US010212940B2

(12) United States Patent
Ambrose et al.

(10) Patent No.: US 10,212,940 B2
(45) Date of Patent: Feb. 26, 2019

(54) ISOLATED COMPLEX ENDOPHYTE COMPOSITIONS AND METHODS FOR IMPROVED PLANT TRAITS

(71) Applicant: Indigo Agriculture, Inc., Cambridge, MA (US)

(72) Inventors: Karen V. Ambrose, Cambridge, MA (US); Brett A. Boghigian, Boston, MA (US); Slavica Djonovic, Malden, MA (US); Paul Andrew Gray, Arlington, MA (US); Gerardo V. Toledo, Belmont, MA (US); Luis Miguel Marquez, Belmont, MA (US); Geoffrey von Maltzahn, Boston, MA (US)

(73) Assignee: Indigo Agriculture, Inc., Boston, MA (US)

( * ) Notice: Subject to any disclaimer, the term of this patent is extended or adjusted under 35 U.S.C. 154(b) by 0 days.

(21) Appl. No.: 15/143,398

(22) Filed: Apr. 29, 2016

(65) Prior Publication Data

US 2016/0316760 A1 Nov. 3, 2016

Related U.S. Application Data

(60) Provisional application No. 62/156,001, filed on May 1, 2015.

(51) Int. Cl.

| | |
|---|---|
| ***A01N 63/00*** | (2006.01) |
| ***A01N 63/04*** | (2006.01) |
| ***A01G 22/00*** | (2018.01) |

(52) U.S. Cl.

CPC ............ *A01N 63/00* (2013.01); *A01G 22/00* (2018.02); *A01N 63/04* (2013.01)

(58) Field of Classification Search

CPC ..................................................... A01N 63/00

See application file for complete search history.

(56) References Cited

U.S. PATENT DOCUMENTS

| | | | |
|---|---|---|---|
| 4,940,834 | A | 7/1990 | Hurley et al. |
| 5,041,290 | A | 8/1991 | Gindrat et al. |

(Continued)

FOREIGN PATENT DOCUMENTS

| | | |
|---|---|---|
| CA | 1041788 | 11/1978 |
| CA | 1229497 | 11/1987 |

(Continued)

OTHER PUBLICATIONS

Sandberg et al., Result 1 from a search in the GenEmbl database, GenEmbl Record No. KF673660, "Fungal endophytes of aquatic macrophytes: diverse host-generalists characterized by tissue preferences and geographic structure," direct submission, 2013.*

(Continued)

*Primary Examiner* — Rosanne Kosson

(74) *Attorney, Agent, or Firm* — Fenwick & West LLP

(57) ABSTRACT

This invention relates to methods and materials for providing a benefit to a plant by associating the plant with a complex endophyte comprising a host fungus further comprising a component bacterium, including benefits to a plant derived from a seed or other plant element treated with a complex endophyte. For example, this invention provides purified complex endophytes, purified complex endophyte components such as bacteria or fungi, synthetic combinations comprising said complex endophytes and/or components, and methods of making and using the same.

21 Claims, 5 Drawing Sheets

Specification includes a Sequence Listing.

(56) References Cited

U.S. PATENT DOCUMENTS

| | | | |
|---|---|---|---|
| 5,113,619 | A | 5/1992 | Leps et al. |
| 5,229,291 | A | 7/1993 | Nielsen et al. |
| 5,292,507 | A | 3/1994 | Charley |
| 5,415,672 | A | 5/1995 | Fahey et al. |
| 5,730,973 | A | 3/1998 | Morales et al. |
| 5,919,447 | A | 7/1999 | Marrone et al. |
| 5,994,117 | A | 11/1999 | Bacon et al. |
| 6,072,107 | A | 6/2000 | Latch et al. |
| 6,077,505 | A | 6/2000 | Parke et al. |
| 6,337,431 | B1 | 1/2002 | Tricoli et al. |
| 6,495,133 | B1 | 12/2002 | Xue |
| 6,681,186 | B1 | 1/2004 | Denisov et al. |
| 6,689,880 | B2 | 2/2004 | Chen et al. |
| 6,823,623 | B2 | 11/2004 | Minato et al. |
| 7,037,879 | B2 | 5/2006 | Imada et al. |
| 7,084,331 | B2 | 8/2006 | Isawa et al. |
| 7,335,816 | B2 | 2/2008 | Kraus et al. |
| 7,341,868 | B2 | 3/2008 | Chopade et al. |
| 7,485,451 | B2 | 2/2009 | VanderGheynst et al. |
| 7,555,990 | B2 | 7/2009 | Beaujot |
| 7,632,985 | B2 | 12/2009 | Malven et al. |
| 7,763,420 | B2 | 7/2010 | Stritzker et al. |
| 7,906,313 | B2 | 3/2011 | Henson et al. |
| 7,977,550 | B2 | 7/2011 | West et al. |
| 8,143,045 | B2 | 3/2012 | Miansnikov et al. |
| 8,455,198 | B2 | 6/2013 | Gao et al. |
| 8,455,395 | B2 | 6/2013 | Miller et al. |
| 8,465,963 | B2 | 6/2013 | Rolston et al. |
| 8,728,459 | B2 | 5/2014 | Isawa et al. |
| 9,113,636 | B2 | 1/2015 | von Maltzahn et al. |
| 8,975,489 | B2 | 3/2015 | Craven |
| 9,277,751 | B2 | 3/2016 | Sword |
| 9,288,995 | B2 | 3/2016 | von Maltzahn et al. |
| 9,295,263 | B2 | 3/2016 | von Maltzahn et al. |
| 9,364,005 | B2 | 6/2016 | Mitter et al. |
| 9,408,394 | B2 | 8/2016 | von Maltzahn et al. |
| 9,532,572 | B2 | 1/2017 | von Maltzahn et al. |
| 9,532,573 | B2 | 1/2017 | von Maltzahn et al. |
| 9,545,111 | B2 | 1/2017 | Sword |
| 9,622,485 | B2 | 4/2017 | von Maltzahn et al. |
| 9,687,001 | B2 | 6/2017 | Vujanovic et al. |
| 9,756,865 | B2 | 9/2017 | Sword |
| 2005/0072047 | A1 | 4/2005 | Conkling et al. |
| 2006/0046246 | A1 | 3/2006 | Zeng et al. |
| 2007/0028318 | A1 | 2/2007 | Livore et al. |
| 2007/0055456 | A1 | 3/2007 | Raftery et al. |
| 2007/0142226 | A1 | 6/2007 | Franco |
| 2007/0292953 | A1 | 12/2007 | Mankin et al. |
| 2008/0229441 | A1 | 9/2008 | Young et al. |
| 2008/0289060 | A1 | 11/2008 | De Beuckeleer et al. |
| 2009/0155214 | A1 | 6/2009 | Isawa et al. |
| 2010/0064392 | A1 | 3/2010 | Yang et al. |
| 2010/0095396 | A1 | 4/2010 | Voeste et al. |
| 2010/0205690 | A1 | 8/2010 | Blasing et al. |
| 2010/0227357 | A1 | 9/2010 | Redman et al. |
| 2011/0182862 | A1 | 7/2011 | Green et al. |
| 2012/0108431 | A1 | 5/2012 | Williams et al. |
| 2012/0131696 | A1 | 5/2012 | Aayal et al. |
| 2012/0144533 | A1 | 6/2012 | Craven |
| 2012/0149571 | A1 | 6/2012 | Kloepper et al. |
| 2012/0178624 | A1 | 7/2012 | Kaminskyj et al. |
| 2012/0324599 | A1 | 12/2012 | Kerns et al. |
| 2013/0031673 | A1 | 1/2013 | Grandlic et al. |
| 2013/0071425 | A1 | 3/2013 | Vidal et al. |
| 2013/0079225 | A1 | 3/2013 | Smith et al. |
| 2013/0150240 | A1 | 6/2013 | Newman et al. |
| 2013/0233501 | A1 | 9/2013 | Van Zyl et al. |
| 2014/0020136 | A1 | 1/2014 | Van Der Wolf et al. |
| 2014/0109249 | A1* | 4/2014 | Turner .................... A01H 1/04 800/260 |
| 2014/0115731 | A1 | 4/2014 | Turner et al. |
| 2014/0147425 | A1 | 5/2014 | Henn et al. |
| 2014/0342905 | A1 | 11/2014 | Bullis et al. |
| 2015/0020239 | A1 | 1/2015 | von Maltzahn et al. |
| 2015/0033420 | A1 | 1/2015 | Rodriguez et al. |
| 2015/0126365 | A1 | 5/2015 | Sword |
| 2015/0230478 | A1 | 8/2015 | Vujanovic et al. |
| 2015/0335029 | A1 | 11/2015 | Mitter et al. |
| 2015/0366217 | A1 | 12/2015 | Vujanovic et al. |
| 2015/0368607 | A1 | 12/2015 | Arnold et al. |
| 2015/0373993 | A1 | 12/2015 | von Maltzahn et al. |
| 2016/0150796 | A1 | 6/2016 | von Maltzahn et al. |
| 2016/0174570 | A1 | 6/2016 | Vujanovic et al. |
| 2016/0192662 | A1 | 7/2016 | Sword |
| 2016/0205947 | A1 | 7/2016 | Sword |
| 2016/0235074 | A1 | 8/2016 | von Maltzahn et al. |
| 2016/0255844 | A1 | 9/2016 | Mitter et al. |
| 2016/0286821 | A1 | 10/2016 | Sword |
| 2016/0316763 | A1 | 11/2016 | Sword |
| 2016/0330976 | A1 | 11/2016 | Mitter et al. |
| 2016/0338360 | A1 | 11/2016 | Mitter et al. |
| 2016/0366892 | A1 | 12/2016 | Ambrose et al. |
| 2017/0020138 | A1 | 1/2017 | von Maltzahn et al. |
| 2017/0164619 | A1 | 6/2017 | von Maltzahn et al. |
| 2017/0164620 | A1 | 6/2017 | von Maltzahn et al. |
| 2017/0215358 | A1 | 8/2017 | Franco et al. |
| 2017/0223967 | A1 | 8/2017 | Mitter et al. |
| 2018/0020677 | A1 | 1/2018 | Ambrose et al. |
| 2018/0092365 | A1 | 4/2018 | Sword |
| 2018/0153174 | A1 | 6/2018 | Riley et al. |

FOREIGN PATENT DOCUMENTS

| | | | |
|---|---|---|---|
| CA | 2562175 | | 1/2013 |
| CN | 1604732 | | 4/2005 |
| CN | 101311262 | A | 11/2008 |
| CN | 101570738 | | 11/2009 |
| CN | 102168022 | A | 8/2011 |
| CN | 102010835 | B | 4/2012 |
| CN | 102533601 | B | 10/2013 |
| CN | 103642725 | A | 3/2014 |
| EP | 0192342 | | 8/1986 |
| EP | 0223662 | | 5/1987 |
| EP | 0378000 | | 7/1990 |
| EP | 0494802 | | 7/1992 |
| EP | 0818135 | | 1/1998 |
| EP | 1935245 | | 6/2008 |
| EP | 2676536 | | 12/2013 |
| JP | 2009/072168 | | 4/2009 |
| KR | 20100114806 | A | 10/2010 |
| KR | 101091151 | | 12/2011 |
| KR | 20130023491 | | 3/2013 |
| WO | WO 1988/009114 | | 1/1988 |
| WO | WO 1994/016076 | | 7/1994 |
| WO | WO 2000/029607 | | 5/2000 |
| WO | WO 2001/083818 | | 11/2001 |
| WO | WO 2002/065836 | | 8/2002 |
| WO | WO 2005/003328 | | 1/2005 |
| WO | WO 2007/021200 | | 2/2007 |
| WO | WO 2007/107000 | | 9/2007 |
| WO | WO 2008/103422 | | 8/2008 |
| WO | WO 2009/012480 | A2 | 1/2009 |
| WO | WO 2009/078710 | A1 | 6/2009 |
| WO | WO 2009/126473 | A1 | 10/2009 |
| WO | WO 2010/109436 | | 9/2010 |
| WO | WO 2010/115156 | | 10/2010 |
| WO | WO 2011/001127 | | 1/2011 |
| WO | WO 2011/082455 | | 7/2011 |
| WO | WO 2011/112781 | | 9/2011 |
| WO | WO 2011/117351 | | 9/2011 |
| WO | WO 2012/034996 | | 3/2012 |
| WO | WO 2013/016361 | | 1/2013 |
| WO | WO 2013/029112 | | 3/2013 |
| WO | WO 2013/090628 | | 6/2013 |
| WO | WO 2013/122473 | | 8/2013 |
| WO | WO 2013/177615 | | 12/2013 |
| WO | WO 2013/190082 | | 12/2013 |
| WO | WO 2014/046553 | | 3/2014 |
| WO | WO 2014/082950 | | 6/2014 |
| WO | WO 2014/121366 | | 8/2014 |
| WO | WO 2014/206953 | | 12/2014 |
| WO | WO 2014/210372 | | 12/2014 |
| WO | WO 2015/035099 | | 3/2015 |
| WO | WO 2015/069938 | | 5/2015 |

(56) References Cited

FOREIGN PATENT DOCUMENTS

| | | |
|---|---|---|
| WO | WO 2015/100431 | 7/2015 |
| WO | WO 2015/100432 | 7/2015 |
| WO | WO 2015/200852 | 12/2015 |
| WO | WO 2015/200902 | 12/2015 |
| WO | WO 2016/109758 | 7/2016 |
| WO | WO 2016/179046 | 11/2016 |
| WO | WO 2016/179047 | 11/2016 |
| WO | WO 2016/200987 | 12/2016 |

OTHER PUBLICATIONS

Huang et al., Result 4 from a search in the GenEmbl database, GenEmbl Record No. KP991588, "Pervasive effects of wildfire on foliar endophyte communities in montane forest trees," Microb Ecol, direct submission, Mar. 2015.*
Abdou et al., "Botryorhodines A-D, antifungal and cytotoxic depsidones from Botryosphaeria rhodina, an endophyte of the medicinal plant Bidens pilosa," Phytochemistry 71:110-116, 2010.*
Alvarez-Perez et al., Result 3 from a search in the GenEmbl database, GenEmbl Record No. JN872548, "Zooming in on floral nectar: a first exploration of nectar-associated bacteria in wild plant communities," FEMS Microbiol Ecol 80(3):591-602, 2012.*
Alvarez-Perez et al., "Zooming in on floral nectar: a first exploration of nectar-associated bacteria in wild plant communities," FEMS Microbiol Ecol 80(3):591-602, 2012.*
Kusari et al. ("Chemical ecology of endophytic fungi: origins of secondary metabolites," Cell Press, Chem & Biol, 19:792-798, 2012.*
PCT Invitation to Pay Additional Fees, PCT Application No. PCT/CA2013/000091, dated Mar. 27, 2013, 2 Pages.
PCT International Search Report and Written Opinion for PCT/CA2013/000091, dated Sep. 20, 2013, 17 Pages.
PCT International Search Report and Written Opinion for PCT/EP2013/062976, dated Dec. 22, 2014, 9 Pages.
PCT International Search Report, Application No. PCT/US2014/044427, dated Dec. 3, 2014, 9 Pages.
PCT International Search Report and Written Opinion, Application No. PCT/US2014/054160, dated Dec. 9, 2014, 21 Pages.
PCT Invitation to Pay Additional Fees, PCT Application No. PCT/US2014/064411, dated Feb. 5, 2015, 2 Pages.
PCT International Search Report and Written Opinion, International Application No. PCT/US2014/064411, dated Mar. 27, 2015, 15 Pages.
PCT Invitation to Pay Additional Fees, PCT Application No. PCT/US2014/072399, dated Apr. 14, 2015, 2 Pages.
PCT International Search Report and Written Opinion, International Application No. PCT/US2014/072399, dated Jun. 26, 2015, 22 Pages.
PCT Invitation to Pay Additional Fees, PCT Application No. PCT/US2014/072400, dated Apr. 16, 2015, 6 Pages.
PCT International Search Report and Written Opinion, Application No. PCT/US2014/072400, dated Jul. 8, 2015, 38 Pages.
PCT Invitation to Pay Additional Fees, PCT Application No. PCT/US2015/038110, dated Sep. 22, 2015, 8 Pages.
PCT Invitation to Pay Additional Fees, PCT Application No. PCT/US2015/038187, dated Oct. 14, 2015, 5 Pages.
PCT International Search Report and Written Opinion, PCT Application No. PCT/US2015/038110, dated Dec. 11, 2015, 36 Pages.
PCT International Search Report and Written Opinion, PCT Application No. PCT/US2015/038187, dated Jan. 22, 2016, 36 Pages.
PCT Invitation to Pay Additional Fees, PCT Application No. PCT/US2015/068206, dated Apr. 12, 2016, 5 Pages.
Abarenkov, K., et al., "PlutoF—A Web Based Workbench for Ecological and Taxonomic Research, with an Online Implementation for Fungal ITS Sequences," Evol Bioinform Online, 2010, pp. 189-196, vol. 6.
Abarenkov, K., et al., "The UNITE Database for Molecular Identification of Fungi—Recent Updates and Future Perspectives," New Phytol., 2010, pp. 281-285, vol. 186.
Abdellatif, L., et al., "Endophytic hyphal compartmentalization is required for successful symbiotic Ascomycota association with root cells," Mycological Research, 2009, pp. 782-791, vol. 113.
Ahmad, F., et al., "Screening of Free-Living Rhizospheric Bacteria for Their Multiple Plant Growth Promoting Activities," Microbiol Res., 2008, pp. 173-181, vol. 163.
Amann, R., et al., "The Identification of Microorganisms by Fluorescence in Situ Hybridisation," Curr Opin Biotechnol., 2001, pp. 231-236, vol. 12.
Apel, K., et al., "Reactive Oxygen Species: Metabolism, Oxidative Stress, and Signal Transduction," Annu Rev Plant Biol., 2004, pp. 373-399, vol. 55.
Arendt, K. R., et al., "Isolation of endohyphal bacteria from foliar Ascomycota and in vitro establishment of their symbiotic associations," Appl. Environ. Microbiol., 2016, pp. 2943-2949, vol. 82, No. 10.
Bacon, C. W., et al., "Isolation, in Planta Detection, and Uses of Endophytic Bacteria for Plant Protection," Manual of Environmental Microbiology, 2007, pp. 638-647.
Baker, K. F., et al., "Dynamics of Seed Transmission of Plant Pathogens," Annu Rev Phytopathol., 1966, pp. 311-334,vol. 4.
Baltruschat, H., et al., "Salt tolerance of barley induced by the root endophyte *Piriformospora indica* is associated with a strong increase in antioxidants," New Phytologist., 2008, pp. 501-510, vol. 180.
Block, C. C., et al., "Seed Transmission of Pantoea stewartii in Field and Sweet Corn," Plant Disease, 1998, pp. 775-780, vol. 82.
Brinkmeyer, R., et al., "Uncultured Bacterium Clone ARKMP-100 16S Ribosomal RNA Gene, Partial Sequence," NCBI GenBank Accession No. AF468334, Submitted Jan. 14, 2002.
Brodie, E.L., et al., "Uncultured Bacterium Clone BANW722 16S Ribosomal RNA Gene, Partial Sequence," NCBI GenBank Accession No. DQ264636, Submitted Oct. 25, 2005.
Bulgarelli, D., et al., "Structure and Functions of the Bacterial Microbiota of Plants," Annu Rev Plant Biol., 2013, pp. 807-838, vol. 64.
Caporaso, J.G., et al., "Ultra-High-Throughput Microbial Community Analysis on the Illumina HiSeq and MiSeq Platforms," ISME J., 2012, pp. 1621-1624, vol. 6.
Castillo, D., et al., "Fungal Entomopathogenic Endophytes: Negative Effects on Cotton Aphid Reproduction in Greenhouse and Field Conditions," Power Point Presentation dated Mar. 23, 2013.
Castillo, D., et al., "Fungal Endophytes: Plant Protective Agents Against Herbivores," Power Point Presentation dated Aug. 4, 2013.
Cavalier-Smith, T., "A Revised Six-Kingdom System of Life," Biol Rev Camb Philos Soc., 1998, pp. 203-266, vol. 73.
Cha, C., et al., "Production of Acyl-Homoserine Lactone Quorum-Sensing Signals by Gram-Negative Plant Associated Bacteria," Mol Plant Microbe Interact., 1998, pp. 1119-1129, vol. 11, No. 11.
Chernin, L. S., et al., "Chitinolytic Activity in Chromobacterium violaceum: Substrate Analysis and Regulation by Quorum Sensing," J Bacteriol., 1998, pp. 4435-4441, vol. 180, No. 17.
Clark, E. M., et al., "Improved Histochemical Techniques for the Detection of Acremonium coenophilum in Tall Fescue and Methods of in vitro Culture of the Fungus," J. Microbiol Methods, 1983, pp. 149-155, vol. 1.
Clay, K., "Effects of fungal endophytes on the seed and seedling biology of Lolium perenne and Festuca arundinacea," Oecologia, 1987, pp. 358-362, vol. 73.
Clough, S. J., et al., "Floral Dip: A Simplified Method for Agrobacterium-mediated Transformation of *Arabidopsis thaliana*," Plant J., 1998, pp. 735-743, vol. 16, No. 6.
Compant, S., et al., "Endophytes of Grapevines Flowers, Berries, and Seeds: Identification of Cultivable Bacteria, Comparison with Other Plant Parts, and Visualization of Niches of Colonization," Microbial Ecology, 2011, pp. 188-197, vol. 62.
Coombs, J. T., et al., "Isolation and Identification of Actinobacteria from Surface-Sterilized Wheat Roots," Applied and Environmental Microbiology, 2003, pp. 5603-5608, vol. 69, No. 9.
Conn, V. M., "Effect of Microbial Inoculants on the Indigenous Actinobacterial Endophyte Population in the Roots of Wheats as Determined by Terminal Restriction Fragment Length Polymorphism," Applied and Environmental Microbiology, 2004, pp. 6407-6413, vol. 70, No. 11.

(56) References Cited

OTHER PUBLICATIONS

Cox, C. D., "Deferration of Laboratory Media and Assays for Ferric and Ferrous Ions," Methods Enzymol., 1994, pp. 315-329, vol. 235.
Craine, J. M., et al., "Global Diversity of Drought Tolerance and Grassland Climate-Change Resilience," Nature Climate Change, 2013, pp. 63-67, vol. 3.
Dalal, J.M., et al., "Utilization of Endophytic Microbes for Induction of Systemic Resistance (ISR) in Soybean (*Glycine max* (L) *Merril*) Against Challenge Inoculation with R. solani," Journal of Applied Science and Research, 2014, pp. 70-84, vol. 2, No. 5.
Danhorn, T., et al., "Biofilm Formation by Plant-Associated Bacteria," Annu Rev Microbiol., 2007, pp. 401-422, vol. 61.
Daniels, R., et al., "Quorum Signal Molecules as Biosurfactants Affecting Swarming in Rhizobium etli," PNAS, 2006, pp. 14965-14970, vol. 103, No. 40.
De Freitas, J. R., et al., "Phosphate-Solubilizing Rhizobacteria Enhance the Growth and Yield but not Phosphorus Uptake of Canola (*Brassica napus* L.)," Biol Fertil Soils, 1997, pp. 358-364, vol. 24.
De Lima Favaro, L. C., et al., "Epicoccum nigrum P16, a Sugarcane Endophyte, Produces Antifungal Compounds and Induces Root Growth," PLoS One, 2012, pp. 1-10, vol. 7, No. 6.
De Melo Pereira, G. V., et al. "A Multiphasic Approach for the Identification of Endophytic Bacterial in Strawberry Fruit and their Potential for Plant Growth Promotion," Microbial Ecology, 2012, pp. 405-417, vol. 63, No. 2.
De Souza, J. J., et al., "Terpenoids from Endophytic Fungi," Molecules, 2011, pp. 10604-10618, vol. 16, No. 12.
Dennis, C., et al., "Antagonistic Properties of Species Groups of Trichoderma," Trans Brit Mycol Soc, 1971, pp. 25-39, vol. 57, No. 1.
Desiro, A., et al., "Detection of a novel intracellular microbiome hosted in arbuscular mycorrhizal fungi," ISME Journal, 2014, pp. 257-270, vol. 8.
Djordjevic, D., et al., "Microtiter Plate Assay for Assessment of Listeria monocytogenes Biofilm Formation," Annl Environ Microbiol., 2002, pp. 2950-2958, vol. 68, No. 6.
Don, R. H., et al., "Properties of Six Pesticide Degradation Plasmids Isolated From Alcaligenes Paradoxus and Alcaligenes eutrophus," J Bacteriol., 1981, pp. 681-686, vol. 145, No. 2.
Dunbar, J, et al., "Uncultured Bacterium Clone NT42a2_20488 16S Ribosomal RNA Gene, Partial Sequence," NCBI GenBank Accession No. JQ378705. Submitted Nov. 8, 2012.
Eberhard, A., et al., "Structural Identification of Autoinducer of Photobacterium fischeri Luciferase," Biochem., 1981, pp. 2444-2449, vol. 20.
Edgar, R. C., "Search and Clustering Orders of Magnitude Faster than BLAST," Bioinformatics, 2010, pp. 2460-2461, vol. 26, No. 19.
Edgar, R. C., "UPARSE: Highly Accurate OTU Sequences From Microbial Amplicon Reads," Nat Methods, 2013, pp. 996-998, vol. 10, No. 10.
Ek-Ramos, M. J., "Ecology, Distribution and Benefits of Fungal Endophytes Isolated from Cultivated Cotton (*Gossypium hirsutum*) in Texas," Power Point Presentation dated Nov. 7, 2012.
Ek-Ramos, M. J., et al., "Spatial and Temporal Variation in Fungal Endophyte Communities Isolated from Cultivated Cotton (*Gossypium hirsutum*)," PLoS One, 2013, vol. 8, No. 6, 13 Pages.
Ek-Ramos, M. J., et al., "Spatial and Temporal Variation in Fungal Endophyte Communities Isolated from Cultivated Cotton (*Gossypium hirsutum*)," Power Point Presentation dated Jan. 7, 2013.
El-Shanshoury, A. R., "Growth Promotion of Wheat Seedlings by Streptomyces atroolivaceus," Journal of Agronomy and Crop Science, 1989, pp. 109-114, vol. 163.
Emerson, D., et al., Identifying and Characterizing Bacteria in an Era of Genomics and Proteomics, BioScience, 2008, pp. 925-936, vol. 58, No. 10.
Endre, G., et al., "A Receptor Kinase Gene Regulating Symbiotic Nodule Development," Nature, 2002, pp. 962-966, vol. 417.
Faria, D. C., et al., "Endophytic Bacteria Isolated from Orchid and Their Potential to Promote Plant Growth," World J Microbiol Biotechnol., 2013, pp. 217-221, vol. 29.
Ferrando, L., et al., "Molecular and Culture-Dependent Analyses Revealed Similarities in the Endophytic Bacterial Community Composition of Leaves from Three Rice (*Oryza sativa*) Varieties," FEMS Microbiol Ecol., 2012, pp. 696-708, vol. 80.
Fiehn, O., et al., "Metabolite Profiling for Plant Functional Genomics," Nature Biotechnol., 2000, pp. 1157-1161, vol. 8.
Fierer, N., et al., "Cross-Biome Metagenomic Analyses of Soil Microbial Communities and Their Functional Attributes," Proc Natl Acad Sci USA, 2012, pp. 21390-21395, vol. 109, No. 52.
Fincher, G. B., "Molecular and Cellular Biology Associated with Endosperm Mobilization in Germinating Cereal Grains," Annu Rev Plant Phvsicl Plant Mol Biol., 1989, pp. 305-346, vol. 40.
Fisher, P. J., et al., "Fungal saprobes and pathogens as endophytes of rice (*Oryza sativa* L.)," New Phytol., 1992, pp. 137-143, vol. 120.
Fisher, P. R., et al., "Isolation and Characterization of the Pesticide-Degrading Plasmid pJP1 from Alcaligenes paradoxus," J Bacteriol., 1978, pp. 798-804, vol. 135, No. 3.
Franco, C., et al., "Actinobacterial Endophytes for Improved Crop Performance," Australasian Plant Pathology, 2007, pp. 524-531, vol. 36.
Fulthorpe, R. R., et al., "Distantly Sampled Soils Carry Few Species in Common," ISME J., 2008, pp. 901-910, vol. 2.
Gantner, S., et al., "Novel Primers for 16S rRNA-based Archaeal Community Analyses in Environmental Samples," J Microbiol Methods, 2011, pp. 12-18, vol. 84.
Gao, Z., et al., "Quantitation of Major Human Cutaneous Bacterial and Fungal Populations," J Clin Microbiol., 2010, pp. 3575-3581, vol. 48, No. 10.
Gasser, I., et al., "Ecology and Characterization of Polyhydroxyalkanoate-Producing Microorganisms on and in Plants," FEMS Microbiol Ecol., 2010, pp. 142-150, vol. 70.
Gavrish, E, et al., "*Lentzea* sp. MS6 16S Ribosomal RNA Gene, Partial Sequence," NCBI GenBank Accession No. EF599958. Submitted May 9, 2007.
Gilmour, S. J., et al., "Overexpression of the *Arabidopsis* CBF3 Transcriptional Activator Mimics Multiple Biochemical Changes Associated with Cold Acclimation," Plant Physiol., 2000, pp. 1854-1865, vol. 124.
Gitaitis, R., et al., "The Epidemiology and Management of Seedborne Bacterial Diseases," Annu Rev Phytopathol., 2007, pp. 371-397, vol. 45.
Gu, O., et al., "*Glycomyces sambucus* sp. nov., an endophytic actinomycete islolated from the stem of Sambucus adnata Wall," International Journal of Systematic and Evolutionary Microbiology, 2007, pp. 1995-1998, vol. 57.
Haake, V., et al., "Transcription Factor CBF4 is a Regulator of Drought Adaptation in *Arabidopsis*," Plant Physiol., 2002, pp. 639-648, vol. 130.
Haas, D., et al., "R Factor Variants with Enhanced Sex Factor Activity in Pseudomonas aeruginosa," Mol Gen Genet., 1976, pp. 243-251, vol. 144.
Hallman, J., et al., "Bacterial Endophytes in Agricultural Crops," Canadian J Microbiol., 1997, pp. 895-914, vol. 43.
Hardegree, S. P. et al., "Effect of Polyethylene Glycol Exclusion on the Water Potential of Solution-Saturated Filter Paper," Plant Physiol., 1990, pp. 462-466, vol. 92.
Hardoim, P. R., et al., "Assessment of Rice Root Endophytes and Their Potential for Plant Growth Promotion," In: Hardoim, P.R., Bacterial Endophytes of Rice—Their Diversity, Characteristics and Perspectives, Groningen, 2011, pp. 77-100.
Hardoim, P. R., et al., "Dynamics of Seed-Borne Rice Endophytes on Early Plant Growth Stages," PLoS One, 2012, vol. 7, No. 2, 13 Pages.
Hepler, P. K., et al., "Polarized Cell Growth in Higher Plants," Annu Rev Cell Dev Biol., 2001, pp. 159-187, vol. 17.
Hiatt, E. E., et al., "Tall Fescue Endophyte Detection: Commerical Immunoblot Test Kit Compared with Microscopic Analysis," Crop Science, 1999, pp. 796-799, vol. 39.
Hibbett, D. S., et al., "A Higher-Level Phylogenetic Classification of the Fungi," Mycol Res., 2007, pp. 509-547, vol. 111.

(56) References Cited

OTHER PUBLICATIONS

Hill, N. S., et al., "Endophyte Survival during Seed Storage: Endophyte-Host Interactions and Heritability," Crop Sci., 2009, pp. 1425-1430, vol. 49.
Hill N. S., et al., "Endophyte Survival during Seed Storage: Endophyte-Host Interactions and Heritability," PowerPoint, Dept. Crop Soil Sciences, University of Georgia, Nov. 16, 2012, 3 Pages.
Hinton, D. M., et al., "Enterobacter cloacae is an endophytic symbiont of corn," Mycopathologia, 1995, pp. 117-125, vol. 129.
Hubbard, M., et al., "Fungal Endophytes Improve Wheat Seed Germination Under Heat and Drought Stress," Botany, 2012, pp. 137-149, vol. 90.
Hung, P.Q., et al., "Isolation and Characterization of Endophytic Bacteria in Soybean (*Glycine* Sp.)," Omonrice, 2004, pp. 92-101, vol. 12.
Idris, A., et al., "Efficacy of Rhizobacteria for Growth Promotion in Sorghum Under Greenhouse Conditions and Selected Modes of Action Studies," J Agr Sci., 2009, pp. 17-30, vol. 147.
Ikeda, S., et al., "The Genotype of the Calcium/Calmodulin-Dependent Protein Kinase Gene (CCaMK) Determines Bacterial Community Diversity in Rice Roots Under Paddy and Upland Field Conditions," Applied and Environmental Microbiology, 2011, pp. 4399-4405, vol. 77, No. 13.
Imoto, K., et al., "Comprehensive Approach to Genes Involved in Cell Wall Modifications in *Arabidopsis thaliana*," Plant Mol Biol., 2005, pp. 177-192, vol. 58.
Jalgaonwala, R., et al., "A Review on Microbial Endophytes from Plants: A Treasure Search for Biologically Active Metabolites," Global Journal of Research on Medicinal Plants & Indigenous Medicine, 2014, pp. 263-277, vol. 3, No. 6.
Janda, J. M., et al., "16S rRNA Gene Sequencing for Bacterial Identification in the Diagnostic Laboratory: Pluses, Perils, and Pitfalls," Journal of Clinical Microbiology, 2007, pp. 2761-2764, vol. 45, No. 9.
Johnston-Monje, D., et al., "Conservation and Diversity of Seed Associated Endophytes in Zea Across Boundaries of Evolution, Ethnography and Ecology," PLoS One, 2011, vol. 6, No. 6, 22 Pages.
Johnston-Monje, D., et al., "Plant and Endophyte Relationships: Nutrient Management," Comprehensive Biotechnol., 2011, pp. 713-727, vol. 4.
Johnston-Monje, D., "Microbial Ecology of Endophytic Bacteria in *Zea* Species as Influenced by Plant Genotype, Seed Origin, and Soil Environment," Thesis, University of Guelph, 2011, 230 Pages.
Jones, K.L., "Fresh Isolates of Actinomycetes in which the Presence of Sporogenous Aerial Mycelia is a Fluctuating Characteristic," J Bacteriol., 1949, pp. 141-145, vol. 57, No. 2.
Kaga, H., et al., "Rice Seeds as Sources of Endophytic Bacteria," Microbes Environ., 2009, pp. 154-162, vol. 24, No. 2.
Kalns, L., et al., "The Effects of Cotton Fungal Endophytes in the Field on Arthropod Community Structure," Power Point Presentation dated Jan. 7, 2013.
Kang, B. H., et al., "Members of the *Arabidopsis* Dynamin-Like Gene Family, ADL1, are Essential for Plant Cytokinesis and Polarized Cell Growth," Plant Cell, 2003, pp. 899-913, vol. 15.
Kasana, R. C., et al., "A Rapid and Easy Method for the Detection of Microbial Cellulases on Agar Plates Using Gram's Iodine," Curr Microbiol., 2008, pp. 503-507, vol. 57.
Kruger, M., et al., "DNA-Based Species Level Detection of Glomeromycota: One PCR Primer Set for All Arbuscular Mycorrhizal Fungi," New Phvtol., 2009, pp. 212-223, vol. 183.
Kuklinsky-Sobral, J., et al., "Isolation and Characterization of Endophytic Bacteria from Soybean (*Glycine max*) Grown in Soil Treated with Glyphosate Herbicide," Plant and Soil, 2005, pp. 91-99, vol. 273.
Lanver, D., et al., "Shot and Msb2-Related Proteins Regulate Appressorium Development in the Smut Fungus *Ustilago aydis*," Plant Cell, 2010, pp. 2085-2101, vol. 22.
Laus, M. C., et al., "Role of Cellulose Fibrils and Exopolysaccharides of Rhizobium leguminosarum in Attachment to and Infection of *Vicia sativa* Root Hairs," Mol Plant Microbe Interact., 2005, pp. 533-538, vol. 18, No. 6.
Leonard, C. A., et al., "Random Mutagenesis of the Aspergillus oryzae Genome Results in Fungal Antibacterial Activity," Int J Microbiol., 2013, vol. 2013, Article ID 901697, 6 Pages.
Li, H. M., et al., "Expression of a Novel Chitinase by the Fungal Endophyte in Poa ampla," Mycologia, 2004, pp. 526-536, vol. 96, No. 3.
Li, Q., "Agrobacterium tumefaciens Strain TA-AT-10 16S Ribosomal RNA Gene, Partial Sequence: GenBank: KF673157.1," Submitted Sep. 17, 2013.
Liu, M., et al., "A Novel Screening Method for Isolating Exopolysaccharide-Deficient Mutants," Appl Environ Microbiol., 1998, pp. 4600-4602, vol. 64, No. 11.
Liu, Y., et al., "Investigation on Diversity and Population Succession Dynamics of Endophytic Bacteria from Seeds of Maize (*Zea mays* L., Nongda108) at Different Growth Stages," Ann Microbiol., 2013, pp. 71-79, vol. 63.
Liu, D., et al., "Osmotin Overexpression in Potato Delays Development of Disease Symptoms," Proc Natl Acad Sci USA, 1994, pp. 1888-1892, vol. 91.
Liu, Y., et al., "Study on Diversity of Endophytic Bacterial Communities in Seeds of Hybrid Maize and their Parental Lines," Arch Microbiol., 2012, pp. 1001-1012, vol. 194.
Long, H. H., et al., "The Structure of the Culturable Root Bacterial Endophyte Community of Nicotiana attenuata is Organized by Soil Composition and Host Plant Ethylene Production and Perception," New Phytol., 2010, pp. 554-567, vol. 185.
Lopez-Lopez, A., et al., "Phaseolus vulgaris Seed-Borne Endophytic Community with Novel Bacterial Species such as *Rhizobium endophyticum* sp. nov.," Systematic Appl Microbiol., 2010, pp. 322-327, vol. 33.
Lorck, H., "Production of Hydrocyanic Acid by Bacteria," Physiol Plant, 1948, pp. 142-146, vol. 1.
Lugtenberg, B., et al., "Plant-Growth-Promoting Rhizobacteria," Ann. Rev. Microbiol., 2009, pp. 541-556, vol. 63.
Lundberg, D. S., et al., "Defining the Core *Arabidopsis thaliana* Root Microbiome," Nature, 2012, pp. 86-90, vol. 488, No. 7409.
Lundberg, D. S., et al., "Practical Innovations for High-Throughput Amplicon Sequencing," Nat Methods, 2013, pp. 999-1002, vol. 10, No. 10.
Ma, Y., et al., "Plant Growth Promoting Rhizobacteria and Endophytes Accelerate Phytoremediation of Metalliferous Soils," Biotechnology Advances, 2011, pp. 248-258, vol. 29.
Madi, L. et al., "Aggregation in Azospirillum brasilense Cd: Conditions and Factors Involved in Cell-to-Cell Adhesion," Plant Soil, 1989, pp. 89-98, vol. 115.
Mannisto, M.K., et al., "Characterization of Psychrotolerant Heterotrophic Bacteria From Finnish Lapland," Svst Appl Microbiol., 2006, pp. 229-243, vol. 29.
Mano, H., et al., "Culturable Surface and Endophytic Bacterial Flora of the Maturing Seeds of Rice Plants (*Oryza sativa*) Cultivated in a Paddy Field," Microbes Environ., 2006, vol. 21, No. 2.
Manter, D. K., et al., "Use of the ITS Primers, ITSIF and ITS4, to Characterize Fungal Abundance and Diversity in Mixed-Template Samples by qPCR and Length Heterogeneity Analysis," J Microbiol Methods, 2007, pp. 7-14, vol. 71.
Mao, W., et al., "Seed Treatment with a Fungal or a Bacterial Antagonist for Reducing Corn Damping-off Caused by Species of *Pythium* and *Fusarium*," Plant Disease, 1997, pp. 450-454, vol. 81, No. 5.
Marasco, R., et al., "A Drought Resistance-Promoting Microbiome is Selected by Root System Under Desert Farming," PLoS One, 2012, vol. 7, No. 10, 14 Pages.
Marquez, L. M., et al., "A Virus in a Fungus in a Plant: Three-Way Symbiosis Required for Thermal Tolerance," Science, 2007, pp. 513-515, vol. 315.
Mastretta, C., et al., "Endophytic Bacteria from Seeds of Nicotiana Tabacum Can Reduce Cadmium Phytotoxicity," Intl J Phytoremediation, 2009, pp. 251-267, vol. 11.

(56) References Cited

OTHER PUBLICATIONS

Mateos, P. F., et al., "Cell-Associated Pectinolytic and Cellulolytic Enzymes in Rhizobium leguminosarum biovar trifolii," Appl Environ Microbiol., 1992, pp. 816-1822, vol. 58, No. 6.
McDonald, D., et al., "An Improved Greengenes Taxonomy with Explicit Ranks for Ecological and Evolutionary Analyses of Bacteria and Archaea," ISME J., 2012, pp. 610-618, vol. 6.
McGuire, K.L., et al., "Digging the New York City Skyline: Soil Fungal Communities in Green Roofs and City Parks," PloS One, 2013, vol. 8, No. 3, 13 Pages.
Medina, P., et al., "Rapid Identification of Gelatin and Casein Hydrolysis Using TCA," J Microbiol Methods, 2007, pp. 391-393, vol. 69.
Mehnaz, S., et al., "Growth Promoting Effects of Corn (*Zea mays*) Bacterial Isolates Under Greenhouse and Field Conditions," Soil Biology and Biochemistry, 2010, pp. 1848-1856, vol. 42.
Michel, B. E., et al., "The Osmotic Potential of Polyethylene Glycol 6000," Plant Physiol., 1973, pp. 914-916, vol. 51.
Moe, L. A., "Amino Acids in the Rhizosphere: From Plants to Microbes," American Journal of Botany, 2013, pp. 1692-1705, vol. 100, No. 9.
Mohiddin, F. A., et al., "Tolerance of Fungal and Bacterial Biocontrol Agents to Six Pesticides Commonly Used in the Control of Soil Borne Plant Pathogens," African Journal of Agricultural Research, 2013, pp. 5331-5334, vol. 8, No. 43.
Mousa, W. K., et al., "The Diversity of Anti-Microbial Secondary Metabolites Produced by Fungal Endophytes: An Interdisciplinary Perspective," Front Microbiol., 2013, vol. 4, No. 65, 18 Pages.
Mundt, J.O., et al., "Bacteria Within Ovules and Seeds," Appl Environ Microbiol., 1976, pp. 694-698, vol. 32, No. 5.
Naik, B. S., et al., "Study on the diversity of endophytic communities from rice (*Oryza sativa* L.) and their antagonistic activities in vitro," Microbiological Research, 2009, pp. 290-296, vol. 164.
Naveed, M., "Maize Endophytes—Diversity, Functionality and Application Potential," University of Natural Resources and Life Sciences, 2013, pp. 1-266 and 81-87; Tables 1-3; Figure 2.
Nejad, P. et al., "Endophytic Bacteria Induce Growth Promotion and Wilt Disease Suppression in Oilseed Rape and Tomato, " Biological Control, 2000, pp. 208-215, vol. 18.
Neslon, E.B., "Microbial Dynamics and Interactions in the Spermosphere," Ann. Rev. Phytopathol., 2004, pp. 271-309, vol. 42.
Nikolcheva, L.G., et al., "Taxon-Specific Fungal Primers Reveal Unexpectedly High Diversity During Leaf Decomposition in a Stream," Mycological Progress, 2004, pp. 41-49, vol. 3, No. 1.
Normander, B., et al., "Bacterial Origin and Community Composition in the Barley Phytosphere as a Function of Habitat and Presowing Conditions," Appl Environ Microbiol., Oct. 2000, pp. 4372-4377, vol. 66, No. 10.
Okunishi, S., et al., "Bacterial Flora of Endophytes in the Maturing Seeds of Cultivated Rice (*Oryza sativa*)," Microbes and Environment, 2005, pp. 168-177, vol. 20, No. 3.
Orole, O. O., et al., "Bacterial and fungal endophytes associated with grains and roots of maize," Journal of Ecology and the Natural Enviornment, 2011, pp. 298-303, vol. 3, No. 9.
Partida-Martinez, L.P., et al., "The Microbe-Free Plant: Fact or Artifact?" Front Plant Sci., 2011, vol. 2, No. 100, 16 Pages.
Pearson, W.R., et al., "Rapid and Sensitive Sequence Comparison With FASTP and FASTA," Methods Enzymol., 2011, pp. 63-98, vol. 183.
Pedraza, R. O., et al., "Azospirillum inoculation and nitrogen fertilization effect on grain yield and on the diversity of endophytic bacteria in the phyllosphere of rice rainfed crop," European Journal of Soil Biology, 2009, pp. 36-43, vol. 45.
Perez-Fernandez, M. A., et al., "Simulation of Germination of Pioneer Species Along an Experimental Drought Gradient," J Environ Biol., 2006, pp. 669-685, vol. 27, No. 4.
Perez-Miranda, S., et al., "O-CAS, A Fast and Universal Method for Siderophore Detection," J Microbiol Methods, 2007, pp. 127-131, vol. 70.
Petti, C. A., "Detection and Identification of Microorganisms by Gene Amplification and Sequencing," Clinical Infectious Diseases, 2007, pp. 1108-1114, vol. 44.
Phalip, V., et al., "A Method for Screening Diacetyl and Acetoin-Producing Bacteria on Agar Plates," J Basic Microbiol., 1994, pp. 277-280, vol. 34.
Philippot, L., et al., "Going Back to the Roots: The Microbial Ecology of the Rhizosphere," Nat Rev Microbiol., Nov. 2013, pp. 789-799, vol. 11.
Pillay, V. K., et al., "Inoculum Density, Temperature, and Genotype Effects on in vitro Growth Promotion and Epiphytic and Endophytic Colonization of Tomato (*Lycopersicon esculentum* L.) Seedlings Inoculated with a Pseudomonad Bacterium," Can J Microbiol., 1997, pp. 354-361, vol. 43.
Powell, W. A., et al., "Evidence of Endophytic Beauveria Bassiana in Seed-Treated Tomato Plants Acting as a Systemic Entomopathogen to Larval *Helicoverpa zea* (Lepidoptera: Noctuidae)," J. Entomol. Sci., 2009, pp. 391-396, vol. 44, No. 4.
Quadt-Hallmann, A., et al., "Bacterial Endophytes in Cotton: Mechanisms of Entering the Plant," Can J Microbiol., 1997, pp. 577-582, vol. 43.
R Core Team, "R: A Language and Environment for Statistical Computing," R Foundation for Statistical Computing, Vienna, Austria, May 2013, ISBN: 3-900051-07-0. Available online at http://www.R- 25project.org/, 3604 Pages.
Ravel, C., et al., "Beneficial effects of Neotyphodium lolii on the growth and the water status in perennial ryegrass cultivated under nitrogen deficiency or drought stress," Agronomie, 1997, pp. 173-181, vol. 17.
Redman, R. S., et al., "Thermotolerance Generated by Plant/Fungal Symbiosis," Science, Nov. 2002, vol. 298, 1 Page (with 4 pages of supplemental material).
Reiter, B., et al., "Response of Endophytic Bacterial Communities in Potato Plants to Infection with *Erwinia carotovora* subsp. *atroseptica*," Appl Environ Microbiol., 2001, pp. 2261-2268, vol. 68, No. 5.
Rodriguez, H., et al., "Expression of a Mineral Phosphate Solubilizing Gene From Erwinia herbicola in Two Rhizobacterial Strains," J Biotechnol., 2001, pp. 155-161, vol. 84.
Rodriguez, R.J., et al., "Stress Tolerance in Plants via Habitat-Adapted Symbiosis," ISME J., 2008, pp. 404-416, vol. 2.
Rodriguez-Navarro, D., et al., "Soybean Interactions with Soil Microbes, Agronomical and Molecular Aspects," Agronomy for Sustainable Development, 2011, pp. 173-190, vol. 31, No. 1.
Roessner, U., et al., "Metabolic Profiling Allows Comprehensive Phenotyping of Genetically or Environmentally Modified Plant Systems," Plant Cell, 2001,pp. 11-29, vol. 13.
Rosado, A. S., et al., "Phenotypic and Genetic Diversity of Paenibacillus azotofixans Strains Isolated from the Rhizoplane or Rhizosphere Soil of Different Grasses," J App Microbiol., 1998, pp. 216-226, vol. 84.
Rosenblueth, A., et al., "Seed Bacterial Endophytes: Common Genera, Seed-to-Seed Variability and Their Possible Role in Plants," Acta Hort., 2012, pp. 39-48, vol. 938.
Rosenblueth, M., et al., "Bacterial Endophytes and Their Interactions With Host," Molecular Plant-Microbe Interactions, 2006, pp. 827-837, vol. 19, No. 8.
Ross, P.L., et al., "Multiplexed Protein Quantitation in *Saccharomyces cerevisiae* Using Amine-Reactive Isobaric Tagging Reagents," Mol Cell Proteomics, 2004, pp. 1154-1169, vol. 3, No. 12.
Saleem, M., et al., "Perspective of Plant Growth Promoting Rhizobacteria (PGRP) Containing ACC Deaminase in Stress Agriculture," J Ind Microbiol Biotechnol., Oct. 2007, pp. 635-648, vol. 34.
Samac, D.A., et al., "Recent Advances in Legume-Microbe Interactions: Recognition, Defense Response, and Symbiosis from a Genomic Perspective," Plant Physiol., 2007, pp. 582-587, vol. 144.
Sardi, P., et al., "Isolation of Endophytic Streptomyces Strains from Surface Sterilized Roots," Applied and Environmental Microbiology, 1992, pp. 2691-2693, vol. 58, No. 8.
Sarwar, M., et al., "Tryptophan Dependent Biosynthesis of Auxins in Soil," Plant Soil, 1992, pp. 207-215, vol. 147.

(56) References Cited

OTHER PUBLICATIONS

Schmieder, R., et al., "Quality Control and Preprocessing of Metagenomic Datasets," Bioinformatics, 2011, pp. 863-864, vol. 27, No. 6.
Schoch, C. L., et al., "Nuclear Ribosomal Internal Transcribed Spacer (ITS) Region as a Universal DNA Barcode Marker for Fungi," Proc Natl Acad Sci USA, 2012, pp. 6241-6246, vol. 109, No. 16.
Schwyn, B. et al., "Universal Chemical Assay for the Detection and Determination of Siderophores," Analytical Biochemistry, 1987, pp. 47-56, vol. 160.
Shapiro-Ilan, D.I., et al., "The Potential for Enhanced Fungicide Resistance in Beauveria Bassiana Through Strain Discovery and Artificial Selection," Journal of Invertebrate Pathology, 2002, pp. 86-93, vol. 81.
Singh, A. K., et al., "Uncultured *Actinomyces* sp. Clone EMLACT 80 IV (New) 16S Ribosomal RNA Gene, Partial Sequence," NCBI GenBank Accession No. JQ285908. Submitted Dec. 13, 2011.
Soares, M. M. C. N., et al., "Screening of Bacterial Strains for Pectinolytic Activity: Characterization of the Polygalacturonase Produced by *Bacillus* Sp," Revista de Microbiolgia, 1999, pp. 299-303, vol. 30.
Song, M., et al., "Effects of Neotyphodium Endophyte on Germination of Hordeum brevisubulatum under Temperature and Water Stress Conditions," Acta Agrestia Sinica, 2010, pp. 834-837, vol. 18, No. 6. (English Abstract).
Souleimanov, A., et al., "The Major Nod Factor of Bradyrhizobium japonicum Promotes Early Growth of Soybean and Corn," J. Exp. Bot., 2002, pp. 1929-1934, vol. 53, No. 376.
Spiekermann, P., et al., "A Sensitive, Viable-Colony Staining Method Using Nile Red for Direct Screening of Bacteria that Accumulate Polyhydroxyalkanoic Acids and Other Lipid Storage Compounds," Arch Microbiol., 1999, pp. 73-80, vol. 171.
Staudt, A. K., et al., "Variations in Exopolysaccharide Production by Rhizobium tropici," Arch Microbiol., 2012, pp. 197-206, vol. 194.
Strobel, G. A., "Endophytes as Sources of Bioactive Products," Microbes and Infection, 2003, pp. 535-544, vol. 5.
Sturz, A. V., et al., "Weeds as a Source of Plant Growth Promoting Rhizobacteria in Agricultural Soils," Can J Microbiol., 2001, pp. 1013-1024, vol. 47, No. 11.
Surette, M. A., et al. "Bacterial Endophytes in Processing Carrots (*Daucus carota* L. var. *sativus*): Their Localization, Population Density, Biodiversity and Their Effects on Plant Growth," Plant and Soil, 2003, pp. 381-390, vol. 253, No. 2.
Suto, M., et al., "Endophytes as Producers of Xylanase," J Biosci Bioeng., 2002, pp. 88-90, vol. 93, No. 1.
Sword, G., "Manipulating Fungal Endophytes to Protect Plants from Insects and Nematodes," Power Point Presentation dated Aug. 7, 2013.
Sword, G., et al., "Manipulating Fungal Endophytes for the Protection of Cotton in the Field," Power Point Presentation dated Jan. 7, 2013.
Sword, G., et al., "Field Trials of Potentially Beneficial Fungal Endophytes in Cotton," Power Point Presentation dated Jan. 7, 2013.
Sword, G., "Fungal Endophytes to Protect Cotton from Insects and Nematodes," Power Point Presentation dated Dec. 7, 2012.
Sword, G., "Natural Enemies—The Forgotten Basis of IPM?," Power Point Presentation dated Sep. 6, 2013.
Taghavi, S., et al., "Genome Survey and Characterization of Endophytic Bacteria Exhibiting a Beneficial Effect on Growth and Development of Poplar Trees," Applied and Environmental Microbiology, 2009, pp. 748-757, vol. 75, No. 3.
Taylor, A. G., et al., "Concepts and Technologies of Selected Seed Treatments," Annu. Rev. Phytopathol., 1990, pp. 321-339, vol. 28.
Teather, R. M., et al., "Use of Congo Red-Polysaccharide Interactions in Enumeration and Characterization of Cellulolytic Bacteria from the Bovine Rumen," Appl Environ Microbiol., 1982, pp. 777-780, vol. 43, No. 4.
Theis, K. R., et al., "Uncultured Bacterium Clone GM2GI8201A64RC 16S Ribosomal RNA Gene, Partial Sequence," NCBI GenBank Accession No. JX051943, Submitted May 14, 2012.
Thomas, L., et al., "Development of Resistance to Chlorhexidine Diacetate in Pseudomonas aeruginosa and the Effect of a "Residual" Concentration," J Hosp Infect., 2000, pp. 297-303, vol. 46.
Thomashow, M. F., "So What's New in the Field of Plant Cold Acclimation? Lots!," Plant Physiol., 2001, pp. 89-93, vol. 125.
Tokala, R. T., et al., "Novel Plant-Microbe Rhizosphere Interaction Involving Streptomyces Lydicus WYEC108 and the Pea Plant (*Pisum Sativum*)," Applied and Environmental Microbiology, May 2002, pp. 2161-2171, vol. 68, No. 5.
Trotel-Aziz, P., et al., "Characterization of New Bacterial Biocontrol Agents *Acinetobacter, Bacillus, Pantoea* and *Pseudomonas* spp. Mediating Grapevine Resistance Against Botrytis cinerea," Environmental and Experimental Botany, 2008, pp. 21-32, vol. 64.
Truyens, S., et al., "Changes in the Population of Seed Bacteria of Transgenerationally Cd-Exposed *Arabidopsis thaliana*," Plant Biol., 2013, pp. 971-981, vol. 15.
Usadel, B., et al., "The Plant Transcriptome-From Integrating Observations to Models," Front Plant Sci., 2013, pp. 1-3, vol. 4., Article 48, 3 Pages.
Vacheron, J., et al., "Plant Growth-Promoting Rhizobacteria and Root System Functioning," Frontiers Plant Sci., 2013, vol. 4, Article 356, 19 Pages.
Valencia, C. U., et al., "Endophytic Establishment as an Unintended Consequence of Biocontrol with Fungal Entomopathogens," Power Point Presentation dated Jan. 7, 2013.
Van Der Lelie, D., et al., "Poplar and its Bacterial Endophytes: Coexistence and Harmony," Critical Rev Plant Sci., 2009, pp. 346-358, vol. 28.
Vining, K., et al., "Methylome Reorganization During in vitro Dedifferentiation and Regeneration of Populus trichocarpa," BMC Plant Biol., 2013, vol. 13, No. 92, 15 Pages.
Viruel, E., et al., "Pseudomonas thiveralensis Strain IEHa 16S Ribosomal RNA Fene, Partial Sequence," NCBI GenBank Accession No. GQ169380.1, Submitted May 15, 2009.
Waller, F., et al., "The Endophytic Fungus *Piriformospora indica* Reprograms Barley to Salt-Stress Tolerance, Disease Resistance, and Higher Yield," PNAS, 2005, pp. 13386-13391, vol. 102, No. 38.
Wang, K., et al., "Monitoring in Planta Bacterial Infection at Both Cellular and Whole-Plant Levels Using the Green Fluorescent Protein Variant GFPuv," New Phytol., 2007, pp. 212-223, vol. 174.
Wang, Q., et al., "Naive Bayesian Classifier for Rapid Assignment of rRNA Sequences into the New Bacterial Taxonomy," Appl. Environ. Microbiol., 2007, pp. 5261-5267, vol. 73, No. 16.
Weaver, P.F., et al., "Characterization of Rhodopseudomonas capsulata," Arch Microbiol., 1975, pp. 207-216, vol. 105.
Welty, R.E., et al., "Influence of Moisture Content, Temperature, and Length of Storage on Seed Germination and Survival of Endophytic Fungi in Seeds of Tall Fescue and Perennial Ryegrass," Phytopathyol., 1987, pp. 893-900, vol. 77, No. 6.
White, J. F., et al., "A Proposed Mechanism for Nitrogen Acquisition by Grass Seedlings Through Oxidation of Symbiotic Bacteria," Symbiosis, 2012, pp. 161-171, vol. 57.
Wiegand, I., et al., "Agar and Broth Dilution Methods to Determine the Minimal Inhibitory Concentration (MIC) of Antimicrobial Substances," Nature Protocols, 2008, pp. 163-175, vol. 3, No. 2.
Xu, M., et al., "Bacterial Community Compositions of Tomato (*Lycopersicum esculentum* Mill.) Seeds and Plant Growth Promoting Activity of ACC Deaminase Producing Bacillus subtilis (HYT-12-1) on Tomato Seedlings," World J Microbiol Biotechnol., 2014, pp. 835-845, vol. 30.
Xu, Y., et al., "Biosynthesis of the Cyclooligomer Despipeptide bassianolide, an Insecticidal Virulence Factor of Beauveria bassiana," Fungal Genetics and Biology, 2009, pp. 353-364, vol. 46.
Xue, Q.Y., et al., "Evaluation of the Strains of Acinetobacter and Enterobacter as potential Biocontrol Agents Against Ralstonia Wilt of Tomato," Biological Control, 2009, vol. 48, pp. 252-258.
Yezerski, A., et al., "The Effects of the Presence of Stored Product Pests on the Microfauna of a Flour Community," Journal of Applied Microbiology, 2005, pp. 507-515, vol. 98.

(56) References Cited

OTHER PUBLICATIONS

You, Y., et al., "Analysis of Genomic Diversity of Endophytic Fungal Strains Isolated from the Roots of *Suaeda japonica* and *S. maritima* for the Restoration of Ecosystems in Buan Salt Marsh," Korean Journal of Microbiology and Biotechnology, 2012, pp. 287-295, vol. 40, No. 4. (with English Abstract).
Zhou, W., et al., "Effects of the Fungal Endophyte *Paecilomyces* sp. in Cotton on the Roo-Knot Nematode Meloidogyne incognita," poster dated Jan. 7, 2013.
Zimmerman, N.B., et al., "Fungal Endophyte Communities Reflect Environmental Structuring Across a Hawaiian Landscape," Proc Natl Acad Sci USA, 2012, pp. 13022-13027, vol. 109, No. 32.
Zuccaro, A., et al., "Endophytic Life Strategies Decoded by Genome and Transcriptome Analyses of the Mutualistic Root Symbiont Piriformospora indica," PLOS Pathogens, 2011, vol. 7, No. 10, e1002290.
Zuniga, A., et al., "Quorum Sensing and Indole-3-Acetic Acid Degradation Play a Role in Colonization and Plant Growth Promotion of *Arabidopsis thaliana* by Burkholderia phytofirmans PsJN," Mol Plant Microbe Interact., 2013, pp. 546-553, vol. 26, No. 5.
PCT International Search Report and Written Opinion, Application No. PCT/AU2014/000360, dated Aug. 5, 2015, 12 Pages.
PCT International Search Report and Written Opinion, PCT Application No. PCT/US2015/068206, dated Jun. 27, 2016, 20 Pages.
PCT International Search Report and Written Opinion, PCT Application No. PCT/US2016/030292, dated Aug. 12, 2016, 20 Pages.
PCT International Preliminary Report on Patentability, PCT Application No. PCT/US2016/030292, dated Aug. 2, 2017, 23 Pages.
PCT International Search Report and Written Opinion, PCT Application No. PCT/US2016/030293, dated Aug. 11, 2016, 23 Pages.
PCT International Search Report and Written Opinion, PCT Application No. PCT/US2016/036504, dated Nov. 4, 2016, 18 Pages.
PCT International Search Report and Written Opinion, PCT Application No. PCT/US2016/039191, dated Nov. 29, 2016, 20 Pages.
PCT International Search Report and Written Opinion, PCT Application No. PCT/US2016/068144, dated May 18, 2017, 30 Pages.
Canadian Patent Office, Office Action, Canadian Patent Application No. CA 2,953,466, dated Dec. 11, 2017, 7 Pages.
Canadian Patent Office, Office Action, Canadian Patent Application No. 2,916,678, dated Feb. 8, 2017, 8 Pages.
Canadian Patent Office, Office Action, Canadian Patent Application No. 2,935,218, dated Jun. 13, 2017, 5 Pages.
Canadian Patent Office, Office Action, Canadian Patent Application No. CA 2,953,697, dated Oct. 12, 2017, 6 Pages.
Canadian Patent Office, Office Action, Canadian Patent Application No. CA 2,952,057, dated Oct. 12, 2017, 4 Pages.
Canadian Patent Office, Office Action, Canadian Patent Application No. CA 2,929,487, dated Dec. 7, 2017, 4 Pages.
Chinese Patent Office, Office Action, Chinese Patent Application No. 201480072142.7, dated Apr. 25, 2017, 14 Pages (with English translation).
Chinese Patent Office, 2nd Office Action for Chinese Patent Application No. CN 201480072142.7, dated Oct. 30, 2017, 13 Pages, (with English translation).
European Patent Office, Supplementary Partial European Search Report, European Patent Application No. 13874703.5, dated Jun. 21, 2016, 3 Pages.
European Patent Office, Supplementary European Search Report, European Patent Application No. 13874703.5, dated Oct. 21, 2016, 16 Pages.
European Patent Office, Communication Pursuant to Article 94(3) EPC for European Patent Application No. 13874703.5, dated Jan. 5, 2018, 4 Pages.
European Patent Office, Supplementary European Search Report, European Patent Application No. 14860187.5, dated May 24, 2017, 9 Pages.
European Patent Office, Supplementary European Search Report, European Patent Application No. 14874589.6, dated Jul. 11, 2017, 9 Pages.
European Patent Office, Examination Report, European Patent Application No. 14748326.7, dated Jul. 19, 2017, 4 Pages.
European Patent Office, Examination Report for European Patent Application No. EP 14777213.1, dated Oct. 20, 2017, 12 Pages.
European Patent Office, Supplementary European Search Report, European Patent Application No. EP 15809264.3, dated Dec. 4, 2017, 16 Pages.
European Patent Office, Communication Pursuant to Article 94(3) EPC for European Patent Application No. 15810847.2, dated Nov. 17, 2017, 17 Pages.
European Patent Office, Supplementary European Search Report, European Patent Application No. EP 15812324.0, dated Nov. 2, 2017, 19 Pages.
Intellectual Property Australia, Examination Report for Australian Patent Application No. 2016202480, dated Apr. 28, 2016, 2 Pages.
Intellectual Property Australia, Examination Report for Australian Patent Application No. 2014346664, dated Nov. 24, 2016, 3 Pages.
Intellectual Property Australia, Examination Report for Australian Patent Application No. 2014315191, dated Jul. 15, 2017, 6 Pages.
Intellectual Property Australia, Examination Report for Australian Patent Application No. 2015279600, dated Jul. 21, 2017, 7 Pages.
Intellectual Property Australia, Examination Report for Australian Patent Application No. 2015278238, dated Jul. 24, 2017, 3 Pages.
Intellectual Property Australia, Examination Report No. 1 for Australian Patent Application No. AU 2017254880, dated Nov. 15, 2017, 2 Pages.
New Zealand Intellectual Property Office, First Examination Report, New Zealand Patent Application No. 715728, dated May 10, 2016, 4 Pages.
New Zealand Intellectual Property Office, First Examination Report, New Zealand Patent Application No. 715728, dated Dec. 5, 2016, 3 Pages.
New Zealand Intellectual Property Office, First Examination Report, New Zealand Patent Application No. 727449, dated Jun. 8, 2017, 7 Pages.
New Zealand Intellectual Property Office, First Examination Report, New Zealand Patent Application No. 726116, dated Jun. 29, 2017, 2 Pages.
New Zealand Intellectual Property Office, First Examination Report, New Zealand Patent Application No. 726116, dated Sep. 26, 2017, 5 Pages.
New Zealand Intellectual Property Office, First Examination Report, New Zealand Patent Application No. 728495, dated Jul. 12, 2017, 5 Pages.
New Zealand Intellectual Property Office, First Examination Report for New Zealand Patent Application No. NZ 728483, dated Dec. 8, 2017, 2 Pages.
Russian Patent Office, Office Action for Russian Patent Application No. RU 2017127214, dated Nov. 22, 2017, 4 Pages, (with English translation).
Russian Patent Office, Office Action for Russian Patent Application No. RU 2015137613, dated Jun. 7, 2017, 14 Pages (with English translation).
Ukraine Patent Office, Office Action for Ukrainian Patent Application No. a201508515, dated May 19, 2017, 14 Pages (with English translation).
Adhikari, M., et al., "A New Record of Pseudeurotium bakeri from Crop Field Soil in Korea," The Korean Journal of Mycology, 2016, pp. 145-149, vol. 44.
Ashrafuzzaman, M., et al., "Efficiency of plant growth-promoting rhizobacteria (PGPR) for the enhancement of rice growth," African Journal of Biotechnology, 2009, pp. 1247-1252, vol. 8, No. 7.
Bensch, K., et al., "Species and ecological diversity within the Cladosporium cladosporioides complex (Davidiellaceae, Capnodiales)," Studies in Mycology, 2010, pp., 1-94, vol. 67.
Buttner, D., et al., "Regulation and secretion of Xanthomonas virulence factors," FEMS Microbiology Reviews, 2010, pp. 107-133, vol. 34, No. 2.
Chagas, F., et al., "A Mixed Culture of Endophytic Fungi Increases Production of Antifungal Polyketides," J. Chem Ecol., Oct. 2013, pp. 1335-1342, vol. 39.

(56) References Cited

OTHER PUBLICATIONS

Clarridge, J., "Impact of 16S rRNA Gene Sequence Analysis for Identification of Bacteria on Clinical Microbiology and Infectious Diseases," Clinical Microbiology Reviews, Oct. 2004, pp. 840-862, vol. 17, No. 4.
Cottyn, B., et al., "Phenotypic and genetic diversity of rice seed-associated bacteria and their role in pathogenicity and biological control," Journal of Applied Microbiology, 2009, pp. 885-897, vol. 107.
Darsonval, A., et al., "Adhesion and Fitness in the Bean Phyllosphere and Transmission to Seed of *Xanthomonas fuscans* subsp. *fuscans*," Molecular Plant-Microbe Interactions, 2009, pp. 747-757, vol. 22, No. 6.
Darsonval, A., et al., "The Type III Secretion System of *Xanthomonas fuscans* subsp. *fuscans* is involved in the Phyllosphere Colonization Process and in Transmission to Seeds of Susceptible Beans," Applied and Envioronmental Mirobiology, 2008, pp. 2669-2678, vol. 74, No. 9.
Dbget, "Orthology: K14454," 2005, 2 pages, can be retrieved at <URL:http://www.genome.jp/dbget-bin/www_bget?ko:K14454>.
Gebhardt, J., et al., "Characterization of a single soybean cDNA encoding cytosolic and glyoxysomal isozymes of aspartate aminostransferase," Plant Molecular Biology, 1998, pp. 99-108, vol. 37.
GenBank: AF034210.1 "Glycine max aspartate aminotransferase glyoxysomal isozyme AAT1 precursor and aspartate aminotransferase cytosolic isozyme AAT2 (AAT) mRNA, complete cds," NCBI, May 26, 1998, 2 Pages, can be retrieved at <URL:https://www.ncbi.nlm.nih.gov/nuccore/AF034210>.
GenBank: JN210900.1, "*Enterobacter* sp. WS05 16S ribosomal RNA gene, partial sequence," NCBI, Sep. 24, 2012, 1 Page, can be retrieved at <URL:https://www.ncbi.nlm.nih.gov/nuccore/jn210900>.
GenBank: NP_001237541.1, "aspartate aminotransferase glyoxysomal isozyme AAT1 precursor [*Glycine max*]," NCBI, Oct. 29, 2016, 2 Pages, can be retrieved at <URL:https://www.ncbi.nlm.nih.gov/protein/NP_001237541.1>.
GenEmbl database, GenEmbl Record No. EU 977189, Jan. 21, 2009, 4 pages, Smith, S.A., et al., "Bioactive endophytes warrant intensified exploration and conservation," PloS One 3(8):E3052, 2008.
GenEmbl database, GenEmbl Record No. KF011597, Paenibacillus strain No. HA 13, Aug. 26, 2013, 5 Pages, Park, H.J., et al., "Isolation and characterization of humic substances-degrading bacteria from the subarctic Alaska grasslands," J Basic Microbiol, 2013.
Giraldo, A., et al., "Phylogeny of Sarocladium (*Hypocreales*)," Persoonia, 2015, pp. 10-24, vol. 34.
Grondona, I., et al., "TUSAL®, a commercial biocontrol formulation based on Trichoderma," Bulletin OILB/SROP, 2004, pp. 285-288, vol. 27, No. 8.
Hahm, M-S., et al., "Biological Control and Plant Growth Promoting Capacity of Rhizobacteria and Pepper Under Greenhouse and Field Conditions," The Journal of Microbiology, The Microbiological Society of Korea, Heidelberg, Jun. 30, 2012, pp. 380-385, vol. 50, No. 3.
Hanson, L.E., "Reduction of Verticillium Wilt Symptoms in Cotton Following Seed Treatment with Trichoderma virens," The Journal of Cotton Science, 2000, pp. 224-231, vol. 4, No. 4.
Hanson, L.E., "Reduction of Verticillium Wilt Symptoms in Cotton Following Seed Treatment with Trichoderma virens," Proceedings Beltwide Cotton Conferences, 2000, vol. 1. (Abstract).
Harman, G.E., et al., "Symposium: biocontrol and biotechnological methods for controlling cotton pests," Proceedings of the Beltwide Cotton Production Research Conf., 1989, Memphis, Tennessee, USA, pp. 15-20. (Abstract).
Howell, C.R., et al., "Induction of Terpenoid Synthesis in Cotton Roots and Control of Rhizoctonia solani by Seed Treatment with Trichoderma virens," Phytopathology, 2000, pp. 248-252, vol. 90, No. 3.
Khan, A.L., et al., "Salinity Stress Resistance Offered by Endophytic Fungal Interaction Between Penicillium minioluteum LHL09 and *Glycine max*. L," J. Microbiol. Biotechnol., 2011, pp. 893-902, vol. 21, No. 9.
Kuklinsky-Sobral, J., et al., "Isolation and characterization of soybean-associated bacteria and their potential for plant growth promotion," Environmental Microbiology, 2004, pp. 1244-1251, vol. 6, No. 12.
Labeda, D.P., et al., "Phylogenetic study of the species within the family Streptomycetaceae," Antonie van Leeuwenhoek, 2012, vol. 101, pp. 73-104, Springer.
Le, X.H., et al., "Effects of endophytic Streptomyces on the lucerne (*Medicago sativa* L.) symbiosis at different levels of nitrogen," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 66-67.
Le, X.H., et al., "Isolation and characterisation of endophytic actinobacteria and their effect on the early growth and nodulation of lucerne (*Medicago sativa* L.)," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 134-136.
Lehman, S.G., "Treat Cotton Seed," Review of Applied Mycology, 1945, 24, 369, 16 Pages.
Lehman, S.G., "Treat Cotton Seed," Research and Farming III, Progr. Rept., 1945, 3, 5, 16 Pages.
Li, H., et al., "Endophytes and their role in phytoremediation," Fungal Diversity, 2012, pp. 11-18, vol. 54.
Mehnaz, S., et al., "Isolation and 16S rRNA sequence analysis of the beneficial bacteria from the rhizosphere of rice," Canada Journal of Microbiology, 2001, pp. 110-117, vol. 47, No. 2.
Mei, C., et al., "The Use of Beneficial Microbial Endophytes for Plant Biomass and Stress Tolerance Improvement," Recent Patents on Biotechnology, 2010, pp. 81-95, vol. 4.
Misk, A., et al., "Biocontrol of chickpea root rot using endophytic actinobacteria", Biocontrol, vol. 56, No. 5, Mar. 12, 2011, pp. 811-822, XP036215297.
Nimnoi, P., et al., "Co-Inoculation of Soybean (*Glycin max*) with Actinomycetes and Bradyrhizobium Japonicum Enhances Plant Growth, Nitrogenase Activity and Plant Nutrition," Journal of Plant Nutrition, 2014, pp. 432-446, vol. 37.
Op De Beeck, M., et al., "Comparison and Validation of Some its Primer Pairs Useful for Fungal Metabarcoding Studies," Plos One, Jun. 2014, vol. 9, Issue 6, e97629, pp. 1-11.
Philrice Batac, Philippine Rice R&D Highlights, 2012, Area-Based R&D Projects, [online][Retrieved Aug. 11, 2016] Retrieved from the Internet <URL:http://www.philrice.gov.ph/2012-rd-highlights/>.
Rasmussen, S., et al., "Grass-endophyte interactions: a note on the role of monosaccharide transport in the Neotyphodium lolii-Lolium perenne symbiosis," New Phytologist, 2012, pp. 7-12, vol. 196.
Riken, GI No. GMFL01-01-003, 2 Pages, [online] [Retrieved on Dec. 18, 2017] Retrieved from the Internet <URL:http://spectra.psc.riken.jp/menta.cgi/rsoy/datail?id=GMFL01-01-D03>.
Senthilkumar, M., et al., "Biocontrol Potential of Soybean Bacterial Endophytes Against Charcoal Rot Fungus, *Rhizoctonia batatiola*," Current Microbiology, 2009, vol. 58, pp. 288-293.
Sessitsch, A., et al., "*Burkholderia phytofirmans* sp. Nov., a novel plant-associated bacterium with plant-beneficial properties," International Journal of Systematic and Evoluntary Microbiology, 2005, pp. 1187-1192, vol. 55.
Shankar, M., et al.,"Root colonization of a rice growth promoting strain of Enterobacter cloacae," Journal of Basic Microbiology, 2011, pp. 523-530, vol. 51.
Soe, K.M., et al., "Effects of endophytic actinomycetes and Bradyrhizobium japonicum strains on growth, nodulation, nitrogen fixation and seed weight of different soybean varieties," Soil Science and Plant Nutrition, 2012, pp. 319-325, vol. 58, No. 3.
Soe, K.M., et al., "Low-Density Co-Inoculation of Myanmar Bradyrhizobium yuanmingense MAS34 and Streptomyces griseoflavus P4 to Enhance Symbiosis and Seed Yield in Soybean Varieties," American Journal of Plant Sciences, 2013, pp. 1879-1892, vol. 4.

(56) References Cited

OTHER PUBLICATIONS

Sogonov, M.V., et al., "The hyphomycete *Teberdinia hygrophila* gen. nov., sp. nov. and related anamorphs of *Pseudeurotium* species," Mycologia, May 2005, pp. 695-709, vol. 97, No. 3.
Thakur, A., et al., "Detrimental effects of endophytic fungus *Nigrospora* sp. on survival and development of Spodoptera litura," Biocontrol Science and Technology, Feb. 1, 2012, pp. 151-161, vol. 22, No. 2.
Thakur, A., et al., "Enhanced Resistance to Spodoptera litura in Endophyte Infected Cauliflower Plants," Environmental Entomology, Apr. 1, 2013, pp. 240-246, vol. 42, No. 2.
Thakur, A., et al., "Suppression of Cellular Immune Response in *Spodoptera litura* (Lepidoptera: Noctuidae) Larvae by Endophytic Fungi Nigrospora oryzae and Cladosporium uredinicola,", Annals of the Entomological Society of America, May 1, 2014, pp. 674-679, vol. 107, No. 3.
Trichoderma definition, 2016, 6 Pages, [online] [Retrieved on Sep. 16, 2016,] Retrieved from the Internet <URL:https://en.wikipedia.org/wiki/Trichoderma>.
Verkley, G., et al., "Paraconiothyrium, a new genus to accommodate the mycoparasite Coniothyrium minitans, anamorphs of Paraphaeosphaeria, and four new species," Studies in Mycology, 2004, pp. 323-335, vol. 50.
Visagie, C.M., et al., "Identification and nomenclature of the genus *Penicillium*," Studies in Mycology, Jun. 2014, pp. 343-371, vol. 78.
Wang, B., et al., "Fungal endophytes of native *Gossypium* species in Australia," Mycological Research, 2007, pp. 347-354, vol. 111, No. 3.
Waqas, M., et al., "Endophytic Fungi Produce Gibberellins and Indoleacetic Acid and Promotes Host-Plant Growth during Stress," Molecules, 2012, pp. 10754-10773, vol. 17.
Weindling, R., "Relation of dosage to control of cotton seedling diseases by seed treatment," Plant Disease Reporter, 1943, 27, pp. 68-70.
Yandigeri, M. S., et al., "Drought-tolerant endophytic actinobacteria promote growth of wheat (*Triticum aestivum*) under water stress conditions," Plant Growth Regulation, 2012, pp. 411-420, vol. 68.
Zhang, J., et al: "Isolation and Characterization of Plant Growth-Promoting Rhizobacteria from Wheat Roots by Wheat Germ Agglutinin Labeled with Fluorescein Isothiocyanate", The Journal of Microbiology, Apr. 27, 2012, vol. 50, No. 2, pp. 191-198, GenBank Accession No. JN210900.
Zhao, J.H., et al., "Bioactive secondary metabolites from Nigrospora sp. LLGLM003, an endophytic fungus of the medicinal plant *Moringa oleifera* Lam." World Journal of Microbiology and Biotechnology, Kluwer Academic Publishers, Feb. 12, 2012, pp. 2107-2112, vol. 28, No. 5.
Garazzino, S., et al., "Osteomyelitis Caused by Enterobacter cancerogenus Infection following a Traumatic Injury: Case Report and Review of the Literature," J Clin Microbiol., Mar. 2005, vol. 43, No. 3, pp. 1459-1461.
Hoffman, M., et al., "Diverse Bacteria Inhabit Living Hyphae of Phylogenetically Diverse Fungal Endophytes," Applied and Environmental Microbiology, Jun. 2010, p. 4063-4075, vol. 76, No. 12.
Hoffman, M., et al., "Endohyphal Bacterium Enhances Production of Indole-3-Acetic Acid by a Foliar Fungal Endophyte," PLOS One, Sep. 24, 2013, pp. 1-8, vol. 8, Issue 9, e73132.
Humann, J., et al., "Complete genome of the onion pathogen Enterobacter cloacae EcWSU1," Standard in Genomic Sciences, Dec. 31, 2011, vol. 5, No. 3, pp. 279-286.
Jung, C., et al., "The Effects of Endohyphal Bacteria on Anti-Cancer and Anti-Malaria Metabolites of Endophytic Fungi," Honors Thesis, University of Arizona, May 2012, 15 Pages.
Kim, M., et al., "Towards a taxonomic coherence between average nucleotide identity and 16S rRNA gene sequence similarity for species demarcation of prokaryotes", Int J Systematic Evolutionary Microbial., 2014, vol. 64, pp. 346-351.
Kumar, S., et al., "MEGA7: Molecular Evolutionary Genetics Analysis version 7.0 for bigger datasets," Molecular Biology and Evolution, Mar. 22, 2016, vol. 33, pp. 1870-1874.
Nishijima, K.A., et al., "Demonstrating Pathogenicity of Enterobacter cloacae on Macadamia and Identifying Associated Volatiles of Gray Kernel of Macadamia in Hawaii," Plant Disease, Oct. 2007, vol. 91, No. 10, pp. 1221-1228.
Ren, Y., et al., "Complete Genome Sequence of *Enterobacter cloacae* subsp. *cloacae* Type Strain ATCC 13047," J. Bacteriol. May 2010, vol. 192, No. 9, pp. 2463-2464.
Tamura, K., et al., "Estimation of the number of nucleotide substitutions in the control region of mitochondrial DNA in humans and chimpanzees," Molecular Biology and Evolution, 1993, vol. 10, No. 3, pp. 512-526.
Yennamalli, R., et al., "Endoglucanases: insights into thermostability for biofuel applications", Biotech Biofuels, 2013, vol. 6, Issue 136, pp. 1-9.
PCT Invitation to Pay Additional Fees, PCT Application No. PCT/US2017/064351, dated Feb. 9, 2018, 18 Pages.
PCT International Search Report and Written Opinion, PCT Application No. PCT/US2017/064351, dated Apr. 9, 2018, 25 Pages.
PCT Invitation to Pay Additional Fees, PCT Application No. PCT/US2017/064361, dated Mar. 7, 2018, 18 Pages.
PCT International Search Report and Written Opinion for PCT/US2017/064361, dated May 11, 2018, 22 Pages.
PCT Invitation to Pay Additional Fees, PCT Application No. PCT/US2017/064292, dated Mar. 5, 2018, 15 Pages.
PCT International Search Report and Written Opinion, PCT Application No. PCT/US2017/064292, dated May 11, 2018, 20 Pages.
PCT International Search Report and Written Opinion, PCT Application No. PCT/USS2017/068255, dated Mar. 19, 2018, 14 Pages.
Canadian Patent Office, Office Action, Canadian Patent Application No. 2,935,218, dated May 8, 2018, 5 Pages.
European Patent Office, Communication Pursuant to Article 94(3) EPC for European Patent Application No. EP 14748326.7, dated Feb. 15, 2018, 7 Pages.
European Patent Office, Supplementary European Search Report for European Patent Application No. 15810847.2, dated Feb. 28, 2018, 19 Pages.
European Patent Office, Extended European Search Report, European Patent Application No. EP 15812324.0, dated Feb. 21, 2018, 23 Pages.
European Patent Office, Extended European Search Report, European Patent Application No. EP 15809264.3, dated Mar. 12, 2018, 14 Pages.
European Patent Office, Extended European Search Report, European Patent Application No. EP 15876324.3, dated Jun. 12, 2018, 9 Pages.
Intellectual Property Australia, Examination Report No. 1 for Australian Patent Application No. AU 2017201009, dated Apr. 4, 2018, 3 Pages.
Intellectual Property Australia, Examination Report No. 1 for Australian Patent Application No. AU 2017210482, dated May 15, 2018, 4 Pages.
New Zealand Intellectual Property Office, Further Examination Report, New Zealand Patent Application No. 726116, dated Feb. 27, 2018, 6 Pages.
Russian Patent Office, Office Action for Russian Patent Application No. RU 2017141758, dated Apr. 17, 2018, 4 Pages (with Concise Explanation of Relevance).
Russian Patent Office, Office Action for Russian Patent Application No. RU 2017141632, dated Apr. 17, 2018, 4 Pages (with Concise Explanation of Relevance).
Ukraine Patent Office, Office Action for Ukrainian Patent Application No. a201508515, dated Feb. 20, 2018, 9 Pages (with English translation).
Office Action for Israel Patent Application No. IL 255682, dated Mar. 15, 2018, 2 Pages (Translation).
Office Action for Israel Patent Application No. IL 255684, dated Mar. 19, 2018, 2 Pages (Translation).
Office Action for Israel Patent Application No. IL 255685, dated Mar. 20, 2018, 2 Pages (Translation).
Office Action for Israel Patent Application No. IL 255688, dated Mar. 22, 2018, 2 Pages (Translation).
Office Action for Israel Patent Application No. IL 245385, dated Mar. 23, 2018, 3 Pages (With Concise Explanation of Relevance).

(56) References Cited

OTHER PUBLICATIONS

Abdellatif, L., et al., "Characterization of virulence and PCR-DGGE profiles of Fusarium avenaceum from western Canadian Prairie Ecozone of Saskatchewan," Canadian Journal of Plant Pathology, 2010, pp. 468-480.
Abou-Shanab, R. A., et al: "Characterization of Ni-resistant bacteria in the rhizosphere of the hyperaccumulator Alyssum murale by 16S rRNA gene sequence analysis", World Journal of Microbiology and Biotechnology, vol. 26, No. 1, Aug. 15, 2009, pp. 101-108.
Amatuzzi, R.F., et al., "Universidade Federal Do Parana," Jan. 1, 2014, 52 Pages. (With English Abstract).
Amatuzzi, R.F., et al., "Potential of endophytic fungi as biocontrol agents of Duponchelia fovealis (Zeller) (Lepidoptera:Crambidae," Brazilian Journal of Biology, Nov. 9, 2017, 7 Pages.
Aveskamp, M., et al., "DNA phylogeny reveals polyphyly of Phoma section Peyronellaea and multiple taxonomic novelties," Mycologia, 2009, vol. 101, No. 3, pp. 363-382.
Bethlenfalvay, G., et al., "Mycorrhizal fungi effects on nutrient composition and yield of soybean seeds", Journal of Plant Nutrition, vol. 20, No. 4-5, Apr. 1, 1997, pp. 581-591.
Bing, La, et al., "Suppression of Ostrinia nubilalis (Hübner) (Lepidoptera: Pyralidae) by endophytic Beauveria bassiana (Balsamo) Vuillemin", Environmental Entomol, Entomological Society of America, College Park, MD, US, vol. 20, Jan. 1, 1991, pp. 1207-1211.
Compant, S., et al., "Endophytic colonization of *Vitis vinfera* L. by Burkholderia phytofirmans strain PsJN: from the rhizosphere to inflorescence tissues," FEMS Microbiol Ecol, 2008, pp. 84-93, vol. 63.
NCBI GenBank: CP000653.1 "*Enterobacter* sp. 638, complete genome" Jan. 28, 2014, 5 Pages, Can be retrieved at <URL:https://www.ncbi.nlm.nih.gov/nuccore/CP000653.1>.
NCBI GenBank: CP000653.1 "*Enterobacter* sp. 638, complete genome" ASM1632v1, Apr. 18, 2007, 2 Pages, Can be retrieved at <URL:https://www.ncbi.nlm.nih.gov/assembly/GCA_000016325.1>.
NCBI GenBank: EU340965.1 "*Enterobacter* sp. 638 16S ribosomal RNA gene, partial sequence" Jan. 30, 2009, 1 Page, Can be retrieved at <URL:https://www.ncbi.nlm.nih.gov/nuccore/EU340965.1>.
NCBI GenBank: EBI accession No. EM STD:JQ759988, "*Dothideomycetes* sp. genotype 226 isolate FL0175 internal transcribed spacer 1, partial sequence; 5.85 ribosomal RNA gene and internal transcribed spacer 2, complete sequence; and 285 ribosomal RNA gene, partial sequence," May 17, 2012, 2 Pages.
NCBI GenBank: EBI accession No. EM STD:GU055658, "Uncultured Periconia clone NG R 806 18S ribosomal RNA gene, partial sequence; internal transcribed spacer 1, 5.8S ribosomal RNA gene, and internal transcribed spacer 2, complete sequence; and 28S ribosomal RNA gene, partial sequence," Oct. 27, 2009, 2 Pages.
Database Geneseq Database accession No. BAP97938 "Pantoea dispersa strain KACC91642P 16S rDNA sequence, Seq ID 1." Aug. 15, 2013, 1 Page.
Database EMBL [Online] Oct. 1, 2001, 2 Pages, "Setosphaeria monoceras 28S ribosomal RNA gene, partial sequence," XP002777918, retrieved from EBI accession No. EM_STD:AY016368 Database accession No. AY016368 sequence.
Hamayun, M., et al., "Cladosporium sphaerospermum as a new plant growth-promoting endophyte from the roots of *Glycine max* (L.) Merr," World Journal of Microbiology and Biotechnology, Kluwer Academic Publishers, Feb. 15, 2009, pp. 627-632, vol. 25, No. 4.
Hubbard, M., et al., 2011. "Agricultural Potential of Fungal Endophytes of Grasses, Cereals and Wheat," In: Wheat: Genetics, Crops and Food Production. Nova Science Publishers Hauppauge, NY, USA. pp. 333-345.
Impullitti, A.E., et al., "Fungal endophyte diversity in soybean", Journal of Applied Microbiolog, vol. 114, No. 5, May 1, 2013, pp. 1500-1506.
Klaubauf, S., et al., "Molecular diversity of fungal communities in agricultural soils from Lower Austria," Fungal Diversity, Aug. 13, 2010, pp. 65-75, vol. 44, No. 1.
Knapp, D., et al., "Inter- and intraspecific functional diversity of fungal root endophytes of semiarid sandy grasslands," Acta Microbiologica et Immunologica Hungarica, Nov. 2017, pp. 1-101, vol. 64, Issue Supplement 1.
Kumar, A., et al., "Bio-control potential of *Cladosporium* sp. (MCPL-461), against a noxious weed *Parthenium hysterophorus* L.," J. Environ Biol., Mar. 2009, pp. 307-312, vol. 30, Issue 2.
Liu, Y., et al., "Phylogenetic relationships among ascomycetes: evidence from an RNA polymerase II subunit," Mol. Biol. Evol. 1999. vol. 16, No. 12, pp. 1799-1808.
Mandyam, K., et al., "Mutualism-parasitism paradigm synthesized from results of root-endophyte models", Frontiers in Microbiology, Jan. 12, 2015, pp. 1-14, vol. 5.
Miyoshi-Akiyama, T., et al., "Multilocus Sequence Typing (MLST) for Characterization of Enterobacter cloacae," PLoS One, 2013, vol. 8, No. 6, 10 Pages, e66358.
Nassar, A., et al., "Promotion of plant growth by an auxin-producing isolate of the yeast *Williopsis saturnus* endophytic in maize (*Zea mays* L.) roots", Biology and Fertility of Soils; Cooperating Journal of International Society of Soil Science, Springer, Berlin, DE, vol. 42, No. 2, Nov. 1, 2005, pp. 97-108.
O'Hanlon, K., et al., "Exploring the potential of symbiotic fungal endophytes in cereal disease suppression", Biological Control, vol. 63, No. 2, Sep. 5, 2012, pp. 69-78.
Rae, R., et al., "A subset of naturally isolated Bacillus strains show extreme virulence to the free-living nematodes Caenorhabditis elegans and Pristionchus pacificus", Environmental Microbiology, 2010, pp. 3007-3021, vol. 12, No. 11.
Riess, K., et al., "High genetic diversity at the regional scale and possible speciation in Sebacina epigaea and S. incrustans," BMC Evolutionary Biology, 2013, vol. 13, No. 102, 17 Pages.
Samways, M.J., et al., "Assessment of the Fungus *Cladosporium Oxyspoum* (Berk. and Curt.) As a Potential BioControl Agent Against Certain Homoptera," Elsevier Science Publioshers B.V., Jan. 1, 1986, pp. 231-239.
Saunders, M., et al., "Host-Synthesized Secondary Compounds Influence the in Vitro Interactions between Fungal Endophytes of Maize", Applied and Environmental Microbiology, Nov. 9, 2007, pp. 136-142, vol. 74, No. 1.
Shiraishi, A., et al., "Nodulation in black locust by the ammaproteobacteria *Pseudomonas* sp. and the Betaproteobacteria *Burkholderia* sp", Systematic and Applied Microbiology, Aug. 2010, pp. 269-274, vol. 33, No. 5.
Simola, L., et al., "The Effect of Some Protein and Non-Protein Amino Acids on the Growth of Cladosporium herbarum and Trichotheeium roseum," Effect of Amino Acids on Fungi, Physiologia Plantarum, 1979, pp. 381-387, vol. 46.
Stielow, J.B., et al., "One fungus, which genes? Development and assessment of universal primers for potential secondary fungal DNA barcodes," Persoonia: Molecular Phylogeny and Evolution of Fungi, 2015, vol. 35, pp. 242-263.
Taghavi, S., et al., "Genome Sequence of the Plant Growth promoting Endophytic Bacterium *Enterobacter* sp. 638", PLoS Genet., May 2010, pp. 1-15, vol. 6, Issue 5, e1000943.
U'Ren, J.M., et al., "Host and geographic structure of endophytic and endolichenic fungi at the continental scale," American Journal of Botany, May 1, 2012, pp. 898-914, vol. 99, No. 5.
Valencia, E., et al., "Mini-review: Brazilian fungi diversity for biomass degradation," Fungal Genetics and Biology, 2013, pp. 9-18, vol. 60.
Vujanovic, V., et al., "Viability Testing of Orchid Seed and the Promotion of Colouration and Germination," Annals of Botany, Mar. 17, 2000, pp. 79-86, vol. 86.
Vujanovic, V., et al., "Endophytic hyphal compartmentalization is required for successful mycobiont-wheat interaction as revealed by confocal laser microscopy," The proceedings of the Soils and Crops conference in Saskatoon (2008) published 2009, 7 Pages.
Vujanovic, V., et al., "A comparative study of endophytic mycobiota in leaves of Acer saccharum in eastern North America," Mycological Progress, May 2002, pp. 147-154, vol. 1, Issue 2.

(56) References Cited

OTHER PUBLICATIONS

Vujanovic, V., et al.,“Orchid seed viability testing by fungal bioassays and molecular phylogeny,” Floriculture, ornamental and plant biotechnology, 2006, vol. 63, pp. 563-569.
Vujanovic, V., et al., “Mycovitality—a new concept of plant biotechnology,” Canadian Journal Plant Pathol, 2007, vol. 29, p. 451.
Vujanovic, V., et al., “19th International Conference on *Arabidopsis*. Research Proceedings—ICAR13,” Jul. 23-27, 2008, 264 Pages, Montreal, QC, Canada.
Vujanovic, V., et al., “Mycovitality and mycoheterotrophy: where lies dormancy in terrestrial orchid and plants with minute seeds?” Symbiosis, 2007, vol. 44, pp. 93-99.
Vujanovic, V., et al., “Seed endosymbiosis: a vital relationship in providing prenatal care to plants,” Can. J. Plant Sci., NRC Research Press, Feb. 6, 2017, pp. 972-981, vol. 97.
Vujanovic, V., et al: “Fungal communities associated with durum wheat production system: A characterization by growth stage, plant organ and preceding crop”, Crop Protection, Elsevier Science, GB, vol. 37, Feb. 19, 2012, pp. 26-34.
Youssef, Y.A., et al., “Production of Plant Growth Substances by *Rhizosphere myoflora* of Broad Bean and Cotton,” Biologia Plantarum, 1975, pp. 175-181, vol. 17, No. 3.
Zhang, Y., et al., BcGsl, a glycoprotein from *Botrytis cinerea*, elicits defence response and improves disease resistance in host plants. Biochemical and biophysical research communications, Biochemical and Biophysical Research Communications, 2015, vol. 457, No. 4, pp. 627-634.
Zhang, W., et al., Host range of Exserohilum monoceras, a potential bioherbicide for the control of *Echinochloa* species, Canadian Journal of Botany/ Journal Canadien De Botan, National Research Council, Ottawa, CA, vol. 75, Jan. 1, 1997, pp. 685-692.
Zhu et al., *Helminthosporium velutinum* and *H. aquaticum* sp. nov. from aquatic habitats in Yunnan Province, China. Phytotaxa, 2016, vol. 253, No. 3, pp. 179-190.
Sarkar, S., et al., “New report of additional *enterobacterial* species causing wilt in West Bengal, India,” Canadian Journal of Microbiology, 2015, vol. 61, No. 7, pp. 477-486.
NCBI GenBank: Accession No. JX880250.1, “Enterobacteriaceae bacterium Clerol 16S ribosomal RNA gene, partial sequence,” NIH, Jun. 24, 2015, 2 Pages, can be retreived at <URL:https://www.ncbi.nlm.nih.gov/nucleotide/JX880250.1?report=genbank&log$=nuclalign&blast_rank=80&RID=KWUPBV08015>.
Azcon, R., et al., “Selective interactions between different species of *mycorrhizal* fungi and *Rhizobium meliloti* strains, and their effects on growth, $N_2$-fixation ($^{15}N$) and nutrition of *Medicago sativa* L.,” New PhytoL., 1991, vol. 117, pp. 399-404.
Intellectual Property Australia, Examination Report No. 2 for Australian Patent Application No. AU 2014315191, dated Jul. 6, 2018, 3 Pages.
Intellectual Property Australia, Examination Report No. 2 for Australian Patent Application No. AU 2015279600, dated Jul. 6, 2018, 3 Pages.
Office Action for Mexican Patent Application No. MX/a/2015/010142, dated May 29, 2018, 5 Pages (With Concise Explanation of Relevance).
New Zealand Intellectual Property Office, Further Examination Report, New Zealand Patent Application No. 734085, dated Jun. 27, 2018, 6 Pages.
New Zealand Intellectual Property Office, Further Examination Report, New Zealand Patent Application No. 727449, dated Jun. 15, 2018, 5 Pages.
European Patent Office, Communication Pursuant to Article 94(3) EPC for European Patent Application No. EP 14777213.1, dated Jun. 18, 2018, 4 Pages.
Artursson, V., et al., “Interactions between arbuscular mycorrhizal fungi and bacteria and their potential for stimulating plant growth”, Environmental Microbiology, vol. 8, No. 1, Jan. 1, 2006, pp. 1-10.

* cited by examiner

FIG. 1

| Complex Endophyte | | Corresponding Bacterial Component | |
|---|---|---|---|
| **SYM16668**<br>*Botryosphaeria*<br>comprising<br>*Dyella* | 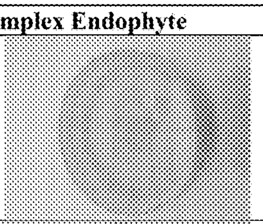 | **SYM16658**<br>*Dyella* | 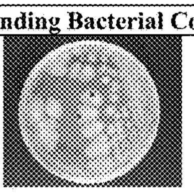 |
| **SYM16669**<br>*Microdiplodia*<br>comprising<br>*Pantoea* | 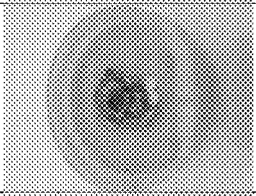 | **SYM16659**<br>*Pantoea* | 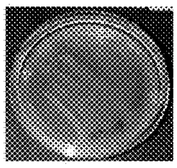 |
| **SYM16670**<br>*Pestalotiposis*<br>comprising<br>*Luteibacter* | 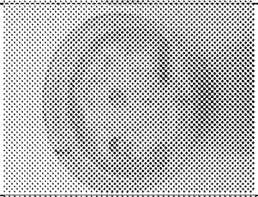 | **SYM16660**<br>*Luteibacter* | 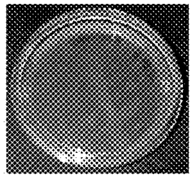 |
| **SYM16671**<br>*Phyllosticta*<br>comprising<br>*Dyella* | 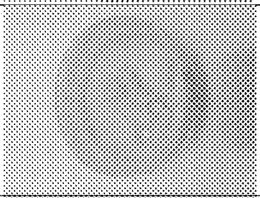 | **SYM16661**<br>*Dyella* | 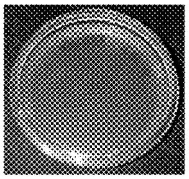 |
| **SYM16672**<br>*Alternaria*<br>comprising<br>*Luteibacter* | 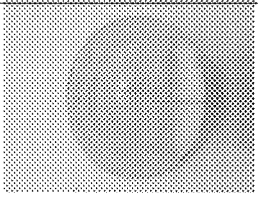 | **SYM16662**<br>*Luteibacter* | 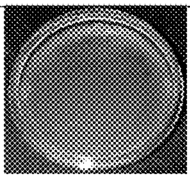 |
| **SYM16673**<br>*Lecythophora*<br>comprising<br>*Ralstonia* | 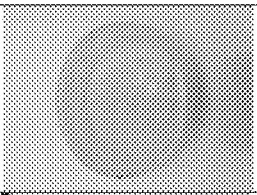 | **SYM16663**<br>*Ralstonia* | 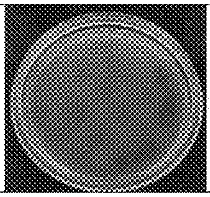 |
| **SYM16674**<br>*Microdiplodia*<br>comprising<br>*Erwinia* | 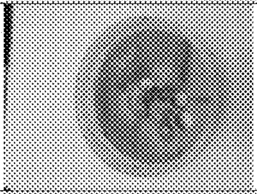 | **SYM16665**<br>*Erwinia* | 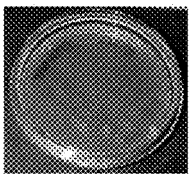 |
| **SYM16675**<br>*Daldinia*<br>comprising<br>*Bacillus* | 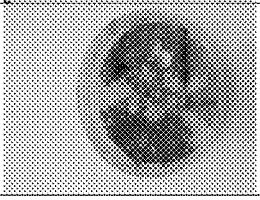 | **SYM16666**<br>*Bacillus* | 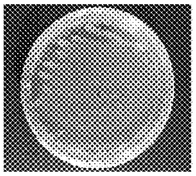 |

ISOLATED COMPLEX ENDOPHYTE COMPOSITIONS AND METHODS FOR IMPROVED PLANT TRAITS

CROSS REFERENCE TO RELATED APPLICATIONS

This application claims the benefit of U.S. Provisional Application No. 62/156,001, filed May 1, 2015, which is hereby incorporated in its entirety by reference.

SEQUENCE LISTING

The instant application contains a Sequence Listing with 333 sequences which has been submitted via EFS-Web and is hereby incorporated by reference in its entirety. Said ASCII copy, created on Apr. 29, 2016, is named 33788_US_sequencelisting.txt, and is 516,096 bytes in size.

FIELD OF THE INVENTION

This invention relates to compositions and methods for improving the cultivation of plants, particularly agricultural plants such as maize, wheat, barley, sorghum, millet, rice, soybean, canola, rapeseed, cotton, alfalfa, sugarcane, cassava, potato, tomato, and vegetables. For example, this invention describes fungal endophytes that comprise additional components, such as bacteria, that may be used to impart improved agronomic traits to plants. The disclosed invention also describes methods of improving plant characteristics by introducing fungal endophytes that comprise additional components to those plants. Further, this invention also provides methods of treating seeds and other plant parts with fungal endophytes that further comprise additional components, to impart improved agronomic characteristics to plants, particularly agricultural plants.

BACKGROUND OF THE INVENTION

According the United Nations Food and Agricultural Organization (UN FAO), the world's population will exceed 9.6 billion people by the year 2050, which will require significant improvements in agriculture to meet growing food demands. At the same time, conservation of resources (such as water, land), reduction of inputs (such as fertilizer, pesticides, herbicides), environmental sustainability, and climate change are increasingly important factors in how food is grown. There is a need for improved agricultural plants and farming practices that will enable the need for a nearly doubled food production with fewer resources, more environmentally sustainable inputs, and with plants with improved responses to various biotic and abiotic stresses (such as pests, drought, disease).

Today, crop performance is optimized primarily via technologies directed towards the interplay between crop genotype (e.g., plant breeding, genetically-modified (GM) crops) and its surrounding environment (e.g., fertilizer, synthetic herbicides, pesticides). While these paradigms have assisted in doubling global food production in the past fifty years, yield growth rates have stalled in many major crops and shifts in the climate have been linked to production instability and declines in important crops, driving an urgent need for novel solutions to crop yield improvement. In addition to their long development and regulatory timelines, public fears of GM-crops and synthetic chemicals have challenged their use in many key crops and countries, resulting in a lack of acceptance for many GM traits and the exclusion of GM crops and many synthetic chemistries from some global markets. Thus, there is a significant need for innovative, effective, environmentally-sustainable, and publically-acceptable approaches to improving the yield and resilience of crops to stresses.

Improvement of crop resilience to biotic and abiotic stresses has proven challenging for conventional genetic and chemical paradigms for crop improvement. This challenge is in part due to the complex, network-level changes that arise during exposure to these stresses. For example, plants under stress can succumb to a variety of physiological and developmental damages, including dehydration, elevated reactive oxygen species, impairment of photosynthetic carbon assimilation, inhibition of translocation of assimilates, increased respiration, reduced organ size due to a decrease in the duration of developmental phases, disruption of seed development, and a reduction in fertility.

Like humans, who utilize a complement of beneficial microbial symbionts, plants have been purported to derive a benefit from the vast array of bacteria and fungi that live both within and around their tissues in order to support the plant's health and growth. Endophytes are symbiotic organisms (typically bacteria or fungi) that live within plants, and inhabit various plant tissues, often colonizing the intercellular spaces of host leaves, stems, flowers, fruits, seeds, or roots. To date, a small number of symbiotic endophyte-host relationships have been analyzed in limited studies to provide fitness benefits to model host plants within controlled laboratory settings, such as enhancement of biomass production and nutrition, increased tolerance to stress such as drought and pests. There is still a need to develop better plant-endophyte systems to confer benefits to a variety of agriculturally-important plants such as maize and soybean, for example to provide improved yield and tolerance to the environmental stresses present in many agricultural situations for such agricultural plants.

There are very few examples of "complex endophytes", or endophytes further comprising another component (such as a virus, or a bacterium), that have been described in the literature, including: a survey of cupressaceous trees (Hoffman and Arnold, 2010 Appl. Environ. Microbiol. 76: 4063-4075, incorporated herein by reference in its entirety) and one species of tropical grasses (Marquez et al., 2007 Science 315: 513-515). Desnò et al. (2014 ISME J. 8: 257-270, incorporated herein by reference in its entirety) describe the existence of more than one species of bacteria residing within a fungal endophyte. It has been demonstrated that at least one of these endofungal bacteria is able to produce a plant hormone that enhances plant growth and others can produce substances with anti-cancer and anti-malaria properties (Hoffman et al., 2013 PLOS One 8: e73132; Jung and Arnold, 2012 The Effects of Endohyphal Bacteria on Anti-Cancer and Anti-Malaria Metabolites of Endophytic Fungi, Honors Thesis, University of Arizona, incorporated herein by reference in their entirety). However, these complex endophytes have not been shown to exist in cultivated plants of agricultural importance such as maize, soybean, wheat, cotton, rice, etc. As such, the complex endophytes, or bacteria isolated from such complex endophytes, have not previously been conceived as a viable mechanism to address the need to provide improved yield and tolerance to environmental stresses for plants of agricultural importance.

Thus, there is a need for compositions and methods of providing agricultural plants with improved yield and tolerance to various biotic and abiotic stresses. Provided herein are novel compositions of complex endophytes, formulations of complex endophytes for treatment of plants and plant parts, novel complex endophyte-plant compositions, and methods of use for the same, created based on the analysis of the key properties that enhance the utility and commercialization of a complex endophyte composition.

SUMMARY OF THE INVENTION

Disclosed herein is a synthetic composition, comprising a plant element heterologously associated with a complex endophyte, wherein the complex endophyte is capable of providing a trait of agronomic importance to the plant element.

In some embodiments, the trait of agronomic importance is selected from the group consisting of: altered oil content, altered protein content, altered seed carbohydrate composition, altered seed oil composition, altered seed protein composition, increased chemical tolerance, increased cold tolerance, delayed senescence, increased disease resistance, increased drought tolerance, increased ear weight, growth improvement, health enhancement, increased heat tolerance, increased herbicide tolerance, increased herbivore resistance, improved nitrogen fixation, improved nitrogen utilization, improved nutrient use efficiency, improved root architecture, improved water use efficiency, increased biomass, increased root length, increased seedling root length, germination rate, increased seed weight, increased shoot length, increased seedling shoot length, increased shoot biomass, increased yield, increased yield under water-limited conditions, increased kernel mass, improved kernel moisture content, increased metal tolerance, increased number of ears, increased number of kernels per ear, increased number of pods, nutrition enhancement, improved pathogen resistance, improved pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased seed germination, increased number of pods per plant, increased length of pods per plant, reduced number of wilted leaves per plant, reduced number of severely wilted leaves per plant, increased number of non-wilted leaves per plant, increased plant height, earlier or increased flowering, increased protein content, increased fermentable carbohydrate content, reduced lignin content, male sterility, and increased antioxidant content. In some embodiments, trait of agronomic importance is selected from the group consisting of: germination rate, emergence rate, shoot biomass, root biomass, seedling root length, seedling shoot length, and yield.

In some embodiments, the synthetic composition further comprises an agronomic formulation that further comprises one or more of the following: a stabilizer, or a preservative, or a carrier, or a surfactant, or an anticomplex agent, fungicide, nematicide, bactericide, insecticide, and herbicide, or any combination thereof. In some embodiments, the complex endophyte is present in an amount of at least about 10^2 CFU per plant element.

In some embodiments, the synthetic compositions described herein comprise a complex endophyte comprising a host fungus from a class selected from the group consisting of: Dothideomycetes, Sordariomycetes, or any of the corresponding anamorph or telomorph taxonomy of the preceding; and/or a bacterium from a class selected from the group consisting of: Bacilli, Betaproteobacteria, Gammaproteobacteria; and/or a host fungus from an order selected from the group consisting of: Botryosphaeriales, Dothideales, Pleosporales, Coniochateles, Xylariales, or any of the corresponding anamorph or telomorph taxonomy of the preceding; and/or a bacterium from an order selected from the group consisting of: Bacillales, Burkholderiales, Enterobacteriales, Xanthomonadales.

10. The synthetic composition of any of Claims 1-5, wherein the complex endophyte comprises a host fungus from a family selected from the group consisting of: Botryosphaeriaceae, Dothioraceae, Montagnulacea, Pleosporacea, Coniochaetaceae, Amphisphaeriaceae, Xylariacea, or any of the corresponding anamorph or telomorph taxonomy of the preceding; and/or a bacterium from a family selected from the group consisting of: Bacillaceae, Burkholderiaceae, Enterobacteriaceae, Xanthomonadaceae; and/or a host fungus from a genus selected from the group consisting of: *Boryosphaeria, Microdiplodia, Pestalotiopsis, Phyllosticta, Alternaria, Lecythophora, Daldinia*, or any of the corresponding anamorph or telomorph taxonomy of the preceding; and/or a bacterium from a genus selected from the group consisting of: *Dyella, Pantoea, Luteibacter, Ralstonia, Erwinia, Bacillus*; and/or a nucleic acid sequence at least 95% identical to a nucletic acid sequence selected from the group consisting of SEQ ID NO: 1 through SEQ ID NO: 333; and/or is selected from those listed in Table 4.

In some embodiments, the complex endophyte is associated with a plant element but is not directly contacting the plant element.

In some embodiments, the plant element is selected from the group consisting of: whole plant, seedling, meristematic tissue, ground tissue, vascular tissue, dermal tissue, seed, leaf, root, shoot, stem, flower, fruit, stolon, bulb, tuber, corm, keikis, and bud. In some embodiments, the plant element is from a plant selected from the group consisting of: wheat, soybean, maize, cotton, canola, barley, sorghum, millet, rice, rapeseed, alfalfa, tomato, sugarbeet, sorghum, almond, walnut, apple, peanut, strawberry, lettuce, orange, potato, banana, sugarcane, potato, cassava, mango, guava, palm, onions, olives, peppers, tea, yams, cacao, sunflower, asparagus, carrot, coconut, lemon, lime, barley, watermelon, cabbage, cucumber, grape, and turfgrass.

Also disclosed herein is a plurality of the synthetic compositions described herein, e.g., confined within an object selected from the group consisting of: bottle, jar, ampule, package, vessel, bag, box, bin, envelope, carton, container, silo, shipping container, truck bed, and case; and/or placed in a medium that promotes plant growth, the medium selected from the group consisting of: soil, hydroponic apparatus, and artificial growth medium, e.g., the medium is soil, wherein the synthetic compositions are placed in the soil with substantially equal spacing between each seed; and/or wherein the synthetic compositions are shelf-stable.

Also disclosed herein is a plant grown from the synthetic combinations described herein, wherein the plant exhibits an improved phenotype of agronomic interest, selected from the group consisting of: altered oil content, altered protein content, altered seed carbohydrate composition, altered seed oil composition, altered seed protein composition, increased chemical tolerance, increased cold tolerance, delayed senescence, increased disease resistance, increased drought tolerance, increased ear weight, growth improvement, health enhancement, increased heat tolerance, increased herbicide tolerance, increased herbivore resistance, improved nitrogen fixation, improved nitrogen utilization, improved nutrient use efficiency, improved root architecture, improved water use efficiency, increased biomass, increased root length, increased seedling root length, germination rate, increased seed weight, increased shoot length, increased seedling shoot length, increased shoot biomass, increased yield, increased yield under water-limited conditions, increased kernel mass, improved kernel moisture content, increased metal tolerance, increased number of ears, increased number of kernels per ear, increased number of pods, nutrition enhancement, improved pathogen resistance, improved pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased seed germination, increased number of pods per plant, increased length of pods per plant, reduced number of wilted leaves per plant, reduced number of severely wilted leaves per plant, increased number of non-wilted leaves per plant, increased plant height, earlier or increased flowering, increased protein content, increased fermentable carbohydrate content, reduced lignin content, male sterility, and increased antioxidant content.

Also disclosed herein is a plant, plant element, or progeny of the plant grown from the synthetic combinations described herein wherein the plant or progeny of the plant comprises in at least one of its plant elements the complex endophyte, fungal host, or bacterial component.

Also disclosed herein is a method of inoculating a plant with a fungal endophyte, comprising contacting a plant element of the plant with a formulation comprising a heterologous complex endophyte, wherein the complex endophyte comprises the fungal endophyte and a method of inoculating a plant with a bacterial endophyte, comprising contacting a plant element of the plant with a formulation comprising a heterologous complex endophyte, wherein the complex endophyte comprises the bacterial endophyte. In some embodiments, the inoculation improves a trait of agronomic importance in the plant.

Also disclosed herein is a method of improving a trait of agronomic importance in a plant, comprising contacting a plant element with a formulation comprising a heterologous complex endophyte; as compared to an isoline plant grown from a plant reproductive element not associated with the complex endophyte and a method of improving a trait of agronomic importance in a plant, comprising growing the plant from a plant reproductive element that has been contacted with a formulation comprising a heterologous complex endophyte; as compared to an isoline plant grown from a plant reproductive element not associated with the complex endophyte. In some embodiments, the complex endophyte comprises a bacterium within a host fungus. In some embodiments, the complex endophyte comprises a fungus within a host fungus Also disclosed herein is a method of improving a trait of agronomic importance in a plant, comprising growing the plant from a plant reproductive element that has been contacted with a formulation comprising a heterologous complex endophyte, wherein the complex endophyte comprises a bacterium within a host fungus; as compared to an isoline plant grown from a plant reproductive element not associated with the bacterium and a method of improving a trait of agronomic importance in a plant, comprising growing the plant from a plant reproductive element that has been contacted with a formulation comprising a heterologous complex endophyte, wherein the complex endophyte comprises a fungus within a host fungus; as compared to an isoline plant grown from a plant reproductive element not associated with the fungus. In some embodiments, the trait of agronomic importance is selected from the group consisting of: altered oil content, altered protein content, altered seed carbohydrate composition, altered seed oil composition, altered seed protein composition, increased chemical tolerance, increased cold tolerance, delayed senescence, increased disease resistance, increased drought tolerance, increased ear weight, growth improvement, health enhancement, increased heat tolerance, increased herbicide tolerance, increased herbivore resistance, improved nitrogen fixation, improved nitrogen utilization, improved nutrient use efficiency, improved root architecture, improved water use efficiency, increased biomass, increased root length, increased seedling root length, germination rate, increased seed weight, increased shoot length, increased seedling shoot length, increased shoot biomass, increased yield, increased yield under water-limited conditions, increased kernel mass, improved kernel moisture content, increased metal tolerance, increased number of ears, increased number of kernels per ear, increased number of pods, nutrition enhancement, improved pathogen resistance, improved pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased seed germination, increased number of pods per plant, increased length of pods per plant, reduced number of wilted leaves per plant, reduced number of severely wilted leaves per plant, increased number of non-wilted leaves per plant, increased plant height, earlier or increased flowering, increased protein content, increased fermentable carbohydrate content, reduced lignin content, male sterility, and increased antioxidant content. In some embodiments, the trait of agronomic importance is selected from the group consisting of: germination rate, emergence rate, shoot biomass, seedling root length, seedling shoot length, and yield. In some embodiments, the trait of agronomic importance is improved under normal watering conditions. In some embodiments, the trait of agronomic importance is improved under conditions of water limitation. In some embodiments, the plant reproductive element is a seed from a soybean plant, and wherein the complex endophyte comprises a fungus of the genus *Dothideomyetes*. In some embodiments, the plant reproductive element is a seed from a wheat plant, and wherein the complex endophyte comprises a fungus of the genus *Sodariomycetes*. In some embodiments, the complex endophyte is present in the formulation in an amount capable of modulating at least one of: a trait of agronomic importance, the transcription of a gene, the expression of a protein, the level of a hormone, the level of a metabolite, and the population of endogenous microbes in plants grown from the seeds, as compared to isoline plants not associated with, or grown from plant elements associated with, the complex endophyte. In some embodiments, the agronomic formulation further comprises one or more of the following: a stabilizer, or a preservative, or a carrier, or a surfactant, or an anticomplex agent, fungicide, nematicide, bactericide, insecticide, and herbicide, or any combination thereof.

In some embodiments of any of the methods described herein, the complex endophyte is present in an amount of at least about 10^2 CFU per plant element.

In some embodiments of any of the methods described herein, the complex endophyte comprises a host fungus from a class selected from the group consisting of: Dothideomycetes, Sordariomycetes, or any of the corresponding anamorph or telomorph taxonomy of the preceding; and/or a bacterium from a class selected from the group consisting of: Bacilli, Betaproteobacteria, Gammaproteobacteria; and/or a host fungus from an order selected from the group consisting of: Botryosphaeriales, Dothideales, Pleosporales, Coniochateles, Xylariales, or any of the corresponding anamorph or telomorph taxonomy of the preceding; and/or a bacterium from an order selected from the group consisting of: Bacillales, Burkholderiales, Enterobacteriales, Xanthomonadales; and/or a host fungus from a family selected from the group consisting of: Botryosphaeriaceae, Dothioraceae, Montagnulacea, Pleosporacea, Coniochaetaceae, Amphisphaeriaceae, Xylariacea, or any of the corresponding anamorph or telomorph taxonomy of the preceding; and/or a bacterium from a family selected from the group consisting of: Bacillaceae, Burkholderiaceae, Enterobacteriaceae, Xanthomonadaceae; and/or a host fungus from a genus selected from the group consisting of: *Boryosphaeria, Microdiplodia, Pestalotiopsis, Phyllosticta, Alternaria, Lecythophora, Daldinia*, or any of the corresponding anamorph or telomorph taxonomy of the preceding; and/or a bacterium from a genus selected from the group consisting of: *Dyella, Pantoea, Luteibacter, Ralstonia, Erwinia, Bacillus*; and/or a nucleic acid sequence at least 95% identical to a nucletic acid sequence selected from the group consisting of SEQ ID NO: 1 through SEQ ID NO: 333; and/or is selected from those listed in Table 4.

In some embodiments of any of the methods described herein, the complex endophyte is associated with a plant element but is not directly contacting the plant element. In some embodiments of any of the methods described herein, the plant element is selected from the group consisting of: whole plant, seedling, meristematic tissue, ground tissue, vascular tissue, dermal tissue, seed, leaf, root, shoot, stem, flower, fruit, stolon, bulb, tuber, corm, keikis, and bud. n some embodiments of any of the methods described herein, the plant element is from a plant selected from the group consisting of: wheat, soybean, maize, cotton, canola, barley, sorghum, millet, rice, rapeseed, alfalfa, tomato, sugarbeet, sorghum, almond, walnut, apple, peanut, strawberry, lettuce, orange, potato, banana, sugarcane, potato, cassava, mango, guava, palm, onions, olives, peppers, tea, yams, cacao, sunflower, asparagus, carrot, coconut, lemon, lime, barley, watermelon, cabbage, cucumber, grape, and turfgrass.

Also disclosed herein is a plant element from the plant produced by any of the methods described herein.

Also disclosed herein is a method of improving a trait of agronomic importance in a plant, comprising isolating a bacterial endophyte from a complex endophyte, and growing the plant from a plant reproductive element onto which the bacterial endophyte is heterologously disposed; as compared to an isoline plant grown from a plant reproductive element not associated with the bacterial endophyte. In some embodiments, the trait of agronomic importance is selected from the group consisting of: altered oil content, altered protein content, altered seed carbohydrate composition, altered seed oil composition, altered seed protein composition, increased chemical tolerance, increased cold tolerance, delayed senescence, increased disease resistance, increased drought tolerance, increased ear weight, growth improvement, health enhancement, increased heat tolerance, increased herbicide tolerance, increased herbivore resistance, improved nitrogen fixation, improved nitrogen utilization, improved nutrient use efficiency, improved root architecture, improved water use efficiency, increased biomass, increased root length, increased seedling root length, germination rate, increased seed weight, increased shoot length, increased seedling shoot length, increased shoot biomass, increased yield, increased yield under water-limited conditions, increased kernel mass, improved kernel moisture content, increased metal tolerance, increased number of ears, increased number of kernels per ear, increased number of pods, nutrition enhancement, improved pathogen resistance, improved pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased seed germination, increased number of pods per plant, increased length of pods per plant, reduced number of wilted leaves per plant, reduced number of severely wilted leaves per plant, increased number of non-wilted leaves per plant, increased plant height, earlier or increased flowering, increased protein content, increased fermentable carbohydrate content, reduced lignin content, male sterility, and increased antioxidant content. In some embodiments, the trait of agronomic importance is selected from the group consisting of: germination rate, emergence rate, shoot biomass, seedling root length, seedling shoot length, and yield. In some embodiments, he trait of agronomic importance is improved under normal watering conditions. In some embodiments, the trait of agronomic importance is improved under conditions of water limitation. In some embodiments, the complex endophyte comprises a host fungus from a class selected from the group consisting of: Dothideomycetes, Sordariomycetes, or any of the corresponding anamorph or telomorph taxonomy of the preceding; and/or a bacterium from a class selected from the group consisting of: Bacilli, Betaproteobacteria, Gammaproteobacteria; and/or a host fungus from an order selected from the group consisting of: Botryosphaeriales, Dothideales, Pleosporales, Coniochateles, Xylariales, or any of the corresponding anamorph or telomorph taxonomy of the preceding; and/or a bacterium from an order selected from the group consisting of: Bacillales, Burkholderiales, Enterobacteriales, Xanthomonadales; and/or a host fungus from a family selected from the group consisting of: Botryosphaeriaceae, Dothioraceae, Montagnulacea, Pleosporacea, Coniochaetaceae, Amphisphaeriaceae, Xylariacea, or any of the corresponding anamorph or telomorph taxonomy of the preceding; and/or a bacterium from a family selected from the group consisting of: Bacillaceae, Burkholderiaceae, Enterobacteriaceae, Xanthomonadaceae; and/or a host fungus from a genus selected from the group consisting of: *Boryosphaeria, Microdiplodia, Pestalotiopsis, Phyllosticta, Alternaria, Lecythophora, Daldinia*, or any of the corresponding anamorph or telomorph taxonomy of the preceding; and/or a bacterium from a genus selected from the group consisting of: *Dyella, Pantoea, Luteibacter, Ralstonia, Erwinia, Bacillus*; and/or a nucleic acid sequence at least 95% identical to a nucletic acid sequence selected from the group consisting of SEQ ID NO: 1 through SEQ ID NO: 333.

Also disclosed herein is a plant produced by any of the methods described herein.

Also disclosed herein is a method for preparing a synthetic composition, comprising associating the surface of a plurality of plant elements with a formulation comprising a purified microbial population that comprises a complex endophyte that is heterologous to the seed, wherein the complex endophyte is present in the formulation in an amount capable of modulating at least one of: a trait of agronomic importance, the transcription of a gene, the expression of a protein, the level of a hormone, the level of a metabolite, and the population of endogenous microbes in plants grown from the seeds, as compared to isoline plants not associated with, or grown from plant elements associated with, the formulation. In some embodiments, the trait of agronomic importance is selected from the group consisting of: altered oil content, altered protein content, altered seed carbohydrate composition, altered seed oil composition, altered seed protein composition, increased chemical tolerance, increased cold tolerance, delayed senescence, increased disease resistance, increased drought tolerance, increased ear weight, growth improvement, health enhancement, increased heat tolerance, increased herbicide tolerance, increased herbivore resistance, improved nitrogen fixation, improved nitrogen utilization, improved nutrient use efficiency, improved root architecture, improved water use efficiency, increased biomass, increased root length, increased seedling root length, germination rate, increased seed weight, increased shoot length, increased seedling shoot length, increased shoot biomass, increased yield, increased yield under water-limited conditions, increased kernel mass, improved kernel moisture content, increased metal tolerance, increased number of ears, increased number of kernels per ear, increased number of pods, nutrition enhancement, improved pathogen resistance, improved pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased seed germination, increased number of pods per plant, increased length of pods per plant, reduced number of wilted leaves per plant, reduced number of severely wilted leaves per plant, increased number of non-wilted leaves per plant, increased plant height, earlier or increased flowering, increased protein content, increased fermentable carbohydrate content, reduced lignin content, male sterility, and increased antioxidant content. In some embodiments, the trait of agronomic importance is selected from the group consisting of: germination rate, emergence rate, shoot biomass, seedling root length, seedling shoot length, and yield. In some embodiments, the trait of agronomic importance is improved under normal watering conditions. In some embodiments, the trait of agronomic importance is improved under conditions of water limitation.

In some embodiments of the methods, the synthetic composition used in the methods described herein further comprises an agronomic formulation that further comprises one or more of the following: a stabilizer, or a preservative, or a carrier, or a surfactant, or an anticomplex agent, fungicide, nematicide, bactericide, insecticide, and herbicide, or any combination thereof.

In some embodiments of the methods, the complex endophyte is present in an amount of at least about 10^2 CFU per plant element; and/or the complex endophyte comprises a host fungus from a class selected from the group consisting of: Dothideomycetes, Sordariomycetes, or any of the corresponding anamorph or telomorph taxonomy of the preceding; and/or a bacterium from a class selected from the group consisting of: Bacilli, Betaproteobacteria, Gammaproteobacteria; and/or a host fungus from an order selected from the group consisting of: Botryosphaeriales, Dothideales, Pleosporales, Coniochateles, Xylariales, or any of the corresponding anamorph or telomorph taxonomy of the preceding; and/or a bacterium from an order selected from the group consisting of: Bacillales, Burkholderiales, Enterobacteriales, Xanthomonadales; and/or a host fungus from a family selected from the group consisting of: Botryosphaeriaceae, Dothioraceae, Montagnulacea, Pleosporacea, Coniochaetaceae, Amphisphaeriaceae, Xylariacea, or any of the corresponding anamorph or telomorph taxonomy of the preceding; and/or a bacterium from a family selected from the group consisting of: Bacillaceae, Burkholderiaceae, Enterobacteriaceae, Xanthomonadaceae; and/or a host fungus from a genus selected from the group consisting of: *Boryosphaeria, Microdiplodia, Pestalotiopsis, Phyllosticta, Alternaria, Lecythophora, Daldinia*, or any of the corresponding anamorph or telomorph taxonomy of the preceding; and/or a bacterium from a genus selected from the group consisting of: *Dyella, Pantoea, Luteibacter, Ralstonia, Erwinia, Bacillus*; and/or a nucleic acid sequence at least 95% identical to a nucletic acid sequence selected from the group consisting of SEQ ID NO: 1 through SEQ ID NO: 333; and/or the complex endophyte is selected from those listed in Table 4.

In some embodiments of the methods, the complex endophyte is associated with a plant element but is not directly contacting the plant element. In some embodiments of the methods, the plant element is selected from the group consisting of: whole plant, seedling, meristematic tissue, ground tissue, vascular tissue, dermal tissue, seed, leaf, root, shoot, stem, flower, fruit, stolon, bulb, tuber, corm, keikis, and bud. In some embodiments of the methods, the plant element is from a plant selected from the group consisting of: wheat, soybean, maize, cotton, canola, barley, sorghum, millet, rice, rapeseed, alfalfa, tomato, sugarbeet, sorghum, almond, walnut, apple, peanut, strawberry, lettuce, orange, potato, banana, sugarcane, potato, cassava, mango, guava, palm, onions, olives, peppers, tea, yams, cacao, sunflower, asparagus, carrot, coconut, lemon, lime, barley, watermelon, cabbage, cucumber, grape, and turfgrass.

Also described herein is a method of improving the efficacy of a bacterial endophyte in an application, comprising utilizing a complex endophyte, wherein the complex endophyte comprises the bacterial endophyte and a method of improving the efficacy of a fungal endophyte in an application, comprising utilizing a complex endophyte, wherein the complex endophyte comprises the fungal endophyte. In some embodiments, the application is selected from the group consisting of: agriculture, plant improvement, water quality improvement, snow or ice production, bioremediation, industrial compound production, pharmaceutical compound production, and production of bioengineered substances. In some embodiments, the application is a production method of a composition belonging to a class of compound selected from the group consisting of: acids, alcohols, amino acids, amylases, antibiotics, biogases, bioplastics, citric acid, enzymes, esters, fatty acids, flavoring agents, glutamic acid, human or animal hormones, human growth hormone, ice, insulin, lactic acid, lipases, lipids, minerals, nitrogen, oils, nucleic acids, pectinases, preservatives, proteins, snow, sugars, vaccines, viruses, vitamins, and waxes.

Also disclosed herein is a method of improving the performance of a bacterial endophyte in an application, comprising identifying a complex endophyte comprising a bacterium comprising a nucleic acid sequence with at least 95% identity to that of the bacterial endophyte, and substituting the complex endophyte for the bacterial endophyte in the application. In some embodiments, the bacterial endophyte is further associated with a plant element, e.g., a Gram-negative bacterial endophyte. In some embodiments, the characteristic is selected from the group consisting of: efficacy, survivability, shelf-stability, tolerance to an antibiotic, tolerance to reduced environmental moisture.

DESCRIPTION OF THE DRAWINGS

FIG. 1: complex endophyte and component bacterial culture phentoypic characteristics.

grown from seeds treated with the complex endophyte SYM166 demonstrated an improved average emergence rate in greenhouse experiments, as compared to plants treated with the formulation control and plants treated with non-complex fungal endophytes. Particular improvement was seen in early emergence rates.

Figure 3A:
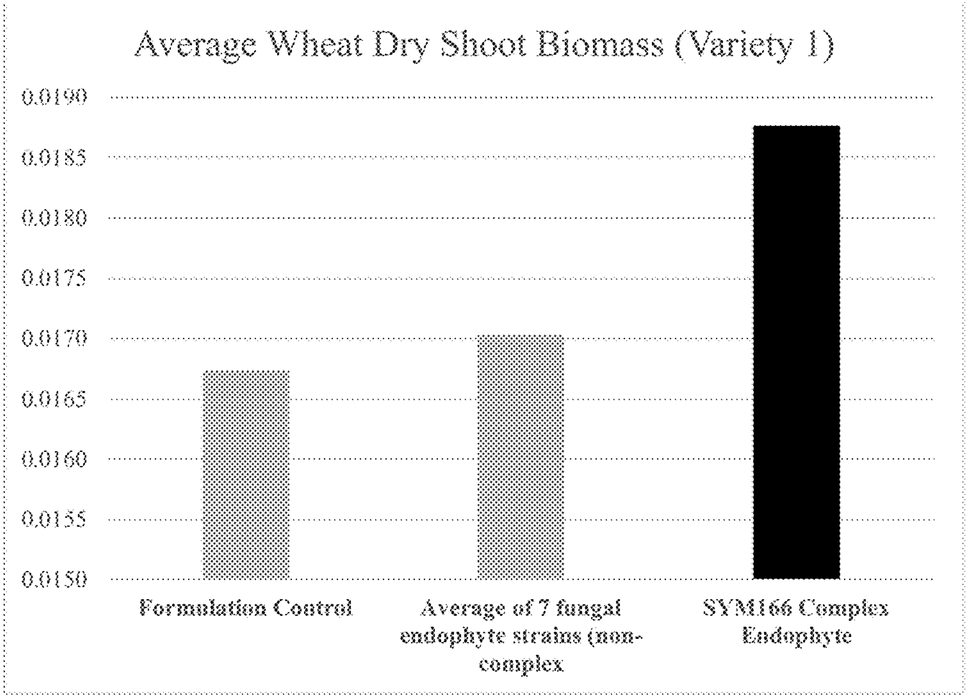
Figure 3B:
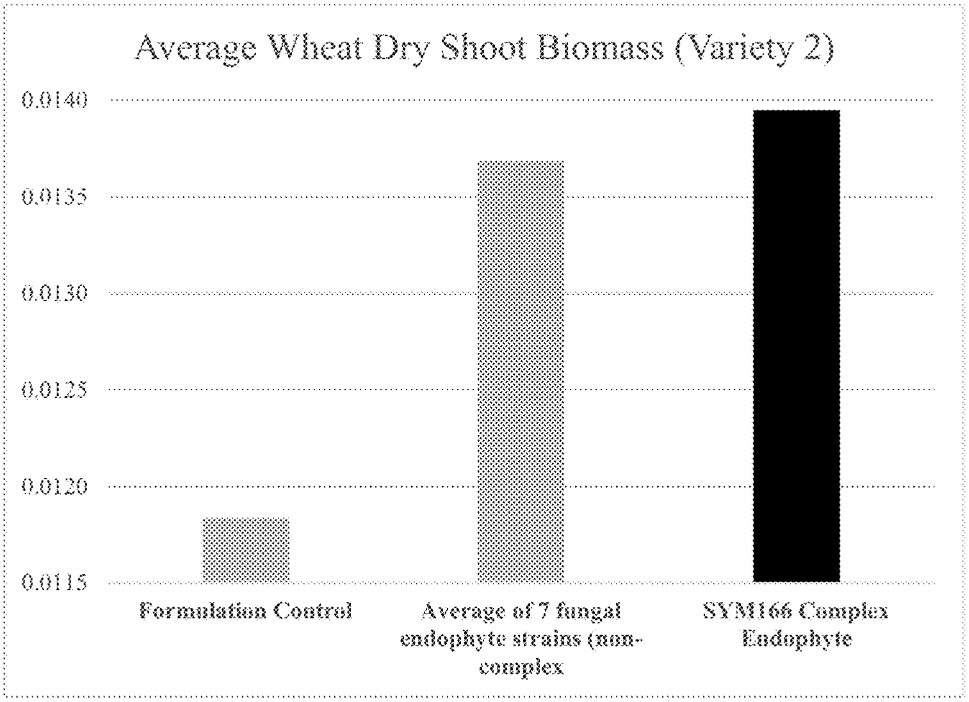

FIG. 3A and FIG. 3B: wheat greenhouse dry shoot biomass. Spring wheat plants (Variety 1, FIG. 3A; Variety 2, FIG. 3B) grown from seeds treated with the complex endophyte SYM166 demonstrated an improved average wheat dry shoot biomass in greenhouse experiments, as compared to plants treated with the formulation control and plants treated with non-complex fungal endophytes.

Figure 4:
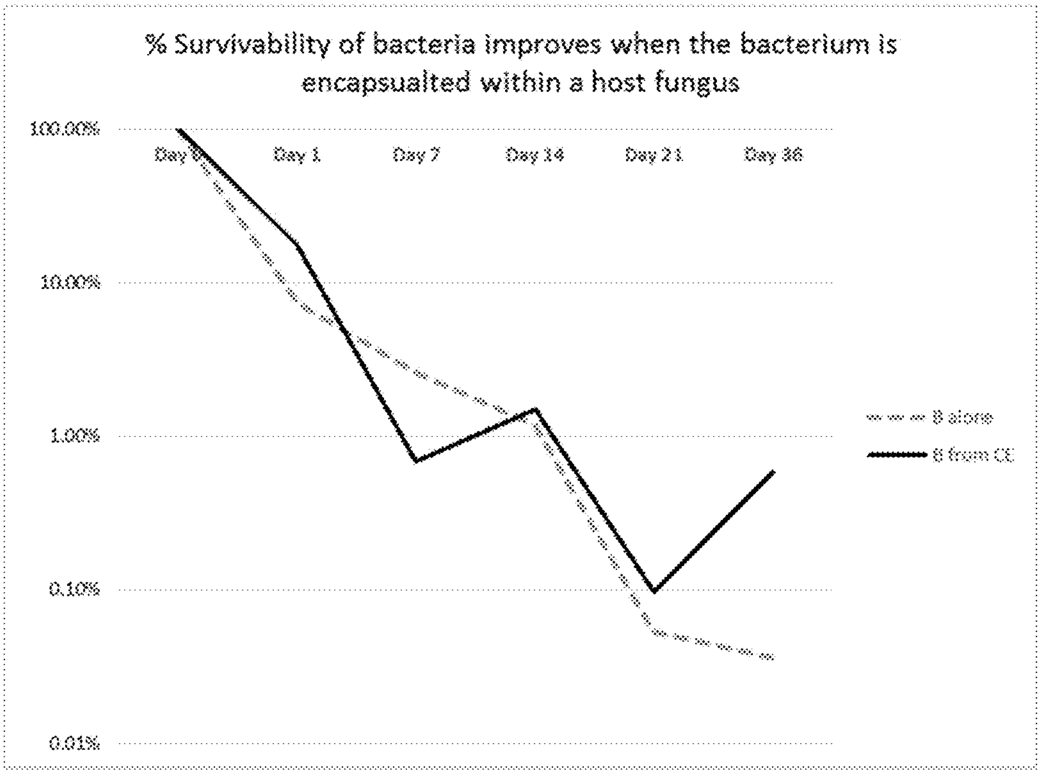

FIG. 4: bacterial survivability is improved when said bacteria are encapsulated within fungal hosts. The bacterial endophyte (B from CE) SYM16660, when encompassed within a fungal host as part of the complex endophyte (CE) SYM16670 (SYM166), displays greater survivability on treated corn seeds than does the isolated bacterial endophyte (B alone) SYM16660.

Figure 5:
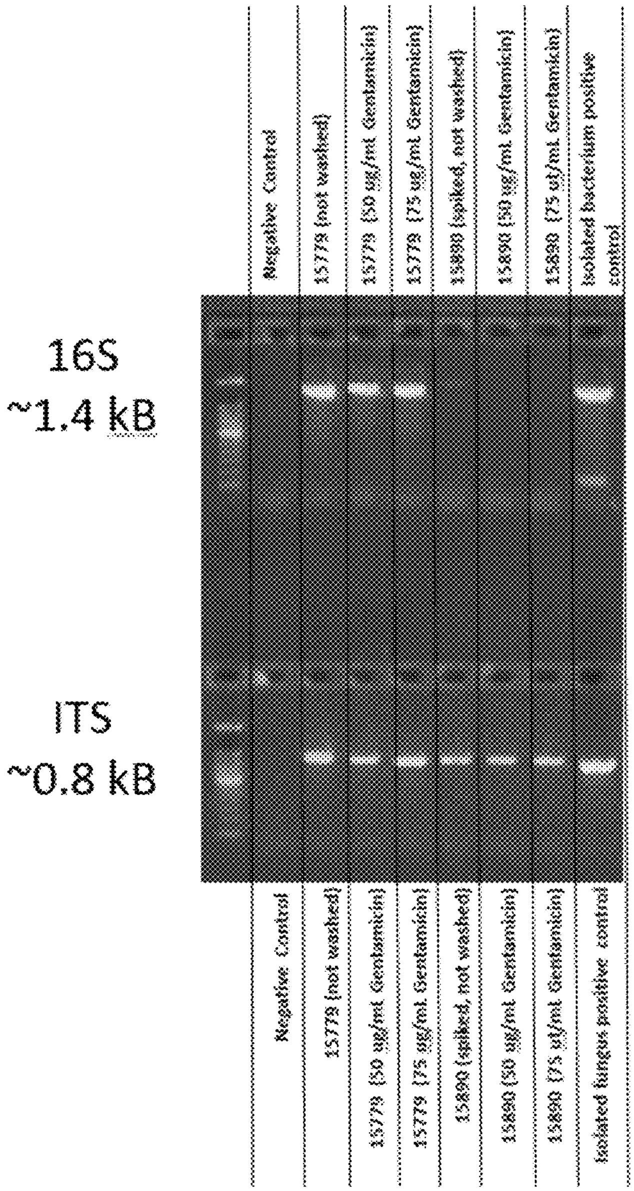

FIG. 5: bacterial endophyte tolerance to antibiotics is improved when said bacteria are encapsulated within fungal hosts. Samples were run on 2% agarose gel. Endofungal bacterium EHB15779 16S remains detectable in its host fungus SYM15779 even after its host fungus is treated with gentamicin washes. Comparison treatments of SYM15779 not washed (presence of both surface and endofungal bacteria) and washed (presence of endofungal bacteria only) demonstrate presence of bacterial 16S sequence. The non-complex endophyte SYM15890 spiked with a bacterial strain and not washed with gentamicin shows a faint band of bacterial 16S sequence, reflecting the presence of surface bacteria. The non-complex endophyte SYM15890 washed with gentamicin does not show presence of bacterial 16S sequence.

DEFINITIONS

An "endophyteis an organism that lives within a plant or is otherwise associated therewith, and does not cause disease or harm the plant otherwise. Endophytes can occupy the intracellular or extracellular spaces of plant tissue, including the leaves, stems, flowers, fruits, seeds, or roots. An endophyte can be for example a bacterial or fungal organism, and can confer a beneficial property to the host plant such as an increase in yield, biomass, resistance, or fitness. As used herein, the term "microbe" is sometimes used to describe an endophyte, particularly a fungal endophyte, that may be isolated from a fungal endophyte, and that may be capable of living within a plant.

The term "complex endophyte" is used to describe a host fungus that encompasses at least one additional organism or composition, and that combination can itself be associated on or within a plant. Such additional organism or composition may be, for example, endofungal bacterial endophytes or endofungal fungal endophytes. As used herein, an "endophytic component" refers to an endofungal bacterial endophyte or an endofungal fungal endophyte.

"Endofungal bacterial endophyte" means a bacterial endophyte that is capable of living inside a fungus, for example within the hyphae. Throughout this document, the term "endofungal bacterial endophyte" is used to denote bacterial endophytic entities originally isolated from a host fungus or those that are capable of living within a host fungus. Likewise, "endofungal fungal endophyte" means a fungal endophyte originally isolated from a host fungus or one capable of living within a host fungusIn such cases, the term "endofungal" denotes either the source of origin (host fungus) or capability of existing within a host fungus, and is not meant to imply that the bacterium or fungus (or bacteria or fungi), is continually encompassed within a host fungus. For example, an endofungal bacterial endophyte may reside within a host fungus for part of its life cycle and reside external to the host fungus for other parts of its life cycle. In some cases, the term "component bacterium" is used to denote a bacterium that exists within a host fungus, or has been isolated from a host fungus.

In some embodiments, the host fungus comprises algae or cyanobacteria, or both, living in symbiosis (lichen), and at least one endofungal bacterial endophyte or endofungal fungal endophyte.

As used herein, the term "capable of" living inside a fungus means that the endophyte has the appropriate features permitting it to live inside a fungus. For example, the endophyte may produce the necessary substances to avoid rejection by the fungus, and be able to use the nutrients provided by the fungus to live.

As used herein, the term "bacterium" or "bacteria" refers in general to any prokaryotic organism, and may reference an organism from either Kingdom *Eubacteria* (Bacteria), Kingdom *Archaebacteria* (Archae), or both. In some cases, bacterial genera have been reassigned due to various reasons (such as but not limited to the evolving field of whole genome sequencing), and it is understood that such nomenclature reassignments are within the scope of any claimed genus. For example, certain species of the genus *Erwinia* have been described in the literature as belonging to genus *Pantoea* (Zhang and Qiu, 2015).

The term 16S refers to the DNA sequence of the 16S ribosomal RNA (rRNA) sequence of a bacterium. 16S rRNA gene sequencing is a well-established method for studying phylogeny and taxonomy of bacteria.

As used herein, the term "fungus" or "fungi" refers in general to any organism from Kingdom Fungi. Historical taxonomic classification of fungi has been according to morphological presentation. Beginning in the mid-1800's, it was became recognized that some fungi have a pleomorphic life cycle, and that different nomenclature designations were being used for different forms of the same fungus. In 1981, the Sydney Congress of the International Mycological Association laid out rules for the naming of fungi according to their status as anamorph, teleomorph, or holomorph (Taylor, 2011). With the development of genomic sequencing, it became evident that taxonomic classification based on molecular phylogenetics did not align with morphological-based nomenclature (Shenoy, 2007). As a result, in 2011 the International Botanical Congress adopted a resolution approving the International Code of Nomenclature for Algae, Fungi, and Plants (Melbourne Code) (2012), with the stated outcome of designating "One Fungus=One Name" (Hawksworth, 2012). However, systematics experts have not aligned on common nomenclature for all fungi, nor are all existing databases and information resources inclusive of updated taxonomies. As such, many fungi referenced herein may be described by their anamorph form but it is understood that based on identical genomic sequencing, any pleomorphic state of that fungus may be considered to be the same organism. For example, the genus *Alternaria* is the anamorph form of the teleomorph genus Lewia (Kwasna 2003), ergo both would be understood to be the same organism with the same DNA sequence. For example, it is understood that the genus *Acremonium* is also reported in the literature as genus *Sarocladium* as well as genus *Tilachilidium* (Summerbell, 2011). For example, the genus *Cla-*

*dosporium* is an anamorph of the teleomorph genus *Davidiella* (Bensch, 2012), and is understood to describe the same organism. In some cases, fungal genera have been reassigned due to various reasons, and it is understood that such nomenclature reassignments are within the scope of any claimed genus. For example, certain species of the genus Microdiplodia have been described in the literature as belonging to genus *Paraconiothyrium* (Crous and Groenveld, 2006).

"Internal Transcribed Spacer" (ITS) refers to the spacer DNA (non-coding DNA) situated between the small-subunit ribosomal RNA (rRNA) and large-subunit (LSU) rRNA genes in the chromosome or the corresponding transcribed region in the polycistronic rRNA precursor transcript. ITS gene sequencing is a well-established method for studying phylogeny and taxonomy of fungi. In some cases, the "Large SubUnit" (LSU) sequence is used to identify fungi. LSU gene sequencing is a well-established method for studying phylogeny and taxonomy of fungi. Some fungal endophytes of the present invention may be described by an ITS sequence and some may be described by an LSU sequence. Both are understood to be equally descriptive and accurate for determining taxonomy.

The terms "pathogen" and "pathogenic" in reference to a bacterium or fungus includes any such organism that is capable of causing or affecting a disease, disorder or condition of a host comprising the organism.

A "spore" or a population of "spores" refers to bacteria or fungi that are generally viable, more resistant to environmental influences such as heat and bactericidal or fungicidal agents than other forms of the same bacteria or fungi, and typically capable of germination and out-growth. Bacteria and fungi that are "capable of forming spores" are those bacteria and fungi comprising the genes and other necessary abilities to produce spores under suitable environmental conditions.

"Biomass" means the total mass or weight (fresh or dry), at a given time, of a plant tissue, plant tissues, an entire plant, or population of plants. Biomass is usually given as weight per unit area. The term may also refer to all the plants or species in the community (community biomass).

The term "isolated" is intended to specifically reference an organism, cell, tissue, polynucleotide, or polypeptide that is removed from its original source and purified from additional components with which it was originally associated. For example, a complex endophyte may be considered isolated from a seed if it is removed from that seed source and purified so that it is isolated from any additional components with which it was originally associated. Similarly, a complex endophyte may be removed and purified from a plant or plant element so that it is isolated and no longer associated with its source plant or plant element. In some cases, the term "isolated" is used to describe a bacterium of a complex endophyte that has been removed from its host fungus A "host plant" includes any plant, particularly a plant of agronomic importance, which a complex endophyte can colonize. As used herein, an endophyte is said to "colonize" a plant or seed when it can be stably detected within the plant or seed over a period time, such as one or more days, weeks, months or years, in other words, a colonizing entity is not transiently associated with the plant or seed. In some embodiments, such host plants are plants of agronomic importance.

A "non-host target" means an organism or chemical compound that is altered in some way after contacting a host plant or host fungus that comprises an endophyte, as a result of a property conferred to the host plant or host fungus by the endophyte.

As used herein, a nucleic acid has "homology" or is "homologous" to a second nucleic acid if the nucleic acid sequence has a similar sequence to the second nucleic acid sequence. The terms "identity," "percent sequence identity" or "identical" in the context of nucleic acid sequences refer to the residues in the two sequences that are the same when aligned for maximum correspondence. There are a number of different algorithms known in the art that can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. (Pearson, 1990, Methods Enzymol. 183: 63-98, incorporated herein by reference in its entirety). The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, or at least about 90%, or at least about 95%, 96%, 97%, 98% 99%, 99.5% or 100% of the nucleotide bases, as measured by any well-known algorithm of sequence identity, such as FASTA, BLAST or Gap, as discussed above. In some embodiments, sequences can be compared using Geneious (Biomatters, Ltd., Auckland, New Zealand). In other embodiments, polynucleotide sequences can be compared using the multiple sequence alignment algorithm MUSCLE (Edgar R C, 2004).

As used herein, the terms "operational taxonomic unit," "OTU," "taxon," "hierarchical cluster," and "cluster" are used interchangeably. An operational taxon unit (OTU) refers to a group of one or more organisms that comprises a node in a clustering tree. The level of a cluster is determined by its hierarchical order. In one embodiment, an OTU is a group tentatively assumed to be a valid taxon for purposes of phylogenetic analysis. In another embodiment, an OTU is any of the extant taxonomic units under study. In yet another embodiment, an OTU is given a name and a rank. For example, an OTU can represent a domain, a sub-domain, a kingdom, a sub-kingdom, a phylum, a sub-phylum, a class, a sub-class, an order, a sub-order, a family, a subfamily, a genus, a subgenus, or a species. In some embodiments, OTUs can represent one or more organisms from the kingdoms eubacteria, protista, or fungi at any level of a hierarchal order. In some embodiments, an OTU represents a prokaryotic or fungal order.

In some embodiments, the invention uses endophytes that are heterologous to a plant element, for example in making synthetic combinations or agricultural formulations. A microbe is considered heterologous to the seed or plant if the seed or seedling that is unmodified (e.g., a seed or seedling that is not treated with an endophyte population described herein) does not contain detectable levels of the microbe. For example, the invention contemplates the synthetic combinations of seeds or seedlings of agricultural plants and an endophytic microbe population (e.g., an isolated bacterium), in which the microbe population is "heterologously disposed" on the exterior surface of or within a tissue of the agricultural seed or seedling in an amount effective to colonize the plant. A microbe is considered "heterologously disposed" on the surface or within a plant (or tissue) when the microbe is applied or disposed on the plant in a number that is not found on that plant before application of the microbe. For example, an endophyte population that is disposed on an exterior surface or within the seed can be an endophytic bacterium that may be associated with the mature plant, but is not found on the surface of or within the seed. As such, a microbe is deemed heterologously disposed when applied on the plant that either does not naturally have the microbe on its surface or within the particular tissue to which the microbe is disposed, or does not naturally have the microbe on its surface or within the particular tissue in the number that is being applied. In another example, an endophyte that is normally associated with leaf tissue of a cupressaceous tree sample would be considered heterologous to leaf tissue of a maize plant. In another example, an endophyte that is normally associated with leaf tissue of a maize plant is considered heterologous to a leaf tissue of another maize plant that naturally lacks said endophyte. In another example, a complex endophyte that is normally associated at low levels in a plant is considered heterologous to that plant if a higher concentration of that endophyte is introduced into the plant.

In some embodiments, a microbe can be "endogenous" to a seed or plant, or a bacterium may be "endogenous" to a fungal host with which it forms a complex endophyte. As used herein, a microbe is considered "endogenous" to a plant or seed, if the endophyte or endophyte component is derived from, or is otherwise found in, a plant element of the plant specimen from which it is sourced. Further, an endophyte is considered "endogenous" to a fungal host, if the endophyte is derived from, or is otherwise found in, a fungal host. For example, a complex endophyte may be isolated and purified, said complex endophyte comprising a host fungus and an endogenous bacterium.

The term "isoline" is a comparative term, and references organisms that are genetically identical, but may differ in treatment. In one example, two genetically identical maize plant embryos may be separated into two different groups, one receiving a treatment (such as transformation with a heterologous polynucleotide, to create a genetically modified plant) and one control that does not receive such treatment. Any phenotypic differences between the two groups may thus be attributed solely to the treatment and not to any inherency of the plant's genetic makeup. In another example, two genetically identical soybean seeds may be treated with a formulation that introduces an endophyte composition. Any phenotypic differences between the plants grown from those seeds may be attributed to the treatment, thus forming an isoline comparison.

Similarly, by the term "reference agricultural plant", it is meant an agricultural plant of the same species, strain, or cultivar to which a treatment, formulation, composition or endophyte preparation as described herein is not administered/contacted. A reference agricultural plant, therefore, is identical to the treated plant with the exception of the presence of the endophyte and can serve as a control for detecting the effects of the endophyte that is conferred to the plant.

A "reference environment" refers to the environment, treatment or condition of the plant in which a measurement is made. For example, production of a compound in a plant associated with an endophyte can be measured in a reference environment of drought stress, and compared with the levels of the compound in a reference agricultural plant under the same conditions of drought stress. Alternatively, the levels of a compound in plant associated with an endophyte and reference agricultural plant can be measured under identical conditions of no stress.

A "plant element" is intended to generically reference either a whole plant or a plant component, including but not limited to plant tissues, parts, and cell types. A plant element may be one of the following: whole plant, seedling, meristematic tissue, ground tissue, vascular tissue, dermal tissue, seed, leaf, root, shoot, stem, flower, fruit, stolon, bulb, tuber, corm, kelkis, shoot, bud. As used herein, a "plant element" is synonymous to a "portion" of a plant, and refers to any part of the plant, and can include distinct tissues and/or organs, and may be used interchangeably with the term "tissue" throughout.

Similarly, a "plant reproductive element" is intended to generically reference any part of a plant that is able to initiate other plants via either sexual or asexual reproduction of that plant, for example but not limited to: seed, seedling, root, shoot, stolon, bulb, tuber, corm, keikis, or bud.

A "progeny seed", as used herein, refers to the seed produced by a host plant that has been inoculated with, or associated with, an endophyte. For example, in the present invention, a seed, plant element, or whole plant may become heterologously associated with an endophyte, and the plant that is grown from said seed, or plant that is grown in heterologous association with said endophyte, may itself produce progeny seeds that comprise altered nutritional composition compared to seeds obtained from plants that were not grown from a plant element associated with an endophyte or obtained from a parental (host) plant that had become associated with an endophyte at some point in its life cycle. In the general sense, the phrase "progeny seed" may be construed to represent any plant propagative unit produced by the host plant that is capable of becoming another individual of that same plant species.

A "population" of plants, as used herein, can refer to a plurality of plants that were subjected to the same inoculation methods described herein, or a plurality of plants that are progeny of a plant or group of plants that were subjected to the inoculation methods. In addition, a population of plants can be a group of plants that are grown from coated seeds. The plants within a population will typically be of the same species, and will also typically share a common genetic derivation.

As used herein, an "agricultural seed" is a seed used to grow a plant typically used in agriculture (an "agricultural plant"). The seed may be of a monocot or dicot plant, and may be planted for the production of an agricultural product, for example feed, food, fiber, fuel, etc. As used herein, an agricultural seed is a seed that is prepared for planting, for example, in farms for growing.

The term "synthetic combination" means a plurality of elements associated by human endeavor, in which said association is not found in nature. In the present invention, "synthetic combination" is used to refer to a treatment formulation associated with a plant element.

A "treatment formulation" refers to a mixture of chemicals that facilitate the stability, storage, and/or application of the endophyte composition(s). In some embodiments, an agriculturally compatible carrier can be used to formulate an agricultural formulation or other composition that includes a purified endophyte preparation. As used herein an "agriculturally compatible carrier" refers to any material, other than water, that can be added to a plant element without causing or having an adverse effect on the plant element (e.g., reducing seed germination) or the plant that grows from the plant element, or the like.

The compositions and methods herein may provide for an improved "agronomic trait" or "trait of agronomic importance" to a host plant, which may include, but not be limited to, the following: disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein content, altered oil content, increased biomass, increased shoot length, increased root length, improved root architecture, modulation of a metabolite, modulation of the proteome, increased seed weight, altered seed carbohydrate composition, altered seed oil composition, altered seed protein composition, altered seed nutritional quality trait, compared to an isoline plant grown from a seed without said seed treatment formulation.

The phrase "nutritional quality trait" includes any measurable parameter of a seed that either directly or indirectly influences the value (nutritional or economic) of said seed, for example, but not limited to: protein, fat, carbohydrate, ash, moisture, fiber, and Calories. In some cases, "nutritional quality trait" is synonymous with "nutritional quality trait" or "seed nutritional quality trait", and can refer to any composition of the associated plant element, most particularly compositions providing benefit to other organisms that consume or utilize said plant element.

As used herein, the terms "water-limited (or water-limiting) condition" and "drought condition", or "water-limited" and "drought", or "water stress" and "drought stress", may all be used interchangeably. For example, a method or composition for improving a plant's ability to grown under drought conditions means the same as the ability to grow under water-limited conditions. In such cases, the plant can be further said to display improved drought tolerance.

Additionally, "altered metabolic function" or "altered enzymatic function" may include, but not be limited to, the following: altered production of an auxin, altered nitrogen fixation, altered production of an antimicrobial compound, altered production of a siderophore, altered mineral phosphate solubilization, altered production of a cellulase, altered production of a chitinase, altered production of a xylanase, altered production of acetoin.

An "increased yield" can refer to any increase in biomass or seed or fruit weight, seed size, seed number per plant, seed number per unit area, bushels per acre, tons per acre, kilo per hectare, or carbohydrate yield. Typically, the particular characteristic is designated when referring to increased yield, e.g., increased grain yield or increased seed size.

In some cases, the present invention contemplates the use of compositions that are "compatible" with agricultural chemicals, for example, a fungicide, an anti-complex compound, or any other agent widely used in agricultural which has the effect of killing or otherwise interfering with optimal growth of another organism. As used herein, a composition is "compatible" with an agricultural chemical when the organism is modified, such as by genetic modification, e.g., contains a transgene that confers resistance to an herbicide, or is adapted to grow in, or otherwise survive, the concentration of the agricultural chemical used in agriculture. For example, an endophyte disposed on the surface of a seed is compatible with the fungicide metalaxyl if it is able to survive the concentrations that are applied on the seed surface.

As used herein, a "colony-forming unit" ("CFU") is used as a measure of viable microorganisms in a sample. A CFU is an individual viable cell capable of forming on a solid medium a visible colony whose individual cells are derived by cell division from one parental cell.

The term "efficacy" (and its synonyms, such as "efficacious") as used herein describes the capability of a microbe to perform its function. In one non-limiting example, a complex endophyte is said to be efficacious if it is capable of performing a function such as improving the yield of a plant with which it becomes associated. In another non-limiting example, a bacterial endophyte is said to display improved efficacy if it is capable of performing a particular function under one condition vs. a control condition.

The terms "decreased", "fewer", "slower" and "increased" "faster" "enhanced" "greater" as used herein refers to a decrease or increase in a characteristic of the endophyte treated seed or resulting plant compared to an untreated seed or resulting plant. For example, a decrease in a characteristic may be at least 1%, between 1% and 2%, at least 2%, between 2% and 3%, at least 3%, between 3% and 4%, at least 4%, between 4% and 5%, at least 5%, between 5% and 10%, at least 10%, between 10% and 15%, at least 15%, between 15% and 20%, at least 20%, between 20% and 25%, at least 25%, between 25% and 30%, at least 30%, between 30% and 35%, at least 35%, between 35% and 40%, at least 40%, between 40% and 45%, at least 45%, between 45% and 50%, at least 50%, between 50% and 60%, at least about 60%, between 60% and 75%, at least 75%, between 75% and 80%, at least about 80%, between 80% and 90%, at least about 90%, between 90% and 100%, at least 100%, between 100% and 200%, at least 200%, between 200% and 300%, at least about 300%, between 300% and 400%, at least about 400% or more lower than the untreated control, and an increase may be at least 1%, between 1% and 2%, at least 2%, between 2% and 3%, at least 3%, between 3% and 4%, at least 4%, between 4% and 5%, at least 5%, between 5% and 10%, at least 10%, between 10% and 15%, at least 15%, between 15% and 20%, at least 20%, between 20% and 25%, at least 25%, between 25% and 30%, at least 30%, between 30% and 35%, at least 35%, between 35% and 40%, at least 40%, between 40% and 45%, at least 45%, between 45% and 50%, at least 50%, between 50% and 60%, at least about 60%, between 60% and 75%, at least 75%, between 75% and 80%, at least about 80%, between 80% and 90%, at least about 90%, between 90% and 100%, at least 100%, between 100% and 200%, at least 200%, between 200% and 300%, at least about 300%, between 300% and 400%, at least about 400% or more higher than the untreated control.

DETAILED DESCRIPTION OF THE INVENTION

As demonstrated herein, agricultural plants associate with symbiotic microorganisms termed endophytes, particularly bacteria and fungi, which may contribute to plant survival and performance. However, modern agricultural processes may have perturbed this relationship, resulting in increased crop losses, diminished stress resilience, biodiversity losses, and increasing dependence on external chemicals, fertilizers, and other unsustainable agricultural practices. There is a need for novel methods for generating plants with novel microbiome properties that can sustainably increase yield, stress resilience, and decrease fertilizer and chemical use.

Currently, the generally accepted view of plant endophytic communities focuses on their homologous derivation, predominantly from the soil communities in which the plants are grown (Hallman et al., (1997) Canadian Journal of Microbiology. 43(10): 895-914). Upon observing taxonomic overlap between the endophytic and soil microbiota in *A. thaliana*, it was stated, “Our rigorous definition of an endophytic compartment microbiome should facilitate controlled dissection of plant-microbe interactions derived from complex soil communities” (Lundberg et al., (2012) Nature. 488, 86-90). There is strong support in the art for soil representing the repository from which plant endophytes are derived (Long et al., 2010, New Phytologist 185: 554-567, incorporated herein by reference in its entirety). Notable plant-microbe interactions such as mycorrhyzal fungi and complex rhizobia fit the paradigm of soil-based colonization of plant hosts and appear to primarily establish themselves independently. As a result of focusing attention on the derivation of endophytes from the soil in which the target agricultural plant is currently growing, there has been an inability to achieve commercially significant improvements in plant yields and other plant characteristics such as increased root biomass, increased root length, increased height, increased shoot length, increased leaf number, increased water use efficiency, increased overall biomass, increase grain yield, increased photosynthesis rate, increased tolerance to drought, increased heat tolerance, increased salt tolerance, increased resistance to insect and nematode stresses, increased resistance to a fungal pathogen, increased resistance to a complex pathogen, increased resistance to a viral pathogen, a detectable modulation in the level of a metabolite, and a detectable modulation in the proteome relative to a reference plant.

Complex endophytes, or endophytes that themselves further comprise an additional organism or composition, are rarely described. Because of the lack of evidence in the literature for both the existence of complex endophytes in crop plant populations, as well as the lack of evidence demonstrating any benefit to the host plant conferred from an endophyte, complex endophytes have not previously been conceived as a viable mechanism to address the need to provide improved yield and tolerance to environmental stresses for plants of agricultural importance.

The inventors herein have conceived of utilizing complex endophyte compositions or compositions comprising endophytic components for use in benefiting plant health and stress tolerance, as well as methods of using said complex endophyte compositions or compositions comprising endophytic components, to impart novel characteristics to a host fungus or a host plant. In one aspect of this invention, endophyte compositions are isolated and purified from plant sources, and synthetically combined with a plant element, such as a seed, to impart improved agronomic potential and/or improved agronomic traits to the host plant. In another aspect of the invention, endophytic components, such as endofungal bacteria or endofungal fungi, are isolated and purified from their native source(s) and synthetically combined with a plant element, to impart improved agronomic potential and/or improved agronomic traits to the host plant. Such endofungal components may be further manipulated or combined with additional elements prior to combining with the plant element(s).

The aspects of the present invention are surprising for a number of reasons. First, crop plants have not been shown to comprise complex endophytes, and even for the few plants in which complex endophytes have been found, no benefit has been described. Secondly, complex endophyte-host associations are hypothesized in the literature to not have evolved for the manifestation of any particular phenotype of the host plant. Rather, the association seems to be driven by an accident of co-localization in the same geographical region.

As described herein, beneficial organisms can be robustly derived from heterologous, endogenous, or engineered sources, optionally cultured, administered heterologously to plant elements, and, as a result of the administration, confer multiple beneficial properties. This is surprising given the variability observed in the art in endophytic microbe isolation and the previous observations of inefficient seed pathogen colonization of plant host's tissues. Further, the ability of heterologously disposed complex endophytes to colonize plant reproductive elements from the outside is surprising, given that isolated complex endophytes have not been previously demonstrated to be capable of penetrating and colonizing host tissues.

In part, the present invention describes preparations of complex endophytes, and the creation of synthetic combinations of seeds and/or seedlings with heterologous complex endophyte compositions, and formulations containing the synthetic combinations, as well as the recognition that such synthetic combinations display a diversity of beneficial properties in the agricultural plants. Such beneficial properties include metabolism, transcript expression, proteome alterations, morphology, and the resilience to a variety of environmental stresses, and the combination of a plurality of such properties. The present invention also describes methods of using such complex endophyte compositions to benefit the host plant with which it is associated.

Isolated Complex Endophyte Compositions and Methods

The isolated complex endophytes described herein provide several key significant advantages over other plant-associated microbes. Different environments can contain significantly different populations of endophytes and thus may provide reservoirs for desired complex endophytes and/or components (such as endofungal bacterial endophytes or endofungal fungal endophytes). Once a choice environment is selected, plant elements of choice plants to be sampled can be identified by their healthy and/or robust growth, or other desired phenotypic characteristics.

In one aspect of the present invention, the complex endophytes useful for the present invention can also be isolated from plants or plant elements adapted to a particular environment, including, but not limited to, an environment with water deficiency, salinity, acute and/or chronic heat stress, acute and/or chronic cold stress, nutrient deprived soils including, but not limited to, micronutrient deprived soils, macronutrient (e.g., potassium, phosphate, nitrogen) deprived soils, pathogen stress, including fungal, nematode, insect, viral, complex pathogen stress.

In one embodiment, a plant comprising a complex endophyte is harvested from a soil type different than that in which the plant is normally grown. In another embodiment, the plant comprising a complex endophyte is harvested from an ecosystem where the agricultural plant is not normally found. In another embodiment, the plant comprising a complex endophyte is harvested from a soil with an average pH range that is different from the optimal soil pH range of the agricultural plant. In one embodiment, the plant comprising a complex endophyte is harvested from an environment with average air temperatures lower than the normal growing temperature of the agricultural plant. In one embodiment, the plant comprising a complex endophyte is harvested from an environment with average air temperatures higher than the normal growing temperature of the agricultural plant. In another embodiment, the plant comprising a complex endophyte is harvested from an environment with average rainfall lower than the optimal average rainfall received by the agricultural plant. In one embodiment, the plant comprising a complex endophyte is harvested from an environment with average rainfall higher than the optimal average rainfall of the agricultural plant. In another embodiment, the plant comprising a complex endophyte is harvested from a soil type with different soil moisture classification than the normal soil type that the agricultural plant is grown on. In one embodiment, the plant comprising a complex endophyte is harvested from an environment with average rainfall lower than the optimal average rainfall of the agricultural plant. In one embodiment, the plant comprising a complex endophyte is harvested from an environment with average rainfall higher than the optimal average rainfall of the agricultural plant. In another embodiment, the plant comprising a complex endophyte is harvested from an agricultural environment with a yield lower than the average yield expected from the agricultural plant grown under average cultivation practices on normal agricultural land. In another embodiment, the plant comprising a complex endophyte is harvested from an agricultural environment with a yield lower than the average yield expected from the agricultural plant grown under average cultivation practices on normal agricultural land. In another embodiment, the plant comprising a complex endophyte is harvested from an environment with average yield higher than the optimal average yield of the agricultural plant. In another embodiment, the plant comprising a complex endophyte is harvested from an environment with average yield higher than the optimal average yield of the agricultural plant. In another embodiment, the plant comprising a complex endophyte is harvested from an environment where soil contains lower total nitrogen than the optimum levels recommended in order to achieve average yields for a plant grown under average cultivation practices on normal agricultural land. In another embodiment, the plant comprising a complex endophyte is harvested from an environment where soil contains higher total nitrogen than the optimum levels recommended in order to achieve average yields for a plant grown under average cultivation practices on normal agricultural land. In another embodiment, the plant comprising a complex endophyte is harvested from an environment where soil contains lower total phosphorus than the optimum levels recommended in order to achieve average yields for a plant grown under average cultivation practices on normal agricultural land. In another embodiment, the plant comprising a complex endophyte is harvested from an environment where soil contains higher total phosphorus than the optimum levels recommended in order to achieve average yields for a plant grown under average cultivation practices on normal agricultural land. In another embodiment, the plant comprising a complex endophyte is harvested from an environment where soil contains lower total potassium than the optimum levels recommended in order to achieve average yields for a plant grown under average cultivation practices on normal agricultural land. In another embodiment, the plant comprising a complex endophyte is harvested from an environment where soil contains higher total potassium than the optimum levels recommended in order to achieve average yields for a plant grown under average cultivation practices on normal agricultural land. In another embodiment, the plant comprising a complex endophyte is harvested from an environment where soil contains lower total sulfur than the optimum levels recommended in order to achieve average yields for a plant grown under average cultivation practices on normal agricultural land. In another embodiment, the plant comprising a complex endophyte is harvested from an environment where soil contains higher total sulfur than the optimum levels recommended in order to achieve average yields for a plant grown under average cultivation practices on normal agricultural land. In another embodiment, the plant comprising a complex endophyte is harvested from an environment where soil contains lower total calcium than the optimum levels recommended in order to achieve average yields for a plant grown under average cultivation practices on normal agricultural land. In another embodiment, the plant comprising a complex endophyte is harvested from an environment where soil contains lower total magnesium than the optimum levels recommended in order to achieve average yields for a plant grown under average cultivation practices on normal agricultural land. In another embodiment, the plant comprising a complex endophyte is harvested from an environment where soil contains higher total sodium chloride (salt) than the optimum levels recommended in order to achieve average yields for a plant grown under average cultivation practices on normal agricultural land.

In some embodiments, this invention relates to purified isolated complex endophytes from, for example, maize, wheat, rice, barley, soybeans, cotton, canola, tomatoes, or other agricultural plants, and compositions such as agricultural formulations or articles of manufacture that include such purified populations, as well as methods of using such populations to make synthetic combinations or agricultural products.

In some embodiments, this invention relates to the usage of a fungus as a carrier of an endophyte, and methods of using said fungus. In such cases, the fungus can act as a protective mechanism for an endophyte, such as a bacterium or another fungus, that otherwise has low survivability in a formulation. Gram-negative bacteria, for example, do not survive well when used to treat plant elements. It may therefore be desirable to identify a complex endophyte comprising a component endofungal bacterium or fungus that is identical to or similar to a bacterium or fungus that provides a benefit to a plant, and introduce such complex endophyte to a plant element in such a manner that the beneficial endophytic bacterium or fungus is protected from dessication, mechanical trauma, or chemical exposure. In another embodiment, this invention relates to the usage of a fungus to deploy a non-spore forming bacterium or fungus. It may be desirable to identify a spore-forming complex endophyte comprising a component endofungal bacteria or fungus that is identical to or similar to a non-spore-forming bacterium or fungus that provides a benefit to a plant. Therefore, one aspect of this invention is a fungus that acts as an endophytic carrier to enable deployment of beneficial bacteria or fungi that could otherwise not be turned into a product.

It is also contemplated that a lichen or lichenized fungus could a host organism in an endophytic complex. The lichen-associated bacteria, cyanobacteria, and/or fungus can be used as endophytes, either as a complex or individually.

Isolated complex endophytes or components thereof, used to make a synthetic composition can be obtained from a plant element of many distinct plants. In one embodiment, the complex endophyte can be obtained a plant element of the same or different crop, and can be from the same or different cultivar or variety as the plant element to which the composition is intended to be association.

In another embodiment, isolated complex endophytes or components thereof, used to make a synthetic composition can be obtained from the same cultivar or species of agricultural plant to which the composition is intended for association, or can be obtained from a different cultivar or species of agricultural plant. For example, complex endophytes from a particular corn variety can be isolated and coated onto the surface of a corn seed of the same variety.

In another embodiment, isolated complex endophytes or components thereof, used to make a synthetic composition can be obtained from a plant element of a plant that is related to the plant element to which the composition is intended to be association. For example, an endophyte isolated from *Triticum monococcum* (einkorn wheat) can be coated onto the surface of a *T. aestivum* (common wheat) seed; or, an endophyte from *Hordeum vulgare* (barley) can be isolated and coated onto the seed of a member of the Triticeae family, for example, seeds of the rye plant, *Secale cereale*).

In still another embodiment, isolated complex endophytes or components thereof, used to make a synthetic composition can be obtained from a plant element of a plant that is distantly related to the seed onto which the endophyte is to be coated. For example, a tomato-derived endophyte can be isolated and coated onto a rice seed.

In some embodiments, a synthetic combination is used that includes two or more (e.g., 3, 4, 5, 6, 7, 8, 9, 10, between 10 and 15, 15, between 15 and 20, 20, between 20 and 25, 25, or greater than 25) different complex endophytes, e.g., obtained from different families or different genera, or from the same genera but different species. The different complex endophytes can be obtained from the same cultivar of agricultural plant (e.g., the same maize, wheat, rice, or barley plant), different cultivars of the same agricultural plant (e.g., two or more cultivars of maize, two or more cultivars of wheat, two or more cultivars of rice, or two or more cultivars of barley), or different species of the same type of agricultural plant (e.g., two or more different species of maize, two or more different species of wheat, two or more different species of rice, or two or more different species of barley). In embodiments in which two or more complex endophytes are used, each of the endophytes can have different properties or activities, e.g., produce different metabolites, produce different enzymes such as different hydrolytic enzymes, confer different beneficial traits, or colonize different elements of a plant (e.g., leaves, stems, flowers, fruits, seeds, or roots). For example, one endophyte can colonize a first tissue and a second endophyte can colonize a tissue that differs from the first tissue. Combinations of endophytes are disclosed in detail below.

In one embodiment, the complex endophyte is isolated from a different plant than the inoculated plant. For example, in one embodiment, the endophyte is an endophyte isolated from a different plant of the same species as the inoculated plant. In some cases, the endophyte is isolated from a species related to the inoculated plant.

In some embodiments, the complex endophyte comprises an endofungal fungal endophyte of one or more of the following taxa: *Alternaria, Aureobasidium, Biscogniauxia, Botryosphaeria, Cladosporium, Coniothyrium, Daldinia, Fusarium, Hormonema, Hypoxylon, Lecythophora, Microdiplodia, Monodictys, Nectria, Neurospora, Paraconiothyrium, Penicillium, Periconia, Pestalotiopsis, Phaeomoniella, Phoma, Phyllosticta, Preussia, Xylaria, Rhizopus, Aspergillus, Gigaspora, Piriformospora, Laccaria, Tuber, Mucor.*

In some embodiments, the complex endophyte comprises a host fungus chosen among those listed in Table 2, or those comprising a fungal ITS or LSU nucleic acid sequence that is at least 97% identical to at least one of the ITS or LSU nucleic acid sequences of the fungi listed in Table 2 (SEQ ID NOs: 250-333).

In some embodiments, the complex endophyte comprises a host fungus from the genus *Botryosphaeria*. In some embodiments, the complex endophyte comprises a host fungus that itself comprises an ITS nucleic acid sequence that is at least 97% identical to SEQ ID NO: 266. In some embodiments, the complex endophyte comprises a host fungus that itself comprises an ITS nucleic acid sequence that is at least 97% identical to SEQ ID NO: 325.

In some embodiments, the complex endophyte comprises a host fungus from the genus *Mucor*. In some embodiments, the complex endophyte comprises a host fungus that itself comprises an ITS nucleic acid sequence that is at least 97% identical to SEQ ID NO: 333.

In some embodiments, the complex endophyte comprises a host fungus from the genus *Microdiplodia* (also known variously as *Paraconiothyrium*). In some embodiments, the complex endophyte comprises a host fungus that itself comprises an ITS nucleic acid sequence that is at least 97% identical to SEQ ID NO: 268. In some embodiments, the complex endophyte comprises a host fungus that itself comprises an ITS nucleic acid sequence that is at least 97% identical to SEQ ID NO: 270. In some embodiments, the complex endophyte comprises a host fungus that itself comprises an ITS nucleic acid sequence that is at least 97% identical to SEQ ID NO: 326. In some embodiments, the complex endophyte comprises a host fungus that itself comprises an ITS nucleic acid sequence that is at least 97% identical to SEQ ID NO: 331.

In some embodiments, the complex endophyte comprises a host fungus from the genus *Pestalotiposis*. In some embodiments, the complex endophyte comprises a host fungus that itself comprises an ITS nucleic acid sequence that is at least 97% identical to SEQ ID NO: 269. In some embodiments, the complex endophyte comprises a host fungus that itself comprises an ITS nucleic acid sequence that is at least 97% identical to SEQ ID NO: 327.

In some embodiments, the complex endophyte comprises a host fungus from the genus *Phyllosticta*. In some embodiments, the complex endophyte comprises a host fungus that itself comprises an ITS nucleic acid sequence that is at least 97% identical to SEQ ID NO: 267. In some embodiments, the complex endophyte comprises a host fungus that itself comprises an ITS nucleic acid sequence that is at least 97% identical to SEQ ID NO: 328.

In some embodiments, the complex endophyte comprises a host fungus from the genus *Alternaria*. In some embodiments, the complex endophyte comprises a host fungus that itself comprises an LSU nucleic acid sequence that is at least 97% identical to SEQ ID NO: 329.

In some embodiments, the complex endophyte comprises a host fungus from the genus *Lecythophora*. In some embodiments, the complex endophyte comprises a host fungus that itself comprises an ITS nucleic acid sequence that is at least 97% identical to SEQ ID NO: 247. In some embodiments, the complex endophyte comprises a host fungus that itself comprises an ITS nucleic acid sequence that is at least 97% identical to SEQ ID NO: 330.

In some embodiments, the complex endophyte comprises a host fungus from the genus *Daldinia*. In some embodiments, the complex endophyte comprises a host fungus that itself comprises an ITS nucleic acid sequence that is at least 97% identical to SEQ ID NO: 242. In some embodiments, the complex endophyte comprises a host fungus that itself comprises an ITS nucleic acid sequence that is at least 97% identical to SEQ ID NO: 260. In some embodiments, the complex endophyte comprises a host fungus that itself comprises an ITS nucleic acid sequence that is at least 97% identical to SEQ ID NO: 263. In some embodiments, the complex endophyte comprises a host fungus that itself comprises an ITS nucleic acid sequence that is at least 97% identical to SEQ ID NO: 332.

In some embodiments, the complex endophyte comprises an endofungal fungal endophyte of one or more of the following taxa: *Alternaria, Aureobasidium, Biscogniauxia, Botryosphaeria, Cladosporium, Coniothyrium, Daldinia, Fusarium, Hormonema, Hypoxylon, Lecythophora, Microdiplodia, Monodictys, Nectria, Neurospora, Paraconiothyrium, Pestalotiopsis, Phaeomoniella, Phoma, Phyllosticta, Preussia, Xylaria, Rhizopus, Aspergillus, Gigaspora, Piriformospora, Laccaria, Tuber, Mucor.*

In some embodiments, the complex endophyte comprises an endofungal fungal endophyte chosen among those listed in Table 2, or those comprising a fungal ITS or LSU nucleic acid sequence that is at least 97% identical to at least one of the ITS or LSU nucleic acid sequences of the fungi listed in Table 2 (SEQ ID NOs: 250-333).

In some embodiments of the present invention, the complex endophyte comprises a bacterium.

In some embodiments of the present invention, the complex endophyte comprises an endofungal bacterial endophyte of one or more of the following taxa: *Acinetobacter, Actinoplanes, Adlercreutzia, Afipia, Atopostipes, Bacillus, Beijerinckia, Bradyrhizobium, Burkholderia, Candidatus Haloredivivus, Caulobacter, Chryseobacterium, Coraliomargarita, Curtobacterium, Delftia, Dyella, Enhydrobacter, Enterobacter, Erwinia, Escherichia/Shigella, Exiguobacterium, Ferroglobus, Filimonas, Halobaculum, Halosimplex, Herbaspirillum, Hymenobacter, Kosakonia, Lactobacillus, Luteibacter, Massilia, Mesorhizobium, Microbacterium, Okibacterium, Oligotropha, Oryzihumus, Paenibacillus, Pantoea, Pelomonas, Perlucidibaca, Polynucleobacter, Propionibacterium, Pseudoclavibacter, Pseudomonas, Ralstonia, Rhizobium, Rhodococcus, Rhodopseudomonas, Sebaldella, Serratia, Sinosporangium, Sphingomonas, Staphylococcus, Stenotrophomonas, Streptococcus, Stygiolobus, Sulfurisphaera, Variovorax*, WPS-2_genera_incertae_sedis, *Zimmermannella, Burkholderia, Streptomyces, Candidatus, Rhizobium, Paenibacillus.*

In some embodiments, the complex endophyte comprises an endofungal bacterial endophyte chosen among those listed in Table 1, or those comprising a 16S nucleic acid sequence that is at least 97% identical to at least one of the 16S nucleic acid sequence of the bacteria listed in Table 1 (SEQ ID NOs: 1-249).

In some embodiments, the complex endophyte comprises a component bacterium from the genus *Luteibacter*. In some embodiments, the complex endophyte comprises a component bacterium from the genus *Dyella*.

In some embodiments, the complex endophyte comprises a host fungus that itself comprises a 16S nucleic acid sequence that is at least 97% identical to SEQ ID NO 45. In some embodiments, the complex endophyte comprises a host fungus that itself comprises a 16S nucleic acid sequence that is at least 97% identical to SEQ ID NO 48. In some embodiments, the complex endophyte comprises a host fungus that itself comprises a 16S nucleic acid sequence that is at least 97% identical to SEQ ID NO 237. In some embodiments, the complex endophyte comprises a host fungus that itself comprises a 16S nucleic acid sequence that is at least 97% identical to SEQ ID NO 240.

In some embodiments, the complex endophyte comprises a component bacterium from the genus *Pantoea*. In some embodiments, the complex endophyte comprises a host fungus that itself comprises a 16S nucleic acid sequence that is at least 97% identical to SEQ ID NO: 55. In some embodiments, the complex endophyte comprises a host fungus that itself comprises a 16S nucleic acid sequence that is at least 97% identical to SEQ ID NO: 238. In some embodiments, the complex endophyte comprises a host fungus that itself comprises a 16S nucleic acid sequence that is at least 97% identical to SEQ ID NO: 249.

In some embodiments, the complex endophyte comprises a component bacterium from the genus *Luteibacter*. In some embodiments, the complex endophyte comprises a host fungus that itself comprises a 16S nucleic acid sequence that is at least 97% identical to SEQ ID NO: 9. In some embodiments, the complex endophyte comprises a host fungus that itself comprises a 16S nucleic acid sequence that is at least 97% identical to SEQ ID NO: 31. In some embodiments, the complex endophyte comprises a host fungus that itself comprises a 16S nucleic acid sequence that is at least 97% identical to SEQ ID NO: 40. In some embodiments, the complex endophyte comprises a host fungus that itself comprises a 16S nucleic acid sequence that is at least 97% identical to SEQ ID NO: 58. In some embodiments, the complex endophyte comprises a host fungus that itself comprises a 16S nucleic acid sequence that is at least 97% identical to SEQ ID NO: 239. In some embodiments, the complex endophyte comprises a host fungus that itself comprises a 16S nucleic acid sequence that is at least 97% identical to SEQ ID NO: 241.

In some embodiments, the complex endophyte comprises a component bacterium from the genus *Ralstonia*. In some embodiments, the complex endophyte comprises a host fungus that itself comprises a 16S nucleic acid sequence that is at least 97% identical to SEQ ID NO: 16. In some embodiments, the complex endophyte comprises a host fungus that itself comprises a 16S nucleic acid sequence that is at least 97% identical to SEQ ID NO: 242.

In some embodiments, the complex endophyte comprises a component bacterium from the genus *Erwinia*. In some embodiments, the complex endophyte comprises a host fungus that itself comprises a 16S nucleic acid sequence that is at least 97% identical to SEQ ID NO: 62. In some embodiments, the complex endophyte comprises a host fungus that itself comprises a 16S nucleic acid sequence that is at least 97% identical to SEQ ID NO: 243.

In some embodiments, the complex endophyte comprises a component bacterium from the genus *Bacillus*. In some embodiments, the complex endophyte comprises a host fungus that itself comprises a 16S nucleic acid sequence that is at least 97% identical to SEQ ID NO: 50. In some embodiments, the complex endophyte comprises a host fungus that itself comprises a 16S nucleic acid sequence that is at least 97% identical to SEQ ID NO: 244.

The isolated complex endophytes of the present invention may individually comprise single additional components (for example, a host fungus may comprise a single endofungal bacterial endophyte), a plurality of components of the same type (for example, a host fungus may comprise multiple endofungal bacterial endophytes of different strains), or a plurality of components of different types (for example, a host fungus may comprise multiple endofungal bacterial endophytes of different strains; in another example, a host fungus may comprise both endofungal bacterial endophytes and endofungal fungal endophytes).

In other embodiments, the complex endophyte is selected from one of the complex endophytes described in Table 3 or Table 4.

In some aspects of the present invention, the complex endophyte, comprising a host fungus and a component bacterium, may be selected from the combination of host fungi and component bacteria represented by the following SEQ ID combinations. For example, a complex endophyte may be a combination of a Bacterium comprising a nucleotide sequence at least 97% identical to SEQ ID NO: 237 and a Fungus comprising a nucleotide sequence at least 97% identical to SEQ ID NO: 325. In another example, a complex endophyte may be a combination of a Bacterium comprising a nucleotide sequence at least 97% identical to SEQ ID NO: 238 and a Fungus comprising a nucleotide sequence at least 97% identical to SEQ ID NO: 326. For example, a complex endophyte may be a combination of a Bacterium comprising a nucleotide sequence at least 97% identical to SEQ ID NO: 239 and a Fungus comprising a nucleotide sequence at least 97% identical to SEQ ID NO: 327. For example, a complex endophyte may be a combination of a Bacterium comprising a nucleotide sequence at least 97% identical to SEQ ID NO: 240 and a Fungus comprising a nucleotide sequence at least 97% identical to SEQ ID NO: 328. For example, a complex endophyte may be a combination of a Bacterium comprising a nucleotide sequence at least 97% identical to SEQ ID NO: 241 and a Fungus comprising a nucleotide sequence at least 97% identical to SEQ ID NO: 329. For example, a complex endophyte may be a combination of a Bacterium comprising a nucleotide sequence at least 97% identical to SEQ ID NO: 242 and a Fungus comprising a nucleotide sequence at least 97% identical to SEQ ID NO: 330. For example, a complex endophyte may be a combination of a Bacterium comprising a nucleotide sequence at least 97% identical to SEQ ID NO: 243 and a Fungus comprising a nucleotide sequence at least 97% identical to SEQ ID NO: 331. For example, a complex endophyte may be a combination of a Bacterium comprising a nucleotide sequence at least 97% identical to SEQ ID NO: 244 and a Fungus comprising a nucleotide sequence at least 97% identical to SEQ ID NO: 332. For example, a complex endophyte may be a combination of a Bacterium comprising a nucleotide sequence at least 97% identical to SEQ ID NO: 249 and a Fungus comprising a nucleotide sequence at least 97% identical to SEQ ID NO: 333.

In some cases, the complex endophyte, or one or more components thereof, is of monoclonal origin, providing high genetic uniformity of the complex endophyte population in an agricultural formulation or within a synthetic seed or plant combination with the endophyte.

In some embodiments, the complex endophyte can be cultured on a culture medium or can be adapted to culture on a culture medium.

In some embodiments, the compositions provided herein are stable. The endofungal bacterial endophyte, endofungal fungal endophyte, or complex endophyte may be shelf stable, where at least 10% of the CFUs are viable after storage in desiccated form (i.e., moisture content of 30% or less) for 1, 2, 3, 4, 5, 6, 7, 8, 9, 10 or greater than 10 weeks at 4° C. or at room temperature. Optionally, a shelf stable formulation is in a dry formulation, a powder formulation, or a lyophilized formulation. In some embodiments, the formulation is formulated to provide stability for the population of endofungal bacterial endophytes, endofungal fungal endophytes, or complex endophytes. In one embodiment, the formulation is substantially stable at temperatures between about 0° C. and about 50° C. for at least about 1, 2, 3, 4, 5, or 6 days, or 1, 2, 3 or 4 weeks, or 1, 2, 3, 4, 5, 6, 7, 8, 9, 10, 11 or 12 months, or one or more years. In another embodiment, the formulation is substantially stable at temperatures between about 4° C. and about 37° C. for at least about 5, 10, 15, 20, 25, 30 or greater than 30 days.

Functional Attributes of Complex Endophytes and Endophytic Components

In some cases, the complex endophyte or endophytic component may produce one or more compounds and/or have one or more activities, e.g., one or more of the following: production of a metabolite, production of a phytohormone such as auxin, production of acetoin, production of an antimicrobial compound, production of a siderophore, production of a cellulase, production of a pectinase, production of a chitinase, production of a xylanase, nitrogen fixation, or mineral phosphate solubilization. For example, a complex endophyte or endophytic component can produce a phytohormone selected from the group consisting of an auxin, a cytokinin, a gibberellin, ethylene, a brassinosteroid, and abscisic acid. In one particular embodiment, the complex endophyte or endophytic component produces auxin (e.g., indole-3-acetic acid (IAA)). Production of auxin can be assayed as described herein. Many of the microbes described herein are capable of producing the plant hormone auxin indole-3-acetic acid (IAA) when grown in culture. Auxin plays a key role in altering the physiology of the plant, including the extent of root growth. Therefore, in another embodiment, the complex endophytic population is disposed on the surface or within a tissue of the seed or seedling in an amount effective to detectably increase production of auxin in the agricultural plant when compared with a reference agricultural plant. In one embodiment, the increased auxin production can be detected in a tissue type selected from the group consisting of the root, shoot, leaves, and flowers.

In some embodiments, the complex endophyte or endophytic component can produce a compound with antimicrobial properties. For example, the compound can have antibacterial properties, as determined by the growth assays provided herein. In one embodiment, the compound with antibacterial properties shows bacteriostatic or bactericidal activity against *E. coli* and/or *Bacillus* sp. In another embodiment, the complex endophyte or endophytic component produces a compound with antifungal properties, for example, fungicidal or fungistatic activity against *S. cerevisiae* and/or *Rhizoctonia*.

In some embodiments, the complex endophyte or endophytic component comprises bacteria capable of nitrogen fixation, and is thus capable of producing ammonium from atmospheric nitrogen. The ability of bacteria to fix nitrogen can be confirmed by testing for growth of the bacteria in nitrogen-free growth media, for example, LGI media, as described in methods known in the art.

In some embodiments, the complex endophyte or endophytic component can produce a compound that increases the solubility of mineral phosphate in the medium, i.e., mineral phosphate solubilization, for example, using the growth assays described herein. In one embodiment, the complex endophyte or endophytic component n produces a compound that allows the bacterium to grow in growth media containing $Ca_3HPO_4$ as the sole phosphate source.

In some embodiments, the complex endophyte or endophytic component can produce a siderophore. Siderophores are small high-affinity iron chelating agents secreted by microorganisms that increase the bioavailability of iron. Siderophore production by the complex endophyte or endophytic component can be detected using methods known in the art.

In some embodiments, the complex endophyte or endophytic component can produce a hydrolytic enzyme. For example, in one embodiment, a complex endophyte or endophytic component can produce a hydrolytic enzyme selected from the group consisting of a cellulase, a pectinase, a chitinase and a xylanase. Hydrolytic enzymes can be detected using methods known in the art.

In some embodiments, the complex endophyte provides an improved attribute to the component fungus or bacterium. In some cases, the presence of one organism is beneficial to the other, and can be a result of any number of mechanisms of either component, or a synergistic effect of the combination of the two organisms. In some embodiments, the improved attribute is an improved ability of the endophytic bacterium to produce crystal proteins. In some embodiments, the improved attribute is an improved ability of the host fungus to sporulate.

Combinations of Complex Endophytes and Complex Endophytic Components

Combinations of complex endophytes or endophytic components can be selected by any one or more of several criteria. In one embodiment, compatible complex endophytes or endophytic components are selected. As used herein, compatibility refers to populations of complex endophytes or endophytic components that do not significantly interfere with the growth, propagation, and/or production of beneficial substances of the other. Incompatible populations can arise, for example, where one of the populations produces or secrets a compound that is toxic or deleterious to the growth of the other population(s). Incompatibility arising from production of deleterious compounds/agents can be detected using methods known in the art, and as described herein elsewhere. Similarly, the distinct populations can compete for limited resources in a way that makes co-existence difficult.

In another embodiment, combinations are selected on the basis of compounds produced by each population of complex endophytes or endophytic components. For example, the first population is capable of producing siderophores, and another population is capable of producing anti-fungal compounds. In one embodiment, the first population of complex endophytes or endophytic components is capable of a function selected from the group consisting of auxin production, nitrogen fixation, production of an antimicrobial compound, siderophore production, mineral phosphate solubilization, cellulase production, chitinase production, xylanase production, and acetoin production. In another embodiment, the second population of complex endophytes or endophytic component is capable of a function selected from the group consisting of auxin production, nitrogen fixation, production of an antimicrobial compound, siderophore production, mineral phosphate solubilization, cellulase production, chitinase production, xylanase production, and acetoin production. In still another embodiment, the first and second populations are capable of at least one different function.

In still another embodiment, the combinations of complex endophytes or endophytic components are selected for their distinct localization in the plant after colonization. For example, the first population of complex endophytes or endophytic components can colonize, and in some cases preferentially colonize, the root tissue, while a second population can be selected on the basis of its preferential colonization of the aerial parts of the agricultural plant. Therefore, in one embodiment, the first population is capable of colonizing one or more of the tissues selected from the group consisting of a root, shoot, leaf, flower, and seed. In another embodiment, the second population is capable of colonizing one or more tissues selected from the group consisting of root, shoot, leaf, flower, and seed. In still another embodiment, the first and second populations are capable of colonizing a different tissue within the agricultural plant.

In still another embodiment, combinations of complex endophytes or endophytic components are selected for their ability to confer one or more distinct fitness traits on the inoculated agricultural plant, either individually or in synergistic association with other endophytes. Alternatively, two or more endophytes induce the colonization of a third endophyte. For example, the first population of complex endophytes or endophytic components is selected on the basis that it confers significant increase in biomass, while the second population promotes increased drought tolerance on the inoculated agricultural plant. Therefore, in one embodiment, the first population is capable of conferring at least one trait selected from the group consisting of thermal tolerance, herbicide tolerance, drought resistance, insect resistance, fungus resistance, virus resistance, bacteria resistance, male sterility, cold tolerance, salt tolerance, increased yield, enhanced nutrient use efficiency, increased nitrogen use efficiency, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, enhanced soil water retention, or a combination thereof. In another embodiment, the second population is capable of conferring a trait selected from the group consisting of thermal tolerance, herbicide tolerance, drought resistance, insect resistance, fungus resistance, virus resistance, bacteria resistance, male sterility, cold tolerance, salt tolerance, increased yield, enhanced nutrient use efficiency, increased nitrogen use efficiency, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, and enhanced soil water retention. In still another embodiment, each of the first and second population is capable of conferring a different trait selected from the group consisting of thermal tolerance, herbicide tolerance, drought resistance, insect resistance, fungus resistance, virus resistance, bacteria resistance, male sterility, cold tolerance, salt tolerance, increased yield, enhanced nutrient use efficiency, increased nitrogen use efficiency, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, and enhanced soil water retention.

The combinations of complex endophytes or endophytic components can also be selected based on combinations of the above criteria. For example, the first population of complex endophytes or endophytic components can be selected on the basis of the compound it produces (e.g., its ability to fix nitrogen, thus providing a potential nitrogen source to the plant), while the second population can be selected on the basis of its ability to confer increased resistance of the plant to a pathogen (e.g., a fungal pathogen).

In some aspects of the present invention, it is contemplated that combinations of complex endophytes or endophytic components can provide an increased benefit to the host plant, as compared to that conferred by a single endophyte, by virtue of additive effects. For example, one endophyte strain that induces a benefit in the host plant may induce such benefit equally well in a plant that is also colonized with a different endophyte strain that also induces the same benefit in the host plant. The host plant thus exhibits the same total benefit from the plurality of different endophyte strains as the additive benefit to individual plants colonized with each individual endophyte of the plurality. In one example, a plant is colonized with two different endophyte strains: one provides a 1× increase in seed protein content when associated with the plant, and the other provides a 2× increase in seed protein content when associated with a different plant. When both endophyte strains are associated with the same plant, that plant would experience a 3× (additive of 1×+2× single effects) increase in seed protein content. Additive effects are a surprising aspect of the present invention, as non-compatibility of endophytes may result in a cancellation of the beneficial effects of both endophytes.

In some aspects of the present invention, it is contemplated that a combination of complex endophytes or endophytic components can provide an increased benefit to the host plant, as compared to that conferred by a single endophyte, by virtue of synergistic effects. For example, one endophyte strain that induces a benefit in the host plant may induce such benefit beyond additive effects in a plant that is also colonized with a different endophyte strain that also induces that benefit in the host plant. The host plant thus exhibits the greater total benefit from the plurality of different endophyte strains than would be expected from the additive benefit of individual plants colonized with each individual endophyte of the plurality. In one example, a plant is colonized with two different endophyte strains: one provides a 1× increase in seed protein content when associated with a plant, and the other provides a 2× increase in seed protein content when associated with a different plant. When both endophyte strains are associated with the same plant, that plant would experience a 5× (greater than an additive of 1×+2× single effects) increase in seed protein content. Synergistic effects are a surprising aspect of the present invention.

Complex Endophytes and Synthetic Combinations with Plants and Plant Elements

It is contemplated that the methods and compositions of the present invention may be used to improve any characteristic of any agricultural plant. The methods described herein can also be used with transgenic plants containing one or more exogenous transgenes, for example, to yield additional trait benefits conferred by the newly introduced endophytic microbes. Therefore, in one embodiment, a plant element of a transgenic maize, wheat, rice, cotton, canola, alfalfa, or barley plant is contacted with a complex endophyte or endophytic component(s).

In some embodiments, the present invention contemplates the use of complex endophytes or endophytic components that can confer a beneficial agronomic trait upon the plant element or resulting plant with which it is associated.

In some cases, the complex endophytes or endophytic components described herein are capable of moving from one tissue type to another. For example, the present invention's detection and isolation of complex endophytes or endophytic components within the mature tissues of plants after coating on the exterior of a seed demonstrates their ability to move from seed exterior into the vegetative tissues of a maturing plant. Therefore, in one embodiment, the population of complex endophytes or endophytic components is capable of moving from the seed exterior into the vegetative tissues of a plant. In one embodiment, the complex endophyte or endophytic component which is coated onto the seed of a plant is capable, upon germination of the seed into a vegetative state, of localizing to a different tissue of the plant. For example, the complex endophyte or endophytic component can be capable of localizing to any one of the tissues in the plant, including: the root, adventitious root, seminal root, root hair, shoot, leaf, flower, bud, tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In one embodiment, the complex endophyte or endophytic component is capable of localizing to the root and/or the root hair of the plant. In another embodiment, the complex endophyte or endophytic component is capable of localizing to the photosynthetic tissues, for example, leaves and shoots of the plant. In other cases, the complex endophyte or endophytic component is localized to the vascular tissues of the plant, for example, in the xylem and phloem. In still another embodiment, the complex endophyte is capable of localizing to the reproductive tissues (flower, pollen, pistil, ovaries, stamen, fruit) of the plant. In another embodiment, the complex endophyte or endophytic component is capable of localizing to the root, shoots, leaves and reproductive tissues of the plant. In still another embodiment, the complex endophyte or endophytic component colonizes a fruit or seed tissue of the plant. In still another embodiment, the complex endophyte or endophytic component is able to colonize the plant such that it is present in the surface of the plant (i.e., its presence is detectably present on the plant exterior, or the episphere of the plant). In still other embodiments, the complex endophyte or endophytic component is capable of localizing to substantially all, or all, tissues of the plant. In certain embodiments, the complex endophyte or endophytic component is not localized to the root of a plant. In other cases, the complex endophyte or endophytic component is not localized to the photosynthetic tissues of the plant.

In some cases, the complex endophytes or endophytic components are capable of replicating within the host plant and colonizing the plant.

In some embodiments, the complex endophytes or endophytic components described herein are capable of colonizing a host plant. Successful colonization can be confirmed by detecting the presence of the fungal population within the plant. For example, after applying the bacteria to the seeds, high titers of the fungus can be detected in the roots and shoots of the plants that germinate from the seeds. Detecting the presence of the complex endophyte or endophytic component inside the plant can be accomplished by measuring the viability of the complex endophyte after surface sterilization of the seed or the plant: complex endophytic colonization results in an internal localization of the complex endophyte or one of its components, rendering it resistant to conditions of surface sterilization. The presence and quantity of the complex endophyte or endophytic component can also be established using other means known in the art, for example, immunofluorescence microscopy using microbe-specific antibodies, or fluorescence in situ hybridization (see, for example, Amann et al. (2001) Current Opinion in Biotechnology 12:231-236, incorporated herein by reference in its entirety). Alternatively, specific nucleic acid probes recognizing conserved sequences from an endofungal bacterial endophyte can be employed to amplify a region, for example by quantitative PCR, and correlated to CFUs by means of a standard curve.

In some cases, plants are inoculated with complex endophytes or endophytic components that are isolated from the same species of plant as the plant element of the inoculated plant. For example, a complex endophyte or endophytic component that is normally found in one variety of *Zea mays* (corn) is associated with a plant element of a plant of another variety of *Zea mays* that in its natural state lacks said complex endophyte or endophytic component. In one embodiment, the complex endophyte or endophytic component is derived from a plant of a related species of plant as the plant element of the inoculated plant. For example, a complex endophyte or endophytic component that is normally found in *Zea diploperennis* Iltis et al., (diploperennial teosinte) is applied to a *Zea mays* (corn), or vice versa. In some cases, plants are inoculated with complex endophytes or endophytic components that are heterologous to the plant element of the inoculated plant. In one embodiment, the complex endophyte or endophytic component is derived from a plant of another species. For example, a complex endophyte that is normally found in dicots is applied to a monocot plant (e.g., inoculating corn with a soy bean-derived endophyte), or vice versa. In other cases, the complex endophyte or endophytic component to be inoculated onto a plant is derived from a related species of the plant that is being inoculated. In one embodiment, the complex endophyte or endophytic component is derived from a related taxon, for example, from a related species. The plant of another species can be an agricultural plant.

In another embodiment, the complex endophyte or endophytic component is disposed, for example, on the surface of a reproductive element of an agricultural plant, in an amount effective to be detecTable ln the mature agricultural plant. In one embodiment, the endophyte is disposed in an amount effective to be detecTable ln an amount of at least about 100 CFU between 100 and 200 CFU, at least about 200 CFU, between 200 and 300 CFU, at least about 300 CFU, between 300 and 400 CFU, at least about 500 CFU, between 500 and 1,000 CFU, at least about 1,000 CFU, between 1,000 and 3,000 CFU, at least about 3,000 CFU, between 3,000 and 10,000 CFU, at least about 10,000 CFU, between 10,000 and 30,000 CFU, at least about 30,000 CFU, between 30,000 and 100,000 CFU, at least about 100,000 CFU or more in the mature agricultural plant.

In some cases, the complex endophyte or endophytic component is capable of colonizing particular plant elements or tissue types of the plant. In one embodiment, the complex endophyte is disposed on the seed or seedling in an amount effective to be detectable within a target tissue of the mature agricultural plant selected from a fruit, a seed, a leaf, or a root, or portion thereof. For example, the complex endophyte or endophytic component can be detected in an amount of at least about 100 CFU, between 100 and 200 CFU, at least about 200 CFU, between 200 and 300 CFU, at least about 300 CFU, between 300 and 500 CFU, at least about 500 CFU, between 500 and 1,000 CFU, at least about 1,000 CFU, between 1,000 and 3,000 CFU, at least about 3,000 CFU, between 3,000 and 10,000 CFU, at least about 10,000 CFU, between 10,000 CFU and 30,000 CFU, at least about 30,000 CFU, between about 30,000 and 100,000 CFU, at least about 100,000 CFU, or more than 100,000 CFU, in the target tissue of the mature agricultural plant.

Endophytes Compatible with Agrichemicals

In certain embodiments, the complex endophyte or endophytic component is selected on the basis of its compatibility with commonly used agrichemicals. As mentioned earlier, plants, particularly agricultural plants, can be treated with a vast array of agrichemicals, including fungicides, biocides (anti-complex agents), herbicides, insecticides, nematicides, rodenticides, fertilizers, and other agents.

In some cases, it can be important for the complex endophyte or endophytic component to be compatible with agrichemicals, particularly those with fungicidal or anticomplex properties, in order to persist in the plant although, as mentioned earlier, there are many such fungicidal or anticomplex agents that do not penetrate the plant, at least at a concentration sufficient to interfere with the complex endophyte. Therefore, where a systemic fungicide or anticomplex agent is used in the plant, compatibility of the complex endophyte to be inoculated with such agents will be an important criterion.

In one embodiment, natural isolates of complex endophytes or endophytic components that are compatible with agrichemicals can be used to inoculate the plants according to the methods described herein. For example, complex endophytes or endophytic components that are compatible with agriculturally employed fungicides can be isolated by plating a culture of the complex endophytes or endophytic components on a petri dish containing an effective concentration of the fungicide, and isolating colonies of the complex endophyte or endophytic component that are compatible with the fungicide. In another embodiment, a complex endophyte or endophytic component that is compatible with a fungicide is used for the methods described herein.

Fungicide- and bactericide-compatible complex endophytes or endophytic components can also be isolated by selection on liquid medium. The culture of complex endophytes or endophytic component scan be plated on petri dishes without any forms of mutagenesis; alternatively, the complex endophytes or endophytic components can be mutagenized using any means known in the art. For example, complex endophyte or endophytic component cultures can be exposed to UV light, gamma-irradiation, or chemical mutagens such as ethylmethanesulfonate (EMS) prior to selection on fungicide containing media. Finally, where the mechanism of action of a particular fungicide or bactericide is known, the target gene can be specifically mutated (either by gene deletion, gene replacement, site-directed mutagenesis, etc.) to generate a complex endophyte or endophytic component that is resilient against that particular chemical. It is noted that the above-described methods can be used to isolate complex endophytes or endophytic components that are compatible with both fungistatic and fungicidal compounds, as well as bacteriostatic and bactericidal compounds.

It will also be appreciated by one skilled in the art that a plant may be exposed to multiple types of fungicides or anticomplex compounds, either simultaneously or in succession, for example at different stages of plant growth. Where the target plant is likely to be exposed to multiple fungicidal and/or anticomplex agents, a complex endophyte or endophytic component that is compatible with many or all of these agrichemicals can be used to inoculate the plant. A complex endophyte or endophytic component that is compatible with several fungicidal agents can be isolated, for example, by serial selection. A complex endophyte or endophytic component that is compatible with the first fungicidal agent can be isolated as described above (with or without prior mutagenesis). A culture of the resulting complex endophyte or endophytic component can then be selected for the ability to grow on liquid or solid media containing the second antifungal compound (again, with or without prior mutagenesis). Colonies isolated from the second selection are then tested to confirm its compatibility to both antifungal compounds.

Likewise, complex endophytes or endophytic components that are compatible to biocides (including herbicides such as glyphosate or anticomplex compounds, whether bacteriostatic or bactericidal) that are agriculturally employed can be isolated using methods similar to those described for isolating fungicide compatible complex endophytes or endophytic components. In one embodiment, mutagenesis of the complex endophyte or endophytic component population can be performed prior to selection with an anticomplex agent. In another embodiment, selection is performed on the complex endophyte or endophytic component population without prior mutagenesis. In still another embodiment, serial selection is performed on a complex endophyte or endophytic component: the complex endophyte or endophytic component is first selected for compatibility to a first anticomplex agent. The isolated compatible complex endophyte or endophytic component is then cultured and selected for compatibility to the second anticomplex agent. Any colony thus isolated is tested for compatibility to each, or both anticomplex agents to confirm compatibility with these two agents.

Compatibility with an antimicrobial agent can be determined by a number of means known in the art, including the comparison of the minimal inhibitory concentration (MIC) of the unmodified and modified endophytes. Therefore, in one embodiment, the present invention discloses an isolated complex endophyte or endophytic component, wherein the endophyte is modified such that it exhibits at least 3 fold greater, for example, at least 5 fold greater, between 5 and 10 fold greater, at least 10 fold greater, between 10 and 20 fold greater, at least 20 fold greater, between 20 and 30 fold greater, at least 30 fold greater or more MIC to an antimicrobial agent when compared with the unmodified endophyte.

In a particular embodiment, disclosed herein are complex endophytes and endophytic components with enhanced compatibility to the herbicide glyphosate. In one embodiment, the complex endophyte or endophytic component has a doubling time in growth medium comprising at least 1 mM glyphosate, for example, between 1 mM and 2 mM glyphosate, at least 2 mM glyphosate, between 2 mM and 5 mM glyphosate, at least 5 mM glyphosate, between 5 mM and 10 mM glyphosate, at least 10 mM glyphosate, between 10 mM and 15 mM glyphosate, at least 15 mM glyphosate or more, that is no more than 250%, between 250% and 100%, for example, no more than 200%, between 200% and 175%, no more than 175%, between 175% and 150%, no more than 150%, between 150% and 125%, or no more than 125%, of the doubling time of the complex endophyte or endophytic component in the same growth medium comprising no glyphosate. In one particular embodiment, the complex endophyte or endophytic component has a doubling time in growth medium comprising 5 mM glyphosate that is no more than 150% the doubling time of the complex endophyte or endophytic component in the same growth medium comprising no glyphosate.

In another embodiment, the complex endophyte or endophytic component has a doubling time in a plant tissue comprising at least 10 ppm glyphosate, between 10 and 15 ppm, for example, at least 15 ppm glyphosate, between 15 and 10 ppm, at least 20 ppm glyphosate, between 20 and 30 ppm, at least 30 ppm glyphosate, between 30 and 40 ppm, at least 40 ppm glyphosate or more, that is no more than 250%, between 250% and 200%, for example, no more than 200%, between 200% and 175%, no more than 175%, between 175% and 150%, no more than 150%, between 150% and 125%, or no more than 125%, of the doubling time of the endophyte in a reference plant tissue comprising no glyphosate. In one particular embodiment, the complex endophyte or endophytic component has a doubling time in a plant tissue comprising 40 ppm glyphosate that is no more than 150% the doubling time of the endophyte in a reference plant tissue comprising no glyphosate.

The selection process described above can be repeated to identify isolates of the complex endophyte or endophytic component that are compatible with a multitude of antifungal or anticomplex agents.

Candidate isolates can be tested to ensure that the selection for agrichemical compatibility did not result in loss of a desired bioactivity. Isolates of the complex endophyte or endophytic component that are compatible with commonly employed fungicides can be selected as described above. The resulting compatible complex endophyte or endophytic component can be compared with the parental complex endophyte on plants in its ability to promote germination.

The agrichemical compatible complex endophytes or endophytic components generated as described above can be detected in samples. For example, where a transgene was introduced to render the complex endophyte compatible with the agrichemical(s), the transgene can be used as a target gene for amplification and detection by PCR. In addition, where point mutations or deletions to a portion of a specific gene or a number of genes results in compatibility with the agrichemical(s), the unique point mutations can likewise be detected by PCR or other means known in the art. Such methods allow the detection of the complex endophyte even if it is no longer viable. Thus, commodity plant products produced using the agrichemical compatible complex endophytes or endophytic components described herein can readily be identified by employing these and related methods of nucleic acid detection.

Beneficial Attributes of Synthetic Combinations of Plant Elements and Complex Endophytes or Endophytic Components Improved Attributes Conferred by the Complex Endophyte The present invention contemplates the establishment of a symbiont in a plant element. In one embodiment, the complex endophyte or endophytic component association results in a detectable change to the plant element, in particular the seed or the whole plant. The detectable change can be an improvement in a number of agronomic traits (e.g., improved general health, increased response to biotic or abiotic stresses, or enhanced properties of the plant or a plant part, including fruits and grains). Alternatively, the detectable change can be a physiological or biological change that can be measured by methods known in the art. The detectable changes are described in more detail in the sections below. As used herein, a complex endophyte or endophytic component is considered to have conferred an improved agricultural trait whether or not the improved trait arose from the plant, the complex endophyte, or endophytic component, or the concerted action between any or all of the preceding. Therefore, for example, whether a beneficial hormone or chemical is produced by the plant or complex endophyte or endophytic component, for purposes of the present invention, the complex endophyte will be considered to have conferred an improved agronomic trait upon the host plant.

In some embodiments, plant-endophyte combinations confer an agronomic benefit in agricultural plants. In some embodiments, the agronomic trait is selected from the group consisting of altered oil content, altered protein content, altered seed carbohydrate composition, altered seed oil composition, and altered seed protein composition, chemical tolerance, cold tolerance, delayed senescence, disease resistance, drought tolerance, increased ear weight, growth improvement, health enhancement, heat tolerance, herbicide tolerance, herbivore resistance, improved nitrogen fixation, improved nitrogen utilization, improved nutrient use efficiency, improved root architecture, improved water use efficiency, increased biomass, increased root length, increased seed weight, increased shoot length, increased yield, increased yield under water-limited conditions, kernel mass, kernel moisture content, metal tolerance, number of ears, number of kernels per ear, number of pods, nutrition enhancement, pathogen resistance, pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased seed germination, increased number of pods per plant, increased length of pods per plant, reduced number of wilted leaves per plant, reduced number of severely wilted leaves per plant, increased number of non-wilted leaves per plant, increased plant height, earlier or increased flowering, increased protein content, increased fermentable carbohydrate content, reduced lignin content, male sterility, increased antioxidant content, modulation in the level of a metabolite, a detectable modulation in the level of a transcript, and a detectable modulation in the proteome relative to a reference plant. In other embodiments, at least two agronomic traits are improved in the agricultural plant.

For example, the endophyte may provide an improved benefit or tolerance to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, or at least 300% or more, when compared with uninoculated plants grown under the same conditions.

In some aspects, provided herein, are methods for producing a seed of a plant with a heritably altered trait. The trait of the plant can be altered without known genetic modification of the plant genome, and comprises the following steps. First, a preparation of an isolated complex endophyte or endophytic component that is heterologous to the seed of the plant is provided, and optionally processed to produce a complex endophyte or endophytic component formulation. The complex endophyte or endophytic component formulation is then contacted with the plant. The plants are then allowed to go to seed, and the seeds are collected.

Improved General Health

Also described herein are plants, and fields of plants, that are associated with beneficial complex endophytes or endophytic components, such that the overall fitness, productivity or health of the plant or a portion thereof, is maintained, increased and/or improved over a period of time. Improvement in overall plant health can be assessed using numerous physiological parameters including, but not limited to, height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof. Improved plant health, or improved field health, can also be demonstrated through improved resistance or response to a given stress, either biotic or abiotic stress, or a combination of one or more abiotic stresses, as provided herein.

Other Abiotic Stresses

Disclosed herein are complex endophyte- or endophytic component-associated plants with increased resistance to an abiotic stress. Exemplary abiotic stresses include, but are not limited to:

Drought and heat tolerance. When soil water is depleted or if water is not available during periods of drought, crop yields are restricted. Plant water deficit develops if transpiration from leaves exceeds the supply of water from the roots. The available water supply is related to the amount of water held in the soil and the ability of the plant to reach that water with its root system. Transpiration of water from leaves is linked to the fixation of carbon dioxide by photosynthesis through the stomata. The two processes are positively correlated so that high carbon dioxide influx through photosynthesis is closely linked to water loss by transpiration. As water transpires from the leaf, leaf water potential is reduced and the stomata tend to close in a hydraulic process limiting the amount of photosynthesis. Since crop yield is dependent on the fixation of carbon dioxide in photosynthesis, water uptake and transpiration are contributing factors to crop yield. Plants which are able to use less water to fix the same amount of carbon dioxide or which are able to function normally at a lower water potential have the potential to conduct more photosynthesis and thereby to produce more biomass and economic yield in many agricultural systems.

In some cases, a plant resulting from seeds or other plant components treated with the complex endophyte or endophytic component can exhibit a physiological change, such as a compensation of the stress-induced reduction in photosynthetic activity (expressed, for example, as $\Delta Fv/Fm$) after exposure to heat shock or drought conditions as compared to a corresponding control, genetically identical plant that does not contain the endophytes grown in the same conditions. In some cases, the complex endophyte- or endophytic component-associated plant as disclosed herein can exhibit an increased change in photosynthetic activity $\Delta Fv$ ($\Delta Fv/Fm$) after heat-shock or drought stress treatment, for example 1, 2, 3, 4, 5, 6, 7 days or more after the heat-shock or drought stress treatment, or until photosynthesis ceases, as compared with corresponding control plant of similar developmental stage but not containing the complex endophyte or endophytic component. For example, a plant having a complex endophyte or endophytic component able to confer heat and/or drought-tolerance can exhibit a $\Delta Fv/Fm$ of from about 0.1 to about 0.8 after exposure to heat-shock or drought stress or a $\Delta Fv/Fm$ range of from about 0.03 to about 0.8 under one day, or 1, 2, 3, 4, 5, 6, 7, or over 7 days post heat-shock or drought stress treatment, or until photosynthesis ceases. In some embodiments, stress-induced reductions in photosynthetic activity can be compensated by at least about 0.25% (for example, at least about 0.5%, between 0.5% and 1%, at least about 1%, between 1% and 2%, at least about 2%, between 2% and 3%, at least about 3%, between 3% and 5%, at least about 5%, between 5% and 10%, at least about 8%, at least about 10%, between 10% and 15%, at least about 15%, between 15% and 20%, at least about 20%, between 20$ and 25%, at least about 25%, between 25% and 30%, at least about 30%, between 30% and 40%, at least about 40%, between 40% and 50%, at least about 50%, between 50% and 60%, at least about 60%, between 60% and 75%, at least about 75%, between 75% and 80%, at least about 80%, between 80% and 85%, at least about 85%, between 85% and 90%, at least about 90%, between 90% and 95%, at least about 95%, between 95% and 99%, at least about 99%, between 99% and 100%, or at least 100%) as compared to the photosynthetic activity decrease in a corresponding reference agricultural plant following heat shock conditions. Significance of the difference between complex endophyte- or endophytic component-associated and reference agricultural plants can be established upon demonstrating statistical significance, for example at $p<0.05$ with an appropriate parametric or non-parametric statistic, e.g., Chi-square test, Student's t-test, Mann-Whitney test, or F-test based on the assumption or known facts that the endophyte-associated plant and reference agricultural plant have identical or near identical genomes (isoline comparison).

In selecting traits for improving crops, a decrease in water use, without a change in growth would have particular merit in an irrigated agricultural system where the water input costs were high. An increase in growth without a corresponding jump in water use would have applicability to all agricultural systems. In many agricultural systems where water supply is not limiting, an increase in growth, even if it came at the expense of an increase in water use also increases yield. Water use efficiency (WUE) is a parameter often correlated with drought tolerance, and is the CO2 assimilation rate per water transpired by the plant. An increased water use efficiency of the plant relates in some cases to an increased fruit/kernel size or number. Therefore, in some embodiments, the plants described herein exhibit an increased water use efficiency when compared with a reference agricultural plant grown under the same conditions. For example, the plants grown from the plant elements comprising the complex endophytes or endophytic components can have at least 3%, between 3% and 5%, at least 5%, between 5% and 10%, at least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, or at least 100% higher WUE than a reference agricultural plant grown under the same conditions. Such an increase in WUE can occur under conditions without water deficit, or under conditions of water deficit, for example, when the soil water content is less than or equal to 60% of water saturated soil, for example, less than or equal to 50%, less than or equal to 40%, less than or equal to 30%, less than or equal to 20%, less than or equal to 10% of water saturated soil on a weight basis. In a related embodiment, the plant comprising the complex endophytes or endophytic component can have at least 10% higher relative water content (RWC), for example, at least 3%, between 3% and 5%, at least 5%, between 5% and 10%, at least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, or at least 100% higher RWC than a reference agricultural plant grown under the same conditions.

In some embodiments, the plants comprise complex endophytes or endophytic components able to increase heat and/or drought-tolerance in sufficient quantity, such that increased growth or improved recovery from wilting under conditions of heat or drought stress is observed. For example, an endofungal bacterial endophyte population described herein can be present in sufficient quantity in a plant, resulting in increased growth as compared to a plant that does not contain the endofungal bacterial endophyte, when grown under drought conditions or heat shock conditions, or following such conditions. Increased heat and/or drought tolerance can be assessed with physiological parameters including, but not limited to, increased height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, wilt recovery, turgor pressure, or any combination thereof, as compared to a reference agricultural plant grown under similar conditions. For example, the endophyte may provide an improved benefit or tolerance to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

Salt Stress. In other embodiments, complex endophytes or endophytic components able to confer increased tolerance to salinity stress can be introduced into plants. The resulting plants comprising endophytes can exhibit increased resistance to salt stress, whether measured in terms of survival under saline conditions, or overall growth during, or following salt stress. The physiological parameters of plant health recited above, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., isogenic plants without the endophytes) grown under identical conditions. For example, the endophyte may provide an improved benefit or tolerance to a plant that is of at least 3%, between 3% and 5%, at least 5%, between 5% and 10%, at least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions. In other instances, endophyte-associated plants and reference agricultural plants can be grown in soil or growth media comprising different concentration of sodium to establish the inhibitory concentration of sodium (expressed, for example, as the concentration in which growth of the plant is inhibited by 50% when compared with plants grown under no sodium stress). Therefore, in another embodiment, a plant resulting from plant elements comprising a complex endophyte or endophytic component able to confer salt tolerance described herein exhibits an increase in the inhibitory sodium concentration by at least 10 mM, between 10 mM and 15 mM, for example at least 15 mM, between 15 mM and 20 mM, at least 20 mM, between 20 mM and 30 mM, at least 30 mM, between 30 mM and 40 mM, at least 40 mM, between 40 mM and 50 mM, at least 50 mM, between 50 mM and 60 mM, at least 60 mM, between 60 mM and 70 mM, at least 70 mM, between 70 mM and 80 mM, at least 80 mM, between 80 mM and 90 mM, at least 90 mM, between 90 mM and 100 mM, at least 100 mM or more, when compared with the reference agricultural plants.

High Metal Content. Plants are sessile organisms and therefore must contend with the environment in which they are placed. Plants have adapted many mechanisms to deal with chemicals and substances that may be deleterious to their health. Heavy metals in particular represent a class of toxins that are highly relevant for plant growth and agriculture, because many of them are associated with fertilizers and sewage sludge used to amend soils and can accumulate to toxic levels in agricultural fields. Therefore, for agricultural purposes, it is important to have plants that are able to tolerate soils comprising elevated levels of toxic heavy metals. Plants cope with toxic levels of heavy metals (for example, nickel, cadmium, lead, mercury, arsenic, or aluminum) in the soil by excretion and internal sequestration. Endophytes that are able to confer increased heavy metal tolerance may do so by enhancing sequestration of the metal in certain compartments away from the seed or fruit and/or by supplementing other nutrients necessary to remediate the stress. Use of such endophytes in a plant would allow the development of novel plant-endophyte combinations for purposes of environmental remediation (also known as phytoremediation). Therefore, in one embodiment, the plant comprising complex endophytes or endophytic components shows increased metal tolerance as compared to a reference agricultural plant grown under the same heavy metal concentration in the soil.

Alternatively, the inhibitory concentration of the heavy metal can be determined for a complex endophyte- or endopytic component-associated plant and compared with a reference agricultural plant under the same conditions. Therefore, in one embodiment, the plants resulting from plant elements comprising complex endophytes or endophytic components able to confer heavy metal tolerance described herein exhibit an increase in the inhibitory metal concentration by at least 0.1 mM, between 0.1 mM and 0.3 mM, for example at least 0.3 mM, between 0.3 mM and 0.5 mM, at least 0.5 mM, between 0.5 mM and 1 mM, at least 1 mM, between 1 mM and 2 mM, at least 2 mM, between 2 mM and 5 mM, at least 5 mM, between 5 mM and 10 mM, at least 10 mM, between 10 mM and 15 mM, at least 15 mM, between 15 mM and 20 mM, at least 20 mM, between 20 mM and 30 mM, at least 30 mM, between 30 mM and 50 mM, at least 50 mM or more, when compared with the reference agricultural plants.

Finally, plants inoculated with complex endophytes or endophytic components that are able to confer increased metal tolerance exhibit an increase in overall metal excretion by at least 3%, between 3% and 5%, at least 5%, between 5% and 10%, at least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

Low Nutrient Stress. Complex endophytes or endophytic components described herein may also confer to the plant an increased ability to grow in nutrient limiting conditions, for example by solubilizing or otherwise making available to the plants macronutrients or micronutrients that are complexed, insoluble, or otherwise in an unavailable form. In one embodiment, a plant is inoculated with an endophyte that confers increased ability to liberate and/or otherwise provide to the plant with nutrients selected from the group consisting of phosphate, nitrogen, potassium, iron, manganese, calcium, molybdenum, vitamins, or other micronutrients. Such a plant can exhibit increased growth in soil comprising limiting amounts of such nutrients when compared with reference agricultural plant. Differences between the endophyte-associated plant and reference agricultural plant can be measured by comparing the biomass of the two plant types grown under limiting conditions, or by measuring the physical parameters described above. Therefore, in one embodiment, the plant comprising endophyte shows increased tolerance to nutrient limiting conditions as compared to a reference agricultural plant grown under the same nutrient limited concentration in the soil, as measured for example by increased biomass or seed yield of at least 3%, between 3% and 5%, at least 5%, between 5% and 10%, at least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

In other embodiments, the plant containing complex endophytes or endophytic components is able to grown under nutrient stress conditions while exhibiting no difference in the physiological parameter compared to a plant that is grown without nutrient stress. In some embodiments, such a plant will exhibit no difference in the physiological parameter when grown with 2-5% less nitrogen than average cultivation practices on normal agricultural land, for example, at least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, or between 75% and 100%, less nitrogen, when compared with crop plants grown under normal conditions during an average growing season. In some embodiments, the microbe capable of providing nitrogen-stress tolerance to a plant is diazotrophic. In other embodiments, the microbe capable of providing nitrogen-stress tolerance to a plant is non-diazotrophic.

Cold Stress. In some cases, complex endophytes or endophytic components described herein can confer to the plant the ability to tolerate cold stress. Many known methods exist for the measurement of a plant's tolerance to cold stress. As used herein, cold stress refers to both the stress induced by chilling (0° C.-15° C.) and freezing (<0° C.). Some cultivars of agricultural plants can be particularly sensitive to cold stress, but cold tolerance traits may be multigenic, making the breeding process difficult. Endophytes able to confer cold tolerance can reduce the damage suffered by farmers on an annual basis. Improved response to cold stress can be measured by survival of plants, production of protectant substances such as anthocyanin, the amount of necrosis of parts of the plant, or a change in crop yield loss, as well as the physiological parameters used in other examples. Therefore, in an embodiment, the plant comprising complex endophytes or endophytic components shows increased cold tolerance exhibits as compared to a reference agricultural plant grown under the same conditions of cold stress. For example, the complex endophytes or endophytic components may provide an improved benefit or tolerance to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

Biotic Stress. In other embodiments, the complex endophyte or endophytic component protects the plant from a biotic stress, for example, insect infestation, nematode infestation, complex infection, fungal infection, bacterial infection, oomycete infection, protozoal infection, viral infection, and herbivore grazing, or a combination thereof. For example, the endophyte may provide an improved benefit or tolerance to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

Insect herbivory. There are an abundance of insect pest species that can infect or infest a wide variety of plants. Pest infestation can lead to significant damage. Insect pests that infest plant species are particularly problematic in agriculture as they can cause serious damage to crops and significantly reduce plant yields. A wide variety of different types of plant are susceptible to pest infestation including commercial crops such as cotton, soybean, wheat, barley, and corn.

In some cases, complex endophytes or endophytic components described herein may confer upon the host plant the ability to repel insect herbivores. In other cases, endophytes may produce, or induce the production in the plant of, compounds which are insecticidal or insect repellant. The insect may be any one of the common pathogenic insects affecting plants, particularly agricultural plants.

The complex endophyte- or endophytic component-associated plant can be tested for its ability to resist, or otherwise repel, pathogenic insects by measuring, for example, insect load, overall plant biomass, biomass of the fruit or grain, percentage of intact leaves, or other physiological parameters described herein, and comparing with a reference agricultural plant. In an embodiment, the endophyte-associated plant exhibits increased biomass as compared to a reference agricultural plant grown under the same conditions (e.g., grown side-by-side, or adjacent to, endophyte-associated plants). In other embodiments, the endophyte-associated plant exhibits increased fruit or grain yield as compared to a reference agricultural plant grown under the same conditions (e.g., grown side-by-side, or adjacent to, endophyte-associated plants). In any of the above, the endophyte may provide an improved benefit or tolerance to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, or at least 100%, when compared with uninoculated plants grown under the same conditions.

Nematodes. Nematodes are microscopic roundworms that feed on the roots, fluids, leaves and stems of more than 2,000 row crops, vegetables, fruits, and ornamental plants, causing an estimated $100 billion crop loss worldwide and accounting for 13% of global crop losses due to disease. A variety of parasitic nematode species infect crop plants, including root-knot nematodes (RKN), cyst- and lesion-forming nematodes. Root-knot nematodes, which are characterized by causing root gall formation at feeding sites, have a relatively broad host range and are therefore parasitic on a large number of crop species. The cyst- and lesion-forming nematode species have a more limited host range, but still cause considerable losses in susceptible crops.

Signs of nematode damage include stunting and yellowing of leaves, and wilting of the plants during hot periods. Nematode infestation, however, can cause significant yield losses without any obvious above-ground disease symptoms. The primary causes of yield reduction are due to underground root damage. Roots infected by SCN are dwarfed or stunted. Nematode infestation also can decrease the number of nitrogen-fixing nodules on the roots, and may make the roots more susceptible to attacks by other soil-borne plant nematodes.

In an embodiment, the complex endophyte- or endophytic component-associated plant has an increased resistance to a nematode when compared with a reference agricultural plant. As before with insect herbivores, biomass of the plant or a portion of the plant, or any of the other physiological parameters mentioned elsewhere, can be compared with the reference agricultural plant grown under the same conditions. Examples of useful measurements include overall plant biomass, biomass and/or size of the fruit or grain, and root biomass. In one embodiment, the endophyte-associated plant exhibits increased biomass as compared to a reference agricultural plant grown under the same conditions (e.g., grown side-by-side, or adjacent to, the endophyte-associated plants, under conditions of nematode challenge). In another embodiment, the endophyte-associated plant exhibits increased root biomass as compared to a reference agricultural plant grown under the same conditions (e.g., grown side-by-side, or adjacent to, the endophyte-associated plants, under conditions of nematode challenge). In still another embodiment, the endophyte-associated plant exhibits increased fruit or grain yield as compared to a reference agricultural plant grown under the same conditions (e.g., grown side-by-side, or adjacent to, the endophyte-associated plants, under conditions of nematode challenge). In any of the above, the endophyte may provide an improved benefit or tolerance to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, or at least 100%, when compared with uninoculated plants grown under the same conditions.

Fungal Pathogens. Fungal diseases are responsible for yearly losses of over $10 Billion on agricultural crops in the US, represent 42% of global crop losses due to disease, and are caused by a large variety of biologically diverse pathogens. Different strategies have traditionally been used to control them. Resistance traits have been bred into agriculturally important varieties, thus providing various levels of resistance against either a narrow range of pathogen isolates or races, or against a broader range. However, this involves the long and labor intensive process of introducing desirable traits into commercial lines by genetic crosses and, due to the risk of pests evolving to overcome natural plant resistance, a constant effort to breed new resistance traits into commercial lines is required. Alternatively, fungal diseases have been controlled by the application of chemical fungicides. This strategy usually results in efficient control, but is also associated with the possible development of resistant pathogens and can be associated with a negative impact on the environment. Moreover, in certain crops, such as barley and wheat, the control of fungal pathogens by chemical fungicides is difficult or impractical.

The present invention contemplates the use of complex endophytes or endophytic componenthat are able to confer resistance to fungal pathogens to the host plant. Increased resistance to fungal inoculation can be measured, for example, using any of the physiological parameters presented above, by comparing with reference agricultural plants. In an embodiment, the endophyte-associated plant exhibits increased biomass and/or less pronounced disease symptoms as compared to a reference agricultural plant grown under the same conditions (e.g., grown side-by-side, or adjacent to, the endophyte-associated plants, infected with the fungal pathogen). In still another embodiment, the endophyte-associated plant exhibits increased fruit or grain yield as compared to a reference agricultural plant grown under the same conditions (e.g., grown side-by-side, or adjacent to, the endophyte-associated plants, infected with the fungal pathogen). In another embodiment, the endophyte-associated plant exhibits decreased hyphal growth as compared to a reference agricultural plant grown under the same conditions (e.g., grown side-by-side, or adjacent to, the endophyte-associated plants, infected with the fungal pathogen). For example, the endophyte may provide an improved benefit to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

Viral Pathogens. Plant viruses are estimated to account for 18% of global crop losses due to disease. There are numerous examples of viral pathogens affecting agricultural productivity. In an embodiment, the complex endophyte or endophytic component provides protection against viral pathogens such that the plant has increased biomass as compared to a reference agricultural plant grown under the same conditions. In still another embodiment, the endophyte-associated plant exhibits greater fruit or grain yield, when challenged with a virus, as compared to a reference agricultural plant grown under the same conditions. In yet another embodiment, the endophyte-associated plant exhibits lower viral titer, when challenged with a virus, as compared to a reference agricultural plant grown under the same conditions.

Complex Pathogens. Likewise, bacterial pathogens are a significant problem negatively affecting agricultural productivity and accounting for 27% of global crop losses due to plant disease. In an embodiment, the complex endophyte or endophytic component described herein provides protection against bacterial pathogens such that the plant has greater biomass as compared to a reference agricultural plant grown under the same conditions. In still another embodiment, the endophyte-associated plant exhibits greater fruit or grain yield, when challenged with a complex pathogen, as compared to a reference agricultural plant grown under the same conditions. In yet another embodiment, the endophyte-associated plant exhibits lower complex count, when challenged with a bacterium, as compared to a reference agricultural plant grown under the same conditions.

Yield and Biomass improvement. In other embodiments, the improved trait can be an increase in overall biomass of the plant or a part of the plant, including its fruit or seed. In some embodiments, a complex endophyte or endophytic component is disposed on the surface or within a tissue of the plant element in an amount effective to increase the biomass of the plant, or a part or tissue of the plant grown from the plant element. The increased biomass is useful in the production of commodity products derived from the plant. Such commodity products include an animal feed, a fish fodder, a cereal product, a processed human-food product, a sugar or an alcohol. Such products may be a fermentation product or a fermentable product, one such exemplary product is a biofuel. The increase in biomass can occur in a part of the plant (e.g., the root tissue, shoots, leaves, etc.), or can be an increase in overall biomass. Increased biomass production, such an increase meaning at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, or at least 100%, when compared with uninoculated plants grown under the same conditions. Such increase in overall biomass can be under relatively stress-free conditions. In other cases, the increase in biomass can be in plants grown under any number of abiotic or biotic stresses, including drought stress, salt stress, heat stress, cold stress, low nutrient stress, nematode stress, insect herbivory stress, fungal pathogen stress, bacterial pathogen stress, and viral pathogen stress. In some embodiments, a complex endophyte or endophytic component is disposed in an amount effective to increase root biomass by at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, or at least 100%, when compared with uninoculated plants grown under the same conditions, when compared with a reference agricultural plant.

In other cases, a complex endophyte or endophytic component is disposed on the plant element in an amount effective to increase the average biomass of the fruit or cob from the resulting plant at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, or at least 100%, when compared with uninoculated plants grown under the same conditions.

Increase in plant growth hormones. Many of the microbes described herein are capable of producing the plant hormone auxin indole-3-acetic acid (IAA) when grown in culture. Auxin may play a key role in altering the physiology of the plant, including the extent of root growth. Therefore, in other embodiments, a complex endophyte or endophytic component is disposed on the surface or within a tissue of the plant element in an amount effective to detectably induce production of auxin in the agricultural plant. For example, the increase in auxin production can be at least 2%, at least 3%, at least 4%, at least 5%, at least 6%, at least 7%, at least 8%, at least 9%, at least 10%, at least 15%, for example, at least 20%, at least 30%, at least 40%, at least 50%, at least 60%, at least 75%, at least 100%, or more, when compared with a reference agricultural plant. In some embodiments, the increased auxin production can be detected in a tissue type selected from the group consisting of the root, shoot, leaves, and flowers.

Improvement of Other Traits

In other embodiments, the inoculated complex endophyte or endophytic component can confer other beneficial traits to the plant. Improved traits can include an improved nutritional content of the plant or plant part used for human consumption. In one embodiment, the complex endophyte- or endophytic component-associated plant is able to produce a detectable change in the content of at least one nutrient. Examples of such nutrients include amino acid, protein, oil (including any one of Oleic acid, Linoleic acid, Alpha-linoleic acid, Saturated fatty acids, Palmitic acid, Stearic acid and Trans fats), carbohydrate (including sugars such as sucrose, glucose and fructose, starch, or dietary fiber), Vitamin A, Thiamine (vit. B1), Riboflavin (vit. B2), Niacin (vit. B3), Pantothenic acid (B5), Vitamin B6, Folate (vit. B9), Choline, Vitamin C, Vitamin E, Vitamin K, Calcium, Iron, Magnesium, Manganese, Phosphorus, Potassium, Sodium, Zinc. In one embodiment, the endophyte-associated plant or part thereof contains at least one increased nutrient when compared with reference agricultural plants.

In other cases, the improved trait can include reduced content of a harmful or undesirable substance when compared with reference agricultural plants. Such compounds include those which are harmful when ingested in large quantities or are bitter tasting (for example, oxalic acid, amygdalin, certain alkaloids such as solanine, caffeine, nicotine, quinine and morphine, tannins, cyanide). As such, in one embodiment, the complex endophyte- or endophytic component-associated plant or part thereof contains less of the undesirable substance when compared with reference agricultural plant. In a related embodiment, the improved trait can include improved taste of the plant or a part of the plant, including the fruit or seed. In a related embodiment, the improved trait can include reduction of undesirable compounds produced by other endophytes in plants, such as degradation of *Fusarium*-produced deoxynivalenol (also known as vomitoxin and a virulence factor involved in *Fusarium* head blight of maize and wheat) in a part of the plant, including the fruit or seed.

The complex endophyte- or endophytic component-associated plant can also have an altered hormone status or altered levels of hormone production when compared with a reference agricultural plant. An alteration in hormonal status may affect many physiological parameters, including flowering time, water efficiency, apical dominance and/or lateral shoot branching, increase in root hair, and alteration in fruit ripening.

The association between the complex endophyte or endophytic component and the plant can also be detected using other methods known in the art. For example, the biochemical, metabolomics, proteomic, genomic, epigenomic and/or transcriptomic profiles of complex endophyte- or endophytic component-associated plants can be compared with reference agricultural plants under the same conditions.

Transcriptome analysis of endophyte-associated and reference agricultural plants can also be performed to detect changes in expression of at least one transcript, or a set or network of genes upon endophyte association. Similarly, epigenetic changes can be detected using methylated DNA immunoprecipitation followed by high-throughput sequencing.

Metabolomic differences between the plants can be detected using methods known in the art. The metabolites, proteins, or other compounds described herein can be detected using any suitable method including, but not limited to gel electrophoresis, liquid and gas phase chromatography, either alone or coupled to mass spectrometry, NMR, immunoassays (enzyme-linked immunosorbent assays (ELISA)), chemical assays, spectroscopy, optical imaging techniques (such as magnetic resonance spectroscopy (MRS), magnetic resonance imaging (MRI), CAT scans, ultra sound, MS-based tissue imaging or X-ray detection methods (e.g., energy dispersive x-ray fluorescence detection)) and the like. In some embodiments, commercial systems for chromatography and NMR analysis are utilized. Such metabolomic methods can be used to detect differences in levels in hormone, nutrients, secondary metabolites, root exudates, phloem sap content, xylem sap content, heavy metal content, and the like. Such methods are also useful for detecting alterations in complex endophyte or endophytic component content and status; for example, the presence and levels of complex/fungal signaling molecules (e.g., autoinducers and pheromones), which can indicate the status of group-based behavior of endophytes based on, for example, population density.

In some embodiments, a biological sample (whole tissue, exudate, phloem sap, xylem sap, root exudate, etc.) from endophyte-associated and reference agricultural plants can be analyzed essentially as known in the art.

In a particular embodiment, the metabolite can serve as a signaling or regulatory molecule. The signaling pathway can be associated with a response to a stress, for example, one of the stress conditions selected from the group consisting of drought stress, salt stress, heat stress, cold stress, low nutrient stress, nematode stress, insect herbivory stress, fungal pathogen stress, complex pathogen stress, and viral pathogen stress.

When the inoculated agricultural plant is grown under conditions such that the level of one or more metabolites is modulated in the plant, wherein the modulation may indicative of increased resistance to a stress selected from the group consisting of drought stress, salt stress, heat stress, cold stress, low nutrient stress, nematode stress, insect herbivory stress, fungal pathogen stress, complex pathogen stress, and viral pathogen stress. The increased resistance can be measured at about 10 minutes after applying the stress, between 10 minutes and 20 minutes, for example about 20 minutes, between 20 and 30 minutes, 30 minutes, between 30 and 45 minutes, about 45 minutes, between 45 minutes and 1 hour, about 1 hour, between 1 and 2 hours, about 2 hours, between 2 and 4 hours, about 4 hours, between 4 and 8 hours, about 8 hours, between 8 and 12 hours, about 12 hours, between 12 and 16 hours, about 16 hours, between 16 and 20 hours, about 20 hours, between 20 and 24 hours, about 24 hours, between 24 and 36 hours, about 36 hours, between 36 and 48 hours, about 48 hours, between 48 and 72 hours, about 72 hours, between 72 and 96 hours, about 96 hours, between 96 and 120 hours, about 120 hours, between 120 hours and one week, or about a week after applying the stress.

In some embodiments, metabolites in plants can be modulated by making synthetic combinations of plants with complex endophytes or endophytic components. For example, complex endophytes or endophytic components can cause a detectable modulation (e.g., an increase or decrease) in the level of various metabolites, e.g., indole-3-carboxylic acid, trans-zeatin, abscisic acid, phaseic acid, indole-3-acetic acid, indole-3-butyric acid, indole-3-acrylic acid, jasmonic acid, jasmonic acid methyl ester, dihydrophaseic acid, gibberellin A3, salicylic acid, upon colonization of a plant.

In some embodiments, complex endophytes or endophytic components modulate the level of the metabolite directly (e.g., the microbes produces the metabolite, resulting in an overall increase in the level of the metabolite found in the plant). In other cases, the agricultural plant, as a result of the association with the complex endophytes or endophytic components, exhibits a modulated level of the metabolite (e.g., the plant reduces the expression of a biosynthetic enzyme responsible for production of the metabolite as a result of the microbe inoculation). In still other cases, the modulation in the level of the metabolite is a consequence of the activity of both the microbe and the plant (e.g., the plant produces increased amounts of the metabolite when compared with a reference agricultural plant, and the endophyte also produces the metabolite). Therefore, as used herein, a modulation in the level of a metabolite can be an alteration in the metabolite level through the actions of the microbe and/or the inoculated plant.

The levels of a metabolite can be measured in an agricultural plant, and compared with the levels of the metabolite in a reference agricultural plant, and grown under the same conditions as the inoculated plant. The uninoculated plant that is used as a reference agricultural plant is a plant that has not been applied with a formulation with the complex endophytes or endophytic components (e.g., a formulation comprising complex endophytes or endophytic components). The uninoculated plant used as the reference agricultural plant is generally the same species and cultivar as, and is isogenic to, the inoculated plant.

The metabolite whose levels are modulated (e.g., increased or decreased) in the endophyte-associated plant may serve as a primary nutrient (i.e., it provides nutrition for the humans and/or animals who consume the plant, plant tissue, or the commodity plant product derived therefrom, including, but not limited to, a sugar, a starch, a carbohydrate, a protein, an oil, a fatty acid, or a vitamin). The metabolite can be a compound that is important for plant growth, development or homeostasis (for example, a phytohormone such as an auxin, cytokinin, gibberellin, a brassinosteroid, ethylene, or abscisic acid, a signaling molecule, or an antioxidant). In other embodiments, the metabolite can have other functions. For example, in some embodiments, a metabolite can have bacteriostatic, bactericidal, fungistatic, fungicidal or antiviral properties. In other embodiments, the metabolite can have insect-repelling, insecticidal, nematode-repelling, or nematicidal properties. In still other embodiments, the metabolite can serve a role in protecting the plant from stresses, may help improve plant vigor or the general health of the plant. In yet another embodiment, the metabolite can be a useful compound for industrial production. For example, the metabolite may itself be a useful compound that is extracted for industrial use, or serve as an intermediate for the synthesis of other compounds used in industry. In a particular embodiment, the level of the metabolite is increased within the agricultural plant or a portion thereof such that it is present at a concentration of at least 0.1 ug/g dry weight, for example, at least 0.3 ug/g dry weight, between 0.3 ug/g and 1.0 ug/g dry weight, at least 1.0 ug/g dry weight, between 1.0 ug/g and 3.0 ug/g dry weight, at least 3.0 ug/g dry weight, between 3.0 ug/g and 10 ug/g dry weight, at least 10 ug/g dry weight, between 10 ug/g and 30 ug/g dry weight, at least 30 ug/g dry weight, between 30 ug/g and 100 ug/g dry weight, at least 100 ug/g dry weight, between 100 ug/g and 300 ug/g dry weight, at least 300 ug/g dry weight, between 300 ug/g and 1 mg/g dry weight, or more than 1 mg/g dry weight, of the plant or portion thereof.

Likewise, the modulation can be a decrease in the level of a metabolite. The reduction can be in a metabolite affecting the taste of a plant or a commodity plant product derived from a plant (for example, a bitter tasting compound), or in a metabolite which makes a plant or the resulting commodity plant product otherwise less valuable (for example, reduction of oxalate content in certain plants, or compounds which are deleterious to human and/or animal health). The metabolite whose level is to be reduced can be a compound that affects quality of a commodity plant product (e.g., reduction of lignin levels).

Non-Agricultural Uses of Isolated Complex Endophytes or Endophytic Components

In one embodiment of the present invention, complex endophytes or endophytic components may be used to improve the efficacy or utility of applications in which single microbe types are typically used. For example, a process that normally utilizes a particular fungus may benefit from substitution of a complex endophyte in that process, where the complex endophyte comprises that particular fungus as a host that itself further comprises a component bacterium. In another example, a process that normally utilizes a particular bacterium may benefit from substitution of a complex endophyte or endophytic component in that process, which comprises a fungal host that itself further comprises that particular bacterium.

It is contemplated that the mechanism of process or application improvement may result from one or more mechanisms, such as but not limited to: the incorporation of an additional organism (host fungus or component bacterium), a synergy between the two organisms (host fungus and component bacterium), a leveraging of a compound produced by one of the organisms that is utilized by the other, an additive effect between the two organisms (host fungus and component bacterium), a protective effect of one organism on the other, the induction, upregulation, or downregulation of a particular biochemical or metabolic pathway in one or both organisms, the utilization of a different energy source as a result of the presence of the other organism, improved survivability of one or both organisms as a result of their association in a host:component relationship, or a combination of effects.

In one example, the efficacy or survivability of a Gram-negative bacterium in an application is improved by the substitution of a complex endophyte comprising said gram-negative bacterium. As Gram-negative bacteria cannot make spores and are particularly sensitive to desiccation because of their thinner peptidoglycan layer (the reason why they do not retain the Gram stain), the potential survivability is decreased when in a non-endofungal state and improved when inside a host fungus. Inside the fungus, or inside fungal spores, they have a better chance of surviving desiccation or other environmental stresses.

In one example, the process of baking bread, brewing beer, or fermenting a fruit or grain for alcohol production, is improved by the substitution of, or addition of, a complex endophyte or endophytic component comprising a component bacterium inside the traditional fungal strain.

In one example, the process pickling or curing foods is improved by the substitution of, or addition of, a complex endophyte or endophytic component comprising a host fungus further comprising the traditional bacterial strain.

In one example, the process of manufacturing or delivering insecticidal bacteria can be improved, by the substitution of, or addition of, a complex endophyte or endophytic component comprising a host fungus further comprising the traditional bacterial strain.

In one example, the process of wastewater treatment can be improved by the substitution of, or addition of, a complex endophyte or endophytic component comprising a host fungus further comprising the traditional bacterial strain.

In one example, the process of bioremediation of oils, plastics, or other chemicals can be improved by the substitution of, or addition of, a complex endophyte or endophytic component comprising a host fungus further comprising the traditional bacterial strain.

In one example, processes related to water quality improvement can be improved by the substitution of, or addition of, a complex endophyte or endophytic component comprising a host fungus further comprising the traditional bacterial strain.

In one example, the process of synthesis of biodegradable plastics can be improved by the substitution of, or addition of, a complex endophyte or endophytic component comprising a host fungus further comprising the traditional bacterial strain.

In one example, the process of composting biodegradable substances can be improved by the substitution of, or addition of, a complex endophyte or endophytic component comprising a host fungus further comprising the traditional bacterial strain.

In one example, the process of manufacturing or delivering pharmaceutical compounds for human or animal usage can be improved by the substitution of, or addition of, a complex endophyte or endophytic component comprising a component bacterium inside the traditional fungal strain.

In one example, the process of manufacturing industrial compounds (such as, but not limited to: enzymes, lipases, amylases, pectinases, amino acids, vitamins, antibiotics, acids, lactic acid, glutamic acid, citric acid alcohols, esters, flavoring agents, preservatives, nitrogen, viruses, sugars, biogas, bioplastic) can be improved by the substitution of, or addition of, a complex endophyte or endophytic component comprising a host fungus further comprising a bacterial strain for either the traditional bacterium or the traditional fungus.

In one example, the process of producing snow or ice can be improved by the substitution of, or addition of, a complex endophyte or endophytic component comprising a host fungus further comprising the traditional bacterial strain.

In one example, the process of manufacturing or delivering pharmaceutical compounds for human or animal usage can be improved by the substitution of, or addition of, a complex endophyte or endophytic component comprising a component bacterium inside the traditional fungal strain.

In one example, the process of manufacturing pharmaceutical compounds (such as, but not limited to: enzymes, amino acids, vitamins, antibiotics, hormones, insulin, human growth hormone, vaccines, preservatives, viruses) can be improved by the substitution of, or addition of, a complex endophyte or endophytic component comprising a host fungus further comprising a bacterial strain for either the traditional bacterium or the traditional fungus.

Formulations for Agricultural Use

The purified populations of complex endophytes or endophytic components described herein are intended to be useful in the improvement of agricultural plants, and as such, may be formulated with other compositions as part of an agriculturally compatible carrier. The carrier composition comprising the endophyte populations may be prepared for agricultural application as a liquid, a solid, or a gas formulation.

In one aspect, the carrier composition is contemplated as a vehicle for a method of association between the agricultural plant element and purified endophyte population. It is contemplated that such methods of association between the agricultural plant element and purified endophyte population can include, but not be limited to: seed treatment, root wash, seedling soak, foliar application, soil inocula, in-furrow application, sidedress application, soil pre-treatement, wound inoculation, drip tape irrigation, vector-mediation via a pollinator, injection, osmopriming, hydroponics, aquaponics, aeroponics.

A variety of applications, including but not limited to single carrier compositions, single methods of association, and combinations of carrier compositions and methods of association, are contemplated. In one non-limiting example, application of the endophyte population to the plant may be achieved, for example, as a powder for surface deposition onto plant leaves, as a spray to the whole plant or selected plant element, as part of a drip to the soil or the roots, or as a coating onto the plant element prior to planting. In another non-limiting example, a plant element may first become associated with a purified endophyte population by virtue of seed treatment with a solid (dry) formulation comprising a purified endophyte population, and upon germination and leaf emergence, the plant then be subjected to a foliar spray of a liquid formulation comprising a purified endophyte population. In another non-limiting example, a plant may become associated with a purified endophyte population by virtue of inoculation of the growth medium (soil or hydroponic) with a liquid or solid formulation comprising a purified endophyte population, and be subjected to repeated (two, three, four, or even five subsequent) inoculations with a liquid or solid formulation comprising a purified endophyte population. Any number of single carrier compositions and single methods of association, as well as combinations of carrier compositions and methods of association, are intended to be within the scope of the present invention, and as such, the examples given are meant to be illustrative and not limiting to the scope of the invention.

The formulation useful for these embodiments generally and typically include at least one member selected from the group consisting of: a buffer, a tackifier, a microbial stabilizer, a fungicide, an anticomplex agent, an herbicide, a nematicide, an insecticide, a bactericide, a virucide, a plant growth regulator, a rodenticide, a desiccant, and a nutrient.

The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in a composition of the invention. Water-in-oil emulsions can also be used to formulate a composition that includes the purified population (see, for example, U.S. Pat. No. 7,485,451, which is incorporated herein by reference in its entirety). Suitable formulations that may be prepared include wettable powders, granules, gels, agar strips or pellets, thickeners, biopolymers, and the like, microencapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or a plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the cultured organisms, such as barley, rice, or other biological materials such as seed, plant elements, sugar cane bagasse, hulls or stalks from grain processing, ground plant material or wood from building site refuse, sawdust or small fibers from recycling of paper, fabric, or wood. Other suitable formulations will be known to those skilled in the art.

In an embodiment, the formulation can include a tackifier, sticker, or adherent. Such agents are useful for combining the complex population of the invention with carriers that can contain other compounds (e.g., control agents that are not biologic), to yield a coating composition. Such compositions help create coatings around the plant or plant element to maintain contact between the endophyte and other agents with the plant or plant element. In one embodiment, adherents (stickers, or tackifiers) are selected from the group consisting of: alginate, gums, starches, lecithins, formononetin, polyvinyl alcohol, alkali formononetinate, hesperetin, polyvinyl acetate, cephalins, Gum Arabic, Xanthan Gum, carragennan, PGA, other biopolymers, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers. Other examples of adherent compositions that can be used in the synthetic preparation include those described in EP 0818135, CA 1229497, WO 2013090628, EP 0192342, WO 2008103422 and CA 1041788, each of which is incorporated herein by reference in its entirety.

It is also contemplated that the formulation may further comprise an anti-caking agent.

The formulation can also contain a surfactant, wetting agent, emulsifier, stabilizer, or anti-foaming agent. Non-limiting examples of surfactants include nitrogen-surfactant blends such as Prefer 28 (Cenex), Surf-N (US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision), polysorbate 20, polysorbate 80, Tween 20, Tween 80, Scattics, Alktest TW20, Canarcel, Peogabsorb 80, Triton X-100, Conco NI, Dowfax 9N, Igebapl CO, Makon, Neutronyx 600, Nonipol NO, Plytergent B, Renex 600, Solar NO, Sterox, Serfonic N, T-DET-N, Tergitol NP, Triton N, IGEPAL CA-630, Nonident P-40, Pluronic. In one embodiment, the surfactant is present at a concentration of between 0.01% v/v to 10% v/v. In another embodiment, the surfactant is present at a concentration of between 0.1% v/v to 1% v/v. An example of an anti-foaming agent would be Antifoam-C.

In certain cases, the formulation includes a microbial stabilizer. Such an agent can include a desiccant. As used herein, a "desiccant" can include any compound or mixture of compounds that can be classified as a desiccant regardless of whether the compound or compounds are used in such concentrations that they in fact have a desiccating effect on the liquid inoculant. Such desiccants are ideally compatible with the population used, and should promote the ability of the endophyte population to survive application on the seeds and to survive desiccation. Examples of suitable desiccants include one or more of trehalose, sucrose, glycerol, and methylene glycol. Other suitable desiccants include, but are not limited to, non-reducing sugars and sugar alcohols (e.g., mannitol or sorbitol). The amount of desiccant introduced into the formulation can range from about 5% to about 50% by weight/volume, for example, between about 10% to about 40%, between about 15% and about 35%, or between about 20% and about 30%.

In some cases, it is advantageous for the formulation to contain agents such as a fungicide, an anticomplex agent, an herbicide, a nematicide, an insecticide, a plant growth regulator, a rodenticide, a bactericide, a virucide, or a nutrient. Such agents are ideally compatible with the agricultural plant element or seedling onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

Nutrient additives to the formulation may include fertilizer compositions such as, but not limited to, nitrogen, phosphorous, or potassium.

In the liquid form, for example, solutions or suspensions, endophyte populations of the present invention can be mixed or suspended in water or in aqueous solutions. Suitable liquid diluents or carriers include water, aqueous solutions, petroleum distillates, or other liquid carriers.

Solid compositions can be prepared by dispersing the endophyte populations of the invention in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil and cottonseed oil, glycerol, ethylene glycol, polyethylene glycol, propylene glycol, polypropylene glycol, etc.

In an embodiment, the formulation is ideally suited for coating of a population of endophytes onto plant elements. The endophytes populations described in the present invention are capable of conferring many fitness benefits to the host plants. The ability to confer such benefits by coating the populations on the surface of plant elements has many potential advantages, particularly when used in a commercial (agricultural) scale.

The endophyte populations herein can be combined with one or more of the agents described above to yield a formulation suitable for combining with an agricultural plant element, seedling, or other plant element. Endophyte populations can be obtained from growth in culture, for example, using a synthetic growth medium. In addition, endophytes can be cultured on solid media, for example on petri dishes, scraped off and suspended into the preparation. Endophytes at different growth phases can be used. For example, endophytes at lag phase, early-log phase, mid-log phase, late-log phase, stationary phase, early death phase, or death phase can be used. Endophytic spores may be used for the present invention, for example but not limited to: arthospores, sporangispores, conidia, chlamadospores, pycnidiospores, endospores, zoospores.

The formulations comprising endophyte populations of the present invention typically contains between about 0.1 to 95% by weight, for example, between about 1% and 90%, between about 3% and 75%, between about 5% and 60%, between about 10% and 50% in wet weight of the endophyte population of the present invention.

In one embodiment, it is contemplated that the formulation comprises at least about 10^2 CFU or spores endophyte population per mL of liquid formulation, between 10^2 and 10^3 CFU or spores per mL, about 10^3 CFU or spores per mL, between 10^3 and 10^4 CFU or spores per mL, about 10^4 CFU or spores per mL, between 10^4 and 10^5 CFU or spores per mL, about 10^5 CFU or spores per mL, between 10^5 and 10^6 and 10^7 CFU or spores per mL, about 10^7 CFU or spores per mL, between 10^7 and 10^8 CFU or spores per mL, about 10^8 CFU or spores per mL, between 10^8 and 10^9 CFU or spores per mL, or even greater than 10^9 CFU or spores endophyte population per mL of liquid formulation.

In one embodiment, it is contemplated that the formulation comprises at least about 10^2 CFU or spores endophyte population per gram of non-liquid formulation, between 10^2 and 10^3 CFU or spores per gram, about 10^3 CFU or spores per gram, between 10^3 and 10^4 CFU or spores per gram, about 10^4 CFU or spores per gram, between 10^4 and 10^5 CFU or spores per gram, about 10^5 CFU or spores per gram, between 10^5 and 10^6 CFU or spores per gram, about 10^6 CFU or spores per gram, between 10^6 and 10^7 CFU or spores per gram, 10^7 CFU or spores per gram, about 10^7 CFU or spores per gram, between 10^7 and 10^8 CFU or spores per gram, about 10^8 CFU or spores per gram, between 10^8 and 10^9 CFU or spores per gram, or even greater than 10^9 CFU or spores endophyte population per gram of non-liquid formulation.

In one embodiment, it is contemplated that the formulation be applied to the plant element at about 10^2 CFU or spores/seed, between 10^2 and 10^3 CFU or spores, at least about 10^3 CFU or spores, between 10^3 and 10^4 CFU or spores, at least about 10^4 CFU or spores, between 10^4 and 10^5 CFU or spores, at least about 10^5 CFU or spores, between 10^5 and 10^6 CFU or spores, at least about 10^6 CFU or spores, between 10^6 and 10^7 CFU or spores, at least about 10^7 CFU or spores, between 10^7 and 10^8 CFU or spores, or even greater than 10^8 CFU or spores per seed.

Populations of Plant Elements

In another embodiment, the invention provides for a substantially uniform population of plant elements (PEs) comprising two or more PEs comprising the endophytic population, as described herein above. Substantial uniformity can be determined in many ways. In some cases, at least 10%, between 10% and 20%, for example, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the PEs in the population, contains the endophytic population in an amount effective to colonize the plant disposed on the surface of the PEs. In other cases, at least 10%, between 10% and 20%, for example, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the plant element s in the population, contains at least 1, between 1 and 10, 10, between 10 and 100, or 100 CFU on the plant element surface or per gram of plant element, for example, between 100 and 200 CFU, at least 200 CFU, between 200 and 300 CFU, at least 300 CFU, between 300 and 1,000 CFU, at least 1,000 CFU, between 1,000 and 3,000 CFU, at least 3,000 CFU, between 3,000 and 10,000 CFU, at least 10,000 CFU, between 10,000 and 30,000 CFU, at least 30,000 CFU, between 30,000 and 100,000 CFU, at least 100,000 CFU, between 100,000 and 300,000 CFU, at least 300,000 CFU, between 300,000 and 1,000,000 CFU, or at least 1,000,000 CFU per plant element or more.

In a particular embodiment, the population of plant elements is packaged in a bag or container suitable for commercial sale. Such a bag contains a unit weight or count of the plant elements comprising the endophytic population as described herein, and further comprises a label. In an embodiment, the bag or container contains at least 100 plant elements, between 100 and 1,000 plant elements, 1,000 plant elements, between 1,000 and 5,000 plant elements, for example, at least 5,000 plant elements, between 5,000 and 10,000 plant elements, at least 10,000 plant elements, between 10,000 and 20,000 plant elements, at least 20,000 plant elements, between 20,000 and 30,000 plant elements, at least 30,000 plant elements, between 30,000 and 50,000 plant elements, at least 50,000 plant elements, between 50,000 and 70,000 plant elements, at least 70,000 plant elements, between 70,000 and 80,000 plant elements, at least 80,000 plant elements, between 80,000 and 90,000, at least 90,000 plant elements or more. In another embodiment, the bag or container can comprise a discrete weight of plant elements, for example, at least 1 lb, between 1 and 2 lbs, at least 2 lbs, between 2 and 5 lbs, at least 5 lbs, between 5 and 10 lbs, at least 10 lbs, between 10 and 30 lbs, at least 30 lbs, between 30 and 50 lbs, at least 50 lbs, between 50 and 70 lbs, at least 70 lbs or more. The bag or container comprises a label describing the plant elements and/or said endophytic population. The label can contain additional information, for example, the information selected from the group consisting of: net weight, lot number, geographic origin of the plant elements, test date, germination rate, inert matter content, and the amount of noxious weeds, if any. Suitable containers or packages include those traditionally used in plant seed commercialization. The invention also contemplates other containers with more sophisticated storage capabilities (e.g., with microbiologically tight wrappings or with gas- or water-proof containments).

In some cases, a sub-population of plant elements comprising the complex endophytic population is further selected on the basis of increased uniformity, for example, on the basis of uniformity of microbial population. For example, individual plant elements of pools collected from individual cobs, individual plants, individual plots (representing plants inoculated on the same day) or individual fields can be tested for uniformity of microbial density, and only those pools meeting specifications (e.g., at least 80% of tested plant elements have minimum density, as determined by quantitative methods described elsewhere) are combined to provide the agricultural plant elements sub-population.

The methods described herein can also comprise a validating step. The validating step can entail, for example, growing some plant elements collected from the inoculated plants into mature agricultural plants, and testing those individual plants for uniformity. Such validating step can be performed on individual s plant elements eeds collected from cobs, individual plants, individual plots (representing plants inoculated on the same day) or individual fields, and tested as described above to identify pools meeting the required specifications.

In some embodiments, methods described herein include planting a synthetic combination described herein. Suitable planters include an air seeder and/or fertilizer apparatus used in agricultural operations to apply particulate materials including one or more of the following, seed, fertilizer and/or inoculants, into soil during the planting operation. Seeder/fertilizer devices can include a tool bar having ground-engaging openers thereon, behind which is towed a wheeled cart that includes one or more containment tanks or bins and associated metering means to respectively contain and meter therefrom particulate materials. See, e.g., U.S. Pat. No. 7,555,990.

In certain embodiments, a composition described herein may be in the form of a liquid, a slurry, a solid, or a powder (wettable powder or dry powder). In another embodiment, a composition may be in the form of a seed coating. Compositions in liquid, slurry, or powder (e.g., wettable powder) form may be suitable for coating seeds. When used to coat seeds, the composition may be applied to the seeds and allowed to dry. In embodiments wherein the composition is a powder (e.g., a wettable powder), a liquid, such as water, may need to be added to the powder before application to a seed.

In still another embodiment, the methods can include introducing into the soil an inoculum of one or more of the endophyte populations described herein. Such methods can include introducing into the soil one or more of the compositions described herein. The inoculum(s) or compositions may be introduced into the soil according to methods known to those skilled in the art. Non-limiting examples include in-furrow introduction, spraying, coating seeds, foliar introduction, etc. In a particular embodiment, the introducing step comprises in-furrow introduction of the inoculum or compositions described herein.

In an embodiment, plant elements may be treated with composition(s) described herein in several ways, for example via spraying or dripping. Spray and drip treatment may be conducted by formulating compositions described herein and spraying or dripping the composition(s) onto a seed(s) via a continuous treating system (which is calibrated to apply treatment at a predefined rate in proportion to the continuous flow of seed), such as a drum-type of treater. Batch systems, in which a predetermined batch size of seed and composition(s) as described herein are delivered into a mixer, may also be employed.

In another embodiment, the treatment entails coating plant elements. One such process involves coating the inside wall of a round container with the composition(s) described herein, adding plant elements, then rotating the container to cause the plant elements to contact the wall and the composition(s), a process known in the art as "container coating." Plant elements can be coated by combinations of coating methods. Soaking typically entails using liquid forms of the compositions described. For example, plant elements can be soaked for about 1 minute to about 24 hours (e.g., for at least 1 min, between 1 and 5 min, 5 min, between 5 and 10 min, 10 min, between 10 and 20 min, 20 min, between 20 and 40 min, 40 min, between 40 and 80 min, 80 min, between 80 min and 3 hrs, 3 hrs, between 3 hrs and 6 hrs, 6 hr, between 6 hrs and 12 hrs, 12 hr, between 12 hrs and 24 hrs, 24 hrs).

Population of Plants/Agricultural Fields

A major focus of crop improvement efforts has been to select varieties with traits that give, in addition to the highest return, the greatest homogeneity and uniformity. While inbreeding can yield plants with substantial genetic identity, heterogeneity with respect to plant height, flowering time, and time to seed, remain impediments to obtaining a homogeneous field of plants. The inevitable plant-to-plant variability is caused by a multitude of factors, including uneven environmental conditions and management practices. Another possible source of variability can, in some cases, be due to the heterogeneity of the complex endophyte or endophytic component population inhabiting the plants. By providing complex endophyte populations onto plant reproductive elements, the resulting plants generated by germinating the plant reproductive elements have a more consistent complex endophyte or endophytic component composition, and thus are expected to yield a more uniform population of plants.

Therefore, in another embodiment, the invention provides a substantially uniform population of plants. The population can include at least 10 plants, between 10 and 100 plants, for example, at least 100 plants, between 100 and 300 plants, at least 300 plants, between 300 and 1,000 plants, at least 1,000 plants, between 1,000 and 3,000 plants, at least 3,000 plants, between 3,000 and 10,000 plants, at least 10,000 plants, between 10,000 and 30,000 plants, at least 30,000 plants, between 30,000 and 100,000 plants, at least 100,000 plants or more. The plants are derived from plant reproductive elements comprising endophyte populations as described herein. The plants are cultivated in substantially uniform groups, for example in rows, groves, blocks, circles, or other planting layout. The plants are grown from plant reproductive elements comprising the complex endophyte or endophytic component population as described herein. The uniformity of the plants can be measured in a number of different ways.

The uniformity of the plants can be measured in a number of different ways. In one embodiment, there is an increased uniformity with respect to endophytes within the plant population. For example, in one embodiment, a substantial portion of the population of plants, for example at least 10%, between 10% and 20%, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the plant elements or plants in a population, contains a threshold number of an endophyte population. The threshold number can be at least 10 CFU, between 10 and 100 CFU, at least 100 CFU, between 100 and 300 CFU, for example at least 300 CFU, between 300 and 1,000 CFU, at least 1,000 CFU, between 1,000 and 3,000 CFU, at least 3,000 CFU, between 3,000 and 10,000 CFU, at least 10,000 CFU, between 10,000 and 30,000 CFU, at least 30,000 CFU, between 30,000 and 100,000 CFU, at least 100,000 CFU or more, in the plant or a part of the plant. Alternatively, in a substantial portion of the population of plants, for example, in at least 1%, between 1% and 10%, at least 10%, between 10% and 20%, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the plants in the population, the endophyte population that is provided to the seed or seedling represents at least 0.1%, between 0.1% and 1% at least 1%, between 1% and 5%, at least 5%, between 5% and 10%, at least 10%, between 10% and 20%, at least 20%, between 20% and 30%, at least 30%, between 30% and 40%, at least 40%, between 40% and 50%, at least 50%, between 50% and 60%, at least 60%, between 60% and 70%, at least 70%, between 70% and 80%, at least 80%, between 80% and 90%, at least 90%, between 90% and 95%, at least 95%, between 95% and 99%, at least 99%, between 99% and 100%, or 100% of the total endophyte population in the plant/seed.

In one embodiment, there is increased genetic uniformity of a substantial proportion or all detectable complex endophytes within the taxa, genus, or species of the complex endophyte fungus or component relative to an uninoculated control. This increased uniformity can be a result of the complex endophyte or endophytic component being of monoclonal origin or otherwise deriving from a population comprising a more uniform genome sequence and plasmid repertoire than would be present in the endophyte population a plant that derives its endophyte community largely via assimilation of diverse soil symbionts.

In another embodiment, there is an increased uniformity with respect to a physiological parameter of the plants within the population. In some cases, there can be an increased uniformity in the height of the plants when compared with a population of reference agricultural plants grown under the same conditions. For example, there can be a reduction in the standard deviation in the height of the plants in the population of at least 5%, between 5% and 10%, for example, at least 10%, between 10% and 15%, at least 15%, between 15% and 20%, at least 20%, between 20% and 30%, at least 30%, between 30% and 40%, at least 40%, between 40% and 50%, at least 50%, between 50% and 60%, at least 60% or more, when compared with a population of reference agricultural plants grown under the same conditions. In other cases, there can be a reduction in the standard deviation in the flowering time of the plants in the population of at least 5%, between 5% and 10%, for example, at least 10%, between 10% and 15%, at least 15%, between 15% and 20%, at least 20%, between 20% and 30%, at least 30%, between 30% and 40%, at least 40%, between 40% and 50%, at least 50%, between 50% and 60%, at least 60% or more, when compared with a population of reference agricultural plants grown under the same conditions.

Commodity Plant Products

The present invention provides a commodity plant product, as well as methods for producing a commodity plant product, that is derived from a plant of the present invention. As used herein, a "commodity plant product" refers to any composition or product that is comprised of material derived from a plant, seed, plant cell, or plant part of the present invention. Commodity plant products may be sold to consumers and can be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal consumption, oil, meal, flour, flakes, bran, fiber, paper, tea, coffee, silage, crushed of whole grain, and any other food for human or animal consumption; and biomasses and fuel products; and raw material in industry. Industrial uses of oils derived from the agricultural plants described herein include ingredients for paints, plastics, fibers, detergents, cosmetics, lubricants, and biodiesel fuel. Soybean oil may be split, inter-esterified, sulfurized, epoxidized, polymerized, ethoxylated, or cleaved. Designing and producing soybean oil derivatives with improved functionality and improved oliochemistry is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils to produce the desired type of oil or fat. Commodity plant products also include industrial compounds, such as a wide variety of resins used in the formulation of adhesives, films, plastics, paints, coatings and foams.

Although the present invention has been described in detail with reference to examples below, it is understood that various modifications can be made without departing from the spirit of the invention. For instance, while the particular examples below may illustrate the methods and embodiments described herein using a specific plant, the principles in these examples may be applied to any agricultural crop. Therefore, it will be appreciated that the scope of this invention is encompassed by the embodiments of the inventions recited herein and the specification rather than the specific examples that are exemplified below. All cited patents and publications referred to in this application are herein incorporated by reference in their entirety.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1: Isolation of Plant-Derived Complex Endophytes

Isolation followed the methods described in Hoffman and Arnold (2010, Appl. Environ. Microbiol. 76: 4063-4075). Briefly, fresh, asymptomatic tissue was collected from at least three healthy, mature individuals of each focal species.

Material was transferred to the laboratory for processing within 6 to 12 h of collection. Tissue samples were washed in running tap water and then cut into 2-mm segments. Segments were surface sterilized by rinsing in 95% ethanol for 30 s, 10% Clorox (0.6% sodium hypochlorite) for 2 min, and 70% ethanol for 2 min, allowed to surface dry under sterile conditions, and plated on 2% malt extract agar (MEA), which encouraged growth by a diversity of endophytes.

Example 2: Identification of Complex Endophyte Host Fungi, Endofungal Bacteria, and Endofungal Fungi Total genomic DNA was extracted from individual fungal isolates obtained as described above, using the Qiagen DNeasy Plant Mini Kit. PCR was used to amplify the nuclear ribosomal internal transcribed spacers (ITS) and the 5.8S gene (ITS ribosomal DNA [rDNA]) and when possible the first 600 bp of the large subunit (LSU rDNA) as a single fragment (ca. 1,000 to 1,200 bp in length) using the primers ITS1F and ITS4 or LR3. Each 25 microliter reaction mixture included 22.5 microliters of Invitrogen Platinum Taq supermix, 0.5 microliter of each primer (10 uM), and 1.5 microliter of DNA template (~2-4 ng). Cycling reactions were run with MJ Research PTC thermocyclers and consisted of 94° C. for 5 min, 35 cycles of 94° C. for 30 s, 54° C. for 30 s, and 72° C. for 1 min, and 72° C. for 10 min. Sanger sequencing was performed using an ABI 3730xl DNA Analyzers for capillary electrophoresis and fluorescent dye terminator detection. Sequences were compared with available sequences in GenBank using BLAST and a 97% similarity with 100% coverage is used as a cutoff threshold for species assignment.

The presence or absence of bacteria within the surrounding matrix was determined initially using light microscopy. Fungal isolates were examined after 1 week of growth in pure culture on 2% MEA using a light microscope with bright-field imaging (400×; numerical aperture [NA]=0.75). Once visual examination ruled out non-endofungal bacteria (i.e., contaminants in the medium or microbes on fungal surfaces), total genomic DNA extracted from fresh mycelia was examined using PCR primers specific to bacterial 16S rRNA genes, 27F and 1429R (1,402 bp). PCR mixes, cycling parameters and sequencing were as described above, except that annealing temperature was 55° C.

Colony PCR was performed on isolates of bacteria from supernatants of mycelial centrifugation (see above), by gently touching the surface of a colony with a sterile toothpick and using it to stir 2 microliters of nuclease-free water that then are used as a template for a 25 microliter PCR. The PCR, cycling parameters and sequencing were performed as described above using the 16S bacterial primers. Sequences were compared with the ones obtained from fungal total genomic DNA and with those deposited in GenBank using BLAST.

Bacterial endophytes of the present invention that are contemplated as being capable of functioning as component bacteria in a complex endophyte are described by their characteristic 16S sequences SEQ ID NO: 1 to 249 in Table 1.

Fungal endophytes of the present invention that are contemplated as being capable of functioning as host fungi in a complex endophyte are described by their characteristic ITS or LSU sequences SEQ ID NO: 250 through 333 in Table 2.

Some examples (non-limiting) of complex endophytes of the present invention, that comprise a host fungus further comprising a component bacterium, are described in Table 3.

Specific endophytes that were used as exemplary complex endophytes, along with their corresponding component bacteria, tested by the methodologies in the following examples are listed and described in Table 4.

Example 3: Characterization of Complex Endophytes

Complex endophytes have unique properties or may produce unique substances that may be beneficial to a plant. Even if an endofungal bacterial endophyte has previously been characterized, its introduction into a host fungus may change its behavior, especially by adding novel functions to the symbiotic coupling. The in vitro activities of complex endophytes can be tested using the following colorimetric or growth-based assays. Host fungi, endofungal bacterial endophytes, and endofungal fungal endophytes may also be tested using these assays.

Growth on Nitrogen Free LGI Media

All glassware is cleaned with 6M HCl before media preparation. A new 48 well plate (600 microliter well volume) is filled with 500 microliters/well of sterile LGI agar [per L, 50 g Sucrose, 0.01 g FeCl3-6H2O, 0.02 g CaCl2, 0.8 g K3PO4, 0.2 g CaCl2, 0.2 g MgSO4-7H2O, 0.002 g Na2MoO4-2H2O, Agar 15 g, pH 7.5]. Microbes are inoculated into the 48 wells with a flame-sterilized metal loop. The plate is sealed with a breathable membrane, incubated at 28° C. for 3 days, and OD600 readings taken with a 48 well plate reader.

ACC Deaminase Activity

Microbes are assayed for growth with ACC as their sole source of nitrogen. Prior to media preparation all glassware is cleaned with 6 M HCl. A 2 M filter sterilized solution of ACC (#1373A, Research Organics, USA) is prepared in water. 2 microliters/mL of this is added to autoclaved LGI agar (see above), and 500 microliter aliquots are placed in a brand new (clean) 48 well plate. The plate is inoculated with a flame sterilized loop, sealed with a breathable membrane, incubated at 28° C. for 3 days, and OD600 readings taken. Only wells that were significantly more turbid than their corresponding nitrogen free LGI wells are considered to display ACC deaminase activity.

Mineral Phosphate Solubilization

Microbes are plated on tricalcium phosphate media. This is prepared as follows: 10 g/L glucose, 0.373 g/L NH4NO3, 0.41 g/L MgSO4, 0.295 g/L NaCl, 0.003 FeCl3, 0.7 g/L Ca3HPO4, 100 mM Tris and 20 g/L Agar, pH 7, then autoclaved and poured into square Petri plates. After 3 days of growth at 28° C. in darkness, clear halos are measured around colonies that are able to solubilize the tricalcium phosphate.

Acetoin and Diacetyl Production 500 ml of autoclaved R2 broth supplemented with 0.5% glucose are aliquoted into a 48 well plate (#07-200-700, Fisher). Microbes are inoculated using a flame-sterilized metal loop, sealed with a breathable membrane, then incubated for 3 days at 28° C. At day 3, 100 microliters/well is added of freshly blended Barritt's Reagents A and B [5 g/L creatine mixed 3:1 (v/v) with freshly prepared ∝-naphthol (75 g/L in 2.5 M sodium hydroxide)]. After 15 minutes, plates are scored for red or pink colouration relative to a copper coloured negative control (measured as 525 nm absorption on a plate reader).

Auxin Production 500 ml of autoclaved R2 broth supplemented with L-tryptophan to a final concentration of 5 mM are autoclaved and poured into a 48 well plate. Using a flame-sterilized loop, all microbes are inoculated into the plate from a fungal stock. The plate is incubated at 28° C. for 3 days, measured for OD525 and OD600 (to assess fungal growth) and finally, 100 microliters per well of Salkowski reagent (0.01 M ferric chloride in 35% perchloric acid, #311421, Sigma) is added. After 15 minutes, plates were scored for red or pink coloration relative to a clear-colored negative controls (measured as 540 nm absorption on a plate reader).

Siderophore Production

To ensure no contaminating iron is carried over from previous experiments, all glassware is deferrated with 6 M HCl and water prior to media preparation. In this cleaned glassware, R2 broth media, which is iron-limited, is prepared and poured (500 microliters/well) into 48 well plates and the plate then inoculated with fungi using a flame sterilized metal loop. After 3 days of incubation at 28° C., to each well is added 200 microliters of O-CAS preparation without gelling agent. Again using the cleaned glassware, 1 liter of O-CAS overlay is made by mixing 60.5 mg of Chrome azurol S (CAS), 72.9 mg of hexadecyltrimethyl ammonium bromide (HDTMA), 30.24 g of finely crushed Piperazine-1,4-bis-2-ethanesulfonic acid (PIPES) with 10 ml of 1 mM FeCl3.6H2O in 10 mM HCl solvent. The PIPES has to be finely powdered and mixed gently with stirring (not shaking) to avoid producing bubbles, until a dark blue colour is achieved. 15 minutes after adding the reagent to each well, color change is scored by looking for purple halos (catechol type siderophores) or orange colonies (hydroxamate siderophores) relative to the deep blue of the O-Cas.

Antibiosis

Agar plates containing bacteria or yeast in the agar are prepared first by adding fresh overnight cultures of *E. coli* DH5α or *Saccharomyces cerevisiae* (yeast) to agar. These are first diluted to OD600=0.2, then 1 microliter/mL of this blended into sterile, cool to the touch, but still liquid R2A agar. These are poured into square Petri dishes, which are then inoculated when solid by using a flame-sterilized metal loop and grown for 3 days at 28° C. At this time, plates are scanned and antibiosis is scored by looking for clear halos around fungal colonies.

Phenotype

Colonies of complex endophytes and individual component bacteria were plated out on agar and grown for 3 days at 28° C. Plates were photographed and phenotypic characteristics were noted. All results are shown in FIG. 1.

Example 4: Creation of Complex Endophyte and Plant Element Associations

Untreated soy and wheat seeds were surface sterilized using chlorine fumes. Briefly, Erlenmyer flasks containing seeds and a bottle with 100 mL of fresh bleach solution were placed in a desiccation jar located in a fume hood. Immediately prior to closing the lid of the desiccation jar, 3 mL hydrochloric acid was carefully pipetted into the bleach. Sterilization was done for 17 hours for soy and 16 hours for wheat. Upon completion the flasks with seeds were removed, sealed in sterile foil, and opened in a sterile biosafety cabinet or laminar flow hood for subsequent work.

Seeds were coated with endophytes as follows. 2% sodium alginate (SA) was prepared and autoclaved. An Erlenmeyer flask was filled with appropriate amount of deionized water and warmed to about 50 degrees on a heat plate with agitation using stirring bar. SA powder was poured slowly until it all dissolved. The solution was autoclaved at 121° C. @15 PSI for 30 minutes.

Talcum powder was autoclaved in a dry cycle (121° C. @15 PSI for 30 minutes) and aliquoted in Ziploc bags or 50 ml falcon tubes.

Endophyte inocula were prepared in the amounts indicated below. For controls, fungal powder was substituted with talc, or liquid fungus with the liquid medium (Yeast Extract Peptone Broth), respectively.

For fungal powder seed treatment, seeds were placed in a large plastic container. 50 mL of the 2% SA was applied per kilogram of seeds to be treated. The container was covered with a hinged lid and shaken slowly in orbital motion for about 20 seconds to disperse the SA. 12.5 g of fungal powder was premixed with 137.5 g of talcum powder, per kg of seed to be treated. A mixture of the fungal inocula and talc was dispersed evenly on top of the seeds, the container covered, and the seeds shaken slowly in orbital motion for about 20 seconds. Excess powder was sieved off and the seeds packed in paper bags for storage prior to planting.

For fungal liquid seed treatment, seeds were placed in a large plastic container. 25 ml of 2% SA per kg of seed and the same amount of fungal culture (25 ml per kg of seed) was poured on the seeds. The container was covered with a hinged lid and shaken slowly in orbital motion for about 20 seconds to disperse the SA. 137.5 g of talcum powder per kg of seed was added and dispersed evenly, the container covered, and the seeds shaken slowly in orbital motion for about 20 seconds. Excess formulation was sieved off and the seeds packed in paper bags for storage prior to planting.

It is contemplated that the described method may be utilized to associate a complex endophyte, or its native fungal host endophyte, or its bacterial endophyte component, with any plant element. Included within the scope of this invention as non-limiting examples of such are methods of associating such endophytes with liquid or powder formulations further comprising a complex endophyte, a bacterial endophyte, or a fungal endophyte, with a seed, a root, a tuber, a keikis, a bud, a stem, a leaf, a flower, a bud, a wound on a plant, a stolon, a pistil, a stamen, a root nodule, a shoot, a seedling, a fruit, or a whole plant or portion thereof.

Seed Treatment

A complex, fungal, or bacterial endophyte was inoculated onto seeds as a liquid or powder using a range of formulations including the following components: sodium alginate and/or methyl cellulose as stickers, talc and flowability polymers. Seeds were air dried after treatment and planted according to common practice for each crop type.

Osmopriming and Hydropriming

A complex, fungal, or bacterial endophyte is inoculated onto seeds during the osmopriming (soaking in polyethylene glycol solution to create a range of osmotic potentials) and/or hydropriming (soaking in de-chlorinated water) process. Osmoprimed seeds are soaked in a polyethylene glycol solution containing a bacterial and/or fungal endophyte for one to eight days and then air dried for one to two days. Hydroprimed seeds are soaked in water for one to eight days containing a bacterial and/or fungal endophyte and maintained under constant aeration to maintain a suitable dissolved oxygen content of the suspension until removal and air drying for one to two days. Talc and or flowability polymer are added during the drying process.

Foliar Application

A complex, fungal, or bacterial endophyte is inoculated onto aboveground plant tissue (leaves and stems) as a liquid suspension in dechlorinated water containing adjuvants, sticker-spreaders and UV protectants. The suspension is sprayed onto crops with a boom or other appropriate sprayer.

Soil Inoculation

A complex, fungal, or bacterial endophyte is inoculated onto soils in the form of a liquid suspension either; pre-planting as a soil drench, during planting as an in furrow application, or during crop growth as a side-dress. A fungal or bacterial endophyte is mixed directly into a fertigation system via drip tape, center pivot or other appropriate irrigation system.

Hydroponic and Aeroponic Inoculation

A complex, fungal, or bacterial endophyte is inoculated into a hydroponic or aeroponic system either as a powder or liquid suspension applied directly to the rockwool substrate, or applied to the circulating or sprayed nutrient solution.

Vector-Mediated Inoculation

A complex, fungal, or bacterial endophyte is introduced in power form in a mixture containing talc or other bulking agent to the entrance of a beehive (in the case of bee-mediation) or near the nest of another pollinator (in the case of other insects or birds. The pollinators pick up the powder when exiting the hive and deposit the inoculum directly to the crop's flowers during the pollination process.

Root Wash

The method includes contacting the exterior surface of a plant's roots with a liquid inoculant formulation containing a purified bacterial population, a purified fungal population, a purified complex endophyte population, or a mixture of any of the preceding. The plant's roots are briefly passed through standing liquid microbial formulation or liquid formulation is liberally sprayed over the roots, resulting in both physical removal of soil and microbial debris from the plant roots, as well as inoculation with microbes in the formulation.

Seedling Soak

The method includes contacting the exterior surfaces of a seedling with a liquid inoculant formulation containing a purified bacterial population, a purified fungal population, or a mixture of any of the preceding. The entire seedling is immersed in standing liquid microbial formulation for at least 30 seconds, resulting in both physical removal of soil and microbial debris from the plant roots, as well as inoculation of all plant surfaces with microbes in the formulation. Alternatively, the seedling can be germinated from seed in or transplanted into media soaked with the microbe(s) of interest and then allowed to grow in the media, resulting in soaking of the plantlet in microbial formulation for much greater time totaling as much as days or weeks. Endophytic microbes likely need time to colonize and enter the plant, as they explore the plant surface for cracks or wounds to enter, so the longer the soak, the more likely the microbes will successfully be installed in the plant.

Wound Inoculation

The method includes contacting the wounded surface of a plant with a liquid or solid inoculant formulation containing a purified bacterial population, a purified fungal population, or a mixture of any of the preceding. Plant surfaces are designed to block entry of microbes into the endosphere, since pathogens attempting to infect plants in this way. In order to introduce beneficial endophytic microbes to plant endospheres, we need a way to access the interior of the plant which we can do by opening a passage by wounding. This wound can take a number of forms, including pruned roots, pruned branches, puncture wounds in the stem breaching the bark and cortex, puncture wounds in the tap root, puncture wounds in leaves, and puncture wounds seed allowing entry past the seed coat. Wounds can be made using needles, hammer and nails, knives, drills, etc. Into the wound can then be contacted the microbial inoculant as liquid, as powder, inside gelatin capsules, in a pressurized capsule injection system, in a pressurized reservoir and tubing injection system, allowing entry and colonization by microbes into the endosphere. Alternatively, the entire wounded plant can be soaked or washed in the microbial inoculant for at least 30 seconds, giving more microbes a chance to enter the wound, as well as inoculating other plant surfaces with microbes in the formulation—for example pruning seedling roots and soaking them in inoculant before transplanting is a very effective way to introduce endophytes into the plant.

Injection

The method includes injecting microbes into a plant in order to successfully install them in the endosphere. Plant surfaces are designed to block entry of microbes into the endosphere, since pathogens attempting to infect plants in this way. In order to introduce beneficial endophytic microbes to endospheres, we need a way to access the interior of the plant which we can do by puncturing the plant surface with a need and injecting microbes into the inside of the plant. Different parts of the plant can be inoculated this way including the main stem or trunk, branches, tap roots, seminal roots, buttress roots, and even leaves. The injection can be made with a hypodermic needle, a drilled hole injector, or a specialized injection system, and through the puncture wound can then be contacted the microbial inoculant as liquid, as powder, inside gelatin capsules, in a pressurized capsule injection system, in a pressurized reservoir and tubing injection system, allowing entry and colonization by microbes into the endosphere.

Example 5: Verification of Complex Endophyte Colonization in Plant Elements or Whole Plants The following methods may be used to verify stable integration of the complex endophyte or components with the target plant host or target plant host plant elements, as well as verification of presence of the complex endophyte or components that have been transmitted to progeny of the target plant host.

Culturing to Confirm Colonization of Plant by Bacteria

The presence of complex endophytes in whole plants or plant elements, such as seeds, roots, leaves, or other parts, can be detected by isolating microbes from plant or plant element homogenates (optionally surface-sterilized) on antibiotic-free media and identifying visually by colony morphotype and molecular methods described herein. Representative colony morphotypes are also used in colony PCR and sequencing for isolate identification via ribosomal gene sequence analysis as described herein. These trials are repeated twice per experiment, with 5 biological samples per treatment.

Culture-Independent Methods to Confirm Colonization of the Plant or Seeds by Complex Endophytes One way to detect the presence of complex endophytes on or within plants or seeds is to use quantitative PCR (qPCR). Internal colonization by the complex endophyte can be demonstrated by using surface-sterilized plant tissue (including seed) to extract total DNA, and isolate-specific fluorescent MGB probes and amplification primers are used in a qPCR reaction. An increase in the product targeted by the reporter probe at each PCR cycle therefore causes a proportional increase in fluorescence due to the breakdown of the probe and release of the reporter. Fluorescence is measured by a quantitative PCR instrument and compared to a standard curve to estimate the number of fungal or bacterial cells within the plant.

The design of both species-specific amplification primers, and isolate-specific fluorescent probes are well known in the art. Plant tissues (seeds, stems, leaves, flowers, etc.) are pre-rinsed and surface sterilized using the methods described herein.

Total DNA is extracted using methods known in the art, for example using commercially available Plant-DNA extraction kits, or the following method.

1. Tissue is placed in a cold-resistant container and 10-50 mL of liquid nitrogen is applied. Tissues are then macerated to a powder.

2. Genomic DNA is extracted from each tissue preparation, following a chloroform:isoamyl alcohol 24:1 protocol (Sambrook, Joseph, Edward F. Fritsch, and Thomas Maniatis. Molecular cloning. Vol. 2. New York: Cold spring harbor laboratory press, 1989.).

Quantitative PCR is performed essentially as described by Gao, Zhan, et al. Journal of clinical microbiology 48.10 (2010): 3575-3581 with primers and probe(s) specific to the desired isolate (the host fungus, the endofungal bacterial endophyte, or the endofungal fungal endophyte) using a quantitative PCR instrument, and a standard curve is constructed by using serial dilutions of cloned PCR products corresponding to the specie-specific PCR amplicon produced by the amplification primers. Data are analyzed using instructions from the quantitative PCR instrument's manufacturer software.

As an alternative to qPCR, Terminal Restriction Fragment Length Polymorphism, (TRFLP) can be performed, essentially as described in Johnston-Monje D, Raizada M N (2011) PLoS ONE 6(6): e20396. Group specific, fluorescently labeled primers are used to amplify a subset of the microbial population, for example bacteria and fungi. This fluorescently labeled PCR product is cut by a restriction enzyme chosen for heterogeneous distribution in the PCR product population. The enzyme cut mixture of fluorescently labeled and unlabeled DNA fragments is then submitted for sequence analysis on a Sanger sequence platform such as the Applied Biosystems 3730 DNA Analyzer.

Immunological Methods to Detect Complex Endophytes in Seeds and Vegetative Tissues A polyclonal antibody is raised against specific the host fungus, the endofungal bacterial endophyte, or the endofungal fungal endophyte via standard methods. Enzyme-linked immunosorbent assay (ELISA) and immunogold labeling is also conducted via standard methods, briefly outlined below.

Immunofluorescence microscopy procedures involve the use of semi-thin sections of seed or seedling or adult plant tissues transferred to glass objective slides and incubated with blocking buffer (20 mM Tris (hydroxymethyl)-aminomethane hydrochloride (TBS) plus 2% bovine serum albumin, pH 7.4) for 30 min at room temperature. Sections are first coated for 30 min with a solution of primary antibodies and then with a solution of secondary antibodies (goat anti-rabbit antibodies) coupled with fluorescein isothiocyanate (FITC) for 30 min at room temperature. Samples are then kept in the dark to eliminate breakdown of the light-sensitive FITC. After two 5-min washings with sterile potassium phosphate buffer (PB) (pH 7.0) and one with double-distilled water, sections are sealed with mounting buffer (100 mL 0.1 M sodium phosphate buffer (pH 7.6) plus 50 mL double-distilled glycerine) and observed under a light microscope equipped with ultraviolet light and a FITC Texas-red filter.

Ultrathin (50- to 70-nm) sections for TEM microscopy are collected on pioloform-coated nickel grids and are labeled with 15-nm gold-labeled goat anti-rabbit antibody. After being washed, the slides are incubated for 1 h in a 1:50 dilution of 5-nm gold-labeled goat anti-rabbit antibody in IGL buffer. The gold labeling is then visualized for light microscopy using a BioCell silver enhancement kit. Toluidine blue (0.01%) is used to lightly counterstain the gold-labeled sections. In parallel with the sections used for immunogold silver enhancement, serial sections are collected on uncoated slides and stained with 1% toluidine blue. The sections for light microscopy are viewed under an optical microscope, and the ultrathin sections are viewed by TEM.

Example 6: Demonstration of Phenotypic Alterations of Host Plants Due to Presence of the Complex Endophyte: Germination Assays Testing for Germination Enhancement in Normal Conditions Standard germination tests are used to assess the ability of the complex endophyte to enhance the seeds' germination and early growth. Briefly, seeds that have been coated with the complex endophyte or bacterial endophyte component as described elsewhere are placed in between wet brown paper towels. An equal number of seeds obtained from control plants that do not contain the endophyte (complex or bacterial) re treated in the same way. The paper towels are placed on top of 1×2 feet plastic trays and maintained in a growth chamber set at 25° C. and 70% humidity for 7 days. The proportion of seeds that germinated successfully is compared between the complex endophyte-treated seeds and the non-complex endophyte-treated.

Testing for Germination Enhancement Under Biotic Stress

A modification of the method developed by Hodgson [Am. Potato. J. 38: 259-264 (1961)] is used to test germination enhancement in complex endophyte-treated seeds under biotic stress. Biotic stress is understood as a concentration of inocula in the form of cell (bacteria) or spore suspensions (fungus) of a known pathogen for a particular crop (e.g., *Pantoea stewartii* or *Fusarium graminearum* for *Zea mays* L.). Briefly, for each level of biotic stress, seeds that have been treated with complex endophyte strains, and seed controls (lacking the complex endophyte strains), are placed in between brown paper towels. Each one of the replicates is placed inside a large petri dish (150 mm in diameter). The towels are then soaked with 10 mL of pathogen cell or spore suspension at a concentration of 10^4 to 10^8 cells/spores per mL. Each level corresponds with an order of magnitude increment in concentration (thus, 5 levels). The petri dishes are maintained in a growth chamber set at 25° C. and 70% humidity for 7 days. The proportion of seeds that germinate successfully is compared between the complex endophyte-treated seeds and the non-complex endophyte-treated for each level of biotic stress.

Testing for Germination Enhancement Under Drought Stress

Polyethylene glycol (PEG) is an inert, water-binding polymer with a non-ionic and virtually impermeable long chain [Couper and Eley, J. Polymer Sci., 3: 345-349 (1984)] that accurately mimics drought stress under dry-soil conditions. The higher the concentration of PEG, the lower the water potential achieved, thus inducing higher water stress in a watery medium. To determine germination enhancement in seeds treated with complex endophytes or bacterial endophyte components, the effect of osmotic potential on germination was tested at a range of water potential representative of drought conditions following Perez-Fernandez et al. [J. Environ. Biol. 27: 669-685 (2006)]. The range of water potentials simulated those that are known to cause drought stress in a range of cultivars and wild plants, (−0.05 MPa to −5 MPa) [Craine et al., Nature Climate Change 3: 63-67 (2013)]. The appropriate concentration of polyethylene glycol (6000) required to achieve a particular water potential was determined following Michel and Kaufmann (Plant Physiol., 51: 914-916 (1973)) and further modifications by Hardegree and Emmerich (Plant Physiol., 92, 462-466 (1990)). The final equation used to determine amounts of PEG was: Ψ=0.130 [PEG]2 T-13.7 [PEG] 2; where the osmotic potential (Ψ) is a function of temperature (T).

Testing for Germination Enhancement Under Drought Stress (Soybean)

Germination experiments for soybean under drought stress experiments were performed using sterile heavy weight germination paper immersed with 8% PEG 6000 solution (Ψ equal to −0.1 MPa; 10 mL solution/plate) in 150 mm Petri plates. Surface sterilized soy seeds were first coated with 2% sodium alginate to enable microbial adhesion, and then treated with equal volume of microbial culture in a 50 mL Falcon tube. Seeds were mixed for homogenous coating. Seed treatment calculations were based on 0.01 mL each of microbial culture and 2% sodium alginate solution for every one gram of seed. Treated seeds were coated were placed on the PEG 6000 saturated germination paper and incubated in the growth chamber at 25° C., 24 hour dark cycle, 65% relative humidity for 4 days. The experiment contained seeds treated with the complex endophyte, in addition to seed controls (lacking the microbial strains). The number of seeds that germinated successfully after four days was compared between the endophyte-treated seeds (complex and bacterial) and the non-endophyte-treated. All treatments were tested in three replicate plates, each containing ten seeds.

Results for the soybean water-stress (drought stress) germination assay are given in Table 5. Complex endophyte treatment improves germination rate of soybean seedlings under drought (water stressed) conditions vs. formulation controls. *Dothideomycetes* as complex endophyte hosts appear to impart greater benefit to soybean seedling germination under water stress (drought stress) conditions vs. their isolated bacterial components, than do *Sodariomycetes.*

Testing for Germination Enhancement Under Drought Stress (Wheat)

Germination experiments were conducted in 90 mm diameter petri dishes for wheat. Replicates consisted of a Petri dish, watered with 10 mL of the appropriate solution and 20 seeds floating in the solution. The experiment contained seeds treated with the complex endophyte, in addition to seed controls (lacking the microbial strains). To prevent large variations in Ψ, dishes were sealed with parafilm and the PEG solutions were renewed weekly by pouring out the existing PEG in the petri dish and adding the same amount of fresh solution. Petri dishes were maintained in a growth chamber set at 25° C., 16:8 hour light:dark cycle, 70% humidity, and least 120 microE/m^2/s light intensity. The proportion of seeds that germinated successfully after three days was compared between the endophyte-treated seeds (complex and bacterial) and the non-endophyte-treated.

Results for the wheat water-stress (drought stress) germination assay are given in Table 6. Complex endophyte treatment, as well as bacterial endophyte treatment, improves germination rate of wheat seedlings under drought (water stressed) conditions vs. formulation controls. Sodariomycetes as complex endophyte hosts appear to impart greater benefit to soybean seedling germination under water stress (drought stress) conditions vs. their isolated bacterial components, than do Dothideomycetes.

Testing for Germination Enhancement in Heat Conditions

Standard germination tests are used to determine if a complex endophyte protects a seedling or plant against heat stress during germination. Briefly, seeds treated with complex endophytes are placed in between wet brown paper towels. An equal number of seeds obtained from control plants that lack the complex endophyte is treated in the same way. The paper towels are placed on top of 1×2 ft plastic trays and maintained in a growth chamber set at 16:8 hour light:dark cycle, 70% humidity, and at least 120 microE/m^2/s light intensity for 7 days. A range of high temperatures (from 35° C. to 45° C., with increments of 2 degrees per assay) is tested to assess the germination of complex endophyte-treated seeds at each temperature. The proportion of seeds that germinate successfully is compared between the complex endophyte-treated seeds and the non-complex endophyte-treated.

Testing for Germination Enhancement in Cold Conditions

Standard germination tests are used to determine if a complex endophyte protects a seedling or plant against cold stress during germination. Briefly, seeds treated with complex endophytes are placed in between wet brown paper towels. An equal number of seeds obtained from control plants that lack the complex endophyte is treated in the same way. The paper towels are placed on top of 1×2 ft plastic trays and maintained in a growth chamber set at 16:8 hour light:dark cycle, 70% humidity, and at least 120 microE/m^2/s light intensity for 7 days. A range of low temperatures (from 0° C. to 10° C., with increments of 2 degrees per assay) is tested to assess the germination of complex endophyte-treated seeds at each temperature. The proportion of seeds that germinate successfully is compared between the complex endophyte-treated seeds and the non-complex endophyte-treated.

Testing for Germination Enhancement in High Salt Concentrations

Germination experiments are conducted in 90 mm diameter petri dishes. Replicates consist of a Petri dish, watered with 10 mL of the appropriate solution and 20 seeds floating in the solution. Seeds treated with complex endophytes and seed controls (lacking the microbial strains) are tested in this way. To prevent large variations in salt concentration due to evaporation, dishes are sealed with parafilm and the saline solutions are renewed weekly by pouring out the existing saline solution in the petri dish and adding the same amount of fresh solution. A range of saline solutions (100-500 mM NaCl) is tested for to assess the germination of complex endophyte-treated seeds at varying salt levels. Petri dishes are maintained in a growth chamber set at 25° C., 16:8 hour light:dark cycle, 70% humidity, and at least 120 microE/m^2/s light intensity. The proportion of seeds that germinates successfully after two weeks is compared between the complex endophyte-treated seeds and the non-complex endophyte-treated.

Testing for Germination Enhancement in Soils with High Metal Content

Standard germination tests are used to determine if a complex endophyte protects a seedling or plant against stress due to high soil metal content during germination. Briefly, seeds treated with complex endophytes, are placed in between wet brown paper towels. An equal number of seeds obtained from control plants that lack the complex endophyte (complex endophyte-free) is treated in the same way. The paper towels are placed on top of 1×2 ft plastic trays with holes to allow water drainage. The paper towels are covered with an inch of sterile sand. For each metal to be tested, the sand needs to be treated appropriately to ensure the release and bioavailability of the metal. For example, in the case of aluminum, the sand is watered with pH 4.0+~1 g/Kg soil Al+3 (~621 microM). The trays are maintained in a growth chamber set at 25° C. and 70% humidity for 7 days. The proportion of seeds that germinates successfully is compared between the complex endophyte-treated seeds and the non-complex endophyte-treated.

Example 7: Demonstration of Phenotypic Alterations of Host Plants Due to Presence of the Complex Endophyte: Growth Chamber Assays Testing for Growth Promotion in Growth Chamber in Normal Conditions Soil is made from a mixture of 60% Sunshine Mix #5 (Sun Gro; Bellevue, Wash., USA) and 40% vermiculite. To determine if a particular complex endophyte is capable of promoting plant growth under normal conditions, pots are prepared in 12-pot no-hole flat trays with 28 grams of dry soil in each pot, and 2 L of filtered water is added to each tray. The water is allowed to soak into the soil and the soil surface is misted before seeding. For each seed-complex endophyte combination, some pots are seeded with 3-5 seeds treated with the complex endophyte and other pots are seeded with 3-5 seeds lacking the complex endophyte (complex endophyte-free plants). The seeded pots are covered with a humidity dome and kept in the dark for 3 days, after which the pots are transferred to a growth chamber set at 25° C., 16:8 hour light:dark cycle, 70% humidity, and at least 120 microE/m^2/s light intensity. The humidity domes are removed on day 5, or when cotyledons are fully expanded. After removal of the domes, each pot is irrigated to saturation with 0.5× Hoagland's solution, then allowing the excess solution to drain. Seedlings are then thinned to 1 per pot. In the following days, the pots are irrigated to saturation with filtered water, allowing the excess water to drain after about 30 minutes of soaking, and the weight of each 12-pot flat tray is recorded weekly. Canopy area is measured at weekly intervals. Terminal plant height, average leaf area and average leaf length are measured at the end of the flowering stage. The plants are allowed to dry and seed weight is measured. Significance of difference in growth between complex endophyte-treated plants and controls lacking the complex endophyte is assessed with the appropriate statistical test depending on the distribution of the data at $p<0.05$.

Testing for Growth Promotion in Growth Chamber Under Biotic Stress

Soil is made from a mixture of 60% Sunshine Mix #5 (Sun Gro; Bellevue, Wash., USA) and 40% vermiculite. To determine if a particular complex endophyte is capable of promoting plant growth in the presence of biotic stress, pots are prepared in 12-pot no-hole flat trays with 28 grams of dry soil in each pot, and 2 L of filtered water is added to each tray. The water is allowed to soak into the soil before planting. For each seed-complex endophyte combination test, some pots are seeded with 3-5 seeds treated with the complex endophyte and other pots are seeded with 3-5 seeds lacking the complex endophyte (complex endophyte-free plants). The seeded pots are covered with a humidity dome and kept in the dark for 3 days, after which the pots are transferred to a growth chamber set at 25° C., 16:8 hour light:dark cycle, 70% humidity, and at least 120 µE/m2/s light intensity. The humidity domes are removed on day 5, or when cotyledons are fully expanded. After removal of the domes, each pot is irrigated to saturation with 0.5× Hoagland's solution, allowing the excess solution to drain. Seedlings are then thinned to 1 per pot. In the following days, the pots are irrigated to saturation with filtered water, allowing the excess water to drain after about 30 minutes of soaking.

Several methods of inoculation are used depending on the lifestyle of the pathogen. For leaf pathogens (e.g., *Pseudomonas syringeae* or *Colletotrichum graminicola*), a suspension of cells for bacteria (10^8 cell/mL) or spores for fungi (10^7 spores/mL) is applied with an applicator on the adaxial surface of each of the youngest fully expanded leaves. Alternatively for fungal pathogens that do not form conidia easily, two agar plugs containing mycelium (~4 mm in diameter) are attached to the adaxial surface of each of the youngest leaves on each side of the central vein. For vascular pathogens (e.g., *Pantoea stewartii* or *Fusarium moniliforme*), the suspension of cells or spores is directly introduced into the vasculature (5-10 microLiters) through a minor injury inflected with a sterile blade. Alternatively, the seedlings can be grown hydroponically in the cell/spore or mycelium suspension. To test the resilience of the plant-complex endophyte combination against insect stresses, such as thrips or aphids, plants are transferred to a specially-designated growth chamber containing the insects. Soil-borne insect or nematode pathogens are mixed into or applied topically to the potting soil. In all cases, care is taken to contain the fungal, insect, nematode or other pathogen and prevent release outside of the immediate testing area.

The weight of each 12-pot flat tray is recorded weekly. Canopy area is measured at weekly intervals. Terminal plant height, average leaf area and average leaf length are measured at the cease of flowering. The plants are allowed to dry and seed weight is measured. Significance of difference in growth between complex endophyte-treated plants and controls lacking the complex endophyte is assessed with the appropriate statistical test depending on the distribution of the data at $p<0.05$.

Example 8: Demonstration of Phenotypic Alterations of Host Plants Due to Presence of the Complex Endophyte: Plant Vigor Seedling Assays Untreated soybean and winter wheat Variety 2 seeds were surface sterilized using chlorine fumes. Briefly, Erlenmyer flasks containing seeds and a bottle with 100 mL of fresh bleach solution were placed in a desiccation jar located in a fume hood. Immediately prior to closing the lid of the desiccation jar, 3 mL hydrochloric acid was carefully pipetted into the bleach. Sterilization was done for 17 hours for soy and 16 hours for wheat. Upon completion the flasks with seeds were removed, sealed in sterile foil, and opened in a sterile biosafety cabinet or laminar flow hood for subsequent work.

Complex endophytes and their corresponding endofungal bacteria were cultured in 4 mL PDB using 12-well plates at 25° C. with constant agitation for 5 days and 3 days, respectively. Fungal samples were briefly sonicated to obtain a homogenous suspension of culture. Surface sterilized soy and wheat seeds were first coated with 2% sodium alginate to enable microbial adhesion, and then treated with equal volume of microbial culture in a 50 mL Falcon tube. Seeds were mixed for homogenous coating. Seed treatment calculations were based on 0.01 mL each of microbial culture and 2% sodium alginate solution for every one gram of seed.

Ten soybean (Variety A) and fifteen wheat (Spring Wheat, Variety 2) treated seeds were placed equidistant to each other on heavy weight germination paper sandwiches saturated with sterile distilled water for each treatment. A total of 50 mL water was added to the germination paper sandwiches for soy and 25 mL for wheat. The germination paper sandwiches were rolled, secured using surgical tape, and placed in two separate airtight plastic containers for each crop. Two replicates per SYM treatment were prepared and placed within each container. All steps were performed under sterile conditions.

All samples were incubated at 24° Celsius with 65% relative humidity in darkness for 4 days to enable seed germination. On day 4, the lid of one airtight container per crop was removed for the seedlings to allow for gradual water stress and the growth chamber setting was changed to 24° Celsius, 70% relative humidity, 250-300 microEinsten light for 12 hours followed by 18° Celsius, 60% relative humidity for 12 hours of darkness for 6 days. The second airtight container with seedlings for both crops remained sealed to maintain plant growth in a non-water stress condition. Placement of germination rolls was randomized periodically to reduce any positional effect throughout the plant growth period.

At the end of the experiment, each seedling was photographed and measured for total root length and mass. Scoring of seedlings were done by manually measuring each seedling's root and shoot length using either a ruler or a measurement grid on which the seedlings were placed for imaging. The total mass of seedlings was recorded by weighing all germinated seedlings within each treatment replicate using an analytical balance. Raw data number averages of each treatment were obtained by computing mean, standard deviation and standard error for all germinated seedlings per replicate. Seedlings that failed to germinate or displayed phenotypic abnormalities were excluded from analysis. Data was represented by four plant vigor parameters including root and shoot length, overall plant growth, and total seedling mass. Analyses were performed relative to seedlings treated with the formulation control (formulation without complex endophyte or the isolated complex endophyte bacterial component).

Wheat Seedling Normal Conditions

Results are shown in Tables 7a-7b.

Plant seedlings grown from seeds treated with complex endophytes or complex endophyte bacterial components display a greater average root length than do plant seedlings grown from seeds treated with the formulation control. No significant difference was observed in average root length between plants grown from seeds treated with complex endophytes vs. isolated bacterial components.

Plant seedlings grown from seeds treated with complex endophytes or complex endophyte bacterial components display a greater average shoot length than do plant seedlings grown from seeds treated with the formulation control. Plant seedlings grown from seeds treated with complex endophytes display a greater average shoot length than do plant seedlings grown from seeds treated with isolated bacterial components.

Wheat Seedling Drought (Water-Stressed) Conditions

Results are shown in Tables 8a-8b.

Plant seedlings grown from seeds treated with complex endophytes or complex endophyte bacterial components display a greater average root length than do plant seedlings grown from seeds treated with the formulation control. No significant difference was observed between plants grown from seeds treated with complex endophytes vs. isolated bacterial components.

Plant seedlings grown from seeds treated with complex endophytes or complex endophyte bacterial components display a greater average shoot length than do plant seedlings grown from seeds treated with the formulation control. Plant seedlings grown from seeds treated with complex endophytes display a greater average shoot length than do plant seedlings grown from seeds treated with isolated bacterial components.

Soy Seedling Normal Conditions

Results are shown in Tables 9a-9b.

Plant seedlings grown from seeds treated with complex endophytes or complex endophyte bacterial components display a greater average root length than do plant seedlings grown from seeds treated with the formulation control. Plant seedlings grown from seeds treated with complex endophytes display a greater average root length than do plant seedlings grown from seeds treated with isolated bacterial components.

Plant seedlings grown from seeds treated with complex endophytes or complex endophyte bacterial components display a greater average shoot length than do plant seedlings grown from seeds treated with the formulation control. Plant seedlings grown from seeds treated with isolated bacterial components display a slightly greater average shoot length than do plant seedlings grown from seeds treated with the complex endophytes.

Soy Seedling Drought (Water-Stressed) Conditions

Results are shown in Tables 10a-10b.

Plant seedlings grown from seeds treated with a complex endophyte or complex endophyte bacterial component display a greater average root length than do plant seedlings grown from seeds treated with the formulation control. Plant seedlings grown from seeds treated with complex endophytes display a greater average root length than do plant seedlings grown from seeds treated with isolated bacterial components.

Plant seedlings grown from seeds treated with complex endophytes or complex endophyte bacterial components display a greater average shoot length than do plant seedlings grown from seeds treated with the formulation control. No significant difference was observed between plants grown from seeds treated with complex endophytes vs. isolated bacterial components.

Example 9: Demonstration of Phenotypic Alterations of Host Plants Due to Presence of the Complex Endophyte: Greenhouse Assessments Seeds were coated with complex endophytes and isolated bacterial endophytes as follows. 2% sodium alginate (SA) was prepared and autoclaved. An Erlenmeyer flask was filled with appropriate amount of deionized water and warmed to about 50 degrees on a heat plate with agitation using stirring bar. SA powder was poured slowly until it all dissolved. The solution was autoclaved at 121° C. @15 PSI for 30 minutes.

Talcum powder was autoclaved in a dry cycle (121° C. @15 PSI for 30 minutes) and aliquoted in Ziploc bags or 50 ml falcon tubes.

Microbial (complex endophyte or fungal endophyte) inocula were prepared in the amounts indicated below. For controls, fungal powder was substituted with talc, or liquid fungus with the liquid medium (Yeast Extract Peptone Broth), respectively.

For wheat fungal powder seed treatment, seeds were placed in a large plastic container. 50 mL of the 2% SA was applied per kilogram of seeds to be treated. The container was covered with a hinged lid and shaken slowly in orbital motion for about 20 seconds to disperse the SA. 12.5 g of fungal powder was premixed with 137.5 g of talcum powder, per kg of seed to be treated. A mixture of the fungal inocula and talc was dispersed evenly on top of the seeds, the container covered, and the seeds shaken slowly in orbital motion for about 20 seconds. Excess powder was sieved off and the seeds packed in paper bags for storage prior to planting.

For wheat fungal liquid seed treatment, seeds were placed in a large plastic container. 25 ml of 2% SA per kg of seed and the same amount of fungal culture (25 ml per kg of seed) was poured on the seeds. The container was covered with a hinged lid and shaken slowly in orbital motion for about 20 seconds to disperse the SA. 137.5 g of talcum powder per kg of seed was added and dispersed evenly, the container covered, and the seeds shaken slowly in orbital motion for about 20 seconds. Excess formulation was sieved off and the seeds packed in paper bags for storage prior to planting.

For each treatment, a standard greenhouse flat divided into 8 compartments with a standard 801 insert was filled with Fafard blend soil (900 mL per compartment) and allowed to soak in 2 L water to provide normal soil moisture conditions. 12 seeds of 2 winter wheat varieties were planted in each compartment at a consistent depth of 2 cm. Pots were watered approximately 2-4 hours prior to planting seeds. The number of seeds planted per pot depends on the type of crop. For example, three seeds can be planted for soy, four for wheat, and one for corn. Plants are grown at a 21° C./18° C. day/night regime with a 14 hour photoperiod at a light intensity of 800 microE/m^2/s and 40% relative humidity.

Drought experiments were performed as described in the art. For example, water was withheld until the plants start wilting, were watered again, then allowed to enter into another drought cycle. The drought cycles were continued until the plant reached maturity.

Plants grown from seeds treated with the complex endophyte SYM166 were tested alongside plants grown from seeds treated with a control formulation (formulation minus endophyte) as well as plants grown from seeds treated control fungal endophytes that are not known to be complex endophytes and are of different genera than SYM166.

Emergence of germinated seeds was observed from days 3 to 8 after planting. Seedlings were harvested at day 8 after planting and dried overnight in a convection oven to collect dry weight and height of each seedling's aerial parts.

Figure 2A:
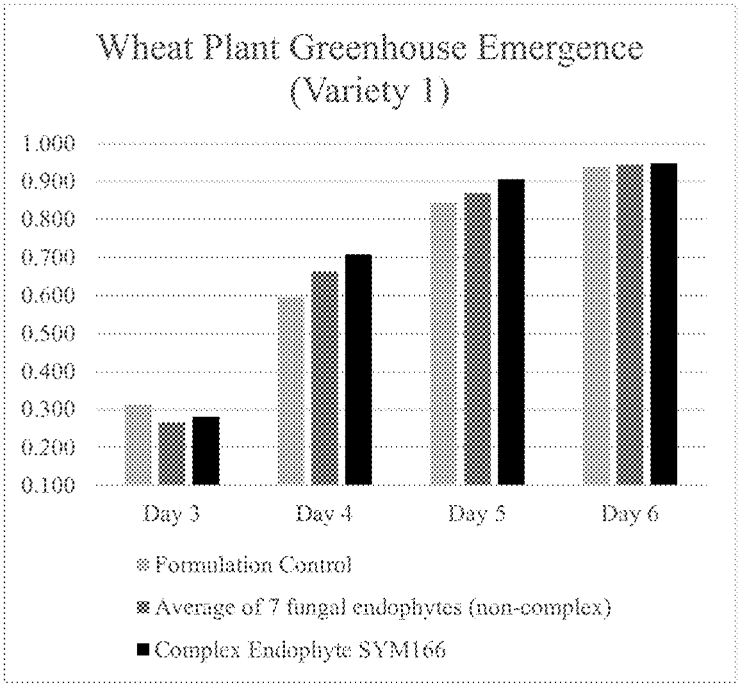
FIG. 2A and FIG. 2B: wheat greenhouse emergence rates. Spring wheat plants (Variety 1, FIG. 2A; Variety 2, FIG. 2B)
Figure 2B:
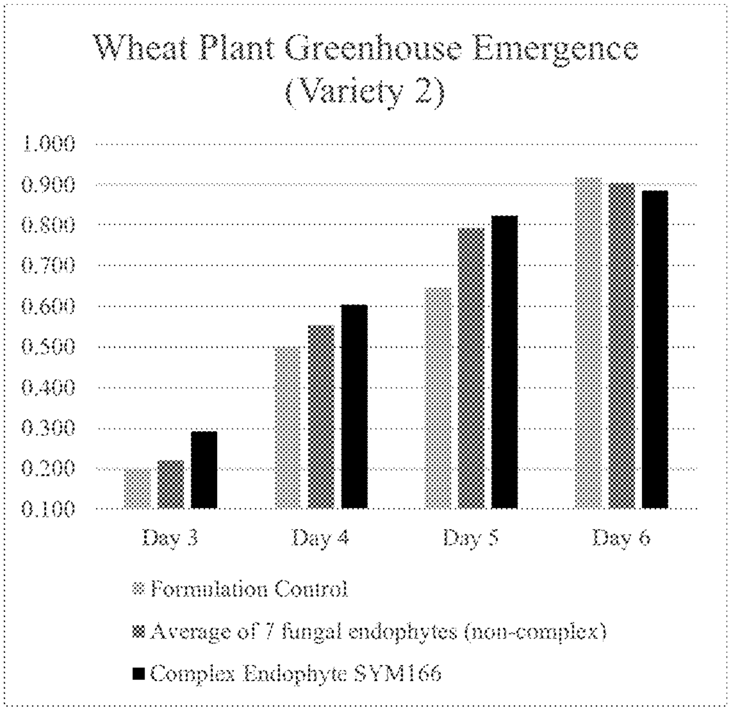

As shown in FIG. 2, the complex endophyte SYM166 demonstrated improved emergence rates in greenhouse wheat plants, versus plants treated with formulation control or fungal endophytes that were not complex. In particular, the complex endophyte appears to improve the early phases of emergence, as demonstrated by improved emergence in Days 3, 4, and 5.

A shown in FIG. 3, the complex endophyte SYM166 demonstrated greater benefit to greenhouse wheat plants with respect to shoot biomass, versus plants treated with formulation control or fungal endophytes that were not complex.

Example 10: Demonstration of Phenotypic Alterations of Host Plants Due to Presence of the Complex Endophyte: Field Trials Winter wheat seed untreated seed was coated with a specific formulation depending on the type of strain, and a formulation control lacking the endophyte was included for each type of formulation. For strains formulated as dry powders (e.g., SYM166, a.k.a. SYM16670; e.g., fungal endophytes that are not known to be complex endophytes and are of different genera as SYM166, as controls), 2% sodium alginate (16.6 mL per kg seed) was applied and the seeds were agitated for 20 s to disperse the sticker. Then a 1:1 mixture of powder and talc (15 g fungal powder per kg seed) was applied and the seeds are agitated for 20 s to disperse the powder. Then FloRite (13.1 mL per kg seed) was applied and seeds were agitated for 20 s to disperse the flowability polymer.

Treated seeds were placed in paper bags and allowed to dry overnight in a well ventilated space before planting.

All fields (2% slopes) were fallow for the previous season, treated with glyphosate pre-planting and managed with conventional tillage. Untreated, formulation-treated and endophyte-treated seeds were drilled in with a plot planter in a randomized complete block design in plots of 7 by 40 ft with 7 rows on 7 in spacing. Seeding rate was 60 lbs per acre and planting depth was 0.5 in. Five interior rows were harvested with a Hege 135 B plot combine for yield assessment with the outer rows used as a buffer between plots. Grain yield (lb per plot), test weight (lb per bushel) and moisture (%) were taken directly on the combine. Yield dry bushels per acre was calculated using per plot test weights and normalized for a grain storage moisture of 13%. Thousand kernel seed weight (TKW g) was established per plot.

Early and mid-season metrics were collected. Emergence counts were taken over 10 feet on two interior rows at a timepoint when the control plots reached 50% emergence and this area was marked for the harvestable head count at the end of the season. A visual assessment of seedling vigor (1-10 rating scale) was taken at emergence. Tillers were counted on 5 individual plants at 30 days after seeding (DAS) both pre- and post-vernalization. A phytotoxicity visual assessment (%) was taken on the same plants used for tiller counts. Directly prior to harvest, harvestable heads were quantified over a square yard.

Yield (wet and dry, per acre) results for winter wheat seeds grown under dryland (non-irrigated) conditions and treated with complex endophyte SYM166 are given in Table 11, compared to winter wheat seeds treated with non-complex fungal endophytes as well as fungal formulation controls. Winter wheat grown from seeds treated with complex endophyte SYM166 demonstrate improved yield (both wet bushels per acre and dry bushels per acre) compared to seeds treated with either the fungal formulation control or with non-complex fungal endophytes.

Yield (wet and dry, per acre) results for spring wheat seeds grown under dryland (non-irrigated) conditions and treated with complex endophyte SYM166 are given in Table 12, compared to winter wheat seeds treated with non-complex fungal endophytes as well as fungal formulation controls. Spring wheat grown from seeds treated with complex endophyte SYM166 demonstrate improved yield (both wet bushels per acre and dry bushels per acre) compared to seeds treated with either the fungal formulation control or with non-complex fungal endophytes.

Example 11: Demonstration of Improved Survivability of Bacteria Associated with Plant Elements, when Said Bacteria are Encapsulated within a Host Fungus This example describes the methods and results for demonstrating that bacteria encompassed within a host fungus display greater survivability on treated seeds than does the identical bacterial strain isolated and treated on seeds.

Corn seeds were associated with individual microbial (endofungal complex endophyte and endofungal bacterial endophyte) cultures as follows. Untreated organic corn seeds were surface sterilized using chlorine fumes. Briefly, Erlenmyer flasks containing seeds and a bottle with 100 mL of fresh bleach solution were placed in a desiccation jar located in a fume hood. Immediately prior to closing the lid of the desiccation jar, 3 mL hydrochloric acid was carefully pipetted into the bleach. Sterilization was done for 14 hours, and upon completion the flasks with seeds were removed, sealed in sterile foil, and opened in a sterile biosafety cabinet or laminar flow hood for subsequent work. Surface sterilized organic corn seeds were first coated with 2% sodium alginate to enable microbial adhesion, and then treated with equal volumes of the appropriate microbial culture in a 50 mL Falcon tube. Seeds were mixed for homogenous coating. Seed treatment calculations were based on 23 mL each of microbial culture and 2% sodium alginate solution for every one kilogram of seed.

All steps of this method were performed under sterile conditions. Complex endophytes (host fungi comprising component bacteria) were grown in cultures in 150 mL of full strength Potato Dextrose Broth (PDB) at 24 grams per liter, in Erlenmyer flasks for 7 days at 25 degrees Celsius with constant agitation (130 RPM).

Endofungal bacteria were isolated from host fungi by plating the complex endohytes onto cycloheximide Lysogeny Broth (LB) plates. Cycloheximide is an antifungal agent that kills the host fungus, allowing the component bacteria to grow alone. SYM166 was grown in full strength Potato Dextrose Broth (PDB) at 24 grams per liter for 5 days. 20 mL from the growth medium was extracted and sonicated to homogenize, and plated in serial dilutions of 1:10, 1:100, and 1:1000. 500 microliters of each dilution was plated in duplicated LB plates with cycloheximide (at 50 micrograms per milliliter). Bacterial colonies were counted and isolated from the serial dilution plates. Pure isolates of the endofungal bacteria were grown as lawns in LB for 1 day.

All results are summarized in FIG. 4. The complex endophyte SYM166 demonstrated a greater than 2 fold survivability at Day 1 post seed treatment, and a 16 fold improvement in bacterial survivability versus the bacterial endophyte alone at Day 36 post seed treatment.

Example 11: Demonstration of Improved Bacterial Tolerance to Environmental Stresses when Encapsulated within a Host Fungus All Bacteria can be sensitive to molecules in the environment, such as antibiotics. The inventors herein developed a method of demonstrating improved tolerance of bacteria to antibiotics, when said bacteria are encapsulated within a host fungus.

Known endofungal endophyte SYM15779, comprising the bacterium EHB15779, was treated with gentamicin, and compared to a control culture of SYM15779 not treated with gentamicin.

Fungal mycelia were washed using 1 mL 10 mM $MgCl_2$ twice in microfuge tubes. Samples were centrifuged at 16,110 RPM at room temperature for 3 minutes and the solution decanted. The residual solution was pipetted out. Samples were incubated in either 0.05 mg/mL or 0.075 mg/mL Gentamicin, prepared with 50 mM Phosphate Saline Buffer, pH 7.0 for 1 hour. 0.2 mL solution was determined to be sufficient.

DNase I cocktail was prepared by the addition of 5 μL of DNase I and 5 μL 10× DNAse Buffer (DNAse I cocktail) per treatment. When five samples were being treated, a microfuge tube of 25 μL (5×5 μL) of each solution was prepared. Solutions were stored in the refrigerator (4° C.) until use.

Following incubation in the antibiotic solution, the solution was decanted. A minimum of 0.1 mL $MgCl_2$ per tube was added to thoroughly immerse the sample, and 10 μL of the DNAse I cocktail was immediately added for each sample. Samples were incubated for 15 minutes.

Proteinase K (10 mg/mL final concentration) in 10 mM $MgCl_2$ (Proteinase K cocktail) was prepared, in enough volume to add 0.2 mL/sample.

DNAse I solution was removed from the tubes after incubation time, via decanting or pipetting.

Proteinase K wash was conducted by adding at least 0.2 mL of the Proteinase K cocktail/sample and the samples were incubated for 15 minutes.

The Proteinase K solution was then pipetted out.

Samples were washed thoroughly 8 to 10 times with 10 mM $MgCl_2$ by pipetting up and down the solution during the procedure, and ensuring that all outer parts of the mycelia were being thoroughly washed.

Samples were stored in the refrigerator at 4° C. until the genomic DNA extraction of fungi was performed, followed by PCR amplification of the bacterial gene relative to control samples.

Presence or absence of bacteria in the washed fungal samples was verified by PCR using 16S rRNA gene amplification, alongside experimental control samples consisting of: (1) control samples of a known native endofungus that is washed the same way to ensure the washing does not strip away internal bacterium, (2) control samples of a known native endofungus that is untreated, and (3) untreated sample of a known non-complex endophyte fungus (fungus not known to comprise a component bacterium, SYM15890) with about 0.1 mL of pure bacterial culture at log phase added on the surface and washed the same way. PCR results were also compared to that of a control isolated bacterium.

Results are show in FIG. 5. The 16S bacterial identification sequence was detected for the control bacterium, SYM15779 before and after the gentamicin treatment and washings described in this example, as well in as the non-complex endophyte fungus SYM15890 that was spiked with the pure bacterial culture, after the gentamicin treatment and washings described in this example. The 16S bacterial identification sequence was not detected in the sample comprising non-complex endophyte fungus SYM15890 after the gentamicin treatment and washings described in this example.

Viability of the endofungal bacterium EHB15779 after gentamicin treatment and wash was confirmed in culture post-treatment: the endofungal bacteria continued to grow and was observed to come out of the fungal hyphae.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents, and patent applications cited within the body of the instant specification are hereby incorporated by reference in their entirety, for all purposes.

TABLE 1

Bacterial endofungal endophytes of the present invention

| SEQ ID | Kingdom | Phylum | Class | Order | Family | Genus |
|---|---|---|---|---|---|---|
| 1 | Bacteria | Firmicutes | Bacilli | Bacillales | Bacillaceae | *Bacillus* |
| 2 | Bacteria | Firmicutes | Bacilli | Bacillales | Bacillaceae | *Bacillus* |
| 3 | Bacteria | Firmicutes | Bacilli | Bacillales | Bacillaceae | *Bacillus* |
| 4 | Bacteria | Firmicutes | Bacilli | Bacillales | Paenibacillaceae | *Paenibacillus* |
| 5 | Bacteria | Firmicutes | Bacilli | Bacillales | Paenibacillaceae | *Paenibacillus* |
| 6 | Bacteria | Proteobacteria | Gammaproteobacteria | Pseudomonadales | Moraxellaceae | *Acinetobacter* |
| 7 | Bacteria | Proteobacteria | Betaproteobacteria | Burkholderiales | Burkholderiaceae | *Burkholderia* |
| 8 | Bacteria | Proteobacteria | Alphaproteobacteria | Sphingomonadales | Sphingomonadaceae | *Sphingomonas* |
| 9 | Bacteria | Proteobacteria | Gammaproteobacteria | Xanthomonadales | Xanthomonadaceae | *Luteibacter* |
| 10 | Bacteria | Proteobacteria | Alphaproteobacteria | Sphingomonadales | Sphingomonadaceae | *Sphingomonas* |
| 11 | Bacteria | Firmicutes | Bacilli | Bacillales | Paenibacillaceae | *Paenibacillus* |
| 12 | Bacteria | Firmicutes | Bacilli | Bacillales | Paenibacillaceae | *Paenibacillus* |
| 13 | Bacteria | Firmicutes | Bacilli | Bacillales | Paenibacillaceae | *Paenibacillus* |
| 14 | Bacteria | Proteobacteria | Betaproteobacteria | Burkholderiales | Burkholderiaceae | *Ralstonia* |
| 15 | Bacteria | Firmicutes | Bacilli | Bacillales | Bacillaceae | *Bacillus* |
| 16 | Bacteria | Proteobacteria | Betaproteobacteria | Burkholderiales | Burkholderiaceae | *Ralstonia* |
| 17 | Bacteria | Firmicutes | Bacilli | Bacillales | Paenibacillaceae | *Paenibacillus* |
| 18 | Bacteria | Firmicutes | Bacilli | Bacillales | Paenibacillaceae | *Paenibacillus* |
| 19 | Bacteria | Firmicutes | Bacilli | Bacillales | Paenibacillaceae | *Paenibacillus* |
| 20 | Bacteria | Firmicutes | Bacilli | Bacillales | Bacillaceae | *Bacillus* |
| 21 | Bacteria | Firmicutes | Bacilli | Bacillales | Paenibacillaceae | *Paenibacillus* |
| 22 | Bacteria | Firmicutes | Bacilli | Bacillales | Paenibacillaceae | *Paenibacillus* |
| 23 | Bacteria | Firmicutes | Bacilli | Bacillales | Paenibacillaceae | *Paenibacillus* |
| 24 | Bacteria | Firmicutes | Bacilli | Bacillales | Paenibacillaceae | *Paenibacillus* |
| 25 | Bacteria | Firmicutes | Bacilli | Bacillales | Paenibacillaceae | *Paenibacillus* |
| 26 | Bacteria | Firmicutes | Bacilli | Bacillales | Paenibacillaceae | *Paenibacillus* |
| 27 | Bacteria | Proteobacteria | Betaproteobacteria | Burkholderiales | Oxalobacteraceae | *Massilia* |
| 28 | Bacteria | Proteobacteria | Betaproteobacteria | Burkholderiales | Oxalobacteraceae | *Massilia* |
| 29 | Bacteria | Proteobacteria | Betaproteobacteria | Burkholderiales | Burkholderiaceae | *Ralstonia* |
| 30 | Bacteria | Proteobacteria | Gammaproteobacteria | Pseudomonadales | Moraxellaceae | *Acinetobacter* |
| 31 | Bacteria | Proteobacteria | Gammaproteobacteria | Xanthomonadales | Xanthomonadaceae | *Luteibacter* |
| 32 | Bacteria | Proteobacteria | Betaproteobacteria | Burkholderiales | Comamonadaceae | *Variovorax* |
| 33 | Bacteria | Proteobacteria | Betaproteobacteria | Burkholderiales | Burkholderiaceae | *Ralstonia* |
| 34 | Bacteria | Firmicutes | Bacilli | Bacillales | Bacillaceae | *Bacillus* |
| 35 | Bacteria | Firmicutes | Bacilli | Bacillales | Bacillaceae | *Bacillus* |
| 36 | Bacteria | Firmicutes | Bacilli | Bacillales | Paenibacillaceae | *Paenibacillus* |
| 37 | Bacteria | Firmicutes | Bacilli | Bacillales | Paenibacillaceae | *Paenibacillus* |
| 38 | Bacteria | Proteobacteria | Betaproteobacteria | Burkholderiales | Burkholderiaceae | *Burkholderia* |
| 39 | Bacteria | Firmicutes | Bacilli | Bacillales | Bacillaceae | *Bacillus* |
| 40 | Bacteria | Proteobacteria | Gammaproteobacteria | Xanthomonadales | Xanthomonadaceae | *Luteibacter* |
| 41 | Bacteria | Proteobacteria | Betaproteobacteria | Burkholderiales | Burkholderiaceae | *Ralstonia* |
| 42 | Bacteria | Firmicutes | Bacilli | Bacillales | Bacillaceae | *Bacillus* |
| 43 | Bacteria | Actinobacteria | Actinobacteria | Actinomycetales | Microbacteriaceae | *Curtobacterium* |
| 44 | Bacteria | Actinobacteria | Actinobacteria | Actinomycetales | Microbacteriaceae | *Curtobacterium* |
| 45 | Bacteria | Proteobacteria | Gammaproteobacteria | Xanthomonadales | Xanthomonadaceae | *Luteibacter* |
| 46 | Bacteria | Proteobacteria | Gammaproteobacteria | Xanthomonadales | Xanthomonadaceae | *Luteibacter* |
| 47 | Bacteria | Proteobacteria | Gammaproteobacteria | Enterobacteriales | Enterobacteriaceae | *Pantoea* |
| 48 | Bacteria | Proteobacteria | Gammaproteobacteria | Xanthomonadales | Xanthomonadaceae | *Luteibacter* |
| 49 | Bacteria | Firmicutes | Bacilli | Bacillales | Bacillaceae | *Bacillus* |
| 50 | Bacteria | Firmicutes | Bacilli | Bacillales | Bacillaceae | *Bacillus* |
| 51 | Bacteria | Firmicutes | Bacilli | Bacillales | Paenibacillaceae | *Paenibacillus* |
| 52 | Bacteria | Firmicutes | Bacilli | Bacillales | Paenibacillaceae | *Paenibacillus* |
| 53 | Bacteria | Firmicutes | Bacilli | Bacillales | Bacillaceae | *Bacillus* |
| 54 | Bacteria | Firmicutes | Bacilli | Bacillales | Bacillaceae | *Bacillus* |
| 55 | Bacteria | Proteobacteria | Gammaproteobacteria | Enterobacteriales | Enterobacteriaceae | *Pantoea* |
| 56 | Bacteria | Proteobacteria | Alphaproteobacteria | Rhizobiales | Rhizobiaceae | *Rhizobium* |
| 57 | Bacteria | Proteobacteria | Gammaproteobacteria | Enterobacteriales | Enterobacteriaceae | *Pantoea* |
| 58 | Bacteria | Proteobacteria | Gammaproteobacteria | Xanthomonadales | Xanthomonadaceae | *Luteibacter* |
| 59 | Bacteria | Proteobacteria | Gammaproteobacteria | Xanthomonadales | Xanthomonadaceae | *Luteibacter* |
| 60 | Bacteria | Proteobacteria | Gammaproteobacteria | Xanthomonadales | Xanthomonadaceae | *Luteibacter* |
| 61 | Bacteria | Proteobacteria | Gammaproteobacteria | Xanthomonadales | Xanthomonadaceae | *Luteibacter* |
| 62 | Bacteria | Proteobacteria | Gammaproteobacteria | Enterobacteriales | Enterobacteriaceae | *Erwinia* |
| 63 | Bacteria | Proteobacteria | Gammaproteobacteria | Xanthomonadales | Xanthomonadaceae | *Luteibacter* |
| 64 | Bacteria | Proteobacteria | Gammaproteobacteria | Xanthomonadales | Xanthomonadaceae | *Luteibacter* |
| 65 | Bacteria | Proteobacteria | Gammaproteobacteria | Xanthomonadales | Xanthomonadaceae | *Luteibacter* |
| 66 | Bacteria | Proteobacteria | Gammaproteobacteria | Xanthomonadales | Xanthomonadaceae | *Luteibacter* |
| 67 | Bacteria | Proteobacteria | Gammaproteobacteria | Xanthomonadales | Xanthomonadaceae | *Luteibacter* |
| 68 | Bacteria | Proteobacteria | Gammaproteobacteria | Xanthomonadales | Xanthomonadaceae | *Luteibacter* |
| 69 | Bacteria | Proteobacteria | Gammaproteobacteria | Enterobacteriales | Enterobacteriaceae | *Erwinia* |
| 70 | Bacteria | Proteobacteria | Betaproteobacteria | Burkholderiales | Burkholderiaceae | *Ralstonia* |
| 71 | Bacteria | Proteobacteria | Gammaproteobacteria | Pseudomonadales | Pseudomonadaceae | *Pseudomonas* |

TABLE 1-continued

Bacterial endofungal endophytes of the present invention

| SEQ ID | Kingdom | Phylum | Class | Order | Family | Genus |
|---|---|---|---|---|---|---|
| 72 | Bacteria | Proteobacteria | Alphaproteobacteria | Caulobacterales | Caulobacteraceae | *Caulobacter* |
| 73 | Bacteria | Proteobacteria | Alphaproteobacteria | Caulobacterales | Caulobacteraceae | *Caulobacter* |
| 74 | Bacteria | Proteobacteria | Gammaproteobacteria | Pseudomonadales | Pseudomonadaceae | *Pseudomonas* |
| 75 | Bacteria | Proteobacteria | Gammaproteobacteria | Xanthomonadales | Xanthomonadaceae | *Stenotrophomonas* |
| 76 | Bacteria | Proteobacteria | Gammaproteobacteria | Pseudomonadales | Pseudomonadaceae | *Pseudomonas* |
| 77 | Bacteria | Proteobacteria | Gammaproteobacteria | Pseudomonadales | Pseudomonadaceae | *Pseudomonas* |
| 78 | Bacteria | Bacteroidetes | Cytophagia | Cytophagales | Cytophagaceae | *Hymenobacter* |
| 79 | Bacteria | Proteobacteria | Gammaproteobacteria | Pseudomonadales | Pseudomonadaceae | *Pseudomonas* |
| 80 | Bacteria | Proteobacteria | Gammaproteobacteria | Pseudomonadales | Pseudomonadaceae | *Pseudomonas* |
| 81 | Bacteria | Proteobacteria | Gammaproteobacteria | Pseudomonadales | Pseudomonadaceae | *Pseudomonas* |
| 82 | Bacteria | Proteobacteria | Gammaproteobacteria | Pseudomonadales | Pseudomonadaceae | *Pseudomonas* |
| 83 | Bacteria | Proteobacteria | Gammaproteobacteria | Pseudomonadales | Pseudomonadaceae | *Pseudomonas* |
| 84 | Bacteria | Proteobacteria | Betaproteobacteria | Burkholderiales | Comamonadaceae | *Pelomonas* |
| 85 | Bacteria | Proteobacteria | Alphaproteobacteria | Sphingomonadales | Sphingomonadaceae | *Sphingomonas* |
| 86 | Bacteria | Proteobacteria | Gammaproteobacteria | Pseudomonadales | Pseudomonadaceae | *Pseudomonas* |
| 87 | Bacteria | Proteobacteria | Gammaproteobacteria | Pseudomonadales | Pseudomonadaceae | *Pseudomonas* |
| 88 | Bacteria | Proteobacteria | Gammaproteobacteria | Pseudomonadales | Pseudomonadaceae | *Pseudomonas* |
| 89 | Bacteria | Proteobacteria | Gammaproteobacteria | Pseudomonadales | Pseudomonadaceae | *Pseudomonas* |
| 90 | Bacteria | Proteobacteria | Gammaproteobacteria | Pseudomonadales | Pseudomonadaceae | *Pseudomonas* |
| 91 | Bacteria | Proteobacteria | Gammaproteobacteria | Pseudomonadales | Pseudomonadaceae | *Pseudomonas* |
| 92 | Bacteria | Proteobacteria | Gammaproteobacteria | Pseudomonadales | Pseudomonadaceae | *Pseudomonas* |
| 93 | Bacteria | Proteobacteria | Gammaproteobacteria | Pseudomonadales | Pseudomonadaceae | *Pseudomonas* |
| 94 | Bacteria | Proteobacteria | Gammaproteobacteria | Pseudomonadales | Pseudomonadaceae | *Pseudomonas* |
| 95 | Bacteria | Proteobacteria | Gammaproteobacteria | Pseudomonadales | Pseudomonadaceae | *Pseudomonas* |
| 96 | Bacteria | Proteobacteria | Alphaproteobacteria | Sphingomonadales | Sphingomonadaceae | *Sphingomonas* |
| 97 | Bacteria | Proteobacteria | Gammaproteobacteria | Pseudomonadales | Pseudomonadaceae | *Pseudomonas* |
| 98 | Bacteria | Proteobacteria | Gammaproteobacteria | Pseudomonadales | Pseudomonadaceae | *Pseudomonas* |
| 99 | Bacteria | Proteobacteria | Gammaproteobacteria | Pseudomonadales | Pseudomonadaceae | *Pseudomonas* |
| 100 | Bacteria | Proteobacteria | Gammaproteobacteria | Pseudomonadales | Pseudomonadaceae | *Pseudomonas* |
| 101 | Bacteria | Proteobacteria | Gammaproteobacteria | Pseudomonadales | Pseudomonadaceae | *Pseudomonas* |
| 102 | Bacteria | Proteobacteria | Gammaproteobacteria | Pseudomonadales | Pseudomonadaceae | *Pseudomonas* |
| 103 | Bacteria | Proteobacteria | Gammaproteobacteria | Pseudomonadales | Pseudomonadaceae | *Pseudomonas* |
| 104 | Bacteria | Proteobacteria | Gammaproteobacteria | Pseudomonadales | Pseudomonadaceae | *Pseudomonas* |
| 105 | Bacteria | Actinobacteria | Actinobacteria | Actinomycetales | Nocardiaceae | *Rhodococcus* |
| 106 | Bacteria | Proteobacteria | Gammaproteobacteria | Pseudomonadales | Moraxellaceae | *Enhydrobacter* |
| 107 | Bacteria | Proteobacteria | Gammaproteobacteria | Pseudomonadales | Moraxellaceae | *Enhydrobacter* |
| 108 | Bacteria | Proteobacteria | Gammaproteobacteria | Pseudomonadales | Moraxellaceae | *Perlucidibaca* |
| 109 | Bacteria | Proteobacteria | Gammaproteobacteria | Xanthomonadales | Xanthomonadaceae | *Dyella* |
| 110 | Bacteria | Proteobacteria | Gammaproteobacteria | Enterobacteriales | Enterobacteriaceae | *Escherichia/Shigella* |
| 111 | Bacteria | Proteobacteria | Betaproteobacteria | Burkholderiales | Comamonadaceae | *Delftia* |
| 112 | Bacteria | Proteobacteria | Alphaproteobacteria | Rhizobiales | Bradyrhizobiaceae | *Oligotropha* |
| 113 | Bacteria | Actinobacteria | Actinobacteria | Actinomycetales | Microbacteriaceae | *Microbacterium* |
| 114 | Bacteria | Proteobacteria | Betaproteobacteria | Burkholderiales | Oxalobacteraceae | *Massilia* |
| 115 | Bacteria | Actinobacteria | Actinobacteria | Actinomycetales | Propionibacteriaceae | *Propionibacterium* |
| 116 | Bacteria | Actinobacteria | Actinobacteria | Actinomycetales | Microbacteriaceae | *Okibacterium* |
| 117 | Bacteria | Actinobacteria | Actinobacteria | Actinomycetales | Microbacteriaceae | *Microbacterium* |
| 118 | Bacteria | Actinobacteria | Actinobacteria | Actinomycetales | Microbacteriaceae | *Microbacterium* |
| 119 | Bacteria | Actinobacteria | Actinobacteria | Actinomycetales | Microbacteriaceae | *Microbacterium* |
| 120 | Bacteria | Bacteroidetes | Flavobacteriia | Flavobacteriales | Flavobacteriaceae | *Chryseobacterium* |
| 121 | Bacteria | Proteobacteria | Betaproteobacteria | Burkholderiales | Oxalobacteraceae | *Herbaspirillum* |
| 122 | Bacteria | Bacteroidetes | Flavobacteriia | Flavobacteriales | Flavobacteriaceae | *Chryseobacterium* |
| 123 | Bacteria | Proteobacteria | Alphaproteobacteria | Rhizobiales | Rhizobiaceae | *Rhizobium* |
| 124 | Bacteria | Proteobacteria | Alphaproteobacteria | Rhizobiales | Phyllobacteriaceae | *Mesorhizobium* |
| 125 | Bacteria | Proteobacteria | Alphaproteobacteria | Rhizobiales | Bradyrhizobiaceae | *Rhodopseudomonas* |
| 126 | Bacteria | Proteobacteria | Betaproteobacteria | Burkholderiales | Burkholderiaceae | *Burkholderia* |
| 127 | Bacteria | Proteobacteria | Betaproteobacteria | Burkholderiales | Oxalobacteraceae | *Herbaspirillum* |
| 128 | Archaea | Crenarchaeota | Thermoprotei | Sulfolobales | Sulfolobaceae | *Sulfurisphaera* |
| 129 | Bacteria | Proteobacteria | Gammaproteobacteria | Enterobacteriales | Enterobacteriaceae | *Kosakonia* |
| 130 | Bacteria | Actinobacteria | Actinobacteria | Actinomycetales | Streptomycetaceae | *Streptomyces* |
| 131 | Bacteria | Fusobacteria | Fusobacteriia | Fusobacteriales | Leptotrichiaceae | *Sebaldella* |
| 132 | Bacteria | Actinobacteria | Actinobacteria | Actinomycetales | Microbacteriaceae | *Curtobacterium* |
| 133 | Bacteria | Proteobacteria | Gammaproteobacteria | Pseudomonadales | Moraxellaceae | *Enhydrobacter* |
| 134 | Bacteria | Proteobacteria | Alphaproteobacteria | Sphingomonadales | Sphingomonadaceae | *Sphingomonas* |
| 135 | Bacteria | Proteobacteria | Alphaproteobacteria | Sphingomonadales | Sphingomonadaceae | *Sphingomonas* |
| 136 | Bacteria | Actinobacteria | Actinobacteria | Actinomycetales | Micromonosporaceae | *Actinoplanes* |
| 137 | Bacteria | Proteobacteria | Alphaproteobacteria | Rhizobiales | Beijerinckiaceae | *Beijerinckia* |
| 138 | Bacteria | Proteobacteria | Gammaproteobacteria | Enterobacteriales | Enterobacteriaceae | *Erwinia* |
| 139 | Bacteria | Proteobacteria | Alphaproteobacteria | Rhizobiales | Bradyrhizobiaceae | *Bradyrhizobium* |
| 140 | Bacteria | Proteobacteria | Alphaproteobacteria | Rhizobiales | Bradyrhizobiaceae | *Bradyrhizobium* |
| 141 | Bacteria | Proteobacteria | Alphaproteobacteria | Rhizobiales | Bradyrhizobiaceae | *Bradyrhizobium* |
| 142 | Bacteria | Proteobacteria | Alphaproteobacteria | Rhizobiales | Bradyrhizobiaceae | *Bradyrhizobium* |
| 143 | Bacteria | Proteobacteria | Alphaproteobacteria | Rhizobiales | Bradyrhizobiaceae | *Bradyrhizobium* |
| 144 | Bacteria | Proteobacteria | Alphaproteobacteria | Rhizobiales | Bradyrhizobiaceae | *Bradyrhizobium* |
| 145 | Bacteria | Proteobacteria | Alphaproteobacteria | Rhizobiales | Bradyrhizobiaceae | *Bradyrhizobium* |
| 146 | Bacteria | Proteobacteria | Alphaproteobacteria | Rhizobiales | Bradyrhizobiaceae | *Bradyrhizobium* |
| 147 | Bacteria | Actinobacteria | Actinobacteria | Actinomycetales | Intrasporangiaceae | *Oryzihumus* |

TABLE 1-continued

Bacterial endofungal endophytes of the present invention

| SEQ ID | Kingdom | Phylum | Class | Order | Family | Genus |
|---|---|---|---|---|---|---|
| 148 | Bacteria | Actinobacteria | Actinobacteria | Coriobacteriales | Coriobacteriaceae | *Adlercreutzia* |
| 149 | Bacteria | Proteobacteria | Betaproteobacteria | Burkholderiales | Comamonadaceae | *Variovorax* |
| 150 | Bacteria | Proteobacteria | Alphaproteobacteria | Rhizobiales | Phyllobacteriaceae | *Mesorhizobium* |
| 151 | Bacteria | Firmicutes | Bacilli | Bacillales | Incertae Sedis XII | *Exiguobacterium* |
| 152 | Bacteria | Firmicutes | Bacilli | Bacillales | Incertae Sedis XII | *Exiguobacterium* |
| 153 | Bacteria | Actinobacteria | Actinobacteria | Actinomycetales | incertae_sedis | *Sinosporangium* |
| 154 | Bacteria | Firmicutes | Bacilli | Bacillales | Staphylococcaceae | *Staphylococcus* |
| 155 | Bacteria | Firmicutes | Bacilli | Bacillales | Staphylococcaceae | *Staphylococcus* |
| 156 | Bacteria | Actinobacteria | Actinobacteria | Actinomycetales | incertae_sedis | *Sinosporangium* |
| 157 | Bacteria | Firmicutes | Bacilli | Bacillales | Bacillaceae | *Bacillus* |
| 158 | Bacteria | Firmicutes | Bacilli | Bacillales | Bacillaceae | *Bacillus* |
| 159 | Bacteria | Proteobacteria | Betaproteobacteria | Burkholderiales | Comamonadaceae | *Variovorax* |
| 160 | Bacteria | Proteobacteria | Betaproteobacteria | Burkholderiales | Comamonadaceae | *Variovorax* |
| 161 | Archaea | Crenarchaeota | Thermoprotei | Sulfolobales | Sulfolobaceae | *Stygiolobus* |
| 162 | Bacteria | Proteobacteria | Betaproteobacteria | Burkholderiales | Comamonadaceae | *Variovorax* |
| 163 | Bacteria | Proteobacteria | Alphaproteobacteria | Rhizobiales | Bradyrhizobiaceae | *Bradyrhizobium* |
| 164 | Bacteria | Proteobacteria | Alphaproteobacteria | Rhizobiales | Bradyrhizobiaceae | *Bradyrhizobium* |
| 165 | Bacteria | Firmicutes | Bacilli | Lactobacillales | Carnobacteriaceae | *Atopostipes* |
| 166 | Bacteria | Firmicutes | Bacilli | Lactobacillales | Carnobacteriaceae | *Atopostipes* |
| 167 | Bacteria | Proteobacteria | Gammaproteobacteria | Enterobacteriales | Enterobacteriaceae | *Serratia* |
| 168 | Bacteria | Proteobacteria | Gammaproteobacteria | Enterobacteriales | Enterobacteriaceae | *Serratia* |
| 169 | Archaea | Crenarchaeota | Thermoprotei | Sulfolobales | Sulfolobaceae | *Sulfurisphaera* |
| 170 | Bacteria | Verrucomicrobia | Opitutae | Puniceicoccales | Puniceicoccaceae | *Coraliomargarita* |
| 171 | Bacteria | Proteobacteria | Gammaproteobacteria | Enterobacteriales | Enterobacteriaceae | *Enterobacter* |
| 172 | Bacteria | Proteobacteria | Gammaproteobacteria | Enterobacteriales | Enterobacteriaceae | *Serratia* |
| 173 | Archaea | Euryarchaeota | Halobacteria | Halobacteriales | Halobacteriaceae | *Halobaculum* |
| 174 | Archaea | Euryarchaeota | Halobacteria | Halobacteriales | Halobacteriaceae | *Halosimplex* |
| 175 | Bacteria | Proteobacteria | Gammaproteobacteria | Xanthomonadales | Xanthomonadaceae | *Luteibacter* |
| 176 | Bacteria | Proteobacteria | Gammaproteobacteria | Xanthomonadales | Xanthomonadaceae | *Luteibacter* |
| 177 | Bacteria | Actinobacteria | Actinobacteria | Actinomycetales | Microbacteriaceae | *Pseudoclavibacter* |
| 178 | Bacteria | Actinobacteria | Actinobacteria | Actinomycetales | Microbacteriaceae | *Zimmermannella* |
| 179 | Bacteria | Proteobacteria | Gammaproteobacteria | Enterobacteriales | Enterobacteriaceae | *Serratia* |
| 180 | Bacteria | Proteobacteria | Gammaproteobacteria | Enterobacteriales | Enterobacteriaceae | *Serratia* |
| 181 | Bacteria | Proteobacteria | Gammaproteobacteria | Enterobacteriales | Enterobacteriaceae | *Serratia* |
| 182 | Bacteria | Proteobacteria | Gammaproteobacteria | Enterobacteriales | Enterobacteriaceae | *Serratia* |
| 183 | Bacteria | Proteobacteria | Gammaproteobacteria | Enterobacteriales | Enterobacteriaceae | *Serratia* |
| 184 | Bacteria | Proteobacteria | Gammaproteobacteria | Enterobacteriales | Enterobacteriaceae | *Serratia* |
| 185 | Bacteria | Proteobacteria | Gammaproteobacteria | Enterobacteriales | Enterobacteriaceae | *Serratia* |
| 186 | Bacteria | Proteobacteria | Gammaproteobacteria | Enterobacteriales | Enterobacteriaceae | *Serratia* |
| 187 | Bacteria | Proteobacteria | Gammaproteobacteria | Enterobacteriales | Enterobacteriaceae | *Serratia* |
| 188 | Bacteria | Proteobacteria | Gammaproteobacteria | Enterobacteriales | Enterobacteriaceae | *Serratia* |
| 189 | Bacteria | Proteobacteria | Gammaproteobacteria | Enterobacteriales | Enterobacteriaceae | *Serratia* |
| 190 | Bacteria | Proteobacteria | Betaproteobacteria | Burkholderiales | Comamonadaceae | *Variovorax* |
| 191 | Bacteria | Proteobacteria | Betaproteobacteria | Burkholderiales | Comamonadaceae | *Variovorax* |
| 192 | Bacteria | Firmicutes | Bacilli | Bacillales | Bacillaceae | *Bacillus* |
| 193 | Archaea | Nanohaloarchaeota | Nanohaloarchaea | Incertae sedis | Incertae sedis | *Candidatus Haloredivivus* |
| 194 | Archaea | Euryarchaeota | Archaeoglobi | Archaeoglobales | Archaeoglobaceae | *Ferroglobus* |
| 195 | Bacteria | Proteobacteria | Gammaproteobacteria | Xanthomonadales | Xanthomonadaceae | *Luteibacter* |
| 196 | Bacteria | Proteobacteria | Gammaproteobacteria | Xanthomonadales | Xanthomonadaceae | *Luteibacter* |
| 197 | Archaea | Nanohaloarchaeota | Nanohaloarchaea | Incertae sedis | Incertae sedis | *Candidatus Haloredivivus* |
| 198 | Archaea | Euryarchaeota | Archaeoglobi | Archaeoglobales | Archaeoglobaceae | *Ferroglobus* |
| 199 | Bacteria | Actinobacteria | Actinobacteria | Actinomycetales | Propionibacteriaceae | *Propionibacterium* |
| 200 | Bacteria | Proteobacteria | Alphaproteobacteria | Rhizobiales | Bradyrhizobiaceae | *Bradyrhizobium* |
| 201 | Bacteria | Proteobacteria | Alphaproteobacteria | Rhizobiales | Bradyrhizobiaceae | *Bradyrhizobium* |
| 202 | Bacteria | Firmicutes | Bacilli | Lactobacillales | Streptococcaceae | *Streptococcus* |
| 203 | Bacteria | Firmicutes | Bacilli | Lactobacillales | Streptococcaceae | *Streptococcus* |
| 204 | Bacteria | Firmicutes | Bacilli | Lactobacillales | Streptococcaceae | *Streptococcus* |
| 205 | Bacteria | Firmicutes | Bacilli | Lactobacillales | Streptococcaceae | *Streptococcus* |
| 206 | Bacteria | candidate division WPS-2 | Incertae sedis | Incertae sedis | Incertae sedis | WPS-2_genera_incertae_sedis |
| 207 | Bacteria | Proteobacteria | Alphaproteobacteria | Rhizobiales | Bradyrhizobiaceae | *Afipia* |
| 208 | Bacteria | Proteobacteria | Alphaproteobacteria | Rhizobiales | Bradyrhizobiaceae | *Rhodopseudomonas* |
| 209 | Bacteria | Firmicutes | Bacilli | Lactobacillales | Streptococcaceae | *Streptococcus* |
| 210 | Bacteria | Firmicutes | Bacilli | Lactobacillales | Streptococcaceae | *Streptococcus* |
| 211 | Bacteria | Cyanobacteria | Incertae sedis | Incertae sedis | Incertae sedis | *Incertae sedis* |
| 212 | Bacteria | Cyanobacteria | Incertae sedis | Incertae sedis | Incertae sedis | *Incertae sedis* |
| 213 | Bacteria | Proteobacteria | Gammaproteobacteria | Pseudomonadales | Pseudomonadaceae | *Pseudomonas* |
| 214 | Bacteria | Proteobacteria | Gammaproteobacteria | Pseudomonadales | Pseudomonadaceae | *Pseudomonas* |
| 215 | Bacteria | Firmicutes | Bacilli | Lactobacillales | Lactobacillaceae | *Lactobacillus* |
| 216 | Bacteria | Firmicutes | Bacilli | Lactobacillales | Lactobacillaceae | *Lactobacillus* |
| 217 | Bacteria | Cyanobacteria | Incertae sedis | Incertae sedis | Incertae sedis | *Incertae sedis* |
| 218 | Bacteria | Cyanobacteria | Incertae sedis | Incertae sedis | Incertae sedis | *Incertae sedis* |
| 219 | Bacteria | Firmicutes | Bacilli | Lactobacillales | Streptococcaceae | *Streptococcus* |
| 220 | Bacteria | Firmicutes | Bacilli | Lactobacillales | Streptococcaceae | *Streptococcus* |
| 221 | Bacteria | Proteobacteria | Alphaproteobacteria | Rhizobiales | Rhizobiaceae | *Rhizobium* |
| 222 | Bacteria | Proteobacteria | Alphaproteobacteria | Rhizobiales | Rhizobiaceae | *Rhizobium* |
| 223 | Bacteria | Proteobacteria | Alphaproteobacteria | Rhizobiales | Rhizobiaceae | *Rhizobium* |

TABLE 1-continued

Bacterial endofungal endophytes of the present invention

| SEQ ID | Kingdom | Phylum | Class | Order | Family | Genus |
|---|---|---|---|---|---|---|
| 224 | Bacteria | Proteobacteria | Alphaproteobacteria | Rhizobiales | Rhizobiaceae | *Rhizobium* |
| 225 | Bacteria | Firmicutes | Bacilli | Lactobacillales | Streptococcaceae | *Streptococcus* |
| 226 | Bacteria | Firmicutes | Bacilli | Lactobacillales | Streptococcaceae | *Streptococcus* |
| 227 | Bacteria | Proteobacteria | Alphaproteobacteria | Rhizobiales | Bradyrhizobiaceae | *Bradyrhizobium* |
| 228 | Bacteria | Proteobacteria | Alphaproteobacteria | Rhizobiales | Bradyrhizobiaceae | *Bradyrhizobium* |
| 229 | Bacteria | Proteobacteria | Alphaproteobacteria | Rhizobiales | Rhizobiaceae | *Rhizobium* |
| 230 | Bacteria | Proteobacteria | Alphaproteobacteria | Rhizobiales | Rhizobiaceae | *Rhizobium* |
| 231 | Bacteria | Proteobacteria | Betaproteobacteria | Burkholderiales | Burkholderiaceae | *Polynucleobacter* |
| 232 | Bacteria | Proteobacteria | Betaproteobacteria | Burkholderiales | Burkholderiaceae | *Polynucleobacter* |
| 233 | Bacteria | Proteobacteria | Alphaproteobacteria | Rhizobiales | Rhizobiaceae | *Rhizobium* |
| 234 | Bacteria | Bacteroidetes | Sphingobacteriia | Sphingobacteriales | Chitinophagaceae | *Filimonas* |
| 235 | Bacteria | Bacteroidetes | Sphingobacteriia | Sphingobacteriales | Chitinophagaceae | *Filimonas* |
| 236 | Bacteria | Bacteroidetes | Sphingobacteriia | Sphingobacteriales | Chitinophagaceae | *Filimonas* |
| 237 | Bacteria | Proteobacteria | Gammaproteobacteria | Xanthomonadales | Xanthomonadaceae | *Dyella* |
| 238 | Bacteria | Proteobacteria | Gammaproteobacteria | Enterobacteriales | Enterobacteriaceae | *Pantoea* |
| 239 | Bacteria | Proteobacteria | Gammaproteobacteria | Xanthomonadales | Xanthomonadaceae | *Luteibacter* |
| 240 | Bacteria | Proteobacteria | Gammaproteobacteria | Xanthomonadales | Xanthomonadaceae | *Dyella* |
| 241 | Bacteria | Proteobacteria | Gammaproteobacteria | Xanthomonadales | Xanthomonadaceae | *Luteibacter* |
| 242 | Bacteria | Proteobacteria | Betaproteobacteria | Burkholderiales | Burkholderiaceae | *Ralstonia* |
| 243 | Bacteria | Proteobacteria | Gammaproteobacteria | Enterobacteriales | Enterobacteriaceae | *Erwinia* |
| 244 | Bacteria | Firmicutes | Bacilli | Bacillales | Bacillaceae | *Bacillus* |
| 245 | Bacteria | Firmicutes | Bacilli | Bacillales | Bacillaceae | *Bacillus* |
| 246 | Bacteria | Firmicutes | Bacilli | Bacillales | Bacillaceae | *Bacillus* |
| 247 | Bacteria | Firmicutes | Bacilli | Bacillales | Bacillaceae | *Bacillus* |
| 248 | Bacteria | Firmicutes | Bacilli | Bacillales | Paenibacillaceae | *Paenibacillus* |
| 249 | Bacteria | Proteobacteria | Gammaproteobacteria | Enterobacteriales | Enterobacteriaceae | *Pantoea* |

TABLE 2

Fungal host endophytes of the present invention

| SEQ ID | Kingdom | Phylum | Class | Order | Family | Genus |
|---|---|---|---|---|---|---|
| 250 | Fungi | Ascomycota | Pezizomycotina | Sordariomycetes | Xylariomycetidae | *Pestalotiopsis* |
| 251 | Fungi | Ascomycota | Eurotiomycetes | Chaetothyriales | Herpotrichiellaceae | *Phaeomoniella* |
| 252 | Fungi | Ascomycota | Sordariomycetes | Sordariomycetes | Xylariomycetidae | *Biscogniauxia* |
| 253 | Fungi | Ascomycota | Eurotiomycetes | Chaetothyriales | Herpotrichiellaceae | *Phaeomoniella* |
| 254 | Fungi | Ascomycota | Sordariomycetes | Sordariomycetes unidentified | Sordariomycetes unidentified | *Sordariomycetes* unidentified |
| 255 | Fungi | Ascomycota | Eurotiomycetes | Chaetothyriales | Chaetothyriales unidentified | *Chaetothyriales* unidentified |
| 256 | Fungi | Ascomycota | Dothideomycetes | Pleosporales | Incertae sedis | *Phoma* |
| 257 | Fungi | Ascomycota | Dothideomycetes | Pleosporales | Pleosporaceae | *Alternaria* |
| 258 | Fungi | Ascomycota | Dothideomycetes | Dothideales | Dothioraceae | *Aureobasidium* |
| 259 | Fungi | Ascomycota | Sordariomycetes | Coniochaetales | Coniochaetaceae | *Lecythophora* |
| 260 | Fungi | Ascomycota | Dothideomycetes | Dothideales | Dothioraceae | *Hormonema* |
| 261 | Fungi | Ascomycota | Dothideomycetes | Pleosporales | Sporormiaceae | *Preussia* |
| 262 | Fungi | Ascomycota | Sordariomycetes | Coniochaetales | Coniochaetaceae | *Lecythophora* |
| 263 | Fungi | Ascomycota | Dothideomycetes | Incertae sedis | Incertae sedis | *Monodictys* |
| 264 | Fungi | Ascomycota | Sordariomycetes | Xylariales | Amphisphaeriaceae | *Pestalotiopsis* |
| 265 | Fungi | Ascomycota | Dothideomycetes | Capnodiales | Mycosphaerellaceae | *Cladosporium* |
| 266 | Fungi | Ascomycota | Dothideomycetes | Botryosphaeriales | Botryosphaeriaceae | *Botryosphaeria* |
| 267 | Fungi | Ascomycota | Dothideomycetes | Botryosphaeriales | Botryosphaeriaceae | *Phyllosticta* |
| 268 | Fungi | Ascomycota | Dothideomycetes | Pleosporales | Montagnulaceae | *Paraconiothyrium* |
| 269 | Fungi | Ascomycota | Sordariomycetes | Xylariales | Amphisphaeriaceae | *Pestalotiopsis* |
| 270 | Fungi | Ascomycota | Dothideomycetes | Pleosporales | Montagnulaceae | *Paraconiothyrium* |
| 271 | Fungi | Ascomycota | Eurotiomycetes | Eurotiales | Trichocomaceae | *Penicillium* |
| 272 | Fungi | Ascomycota | Sordariomycetes | Xylariales | Xylariaceae | *Xylariaceae* unidentified |
| 273 | Fungi | Ascomycota | Sordariomycetes | Xylariales | Xylariaceae | *Xylariaceae* unidentified |
| 274 | Fungi | Ascomycota | Sordariomycetes | Sordariomycetes unidentified | Sordariomycetes unidentified | *Sordariomycetes* unidentified |
| 275 | Fungi | Ascomycota | Sordariomycetes | Xylariales | Xylariaceae | *Xylariaceae* unidentified |
| 276 | Fungi | Ascomycota | Sordariomycetes | Xylariales | Xylariaceae | *Xylariaceae* unidentified |
| 277 | Fungi | Ascomycota | Sordariomycetes | Hypocreales | Nectriaceae | *Fusarium* |
| 278 | Fungi | Ascomycota | Sordariomycetes | Hypocreales | Nectriaceae | *Fusarium* |
| 279 | Fungi | Ascomycota | Sordariomycetes | Hypocreales | Nectriaceae | *Fusarium* |
| 280 | Fungi | Ascomycota | Sordariomycetes | Hypocreales | Nectriaceae | *Nectria* |
| 281 | Fungi | Ascomycota | Sordariomycetes | Hypocreales | Nectriaceae | *Fusarium* |
| 282 | Fungi | Ascomycota | Sordariomycetes | Xylariales | Xylariaceae | *Xylaria* |
| 283 | Fungi | Ascomycota | Sordariomycetes | Xylariales | Xylariaceae | *Hypoxylon* |
| 284 | Fungi | Ascomycota | Sordariomycetes | Hypocreales | Nectriaceae | *Fusarium* |
| 285 | Fungi | Ascomycota | Sordariomycetes | Xylariales | Xylariaceae | *Xylaria* |
| 286 | Fungi | Ascomycota | Sordariomycetes | Xylariales | Xylariaceae | *Xylaria* |
| 287 | Fungi | Ascomycota | Sordariomycetes | Hypocreales | Nectriaceae | *Fusarium* |
| 288 | Fungi | Ascomycota | Dothideomycetes | Pleosporales | Sporormiaceae | *Preussia* |
| 289 | Fungi | Ascomycota | Dothideomycetes | Pleosporales | Sporormiaceae | *Preussia* |

TABLE 2-continued

Fungal host endophytes of the present invention

| SEQ ID | Kingdom | Phylum | Class | Order | Family | Genus |
|---|---|---|---|---|---|---|
| 290 | Fungi | Ascomycota | Dothideomycetes | Pleosporales | Sporormiaceae | *Preussia* |
| 291 | Fungi | Ascomycota | Sordariomycetes | Hypocreales | Nectriaceae | *Fusarium* |
| 292 | Fungi | Ascomycota | Sordariomycetes | Hypocreales | Nectriaceae | *Fusarium* |
| 293 | Fungi | Ascomycota | Sordariomycetes | Hypocreales | Nectriaceae | *Fusarium* |
| 294 | Fungi | Ascomycota | Dothideomycetes | Pleosporales | Sporormiaceae | *Preussia* |
| 295 | Fungi | Ascomycota | Dothideomycetes | Pleosporales | Montagnulaceae | *Paraconiothyrium* |
| 296 | Fungi | Ascomycota | Dothideomycetes | Pleosporales | Montagnulaceae | *Paraconiothyrium* |
| 297 | Fungi | Ascomycota | Dothideomycetes | Pleosporales | Pleosporales unidentified | *Pleosporales* unidentified |
| 298 | Fungi | Ascomycota | Sordariomycetes | Coniochaetales | Coniochaetaceae | *Lecythophora* |
| 299 | Fungi | Ascomycota | Dothideomycetes | Pleosporales | Incertae sedis | *Phoma* |
| 300 | Fungi | Ascomycota | Sordariomycetes | Sordariales | Sordariaceae | *Neurospora* |
| 301 | Fungi | Ascomycota | Dothideomycetes | Dothideomycetes unidentified | Dothideomycetes unidentified | *Dothideomycetes* unidentified |
| 302 | Fungi | Ascomycota | Dothideomycetes | Capnodiales | Davidiellaceae | *Cladosporium* |
| 303 | Fungi | Ascomycota | Dothideomycetes | Pleosporales | Sporormiaceae | *Preussia* |
| 304 | Fungi | Ascomycota | Dothideomycetes | Capnodiales | Davidiellaceae | *Cladosporium* |
| 305 | Fungi | Ascomycota | Dothideomycetes | Pleosporales | Pleosporales Incertae sedis | *Periconia* |
| 306 | Fungi | Ascomycota | Dothideomycetes | Pleosporales | Pleosporales Incertae sedis | *Periconia* |
| 307 | Fungi | Ascomycota | Dothideomycetes | Pleosporales | Pleosporaceae | *Alternaria* |
| 308 | Fungi | Ascomycota | Dothideomycetes | Pleosporales | Pleosporales Incertae sedis | *Periconia* |
| 309 | Fungi | Ascomycota | Dothideomycetes | Pleosporales | Pleosporaceae | *Alternaria* |
| 310 | Fungi | Ascomycota | Dothideomycetes | Pleosporales | Pleosporales Incertae sedis | *Periconia* |
| 311 | Fungi | Ascomycota | Dothideomycetes | Capnodiales | Davidiellaceae | *Cladosporium* |
| 312 | Fungi | Ascomycota | Dothideomycetes | Dothideales | Dothideales unidentified | *Dothideales* unidentified |
| 313 | Fungi | Ascomycota | Dothideomycetes | Pleosporales | Leptosphaeriaceae | *Coniothyrium* |
| 314 | Fungi | Ascomycota | Dothideomycetes | Pleosporales | Pleosporaceae | *Alternaria* |
| 315 | Fungi | Ascomycota | Dothideomycetes | Pleosporales | Pleosporaceae | *Alternaria* |
| 316 | Fungi | Ascomycota | Dothideomycetes | Pleosporales | Pleosporales Incertae sedis | *Periconia* |
| 317 | Fungi | Ascomycota | Dothideomycetes | Pleosporales | Pleosporales Incertae sedis | *Periconia* |
| 318 | Fungi | Ascomycota | Dothideomycetes | Capnodiales | Davidiellaceae | *Cladosporium* |
| 319 | Fungi | Ascomycota | Dothideomycetes | Pleosporales | Pleosporaceae | *Alternaria* |
| 320 | Fungi | Ascomycota | Dothideomycetes | Pleosporales | Pleosporales Incertae sedis | *Periconia* |
| 321 | Fungi | Ascomycota | Dothideomycetes | Pleosporales | Sporormiaceae | *Preussia* |
| 322 | Fungi | Ascomycota | Dothideomycetes | Pleosporales | Sporormiaceae | *Sporormiaceae* unidentified |
| 323 | Fungi | Ascomycota | Dothideomycetes | Pleosporales | Sporormiaceae | *Preussia* |
| 324 | Fungi | Ascomycota | Dothideomycetes | Pleosporales | Sporormiaceae | *Preussia* |
| 325 | Fungi | Ascomycota | Dothideomycetes | Botryosphaeriales | Botryosphaeriaceae | *Botryosphaeria* |
| 326 | Fungi | Ascomycota | Dothideomycetes | Botryosphaeriales | Botryosphaeriaceae | *Microdiplodia* |
| 327 | Fungi | Ascomycota | Sordariomycetes | Xylariales | Amphisphaeriaceae | *Pestalotiposis* |
| 328 | Fungi | Ascomycota | Dothideomycetes | Botryosphaeriales | Botryosphaeriaceae | *Phyllosticta* |
| 329 | Fungi | Ascomycota | Dothideomycetes | Pleosporales | Pleosporaceae | *Alternaria* |
| 330 | Fungi | Ascomycota | Sordariomycetes | Coniochaetales | Coniochaetaceae | *Lecythophora* |
| 331 | Fungi | Ascomycota | Dothideomycetes | Botryosphaeriales | Botryosphaeriaceae | *Microdiplodia* |
| 332 | Fungi | Ascomycota | Sordariomycetes | Xylariales | Xylariaceae | *Daldinia* |
| 333 | Fungi | Zygomycota | Mucoromycotina | Mucorales | Mucoraceae | *Mucor* |

TABLE 3

Examples of Complex Endophytes
The following fungi and associated bacteria are examples of complex endophytes.
These complex endophytes and their components are contemplated to be examples of useful compositions of the present invention.

| Fungal Host | Endofungal Bacterium | Reference |
|---|---|---|
| *Rhizopus microsporus* | *Burkholderia rhizoxinica* | Partida-Martinez LP, Hertweck C. 2005. Pathogenic fungus harbours endosymbiotic bacteria for toxin production. Nature 437: 884-888. doi: 10.1038/nature03997 |
| *Aspergillus nidulans* | *Streptomyces rapamycinicus* | Schroeckh V, et al. (2009) Intimate bacterial-fungal interaction triggers biosynthesis of archetypal polyketides in *Aspergillus nidulans*. Proc Natl Acad Sci USA 106: 14558-14563. |
| *Gigaspora margarita* (mycorrhiza) | *Candidatus Glomeribacter gigasporarum* (related to *Burkholderia*) | Bianciotto V, Lumini E, Lanfranco L, Minerdi D, Bonfante P, et al. 2000. Detection and identification of bacterial endosymbionts in arbuscular mycorrhizal fungi belonging to the family Gigasporaceae. Appl. Environ. Microbiol. 66: 4503-9 |
| *Piriformospora indica* | *Rhizobium radiobacter* (synonym of *Agrobacterium tumefaciens*) | Sharma M, Schmid M, Rothballer M, Hause G, Zuccaro A, et al. 2008. Detection and identification of bacteria intimately associated with fungi of the order Sebacinales. Cell Microbiol. 10: 2235-46 |
| *Laccaria bicolor* | *Paenibacillus* spp. | Bertaux J, Schmid M, Prevost-Boure NC, Churin JL, Hartmann A, et al. 2003. In situ identification of intracellular bacteria related to *Paenibacillus* spp. in the mycelium of the ectomycorrhizal |

TABLE 3-continued

Examples of Complex Endophytes
The following fungi and associated bacteria are examples of complex endophytes. These complex endophytes and their components are contemplated to be examples of useful compositions of the present invention.

| Fungal Host | Endofungal Bacterium | Reference |
|---|---|---|
| | | fungus *Laccaria bicolor* S238N. Appl. Environ. Microbiol. 69: 4243-48 |
| *Tuber borchii* | *Cytophaga-Flexibacter-Bacteroides* (Cytophagales) | Barbieri E, Potenza L, Rossi I, Sisti D, Giomaro G, et al. 2000. Phylogenetic characterization and in situ detection of a *Cytophaga-Flexibacter-Bacteroides* phylogroup bacterium in *Tuber borchii* Vittad. ectomycorrhizal mycelium. Appl. Environ. Microbiol. 66: 5035-42 |
| *Pestalotiposis* sp. | *Luteibacter* sp. | Hoffman MT, Gunatilaka MK, Wijeratne K, Gunatilaka L, Arnold AE (2013) Endohyphal Bacterium Enhances Production of Indole-3-Acetic Acid by a Foliar Fungal Endophyte. PLoS ONE 8(9): e73132. doi: 10.1371/journal.pone.0073132 |
| *Mucor* sp. | *Pantoea* sp. | unpublished |

TABLE 4

Complex Endophytes and Complex Endophyte Components tested in the present invention
The following endophytes (complex endophytes and their corresponding component bacteria) were used as exemplary endophytes in the methods described in the Examples section. These complex endophytes and their components are contemplated to be examples of useful compositions of the present invention.

| ID | Description | Sequence Identifier |
|---|---|---|
| SYM16668 | Complex endophyte fungal host further comprising SYM16658 | Fungal host ITS: SEQ ID NO: 325 (Genus *Botryosphaeria*) |
| SYM16669 | Complex endophyte fungal host further comprising SYM16659 | Fungal host ITS: SEQ ID NO: 326 (Genus *Microdiplodia*) |
| SYM16670 (SYM166) | Complex endophyte fungal host further comprising SYM16660 | Fungal host ITS: SEQ ID NO: 327 (Genus *Pestalotiposis*) |
| SYM16671 | Complex endophyte fungal host further comprising SYM16661 | Fungal host ITS: SEQ ID NO: 328 (Genus *Phyllosticta*) |
| SYM16672 | Complex endophyte fungal host further comprising SYM16662 | Fungal host LSU: SEQ ID NO: 329 (Genus *Alternaria*) |
| SYM16673 | Complex endophyte fungal host further comprising SYM16663 | Fungal host ITS: SEQ ID NO: 330 (Genus *Lecythophora*) |
| SYM16674 | Complex endophyte fungal host further comprising SYM16665 | Fungal host ITS: SEQ ID NO: 331 (Genus *Microdiplodia*) |
| SYM16675 | Complex endophyte fungal host further comprising SYM16666 | Fungal host ITS: SEQ ID NO: 332 (Genus *Daldinia*) |
| SYM16658 | Bacterial component of complex endophyte SYM16668 | Bacterial component 16S: SEQ ID NO: 237 (Genus *Dyella*) |
| SYM16659 | Bacterial component of complex endophyte SYM16669 | Bacterial component 16S: SEQ ID NO: 238 (Genus *Pantoea*) |
| SYM16660 | Bacterial component of complex endophyte SYM16670 | Bacterial component 16S: SEQ ID NO: 239 (Genus *Luteibacter*) |
| SYM16661 | Bacterial component of complex endophyte SYM16671 | Bacterial component 16S: SEQ ID NO: 240 (Genus *Dyella*) |
| SYM16662 | Bacterial component of complex endophyte SYM16672 | Bacterial component 16S: SEQ ID NO: 241 (Genus *Luteibacter*) |
| SYM16663 | Bacterial component of complex endophyte SYM16673 | Bacterial component 16S: SEQ ID NO: 242 (Genus *Ralstonia*) |
| SYM16665 | Bacterial component of complex endophyte SYM16674 | Bacterial component 16S: SEQ ID NO: 243 (Genus *Erwinia*) |

TABLE 4-continued

Complex Endophytes and Complex Endophyte Components tested in the present invention
The following endophytes (complex endophytes and their corresponding component bacteria) were used as exemplary endophytes in the methods described in the Examples section. These complex endophytes and their components are contemplated to be examples of useful compositions of the present invention.

| ID | Description | Sequence Identifier |
|---|---|---|
| SYM16666 | Bacterial component of complex endophyte SYM16675 | Bacterial component 16S: SEQ ID NO: 244 (Genus *Bacillus*) |

TABLE 5

Soybean Seedling Germination Water (Drought) Stress Assay
Complex endophytes and their isolated bacterial endophyte components were compared to each other as well as to control solutions (fungal formulation for the complex endophytes and bacterial formulation for the isolated bacterial endophyte components, respectively) and non-treated, for their ability to improve germination rates in soybean seeds. Complex endophyte treatment improves germination rate of soybean seedlings under drought (water stressed) conditions vs. formulation controls. Dothideomycetes (D) as complex endophyte hosts appear to impart greater benefit to soybean seedling germination under water stress (drought stress) conditions vs. their isolated bacterial components, than do Sodariomycetes (S).
% Germination of soybean seedlings

| Complex Endophyte | | Endofungal Bacterial Endophyte | |
|---|---|---|---|
| SYM16668 (D) | 53.33% | 70.00% | SYM16658 |
| SYM16669 (D) | 63.33% | 33.33% | SYM16659 |
| SYM16670 (S) | 20.00% | 56.67% | SYM16660 |
| SYM16671 (D) | 60.00% | 23.33% | SYM16661 |
| SYM16672 (D) | 40.00% | 23.33% | SYM16662 |
| SYM16673 (S) | 10.00% | 36.67% | SYM16663 |
| SYM16674 (D) | 53.33% | 33.33% | SYM16665 |
| SYM16675 (S) | 30.00% | 80.00% | SYM16666 |
| Average | 41.25% | 44.58% | Average |
| Fungal Formulation Control | 13.33% | 53.33% | Bacterial Formulation Control |

D = Dothideomycetes
S = Sodariomycetes

TABLE 6

Wheat Seedling Germination Water (Drought) Stress Assay
Complex endophytes and their isolated bacterial endophyte components were compared to each other as well as to control solutions (fungal formulation for the complex endophytes and bacterial formulation for the isolated bacterial endophyte components, respectively) and non-treated, for their ability to improve germination rates in wheat seeds. Complex endophyte treatment, as well as bacterial endohpyte treatment, improves germination rate of wheat seedlings under drought (water stressed) conditions vs. formulation controls. Sodariomycetes (S) as complex endophyte hosts appear to impart greater benefit to soybean seedling germination under water stress (drought stress) conditions vs. their isolated bacterial components, than do Dothideomycetes (D).
% Germination of wheat seedlings

| Complex Endophyte | | Endofungal Bacterial Endophyte | |
|---|---|---|---|
| SYM16668 (D) | 35.56% | 53.33% | SYM16658 |
| SYM16669 (D) | 68.89% | 68.89% | SYM16659 |
| SYM16670 (S) | 42.22% | 40.00% | SYM16660 |
| SYM16671 (D) | 42.22% | 48.89% | SYM16661 |
| SYM16672 (D) | 46.67% | 48.89% | SYM16662 |
| SYM16673 (S) | 64.44% | 55.56% | SYM16663 |
| SYM16674 (D) | 53.33% | 55.56% | SYM16665 |
| SYM16675 (S) | 55.56% | 40.00% | SYM16666 |
| Average | 51.11% | 51.39% | Average |
| Fungal Formulation Control | 42.22% | 44.44% | Bacterial Formulation Control |

D = Dothideomycetes
S = Sodariomycetes

TABLE 7

Wheat Plant Vigor Assay: Non-Stressed Conditions

Table 7a: Root Length
Plant seedlings grown from seeds treated with complex endophytes or complex endophyte bacterial components display a greater average root length than do plant seedlings grown from seeds treated with the formulation control. No significant difference was observed in average root length between plants grown from seeds treated with complex endophytes vs. isolated bacterial components.

| Complex Endophyte | Average root length (cm) Formulation Control = 14.48 | | Bacterial Component |
|---|---|---|---|
| SYM 16668 | 16.53 | 15.87 | SYM 16658 |
| SYM 16669 | 18.23 | 15.75 | SYM 16659 |
| SYM 16670 | 15.48 | 16.15 | SYM 16660 |
| SYM 16671 | 14.32 | 17.09 | SYM 16661 |
| SYM 16672 | 17.38 | 17.90 | SYM 16662 |
| SYM 16673 | 17.14 | 17.72 | SYM 16663 |
| SYM 16674 | 16.68 | 17.02 | SYM 16665 |
| SYM 16675 | 16.00 | 14.42 | SYM 16666 |
| Average | 16.47 | 16.49 | Average |

Table 7b: Shoot Length
Plant seedlings grown from seeds treated with complex endophytes or complex endophyte bacterial components display a greater average shoot length than do plant seedlings grown from seeds treated with the formulation control. Plant seedlings grown from seeds treated with complex endophytes display a greater average shoot length than do plant seedlings grown from seeds treated with isolated bacterial components.

| Complex Endophyte | Average shoot length (cm) Formulation Control = 14.31 | | Bacterial Component |
|---|---|---|---|
| SYM 16668 | 15.74 | 14.11 | SYM 16658 |
| SYM 16669 | 16.77 | 15.38 | SYM 16659 |
| SYM 16670 | 16.88 | 15.03 | SYM 16660 |
| SYM 16671 | 17.19 | 14.79 | SYM 16661 |
| SYM 16672 | 15.48 | 15.20 | SYM 16662 |
| SYM 16673 | 14.98 | 14.32 | SYM 16663 |

TABLE 7-continued

Wheat Plant Vigor Assay: Non-Stressed Conditions

| | | | |
|---|---|---|---|
| SYM 16674 | 14.52 | 15.07 | SYM 16665 |
| SYM 16675 | 14.30 | 15.66 | SYM 16666 |
| Average | 15.73 | 14.94 | Average |

Table 7c: Seedling Mass
Average mass of seedlings grown from seeds treated with the endophyte compositions listed below, compared to seedlings grown from seeds treated with only the formulation control.

| Treatment | Average total mass of seedlings (g) |
|---|---|
| Formulation | 2.70 |
| SYM 16658 | 2.89 |
| SYM 16659 | 2.75 |
| SYM 16660 | 2.40 |
| SYM 16661 | 2.48 |
| SYM 16662 | 1.91 |
| SYM 16663 | 2.46 |
| SYM 16665 | 2.08 |
| SYM 16666 | 2.78 |
| SYM 16668 | 2.17 |
| SYM 16669 | 2.73 |
| SYM 16670 | 2.96 |
| SYM 16671 | 2.97 |
| SYM 16672 | 2.67 |
| SYM 16673 | 2.06 |
| SYM 16674 | 2.19 |
| SYM 16675 | 2.20 |

TABLE 8

Wheat Plant Vigor Assay: Water-Stressed (Drought) Conditions

Table 8a: Root Length
Plant seedlings grown from seeds treated with complex endophytes or complex endophyte bacterial components display a greater average root length than do plant seedlings grown from seeds treated with the formulation control. No significant difference was observed between plants grown from seeds treated with complex endophytes vs. isolated bacterial components.

| Complex Endophyte | Average root length (cm) Formulation Control = 12.83 | | Bacterial Component |
|---|---|---|---|
| | | 15.87 | SYM 16658 |
| SYM 16669 | 14.24 | 13.02 | SYM 16659 |
| SYM 16670 | 13.10 | 13.10 | SYM 16660 |
| SYM 16671 | 11.20 | 14.50 | SYM 16661 |
| SYM 16672 | 13.35 | 14.22 | SYM 16662 |
| SYM 16673 | 16.97 | 16.04 | SYM 16663 |
| SYM 16674 | 13.97 | 14.15 | SYM 16665 |
| SYM 16675 | 15.52 | 12.75 | SYM 16666 |
| Average | 14.05 | 14.21 | Average |

Table 8b: Shoot Length
Plant seedlings grown from seeds treated with complex endophytes or complex endophyte bacterial components display a greater average shoot length than do plant seedlings grown from seeds treated with the formulation control. Plant seedlings grown from seeds treated with complex endophytes display a greater average shoot length than do plant seedlings grown from seeds treated with isolated bacterial components.

| Complex Endophyte | Average shoot length (cm) Formulation Control = 9.77 | | Bacterial Component |
|---|---|---|---|
| | | 12.62 | SYM 16658 |
| SYM 16669 | 12.59 | 11.27 | SYM 16659 |
| SYM 16670 | 11.94 | 9.10 | SYM 16660 |
| SYM 16671 | 10.33 | 10.50 | SYM 16661 |
| SYM 16672 | 12.63 | 9.45 | SYM 16662 |
| SYM 16673 | 11.22 | 10.51 | SYM 16663 |
| SYM 16674 | 10.37 | 9.72 | SYM 16665 |

TABLE 8-continued

| Wheat Plant Vigor Assay: Water-Stressed (Drought) Conditions | | | |
|---|---|---|---|
| SYM 16675 | 10.35 | 10.60 | SYM 16666 |
| Average | 11.35 | 10.47 | Average |

Table 8c: Seedling Mass
Average mass of seedlings grown from seeds treated with the endophyte compositions listed below, compared to seedlings grown from seeds treated with only the formulation control.

| Treatment | Average total mass of seedlings (g) |
|---|---|
| Formulation | 1.095 |
| SYM 16658 | 1.77 |
| SYM 16659 | 1.01 |
| SYM 16660 | 0.72 |
| SYM 16661 | 0.765 |
| SYM 16662 | 0.56 |
| SYM 16663 | 0.765 |
| SYM 16665 | 0.555 |
| SYM 16666 | 0.945 |
| SYM 16669 | 1.15 |
| SYM 16670 | 0.92 |
| SYM 16671 | 0.95 |
| SYM 16672 | 1.05 |
| SYM 16673 | 0.895 |
| SYM 16674 | 0.855 |
| SYM 16675 | 0.68 |

TABLE 9

Soybean Plant Vigor Assay: Non-Stressed Conditions

Table 9a: Root Length
Plant seedlings grown from seeds treated with complex endophytes or complex endophyte bacterial components display a greater average root length than do plant seedlings grown from seeds treated with the formulation control. Plant seedlings grown from seeds treated with complex endophytes display a greater average root length than do plant seedlings grown from seeds treated with isolated bacterial components.

| Complex Endophyte | Average root length (cm) Formulation Control = 14.21 | | Bacterial Component |
|---|---|---|---|
| SYM 16668 | 19.30 | 17.36 | SYM 16658 |
| SYM 16669 | 18.00 | 18.06 | SYM 16659 |
| SYM 16670 | 14.00 | 17.90 | SYM 16660 |
| SYM 16671 | 20.96 | 21.00 | SYM 16661 |
| SYM 16672 | 18.33 | 16.00 | SYM 16662 |
| SYM 16673 | 18.40 | 14.40 | SYM 16663 |
| SYM 16674 | 20.86 | 19.51 | SYM 16665 |
| SYM 16675 | 21.47 | 20.00 | SYM 16666 |
| Average | 18.92 | 18.03 | Average |

Table 9b: Shoot Length
Plant seedlings grown from seeds treated with complex endophytes or complex endophyte bacterial components display a greater average shoot length than do plant seedlings grown from seeds treated with the formulation control. Plant seedlings grown from seeds treated with isolated bacterial components display a slightly greater average shoot length than do plant seedlings grown from seeds treated with the complex endophytes.

| Complex Endophyte | Average shoot length (cm) Formulation Control = 5.75 | | Bacterial Component |
|---|---|---|---|
| SYM 16668 | 7.56 | 6.52 | SYM 16658 |
| SYM 16669 | 7.50 | 8.54 | SYM 16659 |
| SYM 16670 | 9.00 | 7.53 | SYM 16660 |
| SYM 16671 | 6.75 | 8.35 | SYM 16661 |
| SYM 16672 | 7.44 | 6.67 | SYM 16662 |
| SYM 16673 | 6.10 | 7.00 | SYM 16663 |

TABLE 9-continued

| Soybean Plant Vigor Assay: Non-Stressed Conditions | | | |
|---|---|---|---|
| SYM 16674 | 5.54 | 7.88 | SYM 16665 |
| SYM 16675 | 6.17 | 7.14 | SYM 16666 |
| Average | 7.01 | 7.45 | Average |

Table 9c: Seedling Mass
Average mass of seedlings grown from seeds treated with the endophyte compositions listed below, compared to seedlings grown from seeds treated with only the formulation control.

| Treatment | Average total mass of seedlings (g) |
|---|---|
| SYM 16668 | 8.645 |
| SYM 16658 | 10.7425 |
| SYM 16669 | 9.6485 |
| SYM 16659 | 9.0095 |
| SYM 16670 | 8.198 |
| SYM 16660 | 10.536 |
| SYM 16671 | 9.411 |
| SYM 16661 | 12.664 |
| SYM 16672 | 10.7265 |
| SYM 16662 | 7.516 |
| SYM 16673 | 10.9655 |
| SYM 16663 | 7.911 |
| SYM 16674 | 12.0485 |
| SYM 16665 | 9.407 |
| SYM 16675 | 13.637 |
| SYM 16666 | 12.0625 |
| Formulation | 10.385 |

TABLE 10

Soybean Plant Vigor Assay: Water-Stressed (Drought) Conditions

Table 10a: Root Length
Plant seedlings grown from seeds treated with a complex endophyte or complex endophyte bacterial component display a greater average root length than do plant seedlings grown from seeds treated with the formulation control. Plant seedlings grown from seeds treated with complex endophytes display a greater average root length than do plant seedlings grown from seeds treated with isolated bacterial components.

| Complex Endophyte | Average root length (cm) Formulation Control = 15.67 | | Bacterial Component |
|---|---|---|---|
| SYM 16668 | 19.12 | 16.06 | SYM 16658 |
| SYM 16669 | 17.98 | 16.46 | SYM 16659 |
| SYM 16670 | 15.89 | 16.81 | SYM 16660 |
| SYM 16671 | 16.03 | 17.16 | SYM 16661 |
| SYM 16672 | 14.60 | 14.50 | SYM 16662 |
| SYM 16673 | 19.03 | 14.00 | SYM 16663 |
| SYM 16674 | 16.07 | 15.63 | SYM 16665 |
| SYM 16675 | 17.79 | 16.01 | SYM 16666 |
| Average | 17.06 | 15.83 | Average |

Table 10b: Shoot Length
Plant seedlings grown from seeds treated with complex endophytes or complex endophyte bacterial components display a greater average shoot length than do plant seedlings grown from seeds treated with the formulation control. No significant difference was observed between plants grown from seeds treated with complex endophytes vs. isolated bacterial components.

| Complex Endophyte | Average shoot length (cm) Formulation Control = 3.69 | | Bacterial Component |
|---|---|---|---|
| SYM 16668 | 5.49 | 5.00 | SYM 16658 |
| SYM 16669 | 4.38 | 5.09 | SYM 16659 |
| SYM 16670 | 4.70 | 6.60 | SYM 16660 |
| SYM 16671 | 6.15 | 6.64 | SYM 16661 |
| SYM 16672 | 5.95 | 4.75 | SYM 16662 |

TABLE 10-continued

| Soybean Plant Vigor Assay: Water-Stressed (Drought) Conditions | | | |
|---|---|---|---|
| SYM 16673 | 4.71 | 5.08 | SYM 16663 |
| SYM 16674 | 5.88 | 4.55 | SYM 16665 |
| SYM 16675 | 4.69 | 4.63 | SYM 16666 |
| Average | 5.24 | 5.29 | Average |

Table 10c: Seedling Mass
Average mass of seedlings grown from seeds treated with the endophyte compositions listed below, compared to seedlings m seeds treated with only the formulation control.

| Treatment | Average total mass of seedlings (g) |
|---|---|
| SYM 16668 | 5.1394 |
| SYM 16658 | 7.07565 |
| SYM 16669 | 7.37525 |
| SYM 16659 | 6.1235 |
| SYM 16670 | 5.9322 |
| SYM 16660 | 4.22315 |
| SYM 16671 | 4.2446 |
| SYM 16661 | 4.367 |
| SYM 16672 | 4.0583 |
| SYM 16662 | 4.94655 |
| SYM 16673 | 5.27775 |
| SYM 16663 | 5.431 |
| SYM 16674 | 5.0386 |
| SYM 16665 | 4.911 |
| SYM 16675 | 6.5926 |
| SYM 16666 | 2.49395 |
| Formulation | 5.4958 |

TABLE 11

Winter Wheat Field Trial Results
Winter wheat grown under non-irrigated (dryland) conditions from winter wheat (Variety 3) seeds treated with complex endophyte SYM166 demonstrate improved yield (both wet bushels per acre and dry bushels per acre) compared to seeds treated with either the fungal formulation control or with non-complex fungal endophytes.

| | Yield (Winter Wheat Variety 3) | |
|---|---|---|
| | Dry Bushels per Acre | Wet Bushels per Acre |
| SYM166 (Complex Endophyte) | 37.24 | 33.70 |
| Average of Fungal Endophyte Controls (non-Complex) | 29.80 | 28.47 |
| Fungal Formulation Control | 26.52 | 25.32 |

TABLE 12

Spring Wheat Field Trial Results
Spring wheat grown under non-irrigated (dryland) conditions from winter wheat (Variety 2) seeds treated with complex endophyte SYM166 demonstrate improved yield (both wet bushels per acre and dry bushels per acre) compared to seeds treated with either the fungal formulation control or with non-complex fungal endophytes.

| | Yield (Spring Wheat Variety 2) | |
|---|---|---|
| | Dry Bushels per Acre | Wet Bushels per Acre |
| SYM166 (Complex Endophyte) | 46.56 | 49.96 |
| Average of Fungal Endophyte Controls (non-Complex) | 45.23 | 48.08 |
| Fungal Formulation Control | 42.92 | 41.12 |

REFERENCES

Amann et al. (2001) Current Opinion in Biotechnology 12:231-236

Bensch et al, "The genus *Cladosporium*" in: Studies in Mycology 72:1-401. 2012 doi:10.3114/sim0003

Couper and Eley, J. Polymer Sci., 3: 345-349 (1948)

Craine et al., Nature Climate Change 3: 63-67 (2013)

Crous and Groenveld, 2006

Desirò et al. (2014 ISME J. 8: 257-270

Edgar R C, 2004

Gao, Zhan, et al. Journal of clinical microbiology 48.10 (2010): 3575-3581

Hallman et al., (1997) Canadian Journal of Microbiology. 43(10): 895-914)

Hardegree and Emmerich (Plant Physiol., 92, 462-466 (1990)

Hawksworth, 2012

Hodgson Am. Potato. J. 38: 259-264 (1961)

Hoffman and Arnold, 2010 Appl. Environ. Microbiol. 76: 4063-4075

Hoffman et al., 2013 PLOS One 8: e73132

International Code of Nomenclature for Algae, Fungi, and Plants (Melbourne Code)

International Botanical Congress (2012)

Johnston-Monje D, Raizada M N (2011) PLoS ONE 6(6): e20396

Jung and Arnold, 2012 The Effects of Endohyphal Bacteria on Anti-Cancer and Anti-Malaria Metabolites of Endophytic Fungi, Honors Thesis, University of Arizona Kwasna 2003

Long et al., 2010, New Phytologist 185: 554-567

Lundberg et al., (2012) Nature. 488, 86-90

Marquez et al., 2007 Science 315: 513-515

Michel and Kaufmann (Plant Physiol., 51: 914-916 (1973)

Pearson, 1990, Methods Enzymol. 183:63-98, incorporated herein by reference in its entirety Perez-Fernandez et al. [J. Environ. Biol. 27: 669-685 (2006)

Sambrook, Joseph, Edward F. Fritsch, and Thomas Maniatis. Molecular cloning. Vol. 2. New York: Cold spring harbor laboratory press, 1989

Shenoy, 2007

Summerbell, 2011

Taylor, 2011

Zhang and Qiu, 2015

U.S. Pat. No. 7,485,451

EP 0818135

CA 1229497

WO 2013090628

EP 0192342

WO 2008103422

CA 1041788

We claim:

1. A synthetic composition, comprising an agricultural plant element heterologously associated with an isolated complex endophyte, wherein said isolated complex endophyte comprises a host fungus comprising an endogenous endofungal bacterial endophyte living inside the host fungal hyphae, wherein the host fungus is of the genus *Botryosphaeria* and the bacterial endophyte is of the genus *Dyella*, and the complex endophyte is capable of providing a trait of agronomic importance to said agricultural plant element.

2. The synthetic composition of claim 1, wherein said trait of agronomic importance is selected from the group consisting of: germination rate, emergence rate, shoot biomass, root biomass, seedling root length, seedling shoot length, seedling mass, root surface area, and yield.

3. The synthetic composition of claim 1, wherein said synthetic composition further comprises an agronomic formulation that further comprises one or more of the following: a stabilizer, preservative, carrier, surfactant, anticomplex agent, fungicide, nematicide, bactericide, insecticide, or herbicide, or any combination thereof.

4. The synthetic composition of claim 1, wherein said isolated complex endophyte is present in an amount of at least 10^2 CFU of complex endophyte per plant element.

5. A plurality of the synthetic compositions of claim 1, placed in a medium that promotes plant growth, wherein said medium is soil, wherein said synthetic compositions are placed in the soil with substantially equal spacing between each seed.

6. A plant grown from the synthetic combination of claim 1, wherein said plant exhibits an improved phenotype of agronomic interest.

7. A method of improving a trait of agronomic importance in an agricultural plant, comprising:

(a) contacting a reproductive element of the agricultural plant with the isolated heterologous complex endophyte of claim 1; and (b) growing the reproductive element comprising complex endophyte into the agricultural plant, wherein the agricultural plant has an improved trait of agronomic importance as compared to an isoline plant grown from a plant reproductive element not contacted with said isolated complex endophyte.

8. The method of claim 7, wherein said trait of agronomic importance is selected from the group consisting of: germination rate, emergence rate, shoot biomass, seedling root length, seedling shoot length, seedling mass, root surface area, and yield.

9. The method of claim 7, wherein the trait of agronomic importance is improved under normal watering conditions.

10. The method of claim 7, wherein the trait of agronomic importance is improved under conditions of water limitation.

11. The method of claim 7, wherein said plant element is selected from the group consisting of: whole plant, seedling, meristematic tissue, ground tissue, vascular tissue, dermal tissue, seed, leaf, root, shoot, stem, flower, fruit, stolon, bulb, tuber, corm, keikis, and bud.

12. The method of claim 7, wherein said plant element is from a plant selected from the group consisting of: wheat, soybean, maize, cotton, canola, barley, sorghum, millet, rice, rapeseed, alfalfa, tomato, sugarbeet, sorghum, almond, walnut, apple, peanut, strawberry, lettuce, orange, potato, banana, sugarcane, potato, cassava, mango, guava, palm, onions, olives, peppers, tea, yams, cacao, sunflower, asparagus, carrot, coconut, lemon, lime, barley, watermelon, cabbage, cucumber, grape, and turfgrass.

13. A method for preparing the synthetic composition of claim 1, comprising:

(a) contacting a surface of a plurality of plant elements with an effective amount of a formulation comprising the isolated complex endophyte of claim 1 that is heterologous to the agricultural plant elements; and (b) growing the plant elements contacted with the effective amount of the isolated complex endophyte to yield plant elements colonized by the complex endophyte, wherein the isolated complex endophyte is capable of modulating at least one of: a trait of agronomic importance, the transcription of a gene, the expression of a protein, the level of a hormone, the level of a metabolite, and the population of endogenous microbes in plants grown from said agricultural plant elements, as compared to isoline plants not associated with, or not grown from plant elements associated with said formulation.

14. The synthetic composition of claim 1, wherein the host fungus comprises an internal transcribed spacer (ITS) nucleic acid sequence at least 95% identical to SEQ ID NO: 325.

15. The synthetic composition of claim 1, wherein the host fungus comprises an internal transcribed spacer (ITS) nucleic acid sequence at least 97% identical to SEQ ID NO: 325.

16. The synthetic composition of claim 1, wherein the host fungus comprises an internal transcribed spacer (ITS) nucleic acid sequence comprising SEQ ID NO: 325.

17. The synthetic composition of claim 1, wherein the endogenous endofungal bacterial endophyte comprises a 16S nucleic acid sequence at least 95% identical to SEQ ID NO: 237.

18. The synthetic composition of claim 1, wherein the endogenous endofungal bacterial endophyte comprises a 16S nucleic acid sequence at least 97% identical to SEQ ID NO: 237.

19. The synthetic composition of claim 1, wherein the endogenous endofungal bacterial endophyte comprises a 16S nucleic acid sequence comprising SEQ ID NO: 237.

20. The synthetic composition of claim 1, wherein the heterologous plant is wheat, the host fungus is of the genus *Botryosphaeria* and comprises an internal transcribed spacer (ITS) nucleic acid sequence comprising SEQ ID NO: 325 and the endogenous endofungal bacterial endophyte is of the genus *Dyella* and comprises a 16S nucleic acid sequence comprising SEQ ID NO: 237.

21. The synthetic composition of claim 1, wherein the heterologous plant is soybean, the host fungus is of the genus *Botryosphaeria* and comprises an internal transcribed spacer (ITS) nucleic acid sequence comprising SEQ ID NO: 325 and the endogenous endofungal bacterial endophyte is of the genus *Dyella* and comprises a 16S nucleic acid sequence comprising SEQ ID NO: 237.

* * * * *

SEQUENCE LISTING

<160> NUMBER OF SEQ ID NOS: 333

<210> SEQ ID NO 1
<211> LENGTH: 1336
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus

<400> SEQUENCE: 1

```
agcttgctcc ctgatgttag cggcggacgg gtgagtaaca cgtgggtaac ctgcctgtaa     60

gactgggata actccgggaa accggggcta ataccggatg cttgtttaac cgcatggttc    120

aaacataaaa ggtggcttcg gctaccactt acagatggac ccgcggcgca ttagctagtt    180

ggtgaggtaa tggctcacca aggcaacgat gcgtagccga cctgagaggg tgatcggcca    240

cactgggact gagacacggc ccagactcct acgggaggca gcagtaggga atcttccgca    300

atggacgaaa gtctgacgga gcaacgccgc gtgagtgatg aaggttttcg gatcgtaaag    360

ctctgttgtt agggaagaac aagtgccgtt caaatagggc ggcaccttga cggtacctaa    420

ccagaaagcc acggctaact acgtgccagc agccgcggta atacgtaggt ggcaagcgtt    480

gtccggaatt attgggcgta aagggctcgc aggcggtttc ttaagtctga tgtgaaagcc    540

cccggctcaa ccggggaggg tcattggaaa ctggggaact tgagtgcaga agaggagagt    600

ggaattccac gtgtagcggt gaaatgcgta gagatgtgga ggaacaccag tggcgaaggc    660

gactctcttc tgtaactgac gctgaggagc gaaagcgtgg ggagcgaaca ggattagata    720

ccctggtagt ccacgccgta aacgatgagt gctaagtgtt agggggtttc cgccccttag    780

tgctgcagct aacgcattaa gcactccgcc tggggagtac ggtcgcaaga ctgaaactca    840

aaggaattga cgggggcccg cacaagcggt ggagcatgtg gtttaattcg aagcaacgcg    900

aagaacctta ccaggtcttg acatcctctg acaccoctag agatagggct tccccttcgg    960

gggcagagtg acaggtggtg catggttgtc gtcagctcgt gtcgtgagat gttgggttaa   1020

gtcccgcaac gagcgcaacc cttgatctta gttgccagca ttcagttggg cactctaagg   1080

tgactgccgg tgacaaaccg gaggaaggtg gggatgacgt caaatcatca tgccccttat   1140

gacctgggct acacacgtgc tacaatggac agaacaaagg gcagcgagac cgcgaggtta   1200

agccaatccc acaaatctgt tctcagttcg gatcgcagtc tgcaactcga ctgcgtgaag   1260

ctggaatcgc tagtaatcgc ggatcagcat gccgcggtga atacgttccc gggccttgta   1320

cacaccgccc gtcaca                                                   1336
```

<210> SEQ ID NO 2
<211> LENGTH: 1295
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus

<400> SEQUENCE: 2

```
gaaaccgggg ctaataccgg atggttgttt gaaccgcatg gttcaaacat aaaaggtggc     60

ttcggctacc acttacagat ggacccgcgg cgcattagct agttggtgag gtaacggctc    120

accaaggcaa cgatgcgtag ccgacctgag agggtgatcg gccacactgg gactgagaca    180

cggcccagac tcctacggga ggcagcagta gggaatcttc cgcaatggac gaaagtctga    240

cggagcaacg ccgcgtgagt gatgaaggtt ttcggatcgt aaagctctgt tgttagggaa    300
```

```
gaacaagtac cgttcgaata gggcggtacc ttgacggtac ctaaccagaa agccacggct    360

aactacgtgc cagcagccgc ggtaatacgt aggtggcaag cgttgtccgg aattattggg    420

cgtaaagggc tcgcaggcgg tttcttaagt ctgatgtgaa agcccccggc tcaaccgggg    480

agggtcattg gaaactgggg aacttgagtg cagaagagga gagtggaatt ccacgtgtag    540

cggtgaaatg cgtagagatg tggaggaaca ccagtggcga aggcgactct ctggtctgta    600

actgacgctg aggagcgaaa gcgtggggag cgaacaggat tagataccct ggtagtccac    660

gccgtaaacg atgagtgcta agtgttaggg ggtttccgcc ccttagtgct gcagctaacg    720

cattaagcac tccgcctggg gagtacggtc gcaagactga aactcaaagg aattgacggg    780

ggcccgcaca agcggtggag catgtggttt aattcgaagc aacgcgaaga accttaccag    840

gtcttgacat cctctgacaa tcctagagat aggacgtccc cttcgggggc agagtgacag    900

gtggtgcatg gttgtcgtca gctcgtgtcg tgagatgttg ggttaagtcc cgcaacgagc    960

gcaacccttg atcttagttg ccagcattca gttgggcact ctaaggtgac tgccggtgac   1020

aaaccggagg aaggtgggga tgacgtcaaa tcatcatgcc ccttatgacc tgggctacac   1080

acgtgctaca atggacagaa caaagggcag cgaaaccgcg aggttaagcc aatcccacaa   1140

atctgttctc agttcggatc gcagtctgca actcgactgc gtgaagctgg aatcgctagt   1200

aatcgcggat cagcatgccg cggtgaatac gttcccgggc cttgtacaca ccgcccgtca   1260

caccacgaga gtttgtaaca cccgaagtcg gtgag                              1295
```

<210> SEQ ID NO 3
<211> LENGTH: 1337
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus

<400> SEQUENCE: 3

```
agcttgctcc ctgatgttag cggcggacgg gtgagtaaca cgtgggtaac ctgcctgtaa     60

gactgggata actccgggaa accggggcta ataccggatg gttgtttacc gcatggttca    120

aacataaaag gtggcttcgg ctaccactta cagatggacc cgcggcgcat tagctagttg    180

gtgaggtaac ggctcaccaa ggcaacgatg cgtagccgac ctgagagggt gatcggccac    240

actgggactg agacacggcc cagactccta cgggaggcag cagtagggaa tcttccgcaa    300

tggacgaaag tctgacggag caacgccgcg tgagtgatga aggttttcgg atcgtaaagc    360

tctgttgtta gggaagaaca agtaccgttc gaatagggcg gtaccttgac ggtacctaac    420

cagaaagcca cggctaacta cgtgccagca gccgcggtaa tacgtaggtg gcaagcgttg    480

tccggaatta ttgggcgtaa agggctcgca ggcggtttct taagtctgat gtgaaagccc    540

ccggctcaac cggggagggt cattggaaac tggggaactt gagtgcagaa gaggagagtg    600

gaattccacg tgtagcggtg aaatgcgtag agatgtggag gaacaccagt ggcgaaggcg    660

actctctggt ctgtaactga cgctgaggag cgaaagcgtg gggagcgaac aggattagat    720

accctggtag tccacgccgt aaacgatgag tgctaagtgt tagggggttt ccgcccctta    780

gtgctgcagc taacgcatta agcactccgc ctggggagta cggtcgcaag actgaaactc    840

aaaggaattg acgggggccc gcacaagcgg tggagcatgt ggtttaattc gaagcaacgc    900

gaagaacctt accaggtctt gacatcctct gacaatccta gagataggac gtccccttcg    960

ggggcagagt gacaggtggt gcatggttgt cgtcagctcg tgtcgtgaga tgttgggtta   1020
```

agtcccgcaa cgagcgcaac ccttgatctt agttgccagc attcagttgg gcactctaag 1080
gtgactgccg gtgacaaacc ggaggaaggt ggggatgacg tcaaatcatc atgcccctta 1140
tgacctgggc tacacacgtg ctacaatgga cagaacaaag ggcagcgaaa ccgcgaggtt 1200
aagccaatcc cacaaatctg ttctcagttc ggatcgcagt ctgcaactcg actgcgtgaa 1260
gctggaatcg ctagtaatcg cggatcagca tgccgcggtg aatacgttcc cgggccttgt 1320
acacaccgcc cgtcaca 1337

<210> SEQ ID NO 4
<211> LENGTH: 1338
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus: Paenibacillus

<400> SEQUENCE: 4
agcttgcttc tccgatggtt agcggcggac gggtgagtaa cacgtaggca acctgccctc 60
aagtttggga caactaccgg aaacggtagc taataccgaa tagttgtttt tctcctgaag 120
gaaactggaa agacggagca atctgtcact tggggatggg cctgcggcgc attagctagt 180
tggtggggta acggctcacc aaggcgacga tgcgtagccg acctgagagg gtgatcggcc 240
acactgggac tgagacacgg cccagactcc tacgggaggc agcagtaggg aatcttccgc 300
aatgggcgaa agcctgacgg agcaatgccg cgtgagtgat gaaggttttc ggatcgtaaa 360
gctctgttgc cagggaagaa cgcttgggag agtaactgct ctcaaggtga cggtacctga 420
gaagaaagcc ccggctaact acgtgccagc agccgcggta atacgtaggg ggcaagcgtt 480
gtccggaatt attgggcgta aagcgcgcgc aggcggtcat ttaagtctgg tgtttaatcc 540
cggggctcaa ccccggatcg cactggaaac tgggtgactt gagtgcagaa gaggagagtg 600
gaattccacg tgtagcggtg aaatgcgtag atatgtggag gaacaccagt ggcgaaggcg 660
actctctggg ctgtaactga cgctgaggcg cgaaagcgtg gggagcaaac aggattagat 720
accctggtag tccacgccgt aaacgatgag tgctaggtgt taggggtttc gatacccttg 780
gtgccgaagt taacacatta agcactccgc ctggggagta cggtcgcaag actgaaactc 840
aaaggaattg acggggaccc gcacaagcag tggagtatgt ggtttaattc gaagcaacgc 900
gaagaacctt accaggtctt gacatccctc tgaccggtac agagatgtac ctttccttcg 960
ggacagagga gacaggtggt gcatggttgt cgtcagctcg tgtcgtgaga tgttgggtta 1020
agtcccgcaa cgagcgcaac ccttgatctt agttgccagc acttcgggtg ggcactctaa 1080
ggtgactgcc ggtgacaaac cggaggaagg tggggatgac gtcaaatcat catgcccctt 1140
atgacctggg ctacacacgt actacaatgg ccggtacaac gggcagtgaa accgcgaggt 1200
ggaacgaatc ctaaaaagcc ggtctcagtt cggattgcag gctgcaactc gcctgcatga 1260
agtcggaatt gctagtaatc gcggatcagc atgccgcggt gaatacgttc ccgggtcttg 1320
tacacaccgc ccgtcaca 1338

<210> SEQ ID NO 5
<211> LENGTH: 1338
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus:

Paenibacillus

<400> SEQUENCE: 5
agcttgcttc tccgatggtt agcggcggac gggtgagtaa cacgtaggca acctgccctc 60
aagtttggga caactaccgg aaacggtagc taataccgaa tagttgtttt tctcctgaag 120
gaaactggaa agacggagca atctgtcact tggggatggg cctgcggcgc attagctagt 180
tggtggggta acggctcacc aaggcgacga tgcgtagccg acctgagagg gtgatcggcc 240
acactgggac tgagacacgg cccagactcc tacgggaggc agcagtaggg aatcttccgc 300
aatgggcgaa agcctgacgg agcaatgccg cgtgagtgat gaaggttttc ggatcgtaaa 360
gctctgttgc cagggaagaa cgcttgggag agtaactgct ctcaaggtga cggtacctga 420
gaagaaagcc ccggctaact acgtgccagc agccgcggta atacgtaggg ggcaagcgtt 480
gtccggaatt attgggcgta aagcgcgcgc aggcggtcat ttaagtctgg tgtttaatcc 540
cggggctcaa ccccggatcg cactggaaac tgggtgactt gagtgcagaa gaggagagtg 600
gaattccacg tgtagcggtg aaatgcgtag atatgtggag gaacaccagt ggcgaaggcg 660
actctctggg ctgtaactga cgctgaggcg cgaaagcgtg gggagcaaac aggattagat 720
accctggtag tccacgccgt aaacgatgag tgctaggtgt taggggtttc gatacccttg 780
gtgccgaagt taacacatta agcactccgc ctggggagta cggtcgcaag actgaaactc 840
aaaggaattg acggggaccc gcacaagcag tggagtatgt ggtttaattc gaagcaacgc 900
gaagaacctt accaggtctt gacatccctc tgaccggtac agagatgtac ctttccttcg 960
ggacagagga gacaggtggt gcatggttgt cgtcagctcg tgtcgtgaga tgttgggtta 1020
agtcccgcaa cgagcgcaac ccttgatctt agttgccagc acttcgggtg ggcactctaa 1080
ggtgactgcc ggtgacaaac cggaggaagg tggggatgac gtcaaatcat catgcccctt 1140
atgacctggg ctacacacgt actacaatgg ccggtacaac gggcagtgaa accgcgaggt 1200
ggaacgaatc ctaaaaagcc ggtctcagtt cggattgcag gctgcaactc gcctgcatga 1260
agtcggaatt gctagtaatc gcggatcagc atgccgcggt gaatacgttc ccgggtcttg 1320
tacacaccgc ccgtcaca 1338

<210> SEQ ID NO 6
<211> LENGTH: 1326
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Moraxellaceae, Genus: Acinetobacter

<400> SEQUENCE: 6
agcttgctac ttgacctagc ggcggacggg cgaagtaatg cttaggaatc tgcctattag 60
tgggggacaa cgtctcgaaa gggatgctaa taccgcatac gtcctacggg agaaagcagg 120
ggaccttcgg gccttgcgct aatagatgag cctaagtcgg attagctagt tggtggggta 180
aaggcctacc aaggcgacga tctgtagcgg gtctgagagg atgatccgcc acactgggac 240
tgagacacgg cccagactcc tacgggaggc agcagtgggg aatattggac aatgggggga 300
agcctgatcc agccatgccg cgtgtgtgaa gaaggccttt tggttgtaaa gcactttaag 360
cgaggaggag gctaccgaga ttaatactct tggatagtgg acgttactcg caaaataagc 420
accggctaac tctgtgccag cagccgcggt aaatacagag ggtgcaagcg ttaatcggat 480
ttactgggcg taaagcgcgc gtaggtggct tattaagtcg aatgtgaaat ccccgagctt 540

```
aacttgggaa ttgcattcaa tactggttgg ctagagtatg ggagaggatg gtaaattcca    600

ggtgtacggt gaaatgcgta agatctggag gaataccgat ggcgaaggca gccatctggc    660

ctaatactga cctgaggtgc gaaagctggg gagcaaacag gattagatac cctggtagtc    720

catgccgtac acgatgtcta ctagccgttg gggcctttga ggctttagtg gcgcagctaa    780

cgcgataagt agaccgcctg gggagtacgg tcgcaagact aaaactcaaa tgaattgacg    840

ggggcccgca ccagcggtgg agcatgtggt ttaattcgat gcaacgcgaa gaaccttacc    900

tggccttgac atagtaagaa ctttccagag atggattggt gccttcggga acttacatac    960

aggtgctgca tggcggtcgt cagctcgtgt cgtgagatgt tgggttaagt cccgcaacga   1020

gcgcaaccct tttccttatt tgccagcggg ttaagccggg aactttaagg atactgccag   1080

tgacaaactg gaggaaggcg gggacgacgt caagtcatca tggcccttac ggccagggct   1140

acacacgtgc tacaatggtc ggtacaaagg gttgccacct cgcgagagga tgctaatctc   1200

aaaaagccga tcgtagtccg gatcgcagtc tgcaactcga ctccgtgaag tcggaatcgc   1260

tagtaatcgc ggatcagaat gccgcggtga atacgttccc gggccttgta cacaccgccc   1320

gtcaca                                                              1326


<210> SEQ ID NO 7
<211> LENGTH: 1409
<212> TYPE: DNA
<213> ORGANISM: Unknown
<220> FEATURE:
<223> OTHER INFORMATION: Kingdom: Bacteria, Phylum: Proteobacteria,
      Class: Betaproteobacteria, Order: Burkholderiales, Family:
      Burkholderiaceae, Genus: Burkholderia

<400> SEQUENCE: 7

ggtgaccgtc ctccttgcgg ttagactagc cacttctggt aaaacccact cccatggtgt     60

gacgggcggt gtgtacaaga cccgggaacg tattcaccgc ggcatgctga tccgcgatta    120

ctagcgattc cagcttcacg cacccgagtt gcagagtgcg atccggacta cgatcggttt    180

tctgggattg gctccacctc gcggcttggc gaccctctgt tccgaccatt gtatgacgtg    240

tgaagcccta cccataaggg ccatgaggac ttgacgtcat ccccaccttc ctccggtttg    300

tcaccggcag tctccctgga gtgctcttgc gtagcaacta gggacaaggg ttgcgctcgt    360

tgcgggactt aacccaacat ctcacgacac gagctgacga cagccatgca gcacctgtgt    420

atcggttccc tttcgggcac tcccacctct cagcaggatt ccgaccatgt caagggtagg    480

taaggttttt cgcgttgcat cgaattaatc cacatcatcc accgcttgtg cgggtccccg    540

tcaattcctt tgagttttaa tcttgcgacc gtactcccca ggcggtcaac ttcacgcgtt    600

agctacgtta ccaagccaat gaaggcccga caaccagttg acatcgttta gggcgtggac    660

taccagggta tctaatcctg tttgctccsc acgctttcgt gcatgagcgt cagtattggc    720

ccagggggct gccttcgcca tcggtattcc tccacatctc tacgcatttc actgctacac    780

gtggaattct acccccctct gccatactct agcccgccag tcacaaatgc agttcccagg    840

ttaagcccgg ggatttcaca tctgtcttag cgaaccgcct gcgcacgctt tacgcccagt    900

aattccgatt aacgcttgca ccctacgtat taccgcggct gctggcacgt agttagccgg    960

tgcttattct tccggtaccg tcatccccca cgggtattaa ccacgaggtt ttctttccgg   1020

acaaaagtgc tttacaaccc gaaggccttc ttcacacacg cggcattgct ggatcaggct   1080

tgcgcccatt gtccaaaatt ccccactgct gcctcccgta ggagtctggg ccgtgtctca   1140
```

-continued

```
gtcccagtgt ggctggtcgt cctctcagac cagctacaga tcgtcgcctt ggtaggcctt   1200

taccccacca actagctaat ctgccatcgg ccgccccttg agcgagaggt ccgaagatcc   1260

ccccctttcc tccacagagc gtatgcggta ttaatccggc tttcgccggg ctatccccca   1320

ctccaggaca cgttccgatg tattactcac ccgttcgcca ctcgccacca gggttgcccc   1380

cgtgctgccg ttcgactgca tgttaagtc                                     1409
```

<210> SEQ ID NO 8
<211> LENGTH: 1281
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Sphingomonadales, Family: Sphingomonadaceae, Genus: Sphingomonas

<400> SEQUENCE: 8

```
ttcggggtct agtggcgcac gggtgcgtaa cgcgtgggaa tctgcccttg ggttcggaat     60

aacagttgga aacgactgct aataccggat gatgacgtaa gtccaaagat ttattgccca    120

gggatgagcc cgcgtaggat tagctagttg gtgaggtaaa ggctcaccaa ggcgacgatc    180

cttagctggt ctgagaggat gatcagccac actgggactg agacacggcc cagactccta    240

cgggaggcag cagtggggaa tattggacaa tgggcgaaag cctgatccag caatgccgcg    300

tgagtgatga aggccttagg gttgtaaagc tcttttaccc gggatgataa tgacagtacc    360

gggagaataa gctccggcta actccgtgcc agcagccgcg gtaatacgga gggagctagc    420

gttgttcgga attactgggc gtaaagcgca cgtaggcggc tttgtaagtt agaggtgaaa    480

gcctggagct caactccaga attgccttta agactgcatc gcttgaatcc aggagaggtg    540

agtggaattc cgagtgtaga ggtgaaattc gtagatattc ggaagaacac cagtggcgaa    600

ggcggctcac tggactggta ttgacgctga ggtgcgaaag cgtggggagc aaacaggatt    660

agataccctg gtagtccacg ccgtaaacga tgataactag ctgtccgggg acttggtctt    720

tgggtggcgc agctaacgca ttaagttatc cgcctgggga gtacggccgc aaggttaaaa    780

ctcaaatgaa ttgacggggg cctgcacaag cggtggagca tgtggtttaa ttcgaagcaa    840

cgcgcagaac cttaccagcg tttgacatgt ccggacgatt tccagagatg gatctcttcc    900

cttcggggac tggaacacag gtgctgcatg gctgtcgtca gctcgtgtcg tgagatgttg    960

ggttaagtcc cgcaacgagc gcaaccctcg cctttagtta ccatcattta gttggggact   1020

ctaaaggaac cgccggtgat aagccggagg aaggtgggga tgacgtcaag tcctcatggc   1080

ccttacgcgc tgggctacac acgtgctaca atggcggtga cagtgggcag caatcccgca   1140

agggtgagct aatctccaaa agccgtctca gttcggattg ttctctgcaa ctcgagagca   1200

tgaaggcgga atcgctagta atcgcggatc agcatgccgc ggtgaatacg ttcccaggcc   1260

ttgtacacac cgcccgtcac a                                             1281
```

<210> SEQ ID NO 9
<211> LENGTH: 1333
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 9

```
agcttgctct gtgggtggcg agtggcggac gggtgagtaa tgcatcggga cctacccaga     60
```

```
cgtgggggat aacgtaggga aacttacgct aataccgcat acgtcctacg ggagaaagcg    120
ggggatcgca agacctcgcg cggttggatg gaccgatgtg cgattagcta gttggtaagg    180
taacggctta ccaaggcgac gatcgctagc tggtctgaga ggatgatcag ccacactggg    240
actgagacac ggcccagact cctacgggag gcagcagtgg ggaatattgg acaatgggcg    300
caagcctgat ccagcaatgc cgcgtgtgtg aagaaggccc tcgggttgta aagcactttt    360
atcaggagcg aaatctgcaa ggttaatacc tttgcagtct gacggtacct gaggaataag    420
caccggctaa ctccgtgcca gcagccgcgg taatacggag ggtgcaagcg ttaatcggaa    480
ttactgggcg taaagcgtgc gtaggcggtt cgttaagtct gttgtgaaag ccccgggctc    540
aacctgggaa tggcaatgga tactggcgag ctagagtgtg tcagaggatg gtggaattcc    600
cggtgtagcg gtgaaatgcg tagagatcgg gaggaacatc agtggcgaag gcggccatct    660
gggacaacac tgacgctgag gcacgaaagc gtggggagca aacaggatta gataccctgg    720
tagtccacgc cctaaacgat gcgaactgga tgttggtctc aactcggaga tcagtgtcga    780
agctaacgcg ttaagttcgc cgcctgggga gtacggtcgc aagactgaaa ctcaaaggaa    840
ttgacggggg cccgcacaag cggtggagta tgtggtttaa ttcgatgcaa cgcgaagaac    900
cttacctggc cttgacatgt ccggaatcca gcagagatgc aggagtgcct tcgggaatcg    960
gaacacaggt gctgcatggc tgtcgtcagc tcgtgtcgtg agatgttggg ttaagtcccg   1020
caacgagcgc aacccttgtc cttagttgcc agcgagtaat gtcgggaact ctaaggagac   1080
tgccggtgac aaaccggagg aaggtgggga tgacgtcaag tcatcatggc ccttacggcc   1140
agggctacac acgtactaca atggtcggta cagagggttg cgataccgcg aggtggagct   1200
aatcccagaa agccgatccc agtccggatt ggagtctgca actcgactcc atgaagtcgg   1260
aatcgctagt aatcgcagat cagctatgct gcggtgaata cgttcccggg ccttgtacac   1320
accgcccgtc aca                                                      1333
```

<210> SEQ ID NO 10
<211> LENGTH: 1295
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Sphingomonadales, Family: Sphingomonadaceae, Genus: Sphingomonas

<400> SEQUENCE: 10

```
cttcgggtct agtggcgcac gggtgcgtaa cgcgtgggaa tctgcccttg ggttcggaat     60
aacagttgga aacgactgct aataccggat gatgacgtaa gtccaaagat ttatcgccca    120
gggatgagcc cgcgtaggat tagctagttg gtgaggtaaa ggctcaccaa ggcgacgatc    180
cttagctggt ctgagaggat gatcagccac actgggactg agacacggcc cagactccta    240
cgggaggcag cagtggggaa tattggacaa tgggcgaaag cctgatccag caatgccgcg    300
tgagtgatga aggccttagg gttgtaaagc tcttttaccc gggatgataa tgacagtacc    360
gggagaataa gctccggcta actccgtgcc agcagccgcg gtaatacgga gggagctagc    420
gttgttcgga attactgggc gtaaagcgca cgtaggcggc tttgtaagtt agaggtgaaa    480
gcctggagct caactccaga attgccttta agactgcatc gcttgaatcc aggagaggtg    540
agtggaattc cgagtgtaga ggtgaaattc gtagatattc ggaagaacac cagtggcgaa    600
ggcggctcac tggactggta ttgacgctga ggtgcgaaag cgtggggagc aaacaggatt    660
```

agataccctg gtagtccacg ccgtaaacga tgataactag ctgtccgggg acttggtctt 720
tgggtggcgc agctaacgca ttaagttatc cgcctgggga gtacggccgc aaggttaaaa 780
ctcaaatgaa ttgacggggg cctgcacaag cggtggagca tgtggtttaa ttcgaagcaa 840
cgcgcagaac cttaccagcg tttgacatgt ccggacgatt tccagagatg gatctcttcc 900
cttcggggac tggaacacag gtgctgcatg gctgtcgtca gctcgtgtcg tgagatgttg 960
ggttaagtcc cgcaacgagc gcaaccctcg cctttagtta ccatcattta gttggggact 1020
ctaaaggaac cgccggtgat aagccggagg aaggtgggga tgacgtcaag tcctcatggc 1080
ccttacgcgc tgggctacac acgtgctaca atggcggtga cagtgggcag caatcccgca 1140
agggtgagct aatctccaaa agccgtctca gttcggattg ttctctgcaa ctcgagagca 1200
tgaaggcgga atcgctagta atcgcggatc agcatgccgc ggtgaatacg ttcccaggcc 1260
ttgtacacac cgcccgtcac accatgggag ttgga 1295

<210> SEQ ID NO 11
<211> LENGTH: 1369
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus: Paenibacillus

<400> SEQUENCE: 11
gcttgcttct ccgatggtta gcggcggacg ggtgagtaac acgtaggcaa cctgccctca 60
agtttgggac aactaccgga aacggtagct aataccgaat agttgttttc ttctcctgaa 120
ggaaactgga aagacggagc aatctgtcac ttggggatgg gcctgcggcg cattagctag 180
ttggtggggt aacggctcac caaggcgacg atgcgtagcc gacctgagag ggtgatcggc 240
cacactggga ctgagacacg gcccagactc ctacgggagg cagcagtagg gaatcttccg 300
caatgggcga aagcctgacg gagcaatgcc gcgtgagtga tgaaggtttt cggatcgtaa 360
agctctgttg ccagggaaga acgcttggga gagtaactgc tctcaaggtg acggtacctg 420
agaagaaagc ccggctaac tacgtgccag cagccgcggt aatacgtagg gggcaagcgt 480
tgtccggaat tattgggcgt aaagcgcgcg caggcggtca tttaagtctg gtgtttaatc 540
ccggggctca accccggatc gcactggaaa ctgggtgact tgagtgcaga agaggagagt 600
ggaattccac gtgtagcggt gaaatgcgta gatatgtgga ggaacaccag tggcgaaggc 660
gactctctgg gctgtaactg acgctgaggc gcgaaagcgt ggggagcaaa caggattaga 720
taccctggta gtccacgccg taaacgatga gtgctaggtg ttaggggttt cgataccctt 780
ggtgccgaag ttaacacatt aagcactccg cctggggagt acggtcgcaa gactgaaact 840
caaaggaatt gacggggacc cgcacaagca gtggagtatg tggtttaatt cgaagcaacg 900
cgaagaacct taccaggtct tgacatccct ctgaccggta cagagatgta cctttccttc 960
gggacagagg agacaggtgg tgcatggttg tcgtcagctc gtgtcgtgag atgttgggtt 1020
aagtcccgca acgagcgcaa cccttgatct tagttgccag cacttcgggt gggcactcta 1080
aggtgactgc cggtgacaaa ccggaggaag gtggggatga cgtcaaatca tcatgcccct 1140
tatgacctgg gctacacacg tactacaatg gccggtacaa cgggcagtga aaccgcgagg 1200
tggaacgaat cctaaaaagc cggtctcagt tcggattgca ggctgcaact cgcctgcatg 1260
aagtcggaat tgctagtaat cgcggatcag catgccgcgg tgaatacgtt cccgggtctt 1320
gtacacaccg cccgtcacac cacgagagtt tataacaccc gaagtcggt 1369

<210> SEQ ID NO 12
<211> LENGTH: 1366
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus: Paenibacillus

<400> SEQUENCE: 12

```
gcttgcttct ccgatggtta gcggcggacg ggtgagtaac acgtaggcaa cctgccctca     60
agtttgggac aactaccgga aacggtagct aataccgaat agttgttttc ttctcctgaa    120
ggaaactgga aagacggagc aatctgtcac ttggggatgg gcctgcggcg cattagctag    180
ttggtggggt aacggctcac caaggcgacg atgcgtagcc gacctgagag ggtgatcggc    240
cacactggga ctgagacacg gcccagactc ctacgggagg cagcagtagg gaatcttccg    300
caatgggcga aagcctgacg gagcaatgcc gcgtgagtga tgaaggtttt cggatcgtaa    360
agctctgttg ccagggaaga acgcttggga gagtaactgc tctcaaggtg acggtacctg    420
agaagaaagc cccggctaac tacgtgccag cagccgcggt aatacgtagg gggcaagcgt    480
tgtccggaat tattgggcgt aaagcgcgcg caggcggtca tttaagtctg gtgtttaatc    540
ccggggctca accccggatc gcactggaaa ctgggtgact tgagtgcaga agaggagagt    600
ggaattccac gtgtagcggt gaaatgcgta gatatgtgga ggaacaccag tggcgaaggc    660
gactctctgg gctgtaactg acgctgaggc gcgaaagcgt ggggagcaaa caggattaga    720
taccctggta gtccacgccg taaacgatga gtgctaggtg ttaggggttt cgataccctt    780
ggtgccgaag ttaacacatt aagcactccg cctggggagt acggtcgcaa gactgaaact    840
caaaggaatt gacggggacc cgcacaagca gtggagtatg tggtttaatt cgaagcaacg    900
cgaagaacct taccaggtct tgacatccct ctgaccggta cagagatgta cctttccttc    960
gggacagagg agacaggtgg tgcatggttg tcgtcagctc gtgtcgtgag atgttgggtt   1020
aagtcccgca acgagcgcaa cccttgatct tagttgccag cacttcgggt gggcactcta   1080
aggtgactgc cggtgacaaa ccggaggaag gtggggatga cgtcaaatca tcatgcccct   1140
tatgacctgg gctacacacg tactacaatg gccggtacaa cgggcagtga aaccgcgagg   1200
tggaacgaat cctaaaaagc cggtctcagt tcggattgca ggctgcaact cgcctgcatg   1260
aagtcggaat tgctagtaat cgcggatcag catgccgcgg tgaatacgtt cccgggtctt   1320
gtacacaccg cccgtcacac cacgagagtt tataacaccc gaagtc                  1366
```

<210> SEQ ID NO 13
<211> LENGTH: 1303
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus: Paenibacillus

<400> SEQUENCE: 13

```
ggtgagtaac acgtaggcaa cctgccctca agtttgggac aactaccgga aacggtagct     60
aataccgaat agttgttttc ttctcctgaa ggaaactgga aagacggagc aatctgtcac    120
ttggggatgg gcctgcggcg cattagctag ttggtggggt aacggctcac caaggcgacg    180
atgcgtagcc gacctgagag ggtgatcggc cacactggga ctgagacacg gcccagactc    240
```

```
ctacgggagg cagcagtagg gaatcttccg caatgggcga aagcctgacg gagcaatgcc    300

gcgtgagtga tgaaggtttt cggatcgtaa agctctgttg ccagggaaga acgcttggga    360

gagtaactgc tctcaaggtg acggtacctg agaagaaagc cccggctaac tacgtgccag    420

cagccgcggt aatacgtagg gggcaagcgt tgtccggaat tattgggcgt aaagcgcgcg    480

caggcggtca tttaagtctg gtgtttaatc ccggggctca accccggatc gcactggaaa    540

ctgggtgact tgagtgcaga agaggagagt ggaattccac gtgtagcggt gaaatgcgta    600

gatatgtgga ggaacaccag tggcgaaggc gactctctgg gctgtaactg acgctgaggc    660

gcgaaagcgt ggggagcaaa caggattaga taccctggta gtccacgccg taaacgatga    720

gtgctaggtg ttaggggttt cgataccctt ggtgccgaag ttaacacatt aagcactccg    780

cctggggagt acggtcgcaa gactgaaact caaaggaatt gacggggacc cgcacaagca    840

gtggagtatg tggtttaatt cgaagcaacg cgaagaacct taccaggtct tgacatccct    900

ctgaccggta cagagatgta cctttccttc gggacagagg agacaggtgg tgcatggttg    960

tcgtcagctc gtgtcgtgag atgttgggtt aagtcccgca acgagcgcaa cccttgatct   1020

tagttgccag cacttcgggt gggcactcta aggtgactgc cggtgacaaa ccggaggaag   1080

gtggggatga cgtcaaatca tcatgcccct tatgacctgg gctacacacg tactacaatg   1140

gccggtacaa cgggcagtga aaccgcgagg tggaacgaat cctaaaaagc cggtctcagt   1200

tcggattgca ggctgcaact cgcctgcatg aagtcggaat tgctagtaat cgcggatcag   1260

catgccgcgg tgaatacgtt cccgggtctt gtacacaccg ccc                     1303
```

<210> SEQ ID NO 14
<211> LENGTH: 1313
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Burkholderiaceae, Genus: Ralstonia

<400> SEQUENCE: 14

```
gattgatggc gagtggcgaa cgggtgagta atacatcgga acgtgccctg tagtggggga     60

taactagtcg aaagattagc taataccgca tacgacctga gggtgaaagt gggggaccgc    120

aaggcctcat gctataggag cggccgatgt ctgattagct agttggtgag gtaaaggctc    180

accaaggcga cgatcagtag ctggtctgag aggacgatca gccacactgg gactgagaca    240

cggcccagac tcctacggga ggcagcagtg gggaattttg gacaatgggc gaaagcctga    300

tccagcaatg ccgcgtgtgt gaagaaggcc ttcgggttgt aaagcacttt tgtccggaaa    360

gaaatggctc cggttaatac ctggggtcga tgacggtacc ggaagaataa ggaccggcta    420

actacgtgcc agcagccgcg gtaatacgta gggtccaagc gttaatcgga attactgggc    480

gtaaagcgtg cgcaggcggt tgtgcaagac cgatgtgaaa tccccgagct taacttggga    540

attgcattgg tgactgcacg gctagagtgt gtcagagggg gtagaattcc acgtgtagca    600

gtgaaatgcg tagagatgtg gaggaatacc gatggcgaag gcagccccct gggataacac    660

tgacgctcat gcacgaaagc gtggggagca aacaggatta gataccctgg tagtccacgc    720

cctaaacgat gtcaactagt tgttggggat tcatttcctt agtaacgtag ctaacgcgtg    780

aagttgaccg cctggggagt acggtcgcaa gattaaaact caaaggaatt gacggggacc    840

cgcacaagcg gtggatgatg tggattaatt cgatgcaacg cgaaaaacct tacctaccct    900

tgacatgcca ctaacgaagc agagatgcat taggtgctcg aaagagaaag tggacacagg    960
```

-continued

```
tgctgcatgg ctgtcgtcag ctcgtgtcgt gagatgttgg gttaagtccc gcaacgagcg   1020

caacccttgt ctctagttgc tacgaaaggg cactctagag agactgccgg tgacaaaccg   1080

gaggaaggtg gggatgacgt caagtcctca tggcccttat gggtagggct tcacacgtca   1140

tacaatggtg catacagagg gttgccaagc cgcgaggtgg agctaatccc agaaaatgca   1200

tcgtagtccg gatcgtagtc tgcaactcga ctacgtggag ctggaatcgc tagtaatcgc   1260

ggatcagcat gccgcggtga atacgttccc gggtcttgta cacaccgccc gtc          1313
```

<210> SEQ ID NO 15
<211> LENGTH: 1337
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus

<400> SEQUENCE: 15

```
tgttagcggc ggacgggtga gtaacacgtg ggtaacctgc ctgtaagact gggataactc     60

cgggaaaccg gggctaatac cggatggttg tttgaaccgc atggttcaaa cataaaaggt    120

ggcttcggct accacttaca gatggacccg cggcgcatta gctagttggt gaggtaacgg    180

ctcaccaagg caacgatgcg tagccgacct gagagggtga tcggccacac tgggactgag    240

acacggccca gactcctacg ggaggcagca gtagggaatc ttccgcaatg gacgaaagtc    300

tgacggagca acgccgcgtg agtgatgaag gttttcggat cgtaaagctc tgttgttagg    360

gaagaacaag taccgttcga atagggcggt accttgacgg tacctaacca gaaagccacg    420

gctaactacg tgccagcagc cgcggtaata cgtaggtggc aagcgttgtc cggaattatt    480

gggcgtaaag ggctcgcagg cggtttctta agtctgatgt gaaagccccc ggctcaaccg    540

gggagggtca ttggaaactg gggaacttga gtgcagaaga ggagagtgga attccacgtg    600

tagcggtgaa atgcgtagag atgtggagga acaccagtgg cgaaggcgac tctctggtct    660

gtaactgacg ctgaggagcg aaagcgtggg gagcgaacag gattagatac cctggtagtc    720

cacgccgtaa acgatgagtg ctaagtgtta gggggtttcc gccccttagt gctgcagcta    780

acgcattaag cactccgcct ggggagtacg gtcgcaagac tgaaactcaa aggaattgac    840

gggggcccgc acaagcggtg gagcatgtgg tttaattcga agcaacgcga agaaccttac    900

caggtcttga catcctctga caatcctaga gataggacgt ccccttcggg ggcagagtga    960

caggtggtgc atggttgtcg tcagctcgtg tcgtgagatg ttgggttaag tcccgcaacg   1020

agcgcaaccc ttgatcttag ttgccagcat tcagttgggc actctaaggt gactgccggt   1080

gacaaaccgg aggaaggtgg ggatgacgtc aaatcatcat gccccttatg acctgggcta   1140

cacacgtgct acaatggaca gaacaaaggg cagcgaaacc gcgaggttaa gccaatccca   1200

caaatctgtt ctcagttcgg atcgcagtct gcaactcgac tgcgtgaagc tggaatcgct   1260

agtaatcgcg gatcagcatg ccgcggtgaa tacgttcccg ggccttgtac acaccgcccg   1320

tcacaccatc gagagtt                                                  1337
```

<210> SEQ ID NO 16
<211> LENGTH: 1326
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Burkholderiaceae, Genus: Ralstonia

<400> SEQUENCE: 16
agcttgctag attgatggcg agtggcgaac gggtgagtaa tacatcggaa cgtgccctgt 60
agtgggggat aactagtcga aagattagct aataccgcat acgacctgag ggtgaaagtg 120
ggggaccgca aggcctcatg ctataggagc ggccgatgtc tgattagcta gttggtgagg 180
taaaggctca ccaaggcgac gatcagtagc tggtctgaga ggacgatcag ccacactggg 240
actgagacac ggcccagact cctacgggag gcagcagtgg ggaattttgg acaatgggcg 300
aaagcctgat ccagcaatgc cgcgtgtgtg aggaaggcct tcgggttgta aagcactttt 360
gtccggaaag aaatggctct ggttaatacc tggggtcgat gacggtaccg gaagaataag 420
gaccggctaa ctacgtgcca gcagccgcgg taatacgtag ggtccaagcg ttaatcggaa 480
ttactgggcg taaagcgtgc gcaggcggtt gtgcaagacc gatgtgaaat ccccgagctt 540
aacttgggaa ttgcattggt gactgcacgg ctagagtgtg tcagaggggg gtagaattcc 600
acgtgtagca gtgaaatgcg tagagatgtg gaggaatacc gatggcgaag gcagcccccct 660 gggataacac tgacgctcat gcacgaaagc gtggggagca aacaggatta gataccctgg 720
tagtccacgc cctaaacgat gtcaactagt tgttggggat tcatttcctt agtaacgtag 780
ctaacgcgtg aagttgaccg cctggggagt acggtcgcaa gattaaaact caaaggaatt 840
gacggggacc cgcacaagcg gtggatgatg tggattaatt cgatgcaacg cgaaaaacct 900
tacctaccct tgacatgcca ctaacgaagc agagatgcat taggtgctcg aaagagaaag 960
tggacacagg tgctgcatgg ctgtcgtcag ctcgtgtcgt gagatgttgg gttaagtccc 1020
gcaacgagcg caacccttgt ctctagttgc tacgaaaggg cactctagag agactgccgg 1080
tgacaaaccg gaggaaggtg gggatgacgt caagtcctca tggcccttat gggtagggct 1140
tcacacgtca tacaatggtg catacagagg gttgccaagc cgcgaggtgg agctaatccc 1200
agaaaatgca tcgtagtccg gatcgtagtc tgcaactcga ctacgtgaag ctggaatcgc 1260
tagtaatcgc ggatcagcat gccgcggtga atacgttccc gggtcttgta cacaccgccc 1320
gtcaca 1326

<210> SEQ ID NO 17
<211> LENGTH: 1368
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus: Paenibacillus

<400> SEQUENCE: 17
cttgcttctc cgatggttag cggcggacgg gtgagtaaca cgtaggcaac ctgccctcaa 60
gtttgggaca actaccggaa acggtagcta ataccgaata gttgttttct tctcctgaag 120
gaaactggaa agacggagca atctgtcact tggggatggg cctgcggcgc attagctagt 180
tggtggggta acggctcacc aaggcgacga tgcgtagccg acctgagagg gtgatcggcc 240
acactgggac tgagacacgg cccagactcc tacgggaggc agcagtaggg aatcttccgc 300
aatgggcgaa agcctgacgg agcaatgccg cgtgagtgat gaaggttttc ggatcgtaaa 360
gctctgttgc cagggaagaa cgcttgggag agtaactgct ctcaaggtga cggtacctga 420
gaagaaagcc ccggctaact acgtgccagc agccgcggta atacgtaggg ggcaagcgtt 480
gtccggaatt attgggcgta aagcgcgcgc aggcggtcat ttaagtctgg tgtttaatcc 540

```
cggggctcaa ccccggatcg cactggaaac tgggtgactt gagtgcagaa gaggagagtg    600

gaattccacg tgtagcggtg aaatgcgtag atatgtggag gaacaccagt ggcgaaggcg    660

actctctggg ctgtaactga cgctgaggcg cgaaagcgtg gggagcaaac aggattagat    720

accctggtag tccacgccgt aaacgatgag tgctaggtgt taggggtttc gataccettg    780

gtgccgaagt taacacatta agcactccgc ctggggagta cggtcgcaag actgaaactc    840

aaaggaattg acggggaccc gcacaagcag tggagtatgt ggtttaattc gaagcaacgc    900

gaagaacctt accaggtctt gacatccctc tgaccggtac agagatgtac ctttccttcg    960

ggacagagga gacaggtggt gcatggttgt cgtcagctcg tgtcgtgaga tgttgggtta   1020

agtcccgcaa cgagcgcaac ccttgatctt agttgccagc acttcgggtg ggcactctaa   1080

ggtgactgcc ggtgacaaac cggaggaagg tggggatgac gtcaaatcat catgcccctt   1140

atgacctggg ctacacacgt actacaatgg ccggtacaac gggcagtgaa accgcgaggt   1200

ggaacgaatc ctaaaaagcc ggtctcagtt cggattgcag gctgcaactc gcctgcatga   1260

agtcggaatt gctagtaatc gcggatcagc atgccgcggt gaatacgttc ccgggtcttg   1320

tacacaccgc ccgtcacacc acgagagttt ataacacccg aagtcggt                1368


<210> SEQ ID NO 18
<211> LENGTH: 1368
<212> TYPE: DNA
<213> ORGANISM: Unknown
<220> FEATURE:
<223> OTHER INFORMATION: Kingdom: Bacteria, Phylum: Firmicutes, Class:
      Bacilli, Order: Bacillales, Family: Paenibacillaceae , Genus:
      Paenibacillus

<400> SEQUENCE: 18

gcttgcttct ccgatggtta gcggcggacg ggtgagtaac acgtaggcaa cctgccctca     60

agtttgggac aactaccgga aacggtagct aataccgaat agttgttttc ttctcctgaa    120

ggaaactgga aagacggagc aatctgtcac ttggggatgg gcctgcggcg cattagctag    180

ttggtggggt aacggctcac caaggcgacg atgcgtagcc gacctgagag ggtgatcggc    240

cacactggga ctgagacacg gcccagactc ctacgggagg cagcagtagg gaatcttccg    300

caatgggcga aagcctgacg gagcaatgcc gcgtgagtga tgaaggtttt cggatcgtaa    360

agctctgttg ccagggaaga acgcttggga gagtaactgc tctcaaggtg acggtacctg    420

agaagaaagc cccggctaac tacgtgccag cagccgcggt aatacgtagg gggcaagcgt    480

tgtccggaat tattgggcgt aaagcgcgcg caggcggtca tttaagtctg gtgtttaatc    540

ccggggctca accccggatc gcactggaaa ctgggtgact tgagtgcaga agaggagagt    600

ggaattccac gtgtagcggt gaaatgcgta gatatgtgga ggaacaccag tggcgaaggc    660

gactctctgg gctgtaactg acgctgaggc gcgaaagcgt ggggagcaaa caggattaga    720

taccctggta gtccacgccg taaacgatga gtgctaggtg ttaggggttt cgataccctt    780

ggtgccgaag ttaacacatt aagcactccg cctggggagt acggtcgcaa gactgaaact    840

caaaggaatt gacggggacc cgcacaagca gtggagtatg tggtttaatt cgaagcaacg    900

cgaagaacct taccaggtct tgacatccct ctgaccggta cagagatgta cctttccttc    960

gggacagagg agacaggtgg tgcatggttg tcgtcagctc gtgtcgtgag atgttgggtt   1020

aagtcccgca acgagcgcaa cccttgatct tagttgccag cacttcgggt gggcactcta   1080

aggtgactgc cggtgacaaa ccggaggaag gtggggatga cgtcaaatca tcatgcccct   1140

tatgacctgg gctacacacg tactacaatg gccggtacaa cgggcagtga aaccgcgagg   1200
```

```
tggaacgaat cctaaaaagc cggtctcagt tcggattgca ggctgcaact cgcctgcatg   1260

aagtcggaat tgctagtaat cgcggatcag catgccgcgg tgaatacgtt cccgggtctt   1320

gtacacaccg cccgtcacac cacgagagtt tataacaccc gaagtcgg                1368


<210> SEQ ID NO 19
<211> LENGTH: 1371
<212> TYPE: DNA
<213> ORGANISM: Unknown
<220> FEATURE:
<223> OTHER INFORMATION: Kingdom: Bacteria, Phylum: Firmicutes, Class:
      Bacilli, Order: Bacillales, Family: Paenibacillaceae , Genus:
      Paenibacillus

<400> SEQUENCE: 19

gcttgcttct ccgatggtta gcggcggacg ggtgagtaac acgtaggcaa cctgccctca     60

agtttgggac aactaccgga aacggtagct aataccgaat agttgttttc ttctcctgaa    120

ggaaactgga aagacggagc aatctgtcac ttggggatgg gcctgcggcg cattagctag    180

ttggtggggt aacggctcac caaggcgacg atgcgtagcc gacctgagag ggtgatcggc    240

cacactggga ctgagacacg gcccagactc ctacgggagg cagcagtagg gaatcttccg    300

caatgggcga aagcctgacg gagcaatgcc gcgtgagtga tgaaggtttt cggatcgtaa    360

agctctgttg ccagggaaga acgcttggga gagtaactgc tctcaaggtg acggtacctg    420

agaagaaagc cccggctaac tacgtgccag cagccgcggt aatacgtagg gggcaagcgt    480

tgtccggaat tattgggcgt aaagcgcgcg caggcggtca tttaagtctg gtgtttaatc    540

ccggggctca accccggatc gcactggaaa ctgggtgact tgagtgcaga agaggagagt    600

ggaattccac gtgtagcggt gaaatgcgta gatatgtgga ggaacaccag tggcgaaggc    660

gactctctgg gctgtaactg acgctgaggc gcgaaagcgt ggggagcaaa caggattaga    720

taccctggta gtccacgccg taaacgatga gtgctaggtg ttaggggttt cgataccctt    780

ggtgccgaag ttaacacatt aagcactccg cctggggagt acggtcgcaa gactgaaact    840

caaaggaatt gacggggacc cgcacaagca gtggagtatg tggtttaatt cgaagcaacg    900

cgaagaacct taccaggtct tgacatccct ctgaccggta cagagatgta cctttccttc    960

gggacagagg agacaggtgg tgcatggttg tcgtcagctc gtgtcgtgag atgttgggtt   1020

aagtcccgca acgagcgcaa cccttgatct tagttgccag cacttcgggt gggcactcta   1080

aggtgactgc cggtgacaaa ccggaggaag gtggggatga cgtcaaatca tcatgcccct   1140

tatgacctgg gctacacacg tactacaatg gccggtacaa cgggcagtga aaccgcgagg   1200

tggaacgaat cctaaaaagc cggtctcagt tcggattgca ggctgcaact cgcctgcatg   1260

aagtcggaat tgctagtaat cgcggatcag catgccgcgg tgaatacgtt cccgggtctt   1320

gtacacaccg cccgtcacac cacgagagtt tataacaccc gaagtcggtg g            1371


<210> SEQ ID NO 20
<211> LENGTH: 1350
<212> TYPE: DNA
<213> ORGANISM: Unknown
<220> FEATURE:
<223> OTHER INFORMATION: Kingdom: Bacteria, Phylum: Firmicutes, Class:
      Bacilli, Order: Bacillales, Family: Bacillaceae , Genus: Bacillus
<220> FEATURE:
<221> NAME/KEY: misc_feature
<222> LOCATION: (1207)..(1207)
<223> OTHER INFORMATION: n is a, c, g, or t

<400> SEQUENCE: 20
```

ttgctccctg atgttagcgg cggacgggtg agtaacacgt gggtaacctg cctgtaagac 60
tgggataact ccgggaaacc ggggctaata ccggatggtt gtttgaaccg catggttcaa 120
acataaaagg tggcttcggc taccacttac agatggaccc gcggcgcatt agctagttgg 180
tgaggtaacg gctcaccaag gcaacgatgc gtagccgacc tgagagggtg atcggccaca 240
ctgggactga gacacggccc agactcctac gggaggcagc agtagggaat cttccgcaat 300
ggacgaaagt ctgacggagc aacgccgcgt gagtgatgaa ggttttcgga tcgtaaagct 360
ctgttgttag ggaagaacaa gtaccgttcg aatagggcgg taccttgacg gtacctaacc 420
agaaagccac ggctaactac gtgccagcag ccgcggtaat acgtaggtgg caagcgttgt 480
ccggaattat tgggcgtaaa gggctcgcag gcggtttctt aagtctgatg tgaaagcccc 540
cggctcaacc ggggagggtc attggaaact ggggaacttg agtgcagaag aggagagtgg 600
aattccacgt gtagcggtga aatgcgtaaa gatgtggagg aacaccagtg gcggtaactg 660
acgttgagga gcgaaagcgt ggggagcgaa caggattaga taccctggta gtccacgccg 720
taaacgatga gtgctaagtg ttagggggtt tccgcccctt agtgctgcag ctaacgcatt 780
aagcactccg cctggggtgt acggtcgcaa gactgaaact caaaggaatt gacgggggcc 840
cgcacaagcg gtggagcatg tggtttaatt cgaagcaacg cgaagaacct taccaggtct 900
tgacatcctc tgacaatcct agagatagga cgtccccttc gggggcagag tgacaggtgg 960
tgcatggttg tcgtcagctc gtgtcgtgag atgttgggtt aagtcccgca acgagcgcaa 1020
cccttgatct tagttgccag cattcagttg ggcactctaa ggtgactgcc ggtgacaaac 1080
cggaggaagg tggggatgac gtcaaatcat catgcccctt atgacctggg ctacacacgt 1140
gctacaatgg acagaacaaa gggcagcgaa accgcgaggt taagccaatc ccacaaatct 1200
gttctcngtt cggatcgcag tctgcaactc gactgcgtga agctggaatc gctagtaatc 1260
gcggatcagc atgccgcggt gaatacgttc ccgggccttg tacacaccgc ccgtcacacc 1320
acgagagttt taacacccga agtcggtgag 1350

<210> SEQ ID NO 21
<211> LENGTH: 1366
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus: Paenibacillus

<400> SEQUENCE: 21
gcttgcttct ccgatggtta gcggcggacg ggtgagtaac acgtaggcaa cctgccctca 60
agtttgggac aactaccgga aacggtagct aataccgaat agttgttttc ttctcctgaa 120
ggaaactgga aagacggagc aatctgtcac ttggggatgg gcctgcggcg cattagctag 180
ttggtggggt aacggctcac caaggcgacg atgcgtagcc gacctgagag ggtgatcggc 240
cacactggga ctgagacacg gcccagactc ctacgggagg cagcagtagg gaatcttccg 300
caatgggcga aagcctgacg gagcaatgcc gcgtgagtga tgaaggtttt cggatcgtaa 360
agctctgttg ccagggaaga acgcttggga gagtaactgc tctcaaggtg acggtacctg 420
agaagaaagc cccggctaac tacgtgccag cagccgcggt aatacgtagg gggcaagcgt 480
tgtccggaat tattgggcgt aaagcgcgcg caggcggtca tttaagtctg gtgtttaatc 540
ccggggctca accccggatc gcactggaaa ctgggtgact tgagtgcaga agaggagagt 600

-continued

```
ggaattccac gtgtagcggt gaaatgcgta gatatgtgga ggaacaccag tggcgaaggc    660

gactctctgg gctgtaactg acgctgaggc gcgaaagcgt ggggagcaaa caggattaga    720

taccctggta gtccacgccg tatacgatga gtgctaggtg ttaggggttt cgataccctt    780

ggtgccgaag ttaacacatt aagcactccg cctggggagt acggtcgcaa gactgaaact    840

caaaggaatt gacggggacc cgcacaagca gtggagtatg tggtttaatt cgaagcaacg    900

cgaagaacct taccaggtct tgacatccct ctgaccggta cagagatgta cctttccttc    960

gggacagagg agacaggtgg tgcatggttg tcgtcagctc gtgtcgtgag atgttgggtt   1020

aagtcccgca acgagcgcaa cccttgatct tagttgccag cacttcgggt gggcactcta   1080

aggtgactgc cggtgacaaa ccggaggaag gtggggatga cgtcaaatca tcatgcccct   1140

tatgacctgg gctacacacg tactacaatg gccggtacaa cgggcagtga aaccgcgagg   1200

tggaacgaat cctaaaaagc cggtctcagt tcggattgca ggctgcaact cgcctgcatg   1260

aagtcggaat tgctagtaat cgcggatcag catgccgcgg tgaatacgtt cccgggtctt   1320

gtacacaccg cccgtcacac cacgagagtt tataacaccc gaagtc                  1366
```

<210> SEQ ID NO 22
<211> LENGTH: 1368
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus: Paenibacillus

<400> SEQUENCE: 22

```
cttgcttctc cgatggttag cggcggacgg gtgagtaaca cgtaggcaac ctgccctcaa     60

gtttgggaca actaccggaa acggtagcta ataccgaata gttgttttct tctcctgaag    120

gaaactggaa agacggagca atctgtcact tggggatggg cctgcggcgc attagctagt    180

tggtggggta acggctcacc aaggcgacga tgcgtagccg acctgagagg gtgatcggcc    240

acactgggac tgagacacgg cccagactcc tacgggaggc agcagtaggg aatcttccgc    300

aatgggcgaa agcctgacgg agcaatgccg cgtgagtgat gaaggttttc ggatcgtaaa    360

gctctgttgc cagggaagaa cgcttgggag agtaactgct ctcaaggtga cggtacctga    420

gaagaaagcc ccggctaact acgtgccagc agccgcggta atacgtaggg ggcaagcgtt    480

gtccggaatt attgggcgta aagcgcgcgc aggcggtcat ttaagtctgg tgtttaatcc    540

cggggctcaa ccccggatcg cactggaaac tgggtgactt gagtgcagaa gaggagagtg    600

gaattccacg tgtagcggtg aaatgcgtag atatgtggag gaacaccagt ggcgaaggcg    660

actctctggg ctgtaactga cgctgaggcg cgaaagcgtg gggagcaaac aggattagat    720

accctggtag tccacgccgt aaacgatgag tgctaggtgt taggggtttc gatacccttg    780

gtgccgaagt taacacatta agcactccgc ctggggagta cggtcgcaag actgaaactc    840

aaaggaattg acggggaccc gcacaagcag tggagtatgt ggtttaattc gaagcaacgc    900

gaagaacctt accaggtctt gacatccctc tgaccggtac agagatgtac ctttccttcg    960

ggacagagga gacaggtggt gcatggttgt cgtcagctcg tgtcgtgaga tgttgggtta   1020

agtcccgcaa cgagcgcaac ccttgatctt agttgccagc acttcgggtg ggcactctaa   1080

ggtgactgcc ggtgacaaac cggaggaagg tggggatgac gtcaaatcat catgcccctt   1140

atgacctggg ctacacacgt actacaatgg ccggtacaac gggcagtgaa accgcgaggt   1200

ggaacgaatc ctaaaaagcc ggtctcagtt cggattgcag gctgcaactc gcctgcatga   1260
```

agtcggaatt gctagtaatc gcggatcagc atgccgcggt gaatacgttc ccgggtcttg 1320
tacacaccgc ccgtcacacc acgagagttt ataacacccg aagtcggt 1368

<210> SEQ ID NO 23
<211> LENGTH: 1367
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus: Paenibacillus

<400> SEQUENCE: 23
gcttgcttct ccgatggtta gcggcggacg ggtgagtaac acgtaggcaa cctgccctca 60
agtttgggac aactaccgga aacggtagct aataccgaat agttgttttc ttctcctgaa 120
ggaaactgga aagacggagc aatctgtcac ttggggatgg gcctgcggcg cattagctag 180
ttggtggggt aacggctcac caaggcgacg atgcgtagcc gacctgagag ggtgatcggc 240
cacactggga ctgagacacg gcccagactc ctacgggagg cagcagtagg gaatcttccg 300
caatgggcga aagcctgacg gagcaatgcc gcgtgagtga tgaaggtttt cggatcgtaa 360
agctctgttg ccagggaaga acgcttggga gagtaactgc tctcaaggtg acggtacctg 420
agaagaaagc cccggctaac tacgtgccag cagccgcggt aatacgtagg gggcaagcgt 480
tgtccggaat tattgggcgt aaagcgcgcg caggcggtca tttaagtctg gtgtttaatc 540
ccggggctca accccggatc gcactggaaa ctgggtgact tgagtgcaga agaggagagt 600
ggaattccac gtgtagcggt gaaatgcgta gatatgtgga ggaacaccag tggcgaaggc 660
gactctctgg gctgtaactg acgctgaggc gcgaaagcgt ggggagcaaa caggattaga 720
taccctggta gtccacgccg taaacgatga gtgctaggtg ttaggggttt cgataccctt 780
ggtgccgaag ttaacacatt aagcactccg cctggggagt acggtcgcaa gactgaaact 840
caaaggaatt gacggggacc cgcacaagca gtggagtatg tggtttaatt cgaagcaacg 900
cgaagaacct taccaggtct tgacatccct ctgaccggta cagagatgta cctttccttc 960
gggacagagg agacaggtgg tgcatggttg tcgtcagctc gtgtcgtgag atgttgggtt 1020
aagtcccgca acgagcgcaa cccttgatct tagttgccag cacttcgggt gggcactcta 1080
aggtgactgc cggtgacaaa ccggaggaag gtggggatga cgtcaaatca tcatgcccct 1140
tatgacctgg gctacacacg tactacaatg gccggtacaa cgggcagtga aaccgcgagg 1200
tggaacgaat cctaaaaagc cggtctcagt tcggattgca ggctgcaact cgcctgcatg 1260
aagtcggaat tgctagtaat cgcggatcag catgccgcgg tgaatacgtt cccgggtctt 1320
gtacacaccg cccgtcacac cacgagagtt tataacaccc gaagtcg 1367

<210> SEQ ID NO 24
<211> LENGTH: 1367
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus: Paenibacillus

<400> SEQUENCE: 24
ttgcttctcc gatggttagc ggcggacggg tgagtaacac gtaggcaacc tgccctcaag 60
tttgggacaa ctaccggaaa cggtagctaa taccgaatag ttgttttctt ctcctgaagg 120

```
aaactggaaa gacggagcaa tctgtcactt ggggatgggc ctgcggcgca ttagctagtt    180

ggtggggtaa cggctcacca aggcgacgat gcgtagccga cctgagaggg tgatcggcca    240

cactgggact gagacacggc ccagactcct acgggaggca gcagtaggga atcttccgca    300

atgggcgaaa gcctgacgga gcaatgccgc gtgagtgatg aaggttttcg gatcgtaaag    360

ctctgttgcc agggaagaac gcttgggaga gtaactgctc tcaaggtgac ggtacctgag    420

aagaaagccc cggctaacta cgtgccagca gccgcggtaa tacgtagggg gcaagcgttg    480

tccggaatta ttgggcgtaa agcgcgcgca ggcggtcatt taagtctggt gtttaatccc    540

ggggctcaac cccggatcgc actggaaact gggtgacttg agtgcagaag aggagagtgg    600

aattccacgt gtagcggtga aatgcgtaga tatgtggagg aacaccagtg gcgaaggcga    660

ctctctgggc tgtaactgac gctgaggcgc gaaagcgtgg ggagcaaaca ggattagata    720

ccctggtagt ccacgccgta aacgatgagt gctaggtgtt aggggtttcg ataccettgg    780

tgccgaagtt aacacattaa gcactccgcc tggggagtac ggtcgcaaga ctgaaactca    840

aaggaattga cggggacccg cacaagcagt ggagtatgtg gtttaattcg aagcaacgcg    900

aagaacctta ccaggtcttg acatccctct gaccggtaca gagatgtacc tttccttcgg    960

gacagaggag acaggtggtg catggttgtc gtcagctcgt gtcgtgagat gttgggttaa   1020

gtcccgcaac gagcgcaacc cttgatctta gttgccagca cttcgggtgg gcactctaag   1080

gtgactgccg gtgacaaacc ggaggaaggt ggggatgacg tcaaatcatc atgcccctta   1140

tgacctgggc tacacacgta ctacaatggc cggtacaacg ggcagtgaaa ccgcgaggtg   1200

gaacgaatcc taaaaagccg gtctcagttc ggattgcagg ctgcaactcg cctgcatgaa   1260

gtcggaattg ctagtaatcg cggatcagca tgccgcggtg aatacgttcc cgggtcttgt   1320

acacaccgcc cgtcacacca cgagagttta taacacccga agtcggt                 1367
```

<210> SEQ ID NO 25
<211> LENGTH: 1363
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus: Paenibacillus

<400> SEQUENCE: 25

```
ttctccgatg gttagcggcg gacgggtgag taacacgtag gcaacctgcc ctcaagtttg     60

ggacaactac cggaaacggt agctaatacc gaatagttgt ttcttctcc tgaaggaaac    120

tggaaagacg gagcaatctg tcacttgggg atgggcctgc ggcgcattag ctagttggtg    180

gggtaacggc tcaccaaggc gacgatgcgt agccgacctg agagggtgat cggccacact    240

gggactgaga cacggcccag actcctacgg gaggcagcag tagggaatct tccgcaatgg    300

gcgaaagcct gacggagcaa tgccgcgtga gtgatgaagg ttttcggatc gtaaagctct    360

gttgccaggg aagaacgctt gggagagtaa ctgctctcaa ggtgacggta cctgagaaga    420

aagccccggc taactacgtg ccagcagccg cggtaatacg taggggggcaa gcgttgtccg    480

gaattattgg gcgtaaagcg cgcgcaggcg gtcatttaag tctggtgttt aatcccgggg    540

ctcaaccccg gatcgcactg gaaactgggt gacttgagtg cagaagagga gagtggaatt    600

ccacgtgtag cggtgaaatg cgtagatatg tggaggaaca ccagtggcga aggcgactct    660

ctgggctgta actgacgctg aggcgcgaaa gcgtggggag caaacaggat tagataccct    720

ggtagtccac gccgtaaacg atgagtgcta ggtgttaggg gtttcgatac ccttggtgcc    780
```

```
gaagttaaca cattaagcac tccgcctggg gagtacggtc gcaagactga aactcaaagg    840

aattgacggg gacccgcaca agcagtggag tatgtggttt aattcgaagc aacgcgaaga    900

accttaccag gtcttgacat ccctctgacc ggtacagaga tgtacctttc cttcgggaca    960

gaggagacag gtggtgcatg gttgtcgtca gctcgtgtcg tgagatgttg ggttaagtcc   1020

cgcaacgagc gcaacccttg atcttagttg ccagcacttc gggtgggcac tctaaggtga   1080

ctgccggtga caaaccggag gaaggtgggg atgacgtcaa atcatcatgc cccttatgac   1140

ctgggctaca cacgtactac aatggccggt acaacgggca gtgaaaccgc gaggtggaac   1200

gaatcctaaa aagccggtct cagttcggat tgcaggctgc aactcgcctg catgaagtcg   1260

gaattgctag taatcgcgga tcagcatgcc gcggtgaata cgttcccggg tcttgtacac   1320

accgcccgtc acaccacgag agtttataac acccgaagtc ggt                     1363
```

<210> SEQ ID NO 26
<211> LENGTH: 1371
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus: Paenibacillus

<400> SEQUENCE: 26

```
gcttgcttct ccgatggtta gcggcggacg ggtgagtaac acgtaggcaa cctgccctca     60

agtttgggac aactaccgga aacggtagct aataccgaat agttgttttc ttctcctgaa    120

ggaaactgga aagacggagc aatctgtcac ttggggatgg gcctgcggcg cattagctag    180

ttggtggggt aacggctcac caaggcgacg atgcgtagcc gacctgagag ggtgatcggc    240

cacactggga ctgagacacg gcccagactc ctacgggagg cagcagtagg gaatcttccg    300

caatgggcga aagcctgacg gagcaatgcc gcgtgagtga tgaaggtttt cggatcgtaa    360

agctctgttg ccagggaaga acgcttggga gagtaactgc tctcaaggtg acggtacctg    420

agaagaaagc cccggctaac tacgtgccag cagccgcggt aatacgtagg gggcaagcgt    480

tgtccggaat tattgggcgt aaagcgcgcg caggcggtca tttaagtctg gtgtttaatc    540

ccggggctca accccggatc gcactggaaa ctgggtgact tgagtgcaga agaggagagt    600

ggaattccac gtgtagcggt gaaatgcgta gatatgtgga ggaacaccag tggcgaaggc    660

gactctctgg gctgtaactg acgctgaggc gcgaaagcgt ggggagcaaa caggattaga    720

taccctggta gtccacgccg taaacgatga gtgctaggtg ttaggggttt cgataccctt    780

ggtgccgaag ttaacacatt aagcactccg cctggggagt acggtcgcaa gactgaaact    840

caaaggaatt gacggggacc cgcacaagca gtggagtatg tggtttaatt cgaagcaacg    900

cgaagaacct taccaggtct tgacatccct ctgaccggta cagagatgta cctttccttc    960

gggacagagg agacaggtgg tgcatggttg tcgtcagctc gtgtcgtgag atgttgggtt   1020

aagtcccgca acgagcgcaa cccttgatct tagttgccag cacttcgggt gggcactcta   1080

aggtgactgc cggtgacaaa ccggaggaag gtggggatga cgtcaaatca tcatgcccct   1140

tatgacctgg gctacacacg tactacaatg gccggtacaa cgggcagtga aaccgcgagg   1200

tggaacgaat cctaaaaagc cggtctcagt tcggattgca ggctgcaact cgcctgcatg   1260

aagtcggaat tgctagtaat cgcggatcag catgccgcgg tgaatacgtt cccgggtctt   1320

gtacacaccg cccgtcacac cacgagagtt tataacaccc gaagtcggtg g            1371
```

<210> SEQ ID NO 27
<211> LENGTH: 1324
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Oxalobacteraceae, Genus: Massilia

<400> SEQUENCE: 27
gcggggcaac ctggcggcga gtggcgaacg ggtgagtaat atatcggaac gtacccagaa 60
gtgggggata acgtagcgaa agttacgcta ataccgcata cgatctacgg atgaaagtgg 120
gggaccttcg ggcctcatgc ttttggagcg gccgatatct gattagctag ttggtgaggt 180
aaaggctcac caaggcgacg atcagtagct ggtctgagag gacgaccagc cacactggga 240
ctgagacacg gcccagactc ctacgggagg cagcagtggg gaattttgga caatgggcgc 300
aagcctgatc cagcaatgcc gcgtgagtga agaaggcctt cgggttgtaa agctcttttg 360
tcagggaaga aacggcctgg gttaatacct tgggctaatg acggtacctg aagaataagc 420
accggctaac tacgtgccag cagccgcggt aatacgtagg gtgcaagcgt taatcggaat 480
tactgggcgt aaagcgtgcg caggcggttt tgtaagtctg acgtgaaatc cccgggctta 540
acctgggaat tgcgttggag actgcaaggc tggagtctgg cagagggggg tagaattcca 600
cgtgtagcag tgaaatgcgt agagatgtgg aggaacaccg atggcgaagg cagcccccctg 660 ggtcaagact gacgctcatg cacgaaagcg tggggagcaa acaggattag ataccctggt 720
agtccacgcc ctaaacgatg tctactagtt gtcgggtctt aattgacttg gtaacgcagc 780
taacgcgtga agtagaccgc ctggggagta cggtcgcaag attaaaactc aaaggaattg 840
acggggaccc gcacaagcgg tggatgatgt ggattaattc gatgcaacgc gaaaaacctt 900
acctaccctt gacatgtcag gaagcctgga gagatccggg tgtgcccgaa agggaacctg 960
aacacaggtg ctgcatggct gtcgtcagct cgtgtcgtga gatgttgggt taagtcccgc 1020
aacgagcgca acccttgtca ttagttgcta cgaaagggca ctctaatgag actgccggtg 1080
acaaaccgga ggaaggtggg gatgacgtca agtcctcatg gcccttatgg gtagggcttc 1140
acacgtcata caatggtaca tacagagggc cgccaacccg cgagggggag ctaatcccag 1200
aaagtgtatc gtagtccgga tcgcagtctg caactcgact gcgtgaagtt ggaatcgcta 1260
gtaatcgcgg atcagcatgc cgcggtgaat acgttcccgg gtcttgtaca caccgcccgt 1320
caca 1324

<210> SEQ ID NO 28
<211> LENGTH: 1353
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Oxalobacteraceae, Genus: Massilia

<400> SEQUENCE: 28
cctggcggcg agtggcgaac gggtgagtaa tatatcggaa cgtacccaga agtgggggat 60
aacgtagcga aagttacgct aataccgcat acgatctacg gatgaaagtg ggggaccttc 120
gggcctcatg cttttggagc ggccgatatc tgattagcta gttggtgagg taaaggctca 180
ccaaggcgac gatcagtagc tggtctgaga ggacgaccag ccacactggg actgagacac 240
ggcccagact cctacgggag gcagcagtgg ggaattttgg acaatgggcg caagcctgat 300
ccagcaatgc cgcgtgagtg aagaaggcct tcgggttgta aagctctttt gtcagggaag 360
aaacggcctg ggttaatacc ttgggctaat gacggtacct gaagaataag caccggctaa 420
ctacgtgcca gcagccgcgg taatacgtag ggtgcaagcg ttaatcggaa ttactgggcg 480
taaagcgtgc gcaggcggtt ttgtaagtct gacgtgaaat ccccgggctt aacctgggaa 540
ttgcgttgga gactgcaagg ctggagtctg gcagaggggg gtagaattcc acgtgtagca 600
gtgaaatgcg tagagatgtg gaggaacacc gatggcgaag gcagcccct gggtcaagac 660 tgacgctcat gcacgaaagc gtggggagca aacaggatta gataccctgg tagtccacgc 720
cctaaacgat gtctactagt tgtcgggtct taattgactt ggtaacgcag ctaacgcgtg 780
aagtagaccg cctggggagt acggtcgcaa gattaaaact caaaggaatt gacggggacc 840
cgcacaagcg gtggatgatg tggattaatt cgatgcaacg cgaaaaacct tacctaccct 900
tgacatgtca ggaagcctgg agagatccgg gtgtgcccga aagggaacct gaacacaggt 960
gctgcatggc tgtcgtcagc tcgtgtcgtg agatgttggg ttaagtcccg caacgagcgc 1020
aacccttgtc attagttgct acgaaagggc actctaatga gactgccggt gacaaaccgg 1080
aggaaggtgg ggatgacgtc aagtcctcat ggcccttatg ggtagggctt cacacgtcat 1140
acaatggtac atacagaggg ccgccaaccc gcgagggga gctaatccca gaaagtgtat 1200
cgtagtccgg atcgcagtct gcaactcgac tgcgtgaagt tggaatcgct agtaatcgcg 1260
gatcagcatg ccgcggtgaa tacgttcccg ggtcttgtac acaccgcccg tcacaccatg 1320
ggagcgggtt ataccagaag taggtagcta acc 1353

<210> SEQ ID NO 29
<211> LENGTH: 1317
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Burkholderiaceae, Genus: Ralstonia

<400> SEQUENCE: 29
gattgatggc gagtggcgaa cgggtgagta atacatcgga acgtgccctg tagtggggga 60
taactagtcg aaagattagc taataccgca tacgacctga gggtgaaagt gggggaccgc 120
aaggcctcat gctataggag cggccgatgt ctgattagct agttggtgag gtaaaggctc 180
accaaggcga cgatcagtag ctggtctgag aggacgatca gccacactgg gactgagaca 240
cggcccagac tcctacggga ggcagcagtg gggaattttg gacaatgggc gaaagcctga 300
tccagcaatg ccgcgtgtgt gaagaaggcc ttcgggttgt aaagcacttt tgtccggaaa 360
gaaatggctc tggttaatac ctggggtcga tgacggtacc ggaagaataa ggaccggcta 420
actacgtgcc agcagccgcg gtaatacgta gggtccaagc gttaaccgga attactgggc 480
gtaaagcgtg cgcaggcggt tgtgcaagac cgatgtgaaa tccccgagct taacttggga 540
attgcattgg tgactgcacg gctagagtgt gtcagagggg ggtagaattc cacgtgtagc 600
agtgaaatgc gtagagatgt ggaggaatac cgatggcgaa ggcagccccc tgggataaca 660
ctgacgctca tgcacgaaag cgtggggagc aaacaggatt agataccctg gtagtccacg 720
ccctaaacga tgtcaactag ttgttgggga ttcatttcct tagtaacgta gctaacgcgc 780
gaagttgacc gcctggggag tacggtcgca agattaaaac tcaaaggaat tgacggggac 840
ccgcacaagc ggtggatgat gtggattaat tcgatgcaac gcgaaaaacc ttacctaccc 900
ttgacatgcc actaacgaag cagagatgca ttaggtgctc gaaagagaaa gtggacacag 960
gtgctgcatg gctgtcgtca gctcgtgtcg tgagatgttg ggttaagtcc cgcaacgagc 1020
gcaacccttg tctctagttg ctacgaaagg gcactctaga gagactgccg gtgacaaacc 1080
ggaggaaggt ggggatgacg tcaagtcctc atggccctta tgggtagggc ttcacacgtc 1140
atacaatggt gcatacagag ggttgccaag ccgcgaggtg gagctaatcc cagaaaatgc 1200
atcgtagtcc ggatcgtagt ctgcaactcg actacgtgaa gctggaatcg ctagtaatcg 1260
cggatcagca tgccgcggtg aatacgttcc cgggtcttgt acacaccgcc cgtcaca 1317

<210> SEQ ID NO 30
<211> LENGTH: 1326
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Moraxellaceae, Genus: Acinetobacter

<400> SEQUENCE: 30
ttgctacatt acctaacggc ggacgggtga gtaatgctta ggaatctgcc tattagtggg 60
agacaacatt ccgaaaggaa tgctaatact gcatacgtcc tacgggagaa agcaggggac 120
cttcgggcct tgcgctaata gatgagccta agtcggatta gctagttggt ggggtaaagg 180
cctaccaagg cgacgatctg tagcgggtct gagaggatga tccgccacac tgggactgag 240
acacggccca gactcctacg ggaggcagca gtggggaata ttggacaatg gggggaaccc 300
tgatccagcc atgccgcgtg tgtgaagaag gccttttggt tgtaaagcac tttaagcgag 360
gaggaggcta ctagtattaa tactactgga tagtggacgt tactcgcaga ataagcaccg 420
gctaactctg tgccagcagc cgcggtaata cagagggtgc gagcgttaat cggatttact 480
gggcgtaaag cgtgcgtagg cggctgatta agtcggatgt gaaatccctg agcttaactt 540
aggaattgca ttcgatactg gtcagctaga gtatgggaga ggatggtaga attccaggtg 600
tagcggtgaa atgcgtagag atctggagga ataccgatgg cgaaggcagc catctggcct 660
aatactgacg ctgaggtacg aaagcatggg gagcaaacag gattagatac cctggtagtc 720
catgccgtaa acgatgtcta ctagccgttg gggcctttga ggctttagtg gcgcagctaa 780
cgcgataagt agaccgcctg gggagtacgg tcgcaagact aaaactcaaa tgaattgacg 840
ggggcccgca caagcggtgg agcatgtggt ttaattcgat gcaacgcgaa gaaccttacc 900
tggtcttgac atagtaagaa ctttccagag atggattggt gccttcggga acttacatac 960
aggtgctgca tggctgtcgt cagctcgtgt cgtgagatgt tgggttaagt cccgcaacga 1020
gcgcaaccct tttccttatt tgccagcggg ttaagccggg aactttaagg atactgccag 1080
tgacaaactg gaggaaggcg gggacggcgt caagtcatca tggcccttac gtccagggct 1140
acacacgtgc tacaatggtc ggtacaaagg gttgctacct agcgatagga tgctaatctc 1200
aaaaagccga tcgtagtccg gattggagtc tgcaactcga ctccatgaag tcggaatcgc 1260
tagtaatcgc ggatcagaat gccgcggtga atacgttccc gggccttgta cacaccgccc 1320
gtcaca 1326

<210> SEQ ID NO 31
<211> LENGTH: 1333
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 31
agcttgctct gtgggtggcg agtggcggac gggtgagtaa tgcatcggga cctacccaga 60
cgtgggggat aacgtaggga aacttacgct aataccgcat acgtcctacg ggagaaagcg 120
ggggatcgca agacctcgcg cggttggatg gaccgatgtg cgattagcta gttggtaagg 180
taacggctta ccaaggcgac gatcgctagc tggtctgaga ggatgatcag ccacactggg 240
actgagacac ggcccagact cctacgggag gcagcagtgg ggaatattgg acaatgggcg 300
caagcctgat ccagcaatgc cgcgtgtgtg aagaaggccc tcgggttgta aagcactttt 360
atcaggagcg aaatctgcaa ggttaatacc tttgcagtct gacggtacct gaggaataag 420
caccggctaa ctccgtgcca gcagccgcgg taatacggag ggtgcaagcg ttaatcggaa 480
ttactgggcg taaagcgtgc gtaggcggtt cgttaagtct gttgtgaaag ccccgggctc 540
aacctgggaa tggcaatgga tactggcgag ctagagtgtg tcagaggatg gtggaattcc 600
cggtgtagcg gtgaaatgcg tagagatcgg gaggaacatc agtggcgaag gcggccatct 660
gggacaacac tgacgctgag gcacgaaagc gtggggagca aacaggatta gataccctgg 720
tagtccacgc cctaaacgat gcgaactgga tgttggtctc aactcggaga tcagtgtcga 780
agctaacgcg ttaagttcgc cgcctgggga gtacggtcgc aagactgaaa ctcaaaggaa 840
ttgacggggg cccgcacaag cggtggagta tgtggtttaa ttcgatgcaa cgcgaagaac 900
cttacctggc cttgacatgt ccggaatcca gcagagatgc aggagtgcct tcgggaatcg 960
gaacacaggt gctgcatggc tgtcgtcagc tcgtgtcgtg agatgttggg ttaagtcccg 1020
caacgagcgc aacccttgtc cttagttgcc agcgagtaat gtcgggaact ctaaggagac 1080
tgccggtgac aaaccggagg aaggtgggga tgacgtcaag tcatcatggc ccttacggcc 1140
agggctacac acgtactaca atggtcggta cagagggttg cgataccgcg aggtggagct 1200
aatcccagaa agccgatccc agtccggatt ggagtctgca actcgactcc atgaagtcgg 1260
aatcgctagt aatcgcagat cagctatgct gcggtgaata cgttcccggg ccttgtacac 1320
accgcccgtc aca 1333

<210> SEQ ID NO 32
<211> LENGTH: 1296
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Comamonadaceae, Genus: Variovorax

<400> SEQUENCE: 32
gtgagtaata catcggaacg tgcccaatcg tgggggataa cgcagcgaaa gctgtgctaa 60
taccgcatac gatctacgga tgaaagcagg ggaccgcaag gccttgcgcg aatggagcgg 120
ccgatggcag attaggtagt tggtgaggta aaggctcacc aagccttcga tctgtagctg 180
gtctgagagg acgaccagcc acactgggac tgagacacgg cccagactcc tacgggaggc 240
agcagtgggg aattttggac aatgggcgaa agcctgatcc agcaatgccg cgtgcaggat 300
gaaggccttc gggttgtaaa ctgcttttgt acggaacgaa acggttcttt ctaataaaga 360
gagctaatga cggtaccgta agaataagca ccggctaact acgtgccagc agccgcggta 420
atacgtaggg tgcaagcgtt aatcggaatt actgggcgta aagcgtgcgc aggcggttat 480

```
gtaagacagt tgtgaaatcc ccgggctcaa cctgggaatt gcatctgtga ctgcatagct    540
agagtacggt agaggggat ggaattccgc gtgtagcagt gaaatgcgta gatatgcgga    600
ggaacaccga tggcgaaggc aatcccctgg acctgtactg acgctcatgc acgaaagcgt    660
ggggagcaaa caggattaga taccctggta gtccacgccc taaacgatgt caactggttg    720
ttgggtcttc actgactcag taacgaagct aacgcgtgaa gttgaccgcc tggggagtac    780
ggccgcaagg ttgaaactca aaggaattga cggggacccg cacaagcggt ggatgatgtg    840
gtttaattcg atgcaacgcg aaaaacctta cccacctttg acatgtacgg aatttaccag    900
agatggttta gtgctcgaaa gagaaccgta acacaggtgc tgcatggctg tcgtcagctc    960
gtgtcgtgag atgttgggtt aagtcccgca acgagcgcaa cccttgtcat tagttgctac   1020
atttagttgg gcactctaat gagactgccg gtgacaaacc ggaggaaggt ggggatgacg   1080
tcaagtcctc atggccctta taggtggggc tacacacgtc atacaatggc tggtacaaag   1140
ggttgccaac ccgcgagggg gagctaatcc cataaaacca gtcgtagtcc ggatcgcagt   1200
ctgcaactcg actgcgtgaa gtcggaatcg ctagtaatcg tggatcagaa tgtcacggtg   1260
aatacgttcc cgggtcttgt acacaccgcc cgtcac                             1296
```

<210> SEQ ID NO 33
<211> LENGTH: 1317
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Burkholderiaceae, Genus: Ralstonia

<400> SEQUENCE: 33

```
gattgatggc gagtggcgaa cgggtgagta atacgtcgga acgtgccctg tagtggggga     60
taactagtcg aaagattagc taataccgca tacgacctga gggtgaaagt gggggaccgc    120
aaggcctcat gctataggag cggccgatgt ctgattagct agttggtgag gtaaaggctc    180
accaaggcga cgatcagtag ctggtctgag aggacgatca gccacactgg gactgagaca    240
cggcccagac tcctacggga ggcagcagtg gggaattttg gacaatgggc gaaagcctga    300
tccagcaatg ccgcgtgtgt gaagaaggcc ttcgggttgt aaagcacttt tgtccggaaa    360
gaaatggctc tggttaatac ctggggtcga tgacggtacc ggaagaataa ggaccggcta    420
actacgtgcc agcagccgcg gtaatacgta gggtccaagc gttaatcgga attactgggc    480
gtaaagcgtg cgcaggcggt tgtgcaagac cgatgtgaaa tccccgagct taacttggga    540
attgcattgg tgactgcacg gctagagtgt gtcagagggg ggtagaattc cacgtgtagc    600
agtgaaatgc gtagagatgt ggaggaatac cgatggcgaa ggcagccccc tgggataaca    660
ctgacgctca tgcacgaaag cgtggggagc aaacaggatt agataccctg gtagtccacg    720
ccctaaacga tgtcaactag ttgttgggga ttcatttcct tagtaacgta gctaacgcgt    780
gaagttgacc gcctggggag tacggtcgca agattaaaac tcaaaggaat tgacggggac    840
ccgcacaagc ggtggatgat gtggattaat tcgatgcaac gcgaaaaacc ttacctaccc    900
ttgacatgcc actaacgaag cagagatgca ttaggtgctc gaaagagaaa gtggacacag    960
gtgctgcatg gctgtcgtca gctcgtgtcg tgagatgttg ggttaagtcc cgcaacgagc   1020
gcaacccttg tctctagttg ctacgaaagg gcactctaga gagactgccg gtgacaaacc   1080
ggaggaaggt ggggatgacg tcaagtcctc atggccctta tgggtagggc ttcacacgtc   1140
atacaatggt gcatacagag ggttgccaag ccgcgaggtg gagctaatcc cagaaaatgc   1200
```

atcgtagtcc ggatcgtagt ctgcaactcg actacgtgaa gctggaatcg ctagtaatcg 1260
cggatcagca tgccgcggtg aatacgttcc cgggtcttgt acacaccgcc cgtcaca 1317

<210> SEQ ID NO 34
<211> LENGTH: 1369
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus

<400> SEQUENCE: 34
agcttgctct tatgaagtta gcggcggacg ggtgagtaac acgtgggtaa cctgcccata 60
agactgggat aactccggga aaccggggct aataccggat aacattttga accgcatggt 120
tcgaaattga aaggcggctt cggctgtcac ttatggatgg acccgcgtcg cattagctag 180
ttggtgaggt aacggctcac caaggcaacg atgcgtagcc gacctgagag ggtgatcggc 240
cacactggga ctgagacacg gcccagactc ctacgggagg cagcagtagg gaatcttccg 300
caatggacga aagtctgacg gagcaacgcc gcgtgagtga tgaaggcttt cgggtcgtaa 360
aactctgttg ttagggaaga acaagtgcta gttgaataag ctggcacctt gacggtacct 420
aaccagaaag ccacggctaa ctacgtgcca gcagccgcgg taatacgtag gtggcaagcg 480
ttatccggaa ttattgggcg taaagcgcgc gcaggtggtt tcttaagtct gatgtgaaag 540
cccacggctc aaccgtggag ggtcattgga aactgggaga cttgagtgca gaagaggaaa 600
gtggaattcc atgtgtagcg gtgaaatgcg tagagatatg gaggaacacc agtggcgaag 660
gcgactttct ggtctgtaac tgacactgag gcgcgaaagc gtggggagca aacaggatta 720
gataccctgg tagtccacgc cgtaaacgat gagtgctaag tgttagaggg tttccgccct 780
ttagtgctga agttaacgca ttaagcactc cgcctgggga gtacggccgc aaggctgaaa 840
ctcaaaggaa ttgacggggg cccgcacaag cggtggagca tgtggtttaa ttcgaagcaa 900
cgcgaagaac cttaccaggt cttgacatcc tctgaaaacc ctagagatag ggcttctcct 960
tcgggagcag agtgacaggt ggtgcatggt tgtcgtcagc tcgtgtcgtg agatgttggg 1020
ttaagtcccg caacgagcgc aacccttgat cttagttgcc atcattaagt tgggcactct 1080
aaggtgactg ccggtgacaa accggaggaa ggtggggatg acgtcaaatc atcatgcccc 1140
ttatgacctg ggctacacac gtgctacaat ggacggtaca aagagctgca agaccgcgag 1200
gtggagctaa tctcataaaa ccgttctcag ttcggattgt aggctgcaac tcgcctacat 1260
gaagctggaa tcgctagtaa tcgcggatca gcatgccgcg gtgaatacgt tcccgggcct 1320
tgtacacacc gcccgtcaca ccacgagagt ttgtaacacc cgaagtcgg 1369

<210> SEQ ID NO 35
<211> LENGTH: 1376
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus

<400> SEQUENCE: 35
gcttgctctt atgaagttag cggcggacgg gtgagtaaca cgtgggtaac ctgcccataa 60
gactgggata actccgggaa accggggcta ataccggata acattttgaa ccgcatggtt 120
cgaaattgaa aggcggcttc ggctgtcact tatggatgga cccgcgtcgc attagctagt 180
tggtgaggta acggctcacc aaggcaacga tgcgtagccg acctgagagg gtgatcggcc 240
acactgggac tgagacacgg cccagactcc tacgggaggc agcagtaggg aatcttccgc 300
aatggacgaa agtctgacgg agcaacgccg cgtgagtgat gaaggctttc gggtcgtaaa 360
actctgttgt tagggaagaa caagtgctag ttgaataagc tggcaccttg acggtaccta 420
accagaaagc cacggctaac tacgtgccag cagccgcggt aatacgtagg tggcaagcgt 480
tatccggaat tattgggcgt aaagcgcgcg caggtggttt cttaagtctg atgtgaaagc 540
ccacggctca accgtggagg gtcattggaa actgggagac ttgagtgcag aagaggaaag 600
tggaattcca tgtgtagcgg tgaaatgcgt agagatatgg aggaacacca gtggcgaagg 660
cgactttctg gtctgtaact gacactgagg cgcgaaagcg tggggagcaa acaggattag 720
ataccctggt agtccacgcc gtaaacgatg agtgctaagt gttagagggt ttccgccctt 780
tagtgctgaa gttaacgcat taagcactcc gcctggggag tacggccgca aggctgaaac 840
tcaaaggaat tgacgggggc ccgcacaagc ggtggagcat gtggtttaat tcgaagcaac 900
gcgaagaacc ttaccaggtc ttgacatcct ctgaaaaccc tagagatagg gcttctcctt 960
cgggagcaga gtgacaggtg gtgcatggtt gtcgtcagct cgtgtcgtga gatgttgggt 1020
taagtcccgc aacgagcgca acccttgatc ttagttgcca tcattaagtt gggcactcta 1080
aggtgactgc cggtgacaaa ccggaggaag gtggggatga cgtcaaatca tcatgcccct 1140
tatgacctgg gctacacacg tgctacaatg gacggtacaa agagctgcaa gaccgcgagg 1200
tggagctaat ctcataaaac cgttctcagt tcggattgta ggctgcaact cgcctacatg 1260
aagctggaat cgctagtaat cgcggatcag catgccgcgg tgaatacgtt cccgggcctt 1320
gtacacaccg cccgtcacac cacgagagtt tgtaacaccc gaagtcggtg gggaac 1376

<210> SEQ ID NO 36
<211> LENGTH: 1386
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus: Paenibacillus
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (389)..(389)
<223> OTHER INFORMATION: n is a, c, g, or t
<220> FEATURE:
<221> NAME/KEY: misc_feature
<222> LOCATION: (931)..(931)
<223> OTHER INFORMATION: n is a, c, g, or t
<220> FEATURE:
<221> NAME/KEY: misc_feature
<222> LOCATION: (941)..(941)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t

<400> SEQUENCE: 36
gcttgcttcn ctgatggtta gcggcggacg ggtgagtaac acgtaggcaa cctgccctca 60
agcttgggac aactaccgga aacggtagct aataccgaat acttgcttnc ttcgcctgaa 120

```
gggagctgga aagacggagc aatctgtcac ttgaggatgg gcctgcggcg cattagctag    180
ttggtgaggt aacggctcac caaggcgacg atgcgtagcc gacctgagag ggtgatcggc    240
cacactggga ctgagacacg gcccagactc ctacgggagg cagcagtagg gaatcttccg    300
caatgggcga aagcctgacg gagcaatgcc gcgtgagtga tgaaggtttt cggatcgtaa    360
agctctgttg ccagggaaga acgtccttna gagtaactgc ttaaggagtg acggtacctg    420
agaagaaagc cccggctaac tacgtgccag cagccgcggt aatacgtagg gggcaagcgt    480
tgtccggaat tattgggcgt aaagcgcgcg caggcggtca tttaagtctg gtgtttaatc    540
ccggggctca accccggatc gcactggaaa ctggatgact tgagtgcaga agaggagagt    600
ggaattccac gtgtagcggt gaaatgcgta gagatgtgga ggaacaccag tggcgaaggc    660
gactctctgg gctgtaactg acgctgaggc gcgaaagcgt ggggagcaaa caggattaga    720
taccctggta gtccacgccg taaacgatga atgctaggtg ttaggggttt cgataccctt    780
ggtgccgaag ttaacacatt aagcattccg cctggggagt acggtcgcaa gactgaaact    840
caaaggaatt gacggggacc cgcacaagca gtggagtatg tggtttaatt cgaagcaacg    900
cgaagaacct taccaggtct tgacatccct ntgaccgtcc nagagatagg nctttccttc    960
gggacagagg agacaggtgg tgcatggttg tcgtcagctc gtgtcgtgag atgttgggtt   1020
aagtcccgca acgagcgcaa cccttgatct tagttgccag cacttcgggt gggcactcta   1080
aggtgactgc cggtgacaaa ccggaggaag gtggggatga cgtcaaatca tcatgcccct   1140
tatgacctgg gctacacacg tactacaatg gccggtacaa cgggcagtga agccgcgagg   1200
tggaacgaat cctaaaaagc cggtctcagt tcggattgca ggctgcaact cgcctgcatg   1260
aagtcggaat tgctagtaat cgcggatcag catgccgcgg tgaatacgtt cccgggtctt   1320
gtacacaccg cccgtcacac cacgagagtt tataacaccc gaagtcggtg gggtaaccgc   1380
aagagc                                                               1386
```

```
<210> SEQ ID NO 37
<211> LENGTH: 1212
<212> TYPE: DNA
<213> ORGANISM: Unknown
<220> FEATURE:
<223> OTHER INFORMATION: Kingdom: Bacteria, Phylum: Firmicutes, Class:
      Bacilli, Order: Bacillales, Family: Paenibacillaceae , Genus:
      Paenibacillus

<400> SEQUENCE: 37
```

```
gcctgcggcg cattagctag ttggtggggt aacggctcac caaggcgacg atgcgtagcc     60
gacctgagag ggtgaacggc cacactggga ctgagacacg gcccagactc ctacgggagg    120
cagcagtagg gaatcttccg caatgggcga aagcctgacg gagcaacgcc gcgtgagtga    180
tgaaggtttt cggatcgtaa agctctgttg ccaaggaaga acgtcttcta gagtaactgc    240
taggagagtg acggtacttg agaagaaagc cccggctaac tacgtgccag cagccgcggt    300
aatacgtagg gggcaagcgt tgtccggaat tattgggcgt aaagcgcgcg caggcggttc    360
tttaagtctg gtgtttaaac ccgaggctca acttcgggtc gcactggaaa ctggggaact    420
tgagtgcaga agaggagagt ggaattccac gtgtagcggt gaaatgcgta gatatgtgga    480
ggaacaccag tggcgaaggc gactctctgg gctgtaactg acgctgaggc gcgaaagcgt    540
ggggagcaaa caggattaga taccctggta gtccacgccg taaacgatga atgctaggtg    600
ttaggggttt cgataccctt ggtgccgaag ttaacacatt aagcattccg cctggggagt    660
```

-continued

```
acggtcgcaa gactgaaact caaaggaatt gacggggacc cgcacaagca gtggagtatg    720

tggtttaatt cgaagcaacg cgaagaacct taccaagtct tgacatccct ctgaatcctc    780

tagagataga ggcggccttc gggacagagg tgacaggtgg tgcatggttg tcgtcagctc    840

gtgtcgtgag atgttgggtt aagtcccgca acgagcgcaa cccttgattt tagttgccag    900

cactttgggt gggcactcta gaatgactgc cggtgacaaa ccggaggaag gcggggatga    960

cgtcaaatca tcatgcccct tatgacttgg gctacacacg tactacaatg gctggtacaa   1020

cgggaagcga agccgcgagg tggagccaat cctataaaag ccagtctcag ttcggattgc   1080

aggctgcaac tcgcctgcat gaagtcggaa ttgctagtaa tcgcggatca gcatgccgcg   1140

gtgaatacgt tcccgggtct tgtacacacc gcccgtcaca ccacgagagt ttacaacacc   1200

cgaagtcggt gg                                                       1212
```

<210> SEQ ID NO 38
<211> LENGTH: 1328
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Burkholderiaceae, Genus: Burkholderia

<400> SEQUENCE: 38

```
cctggtggcg agtggcgaac gggtgagtaa tacatcggaa cgtgtcctgt agtgggggat     60

agcccggcga aagccggatt aataccgcat acgctctacg gaggaaaggg ggggatctta    120

ggacctctcg ctacaggggc ggccgatggc agattagcta gttggtgggg taaaggccta    180

ccaaggcgac gatctgtagc tggtctgaga ggacgaccag ccacactggg actgagacac    240

ggcccagact cctacgggag gcagcagtgg ggaattttgg acaatgggcg aaagcctgat    300

ccagcaatgc cgcgtgtgtg aagaaggcct tcgggttgta aagcactttt gtccggaaag    360

aaaacttctg tcctaatacg gcgggaggat gacggtaccg gaagaataag caccggctaa    420

ctacgtgcca gcagccgcgg taatacgtag ggtgcaagcg ttaatcggaa ttactgggcg    480

taaagcgtgc gcaggcggtc cgctaagaca gatgtgaaat ccccgggctt aacctgggaa    540

ctgcatttgt gactggcggg ctagagtatg gcagaggggg gtagaattcc acgtgtagca    600

gtgaaatgcg tagagatgtg gaggaatacc gatggcgaag gcagcccccct gggccaatac    660

tgacgctcat gcacgaaagc gtggggagca aacaggatta gataccctgg tagtccacgc    720

cctaaacgat gtcaactagt tgttgggtct tcattgactt agtaacgtag ctaacgcgtg    780

aagttgaccg cctggggagt acggtcgcaa gattaaaact caaaggaatt gacggggacc    840

cgcacaagcg gtggatgatg tggattaatt cgatgcaacg cgaaaaacct tacctaccct    900

tgacatgtat ggaagtctgc cgagaggtgg atgtgcccga aagggagcca taacacaggt    960

gctgcatggc tgtcgtcagc tcgtgtcgtg agatgttggg ttaagtcccg caacgagcgc   1020

aacccttgtc cctagttgct acgcaagagc actccaggga gactgccggt gacaaaccgg   1080

aggaaggtgg ggatgacgtc aagtcctcat ggcccttatg ggtagggctt cacacgtcat   1140

acaatggtcg gaacagaggg ttgccaagcc gcgaggtgga gccaatccca gaaaaccgat   1200

cgtagtccgg atcgcactct gcaactcgag tgcgtgaagc tggaatcgct agtaatcgcg   1260

gatcagcatg ccgcggtgaa tacgttcccg ggtcttgtac acaccgcccg tcacaccatg   1320

ggagtggg                                                            1328
```

<210> SEQ ID NO 39
<211> LENGTH: 1377
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus

<400> SEQUENCE: 39
agcttgctct tatgaagtta gcggcggacg ggtgagtaac acgtgggtaa cctgcccata 60
agactgggat aactccggga aaccggggct aataccggat aacattttga accgcatggt 120
tcgaaattga aaggcggctt cggctgtcac ttatggatgg acccgcgtcg cattagctag 180
ttggtgaggt aacggctcac caaggcaacg atgcgtagcc gacctgagag ggtgatcggc 240
cacactggga ctgagacacg gcccagactc ctacgggagg cagcagtagg gaatcttccg 300
caatggacga aagtctgacg gagcaacgcc gcgtgagtga tgaaggcttt cgggtcgtaa 360
aactctgttg ttagggaaga acaagtgcta gttgaataag ctggcacctt gacggtacct 420
aaccagaaag ccacggctaa ctacgtgcca gcagccgcgg taatacgtag gtggcaagcg 480
ttatccggaa ttattgggcg taaagcgcgc gcaggtggtt tcttaagtct gatgtgaaag 540
cccacggctc aaccgtggag ggtcattgga aactgggaga cttgagtgca gaagaggaaa 600
gtggaattcc atgtgtagcg gtgaaatgcg tagagatatg gaggaacacc agtggcgaag 660
gcgactttct ggtctgtaac tgacactgag gcgcgaaagc gtggggagca aacaggatta 720
gataccctgg tagtccacgc cgtaaacgat gagtgctaag tgttagaggg tttccgccct 780
ttagtgctga agttaacgca ttaagcactc cgcctgggga gtacggccgc aaggctgaaa 840
ctcaaaggaa ttgacggggg cccgcacaag cggtggagca tgtggtttaa ttcgaagcaa 900
cgcgaagaac cttaccaggt cttgacatcc tctgaaaacc ctagagatag ggcttctcct 960
tcgggagcag agtgacaggt ggtgcatggt tgtcgtcagc tcgtgtcgtg agatgttggg 1020
ttaagtcccg caacgagcgc aacccttgat cttagttgcc atcattaagt tgggcactct 1080
aaggtgactg ccggtgacaa accggaggaa ggtggggatg acgtcaaatc atcatgcccc 1140
ttatgacctg ggctacacac gtgctacaat ggacggtaca aagagctgca agaccgcgag 1200
gtggagctaa tctcataaaa ccgttctcag ttcggattgt aggctgcaac tcgcctacat 1260
gaagctggaa tcgctagtaa tcgcggatca gcatgccgcg gtgaatacgt tcccgggcct 1320
tgtacacacc gcccgtcaca ccacgagagt ttgtaacacc cgaagtcggt ggggtaa 1377

<210> SEQ ID NO 40
<211> LENGTH: 1333
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 40
agcttgctct gtgggtggcg agtggcggac gggtgagtaa tgcatcggga cctacccaga 60
cgtgggggat aacgtaggga aacttacgct aataccgcat acgtcctacg ggagaaagcg 120
ggggatcgca agacctcgcg cggttggatg gaccgatgtg cgattagcta gttggtaagg 180
taacggctta ccaaggcgac gatcgctagc tggtctgaga ggatgatcag ccacactggg 240
actgagacac ggcccagact cctacgggag gcagcagtgg ggaatattgg acaatgggcg 300
caagcctgat ccagcaatgc cgcgtgtgtg aagaaggccc tcgggttgta aagcactttt 360
atcaggagcg aaatctgcaa ggttaatacc tttgcagtct gacggtacct gaggaataag 420
caccggctaa ctccgtgcca gcagccgcgg taatacggag ggtgcaagcg ttaatcggaa 480
ttactgggcg taaagcgtgc gtaggcggtt cgttaagtct gttgtgaaag ccccgggctc 540
aacctgggaa tggcaatgga tactggcgag ctagagtgtg tcagaggatg gtggaattcc 600
cggtgtagcg gtgaaatgcg tagagatcgg gaggaacatc agtggcgaag gcggccatct 660
gggacaacac tgacgctgag gcacgaaagc gtggggagca aacaggatta gataccctgg 720
tagtccacgc cctaaacgat gcgaactgga tgttggtctc aactcggaga tcagtgtcga 780
agctaacgcg ttaagttcgc cgcctgggga gtacggtcgc aagactgaaa ctcaaaggaa 840
ttgacggggg cccgcacaag cggtggagta tgtggtttaa ttcgatgcaa cgcgaagaac 900
cttacctggc cttgacatgt ccggaatcca gcagagatgc aggagtgcct tcgggaatcg 960
gaacacaggt gctgcatggc tgtcgtcagc tcgtgtcgtg agatgttggg ttaagtcccg 1020
caacgagcgc aacccttgtc cttagttgcc agcgagtaat gtcgggaact ctaaggagac 1080
tgccggtgac aaaccggagg aaggtgggga tgacgtcaag tcatcatggc ccttacggcc 1140
agggctacac acgtactaca atggtcggta cagagggttg cgataccgcg aggtggagct 1200
aatcccagaa agccgatccc agtccggatt ggagtctgca actcgactcc atgaagtcgg 1260
aatcgctagt aatcgcagat cagctatgct gcggtgaata cgttcccggg ccttgtacac 1320
accgcccgtc aca 1333

<210> SEQ ID NO 41
<211> LENGTH: 1317
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Burkholderiaceae, Genus: Ralstonia

<400> SEQUENCE: 41
gattgatggc gagtggcgaa cgggtgagta atacatcgga acgtgccctg tagtggggga 60
taactagtcg aaagattagc taataccgca tacgacctga gggtgaaagt gggggaccgc 120
aaggcctcat gctataggag cggccgatgt ctgattagct agttggtgag gtaaaggctc 180
accaaggcga cgatcagtag ctggtctgag aggacgatca gccacactgg gactgagaca 240
cggcccagac tcctacggga ggcagcagtg gggaattttg gacaatgggc gaaagcctga 300
tccagcaatg ccgcgtgtgt gaagaaggcc ttcgggttgt aaagcacttt tgtccggaaa 360
gaaatggctc tggttaatac ctggggtcga tgacggtacc ggaagaataa ggaccggcta 420
actacgtgcc agcagccgcg gtaatacgta gggtccaagc gttaatcgga attactgggc 480
gtaaagcgtg cgcaggcggt tgtgcaagac cgatgtgaaa tccccgagct taacttggga 540
attgcattgg tgactgcacg gctagagtgt gtcagagggg ggtagaattc cacgtgtagc 600
agtgaaatgc gtagagatgt ggaggaatac cgatggcgaa ggcagccccc tgggataaca 660
ctgacgctca tgcacgaaag cgtggggagc aaacaggatt agataccctg gtagtccacg 720
ccctaaacga tgtcaactag ttgttgggga ttcatttcct tagtaacgta gctaacgcgt 780
gaagttgacc gcctggggag tacggtcgca agattaaaac tcaaaggaat tgacggggac 840
ccgcacaagc ggtggatgat gtggattaat tcgatgcaac gcgaaaaacc ttacctaccc 900
ttgacatgcc actaacgaag cagagatgca ttaggtgctc gaaagagaaa gtggacacag 960

```
gtgctgcatg gctgtcgtca gctcgtgtcg tgagatgttg ggttaagtcc cgcaacgagc   1020

gcaacccttg tctctagttg ctacgaaagg gcactctaga gggactgccg gtgacaaacc   1080

ggaggaaggt ggggatgacg tcaagtcctc atggccctta tgggtagggc ttcacacgtc   1140

atacaatggt gcatacagag ggttgccaag ccgcgaggtg gagctaatcc cagaaaatgc   1200

atcgtagtcc ggatcgtagt ctgcaactcg actacgtgaa gctggaatcg ctagtaatcg   1260

cggatcagca tgccgcggtg aatacgttcc cgggtctcgt acacaccgcc cgtcaca      1317
```

<210> SEQ ID NO 42
<211> LENGTH: 1258
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus

<400> SEQUENCE: 42

```
ctgtaagact gggataactc cgggaaaccg gggctaatac cggatggttg tttgaaccgc     60

atggttcaaa cataaaaggt ggcttcggct accacttaca gatggacccg cggcgcatta    120

gctagttggt gaggtaacgg ctcaccaagg caacgatgcg tagccgacct gagagggtga    180

tcggccacac tgggactgag acacggccca gactcctacg ggaggcagca gtagggaatc    240

ttccgcaatg gacgaaagtc tgacggagca acgccgcgtg agtgatgaag gttttcggat    300

cgtaaagctc tgttgttagg gaagaacaag taccgttcga atagggcggt accttgacgg    360

tacctaacca gaaagccacg gctaactacg tgccagcagc cgcggtaata cgtaggtggc    420

aagcgttgtc cggaattatt gggcgtaaag ggctcgcagg cggtttctta agtctgatgt    480

gaaagccccc ggctcaaccg gggagggtca ttggaaactg gggaacttga gtgcagaaga    540

ggagagtgga attccacgtg tagcggtgaa atgcgtagag atgtggagga acaccagtgg    600

cgaaggcgac tctctggtct gtaactgacg ctgaggagcg aaagcgtggg gagcgaacag    660

gattagatac cctggtagtc cacgccgtaa acgatgagtg ctaagtgtta gggggtttcc    720

gccccttagt gctgcagcta acgcattaag cactccgcct ggggagtacg gtcgcaagac    780

tgaaactcaa aggaattgac gggggcccgc acaagcggtg gagcatgtgg tttaattcga    840

agcaacgcga agaaccttac caggtcttga catcctctga caatcctaga gataggacgt    900

ccccttcggg ggcagagtga caggtggtgc atggttgtcg tcagctcgtg tcgtgagatg    960

ttgggttaag tcccgcaacg agcgcaaccc ttgatcttag ttgccagcat tcagttgggc   1020

actctaaggt gactgccggt gacaaaccgg aggaaggtgg ggatgacgtc aaatcatcat   1080

gccccttatg acctgggcta cacacgtgct acaatggaca gaacaaaggg cagcgaaacc   1140

gcgaggttaa gccaatccca caaatctgtt ctcagttcgg atcgcagtct gcaactcgac   1200

tgcgtgaagc tggaatcgct agtaatcgcg gatcagcatg ccgcggtgaa tacgtccc     1258
```

<210> SEQ ID NO 43
<211> LENGTH: 1362
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Actinomycetales, Family: Microbacteriaceae, Genus: Curtobacterium

<400> SEQUENCE: 43

```
agtcgacgat gatgcccagc ttgctgggtg gattagtggc gaacgggtga gtaacacgtg     60
```

```
agtaacctgc ccctgactct gggataagcg ttggaaacga cgtctaatac tggatatgat    120

cgccggccgc atggtctggt ggtggaaaga ttttttggtt ggggatggac tcgcggccta    180

tcagcttgtt ggtgaggtaa tggctcacca aggcgacgac gggtagccgg cctgagaggg    240

tgaccggcca cactgggact gagacacggc ccagactcct acgggaggca gcagtgggga    300

atattgcaca atgggcgaaa gcctgatgca gcaacgccgc gtgagggatg acggccttcg    360

ggttgtaaac ctcttttagt agggaagaag cgaaagtgac ggtacctgca gaaaaagcac    420

cggctaacta cgtgccagca gccgcggtaa tacgtagggt gcaagcgttg tccggaatta    480

ttgggcgtaa agagctcgta ggcggtttgt cgcgtctgct gtgaaatccc gaggctcaac    540

ctcgggcttg cagtgggtac gggcagacta gagtgcggta ggggagattg gaattcctgg    600

tgtagcggtg gaatgcgcag atatcaggag gaacaccgat ggcgaaggca gatctctggg    660

ccgtaactga cgctgaggag cgaaagcatg gggagcgaac aggattagat accctggtag    720

tccatgccgt atacgttggg cgctagatgt agggaccttt ccacggtttc tgtgtcgtag    780

ctaacgcatt aagcgccccg cctggggagt acggccgcaa ggctaaaact caaaggaatt    840

gacgggggcc cgcacaagcg gcggagcatg cggattaatt cgatgcaacg cgaagaacct    900

taccaaggct tgacatacac cggaaacggc cagagatggt cgcccccttg tggtcggtgt    960

acaggtggtg catggttgtc gtcagctcgt gtcgtgagat gttgggttaa gtcccgcaac   1020

gagcgcaacc ctcgttctat gttgccagcg ggttatgccg ggactcata ggagactgcc   1080

ggggtcaact cggaggaagg tggggatgac gtcaaatcat catgcccctt atgtcttggg   1140

cttcacgcat gctacaatgg ccggtacaaa gggctgcgat accgtaaggt ggagcgaatc   1200

ccaaaaagcc ggtctcagtt cggattgagg tctgcaactc gacctcatga agtcggagtc   1260

gctagtaatc gcagatcagc aacgctgcgg tgaatacgtt cccgggcctt gtacacaccg   1320

cccgtcaagt catgaaagtc ggtaacaccc gaagccggtg gc                      1362
```

<210> SEQ ID NO 44
<211> LENGTH: 1284
<212> TYPE: DNA
<213> ORGANISM: Unknown
<220> FEATURE:
<223> OTHER INFORMATION: Kingdom: Bacteria, Phylum: Actinobacteria,
      Class: Actinobacteria, Order: Actinomycetales, Family:
      Microbacteriaceae, Genus: Curtobacterium
<220> FEATURE:
<221> NAME/KEY: misc_feature
<222> LOCATION: (53)..(53)
<223> OTHER INFORMATION: n is a, c, g, or t

<400> SEQUENCE: 44

```
cttgctgggt ggattagtgg cgaacgggtg agtaacacgt gagtaacctg ccnctgactc     60

tgggataagc gttggaaacg acgtctaata ctggatatga tcgccggccg catggtctgg    120

tggtggaaag atttttggt tggggatgga ctcgcggcct atcagcttgt tggtgaggta    180

atggctcacc aaggcgacga cgggtagccg gcctgagagg gtgaccggcc acactgggac    240

tgagacacgg cccagactcc tacgggaggc agcagtgggg aatattgcac aatgggcgaa    300

agcctgatgc agcaacgccg cgtgagggat gacggccttc gggttgtaaa cctcttttag    360

tagggaagaa gcgaaagtga cggtacctgc agaaaaagca ccggctaact acgtgccagc    420

agccgcggta atacgtaggg tgcaagcgtt gtccggaatt attgggcgta aagagctcgt    480

aggcggtttg tcgcgtctgc tgtgaaatcc cgaggctcaa cctcgggctt gcagtgggta    540

cgggcagact agagtgcggt aggggagatt ggaattcctg gtgtagcggt ggaatgcgca    600
```

gatatcagga ggaacaccga tggcgaaggc agatctctgg gccgtaactg acgctgagga 660
gcgaaagcat ggggagcgaa caggattaga taccctggta gtccatgccg taaacgttgg 720
gcgctagatg tagggacctt tccacggttt ctgtgtcgta gctaacgcat taagcgcccc 780
gcctggggag tacggccgca aggctaaaac tcaaaggaat tgacgggggc ccgcacaagc 840
ggcggagcat gcggattaat tcgatgcaac gcgaagaacc ttaccaaggc ttgacataca 900
ccggaaacgg ccagagatgg tcgccccctt gtggtcggtg tacaggtggt gcatggttgt 960
cgtcagctcg tgtcgtgaga tgttgggtta agtcccgcaa cgagcgcaac cctcgttcta 1020
tgttgccagc gggttatgcc ggggactcat aggagactgc cggggtcaac tcggaggaag 1080
gtggggatga cgtcaaatca tcatgcccct tatgtcttgg gcttcacgca tgctacaatg 1140
gccggtacaa agggctgcga taccgtaagg tggagcgaat cccaaaaagc cggtctcagt 1200
tcggattgag gtctgcaact cgacctcatg aagtcggagt cgctagtaat cgcagatcag 1260
caacgctgcg gtgaatacgt tccc 1284

<210> SEQ ID NO 45
<211> LENGTH: 1333
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 45
agcttgctct gtgggtggcg agtggcggac gggtgagtaa tgcatcggga cctacccaga 60
cgtgggggat aacgtaggga aacttacgct aataccgcat acgtcctacg ggagaaagcg 120
ggggatcgca agacctcgcg cggttggatg gaccgatgtg cgattagctt gttggtgagg 180
taacggctca ccaaggcgac gatcgctagc tggtctgaga ggatgatcag ccacactggg 240
actgagacac ggcccagact cctacgggag gcagcagtgg ggaatattgg acaatgggcg 300
caagcctgat ccagcaatgc cgcgtgtgtg aagaaggccc tcgggttgta aagcactttt 360
atcaggagcg aaatctgcaa ggttaatacc tttgcagtct gacggtacct gaggaataag 420
caccggctaa ctccgtgcca gcagccgcgg taatacggag ggtgcaagcg ttaatcggaa 480
ttactgggcg taaagcgtgc gtaggcggtt cgttaagtct gttgtgaaag ccccgggctc 540
aacctgggaa tggcaatgga tactggcgag ctagagtgtg tcagaggatg gtggaattcc 600
cggtgtagcg gtgaaatgcg tagagatcgg gaggaacatc agtggcgaag gcggccatct 660
gggacaacac tgacgctgag gcacgaaagc gtggggagca aacaggatta gataccctgg 720
tagtccacgc cctaaacgat gcgaactgga tgttggtctc aactcggaga tcagtgtcga 780
agctaacgcg ttaagttcgc cgcctgggga gtacggtcgc aagactgaaa ctcaaaggaa 840
ttgacggggg cccgcacaag cggtggagta tgtggtttaa ttcgatgcaa cgcgaagaac 900
cttacctggc cttgacatgt ccggaatcca gcagagatgc aggagtgcct tcgggaatcg 960
gaacacaggt gctgcatggc tgtcgtcagc tcgtgtcgtg agatgttggg ttaagtcccg 1020
caacgagcgc aacccttgtc cttagttgcc agcgagtaat gtcgggaact ctaaggagac 1080
tgccggtgac aaaccggagg aaggtgggga tgacgtcaag tcatcatggc ccttacggcc 1140
agggctacac acgtactaca atggtcggta cagagggttg cgataccgcg aggtggagct 1200
aatcccagaa agccgatccc agtccggatt ggagtctgca actcgactcc atgaagtcgg 1260
aatcgctagt aatcgcagat cagctatgct gcggtgaata cgttcccggg ccttgtacac 1320
accgcccgtc aca 1333

<210> SEQ ID NO 46
<211> LENGTH: 1355
<212> TYPE: DNA
<213> ORGANISM: Unknown
<220> FEATURE:
<223> OTHER INFORMATION: Kingdom: Bacteria, Phylum: Proteobacteria,
Class: Gammaproteobacteria, Order: Xanthomonadales, Family:
Xanthomonadaceae, Genus: Luteibacter

<400> SEQUENCE: 46
cttgctctgt gggtggcgag tggcggacgg gtgagtaatg catcgggacc tacccagacg 60
tgggggataa cgtagggaaa cttacgctaa taccgcatac gtcctacggg agaaagcggg 120
ggatcgcaag acctcgcgcg gttggatgga ccgatgtgcg attagctagt tggtaaggta 180
acggcttacc aaggcgacga tcgctagctg gtctgagagg atgatcagcc acactgggac 240
tgagacacgg cccagactcc tacgggaggc agcagtgggg aatattggac aatgggcgca 300
agcctgatcc agcaatgccg cgtgtgtgaa gaaggccctc gggttgtaaa gcacttttat 360
caggagcgaa atctgcaagg ttaatacctt tgcagtctga cggtacctga ggaataagca 420
ccggctaact ccgtgccagc agccgcggta atacggaggg tgcaagcgtt aatcggaatt 480
actgggcgta aagcgtgcgt aggcggttcg ttaagtctgt tgtgaaagcc ccgggctcaa 540
cctgggaatg gcaatggata ctggcgagct agagtgtgtc agaggatggt ggaattcccg 600
gtgtagcggt gaaatgcgta gagatcggga ggaacatcag tggcgaaggc ggccatctgg 660
gacaacactg acgctgaggc acgaaagcgt ggggagcaaa caggattaga taccctggta 720
gtccacgccc taaacgatgc gaactggatg ttggtctcaa ctcggagatc agtgtcgaag 780
ctaacgcgtt aagttcgccg cctggggagt acggtcgcaa gactgaaact caaaggaatt 840
gacgggggcc cgcacaagcg gtggagtatg tggtttaatt cgatgcaacg cgaagaacct 900
tacctggcct tgacatgtcc ggaatccagc agagatgcag gagtgccttc gggaatcgga 960
acacaggtgc tgcatggctg tcgtcagctc gtgtcgtgag atgttgggtt aagtcccgca 1020
acgagcgcaa cccttgtcct tagttgccag cgagtaatgt cgggaactct aaggagactg 1080
ccggtgacaa accggaggaa ggtggggatg acgtcaagtc atcatggccc ttacggccag 1140
ggctacacac gtactacaat ggtcggtaca gagggttgcg ataccgcgag gtggagctaa 1200
tcccagaaag ccgatcccag tccggattgg agtctgcaac tcgactccat gaagtcggaa 1260
tcgctagtaa tcgcagatca gctatgctgc ggtgaatacg ttccctggcc ttgtacacac 1320
cgcccgtcac accatgggag tgagctgctc cagaa 1355

<210> SEQ ID NO 47
<211> LENGTH: 641
<212> TYPE: DNA
<213> ORGANISM: Unknown
<220> FEATURE:
<223> OTHER INFORMATION: Kingdom: Bacteria, Phylum: Proteobacteria,
Class: Gammaproteobacteria, Order: Enterobacteriales, Family:
Enterobacteriaceae, Genus: Pantoea
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (344)..(345)
<223> OTHER INFORMATION: n is a, c, g, or t
<220> FEATURE:
<221> NAME/KEY: misc_feature
<222> LOCATION: (351)..(352)
<223> OTHER INFORMATION: n is a, c, g, or t
<220> FEATURE:
<221> NAME/KEY: misc_feature
<222> LOCATION: (619)..(619)
<223> OTHER INFORMATION: n is a, c, g, or t
<220> FEATURE:
<221> NAME/KEY: misc_feature
<222> LOCATION: (626)..(626)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t

<400> SEQUENCE: 47
gtcgaagcta aattccgact tcacggagtc gagttgcaga ctccgatccg gactacgacg 60
cactttgtga ggtccgcttg ctctcgcgag gtcgcttctc tttgtatgcg ccattgtagc 120
acgtgtgtag ccctactcgt aagggccatg atgacttgac gtcatcccca ccttcctccg 180
gtttatcacc ggcagtctcc tttgagttcc cgaccgaatc gctggcaaca aaggataagg 240
gttgcgctcg ttgcgggact taacccaaca tttcacaaca cgagctgacg acagccatgc 300
agcacctgtc tcacagttcc cgaaggcact aangcatctc tgcnnaattc nntggatgtc 360
aagagtaggt aaggttcttc gcgttgcatc gaattaaacc acatgctcca ccgcttgtgc 420
gggcccccgt caattcattt gagttttaac cttgcggccg tactccccag gcggtcgact 480
taacgcgtta gctccggaag ccactcctca agggaacaac ctccaagtcg acatcgttta 540
cggcgtggac taccagggta tctaatcctg tttgctcccc acgctttcgc acctgagcgt 600
cagtctttgt ccaccctcng tattancgcg ggtgntggca g 641

<210> SEQ ID NO 48
<211> LENGTH: 1333
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 48
agcttgctct gtgggtggcg agtggcggac gggtgagtaa tgcatcggga cctacccaga 60
cgtgggggat aacgtaggga aacttacgct aataccgcat acgtcctacg ggagaaagcg 120
ggggatcgca agacctcgcg cggttggatg gaccgatgtg cgattagctt gttggtgagg 180
taacggctca ccaaggcgac gatcgctagc tggtctgaga ggatgatcag ccacactggg 240
actgagacac ggcccagact cctacgggag gcagcagtgg ggaatattgg acaatgggcg 300
caagcctgat ccagcaatgc cgcgtgtgtg aagaaggccc tcgggttgta aagcactttt 360
atcaggagcg aaatctgcaa ggttaatacc tttgcagtct gacggtacct gaggaataag 420
caccggctaa ctccgtgcca gcagccgcgg taatacggag ggtgcaagcg ttaatcggaa 480
ttactgggcg taaagcgtgc gtaggcggtt cgttaagtct gttgtgaaag ccccgggctc 540
aacctgggaa tggcaatgga tactggcgag ctagagtgtg tcagaggatg gtggaattcc 600
cggtgtagcg gtgaaatgcg tagagatcgg gaggaacatc agtggcgaag gcggccatct 660
gggacaacac tgacgctgag gcacgaaagc gtggggagca aacaggatta gataccctgg 720
tagtccacgc cctaaacgat gcgaactgga tgttggtctc aactcggaga tcagtgtcga 780
agctaacgcg ttaagttcgc cgcctgggga gtacggtcgc aagactgaaa ctcaaaggaa 840
ttgacggggg cccgcacaag cggtggagta tgtggtttaa ttcgatgcaa cgcgaagaac 900
cttacctggc cttgacatgt ccggaatcca gcagagatgc aggagtgcct tcgggaatcg 960
gaacacaggt gctgcatggc tgtcgtcagc tcgtgtcgtg agatgttggg ttaagtcccg 1020
caacgagcgc aacccttgtc cttagttgcc agcgagtaat gtcgggaact ctaaggagac 1080
tgccggtgac aaaccggagg aaggtgggga tgacgtcaag tcatcatggc ccttacggcc 1140
agggctacac acgtactaca atggtcggta cagagggttg cgataccgcg aggtggagct 1200
aatcccagaa agccgatccc agtccggatt ggagtctgca actcgactcc atgaagtcgg 1260
aatcgctagt aatcgcagat cagctatgct gcggtgaata cgttcccggg ccttgtacac 1320
accgcccgtc aca 1333

<210> SEQ ID NO 49
<211> LENGTH: 1374
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus

<400> SEQUENCE: 49
cttgctccct gatgttagcg gcggacgggt gagtaacacg tgggtaacct gcctgtaaga 60
ctgggataac tccgggaaac cggggctaat accggatggt tgtttgaacc gcatggttca 120
aacataaaag gtggcttcgg ctaccactta cagatggacc cgcggcgcat tagctagttg 180
gtgaggtaac ggctcaccaa ggcaacgatg cgtagccgac ctgagagggt gatcggccac 240
actgggactg agacacggcc cagactccta cgggaggcag cagtagggaa tcttccgcaa 300
tggacgaaag tctgacggag caacgccgcg tgagtgatga aggttttcgg atcgtaaagc 360
tctgttgtta gggaagaaca agtaccgttc gaatagggcg gtaccttgac ggtacctaac 420
cagaaagcca cggctaacta cgtgccagca gccgcggtaa tacgtaggtg gcaagcgttg 480
tccggaatta ttgggcgtaa agggctcgca ggcggtttct taagtctgat gtgaaagccc 540
ccggctcaac cggggagggt cattggaaac tggggaactt gagtgcagaa gaggagagtg 600
gaattccacg tgtagcggtg aaatgcgtag agatgtggag gaacaccagt ggcgaaggcg 660
actctctggt ctgtaactga cgctgaggag cgaaagcgtg gggagcgaac aggattagat 720
accctggtag tccacgccgt aaacgatgag tgctaagtgt tagggggttt ccgcccctta 780
gtgctgcagc taacgcatta agcactccgc ctggggagta cggtcgcaag actgaaactc 840
aaaggaattg acgggggccc gcacaagcgg tggagcatgt ggtttaattc gaagcaacgc 900
gaagaacctt accaggtctt gacatcctct gacaatccta gagataggac gtccccttcg 960 gggcagagt gacaggtggt gcatggttgt cgtcagctcg tgtcgtgaga tgttgggtta 1020
agtcccgcaa cgagcgcaac ccttgatctt agttgccagc attcagttgg gcactctaag 1080
gtgactgccg gtgacaaacc ggaggaaggt ggggatgacg tcaaatcatc atgcccctta 1140
tgacctgggc tacacacgtg ctacaatgga cagaacaaag ggcagcgaaa ccgcgaggtt 1200
aagccaatcc cacaaatctg ttctcagttc ggatcgcagt ctgcaactcg actgcgtgaa 1260
gctggaatcg ctagtaatcg cggatcagca tgccgcggtg aatacgttcc cgggccttgt 1320
acacaccgcc cgtcacacca cgagagtttg taacacccga agtcggtgag gaac 1374

<210> SEQ ID NO 50

<211> LENGTH: 1322
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (406)..(406)
<223> OTHER INFORMATION: n is a, c, g, or t
<220> FEATURE:
<221> NAME/KEY: misc_feature
<222> LOCATION: (1152)..(1152)
<223> OTHER INFORMATION: n is a, c, g, or t

<400> SEQUENCE: 50

```
atgggagctt gctccctgat gttagcggcg gacgggtgag taacacgtgg gtaacctgcc     60

tgtaagactg ggataactcc gggaaaccgg ggctaatacc ggatggttgt ttgaaccgca    120

tggttcaaac ataaaaggtg gcttcggcta ccacttacag atggacccgc ggcgcattag    180

ctagttggtg aggtaacggc tcaccaaggc aacgatgcnt agccgacctg agagggtgat    240

cggccacact gggactgaga cacggcccag actcctacgg gaggcagcag tanggaatct    300

tcngcaatgg acgaaagtct gacggagcaa cgccgcgtga gtgatgaagg ttttcggatc    360

gtaaagctct gttgttaggg aagaacaagt accgttcgaa tagggnggta ccttgacggt    420

acctaaccag aaagccacgg ctaactacgt gccagcagcc gcggtaatac gtaggtggca    480

agcgttgtcc ggaattattg ggcgtaaagg gctcgcaggc ggtttcttaa gtctgatgtg    540

aaagcccccg gctcaaccgg ggagggtcat tggaaactgg ggaacttgag tgcagaagag    600

gagagtggaa ttccacgtgt agcggtgaaa tgcgtagaga tgtggaggaa caccagtggc    660

gaaggcgact ctctggtctg taactgacgc tgaggagcga aagcgtgggg agcgaacagg    720

attagatacc ctggtagtcc acgccgtaaa cgatgagtgc taagtgttag ggggtttccg    780

ccccttagtg ctgcagctaa cgcattaagc actccgcctg gggagtacgg tcgcaagact    840

gaaactcaaa ggaattgacg ggggcccgca caagcggtgg agcatgtggt ttaattcgaa    900

gcaacgcgaa gaaccttacc aggtcttgac atcctctgac aatcctagag ataggacgtc    960

cccttcgggg tcagagtgac aggtggtgca tggttgtcgt cagctcgtgt cgtgagatgt   1020

tgggttaagt cccgcaacga gcgcaaccct tgatcttagt tgccagcatt cagttgggca   1080

ctctaaggtg actgccggtg acaaaccgga ggaaggtggg gatgacgtca aatcatcatg   1140

ccccttatga cntgggctac acacgtgcta caatggacag aacaaagggc agcgaaaccg   1200

cgaggttaag ccaatcccac aaatctgttc tcagttcgga tcgcagtctg caactcgact   1260

gcgtgaagct ggaatcgcta gtaatcgcgg atcagcatgc cgcggtgaat acgttcccgg   1320

gc                                                                  1322
```

<210> SEQ ID NO 51
<211> LENGTH: 1368
<212> TYPE: DNA

<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus: Paenibacillus

<400> SEQUENCE: 51

```
gcttgcttct ccgatggtta gcggcggacg ggtgagtaac acgtaggcaa cctgccctca     60
agtttgggac aactaccgga aacggtagct aataccgaat agttgttttc ttctcctgaa    120
ggaaactgga aagacggagc aatctgtcac ttggggatgg gcctgcggcg cattagctag    180
ttggtggggt aacggctcac caaggcgacg atgcgtagcc gacctgagag ggtgatcggc    240
cacactggga ctgagacacg gcccagactc ctacgggagg cagcagtagg gaatcttccg    300
caatgggcga aagcctgacg gagcaatgcc gcgtgagtga tgaaggtttt cggatcgtaa    360
agctctgttg ccagggaaga acgcttggga gagtaactgc tctcaaggtg acggtacctg    420
agaagaaagc cccggctaac tacgtgccag cagccgcggt aatacgtagg gggcaagcgt    480
tgtccggaat tattgggcgt aaagcgcgcg caggcggtca tttaagtctg gtgtttaatc    540
ccggggctca accccggatc gcactggaaa ctgggtgact tgagtgcaga agaggagagt    600
ggaattccac gtgtagcggt gaaatgcgta gatatgtgga ggaacaccag tggcgaaggc    660
gactctctgg gctgtaactg acgctgaggc gcgaaagcgt ggggagcaaa caggattaga    720
taccctggta gtccacgccg taaacgatga gtgctaggtg ttaggggttt cgataccctt    780
ggtgccgaag ttaacacatt aagcactccg cctggggagt acggtcgcaa gactgaaact    840
caaaggaatt gacggggacc cgcacaagca gtggagtatg tggtttaatt cgaagcaacg    900
cgaagaacct taccaggtct tgacatccct ctgaccggta cagagatgta cctttccttc    960
gggacagagg agacaggtgg tgcatggttg tcgtcagctc gtgtcgtgag atgttgggtt   1020
aagtcccgca acgagcgcaa cccttgatct tagttgccag cacttcgggt gggcactcta   1080
aggtgactgc cggtgacaaa ccggaggaag gtggggatga cgtcaaatca tcatgcccct   1140
tatgacctgg gctacacacg tactacaatg gccggtacaa cgggcagtga aaccgcgagg   1200
tggaacgaat cctaaaaagc cggtctcagt tcggattgca ggctgcaact cgcctgcatg   1260
aagtcggaat tgctagtaat cgcggatcag catgccgcgg tgaatacgtt cccgggtctt   1320
gtacacaccg cccgtcacac cacgagagtt tataacaccc gaagtcgg                1368
```

<210> SEQ ID NO 52
<211> LENGTH: 1371
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus: Paenibacillus

<400> SEQUENCE: 52

```
gcttgcttct ccgatggtta gcggcggacg ggtgagtaac acgtaggcaa cctgccctca     60
agtttgggac aactaccgga aacggtagct aataccgaat agttgttttc ttctcctgaa    120
ggaaactgga aagacggagc aatctgtcac ttggggatgg gcctgcggcg cattagctag    180
ttggtggggt aacggctcac caaggcgacg atgcgtagcc gacctgagag ggtgatcggc    240
cacactggga ctgagacacg gcccagactc ctacgggagg cagcagtagg gaatcttccg    300
caatgggcga aagcctgacg gagcaatgcc gcgtgagtga tgaaggtttt cggatcgtaa    360
agctctgttg ccagggaaga acgcttggga gagtaactgc tctcaaggtg acggtacctg    420
```

```
agaagaaagc cccggctaac tacgtgccag cagccgcggt aatacgtagg gggcaagcgt    480

tgtccggaat tattgggcgt aaagcgcgcg caggcggtca tttaagtctg gtgtttaatc    540

ccggggctca accccggatc gcactggaaa ctgggtgact tgagtgcaga agaggagagt    600

ggaattccac gtgtagcggt gaaatgcgta gatatgtgga ggaacaccag tggcgaaggc    660

gactctctgg gctgtaactg acgctgaggc gcgaaagcgt ggggagcaaa caggattaga    720

taccctggta gtccacgccg taaacgatga gtgctaggtg ttaggggttt cgataccctt    780

ggtgccgaag ttaacacatt aagcactccg cctggggagt acggtcgcaa gactgaaact    840

caaaggaatt gacggggacc cgcacaagca gtggagtatg tggtttaatt cgaagcaacg    900

cgaagaacct taccaggtct tgacatccct ctgaccggta cagagatgta cctttccttc    960

gggacagagg agacaggtgg tgcatggttg tcgtcagctc gtgtcgtgag atgttgggtt   1020

aagtcccgca acgagcgcaa cccttgatct tagttgccag cacttcgggt gggcactcta   1080

aggtgactgc cggtgacaaa ccggaggaag gtggggatga cgtcaaatca tcatgcccct   1140

tatgacctgg gctacacacg tactacaatg gccggtacaa cgggcagtga aaccgcgagg   1200

tggaacgaat cctaaaaagc cggtctcagt tcggattgca ggctgcaact cgcctgcatg   1260

aagtcggaat tgctagtaat cgcggatcag catgccgcgg tgaatacgtt cccgggtctt   1320

gtacacaccg cccgtcacac cacgagagtt tataacaccc gaagtcggtg g             1371
```

```
<210> SEQ ID NO 53
<211> LENGTH: 1374
<212> TYPE: DNA
<213> ORGANISM: Unknown
<220> FEATURE:
<223> OTHER INFORMATION: Kingdom: Bacteria, Phylum: Firmicutes, Class:
      Bacilli, Order: Bacillales, Family: Bacillaceae , Genus: Bacillus

<400> SEQUENCE: 53

cttgctccct gatgttagcg gcggacgggt gagtaacacg tgggtaacct gcctgtaaga     60

ctgggataac tccgggaaac cggggctaat accggatggt tgtttgaacc gcatggttca    120

aacataaaag gtggcttcgg ctaccactta cagatggacc cgcggcgcat tagctagttg    180

gtgaggtaac ggctcaccaa ggcaacgatg cgtagccgac ctgagagggt gatcggccac    240

actgggactg agacacggcc cagactccta cgggaggcag cagtagggaa tcttccgcaa    300

tggacgaaag tctgacggag caacgccgcg tgagtgatga aggttttcgg atcgtaaagc    360

tctgttgtta gggaagaaca agtaccgttc gaatagggcg gtaccttgac ggtacctaac    420

cagaaagcca cggctaacta cgtgccagca gccgcggtaa tacgtaggtg gcaagcgttg    480

tccggaatta ttgggcgtaa agggctcgca ggcggtttct taagtctgat gtgaaagccc    540

ccggctcaac cggggagggt cattggaaac tggggaactt gagtgcagaa gaggagagtg    600

gaattccacg tgtagcggtg aaatgcgtag agatgtggag gaacaccagt ggcgaaggcg    660

actctctggt ctgtaactga cgctgaggag cgaaagcgtg gggagcgaac aggattagat    720

accctggtag tccacgccgt aaacgatgag tgctaagtgt tagggggttt ccgcccctta    780

gtgctgcagc taacgcatta agcactccgc ctggggagta cggtcgcaag actgaaactc    840

aaaggaattg acgggggccc gcacaagcgg tggagcatgt ggtttaattc gaagcaacgc    900

gaagaacctt accaggtctt gacatcctct gacaatccta gagataggac gtccccttcg    960

gggcagagt gacaggtggt gcatggttgt cgtcagctcg tgtcgtgaga tgttgggtta   1020

agtcccgcaa cgagcgcaac ccttgatctt agttgccagc attcagttgg gcactctaag   1080
```

gtgactgccg gtgacaaacc ggaggaaggt ggggatgacg tcaaatcatc atgcccctta 1140
tgacctgggc tacacacgtg ctacaatgga cagaacaaag ggcagcgaaa ccgcgaggtt 1200
aagccaatcc cacaaatctg ttctcagttc ggatcgcagt ctgcaactcg actgcgtgaa 1260
gctggaatcg ctagtaatcg cggatcagca tgccgcggtg aatacgttcc cgggccttgt 1320
acacaccgcc cgtcacacca cgagagtttg taacacccga agtcggtgag gtaa 1374

<210> SEQ ID NO 54
<211> LENGTH: 1381
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus
<220> FEATURE:
<221> NAME/KEY: misc_feature
<222> LOCATION: (106)..(106)
<223> OTHER INFORMATION: n is a, c, g, or t

<400> SEQUENCE: 54
atgggagctt gctccctgat gttagcggcg gacgggtgag taacacgtgg gtaacctgcc 60
tgtaagactg ggataactcc gggaaaccgg ggctaatacc ggatgnttgt ttgaaccgca 120
tggttcagac ataaaaggtg gcttcggcta ccacttacag atggacccgc ggcgcattag 180
ctagttggtg aggtaacggc tcaccaaggc gacgatgcgt agccgacctg agagggtgat 240
cggccacact gggactgaga cacggcccag actcctacgg gaggcagcag tagggaatct 300
tccgcaatgg acgaaagtct gacggagcaa cgccgcgtga gtgatgaagg ttttcggatc 360
gtaaagctct gttgttaggg aagaacaagt gccgttcaaa tagggcggca ccttgacggt 420
acctaaccag aaagccacgg ctaactacgt gccagcagcc gcggtaatac gtaggtggca 480
agcgttgtcc ggaattattg ggcgtaaagg gctcgcaggc ggtttcttaa gtctgatgtg 540
aaagcccccg gctcaaccgg ggagggtcat tggaaactgg ggaacttgag tgcagaagag 600
gagagtggaa ttccacgtgt agcggtgaaa tgcgtagaga tgtggaggaa caccagtggc 660
gaaggcgact ctctggtctg taactgacgc tgaggagcga aagcgtgggg agcgaacagg 720
attagatacc ctggtagtcc acgccgtaaa cgatgagtgc taagtgttag ggggtttccg 780
ccccttagtg ctgcagctaa cgcattaagc actccgcctg gggagtacgg tcgcaagact 840
gaaactcaaa ggaattgacg ggggcccgca caagcggtgg agcatgtggt ttaattcgaa 900
gcaacgcgaa gaaccttacc aggtcttgac atcctctgac aatcctagag ataggacgtc 960
cccttcgggg gcagagtgac aggtggtgca tggttgtcgt cagctcgtgt cgtgagatgt 1020
tgggttaagt cccgcaacga gcgcaaccct tgatcttagt tgccagcatt cagttgggca 1080
ctctaaggtg actgccggtg acaaaccgga ggaaggtggg gatgacgtca aatcatcatg 1140
ccccttatga cctgggctac acacgtgcta caatggacag aacaaagggc agcgaaaccg 1200
cgaggttaag ccaatcccac aaatctgttc tcagttcgga tcgcagtctg caactcgact 1260
gcgtgaagct ggaatcgcta gtaatcgcgg atcagcatgc cgcggtgaat acgttcccgg 1320
gccttgtaca caccgcccgt cacaccacga gagtttgtaa cacccgaagt cggtgaggta 1380
a 1381

<210> SEQ ID NO 55
<211> LENGTH: 1177
<212> TYPE: DNA
<213> ORGANISM: Unknown

<220> FEATURE:
<223> OTHER INFORMATION: Kingdom: Bacteria, Phylum: Proteobacteria,
Class: Gammaproteobacteria, Order: Enterobacteriales, Family:
Enterobacteriaceae, Genus: Pantoea

<400> SEQUENCE: 55

```
tggggggta aaggcccact tggggaggat cccagtttgt gtgaggggtg accagcccac     60

cggaaatggg acccggtccc gactcttacg gagggagcag tgggaatatt gcacaatggg    120

cccaaccctg atgcagccat gccgggttat gaagaggcct ttgggttgta aagtactttc    180

agcggggagg aaggcgatgc ggttataacc gcaccgattg acgttacccg cagaagaagc    240

acgggctaac tccgtgccag cagccgcggt aatacggagg gtgcaagcgt taatcggaat    300

tactgggcgt aaagcgcacg caggcggtct gttaagtcag atgtgaaatc cccgggctta    360

acctgggaac tgcatttgaa actggcaggc ttgagtcttg tagagggggg tagaattcca    420

ggtgtagcgg tgaaatgcgt agagatctgg aggaataccg gtggcgaagg cggccccctg    480

gacaaagact gacgctcagg tgcgaaagcg tggggagcaa acaggattag ataccctggt    540

agtccacgcc gtaaacgatg tcgacttgga ggttgttccc ttgaggagtg gcttccggag    600

ctaacgcgtt aagtcgaccg cctggggagt acggccgcaa ggttaaaact caaatgaatt    660

gacgggggcc cgcacaagcg gtggagcatg tggtttaatt cgatgcaacg cgaagaacct    720

tacctactct tgacatccag agaattcggc agagatgctt tagtgccttc gggaactgtg    780

agacaggtgc tgcatggctg tcgtcagctc gtgttgtgaa atgttgggtt aagtcccgca    840

acgagcgcaa cccttatcct ttgttgccag cgattcggtc gggaactcaa aggagactgc    900

cggtgataaa ccggaggaag gtggggatga cgtcaagtca tcatggccct tacgagtagg    960

gctacacacg tgctacaatg gcgcatacaa agagaagcga cctcgcgaga gcaagcggac   1020

ctcacaaagt gcgtcgtagt ccggatcgga gtctgcaact cgactccgtg aagtcggaat   1080

cgctagtaat cgtggatcag aatgccacgg tgaatacgtt cccgggcctt gtacacaccg   1140

cccgtcacac catgggagtg ggtgcaaaag aagtagg                            1177
```

<210> SEQ ID NO 56
<211> LENGTH: 1345
<212> TYPE: DNA
<213> ORGANISM: Unknown
<220> FEATURE:
<223> OTHER INFORMATION: Kingdom: Bacteria, Phylum: Proteobacteria,
Class: Alphaproteobacteria, Order: Rhizobiales, Family:
Rhizobiaceae, Genus: Rhizobium

<400> SEQUENCE: 56

```
cagtcgagcg catccttcgg ggtgagcggc agacgggtga gtaacgcgtg ggaatctacc     60

ttttgctacg gaatagctcc gggaaactgg aattaatacc gtatgtgccc tttggcggtg    120

gacgctggag gggaaagatt tatcggcaaa ggatgagccc gcgttggatt agctagttgg    180

tggggtaaag gcctaccaag gcgacgatcc atagctggtc tgagaggatg atcagccaca    240

ttgggactga gacacggccc aaactcctac gggaggcagc agtggggaat attggacaat    300

gggcgcaagc ctgatccagc catgccgcgt gtgtgatgaa ggccttaggg ttgtaaagca    360

ctttcaccgg tgaagataat gacggtaacc ggagaagaag ccccggctaa cttcgtgcca    420

gcagccgcgg taatacgaag gggctagcg ttgttcggaa ttactgggcg taaagcgcac    480

gtaggcggat atttaagtca ggggtgaaat cccagagctc aactctggaa ctgcctttga    540

tactgggtat cttgagtatg gaagaggtga gtggaattcc gagtgtagag gtgaaattcg    600
```

```
tagatattcg gaggaacacc agtggcgaag gcggctcact ggtccataac tgacgctgag    660

gtgcgaaagc gtggggagca aacaggatta gataccctgg tagtccacgc cgtaaacgat    720

gaatgttagc cgtcgggcag tttactgttc ggtggcgcag ctaacgcatt aaacattccg    780

cctggggagt acggtcgcaa gattaaaact caaaggaatt gacgggggcc cgcacaagcg    840

gtggagcatg tggtttaatt cgaagcaacg cgcagaacct taccagccct tgacatgtcc    900

ggctagctag agagatctag tgttcccttc ggggaccgga gcacaggtgc tgcatggctg    960

tcgtcagctc gtgtcgtgag atgttgggtt aagtcccgca acgagcgcaa ccctcgccct   1020

tagttgccag cattaggttg ggcactctaa ggggactgcc ggtgataagc cgagaggaag   1080

gtggggatga cgtcaagtcc tcatggccct tacgggctgg gctacacacg tgctacaatg   1140

gtggtgacag tgggcagcga gaccgcgagg tcgagctaat ctccaaaagc catctcagtt   1200

cggattgcac tctgcaactc gagtgcatga agttggaatc gctagtaatc gcagatcagc   1260

atgctgcggt gaatacgttc ccgggccttg tacacaccgc ccgtcacacc atgggagttg   1320

gttttacccg aaggcgctgc gctaa                                         1345
```

<210> SEQ ID NO 57
<211> LENGTH: 707
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family: Enterobacteriaceae, Genus: Pantoea
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t

<400> SEQUENCE: 57

```
gttagctacc tacttctttt gcacccactc ccatggtgtg acgggcggtg tgtacaaggc     60

ccgggaacgt attcaccgtg gcattctgat ccacgattac tagcgattcc gacttcacgg    120

agtcgagttg cagactccga tccggactac gacgcacttt gtgaggtccg cttgctctcg    180

cgaggtcgct tctctttgta tgcgccattg tagcacgtgt gtagccctac tcgtaagggc    240

catgatgact tgacgtcatc cccaccttcc tccggtttat caccggcagt ctcctttgag    300

ttcccgaccg aatcgctggc aacaaaggat aagggttgcg ctcgttgcgg gacttaaccc    360

aacatttcac aacacgagct gacgacagcc atgcagcacc tgtctcacag ttcccgaagg    420

cactaangca tctctgccna attctntgga tgtcaagagt aggtaaggtt cttcgcgttg    480

catcgaatta aaccacatgc tccaccgctt gtgcgggccc ccgtcaattc atttgagttt    540

taaccttgcg gccgtactcc ccaggcggtc gacttaacgc gttagctccg gaagccactc    600

ctcaagggaa caacctccaa gtcgacatcg tttacggcgt ggactaccag ggtatctaat    660

cctgtttgct ccccacgctt tcgcacctga gcgtcagtct ttgtcca                 707
```

<210> SEQ ID NO 58
<211> LENGTH: 1333
<212> TYPE: DNA
<213> ORGANISM: Unknown

<220> FEATURE:
<223> OTHER INFORMATION: Kingdom: Bacteria, Phylum: Proteobacteria,
      Class: Gammaproteobacteria, Order: Xanthomonadales, Family:
      Xanthomonadaceae, Genus: Luteibacter

<400> SEQUENCE: 58

```
agcttgctct gtgggtggcg agtggcggac gggtgagtaa tgcatcggga cctacccaga     60

cgtgggggat aacgtaggga aacttacgct aataccgcat acgtcctacg ggagaaagcg    120

ggggatcgca agacctcgcg cggttggatg gaccgatgtg cgattagcta gttggtaagg    180

taacggctta ccaaggcgac gatcgctagc tggtctgaga ggatgatcag ccacactggg    240

actgagacac ggcccagact cctacgggag gcagcagtgg ggaatattgg acaatgggcg    300

caagcctgat ccagcaatgc cgcgtgtgtg aagaaggccc tcgggttgta aagcactttt    360

atcaggagcg aaatctgcaa ggttaatacc tttgcagtct gacggtacct gaggaataag    420

caccggctaa ctccgtgcca gcagccgcgg taatacggag ggtgcaagcg ttaatcggaa    480

ttactgggcg taaagcgtgc gtaggcggtt cgttaagtct gttgtgaaag ccccgggctc    540

aacctgggaa tggcaatgga tactggcgag ctagagtgtg tcagaggatg gtggaattcc    600

cggtgtagcg gtgaaatgcg tagagatcgg gaggaacatc agtggcgaag gcggccatct    660

gggacaacac tgacgctgag gcacgaaagc gtggggagca aacaggatta gataccctgg    720

tagtccacgc cctaaacgat gcgaactgga tgttggtctc aactcggaga tcagtgtcga    780

agctaacgcg ttaagttcgc cgcctgggga gtacggtcgc aagactgaaa ctcaaaggaa    840

ttgacggggg cccgcacaag cggtggagta tgtggtttaa ttcgatgcaa cgcgaagaac    900

cttacctggc cttgacatgt ccggaatcca gcagagatgc aggagtgcct tcgggaatcg    960

gaacacaggt gctgcatggc tgtcgtcagc tcgtgtcgtg agatgttggg ttaagtcccg   1020

caacgagcgc aacccttgtc cttagttgcc agcgagtaat gtcgggaact ctaaggagac   1080

tgccggtgac aaaccggagg aaggtgggga tgacgtcaag tcatcatggc ccttacggcc   1140

agggctacac acgtactaca atggtcggta cagagggttg cgataccgcg aggtggagct   1200

aatcccagaa agccgatccc agtccggatt ggagtctgca actcgactcc atgaagtcgg   1260

aatcgctagt aatcgcagat cagctatgct gcggtgaata cgttcccggg ccttgtacac   1320

accgcccgtc aca                                                      1333
```

<210> SEQ ID NO 59
<211> LENGTH: 1361
<212> TYPE: DNA
<213> ORGANISM: Unknown
<220> FEATURE:
<223> OTHER INFORMATION: Kingdom: Bacteria, Phylum: Proteobacteria,
      Class: Gammaproteobacteria, Order: Xanthomonadales, Family:
      Xanthomonadaceae, Genus: Luteibacter

<400> SEQUENCE: 59

```
ttgctctgtg ggtggcgagt ggcggacggg tgagtaatgc atcgggacct acccagacgt     60

gggggataac gtagggaaac ttacgctaat accgcatacg tcctacggga gaaagcgggg    120

gatcgcaaga cctcgcgcgg ttggatggac cgatgtgcga ttagctagtt ggtaaggtaa    180

cggcttacca aggcgacgat cgctagctgg tctgagagga tgatcagcca cactgggact    240

gagacacggc ccagactcct acgggaggca gcagtgggga atattggaca atgggcgcaa    300

gcctgatcca gcaatgccgc gtgtgtgaag aaggccctcg ggttgtaaag cacttttatc    360

aggagcgaaa tctgcaaggt taatacettt gcagtctgac ggtacctgag gaataagcac    420
```

-continued

```
cggctaactc cgtgccagca gccgcggtaa tacggagggt gcaagcgtta atcggaatta    480

ctgggcgtaa agcgtgcgta ggcggttcgt taagtctgtt gtgaaagccc cgggctcaac    540

ctgggaatgg caatggatac tggcgagcta gagtgtgtca gaggatggtg gaattcccgg    600

tgtagcggtg aaatgcgtag agatcgggag gaacatcagt ggcgaaggcg gccatctggg    660

acaacactga cgctgaggca cgaaagcgtg gggagcaaac aggattagat accctggtag    720

tccacgccct aaacgatgcg aactggatgt tggtctcaac tcggagatca gtgtcgaagc    780

taacgcgtta agttcgccgc ctggggagta cggtcgcaag actgaaactc aaaggaattg    840

acgggggccc gcacaagcgg tggagtatgt ggtttaattc gatgcaacgc gaagaacctt    900

acctggcctt gacatgtccg gaatccagca gagatgcagg agtgccttcg ggaatcggaa    960

cacaggtgct gcatggctgt cgtcagctcg tgtcgtgaga tgttgggtta agtcccgcaa   1020

cgagcgcaac ccttgtcctt agttgccagc gagtaatgtc gggaactcta aggagactgc   1080

cggtgacaaa ccggaggaag gtggggatga cgtcaagtca tcatggccct tacggccagg   1140

gctacacacg tactacaatg gtcggtacag agggttgcga taccgcgagg tggagctaat   1200

cccagaaagc cgatcccagt ccggattgga gtctgcaact cgactccatg aagtcggaat   1260

cgctagtaat cgcagatcag ctatgctgcg gtgaatacgt tcccgggcct tgtacacacc   1320

gcccgtcaca ccatgggagt gagctgctcc agaagccgta g                        1361
```

<210> SEQ ID NO 60
<211> LENGTH: 1360
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 60

```
gcttgctctg tgggtggcga gtggcggacg ggtgagtaat gcatcgggac ctacccagac     60

gtgggggata acgtagggaa acttacgcta ataccgcata cgtcctacgg gagaaagcgg    120

gggatcgcaa gacctcgcgc ggttggatgg accgatgtgc gattagctag ttggtaaggt    180

aacggcttac caaggcgacg atcgctagct ggtctgagag gatgatcagc cacactggga    240

ctgagacacg gcccagactc ctacgggagg cagcagtggg gaatattgga caatgggcgc    300

aagcctgatc cagcaatgcc gcgtgtgtga agaaggccct cgggttgtaa agcactttta    360

tcaggagcga aatctgcaag gttaatacct ttgcagtctg acggtacctg aggaataagc    420

accggctaac tccgtgccag cagccgcggt aatacggagg gtgcaagcgt taatcggaat    480

tactgggcgt aaagcgtgcg taggcggttc gttaagtctg ttgtgaaagc cccgggctca    540

acctgggaat ggcaatggat actggcgagc tagagtgtgt cagaggatgg tggaattccc    600

ggtgtagcgg tgaaatgcgt agagatcggg aggaacatca gtggcgaagg cggccatctg    660

ggacaacact gacgctgagg cacgaaagcg tggggagcaa acaggattag ataccctggt    720

agtccacgcc ctaaacgatg cgaactggat gttggtctca actcggagat cagtgtcgaa    780

gctaacgcgt taagttcgcc gcctggggag tacggtcgca agactgaaac tcaaaggaat    840

tgacgggggc ccgcacaagc ggtggagtat gtggtttaat tcgatgcaac gcgaagaacc    900

ttacctggcc ttgacatgtc cggaatccag cagagatgca ggagtgcctt cgggaatcgg    960

aacacaggtg ctgcatggct gtcgtcagct cgtgtcgtga gatgttgggt taagtcccgc   1020

aacgagcgca acccttgtcc ttagttgcca gcgagtaatg tcgggaactc taaggagact   1080
```

gccggtgaca aaccggagga aggtggggat gacgtcaagt catcatggcc cttacggcca 1140
gggctacaca cgtactacaa tggtcggtac agagggttgc gataccgcga ggtggagcta 1200
atcccagaaa gccgatccca gtccggattg gagtctgcaa ctcgactcca tgaagtcgga 1260
atcgctagta atcgcagatc agctatgctg cggtgaatac gttcccgggc cttgtacaca 1320
ccgcccgtca caccatggga gtgagctgct ccagaagccg 1360

<210> SEQ ID NO 61
<211> LENGTH: 1357
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 61
ttgctctgtg ggtggcgagt ggcggacggg tgagtaatgc atcgggacct acccagacgt 60
gggggataac gtagggaaac ttacgctaat accgcatacg tcctacggga gaaagcgggg 120
gatcgcaaga cctcgcgcgg ttggatggac cgatgtgcga ttagctagtt ggtaaggtaa 180
cggcttacca aggcgacgat cgctagctgg tctgagagga tgatcagcca cactgggact 240
gagacacggc ccagactcct acgggaggca gcagtgggga atattggaca atgggcgcaa 300
gcctgatcca gcaatgccgc gtgtgtgaag aaggccctcg ggttgtaaag cacttttatc 360
aggagcgaaa tctgcaaggt taataccttt gcagtctgac ggtacctgag gaataagcac 420
cggctaactc cgtgccagca gccgcggtaa tacggagggt gcaagcgtta atcggaatta 480
ctgggcgtaa agcgtgcgta ggcggttcgt taagtctgtt gtgaaagccc cgggctcaac 540
ctgggaatgg caatggatac tggcgagcta gagtgtgtca gaggatggtg gaattcccgg 600
tgtagcggtg aaatgcgtag agatcgggag gaacatcagt ggcgaaggcg gccatctggg 660
acaacactga cgctgaggca cgaaagcgtg gggagcaaac aggattagat accctggtag 720
tccacgccct aaacgatgcg aactggatgt tggtctcaac tcggagatca gtgtcgaagc 780
taacgcgtta agttcgccgc ctggggagta cggtcgcaag actgaaactc aaaggaattg 840
acgggggccc gcacaagcgg tggagtatgt ggtttaattc gatgcaacgc gaagaacctt 900
acctggcctt gacatgtccg gaatccagca gagatgcagg agtgccttcg ggaatcggaa 960
cacaggtgct gcatggctgt cgtcagctcg tgtcgtgaga tgttgggtta agtcccgcaa 1020
cgagcgcaac ccttgtcctt agttgccagc gagtaatgtc gggaactcta aggagactgc 1080
cggtgacaaa ccggaggaag gtggggatga cgtcaagtca tcatggccct tacggccagg 1140
gctacacacg tactacaatg gtcggtacag agggttgcga taccgcgagg tggagctaat 1200
cccagaaagc cgatcccagt ccggattgga gtctgcaact cgactccatg aagtcggaat 1260
cgctagtaat cgcagatcag ctatgctgcg gtgaatacgt tcccgggcct tgtacacacc 1320
gcccgtcaca ccatgggagt gagctgctcc agaagcc 1357

<210> SEQ ID NO 62
<211> LENGTH: 1330
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family: Enterobacteriaceae, Genus: Erwinia

<400> SEQUENCE: 62
agcttgctcc tcgggtgacg agtggcggac gggtgagtaa tgtctgggga tctgcccggt 60
agagggggat aaccactgga aacggtggct aataccgcat aatctcgcaa gagcaaagtg 120
ggggaccttc gggcctcaca ctaccggatg aacccagatg ggattagcca gctggtgagg 180
taacggctca ccagggcgac gatccctagc tggtctgaga ggatgaccag ccacactgga 240
actgagacac ggtccagact cctacgggag gcagcagtgg ggaatattgc acaatgggcg 300
caagcctgat gcagccatgc cgcgtgtatg aagaaggcct tcgggttgta aagtactttc 360
agcggggagg aagggtgaag agcgaataac ttttcacatt gacgttaccc gcagaagaag 420
caccggctaa ctccgtgcca gcagccgcgg taatacggag ggtgcaagcg ttaatcggaa 480
ttactgggcg taaagcgcac gcaggcggtc tgttaagtca gatgtgaaat ccccgggctc 540
aacccgggaa ctgcatttga aactggcagg cttgagtctc gtagaggggg gtggaattcc 600
aggtgtagcg gtgaaatgcg tagagatctg gaggaatacc ggtggcgaag gcggcccccct 660 ggacgaagac tgacgctcag gtgcgaaagc gtggggagca aacaggatta gataccctgg 720
tagtccacgc cgtaaacgat gtcgatttgg aggctgtgag cttgactcgt ggcttccgta 780
gctaacgcgt taaatcgacc gcctggggag tacggccgca aggttaaaac tcaaatgaat 840
tgacgggggc ccgcacaagc ggtggagcat gtggtttaat tcgatgcaac gcgaagaacc 900
ttacctggtc ttgacatcca cggaatcggg cagagatgcc tgagtgcctt cgggagccgt 960
gagacaggtg ctgcatggct gtcgtcagct cgtgttgtga aatgttgggt taagtcccgc 1020
aacgagcgca acccttatcc tttgttgcca gcgattcggt cgggaactca aaggagactg 1080
ccggtgataa accggaggaa ggtggggatg acgtcaagtc atcatggccc ttacgaccag 1140
ggctacacac gtgctacaat ggcgcataca aagagaagcg acctcgcgag agcaagcgga 1200
cctcataaag tgcgtcgtag tccggatcgg agtctgcaac ccgactccgt gaagtcggaa 1260
tcgctagtaa tcgtggatca gaatgccacg gtgaatacgt tcccgggcct tgtacacacc 1320
gcccgtcaca 1330

<210> SEQ ID NO 63
<211> LENGTH: 1253
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 63
tacccagacg tgggggataa cgtagggaaa cttacgctaa taccgcatac gtcctacggg 60
agaaagcggg ggatcgcaag acctcgcgcg gttggatgga ccgatgtgcg attagctagt 120
tggtaaggta acggcttacc aaggcgacga tcgctagctg gtctgagagg atgatcagcc 180
acactgggac tgagacacgg cccagactcc tacgggaggc agcagtgggg aatattggac 240
aatgggcgca agcctgatcc agcaatgccg cgtgtgtgaa gaaggccctc gggttgtaaa 300
gcacttttat caggagcgaa atctgcaagg ttaatacctt tgcagtctga cggtacctga 360
ggaataagca ccggctaact ccgtgccagc agccgcggta atacggaggg tgcaagcgtt 420
aatcggaatt actgggcgta aagcgtgcgt aggcggttcg ttaagtctgt tgtgaaagcc 480
ccgggctcaa cctgggaatg gcaatggata ctggcgagct agagtgtgtc agaggatggt 540
ggaattcccg gtgtagcggt gaaatgcgta gagatcggga ggaacatcag tggcgaaggc 600
ggccatctgg gacaacactg acgctgaggc acgaaagcgt ggggagcaaa caggattaga 660
taccctggta gtccacgccc taaacgatgc gaactggatg ttggtctcaa ctcggagatc 720
agtgtcgaag ctaacgcgtt aagttcgccg cctggggagt acggtcgcaa gactgaaact 780
caaaggaatt gacgggggcc cgcacaagcg gtggagtatg tggtttaatt cgatgcaacg 840
cgaagaacct tacctggcct tgacatgtcc ggaatccagc agagatgcag gagtgccttc 900
gggaatcgga acacaggtgc tgcatggctg tcgtcagctc gtgtcgtgag atgttgggtt 960
aagtcccgca acgagcgcaa cccttgtcct tagttgccag cgagtaatgt cgggaactct 1020
aaggagactg ccggtgacaa accggaggaa ggtggggatg acgtcaagtc atcatggccc 1080
ttacggccag ggctacacac gtactacaat ggtcggtaca gagggttgcg ataccgcgag 1140
gtggagctaa tcccagaaag ccgatcccag tccggattgg agtctgcaac tcgactccat 1200
gaagtcggaa tcgctagtaa tcgcagatca gctatgctgc ggtgaatacg ttc 1253

<210> SEQ ID NO 64
<211> LENGTH: 463
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 64
atggaccgat gtgcgattag ctagttggta aggtaacggc ttaccaaggc gacgatcgct 60
agctggtctg agaggatgat cagccacact gggactgaac acggcccaga ctcctacggg 120
aggcacagtg gggaatattg gacaatgggc gcaagcctga tccagcaatg ccgcgtgtgt 180
gaagaaggcc ctcgggttgt aaagcacttt tatcaggagc gaaatctgca aggttaatac 240
ctttgcatct gacggtacct gaggaataag caccggctaa ctccgtgcca gcagccgcgg 300
taatacggag ggtgcaagcg ttaatcggaa ttactgggcg taaagcgtgc gtaggcggtt 360
cgttaagtct gttgtgaaag ccccgggctc aacctgggaa tggcaatgga tactggcgag 420
ctagagtgtg tcagaggatg gtggaattcc cggtgtagcg gtg 463

<210> SEQ ID NO 65
<211> LENGTH: 1250
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 65
tacccagacg tgggggataa cgtagggaaa cttacgctaa taccgcatac gtcctacggg 60
agaaagcggg ggatcgcaag acctcgcgcg gttggatgga ccgatgtgcg attagctagt 120
tggtaaggta acggcttacc aaggcgacga tcgctagctg gtctgagagg atgatcagcc 180
acactgggac tgagacacgg cccagactcc tacgggaggc agcagtgggg aatattggac 240
aatgggcgca agcctgatcc agcaatgccg cgtgtgtgaa gaaggccctc gggttgtaaa 300
gcacttttat caggagcgaa atctgcaagg ttaatacctt tgcagtctga cggtacctga 360
ggaataagca ccggctaact ccgtgccagc agccgcggta atacggaggg tgcaagcgtt 420
aatcggaatt actgggcgta aagcgtgcgt aggcggttcg ttaagtctgt tgtgaaagcc 480

```
ccgggctcaa cctgggaatg gcaatggata ctggcgagct agagtgtgtc agaggatggt    540

ggaattcccg gtgtagcggt gaaatgcgta gagatcggga ggaacatcag tggcgaaggc    600

ggccatctgg gacaacactg acgctgaggc acgaaagcgt ggggagcaaa caggattaga    660

taccctggta gtccacgccc taaacgatgc gaactggatg ttggtctcaa ctcggagatc    720

agtgtcgaag ctaacgcgtt aagttcgccg cctggggagt acggtcgcaa gactgaaact    780

caaaggaatt gacgggggcc cgcacaagcg gtggagtatg tggtttaatt cgatgcaacg    840

cgaagaacct tacctggcct tgacatgtcc ggaatccagc agagatgcag gagtgccttc    900

gggaatcgga acacaggtgc tgcatggctg tcgtcagctc gtgtcgtgag atgttgggtt    960

aagtcccgca acgagcgcaa cccttgtcct tagttgccag cgagtaatgt cgggaactct   1020

aaggagactg ccggtgacaa accggaggaa ggtggggatg acgtcaagtc atcatggccc   1080

ttacggccag ggctacacac gtactacaat ggtcggtaca gagggttgcg ataccgcgag   1140

gtggagctaa tcccagaaag ccgatcccag tccggattgg agtctgcaac tcgactccat   1200

gaagtcggaa tcgctagtaa tcgcagatca gctatgctgc ggtgaatacg              1250
```

<210> SEQ ID NO 66
<211> LENGTH: 1254
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 66

```
tacccagacg tgggggataa cgtagggaaa cttacgctaa taccgcatac gtcctacggg     60

agaaagcggg ggatcgcaag acctcgcgcg gttggatgga ccgatgtgcg attagctagt    120

tggtaaggta acggcttacc aaggcgacga tcgctagctg gtctgagagg atgatcagcc    180

acactgggac tgagacacgg cccagactcc tacgggaggc agcagtgggg aatattggac    240

aatgggcgca agcctgatcc agcaatgccg cgtgtgtgaa gaaggccctc gggttgtaaa    300

gcacttttat caggagcgaa atctgcaagg ttaatacctt tgcagtctga cggtacctga    360

ggaataagca ccggctaact ccgtgccagc agccgcggta atacggaggg tgcaagcgtt    420

aatcggaatt actgggcgta aagcgtgcgt aggcggttcg ttaagtctgt tgtgaaagcc    480

ccgggctcaa cctgggaatg gcaatggata ctggcgagct agagtgtgtc agaggatggt    540

ggaattcccg gtgtagcggt gaaatgcgta gagatcggga ggaacatcag tggcgaaggc    600

ggccatctgg gacaacactg acgctgaggc acgaaagcgt ggggagcaaa caggattaga    660

taccctggta gtccacgccc taaacgatgc gaactggatg ttggtctcaa ctcggagatc    720

agtgtcgaag ctaacgcgtt aagttcgccg cctggggagt acggtcgcaa gactgaaact    780

caaaggaatt gacgggggcc cgcacaagcg gtggagtatg tggtttaatt cgatgcaacg    840

cgaagaacct tacctggcct tgacatgtcc ggaatccagc agagatgcag gagtgccttc    900

gggaatcgga acacaggtgc tgcatggctg tcgtcagctc gtgtcgtgag atgttgggtt    960

aagtcccgca acgagcgcaa cccttgtcct tagttgccag cgagtaatgt cgggaactct   1020

aaggagactg ccggtgacaa accggaggaa ggtggggatg acgtcaagtc atcatggccc   1080

ttacggccag ggctacacac gtactacaat ggtcggtaca gagggttgcg ataccgcgag   1140

gtggagctaa tcccagaaag ccgatcccag tccggattgg agtctgcaac tcgactccat   1200

gaagtcggaa tcgctagtaa tcgcagatca gctatgctgc ggtgaatacg ttcc         1254
```

<210> SEQ ID NO 67
<211> LENGTH: 1295
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 67
gggtggcgag tggcggacgg gtgagtaatg catcgggaca tacccagacg tgggggataa 60
cgtagggaaa cttacgctaa taccgcatac gtcctacggg agaaagcggg ggatcgcaag 120
acctcgcgcg gttggatgga ccgatgtgcg attagctagt tggtaaggta acggcttacc 180
aaggcgacga tcgctagctg gtctgagagg atgatcagcc acactgggac tgagacacgg 240
cccagactcc tacgggaggc agcagtgggg aatattggac aatgggcgca agcctgatcc 300
agcaatgccg cgtgtgtgaa gaaggccctc gggttgtaaa gcacttttat caggagcgaa 360
atctgcaagg ttaatacctt tgcagtctga cggtacctga ggaataagca ccggctaact 420
ccgtgccagc agccgcggta atacggaggg tgcaagcgtt aatcggaatt actgggcgta 480
aagcgtgcgt aggcggttcg ttaagtctgt tgtgaaagcc ccgggctcaa cctgggaatg 540
gcaatggata ctggcgagct agagtgtgtc agaggatggt ggaattcccg gtgtagcggt 600
gaaatgcgta gagatcggga ggaacatcag tggcgaaggc ggccatctgg gacaacactg 660
acgctgaggc acgaaagcgt ggggagcaaa caggattaga taccctggta gtccacgccc 720
taaacgatgc gaactggatg ttggtctcaa ctcggagatc agtgtcgaag ctaacgcgtt 780
aagttcgccg cctggggagt acggtcgcaa gactgaaact caaaggaatt gacgggggcc 840
cgcacaagcg gtggagtatg tggtttaatt cgatgcaacg cgaagaacct tacctggcct 900
tgacatgtcc ggaatccagc agagatgcag gagtgccttc gggaatcgga acacaggtgc 960
tgcatggctg tcgtcagctc gtgtcgtgag atgttgggtt aagtcccgca acgagcgcaa 1020
cccttgtcct tagttgccag cgagtaatgt cgggaactct aaggagactg ccggtgacaa 1080
accggaggaa ggtggggatg acgtcaagtc atcatggccc ttacggccag ggctacacac 1140
gtactacaat ggtcggtaca gagggttgcg ataccgcgag gtggagctaa tcccagaaag 1200
ccgatcccag tccggattgg agtctgcaac tcgactccat gaagtcggaa tcgctagtaa 1260
tcgcagatca gctatgctgc ggtgaatacg ttccc 1295

<210> SEQ ID NO 68
<211> LENGTH: 1364
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 68
cttgctctgt gggtggcgag tggcggacgg gtgagtaatg catcgggacc tacccagacg 60
tgggggataa cgtagggaaa cttacgctaa taccgcatac gtcctacggg agaaagcggg 120
ggatcgcaag acctcgcgcg gttggatgga ccgatgtgcg attagctagt tggtaaggta 180
acggcttacc aaggcgacga tcgctagctg gtctgagagg atgatcagcc acactgggac 240
tgagacacgg cccagactcc tacgggaggc agcagtgggg aatattggac aatgggcgca 300

-continued

```
agcctgatcc agcaatgccg cgtgtgtgaa gaaggccctc gggttgtaaa gcacttttat    360

caggagcgaa atctgcaagg ttaatacctt tgcagtctga cggtacctga ggaataagca    420

ccggctaact ccgtgccagc agccgcggta atacggaggg tgcaagcgtt aatcggaatt    480

actgggcgta aagcgtgcgt aggcggttcg ttaagtctgt tgtgaaagcc ccgggctcaa    540

cctgggaatg gcaatggata ctggcgagct agagtgtgtc agaggatggt ggaattcccg    600

gtgtagcggt gaaatgcgta gagatcggga ggaacatcag tggcgaaggc ggccatctgg    660

gacaacactg acgctgaggc acgaaagcgt ggggagcaaa caggattaga taccctggta    720

gtccacgccc taaacgatgc gaactggatg ttggtctcaa ctcggagatc agtgtcgaag    780

ctaacgcgtt aagttcgccg cctggggagt acggtcgcaa gactgaaact caaaggaatt    840

gacgggggcc cgcacaagcg gtggagtatg tggtttaatt cgatgcaacg cgaagaacct    900

tacctggcct tgacatgtcc ggaatccagc agagatgcag gagtgccttc gggaatcgga    960

acacaggtgc tgcatggctg tcgtcagctc gtgtcgtgag atgttgggtt aagtcccgca   1020

acgagcgcaa cccttgtcct tagttgccag cgagtaatgt cgggaactct aaggagactg   1080

ccggtgacaa accggaggaa ggtggggatg acgtcaagtc atcatggccc ttacggccag   1140

ggctacacac gtactacaat ggtcggtaca gagggttgcg ataccgcgag gtggagctaa   1200

tcccagaaag ccgatcccag tccggattgg agtctgcaac tcgactccat gaagtcggaa   1260

tcgctagtaa tcgcagatca gctatgctgc ggtgaatacg ttcccgggcc ttgtacacac   1320

cgcccgtcac accatgggag tgagctgctc cagaagccgt tagt                    1364
```

```
<210> SEQ ID NO 69
<211> LENGTH: 1356
<212> TYPE: DNA
<213> ORGANISM: Unknown
<220> FEATURE:
<223> OTHER INFORMATION: Kingdom: Bacteria, Phylum: Proteobacteria,
      Class: Gammaproteobacteria, Order: Enterobacteriales, Family:
      Enterobacteriaceae, Genus: Erwinia

<400> SEQUENCE: 69

cttgctcctc gggtgacgag tggcggacgg gtgagtaatg tctggggatc tgcccggtag     60

agggggataa ccactggaaa cggtggctaa taccgcataa tctcgcaaga gcaaagtggg    120

ggaccttcgg gcctcacact accggatgaa cccagatggg attagccagc tggtgaggta    180

acggctcacc agggcgacga tccctagctg gtctgagagg atgaccagcc acactggaac    240

tgagacacgg tccagactcc tacgggaggc agcagtgggg aatattgcac aatgggcgca    300

agcctgatgc agccatgccg cgtgtatgaa gaaggccttc gggttgtaaa gtactttcag    360

cggggaggaa gggtgaagag cgaataactt ttcacattga cgttacccgc agaagaagca    420

ccggctaact ccgtgccagc agccgcggta atacggaggg tgcaagcgtt aatcggaatt    480

actgggcgta aagcgcacgc aggcggtctg ttaagtcaga tgtgaaatcc ccgggctcaa    540

cccgggaact gcatttgaaa ctggcaggct tgagtctcgt agaggggggt ggaattccag    600

gtgtagcggt gaaatgcgta gagatctgga ggaataccgg tggcgaaggc ggccccctgg    660

acgaagactg acgctcaggt gcgaaagcgt ggggagcaaa caggattaga taccctggta    720

gtccacgccg taaacgatgt cgatttggag gctgtgagct tgactcgtgg cttccgtagc    780

taacgcgtta aatcgaccgc ctggggagta cggccgcaag gttaaaactc aaatgaattg    840

acgggggccc gcacaagcgg tggagcatgt ggtttaattc gatgcaacgc gaagaacctt    900

acctggtctt gacatccacg gaatcgggca gagatgcctg agtgccttcg ggagccgtga    960
```

gacaggtgct gcatggctgt cgtcagctcg tgttgtgaaa tgttgggtta agtcccgcaa 1020
cgagcgcaac ccttatcctt tgttgccagc gattcggtcg ggaactcaaa ggagactgcc 1080
ggtgataaac cggaggaagg tggggatgac gtcaagtcat catggccctt acgaccaggg 1140
ctacacacgt gctacaatgg cgcatacaaa gagaagcgac ctcgcgagag caagcggacc 1200
tcataaagtg cgtcgtagtc cggatcggag tctgcaaccc gactccgtga agtcggaatc 1260
gctagtaatc gtggatcaga atgccacggt gaatacgttc ccgggccttg tacacaccgc 1320
ccgtcacacc atgggagtgg gttgcaaaag aagtag 1356

<210> SEQ ID NO 70
<211> LENGTH: 1326
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Burkholderiaceae, Genus: Ralstonia

<400> SEQUENCE: 70
agcttgctac attgatggcg agtggcgaac gggtgagtaa tacatcggaa cgtgccctgt 60
agtgggggat aactagtcga aagattagct aataccgcat acgacctgag ggtgaaagtg 120
ggggaccgca aggcctcatg ctataggagc ggccgatgtc tgattagcta gttggtgagg 180
taaaggctca ccaaggcgac gatcactagc tggtctgaga ggacgatcag ccacactggg 240
actgagacac ggcccagact cctacgggag gcagcagtgg ggaattttgg acaatgggcg 300
aaagcctgat ccagcaatgc cgcgtgtgtg aagaaggcct tcgggttgta aagcactttt 360
gtccggaaag aaatggctct ggttaatacc tggggtcgat gacggtaccg gaagaataag 420
gaccggctaa ctacgtgcca gcagccgcgg taatacgtag ggtccaagcg ttaatcggaa 480
ttactgggcg taaagcgtgc gcaggcggtt gtgcaagacc gatgtgaaat ccccgagctt 540
aacttgggaa ttgcattggt gactgcacgg ctagagtgtg tcagaggggg gtagaattcc 600
acgtgtagca gtgaaatgcg tagagatgtg gaggaatacc gatggcgaag gcagccccct 660
gggataacac tgacgctcat gcacgaaagc gtggggagca aacaggatta gataccctgg 720
tagtccacgc cctaaacgat gtcaactagt tgttggggat tcatttcctt agtaacgtag 780
ctaacgcgtg aagttgaccg cctggggagt acggtcgcaa gattaaaact caaaggaatt 840
gacggggacc cgcacaagcg gtggatgatg tggattaatt cgatgcaacg cgaacaacct 900
tacctaccct tgacatgcca ctaacgaagc agagatgcat tacgtgctcg aaagagaaag 960
cggacacagg tgctgcatgg ctgtcgtcag ctcgtgtcgt gagatgttgg gttaagtccc 1020
gcaacgagcg caacccttgt ctgtagttgc tacgaaaggg cactctagag agactgccgg 1080
tgacaaaccg gaggaaggtg gggatgacgt caagtcctca tggcccttat gggtagggct 1140
tcacacgtca tacaatggtg catacagagg gttgccaagc cgcgaggtgg agctaatccc 1200
agaaaatgca tcgtagtccg gatcgtagtc tgcaactcga ctacgtgaag ctggaatcgc 1260
tagtaatcgc ggatcagcat gccgcggtga atacgttccc gggtcttgta cacaccgccc 1320
gtcaca 1326

<210> SEQ ID NO 71
<211> LENGTH: 1394
<212> TYPE: DNA
<213> ORGANISM: Unknown
<220> FEATURE:

<223> OTHER INFORMATION: Kingdom: Bacteria, Phylum: Proteobacteria,
      Class: Gammaproteobacteria, Order: Pseudomonadales, Family:
      Pseudomonadaceae, Genus: Pseudomonas
<220> FEATURE:
<221> NAME/KEY: misc_feature
<222> LOCATION: (1384)..(1384)
<223> OTHER INFORMATION: n is a, c, g, or t

<400> SEQUENCE: 71
agtcgagcgg atgacgggag cttgctcctt gattcagcgg cggacgggtg agtaatgcct 60
aggaatctgc ctggtagtgg gggacaacgt ttcgaaagga acgctaatac cgcatacgtc 120
ctacgggaga aagcagggga ccttcgggcc ttgcgctatc agatgagcct aggtcggatt 180
agctagttgg tgaggtaatg gctcaccaag gcgacgatcc gtaactggtc tgagaggatg 240
atcagtcaca ctggaactga gacacggtcc agactcctac gggaggcagc agtggggaat 300
attggacaat gggcgaaagc ctgatccagc catgccgcgt gtgtgaagaa ggtcttcgga 360
ttgtaaagca ctttaagttg ggaggaaggg cagtaagcca ataccttgct gttttgacgt 420
taccgacaga ataagcaccg gctaactctg tgccagcagc cgcggtaata cagagggtgc 480
aagcgttaat cggaattact gggcgtaaag cgcgcgtagg tggttcgtta agttggatgt 540
gaaagccccg ggctcaacct gggaactgca tccaaaactg gcgagctaga gtacggtaga 600
gggtggtgga atttcctgtg tagcggtgaa atgcgtagat ataggaagga acaccagtgg 660
cgaaggcgac cacctggact gatactgaca ctgaggtgcg aaagcgtggg gagcaaacag 720
gattagatac cctggtagtc cacgccgtaa acgatgtcaa ctagccgttg gaatccttga 780
gattttagtg gcgcagctaa cgcattaagt tgaccgcctg gggagtacgg ccgcaaggtt 840
aaaactcaaa tgaattgacg ggggcccgca caagcggtgg agcatgtggt ttaattcgaa 900
gcaacgcgaa gaaccttacc aggccttgac atgcagagaa ctttccagag atggattggt 960
gccttaggga actctgacac aggtgctgca tggctgtcgt cagctcgtgt cgtgagatgt 1020
tgggttaagt cccgcaacga gcgcaaccct tgtccttagt taccagcacg ttatggtggg 1080
cactctaagg agactgccgg tgacaaaccg gaggaaggtg gggatgacgt caagtcatca 1140
tggcccttac ggcctgggct acacacgtgc tacaatggtc ggtacagagg gttgccaagc 1200
cgcgaggtgg agctaatctc acaaaaccga tcgtagtccg gatcgcagtc tgcaactcga 1260
ctgcgtgaag tcggaatcgc tagtaatcgc gaatcagaat gtcgcggtga atacgttccc 1320
gggccttgta cacaccgccc gtcacaccat gggagtgggt tgcaccagaa gtagctagtc 1380
taancttcgg gagg 1394

<210> SEQ ID NO 72
<211> LENGTH: 1344
<212> TYPE: DNA
<213> ORGANISM: Unknown
<220> FEATURE:
<223> OTHER INFORMATION: Kingdom: Bacteria, Phylum: Proteobacteria,
      Class: Alphaproteobacteria, Order: Caulobacterales, Family:
      Caulobacteraceae, Genus: Caulobacter

<400> SEQUENCE: 72
ggctgcctcc ttgcggttag cacaccgtct tcgggtaaag ccaactccca tggtgtgacg 60
ggcggtgtgt acaaggcccg ggaacgtatt caccgcggca tgctgatccg cgattactag 120
cgattccaac ttcatgcact cgagttgcag agtgcaatcc gaactgagac gacttttagg 180
gattggctcc ccctcgcggg attgcagccc tctgtagtcg ccattgtagc acgtgtgtag 240
cccaccctgt aagggccatg aggacttgac gtcatcccca ccttcctccg gcttaccacc 300

```
ggcggtcctg ttagagtgcc cagccaaacc tggtagcaac taacagcgag ggttgcgctc    360

gttgcgggac ttaacccaac atctcacgac acgagctgac gacagctatg cagcacctgt    420

gtcccagtcc ccgaagggaa agccacatct ctgtggcggt ccgggcatgt caaaaggtgg    480

taaggttctg cgcgttgctt cgaattaaac cacatgctcc accgcttgtg cgggcccccg    540

tcaattcctt tgagttttaa tcttgcgacc gtactcccca ggcggagtgc ttaatgcgtt    600

agctgcgtca ccgacatgca tgcatgccga caactagcac tcatcgttta cggcgtggac    660

taccagggta tctaatcctg tttgctcccc acgctttcgc gcctcagcgt cagtaacggg    720

ccagtgagtc gccttcgcca ctggtgttct tccgaatatc tacgaatttc acctctacac    780

tcggagttcc actcacctct cccgtactca agacagccag tattgaaggc atttccgagg    840

ttgagccccg ggctttcacc cccaacttaa ctgtccgcct acgcgccctt tacgcccagt    900

aattccgagc aacgctagcc cccttcgtat taccgcggct gctggcacga agttagccgg    960

ggcttcttct ccgggtaccg tcattatcgt ccacggtgaa aggattttac aatcctaaga   1020

ccttcatcat ccacgcggca tggctgcgtc aggctttcgc ccattgcgca agattcccca   1080

ctgctgcctc ccgtaggagt ctgggccgtg tctcagtccc agtgtggctg gccatcctct   1140

cagaccagct actgatcgta gccttggtga gccattacct caccaacaag ctaatcagac   1200

gcgggccgct ccaaaggcga taaatctttc ccccgaaggg cttatccggt attagcacaa   1260

gtttccctgt gttgttccga acctaagggt acgttcccac gtgttactca cccgtccgcc   1320

actatcccga aggaccgttc gact                                          1344
```

```
<210> SEQ ID NO 73
<211> LENGTH: 1344
<212> TYPE: DNA
<213> ORGANISM: Unknown
<220> FEATURE:
<223> OTHER INFORMATION: Kingdom: Bacteria, Phylum: Proteobacteria,
      Class: Alphaproteobacteria, Order: Caulobacterales, Family:
      Caulobacteraceae, Genus: Caulobacter

<400> SEQUENCE: 73
```

```
ggctgcctcc ttgcggttag cacaccgtct tcgggtaaag ccaactccca tggtgtgacg     60

ggcggtgtgt acaaggcccg ggaacgtatt caccgcggca tgctgatccg cgattactag    120

cgattccaac ttcatgcact cgagttgcag agtgcaatcc gaactgagac gacttttagg    180

gattggctcc ccctcgcggg attgcagccc tctgtagtcg ccattgtagc acgtgtgtag    240

cccaccctgt aagggccatg aggacttgac gtcatcccca ccttcctccg gcttaccacc    300

ggcggtcctg ttagagtgcc cagccaaacc tggtagcaac taacagcgag ggttgcgctc    360

gttgcgggac ttaacccaac atctcacgac acgagctgac gacagccatg cagcacctgt    420

gtcccagtcc ccgaagggaa agccacatct ctgtggcggt ccgggcatgt caaaaggtgg    480

taaggttctg cgcgttgctt cgaattaaac cacatgctcc accgcttgtg cgggcccccg    540

tcaattcctt tgagttttaa tcttgcgacc gtactcccca ggcggagtgc ttaatgcgtt    600

agctgcgtca ccgacatgca tgcatgccga caactagcac tcatcgttta cggcgtggac    660

taccagggta tctaatcctg tttgctcccc acgctttcgc gcctcagcgt cagtaacggg    720

ccagtgagtc gccttcgcca ctggtgttct tccgaatatc tacgaatttc acctctacac    780

tcggagttcc actcacctct cccgtactca agacagccag tattgaaggc atttccgagg    840

ttgagccccg ggctttcacc cccaacttaa ctgtccgcct acgcgccctt tacgcccagt    900
```

-continued

```
aattccgagc aacgctagcc cccttcgtat taccgcggct gctggcacga agttagccgg    960

ggcttcttct ccgggtaccg tcattatcgt ccccggtgaa aggattttac aatcctaaga   1020

ccttcatcat ccacgcggca tggctgcgtc aggctttcgc ccattgcgca agattcccca   1080

ctgctgcctc ccgtaggagt ctgggccgtg tctcagtccc agtgtggctg gccatcctct   1140

cagaccagct actgatcgta gccttggtga gccattacct caccaacaag ctaatcagac   1200

gcgggccgct ccaaaggcga taaatctttc ccccgaaggg cttatccggt attagcacaa   1260

gtttccctgt gttgttccga acctaagggt acgttcccac gtgttactca cccgtccgcc   1320

actatcccga aggaccgttc gact                                          1344
```

<210> SEQ ID NO 74
<211> LENGTH: 1398
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 74

```
tgcaagtcga gcggatgacg ggagcttgct ccttgattca gcggcggacg ggtgagtaat     60

gcctaggaat ctgcctggta gtgggggaca acgtttcgaa aggaacgcta ataccgcata    120

cgtcctacgg gagaaagcag gggaccttcg ggccttgcgc tatcagatga gcctaggtcg    180

gattagctag ttggtgaggt aatggctcac caaggcgacg atccgtaact ggtctgagag    240

gatgatcagt cacactggaa ctgagacacg gtccagactc ctacgggagg cagcagtggg    300

gaatattgga caatgggcga aagcctgatc cagccatgcc gcgtgtgtga agaaggtctt    360

cggattgtaa agcactttaa gttgggagga agggcagtaa gctaatacct tgctgttttg    420

acgttaccga cagaataagc accggctaac tctgtgccag cagccgcggt aatacagagg    480

gtgcgagcgt taatcggaat tactgggcgt aaagcgcgcg taggtggttc gttaagttgg    540

atgtgaaagc cccgggctca acctgggaac tgcatccaaa actggcgagc tagagtacgg    600

tagagggtgg tggaatttcc tgtgtagcgg tgaaatgcgt agatatagga aggaacacca    660

gtggcgaagg cgaccacctg gactggtact gacactgagg tgcgaaagcg tggggagcaa    720

acaggattag ataccctggt agtccacgcc gtaaacgatg tcaactagcc gttggaatcc    780

ttgagatttt agtggcgcag ctaacgcatt aagttgaccg cctggggagt acggccgcaa    840

ggttaaaact caaatgaatt gacgggggcc cgcacaagcg gtggagcatg tggtttaatt    900

cgaagcaacg cgaagaacct taccaggcct tgacatgcag agaactttcc agagatggat    960

tggtgcctta gggaactctg acacaggtgc tgcatggctg tcgtcagctc gtgtcgtgag   1020

atgttgggtt aagtcccgta acgagcgcaa cccttgtcct tagttaccag cacgttatgg   1080

tgggcactct aaggagactg ccggtgacaa accggaggaa ggtggggatg acgtcaagtc   1140

atcatggccc ttacggcctg ggctacacac gtgctacaat ggtcggtaca gagggttgcc   1200

aagccgcgag gtggagctaa tctcacaaaa ccgatcgtag tccggatcgc agtctgcaac   1260

tcgactgcgt gaagtcggaa tcgctagtaa tcgcgaatca gaatgtcgcg gtgaatacgt   1320

tcccgggcct tgtacacacc gcccgtcaca ccatgggagt gggttgcacc agaagtagct   1380

agtctaacct tcgggagg                                                 1398
```

<210> SEQ ID NO 75
<211> LENGTH: 1409

<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Stenotrophomonas

<400> SEQUENCE: 75
cgccctcccg aaggttaagc tacctgcttc tggtgcaaca aactcccatg gtgtgacggg 60
cggtgtgtac aaggcccggg aacgtattca ccgcagcaat gctgatctgc gattactagc 120
gattccgact tcatggagtc gagttgcaga ctccaatccg gactgagata gggtttctgg 180
gattggctta ccgtcgccgg cttgcagccc tctgtcccta ccattgtagt acgtgtgtag 240
ccctggccgt aagggccatg atgacttgac gtcatcccca ccttcctccg gtttgtcacc 300
ggcggtctcc ttagagttcc caccattacg tgctggcaac taaggacaag ggttgcgctc 360
gttgcgggac ttaacccaac atctcacgac acgagctgac gacagccatg cagcacctgt 420
gttcgagttc ccgaaggcac caatccatct ctggaaagtt ctcgacatgt caaggccagg 480
taaggttctt cgcgttgcat cgaattaaac cacatactcc accgcttgtg cgggcccccg 540
tcaattcctt tgagtttcag tcttgcgacc gtactcccca ggcggcgaac ttaacgcgtt 600
agcttcgata ctgcgtgcca aattgcaccc aacatccagt tcgcatcgtt tagggcgtgg 660
actaccaggg tatctaatcc tgtttgctcc ccacgctttc gtgcctcagt gtcagtgttg 720
gtccaggtag ctgcgttcgc catggatgtt cctcgtgatc tctacgcatt tcactgctac 780
accaggaatt ccgctaccct ctaccacact ctagtcgtcc agtatccact gcagttccca 840
ggttgagccc agggctttca caacggactt aaacgaccac ctacgcacgc tttacgccca 900
gtaattccga gtaacgcttg cacccttcgt attaccgcgg ctgctggcac gaagttagcc 960
ggtgcttatt ctttgggtac cgtcatccca accgggtatt aaccagctgg atttctttcc 1020
caacaaaagg gctttacaac ccgaaggcct tcttcaccca cgcggtatgg ctggatcagg 1080
cttgcgccca ttgtccaata ttccccactg ccgcctcccg taggagtctg gaccgtgtct 1140
cagttccagt gtggctgatc atcctctcag accagctacg gatcgtcgcc ttggtgggcc 1200
tttaccccgc caactagcta atccgacatc ggctcattca atcgcgcaag gtccgaagat 1260
cccctgcttt cacccgtagg tcgtatgcgg tattagcgta agtttcccta cgttatcccc 1320
cacgaaaaag tagattccga tgtattcctc acccgtccgc cactcgccac ccagagagca 1380
agctctcctg tgctgccgtt cgacttgca 1409

<210> SEQ ID NO 76
<211> LENGTH: 1396
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 76
cctcccgaag gttagactag ctacttctgg tgcaacccac tcccatggtg tgacgggcgg 60
tgtgtacaag gcccgggaac gtattcaccg cgacattctg attcgcgatt actagcgatt 120
ccgacttcac gcagtcgagt tgcagactgc gatccggact acgatcggtt ttgtgagatt 180
agctccacct cgcggcttgg caaccctctg taccgaccat tgtagcacgt gtgtagccca 240
ggccgtaagg gccatgatga cttgacgtca tccccacctt cctccggttt gtcaccggca 300
gtctccttag agtgcccacc ataacgtgct ggtaactaag gacaagggtt gcgctcgtta 360
cgggacttaa cccaacatct cacgacacga gctgacgaca gccatgcagc acctgtgtca 420
gagttcccga aggcaccaat ccatctctgg aaagttctct gcatgtcaag gcctggtaag 480
gttcttcgcg ttgcttcgaa ttaaaccaca tgctccaccg cttgtgcggg cccccgtcaa 540
ttcatttgag ttttaacctt gcggccgtac tccccaggcg gtcaacttaa tgcgttagct 600
gcgccactaa aatctcaagg attccaacgg ctagttgaca tcgtttacgg cgtggactac 660
cagggtatct aatcctgttt gctccccacg ctttcgcact cagtgtcagt atcagtccag 720
gtggtcgcgt tcgccactgg tgttccttcc tatatctacg catttcaccg ctacacagga 780
aattccacca ccctctaccg tactctagct cgccagtttt ggatgcagtt cccaggttga 840
gcccggggct ttcacatcca acttaacgaa ccacctacgc gcgctttacg cccagtaatt 900
ccgattaacg cttgcaccct ctgtattacc gcggctgctg gcacagagtt agccggtgct 960
tattctgtcg gtaacgtcaa aacagcaagg tattagctta ctgcccttcc tcccaactta 1020
aagtgcttta caatccgaag accttcttca cacacgcggc atggctggat caggctttcg 1080
cccattgtcc aatattcccc actgctgcct cccgtaggag tctggaccgt gtctcagttc 1140
cagtgtgact gatcatcctc tcagaccagt tacggatcgt cgccttggtg agccattacc 1200
tcaccaacta gctaatccga cctaggctca tctgatagcg caaggcccga aggtcccctg 1260
ctttctcccg taggacgtat gcggtattag cgttcctttc gaaacgttgt cccccactac 1320
caggcagatt cctaggcatt actcacccgt ccgccgctga atcaaggagc aagctcccgt 1380
catccgctcg acttgc 1396

<210> SEQ ID NO 77
<211> LENGTH: 1400
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 77
cgtcctcccg aaggttagac tagctacttc tggtgcaacc cactcccatg gtgtgacggg 60
cggtgtgtac aaggcccggg aacgtattca ccgcgacatt ctgattcgcg attactagcg 120
attccgactt cacgcagtcg agttgcagac tgcgatccgg actacgatcg gttttgtgag 180
attagctcca cctcgcggct tggcaaccct ctgtaccgac cattgtagca cgtgtgtagc 240
ccaggccgta agggccatga tgacttgacg tcatccccac cttcctccgg tttgtcaccg 300
gcagtctcct tagagtgccc accataacgt gctggtaact aaggacaagg gttgcgctcg 360
ttacgggact taacccaaca tctcacgaca cgagctgacg acagccatgc agcacctgtg 420
tcagagttcc ctaaggcacc aatccatctc tggaaagttc tctgcatgtc aaggcctggt 480
aaggttcttc gcgttgcttc gaattaaacc acatgctcca ccgcttgtgc gggcccccgt 540
caattcattt gagttttaac cttgcggccg tactccccag gcggtcaact taatgcgtta 600
gctgcgccac taaaatctca aggattccaa cggctagttg acatcgttta cggcgtggac 660
taccagggta tctaatcctg tttgctcccc acgctttcgc acctcagtgt cagtatcagt 720
ccaggtggtc gctttcgcca ctggtgttcc ttcctatatc tacgcatttc accgctacac 780
aggaaattcc accaccctct accgtactct agctcgccag ttttggatgc agttcccagg 840
ttgagcccgg ggctttcaca tccaacttaa cgaaccacct acgcgcgctt tacgcccagt 900
aattccgatt aacgcttgca ccctctgtat taccgcggct gctggcacag agttagccgg 960
tgcttattct gtcagtaacg tcaaaacagc aaggtattag cttactgccc ttcctcccaa 1020
cttaaagtgc tttacaatcc gaagaccttc ttcacacacg cggcatggct ggatcaggct 1080
ttcgcccatt gtccaatatt ccccactgct gcctcccgta ggagtctgga ccgtgtctca 1140
gttccagtgt gactgatcat cctctcagac cagttacgga tcgtcgcctt ggtgagccat 1200
taccccacca actagctaat ccgacctagg ctcatctgat agcgcaaggc ccgaaggtcc 1260
cctgctttct cccgtaggac gtatgcggta ttagcgttcc tttcgaaacg ttgtccccca 1320
ctaccaggca gattcctagg cattactcac ccgtccgccg ctgaatcaag gagcaagctc 1380
ccgtcatccg ctcgacttgc 1400

<210> SEQ ID NO 78
<211> LENGTH: 1377
<212> TYPE: DNA
<213> ORGANISM: Unknown
<220> FEATURE:
<223> OTHER INFORMATION: Kingdom: Bacteria, Phylum: Bacteroidetes,
Class: Cytophagia, Order: Cytophagales, Family: Cytophagaceae,
Genus: Hymenobacter

<400> SEQUENCE: 78
ttcgttgcgg agcaccggct tcaggtctac caaactttca tggcttgacg ggcggtgtgt 60
acaaggcccg ggaacgtatt caccgcgtca ttgctgatac gcgattacta gtgattccag 120
cttcacggag tcgagttgca gactccgatc cgaactgaga acggcttttc gggattggcg 180
caccatcgct ggttggcaac ccgctgtacc gtccattgta gcacgtgtgt agccctaggc 240
gtaagggcca tgatgacctg acgtcgtccc cgccttcctc actgcttgcg caggcagtcc 300
atctagagtc cccgccttga cgcgctggca actaaatgta ggggttgcgc tcgttgcggg 360
acttaaccca acacctcacg gcacgagctg acgacggcca tgcagcacct tgctttgtgt 420
cccgaaggaa agcgccatct ctggcgcggt cacgcgcatt ctagcctagg taaggttcct 480
cgcgtatcat cgaattaaac cacatgctcc accacttgtg cgggcccccg tcaattcctt 540
tgagtttcac ccttgcgggc gtactcccca ggtgggatac ttaacgcttt cgctaagcca 600
ccgacattgt atcgccggca gcgagtatcc atcgtttacg gcgtggacta ccagggtatc 660
taatcctgtt cgctccccac gctttcgtgc ctcagcgtca gttacagcct agtcagctgc 720
cttcgcaatc ggggttctgg atgctatcta tgcatttcac cgctacagca tccattccgc 780
caacctcgtc tgtactcaag ccaaccagtt tccagggcag ttccgttgtt gagcaacggg 840
ctttcacccc agacttaatc ggccgcctac gcacccttta aacccaataa atccggacaa 900
cgcttgcacc ctccgtatta ccgcggctgc tggcacggag ttagccggtg cttattcacc 960
aggtaccgtc agtagcggac gcatccgctt ttttcttccc tggcaaaagc agtttacgac 1020
tcagaaagcc ttcatcctgc acgcggcatg gctgggtcag gctctcgccc attgcccaat 1080
attccctact gctgcctccc gtaggagtcg ggcccgtatc tcagtgcccg tgtgggggac 1140
cagcctctca gctcccctaa gcatcgtcgc cttggtgggc cgttaccccg ccaaccagct 1200
aatgctacgc aaccccatcc ttgaccaata aatctttaat aaagagacga tgccgccacc 1260
ttattttatg cggtattaat ccgcctttcg gcgggctatc cccagtcaa gggcaggttg 1320 gttacgcgtt acgcacccgt gcgccactat cgtattgcta cgaccgttcg acttgca 1377

<210> SEQ ID NO 79

<211> LENGTH: 1395
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 79
gtcctcccga aggttagact agctacttct ggtgcaaccc actcccatgg tgtgacgggc 60
ggtgtgtaca aggcccggga acgtattcac cgcgacattc tgattcgcga ttactagcga 120
ttccgacttc acgcagtcga gttgcagact gcgatccgga ctacgatcgg ttttgtgaga 180
ttagctccac ctcgcggctt ggcaaccctc tgtaccgacc actgtagcac gtgtgtagcc 240
caggccgtaa gggccatgat gacttgacgt catccccacc ttcctccggt ttgtcaccgg 300
cagtctcctt agagtgccca ccataacgtg ctggtaacta aggacaaggg ttgcgctcgt 360
tacgggactt aacccaacat ctcacgacac gagctgacga cagccatgca gcacctgtgt 420
cagagttccc gaaggcacca atccatctct ggaaagttct ctgcatgtca aggcctggta 480
aggttcttcg cgttgcttcg aattaaacca catgctccac cgcttgtgcg ggcccccgtc 540
aattcatttg agttttaacc ttgcggccgt actccccagg cggtcaactt aatgcgttag 600
ctgcgccact aaaatctcaa ggattccaac ggctagttga catcgtttac ggcgtggact 660
accagggtat ctaatcctgt ttgctcccca cgctttcgca cctcagtgtc agtatcagtc 720
caggtggtcg ccttcgccac tggtgttcct tcctatatct acgcatttca ccgctacaca 780
ggaaattcca ccaccctcta ccgtactcta gctcgccagt tttggatgca gttcccaggt 840
tgagcccggg gctttcacat ccaacttaac gaaccaccta cgcgcgcttt acgcccagta 900
attccgatta acgcttgcac cctctgtatt accgcggctg ctggcacaga gttagccggt 960
gcttattctg tcggtaacgt caaaacagta aggtattagc ttactgccct tcctcccaac 1020
ttaaagtgct ttacaatccg aagaccttct tcacacacgc ggcatggctg gatcaggctt 1080
tcgcccattg tccaatattc cccactgctg cctcccgtag gagtctggac cgtgtctcag 1140
ttccagtgtg actgatcatc ctctcagacc agtcacggat cgtcgccttg gtgagccatt 1200
accccaccaa ctagctaatc cgacctaggc tcatctgata gcgcaaggcc cgaaggtccc 1260
ctgctttctc ccgtaggacg tatgcggtat tagcgttcct ttcgaaacgt tgtcccccac 1320
taccaggcag attcctaggc attactcacc cgtccgccgc tgaatcaagg agcaagctcc 1380
cgtcatccgc tcgac 1395

<210> SEQ ID NO 80
<211> LENGTH: 1384
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 80
gtcctcccga aggttagact agctacttct ggtgcaaccc actcccatgg tgtgacgggc 60
ggtgtgtaca aggcccggga acgtattcac cgcgacattc tgattcgcga ttactagcga 120
ttccgacttc acgcagtcga gttgcagact gcgatccgga ctacgatcgg ttttgtgaga 180
ttagctccac ctcgcggctc ggcaaccctc tgtaccgacc attgtagcac gtgtgtagcc 240
caggccgtaa gggccatgat gacttgacgt catccccacc ttcctccggt ttgtcaccgg 300

```
cagtctcctt agagtgccca ccataacgtg ctggtaacta aggacaaggg ttgcgctcgt    360

tacgggactt aacccaacat ctcacgacac gagctgacga cagccatgcg gcacctgtgt    420

cagagttccc taaggcacca atccatctct ggaaagttct ctgcatgtca aggcctggta    480

aggttcttcg cgttgcttcg aattaaacca catgctccac cgcttgtgcg ggcccccgtc    540

aattcatttg agttttaacc ttgcggccgt actccccagg cggtcaactt aatgcgttgg    600

ctgcgccact aaaatctcaa ggattccaac ggctagttga catcgtttac ggtgtggact    660

accagggtat ctaatcctgt ttgctcccca cgctttcgca cctcagtgtc agtatcagtc    720

caggtggtcg ccttcgccac tggtgttcct tcctatatct acgcatttca ccgctacaca    780

ggaaattcca ccaccctcta ccgtactcta gctcgccagt tttggatgca gttcccaggt    840

tgagcccggg gctttcacat ccaacttaac gaaccaccta cgcgcgcttt acgcccagta    900

attccgatta acgcttgcac cctctgtatt accgcggctg ctggcacaga gttagccggt    960

gcttattctg tcggtaacgt caaaacagca aggtattagc ttactgccct tcctcccaac   1020

ttaaagtgct ttacaatccg aagaccttct tcacacacgc ggcatggctg gatcaggctt   1080

tcgcccattg tccaatattc cccactgctg cctcccgtag gagtctggac cgtgtctcag   1140

ttccagtgtg actgatcatc ctctcagacc agttacggat cgtcgccttg gtgagccatt   1200

acctcaccaa ctagctaatc cgacctaggc tcatctgata gcgcaaggcc cgaaggtccc   1260

ctgctttctc ccgtaggacg tatgcggtat tagcgttcct ttcgaaacgt tgtcccccac   1320

taccaggcag attcctaggc attactcacc cgtccgccgc tgaatcaagg agcaagctcc   1380

cgtc                                                                1384
```

```
<210> SEQ ID NO 81
<211> LENGTH: 1400
<212> TYPE: DNA
<213> ORGANISM: Unknown
<220> FEATURE:
<223> OTHER INFORMATION: Kingdom: Bacteria, Phylum: Proteobacteria,
      Class: Gammaproteobacteria, Order: Pseudomonadales, Family:
      Pseudomonadaceae, Genus: Pseudomonas
<220> FEATURE:
<221> NAME/KEY: misc_feature
<222> LOCATION: (445)..(445)
<223> OTHER INFORMATION: n is a, c, g, or t

<400> SEQUENCE: 81

gtcctcccga aggttagact agctacttct ggtgcaaccc actcccatgg tgtgacgggc     60

ggtgtgtaca aggcccggga acgtattcac cgcgacattc tgattcgcga ttactagcga    120

ttccgacttc acgcagtcga gttgcagact gcgatccgga ctacgatcgg ttttgtgaga    180

ttagcaccac ctcgcggctt ggcaaccctc tgtaccgacc attgtagcac gtgtgtagcc    240

caggccgtaa gggccatgat gacttgacgt catccccacc ttcctccggt ttgtcaccgg    300

cagtctcctt agagtgccca ccataacgtg ctggtaacta aggacaaggg ttgcgctcgt    360

tacgggactt aacccgacat ctcacgacac gagctgacga cagccatgca gcacctgtgt    420

cagagttccc gaaggcacca atccntctct ggaaagttct ctgcatgtca aggcctggta    480

aggttcttcg cgttgcttcg aattaaacca catgctccac cgcttgtgcg ggcccccgtc    540

aattcatttg agttttaacc ttgcggccgt actccccagg cggtcaactt aatgcgttag    600

ctgcgccact aaaatctcaa ggattccaac ggctagttga catcgtttac ggcgtggact    660

accagggtgt ctaatcctgt ttgctcccca cgctttcgca cctcagtgtc agtatcagtc    720
```

```
caggcggtcg ctttcgccac tggtgttcct tcctatatct acgcatttca ccgctacaca    780

ggaaattcca ccaccctcta ccgtactcta gctcgccagt tttggatgca gttcccaggt    840

tgagcccggg gctttcacat ccaacttaac gaaccaccta cgcgcgcttt acgcccagta    900

attccgatta acgcttgcac cctctgtatt accgcggctg ctggcacaga gttagccggt    960

gcttattctg tcggtaacgt caaaacagta aggtattagc ttactgccct tcctcccaac   1020

ttaaagtgct ttacaatccg aagaccttct tcacacacgc ggcatggctg gatcaggctt   1080

tcgcccattg tccaatattc cccactgctg cctcccgtag gagtctggac cgtgtctcag   1140

ttccagtgtg actgatcatc ctctcagacc agttacggat cgtcgccttg gtgagccatt   1200

accccaccaa ctagctaatc cgacctaggc tcatctgata gcgcaaggcc cgaaggtccc   1260

ctgctttctc ccgtaggacg tatgcggtat tagcgttcct ttcgaaacgt tgtcccccac   1320

taccaggcag attcctaggc attactcacc cgtccgccgc tgaatcaagg agcaagctcc   1380

cgtcatccgc tcgacttgca                                                1400
```

<210> SEQ ID NO 82
<211> LENGTH: 1381
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 82

```
gtcctcccga aggttagact agctacttct ggtgcaaccc actcccatgg tgtgacgggc     60

ggtgtgtaca aggcccggga acgtattcac cgcgacattc tgattcgcga ttactagcga    120

ttccgacttc acgcagtcga gttgcagact gcgatccgga ctacgatcgg ttttgtgaga    180

ttagctccac ctcgcggctt ggcaaccctc tgtaccgacc attgtagcac gtgtgtagcc    240

caggccgtaa gggccatgat gacttgacgt catccccacc ttcctccggt ttgtcaccgg    300

cagtctcctt agagtgccca ccataacgtg ctggtaacta aggacaaggg ttgcgctcgt    360

tacgggactt aacccaacat ctcacgacac gagctgacga cagccatgca gcacctgtgt    420

cagagttccc gaaggcacca atccatctct ggaaagttct ctgcatgtca aggcctggta    480

aggttcttcg cgttgcttcg aattaaacca catgctccac cgcttgtgcg ggcccccgtc    540

aattcatttg agttttaacc ttgcggccgt actccccagg cggtcaactt aatgcgttag    600

ctgcgccact aaaatctcaa ggattccaac ggctagttga catcgtttac ggcgtggact    660

accagggtat ctaatcctgt ttgctcccca cgctttcgca cctcagtgtc agtatcagtc    720

caggtggtcg ctttcgccac tggtgttcct tcctatatct acgcatttca ccgctacaca    780

ggaaattcca ccaccctcta ccgtactcta gctcgccagt tttggatgca gttcccaggt    840

tgagcccggg gctttcacat ccgacttaac gaaccaccta cgcgcgcttt acgcccagta    900

attccgatta acgcttgcac cctctgtatt accgcggctg ctggcacaga gttagccggt    960

gcttattctg tcggtaacgt caaaacagca aggtattagc ttactgccct tcctcccaac   1020

ttaaagtgct ttacaatccg aagaccttct tcacacacgc ggcatggctg gatcaggctt   1080

tcgcccattg tccaatattc cccactgctg cctcccgtag gagtctggac cgtgtctcag   1140

ttccagtgtg actgatcatc ctctcagacc agttacggat cgtcgccttg gtgagccatt   1200

acctcaccaa ctagctaatc cgacctaggc tcatctgata gcgcaaggcc cgaaggtccc   1260

ctgctttctc ccgtaggacg tatgcggtat tagcgttcct ttcgaaacgt tgtcccccac   1320
```

taccaggcag attcctaggc attactcacc cgtccgccgc tgaatcaagg agcaagctcc 1380
c 1381

<210> SEQ ID NO 83
<211> LENGTH: 1402
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 83
ccgtcctccc gaaggttaga ctagctactt ctggtgcaac ccactcccat ggtgtgacgg 60
gcggtgtgta caaggcccgg gaacgtattc accgcgacat tctgattcgc gattactagc 120
gattccgact tcacgcagtc gagttgcaga ctgcgatccg gactacgatc ggttttgtga 180
gattagctcc acctcgcggc ttggcaaccc tctgtaccga ccattgtagc acgtgtgtag 240
cccaggccgt aagggccatg atgacttgac gtcatcccca ccttcctccg gtttgtcacc 300
ggcagtctcc ttagagtgcc caccataacg tgctggtaac taaggacaag ggttgcgctc 360
gttacgggac ttaacccaac atctcacgac acgagctgac gacagccatg cagcacctgt 420
gtcagagttc ccgaaggcac caatccatct ctggaaagtt ctctgcatgt caaggcctgg 480
taaggttctt cgcgttgctt cgaattaaac cacatgctcc accgcttgtg cgggcccccg 540
tcaattcatt tgagttttaa ccttgcggcc gtactcccca ggcggtcaac ttaatgcgtc 600
agctgcgcca ctaaaatctc aaggattcca acggctagtt gacatcgttt acggcgtgga 660
ctaccagggt atctaatcct gtttgctccc cacgctttcg cacctcagtg tcagtatcag 720
tccaggtggt cgccttcgcc actggtgttc cttcctatat ctacgcattt caccgctaca 780
caggaaattc caccaccctc taccgtactc tagctcgcca gttttggatg cagttcccag 840
gttgagcccg gggctttcac atccaactta acgaaccacc tacgcgcgct ttacgcccag 900
taattccgat taacgcttgc accctctgta ttaccgcggc tgctggcaca gagttagccg 960
gtgcttattc tgtcggtaac gtcaaaacag caaggtatta gcttactgcc cttcctccca 1020
acttaaagtg ctttacaatc cgaagacctt cttcacacac gcggcatggc tggatcaggc 1080
tttcgcccat tgtccaatat tccccactgc tgcctcccgt aggagtctgg accgtgtctc 1140
agttccagtg tgactgatca tcctctcaga ccagttacgg atcgtcgcct tggtgagcca 1200
ttacctcacc aactagctaa tccgacctag gctcatctga tagcgcaagg cccgaaggtc 1260
ccctgctttc tcccgtagga cgtatgcggt attagcgttc ctttcgaaac gttgtccccc 1320
actaccaggc agattcctag gcattactca cccgtccgcc gctgaatcaa ggagcaagct 1380
cccgtcatcc gctcgacttg ca 1402

<210> SEQ ID NO 84
<211> LENGTH: 1393
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Comamonadaceae, Genus: Pelomonas

<400> SEQUENCE: 84
ggtatcgccc tccttgcggt taggctaact acttctggca gaacccgctc ccatggtgtg 60
acgggcggtg tgtacaagac ccgggaacgt attcaccgcg gcaagctgat ctgcgattac 120
tagcgattcc gacttcacgc agtcgagttg cagactacga tccggactac gaccgggttt 180
ctgggattag ctccccctcg cgggttggca gccctctgtc ccggccattg tatgacgtgt 240
gtagccctac ccataagggc catgatgacc tgacgtcatc cccaccttcc tccggtttgt 300
caccggcagt ctcattagag tgccctttcg tagcaactaa tgacaagggt tgcgctcgtt 360
gcgggactta acccaacatc tcacgacacg agctgacgac ggccatgcag cacctgtgtc 420
caggctctct ttcgagcact cccaaatctc ttcaggattc ctggcatgtc aagggtaggt 480
aaggtttttc gcgttgcatc gaattaaacc acatcatcca ccgcttgtgc gggtccccgt 540
caattccttt gagtttcaac cttgcggccg tactccccag gcggtcaact tcacgcgtta 600
gctacgttac tgagaagaaa ccctcccaac aaccagttga catcgtttag ggcgtggact 660
accagggtat ctaatcctgt ttgctcccca cgctttcgtg catgagcgtc agtacaggtc 720
caggggattg ccttcgccat cggtgttcct ccgcatatct acgcatttca ctgctacacg 780
cggaattcca tccccctcta ccgtactcta gccatgcagt cacaaaggca gttcccaggt 840
tgagcccggg gatttcacct ctgtcttgca taaccgcctg cgcacgcttt acgcccagta 900
attccgatta acgcttgcac cctacgtatt accgcggctg ctggcacgta gttagccggt 960
gcttattctt caggtaccgt catgagtccc aggtattaac cagaaccttt tcttccctga 1020
caaaagcggt ttacaacccg aaggccttct tcccgcacgc ggcatggctg gatcaggctt 1080
gcgcccattg tccaaaattc cccactgctg cctcccgtag gagtctgggc cgtgtctcag 1140
tcccagtgtg gctggtcgtc ctctcagacc agctacagat cgttggcttg gtgggccttt 1200
accccaccga ctacctaatc tgatatcggc cgctccaatc gcgcgaggtc ttgcgatccc 1260
ccgctttcac cctcaggtcg tatgcggtat tagctgctct tccgagcagt tatcccccac 1320
gactgggcac gttccgatat attactcacc cgttcgccac tcgtcagctt aacctgttac 1380
cgttcgactt gca 1393

<210> SEQ ID NO 85
<211> LENGTH: 1353
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Sphingomonadales, Family: Sphingomonadaceae, Genus: Sphingomonas

<400> SEQUENCE: 85
gcctgcctct cttgcgagtt agcgcaacgc cttcgggtga acccaactcc catggtgtga 60
cgggcggtgt gtacaaggcc tgggaacgta ttcaccgcgg catgctgatc cgcgattact 120
agcgattccg ccttcatgct ctcgagttgc agagaacaat ccgaactgag acaacttttg 180
gagattagct caccctcgcg ggattgctgc ccactgtagt tgccattgta gcacgtgtgt 240
agcccagcgc gtaagggcca tgaggacttg acgtcatccc caccttcctc cggcttatca 300
ccggcggttc ctttagagta cccaactaaa tgatggtaac taaaggcgag ggttgcgctc 360
gttgcgggac ttaacccaac atctcacgac acgagctgac gacagccatg cagcacctgt 420
gttccagtcc ccgaagggaa gaaatccatc tctggaaatc gtccggacat gtcaaacgct 480
ggtaaggttc tgcgcgttgc ttcgaattaa accacatgct ccaccgcttg tgcaggcccc 540
cgccaattcc tttgagtttt aatcttgcga ccgtactccc caggcggata acttaatgcg 600
ttagctgcgc cacccaagca ccaagtgccc ggacagctag ttatcatcgt ttacggcgtg 660
gactaccagg gtatctaatc ctgtttgctc cccacgcttt cgcacctcag cgtcaatacc 720
agtccagtga gccgccttcg ccactggtgt tcttccgaat atctacgaat ttcacctcta 780
cactcggaat tccactcacc tctcctggat tcaagcgatg cagtcttaaa ggcaattccg 840
gagttgagcc ccgggctttc acctctaact tacagagccg cctacgtgcg ctttacgccc 900
agtaattccg aataacgcta gctcccctcg tattaccgcg gctgctggca cgaagttagc 960
cggagcttat tctcccggta ctgtcattat catcccgggt aaaagagctt tacaacccta 1020
aggccttcat cactcacgcg gcattgctgg atcaggcttt cgcccattgt ccaatattcc 1080
ccactgctgc ctcccgtagg agtctgggcc gtgtctcagt cccagtgtgg ctgatcatcc 1140
tctcagacca gctaaggatc gtcgccttgg tgagctttta cctcaccaac tagctaatcc 1200
tacgcgggct catccttggg cgataaatct ttggtcttac gacatcatcc ggtattagca 1260
gtcatttcta actgttattc cgaacccaag ggcagattcc cacgcgttac gcacccgtgc 1320
gccactaagg ccgaagcctt cgttcgactt gca 1353

<210> SEQ ID NO 86
<211> LENGTH: 1401
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 86
cgtcctcccg aaggttagac tagctacttc tggtgcaacc cactcccatg gtgtgacggg 60
cggtgtgtac aaggcccggg aacgtattca ccgcgacatt ctgattcgcg attactagcg 120
attccgactt cacgcagtcg agttgcagac tgcgatccgg actacgatcg gttttgtgag 180
attagctcca cctcgcggct tggcaaccct ctgtaccgac cattgtagca cgtgtgtagc 240
ccaggccgta agggccatga tgacttgacg tcatccccac cttcctccgg tttgtcaccg 300
gcagtctcct tagagtgccc accataacgt gctggtaact aaggacaagg gttgcgctcg 360
ttacgggact taacccaaca tctcacgaca cgagctgacg acagccatgc agcacctgtg 420
tcagagttcc cgaaggcacc aatccatctc tggaaagttc tctgcatgtc aaggcctggt 480
aaggttcttc gcgttgcctc gaattaaacc acatgctcca ccgcttgtgc gggcccccgt 540
caattcattt gagttttaac cttgcggccg tactccccag gcggtcaact taatgcgtta 600
gctgcgccac taaaatctca aggattccaa cggctagttg acatcgttta cggcgtggac 660
taccagggta tctaatcctg tttgctcccc acgctttcgc acctcagtgt cagtatcagt 720
ccaggtggtc gccttcgcca ctggtgttcc ttcctatatc tacgcatttc accgctacac 780
aggaaattcc accaccctct accgtactct agctcgccag ttttggatgc agttcccagg 840
ttgagcccgg ggctttcaca tccaacttaa cgaaccacct acgcgcgctt tacgcccagt 900
aattccgatt aacgcttgca ccctctgtat taccgcggct gctggcacag agttagccgg 960
tgcttattct gtcggtaacg tcaaaacagc aaggtattag cttactgccc ttcctcccaa 1020
cttaaagtgc tttacaatcc gaagaccttc ttcacacacg cggcatggct ggatcaggct 1080
ttcgcccatt gtccaatatt ccccactgct gcctcccgta ggagtctgga ccgtgtctca 1140
gttccagtgt gactgatcat cctctcagac cagttacgga tcgtcgcctt ggtgagccat 1200
tacctcacca actagctaat ccgacctagg ctcatctgat agcgcaaggc ccgaaggtcc 1260

```
cctgctttct cccgtaggac gtatgcggta ttagcgttcc tttcgaaacg ttgcccccca   1320

ctaccaggca gattcctagg cattactcac ccgtccgccg ctgaatcaag gagcaagctc   1380

ccgtcatccg ctcgacttgc a                                              1401


<210> SEQ ID NO 87
<211> LENGTH: 1396
<212> TYPE: DNA
<213> ORGANISM: Unknown
<220> FEATURE:
<223> OTHER INFORMATION: Kingdom: Bacteria, Phylum: Proteobacteria,
      Class: Gammaproteobacteria, Order: Pseudomonadales, Family:
      Pseudomonadaceae, Genus: Pseudomonas

<400> SEQUENCE: 87

tcccgaaggt tagactagct acttctggtg caacccactc ccatggtgtg acgggcggtg     60

tgtacaaggc ccgggaacgt attcaccgcg acattctgat tcgcgattac tagcgattcc    120

gacttcacgc agtcgagttg cagactgcga tccggactac gatcggtttt gtgagattag    180

ctccacctcg cggcttggca accctctgta ccgaccattg tagcacgtgt gtagcccagg    240

ccgtaagggc catgatgact tgacgtcatc cccaccttcc tccggtttgt caccggcagt    300

ctccttagag tgcccaccat aacgtgctgg taactaagga caagggttgc gctcgttacg    360

ggacttaacc caacatctca cgacacgagc tgacgacagc catgcagcac ctgtgtcaga    420

gttcccgaag gcaccaatcc atctctggaa agttctctgc atgtcaaggc ctggtaaggt    480

tcttcgcgtt gcttcgaatt aaaccacatg ctccaccgct tgtgcgggcc cccgtcaatt    540

catttgagtt ttaaccttgc ggccgtactc cccaggcggt caacttaatg cgctagctgc    600

gccactaaaa tctcaaggat tccaacggct agttgacatc gtttacggcg tggactacca    660

gggtatctaa tcctgtttgc tccccacgct ttcgcacctc agtgtcagta tcagtccagg    720

tggtcgcctt cgccactggt gttccttcct atatctacgc atttcaccgc tacacaggaa    780

attccaccac cctctaccgt actctagctc gccagttttg gatgcagttc ccaggttgag    840

cccggggctt tcacatccaa cttaacgaac cacctacgcg cgctttacgc ccagtaattc    900

cgattaacgc ttgcaccctc tgtattaccg cggctgctgg cacagagtta gccggtgctt    960

attctgtcgg taacgtcaaa acagtaaggt attagcttac tgcccttcct cccaacttaa   1020

agtgctttac aatccgaaga ccttcttcac acacgcggca tggctggatc aggctttcgc   1080

ccattgtcca atattcccca ctgctgcctc ccgtaggagt ctggaccgtg tctcagttcc   1140

agtgtgactg atcatcctct cagaccagtt acggatcgtc gccttggtga gccattaccc   1200

caccaactag ctaatccgac ctaggctcat ctgatagcgc aaggcccgaa ggtcccctgc   1260

tttctcccgt aggacgtatg cggtattagc gttcctttcg aaacgttgtc cccccactacc   1320

aggcagattc ctaggcatta ctcacccgtc cgccgctgaa tcaaggagca agctcccgtc   1380

atccgctcga cttgca                                                   1396


<210> SEQ ID NO 88
<211> LENGTH: 1409
<212> TYPE: DNA
<213> ORGANISM: Unknown
<220> FEATURE:
<223> OTHER INFORMATION: Kingdom: Bacteria, Phylum: Proteobacteria,
      Class: Gammaproteobacteria, Order: Pseudomonadales, Family:
      Pseudomonadaceae, Genus: Pseudomonas

<400> SEQUENCE: 88

tgcaagtcga gcggatgacg ggagcttgct ccttgattca gcggcggacg ggtgagtaat     60
```

```
gcctaggaat ctgcctggta gtgggggaca acgtttcgaa aggaacgcta ataccgcata    120
cgtcctacgg gagaaagcag gggaccttcg ggccttgcgc tatcagatga gcctaggtcg    180
gattagctag ttggtggggt aatggctcac caaggcgacg atccgtaact ggtctgagag    240
gatgatcagt cacactggaa ctgagacacg gtccagactc ctacgggagg cagcagtggg    300
gaatattgga caatgggcga aagcctgatc cagccatgcc gcgtgtgtga agaaggtctt    360
cggattgtaa agcactttaa gttgggagga agggcagtaa gctaatacct tactgttttg    420
acgttaccga cagaataagc accggctaac tctgtgccag cagccgcggt aatacagagg    480
gtgcaagcgt taatcggaat tactgggcgt aaagcgcgcg taggtggttc gttaagttgg    540
atgtgaaagc cccgggctca acctgggaac tgcatccaaa actggcgagc tagagtacgg    600
tagagggtgg tggaatttcc tgtgtagcgg tgaaatgcgt agatatagga aggaacacca    660
gtggcgaagg cgaccacctg gactgatact gacactgagg tgcgaaagcg tggggagcaa    720
acaggattag ataccctggt agtccacgcc gtaaacgatg tcaactagcc gttggaatcc    780
ttgagatttt agtgacgcag ctaacgcatt aagttgaccg cctggggagt acggccgcaa    840
ggttaaaact caaatgaatt gacgggggcc cgcacaagcg gtggagcatg tggtttaatt    900
cgaagcaacg cgaagaacct taccaggcct tgacatgcag agaactttcc agagatggat    960
tggtgccttc gggaattctg acacaggtgc tgcatggctg tcgtcagctc gtgtcgtgag   1020
atgttgggtt aagtcccgta acgagcgcaa cccttgtcct tagttaccag cacgttatgg   1080
tgggcactct aaggagactg ccggtgacaa accggaggaa ggtggggatg acgtcaagtc   1140
atcatggccc ttacggcctg ggctacacac gtgctacaat ggtcggtaca gagggttgcc   1200
aagccgcgag gtggagctaa tctcacaaaa ccgatcgtag tccggatcgc agtctgcaac   1260
tcgactgcgt gaagtcggaa tcgctagtaa tcgcgaatca gaatgtcgcg gtgaatacgt   1320
tcccgggcct tgtacacacc gcccgtcaca ccatgggagt gggttgcacc agaagtagct   1380
agtctaacct tcgggggggac ggttaccac                                      1409
```

<210> SEQ ID NO 89
<211> LENGTH: 1397
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 89

```
ctcccgaagg ttagactagc tacttctggt gcaacccact cccatggtgt gacgggcggt     60
gtgtacaagg cccgggaacg tattcaccgc gacattctga ttcgcgatta ctagcgattc    120
cgacttcacg cagtcgagtt gcagactgcg atccggacta cgatcggttt tgtgagatta    180
gctccacctc gcggcttggc aaccctctgt accgaccatt gtagcacgtg cgtagcccag    240
gccgtaaggg ccatgatgac ttgacgtcat ccccaccttc ctccggtttg tcaccggcag    300
tctccttaga gtgcccacca taacgtgctg gtaactaagg acaagggttg cgctcgttac    360
gggacttaac ccaacatctc acgacacgag ctgacgacag ccatgcagca cctgtgtcag    420
agttcccgaa ggcaccaatc catctctgga aagttctctg catgtcaagg cctggtaagg    480
ttcttcgcgt tgcttcgaat taaaccacat gctccaccgc ttgtgcgggc ccccgtcaat    540
tcatttgagt tttaaccttg cggccgtact ccccaggcgg tcaacttaat gcgttagctg    600
```

-continued

```
cgccactaaa atctcaagga ttccaacggc tagttgacat cgtttacggc gtggactacc    660

agggtatcta atcctgtttg ctccccacgc tttcgcacct cagtgtcagt atcagtccag    720

gtggtcgctt tcgccactgg tgttccttcc tatatctgcg catttcaccg ctacacagga    780

aattccacca ccctctaccg tactctagct cgccagtttt ggatgcagtt cccaggttga    840

gcccggggct ttcacatcca acttaacgaa ccacctacgc gcgctttacg cccagtaatt    900

ccgattaacg cttgcaccct ctgtattacc gcggctgctg gcacagagtt agccggtgct    960

tattctgtcg gtaacgtcaa aacagtaagg tattagctta ctgcccttcc tcccaactta   1020

aagtgcttta caatccgaag accttcttca cacacgcggc atggctggat caggctttcg   1080

cccattgtcc aatattcccc actgctgcct cccgtaggag tctggaccgt gtctcagttc   1140

cagtgtgact gatcatcctc tcagaccagt tacggatcgt cgccttggtg agccattacc   1200

ccaccaacta gctaatccga cctaggctca tctgatagcg caaggcccga aggtcccctg   1260

ctttctcccg taggacgtat gcggtattag cgttcctttc gaaacgttgt cccccactac   1320

caggcagatt cctaggcatt actcacccgt ccgccgctga atcaaggagc aagctcccgt   1380

catccgctcg acttgca                                                  1397
```

```
<210> SEQ ID NO 90
<211> LENGTH: 1396
<212> TYPE: DNA
<213> ORGANISM: Unknown
<220> FEATURE:
<223> OTHER INFORMATION: Kingdom: Bacteria, Phylum: Proteobacteria,
      Class: Gammaproteobacteria, Order: Pseudomonadales, Family:
      Pseudomonadaceae, Genus: Pseudomonas

<400> SEQUENCE: 90
```

```
gtcctcccga aggttagact agctacttct ggtgcaaccc actcccatgg tgtgacgggc     60

ggtgtgtaca aggcccggga acgtattcac cgcgacattc tgattcgcga ttactagcga    120

ttccgacttc acgcagtcga gttgcagact gcgatccgga ctacgatcgg ttttgtgaga    180

ttagctccac ctcgcggctt ggcaaccctc tgtaccgacc attgtagcac gtgtgtagcc    240

caggccgtaa gggccatgat gacttgacgt catccccacc ttcctccggt ttgtcaccgg    300

cagtctcctt agagtgccca ccataacgtg ctggtaacta aggacaaggg ctgcgctcgt    360

tacgggactt aacccaacat ctcacgacac gagctgacga cagccatgca gcacctgtgt    420

cagagttccc gaaggcacca atccatctct ggaaagttct ctgcatgtca aggcctggta    480

aggttcttcg cgttgcttcg aattaaacca catgctccac cgcttgtgcg ggcccccgtc    540

aattcatttg agttttaacc ttgcggccgt actccccagg cggtcaactt aatgcgttag    600

ctgcgccact aaaatctcaa ggattccaac ggctagttga catcgtttac ggcgtggact    660

accagggtat ctaatcctgt ttgctcccca cgctttcgca cctcagtgtc agtatcagtc    720

caggtggtcg ctttcgccac tggtgttcct tcctatatct acgcatttca ccgctacaca    780

ggaaattcca ccaccctcta ccgtactcta gctcgccagt tttggatgca gttcccaggt    840

tgagcccggg gctttcacat ccaacttaac gaaccaccta cgcgcgcttt acgcccagta    900

attccgatta acgcttgcac cctctgtatt accgcggctg ctggcacaga gttagccggt    960

gcttattctg tcggtaacgt caaaacagta aggtattagc ttactgccct tcctcccaac   1020

ttaaagtgct ttacaatccg aagaccttct tcacacacgc ggcatggctg gatcaggctt   1080

tcgcccattg tccaatattc cccactgctg cctctcgtag gagtctggac cgtgtctcag   1140

ttccagtgtg actgatcatc ctctcagacc agttacggat cgtcgccttg gtgagccatt   1200
```

accccaccaa ctagctaatc cgacctaggc tcatctgata gcgcaaggcc cgaaggtccc 1260
ctgctttctc ccgtaggacg tatgcggtat tagcgttcct ttcgaaacgt tgtcccccac 1320
taccaggcag attcctaggc attactcacc cgtccgccgc tgaatcaagg agcaagctcc 1380
cgtcatccgc tcgact 1396

<210> SEQ ID NO 91
<211> LENGTH: 1395
<212> TYPE: DNA
<213> ORGANISM: Unknown
<220> FEATURE:
<223> OTHER INFORMATION: Kingdom: Bacteria, Phylum: Proteobacteria,
Class: Gammaproteobacteria, Order: Pseudomonadales, Family:
Pseudomonadaceae, Genus: Pseudomonas

<400> SEQUENCE: 91
tcccgaaggt tagactagct acttctggtg caacccactc ccatggtgtg acgggcggtg 60
tgtacaaggc ccgggaacgt attcaccgcg acattctgat tcgcgattac tagcgattcc 120
gacttcacgc agtcgagttg cagactgcga tccggactac gatcggtttt gtgagattag 180
ctccacctcg cggcttggca accctctgta ccgaccattg tagcacgtgt gtagcccagg 240
ccgtaagggc catgatgact tgacgtcatc cccaccttcc tccggtttgt caccggcagt 300
ctccttagag tgcccaccat aacgtgctgg taactaagga caagggttgc gctcgttacg 360
ggacttaacc caacatctca cgacacgagc tgacgacagc catgcagcac ctgtgtcaga 420
gttcccgaag gcaccaatcc atctctggaa agttctctgc atgtcaaggc ctggtaaggt 480
tcttcgcgtt gcttcgaatt aaaccacatg ctccaccgct tgtgcgggcc cccgtcaatt 540
catttgagtt ttaaccttgc ggccgtactc cccaggcggt caacttaatg cgttagctgc 600
gccactaaaa tctcaaggat tccaacggct agttgacatc gtttacggcg tggactacca 660
gggtatctaa tcctgtttgc tccccacgct ttcgcacctc agtgtcagta tcagtccagg 720
tggtcgcctt cgccgctggt gttccttcct atatctacgc atttcaccgc tacacaggaa 780
attccaccac cctctaccgt actctagctc gccagttttg gatgcagttc ccaggttgag 840
cccggggctt tcacatccaa cttaacgaac cacctacgcg cgctttacgc ccagtaattc 900
cgattaacgc ttgcaccctc tgtattaccg cggctgctgg cacagagtta gccggtgctt 960
attctgtcgg taacgtcaaa acagtaaggt attagcttac tgcccttcct cccaacttaa 1020
agtgctttac aatccgaaga ccttcttcac acacgcggca tggctggatc aggctttcgc 1080
ccattgtcca atattcccca ctgctgcctc ccgtaggagt ctggaccgtg tctcagttcc 1140
agtgtgactg atcatcctct cagaccagtt acggatcgtc gccttggtga gccattaccc 1200
caccaactag ctaatccgac ctaggctcat ctgatagcgc aaggcccgaa ggtcccctgc 1260
tttctcccgt aggacgtatg cggtattagc gttcctttcg aaacgttgcc ccccactacc 1320
aggcagattc ctaggcatta ctcacccgtc cgccgctgaa tcaaggagca agctcccgtc 1380
atccgctcga cttgc 1395

<210> SEQ ID NO 92
<211> LENGTH: 1401
<212> TYPE: DNA
<213> ORGANISM: Unknown
<220> FEATURE:
<223> OTHER INFORMATION: Kingdom: Bacteria, Phylum: Proteobacteria,
Class: Gammaproteobacteria, Order: Pseudomonadales, Family:
Pseudomonadaceae, Genus: Pseudomonas
<220> FEATURE:

<221> NAME/KEY: misc_feature
<222> LOCATION: (30)..(32)
<223> OTHER INFORMATION: n is a, c, g, or t

<400> SEQUENCE: 92

```
gtcctcccga aggttagact agctacttcn nngtgcaacc cactcccatg gtgtgacggg     60

cggtgtgtac aaggcccggg aacgtattca ccgcgacatt ctgattcgcg attactagcg    120

attccgactt cacgcagtcg agttgcagac tgcgatccgg actacgatcg gttttgtgag    180

attagctcca cctcgcggct tggcaaccct ctgtaccgac cattgtagca cgtgtgtagc    240

ccaggccgta agggccatga tgacttgacg tcatccccac cttcctccgg tttgtcaccg    300

gcagtctcct tagagtgccc accataacgt gctggtaact aaggacaagg gttgcgctcg    360

ttacgggact taacccaaca tctcacgaca cgagctgacg acagccatgc agcacctgtg    420

tcagagttcc cgaaggcacc aatccatctc tggaaagttc tctgcatgtc aaggcctggt    480

aaggttcttc gcgttgcttc gaattaaacc acatgctcca ccgcttgtgc gggcccccgt    540

caattcattt gagttttaac cttgcggccg tactccccag gcggtcaact taatgcgtta    600

gctgcgccac taaaatctca aggattccaa cggctagttg acatcgttta cggcgtggac    660

taccagggta tctaatcctg tttgctcccc acgctttcgc acctcagtgt cagtatcagt    720

ccaggtggtc gctttcgcca ctggtgttcc ttcctatatc tacgcatttc accgctacac    780

aggaaattcc accaccctct accgtactct agctcgccag ttttggatgc agttcccagg    840

ttgagcccgg ggctttcaca tccaacttaa cgaaccacct acgcgcgctt tacgcccagt    900

aattccgatt aacgcttgca ccctctgtat taccgcggct gctggcacag agttagccgg    960

tgcttattct gtcggtaacg tcaaaacagc aaggtattag cttactgccc ttcctcccaa   1020

cttaaagtgc tttacaatcc gaagaccttc ttcacacacg cggcatggct ggatcaggct   1080

ttcgcccatt gtccaatatt ccccactgct gcctcccgta ggagtctgga ccgtgtctca   1140

gttccagtgt gactgatcat cctctcagac cagttacgga tcgtcgcctt ggtgagccat   1200

tacctcacca actagctaat ccgacctagg ctcatctgat agcgcaaggc ccgaaggtcc   1260

cctgctttct cccgtaggac gtatgcggta ttagcgttcc tttcgaaacg ttgtccccca   1320

ctaccaggca gattcctagg cattactcac ccgtccgccg ctgaatcaag gagcaagctc   1380

ccgtcatccg ctcgacttgc a                                              1401
```

<210> SEQ ID NO 93
<211> LENGTH: 1400
<212> TYPE: DNA
<213> ORGANISM: Unknown
<220> FEATURE:
<223> OTHER INFORMATION: Kingdom: Bacteria, Phylum: Proteobacteria,
      Class: Gammaproteobacteria, Order: Pseudomonadales, Family:
      Pseudomonadaceae, Genus: Pseudomonas

<400> SEQUENCE: 93

```
cgtcctcccg aaggttagac tagctacttc tggtgcaacc cactcccatg gtgtgacggg     60

cggtgtgtac aaggcccggg aacgtattca ccgcgacatt ctgattcgcg attactagcg    120

attccgactt cacgcagtcg agttgcagac tgcgatccgg actacgatcg gttttgtgag    180

attagctcca cctcgcggct tggcaaccct ctgtaccgac cattgtagca cgtgtgtagc    240

ccaggccgta agggccatga tgacttgacg tcatccccac cttcctccgg tttgtcaccg    300

gcagtctcct tagagtgccc accataacgt gctggtaact aaggacaagg gttgcgctcg    360

ttacgggact taacccaaca tctcacgaca cgagctgacg acagccatgc agcacctgtg    420
```

-continued

```
tcagagttcc ctaaggcacc aatccatctc tggaaagttc tctgcatgtc aaggcctggt    480

aaggttcttc gcgttgcttc gaattaaacc acatgctcca ccgcttgtgc gggcccccgt    540

caattcattt gagttttaac cttgcggccg tactccccag gcggtcaact taatgcgtta    600

gctgcgccac taaaatctca aggattccaa cggctagttg acatcgttta cggcgtggac    660

taccagggta tctaatcctg tttgctcccc acgctttcgc acctcagtgt cagtatcagt    720

ccaggtggtc gccttcgcca ctggtgttcc ttcctatatc tacgcattca ccgctacaca    780

ggaaattcca ccaccctcta ccgtactcca gctcgccagt tttggatgca gttcccaggt    840

tgagcccggg gctttcacat ccaacttaac gaaccaccta cgcgcgcttt acgcccagta    900

attccgatta acgcttgcac cctctgtatt accgcggctg ctggcacaga gctagccggt    960

gcttattctg tcagtaacgt caaaacagca aggtattagc ttactgccct tcctcccaac   1020

ttaaagtgct ttacaatccg aagaccttct tcacacacgc ggcatggctg gatcaggctt   1080

tcgcccattg tccaatattc cccactgctg cctcccgtag gagtctggac cgtgtctcag   1140

ttccagtgtg actgatcatc ctctcagacc agttacggat cgtcgccttg gtgagccatt   1200

accccaccaa ctagctaatc cgacctaggc tcatctgata gcgcaaggcc cgaaggtccc   1260

ctgctttctc ccgtaggacg tatgcggtat tagcgttcct ttcgaaacgt tgtcccccac   1320

taccaggcag attcctaggc attactcacc cgtccgccgc tgaatcaagg agcaagctcc   1380

cgtcatccgc tcgacttgca                                               1400
```

<210> SEQ ID NO 94
<211> LENGTH: 1399
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 94

```
gtcctcccga aggttagact agctacttct ggtgcaaccc actcccatgg tgtgacgggc     60

ggtgtgtaca aggcccggga acgtattcac cgcgacattc tgattcgcga ttactagcga    120

ttccgacttc acgcagtcga gttgcagact gcgatccgga ctacgatcgg ttttgtgaga    180

ttagctccac ctcgcggctt ggcaaccctc tgtaccgacc attgtagcac gtgtgtagcc    240

caggccgtaa gggccatgat gacttgacgt catccccacc ttcctccggt ttgtcaccgg    300

cagtctcctt agagtgccca ccataacgtg ctggtaacta aggacaaggg ttgcgctcgt    360

tacgggactt aacccaacat ctcacgacac gagctgacga cagccatgca gcacctgtgt    420

cagagttccc taaggcacca atccatctct ggaaagttct ctgcatgtca aggcctggta    480

aggttcttcg cgttgcttcg aattaaacca catgctccac cgcttgtgcg ggcccccgtc    540

aattcatttg agttttaacc ttgcggccgt gctccccagg cggtcaactt aatgcgttag    600

ctgcgccact aaaatctcaa ggattccaac ggctagttga catcgtttac ggcgtggact    660

accagggtat ctaatcctgt ttgctcccca cgctttcgca cctcagtgtc agtatcagtc    720

caggtggtcg ccttcgccac tggtgttcct tcctatatct acgcatttca ccgctacaca    780

ggaaattcca ccaccctcta ccgtactcta gctcgccagt tttggatgca gttcccaggt    840

tgagcccggg gctttcacat ccaacttaac gaaccaccta cgcgcgcttt acgcccagta    900

attccgatta acgcttgcac cctctgtatt accgcggctg ctggcacaga gttagccggt    960
```

gcttattctg tcagtaacgt caaaacagca aggtattagc ttactgccct tcctcccaac 1020
ttaaagtgct ttacaatccg aagaccttct tcacacacgc ggcatggctg gatcaggctt 1080
tcgcccattg tccaatattc cccactgctg cctcccgtag gagtctggac cgtgtctcag 1140
ttccagtgtg actgatcatc ctctcagacc agttacggat cgtcgccttg gtgagccatt 1200
accccaccaa ctagctaatc cgacctaggc tatctgatag cgcaaggccc gaaggtcccc 1260
tgctttctcc cgtaggacgt atgcggtatt agcgttcctt tcgaaacgtt gtcccccact 1320
accaggcaga ttcctaggca ttactcaccc gtccgccgct gaatcaagga gcaagctccc 1380
gtcatccgct cgacttgca 1399

<210> SEQ ID NO 95
<211> LENGTH: 1400
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 95
gtcctcccga aggttagact agctacttct ggtgcaaccc actcccatgg tgtgacgggc 60
ggtgtgtaca aggcccggga acgtattcac cgcgacattc tgattcgcga ttactagcga 120
ttccgacttc acgcagtcga gttgcagact gcggtccgga ctacgatcgg ttttgtgaga 180
ttagctccac ctcgcggctt ggcaaccctc tgtaccgacc attgtagcac gtgtgtagcc 240
caggccgtaa gggccatgat gacttgacgt catccccacc ttcctccggt ttgtcaccgg 300
cagtctcctt agagtgccca ccataacgtg ctggtaacta aggacaaggg ttgcgctcgt 360
tacgggactt aacccaacat ctcacgacac gagctgacga cagccatgca gcacctgtgt 420
cagagttccc taaggcacca atccatctct ggaaagttct ctgcatgtca aggcctggta 480
aggttcttcg cgttgcttcg aattaaacca catgctccac cgcttgtgcg ggcccccgtc 540
aattcatttg agttttaacc ttgcggccgt actccccagg cggtcaactt aatgcgttag 600
ctgcgccact aaaatctcaa ggattccaac ggctagttga catcgtttac ggcgtggact 660
accagggtat ctaatcctgt ttgctcccca cgctttcgca cctcagtgtc agtatcagtc 720
caggtggtcg ctttcgccac tggtgttcct tcctatatct acgcatttca ccgctacaca 780
ggaaattcca ccaccctcta ccgtactcta gctcgccagt tttggatgca gttcccaggt 840
tgagcccggg gctttcacat ccaacttaac gaaccaccta cgcgcgcttt acgcccagta 900
attccgatta acgcttgcac cctctgtatt accgcggctg ctggcacaga gttagccggt 960
gcttattctg tcggtaacgt caaaacagca aggtattagc ttactgccct tcctcccaac 1020
ttaaagtgct ttacaatccg aagaccttct tcacacacgc ggcatggctg gatcaggctt 1080
tcgcccattg tccaatattc cccactgctg cctcccgtag gagtctggac cgtgtctcag 1140
ttccagtgtg actgatcatc ctctcagacc agttacggat cgtcgccttg gtgagccatt 1200
acctcaccaa ctagctaatc cgacctaggc tcatctgata gcgcaaggcc cgaaggtccc 1260
ctgctttctc ccgtaggacg tatgcggtat tagcgttcct ttcgaaacgt tgtcccccac 1320
taccaggcag attcctaggc attactcacc cgtccgccgc tgaatcaagg agcaagctcc 1380
cgtcatccgc tcgacttgca 1400

<210> SEQ ID NO 96
<211> LENGTH: 1353

-continued

<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Sphingomonadales, Family: Sphingomonadaceae, Genus: Sphingomonas

<400> SEQUENCE: 96
gcctgcctct cttgcgagtt agcgcaacgc cttcgggtga acccaactcc catggtgtga 60
cgggcggtgt gtacaaggcc tgggaacgta ttcaccgcgg catgctgatc cgcgattact 120
agcgattccg ccttcatgct ctcgagttgc agagaacaat ccgaactgag acaacttttg 180
gagattagct caccctcgcg ggattgctgc ccactgtagt tgccattgta gcacgtgtgt 240
agcccagcgc gtaagggcca tgaggacttg acgtcatccc caccttcctc cggcttatca 300
ccggcggttc ctttagagta cccaactaaa tgatggtaac taaaggcgag ggttgcgctc 360
gttgcgggac ttaacccaac atctcacgac acgagctgac gacagccatg cagcacctgt 420
gttccagtcc ccgaagggaa gaaatccatc tctggaaatc gtccggacat gtcaaacgct 480
ggtaaggttc tgcgcgttgc ttcgaattaa accacatgct ccaccgcttg tgcaggcccc 540
cgtcaattcc tttgagtttt aatcttgcga ccgtactccc caggcggata acttaatgcg 600
ttagctgcgc cacccaagca ccaagtgccc ggacagctag ttatcatcgt ttacggcgtg 660
gactaccagg gtatctaatc ctgtttgctc cccacgcttt cgcacctcag cgtcaatacc 720
agtccagtga gccgccttcg ccactggtgt tcttccgaat atctacgaat ttcacctcta 780
cactcggaat tccactcacc tctcctggat tcaagcgatg cagtcttaaa ggcaattccg 840
gagttgagtc ccgggctttc acctctaact tacaaagccg cctacgtgcg ctttacgccc 900
agtaattccg aataacgcta gctcccctcg tattaccgcg gctgctggca cgaagttagc 960
cggagcttat tctcccggta ctgtcattat catcccgggt aaaagagctt tacaacccta 1020
aggccttcat cactcacgcg gcattgctgg atcaggcttt cgcccattgt ccaatattcc 1080
ccactgctgc ctcccgtagg agtctgggcc gtgtctcagt cccagtgtgg ctgatcatcc 1140
tctcagacca gctaaggatc gtcgccttgg tgagctttta cctcaccaac tagctaatcc 1200
tacgcgggct catccttggg cgataaatct ttggtcttac gacatcatcc ggtattagca 1260
gtcatttcta actgttattc cgaacccaag ggcagattcc cacgcgttac gcacccgtgc 1320
gccactaagg ccgaagcctt cgttcgactt gca 1353

<210> SEQ ID NO 97
<211> LENGTH: 1397
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 97
ctcccgaagg ttagactagc tacttctggt gcaacccact cccatggtgt gacgggcggt 60
gtgtacaagg cccgggaacg tattcaccgc gacattctga ttcgcgatta ctagcgattc 120
cgacttcacg cagtcgagtt gcagactgcg atccggacta cgatcggttt tgtgagatta 180
gctccacctc gcggcttggc aaccctctgt accgaccatt gtagcacgtg tgtagcccag 240
gccgtaaggg ccatgatgac ttgacgtcat ccccaccttc ctccggcttg tcaccggcag 300
tctccttaga gtgcccacca taacgtgctg gtaactaagg acaagggttg cgctcgttac 360

-continued

```
gggacttaac ccaacatctc acgacacgag ctgacgacag ccatgcagca cctgtgtcag    420

agttcccgaa ggcaccaatc catctctgga aagttctctg catgtcaagg cctggtaagg    480

ttcttcgcgt tgcttcgaat taaaccacat gctccaccgc ttgtgcgggc ccccgtcaat    540

tcatttgagt tttaaccttg cggccgtact ccccaggcgg tcaacttaat gcgttagctg    600

cgccactaaa atctcaagga ttccaacggc tagttgacat cgtttacggc gtggactacc    660

agggtatcta atcctgtttg ctccccacgc tttcgcacct cagtgtcagt atcagtccag    720

gtggtcgctt tcgccactgg tgttccttcc tatatctacg catttcaccg ctacacagga    780

aattccacca ccctctaccg tactctagct cgccagtttt ggatgcagtt cccaggttga    840

gcccggggct ttcacatcca acttaacgaa ccacctacgc gcgctttacg cccagtaatt    900

ccgattaacg cttgcaccct ctgtattact gcggctgctg gcacagagtt agccggtgct    960

tattctgtcg gtaacgtcaa aacagcaagg tattagctta ctgcccttcc tcccaactta   1020

aagtgcttta caatccgaag accttcttca cacacgcggc atggctggat caggctttcg   1080

cccattgtcc aatattcccc actgctgcct cccgtaggag tctggaccgt gtctcagttc   1140

cagtgtgact gatcatcctc tcagaccagt tacggatcgt cgccttggtg agccattacc   1200

tcaccaacta gctaatccga cctaggctca tctgatagcg caaggcccga aggtcccctg   1260

ctttctcccg taggacgtat gcggtattag cgttcctttc gaaacgttgt cccccactac   1320

caggcagatt cctaggcatt actcacccgt ccgccgctga atcaaggagc aagctcccgt   1380

catccgctcg acttgca                                                  1397
```

<210> SEQ ID NO 98
<211> LENGTH: 1400
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 98

```
gtcctcccga aggttagact agctacttct ggtgcaaccc actcccatgg tgtgacgggc     60

ggtgtgtaca aggcccggga acgtattcac cgcgacattc tgattcgcga ttactagcga    120

ttccgacttc acgcagtcga gttgcagact gcgatccgga ctacgatcgg ttttgtgaga    180

ttagctccac ctcgcggctt ggcaaccctc tgtaccgacc attgtagcac gtgtgtagcc    240

caggccgtaa gggccatgat gacttgacgt catccccacc ttcctccggt ttgtcaccgg    300

cagtctcctt agagtgccca ccataacgtg ctggtaacta aggacaaggg ttgcgctcgt    360

tacgggactt aacccaacat ctcacgacac gagctgacga cagccatgca gcacctgtgt    420

cagagttccc gaaggcacca atccatctct ggaaagttct ctgcatgtca aggcctggta    480

aggttcttcg cgttgcttcg aattaaacca catgctccac cgcttgtgcg ggcccccgtc    540

aattcatttg agttttaacc ttgcggccgt actccccagg cggtcaactt aatgcgttag    600

ctgcgccact aaaatctcaa ggattccaac ggctagttga catcgtttac ggcgtggact    660

accagggtat ctaatcctgt ttgctcccca cgctttcgca cctcagtgtc agtatcagtc    720

caggtggtcg ctttcgccac tggtgttcct tcctatatct acgcatttca ccgctacaca    780

ggaaattcca ccaccctcta ccgtactcta gctcgccagt tttggatgca gttcccaggt    840

tgagcccggg gctttcacat ccaacttaac gaaccaccta cgcgcgcttt acgcccagta    900

attccgatta acgcttgcac cctctgtatt accgcggctg ctggcacaga gttagccggt    960
```

```
gcttattctg tcggtaacgt caaaacagca aggtattagc ttactgccct tcctcccaac   1020

ttaaagtact ttacaatccg aagaccttct tcacacacgc ggcatggctg gatcaggctt   1080

tcgcccattg tccaatattc cccactgctg cctcccgtag gagtctggac cgtgtctcag   1140

ttccagtgtg actgatcatc ctctcagacc agttacggat cgtcgccttg gtgagccatt   1200

acctcaccaa ctagctaatc cgacctaggc tcatctgata gcgcaaggcc cgaaggtccc   1260

ctgctttctc ccgtaggacg tatgcggtat tagcgttcct ttcgaaacgt tgtcccccac   1320

taccaggcag attcctaggc attactcacc cgtccgccgc tgaatcaagg agcaagctcc   1380

cgtcatccgc tcgacttgca                                                1400
```

<210> SEQ ID NO 99
<211> LENGTH: 1394
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 99

```
gtcctcccga aggttagact agctacttct ggtgcaaccc actcccatgg tgtgacgggc     60

ggtgtgtaca aggcccggga acgtattcac cgcgacattc tgattcgcga ttactagcga    120

ttccgacttc acgcagtcga gttgcagact gcgatccgga ctacgatcgg ttttgtgaga    180

ttagctccac ctcgcggctt ggcaaccctc tgtaccgacc attgtagcac gtgtgtagcc    240

caggccgtaa gggccatgat gacttgacgt catccccacc ttcctccggt ttgtcaccgg    300

cagtctcctt agagtgccca ccataacgtg ctggtaacta aggacaaggg ttgcgctcgt    360

tacgggactt aacccaacat ctcacgacgc gagctgacga cagccatgca gcacctgtgt    420

cagagttccc taaggcacca atccatctct ggaaagttct ctgcatgtca aggcctggta    480

aggttcttcg cgttgcttcg aattaaacca catgctccac cgcttgtgcg ggcccccgtc    540

aattcatttg agttttaacc ttgcggccgt actccccagg cggtcaactt aatgcgttag    600

ctgcgccact aaaatctcaa ggattccaac ggctagttga catcgtttac ggcgtggact    660

accagggtat ctaatcctgt ttgctcccca cgctttcgca cctcagtgtc agtatcagtc    720

caggtggtcg ccttcgccac tggtgttcct tcctatatct acgcatttca ccgctgcaca    780

ggaaattcca ccaccctcta ccgtactcta gctcgccagt tttggatgca gttcccaggt    840

tgagcccggg gctttcacat ccaacttaac gaaccaccta cgcgcgcttt acgcccagta    900

attccgatta acgcttgcac cctctgtatt accgcggctg ctggcacaga gttagccggt    960

gcttattctg tcagtaacgt caaaacagca aggtattagc ttactgccct tcctcccaac   1020

ttaaagtgct ttacaatccg aagaccttct tcacacacgc ggcatggctg gatcaggctt   1080

tcgcccattg tccaatattc cccactgctg cctcccgtag gagtctgggc cgtgtctcag   1140

ttccagtgtg actgatcatc ctctcagacc agttacggat cgtcgccttg gtgagccatt   1200

accccaccaa ctagctaatc cgacctaggc tcatctgata gcgcaaggcc cgaaggtccc   1260

ctgctttctc ccgtaggacg tatgcggtat tagcgttcct ttcgaaacgt tgtcccccac   1320

taccaggcag attcctaggc attactcacc cgtccgccgc tgaatcaagg agcaagctcc   1380

cgtcatccgc tcga                                                      1394
```

<210> SEQ ID NO 100

<211> LENGTH: 1399
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 100

```
gtcctcccga aggttagact agctacttct ggtgcaaccc actcccatgg tgtgacgggc     60

ggtgtgtaca aggcccggga acgtattcac cgcgacattc tgattcgcga ttactagcga    120

ttccgacttc acgcagtcga gttgcagact gcgatccgga ctacgatcgg ttttgtgaga    180

ttagctccac ctcgcggctt ggcaaccctc tgtaccgacc attgtagcac gtgtgtagcc    240

caggccgtaa gggccatgat gacttgacgt catccccacc ttcctccggt ttgtcaccgg    300

cagtctcctt agagtgccca ccataacgtg ctggtaacta aggacaaggg ttgcgctcgt    360

tacgggactt aacccaacat ctcacgacac gagctgacga cagccatgca gcacctgtgt    420

cagagttccc taaggcacca atccatctct ggaaagttct ctgcatgtca aggcctggta    480

aggttcttcg cgttgcttcg aattaaacca catgctccac cgcttgtgcg ggcccccgtc    540

aattcatttg agttttaacc ttgcggccgt actccccagg cggtcaactt aatgcgttag    600

ctgcgccact aaaatctcaa ggattccaac ggctagttga catcgtttac ggcgtggact    660

accagggtat ctaatcctgt ttgctcccca cgctttcgca cctcagtgtc agtatcagtc    720

caggtggtcg ccttcgccac tggtgttcct tcctatatct acgcatttca ccgctacaca    780

ggaaattcca ccaccctcta ccgtactcta gctcgccagt tttggatgca gttcccaggt    840

tgagcccggg gctttcacat ccaacttaac gaaccaccta cgcgcgcttt acgcccagta    900

attccgatta acgcttgcac cctctgtatt accgcggctg ctggcacaga gttagccggt    960

gcttattctg tcggtaacgt caaaacagca aggtattagc ttactgccct tcctcccaac   1020

ttaaagtgct ttacaatccg aagaccttct tcacacacgc ggcatggctg gatcaggctt   1080

tcgcccattg tccaatattc cccactgctg cctcccgtag gagtctggac cgtgtctcag   1140

ttccagtgtg actgatcatc ctctcagacc agttacggat cgtcgccttg gtgagccatt   1200

acctcaccaa ctagctaatc cgacctaggc tcatctgata gcgcaaggcc cgaaggcccc   1260

ctgctttctc ccgtaggacg tatgcggtat tagcgttcct ttcgaaacgt tgtcccccac   1320

taccaggcag attcctaggc attactcacc cgtccgccgc tgaatcaagg agcaagctcc   1380

cgtcgtccgc tcgacttgc                                                1399
```

<210> SEQ ID NO 101
<211> LENGTH: 1400
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 101

```
gtcctcccga aggttagact agctacttct ggtgcaaccc actcccatgg tgtgacgggc     60

ggtgtgtaca aggcccggga acgtattcac cgcgacattc tgattcgcga ttactagcga    120

ttccgacttc acgcagtcga gttgcagact gcgatccgga ctacgatcgg ttttgtgaga    180

ttagctccac ctcgcggctt ggcaaccctc tgtaccgacc attgtagcac gtgtgtagcc    240

caggccgtaa gggccatgat gacttgacgt catccccacc ttcctccggt ttgtcaccgg    300
```

```
cagtctcctt agagtgccca ccataacgtg ctggtaacta aggacaaggg ttgcgctcgt    360

tacgggactt aacccaacat ctcacgacac gagctgacga cagccatgca gcacctgtgt    420

cagagttccc taaggcacca atccatctct ggaaagttct ctgcatgtca aggcctggta    480

aggttcttcg cgttgcttcg aattaaacca catgctccac cgcttgtgcg ggcccccgtc    540

aattcatttg agttttaacc ttgcggccgt actccccagg cggtcaactt aatgcgttag    600

ctgcgccact aaaatctcaa ggattccaac ggctagttga catcgtttac ggcgtggact    660

accagggtat ctaatcctgt ttgctcccca cgctttcgca cctcagtgtc agtatcagtc    720

caggtggtcg ccttcgccac tggtgttcct tcctatatct acgcatttca ccgctacaca    780

ggaaattcca ccaccctcta ccgtactcta gctcgccagt tttggatgca gttcccaggt    840

tgagcccggg gctttcacat ccaacttaac gaaccaccta cgcgcgcttt acgcccagta    900

attccgatta acgcttgcac cctctgtatt accgcggctg ctggcacaga gttagccggt    960

gcttattctg tcggtaacgt caaaacagca aggtattagc ttactgccct tcctcccaac   1020

ttaaagtgct ttacaatccg aagaccttct tcacacacgc ggcatggctg gatcaggctt   1080

tcgcccattg tccaatattc cccactgctg cctcccgtag gagtctggac cgtgtctcag   1140

ttccagtgtg actgatcatc ctctcagacc agttacggat cgtcgccttg gtgagccatt   1200

acctcaccaa ctagctaatc cgacctaggc tcatctgata gcgcaaggcc cgaaggcccc   1260

ctgctttctc ccgtaggacg tatgcggtat tagcgttcct ttcgaaacgt tgtcccccac   1320

taccaggcag attcctaggc attactcacc cgtccgccgc tgaatcaagg agcaagctcc   1380

cgtcatccgc tcgacttgca                                               1400
```

```
<210> SEQ ID NO 102
<211> LENGTH: 1401
<212> TYPE: DNA
<213> ORGANISM: Unknown
<220> FEATURE:
<223> OTHER INFORMATION: Kingdom: Bacteria, Phylum: Proteobacteria,
      Class: Gammaproteobacteria, Order: Pseudomonadales, Family:
      Pseudomonadaceae, Genus: Pseudomonas

<400> SEQUENCE: 102

cgtcctcccg aaggttagac tagctacttc tggtgcaacc cactcccatg gtgtgacggg     60

cggtgtgtac aaggcccggg aacgtattca ccgcgacatt ctgattcgcg attactagcg    120

attccgactt cacgcagtcg agttgcagac tgcgatccgg actacgatcg gttttgtgag    180

attagctcca cctcgcggct tggcaaccct ctgtaccgac cattgtagca cgtgtgtagc    240

ccaggccgta agggccatga tgacttgacg tcatccccac cttcctccgg tttgtcaccg    300

gcagtctcct tagagtgccc accataacgt gctggtaact aaggacaagg gttgcgctcg    360

ttacgggact taacccaaca tctcacgaca cgagctgacg acagccatgc agcacctgtg    420

tcagagttcc ctaaggcacc aatccatctc tggaaagttc tctgcatgtc aaggcctggt    480

aaggttcttc gcgttgcttc gaattaaacc acatgctcca ccgcttgtgc gggcccccgt    540

caattcattt gagttttaac cttgcggccg tactccccag gcggtcaact taatgcgtta    600

gctgcgccac taaaatctca aggattccaa cggctagttg acatcgttta cggcgtggac    660

taccagggta tctaatcctg tttgctcccc acgctttcgc acctcagtgt cagtatcagt    720

ccaggtggtc gccttcgcca ctggtgttcc ttcctatatc tacgcatttc accgctacac    780

aggaaattcc accaccctct accgtactct agctcgccag ttttggatgc agttcccagg    840
```

-continued

```
ttgagcccgg ggctttcgca tccaacttaa cgaaccacct acgcgcgctt tacgcccagt     900

aattccgatt aacgcttgca ccctctgtat taccgcggct gctggcacag agttagccgg     960

tgcttattct gtcagtagcg tcaaaacagc aaggtattag cttactgccc ttcctcccaa    1020

cttaaagtgc tttacaatcc gaagaccttc ttcacacacg cggcatggct ggatcaggtt    1080

ttcgcccatt gtccaatatt ccccactgct gcctcccgta ggagtctgga ccgtgtctca    1140

gttccagtgt gactgatcat cctctcagac cagttacgga tcgtcgcctt ggtgagccat    1200

taccccacca actagctaat ccgacctagg ctcatctgat agcgcaaggc ccgaaggtcc    1260

cctgctttct cccgtaggac gtatgcggta ttagcgttcc tttcgaaacg ttgtccccca    1320

ctaccaggca gattcctagg cattactcac ccgtccgccg ctgaatcaag gagcaagctc    1380

ccgtcatccg ctcgacttgc a                                              1401


<210> SEQ ID NO 103
<211> LENGTH: 1396
<212> TYPE: DNA
<213> ORGANISM: Unknown
<220> FEATURE:
<223> OTHER INFORMATION: Kingdom: Bacteria, Phylum: Proteobacteria,
      Class: Gammaproteobacteria, Order: Pseudomonadales, Family:
      Pseudomonadaceae, Genus: Pseudomonas

<400> SEQUENCE: 103

ctcccgaagg ttagactagc tacttctggt gcaacccact cccatggtgt gacgggcggt      60

gtgtacaagg cccgggaacg tattcaccgc gacattctga ttcgcgatta ctagcgattc     120

cgacttcacg cagtcgagtt gcagactgcg atccggacta cgatcggttt tgtgagatta     180

gctccacctc gcggcttggc aaccctctgt accgaccatt gtagcacgtg tgtagcccag     240

gccgtaaggg ccatgatgac ttgacgtcat ccccaccttc ctccggtttg tcaccggcag     300

tctccttaga gtgcccacca taacgtgctg gtaactaagg acaagggttg cgctcgttac     360

gggacttaac ccaacatctc acgacacgag ctgacgacag ccatgcagca cctgtgtcag     420

agttccctaa ggcaccaatc catctctgga aagttctctg catgtcaagg cctggtaagg     480

ttcttcgcgt tgcttcgaat taaaccacat gctccaccgc ttgtgcgggc ccccgtcaat     540

tcatttgagt tttaaccttg cggccgtact ccccaggcgg tcaacttaat gcgttagctg     600

cgccactaaa atctcaagga ttccaacggc tagttgacat cgtttacggc gtggactacc     660

agggtatcta atcctgtttg ctccccacgc tttcgcacct cagtgtcagt atcagtccag     720

gtggtcgcgt tcgccactgg tgttccttcc tatatctacg catttcaccg ctacacagga     780

aattccacca ccctctaccg tactctagct cgccagtttt ggatgcagtt cccaggttga     840

gcccggggct ttcacatcca acttaacgaa ccacctacgc gcgctttacg cccagtaatt     900

ccgattaacg cttgcaccct ctgtattacc gcggctgctg gcacagagtt agccggtgct     960

tattctgtca gtaacgtcaa aacagcaagg tattagctta ctgcccttcc tcccaactta    1020

aagtgcttta caatccgaag accttcttca cacacgcggt atggctggat caggctttcg    1080

cccattgtcc aatattcccc actgctgcct cccgtaggag tctggaccgt gtctcagttc    1140

cagtgtgact gatcatcctc tcagaccagt tacggatcgt cgccttggtg agccattacc    1200

ccaccaacta gctaatccga cctaggctca tctgatagcg caaggcccga aggtcccctg    1260

ctttctcccg taggacgtat gcggtattag cgttcctttc gaaacgttgt cccccactac    1320

caggcagatt cctaggcatt actcacccgt ccgccgctga atcaaggagc aagctcccgt    1380

catccgctcg acttgc                                                    1396
```

<210> SEQ ID NO 104
<211> LENGTH: 1400
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 104
gtcctcccga aggttagact agctacttct ggtgcaaccc actcccatgg tgtgacgggc 60
ggtgtgtaca aggcccggga acgtactcac cgcgacattc tgattcgcga ttactagcga 120
ttccgacttc acgcagtcga gttgcagact gcgatccgga ctacgatcgg ttttgtgaga 180
ttagctccac ctcgcggctt ggcaaccctc tgtaccgacc attgtagcac gtgtgtagcc 240
caggccgtaa gggccatgat gacttgacgt catccccacc ttcctccggt ttgtcaccgg 300
cagtctcctt agagtgccca ccataacgtg ctggtaacta aggacaaggg ttgcgctcgt 360
tacgggactt aacccaacat ctcacgacac gagctgacga cagccatgca gcacctgtgt 420
cagagttccc gaaggcacca atccatctct ggaaagttct ctgcatgtca aggcctggta 480
aggttcttcg cgttgcttcg aattaaacca catgctccac cgcttgtgcg ggcccccgtc 540
aattcatttg agttttaacc ttgcggccgt actccccagg cggtcaactt aatgcgttag 600
ctgcgccact aaaatctcaa ggattccaac ggctagttga catcgtttac ggcgtggact 660
accagggtat ctaatcctgt ttgctcccca cgctttcgca cctcagtgtc agtatcagtc 720
caggtggtcg ctttcgccac tggtgttcct tcctatatct acgcatttca ccgctacaca 780
ggaaattcca ccaccctcta ccgtactcta gctcgccagt tttggatgca gttcccaggt 840
tgagcccggg gctttcacat ccaacttaac gaaccaccta cgcgcgcttt acgcccagta 900
attccgatta acgcttgcac cctctgtatt accgcggctg ctggcacaga gttagccggt 960
gcttattctg tcggtaacgt caaaacagta aggtattagc ttactgccct tcctcccaac 1020
ttaaagtgct ttacaatccg aagaccttct tcacacacgc ggcatggctg gatcaggctt 1080
tcgcccattg tccaatattc cccactgctg cctcccgtag gagtctggac cgtgtctcag 1140
ttccagtgtg actgatcatc ctctcagacc agttacggat cgtcgccttg gtgagccatt 1200
accccaccaa ctagctaatc cgacctaggc tcatctgata gcgcaaggcc cgaaggtccc 1260
ctgctttctc ccgtaggacg tatgcggtat tagcgttcct ttcgaaacgt tgtcccccac 1320
taccaggcag attcctaggc attactcacc cgtccgccgc tgaatcaagg agcaagctcc 1380
cgtcatccgc tcgacttgca 1400

<210> SEQ ID NO 105
<211> LENGTH: 1548
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Actinomycetales, Family: Nocardiaceae, Genus: Rhodococcus

<400> SEQUENCE: 105
gggtaccggg cccccctcg aggtcgacgg tatcgataag cttgatatcc actgtggaat 60
tcgcccttag agtttgatcc tggctcagga cgaacgctgg cggcgtgctt aacacatgca 120
agtcgagcgg taaggccttt cggggtacac gagcggcgaa cgggtgagta acacgtgggt 180

```
gatctgccct gcacttcggg ataagcctgg gaaactgggt ctaataccgg atatgacctc    240

ctatcgcatg gtgggtggtg gaaagattta tcggtgcagg atgggcccgc ggcctatcag    300

cttgttggtg ggtaatggc ctaccaaggc gacgacgggt agccgacctg agagggtgac    360

cggccacact gggactgaga cacggcccag actcctacgg gaggcagcag tggggaatat    420

tgcacaatgg gcgaaagcct gatgcagcga cgccgcgtga gggatgacgg ccttcgggtt    480

gtaaacctct ttcagcaggg acgaagcgca agtgacggta cctgcagaag aagcaccggc    540

tagctacgtg ccagcagccg cggtaatacg tagggtgcaa gcgttgtccg gaattactgg    600

gcgtaaagag ttcgtaggcg gtttgtcgcg tcgtttgtga aaaccagcag ctcaactgct    660

ggcttgcagg cgatacgggc agacttgagt actgcagggg agactggaat tcctgggtgt    720

agcggtgaaa tgcgcagata tcaggaggaa caccggtggc gaaggcgggt ctctgggcag    780

taactgacgc tgaggaacga aagcgtgggt agcgaacagg attagatacc ctggtagtcc    840

acgccgtaaa cggtgggcgc taggtgtggg ttccttccac ggaatccgtg ccgtagctaa    900

cgcattaagc gccccgcctg gggagtacgg ccgcaaggct aaaactcaaa ggaattgacg    960

ggggcccgca caagcggcgg agcatgtgga ttaattcgat gcaacgcgaa gaaccttacc   1020

tgggtttgac atataccgga aagctgcaga gatgtggccc cccttgtggt cggtatacag   1080

gtggtgcatg gctgtcgtca gctcgtgtcg tgagatgttg ggttaagtcc cgcaacgagc   1140

gcaaccccta tcttatgttg ccagcacgtt atggtgggga ctcgtaagag actgccgggg   1200

tcaactcgga ggaaggtggg gacgacgtca agtcatcatg ccccttatgt ccagggcttc   1260

acacatgcta caatggccag tacagagggc tgcgagaccg tgaggtggag cgaatccctt   1320

aaagctggtc tcagttcgga tcggggtctg caactcgacc ccgtgaagtc ggagtcgcta   1380

gtaatcgcag atcagcaacg ctgcggtgaa tacgttcccg ggccttgtac acaccgcccg   1440

tcacgccatg aaagtcggta acacccgaag ccggtggctt aacccccttgt gggagggagc   1500

cgtcgaaggt gggatcggcg attgggacga agtcgtaaca aggtaacc                1548
```

<210> SEQ ID NO 106
<211> LENGTH: 1452
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Moraxellaceae, Genus: Enhydrobacter

<400> SEQUENCE: 106

```
agagtttgat cctggctcag attgaacgct ggcggcaggc ttaacacatg caagtcgaac     60

gatgaaactc tagcttgcta gagatgatta gtggcggacg ggtgagtaac atttaggaat    120

ctacctagta gtgggggata gctcggggaa actcgaatta ataccgcata cgacctacgg    180

gtgaaagggg gcgcaagctc ttgctattag atgagcctaa atcagattag ctagttggtg    240

gggtaaaggc ccaccaaggc gacgatctgt aactggtctg agaggatgat cagtcacacc    300

ggaactgaga cacggtccgg actcctacgg gaggcagcag tggggaatat tggacaatgg    360

gggcaaccct gatccagcca tgccgcgtgt gtgaagaagg ccttttggtt gtaaagcact    420

ttaagcaggg aggagaggct aatggttaat acccattaga ttagacgtta cctgcagaat    480

aagcgccggc taactctgtg ccagcagccg cggtaataca gagggtgcga gcgttaatcg    540

gaattactgg gcgtaaagcg agtgtaggtg gctcattaag tcacatgtga aatccccggg    600

cttaacctgg gaactgcatg tgatactggt ggtgctagaa tatgtgagag ggaagtagaa    660
```

ttccaggtgt agcggtgaaa tgcgtagaga tctggaggaa taccgatggc gaaggcagct 720
tcctggcata atattgacac tgtagtccac gccgtaaacg atgtctacta gccgttgggg 780
tccttgagac tttagtggcg cagttaacgc gataagtaga ccgcctgggg agtacggccg 840
caaggttaaa actcaaatga attgacgggg gcccgcacaa gcggtggagc atgtggttta 900
attcgatgca acgcgaagaa ccttacctgg tcttgacata gtgagaatct ttcagagatg 960
agagagtgcc tttgggaact cacatacagg tgctgcatgg ctgtcgtcag ctcgtgtcgt 1020
gagatgttgg gttaagtccc gcaacgagcg caaccctttt ccttatttgc cagcgggtta 1080
agccgggaac tttaaggata ctgccagtga caaactggag gaaggcgggg acgacgtcaa 1140
gtcatcatgg cccttacgac cagggctaca cacgtgctac aatggtaggt acagagggtt 1200
gctacacagc gatgtgatgc taatctcaaa aagcctatcg tagtccggat tggagtctgc 1260
aactcgactc catgaagtcg gaatcgctag taatcgcgga tcagaatgcc gcggtgaata 1320
cgttcccggg ccttgtacac accgcccgtc acaccatggg agtctattgc accagaagta 1380
ggtagcctaa tgcaagaggg cgcttaccac ggtgtggtcg atgactgggg tgaagtcgta 1440
acaaggtaac ca 1452

<210> SEQ ID NO 107
<211> LENGTH: 1623
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Moraxellaceae, Genus: Enhydrobacter

<400> SEQUENCE: 107
cggccgctct agaactagtg gatcccccgg gctgcagccc aatgtggaat tcgcccttag 60
agtttgatcc tggctcagat tgaacgctgg cggcaggctt aacacatgca agtcgaacga 120
tgaaactcta gcttgctaga gatgattagt ggcggacggg tgagtaacat ttaggaatct 180
acctagtagt gggggatagc tcggggaaac tcgaattaat accgcatacg acctacgggt 240
gaaagggggc gcaagctctt gctattagat gagcctaaat cagattagct agttggtggg 300
gtaaaggccc accaaggcga cgatctgtaa ctggtctgag aggatgatca gtcacaccgg 360
aactgagaca cggtccggac tcctacggga ggcagcagtg gggaatattg gacaatgggg 420
gcaaccctga tccagccatg ccgcgtgtgt gaagaaggcc ttttggttgt aaagcacttt 480
aagcagggag gagaggctaa tggttaatac ccattagatt agacgttacc tgcagaataa 540
gcaccggcta actctgtgcc agcagccgcg gtaatacaga gggtgcgagc gttaatcgga 600
attactgggc gtaaagcgag tgtaggtggc tcattaagtc acatgtgaaa tccccgggct 660
taacctggga actgcatgtg atactggtgg tgctagaata tgtgagaggg aagtagaatt 720
ccaggtgtag cggtgaaatg cgtagagatc tggaggaata ccgatggcga aggcagcttc 780
ctggcataat atcgacactg agattcgaaa gcgtgggtag caaacaggat tagataccct 840
ggtagtccac gccgtaaacg atgtctacta gccgttgggg tccttgagac tttagtggcg 900
cagttaacgc gataagtaga ccgcctgggg agtacggccg caaggttaaa actcaaatga 960
attgacgggg gcccgcacaa gcggtggagc atgtggttta attcgatgca acgcgaagaa 1020
ccttacctgg tcttgacata gtgagaatct ttcagagatg agagagtgcc tttgggaact 1080
cacatacagg tgctgcatgg ctgtcgtcag ctcgtgtcgt gagatgttgg gttaagtccc 1140

-continued

```
gcaacgagcg caacccttttt ccttatttgc cagcgggtta agccgggaac tttaaggata   1200

ctgccagtga caaactggag gaaggcgggg acgacgtcaa gtcatcatgg cccttacgac   1260

cagggctaca cacgtgctac aatggtaggt acagagggtt gctacacagc gatgtgatgc   1320

taatctcaaa aagcctatcg tagtccggat tggagtctgc aactcgactc catgaagtcg   1380

gaatcgctag taatcgcgga tcagaatgcc gcggtgaata cgttcccggg ccttgtacac   1440

accgcccgtc acaccatggg agtctattgc accagaagta ggtagcctaa cgcaagaggg   1500

cgcttaccac ggtgtggtcg atgactgggg tgaagtcgta acaaggtaac caagggcgaa   1560

ttccacagtg gatatcaagc ttatcgatac cgtcgacctc gagggggggc ccggtaccca   1620

gct                                                                 1623
```

<210> SEQ ID NO 108
<211> LENGTH: 1405
<212> TYPE: DNA
<213> ORGANISM: Unknown
<220> FEATURE:
<223> OTHER INFORMATION: Kingdom: Bacteria, Phylum: Proteobacteria,
      Class: Gammaproteobacteria, Order: Pseudomonadales, Family:
      Moraxellaceae, Genus: Perlucidibaca

<400> SEQUENCE: 108

```
agagtttgat cctggctcag attgaacgct ggcggcaggc ctaacacatg caagtcgagc     60

gggggtagca ataccctagc ggcgaacggg tgaggaatgc ttgggaatct gcctggtagt    120

gggggataac gttccgaaag gaacgctaat accgcatacg tcctacggga gaaagggggg    180

gatcttcgga cctctcgcta tcagatgagc ccaagcggga ttagctagtt ggtgaggtaa    240

aggctcacca aggcgacgat ccctagctgg tctgagagga tgatcagcca cactggaact    300

gagacacggt ccagactcct acgggaggca gcagtgggga atattggaca atgggcgaaa    360

gcctgatcca gccatgccgc gtgtgtgaag aaggccttcg ggttgtaaag cactttaagc    420

ggggaggaag gttcgttact taatacgtaa cggaattgac gttacccgca gaataagcac    480

cggctaactc tgtgccagca gccgcggtaa tacagagggt gcaagcgtta atcggaatta    540

ctgggcgtaa agcgcgcgta ggcggttgtg taagttggat gtgaaatccc cgggcttaac    600

ctgggcactg cattcaaaac tgcacggcta gagtatgggc tgacgctgag gtgcgaaagc    660

atggggagca aacaggatta gataccctgg tagtccatgc cgtaaacgat gtcgactagg    720

tgttggggaa cttgattcct tagtgccgca gctaacgcat taagtcgacc gcctggggag    780

tacgaccgca aggttaaaac tcaaatgaat tggcgggggc ccgcacaagc ggtggagcat    840

gtggtttaat tcgatgcaac gcgaagaacc ttacctactc ttgacatcca gagaatcctg    900

cagagatgcg ggagtgcctt cgggaattct gagacaggtg ctacatggct gtcgtcagct    960

cgtgtcgtga gatgttgggt taagtcccgc aacgagcgca acccttatcc ttagttgcca   1020

gcacgtaatg gtgggaactc tagggagact gccggtgaca aaccggagga aggcggggac   1080

gacgtcaagt catcatggcc cttacgagta gggctacaca cgtgctacaa tggtcggtac   1140

agagggtcgc aagcctgcga gggtgagcca atctcaaaaa gccgatcgta gtccggattg   1200

gagtctgcaa ctcgactcca tgaagtcgga atcgctagta atcgcggatc agaatgccgc   1260

ggtgaatacg ttcccgggcc ttgtacacac cgcccgtcac accatgggag tctgttgcac   1320

cagaagtagg tagcttaacc gcaaggaggg cgcttaccac ggtgtggccg atgactgggg   1380

tgaagtcgta acaaggtaac caagg                                         1405
```

<210> SEQ ID NO 109
<211> LENGTH: 1469
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Dyella

<400> SEQUENCE: 109

```
ccttagagtt tgatcctggc tcagattgaa cgctggcggc atgcctaaca catgcaagtc     60
gaacggcagc acagcagtag caatactgtg ggtggcgagt ggcggacggg tgagtaatgc    120
atcgggatct acccaaacgt gggggataac gtagggaaac ttacgctaat accgcatacg    180
tcctatggga gaaagcgggg gatcgcaaga cctcgcgcgg ttggacgaac cgatgtgcga    240
ttagctagtt ggtagggtaa tggcctacca aggcgacgat cgctagctgg tctgagagga    300
tgatcagcca cactggaact gagacacggt ccagactcct acgggaggca gcagtgggga    360
atattggaca atgggcgcaa gcctgatcca gcaatgccgc gtgtgtgaag aaggccttcg    420
ggttgtaaag cacttttatc aggagcgaaa tgccattggt taatacccgg tggagctgac    480
ggtacctgag gaataagcac cggctaactt cgtgccagca gccgcggtaa tacgaagggt    540
gcaagcgtta atcggaatta ctgggcgtaa agcgtgcgta ggcggtgatt taagtctgct    600
gtgaaatccc cgggctcaac ctgggaatgg cagtggatac tggatcgcta gagtgtgata    660
gaggatggtg gaattcccgg tgtagcggtg aaatgcgtat caacactgac gctgaggcac    720
gaaagcgtgg ggagcaaaca ggattagata ccctggtagt ccacgcccta aacgatgcga    780
actggatgtt ggtctcaact cggagatcag tgtcgaagct aacgcgttaa gttcgccgcc    840
tggggagtac ggtcgcaaga ctgaaactca aaggaattga cgggggcccg cacaagcggt    900
ggagtatgtg gtttaattcg atgcaacgcg aagaacctta cctggccttg acatgtctgg    960
aatcctgcag agatgcggga gtgccttcgg gaatcagaac acaggtgctg catggctgtc   1020
gtcagctcgt gtcgtgagat gttgggttaa gtcccgcaac gagcgcaacc cttgtcctta   1080
gttgccagca cgtaatggtg ggaactctaa ggagactgcc ggtgacaaac cggaggaagg   1140
tggggatgac gtcaagtcat catggccctt acggccaggg ctacacacgt actacaatgg   1200
tcggtacaga gggttgcaat accgcgaggt ggagccaatc ccagaaagcc gatcccagtc   1260
cggatcgaag tctgcaactc gacttcgtga agtcggaatc gctagtaatc gcagatcagc   1320
tatgctgcgg tgaatacgtt cccgggcctt gtacacaccg cccgtcacac catgggagtg   1380
agttgctcca gaagccgtta gtctaaccgc aagggggacg acgaccacgg agtggttcat   1440
gactggggtg aagtcgtaac aaggtaacc                                     1469
```

<210> SEQ ID NO 110
<211> LENGTH: 1448
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family: Enterobacteriaceae, Genus: Escherichia/Shigella

<400> SEQUENCE: 110

```
agagtttgat cctggctcag attgaacgct ggcggcaggc ctaacacatg caagtcgaat     60
ggtaacagga aacagcttgc tgtttcgctg acgagtggcg gacgggtgag taatgtctgg    120
gaaactgcct gatggagggg gataactact ggaaacggta gctaataccg cataacgtcg    180
```

-continued

```
caagaccaaa gacggggacc ttcgggcctc ttgccatcag atgtgcccag atgggattag    240

ctagtaggtg gggtaacggc tcacctaggc gacgatccct agctggtctg agaggatgac    300

cagccacact ggaactgaga cacggtccag actcctacgg gaggcagcag tggggaatat    360

tgcacaatgg gcgcaagccc gatgcagcca tgccgcgtgt atgaagaagg ccttcgggtt    420

gtaaagtact ttcagcgggg aggaagggag taaagttaat acctttgctc attgacgtta    480

cccgcagaag aagcaccggc taactccgtg ccagcagccg cggtaatacg gagggtgcaa    540

gcgttaatcg gaattactgg gcgtaaagcg cacgcaggcg gtttgttaag tcagatgtga    600

aatccccggg ctcaacctgg gaactgcatc tgatactggc aagcttgagt ctcgtagagg    660

ggggtagaat tccaggtgta gcggtgaaat gcgtagagat ctggaggaat accggtggcg    720

aaagcggccc cctggatagt ccacgccgta aacgatgtcg acttggaggt tgtgcccttg    780

aggcgtggct tccggagcta acgcgttaag tcgaccgcct ggggagtacg gccgcaaggt    840

taaaactcaa atgaattgac gggggcccgc acaagcggtg gagcatgtgg tttaattcga    900

tgcaacgcga agaaccttac ctggtcttga catccacgga agttttcaga gatgagaatg    960

tgccttcggg aaccgtgaga caggtgctgc atggctgtcg tcagctcgtg ttgtgaaatg   1020

ctgggttaag tcccgcaacg agcgcaaccc ttatcctttg ttgccagcgg tccggccggg   1080

aactcaaagg agactgccag tgataaactg gaggaaggtg gggatgacgt caagtcatca   1140

tggcccttac gaccagggct acacacgtgc tacaatggcg catacaaaga gaagcgacct   1200

cgcgagagca agcggacctc ataaagtgcg tcgtagtccg gattggagtc tgcaactcga   1260

ctccatgaag tcggaatcgc tagtaatcgt ggatcagaat gccacggtga atacgttccc   1320

gggccttgta cacaccgccc gtcacaccat gggagtgggt tgcaaaagaa gtaggtagct   1380

taatcttcgg gagggcgctt accactttgt gattcatgac tggggtgaag tcgtaacaag   1440

gtaaccaa                                                            1448
```

<210> SEQ ID NO 111
<211> LENGTH: 1495
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Comamonadaceae, Genus: Delftia

<400> SEQUENCE: 111

```
agagtttgat cctggctcag attgaacgct ggcggcatgc cttacacatg caagtcgaac     60

ggtaacaggt cttcggacgc tgacgagtgg cgaacgggtg agtaatacat cggaacgtgc    120

ccagtcgtgg gggataacta ctcgaaagag tagctaatac cgcatacgat ctgaggatga    180

aagcggggga ccttcgggcc tcgcgcgatt ggagcggccg atggcagatt aggtagttgg    240

tgggataaaa gcttaccaag ccgacgatct gtagctggtc tgagaggacg accagccaca    300

ctgggactga gacacggccc agactcctac gggaggcagc agtggggaat tttggacaat    360

gggcgaaagc ctgatccagc aatgccgcgt gcaggatgaa ggccttcggg ttgtaaactg    420

cttttgtacg gaacgaaaaa gcttctccta atacgagagg cccatgacgg taccgtaaga    480

ataagcaccg gctaactacg tgccagcagc cgcggtaata cgtagggtgc aagcgttaat    540

cggaattact gggcgtaaag cgtgcgcagg cggttatgta agacagatgt gaaatccccg    600

ggctcaacct gggaactgca tttgtgactg catggctaga gtacggtaga gggggatgga    660

attccgcgtg tagcagtgaa atgcgtagat atgcggagga acaccgatgg cgaaggcaat    720
```

```
cccctggacc tgtactgacg ctcatgcacg aaagcgtggg gagcaaacag gattagatac    780

cctggtagtc cacgccctaa acgatgtcaa ctggttgttg ggaattagtt ttctcagtaa    840

cgaagctaac gcgtgaagtt gaccgcctgg ggagtacggc cgcaaggttg aaactcaaag    900

gaattgacgg ggacccgcac aagcggtgga tgatgtggtt taattcgatg caacgcgaaa    960

aaccttaccc acctttgaca tggcaggaag tttccagaga tggattcgtg ctcgaaagag   1020

aacctgcaca caggtgctgc atggctgtcg tcagctcgtg tcgtgagatg ttgggttaag   1080

tcccgcaacg agcgcaaccc ttgtcattag ttgctacatt cagttgggca ctctaatgag   1140

actgccggtg acaaaccgga ggaaggtggg gatgacgtca agtcctcatg gcccttatag   1200

gtggggctac acacgtcata caatggctgg tacagagggt tgccaacccg cgagggggag   1260

ctaatcccat aaaaccagtc gtagtccgga tcgcagtctg caactcgact gcgtgaagtc   1320

ggaatcgcta gtaatcgcgg atcagcatgc cgcggtgaat acgttcccgg gtcttgtaca   1380

caccgcccgt cacaccatgg gagcgggtct cgccagaagt aggtagccta accgcaagga   1440

gggcgcttac cacggcgggg ttcgtgactg gggtgaagtc gtaacaaggt aacca        1495
```

<210> SEQ ID NO 112
<211> LENGTH: 464
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Bradyrhizobiaceae, Genus: Oligotropha

<400> SEQUENCE: 112

```
tccatccatg ccgcgtgatt gatgaccgcc ctatggttgt atctctcttt tgagacgcga     60

cgttctcttc ggagcccgga acacaggtgc tgcatggctg tcgtcagctc gtgtcgtgag    120

atgttgggtt aagtcccgca acgagcgcaa cccccgtcct tagttgctac cattcagttg    180

agcactctaa ggagactgcc ggtgataagc cgcgaggaag gtggggatga cgtcaagtcc    240

tcatggccct tacgggctgg gctacacacg tgctacaatg gcggtgacaa tgggctgcga    300

ggacgcgagt cctagcaaat ctccaaaagc cgtctcagtt cggattgcgc tctgcaactc    360

gagcccatga agttggaatc gctagtaatc gtggatcagc acgccacggt gaatacgttc    420

ccgggccttg tacacaccgc ccgtcacacc atgggagttg gttt                     464
```

<210> SEQ ID NO 113
<211> LENGTH: 1414
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Actinomycetales, Family: Microbacteriaceae, Genus: Microbacterium

<400> SEQUENCE: 113

```
agagtttgat cctggctcag gatgaacgct ggcggcgtgc ttaacacatg caagtcgaac     60

ggtgaacacg gagcttgctc tgtgggatca gtggcgaacg ggtgagtaac acgtgagcaa    120

cctgcccctg actctgggat aagcgctgga aacggcgtct aatactggat atgtgacgtg    180

accgcatggt ctgcgtctgg aaagaatttc ggttggggat gggctcgcgg cctatcagct    240

tgttggtgag gtaatggctc accaaggcgt cgacgggtag ccggcctgag agggtgaccg    300

gccacactgg gactgagaca cggcccagac tcctacggga ggcagcagtg gggaatattg    360
```

-continued

```
cacaatgggc gcaagcctga tgcagcaacg ccgcgtgagg gacgacggcc ttcgggttgt    420

aaacctcttt tagcagggaa gaagcgaaag tgacggtacc tgcagaaaaa gcgccggcta    480

actacgtgcc agcagccgcg gtaatacgta gggcgcaagc gttatccgga attattgggc    540

gtaaagagct cgtaggcggt ttgtcgcgtc tgctgtgaaa tccggaggct caacctccgg    600

cctgcagtgg gtacgggcag actagagtgc ggtaggggag attggaattc ctggtgtagc    660

ggtggaatgc gcagatatca ggaggaacac cgatggcgaa ggcagatctc tgggccgtaa    720

ctgacgcttt gtggggtcca ttccacggat tccgtgacgc agctaacgca ttaagttccc    780

cgcctgggga gtacggccgc aaggctaaaa ctcaaaggaa ttgacgggga cccgcacaag    840

cggcggagca tgcggattaa ttcgatgcaa cgcgaagaac cttaccaagg cttgacatat    900

acgagaacgg gccagaaatg gtcaactctt tggacactcg taaacaggtg gtgcatggtt    960

gtcgtcagct cgtgtcgtga gatgttgggt taagtcccgc aacgagcgca accctcgttc   1020

tatgttgcca gcacgtaatg gtgggaactc atgggatact gccggggtca actcggagga   1080

aggtggggat gacgtcaaat catcatgccc cttatgtctt gggcttcacg catgctacaa   1140

tggccggtac aaagggctgc aataccgcga ggtggagcga atcccaaaaa gccggtccca   1200

gttcggattg aggtctgcaa ctcgacctca tgaagtcgga gtcgctagta atcgcagatc   1260

agcaacgctg cggtgaatac gttcccgggt cttgtacaca ccgcccgtca agtcatgaaa   1320

gtcggtaaca cctgaagccg gtggcctaac ccttgtggag ggagccgtcg aaggtgggat   1380

cggtaattag gactaagtcg taacaaggta acca                               1414
```

<210> SEQ ID NO 114
<211> LENGTH: 1535
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Oxalobacteraceae, Genus: Massilia

<400> SEQUENCE: 114

```
agagtttgat cctggctcag attgaacgct ggcggcatgc tttacacatg caagtcgaac     60

ggcagcgcgg ggtaacctgg cggcgagtgg cgaacgggtg agtaatatat cggaacgtac    120

ccaagagtgg gggataacgt agcgaaagtt acgctaatac cgcatacgat ccaaggatga    180

aagcggggga tcgcaagacc tcgtgctcct ggagcggccg atatctgatt agctagttgg    240

tgaggtaaag gctcaccaag gcgacgatca gtagctggtc tgagaggacg accagccaca    300

ctggaactga gacacggtcc agactcctac gggaggcagc agtggggaat tttggacaat    360

gggcgcaagc ctgatccagc aatgccgcgt gagtgaagaa ggccttcggg ttgtaaagct    420

cttttgtcag ggaagaaacg gtagaggcta atatcctttg ctaatgacgg tacctgaaga    480

ataagcaccg gctaactacg tgccagcagc cgcggtaata cgtagggtgc aagcgttaat    540

cggaattact gggcgtaaag cgtgcgcagg cggttttgta agtctgtcgt gaaagccccg    600

ggctcaacct gggaattgcg atggagactg caatgcttga atctggcaga ggggggtaga    660

attccacgtg tagcagtgaa atgcgtagag atgtggagga acaccgatgg cgaaggcagc    720

cccctgggtc aagattgacg ctcatgcacg aaagcgtggg gagcaaacag gattagatac    780

cctggtagtc cacgccctaa acgatgtcta ctagttgtcg ggttttaatt aacttggtaa    840

cgcagctaac gcgtgaagta gaccgcctgg ggagtacggt cgcaagatta aaactcaaag    900

gaattgacgg ggacccgcac aagcggtgga tgatgtggat taattcgatg caacgcgaaa    960
```

aaccttacct acccttgaca tgtcaggaag tctggagaga tctggatgtg cccgaaaggg 1020
agcctgaaca caggtgctgc atggctgtcg tcagctcgtg tcgtgagatg ttgggttaag 1080
tcccgcaacg agcgcaaccc ttgtcattag ttgctacgca agagcactct aatgagactg 1140
ccggtgacaa accggaggaa ggtggggatg acgtcaagtc ctcatggccc ttatgggtag 1200
ggcttcacac gtcatacaat ggtacataca gagggccgcc aacccgcgag gggggagctaa 1260 tcccagaaag tgtatcgtag tccggatcgc agtctgcaac tcgactgcgt gaagttggaa 1320
tcgctagtaa tcgcggatca gcatgccgcg gtgaatacgt tcccgggtct tgtacacacc 1380
gcccgtcaca ccatgggagc gggttttacc agaagtaggt agcttaaccg taaggagggc 1440
gcttaccacg gtaggattcg tgactggggt gaagtcgtaa caaggtaacc aagggcgaat 1500
tccacagtgg atatcaagct tatcgatacc gtcga 1535

<210> SEQ ID NO 115
<211> LENGTH: 1435
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Actinomycetales, Family: Propionibacteriaceae, Genus: Propionibacterium

<400> SEQUENCE: 115
agagtttgat cctggctcag gacgaacgct ggcggcgtgc ttaacacatg caagtcgaac 60
ggaaaggccc tgcttttgtg gggtgctcga gtggcgaacg ggtgagtaac acgtgagtaa 120
cctgcccttg actttgggat aacttcagga aactggggct aataccggat aggagctcct 180
gctgcatggt gggggttgga aagtttcggc ggttggggat ggactcgcgg cttatcagct 240
tgttggtggg gtagtggctt accaaggctt tgacgggtag ccggcctgag agggtgaccg 300
gccacattgg gactgagata cggcccagac tcctacggga ggcagcagtg gggaatattg 360
cacaatgggc ggaagcctga tgcagcaacg ccgcgtgcgg gatgacggcc ttcgggttgt 420
aaaccgcttt cgcctgtgac gaagcgtgag tgacggtaat gggtaaagaa gcaccggcta 480
actacgtgcc agcagccgcg gtgatacgta gggtgcgagc gttgtccgga tttattgggc 540
gtaaagggct cgtaggtggt tgatcgcgtc ggaagtgtaa tcttggggct taaccctgag 600
cgtgctttcg atacgggttg acttgaggaa ggtaggggag aatggaattc ctggtggagc 660
ggtggaatgc gccgaaagcg tggggagcga acaggcttag ataccctggt agtccacgct 720
gtaaacggtg ggtactaggt gtggggtcca ttccacgggt tccgcgccgt agctaacgct 780
ttaagtaccc cgcctgggga gtacggccgc aaggctaaaa ctcaaaggaa ttgacggggc 840
cccgcacaag cggcggagca tgcggattaa ttcgatgcaa cgcgtagaac cttacctggg 900
tttgacatgg atcgggagtg ctcagagatg ggtgtgcctc ttttggggtc ggttcacagg 960
tggtgcatgg ctgtcgtcag ctcgtgtcgt gagatgttgg gttaagtccc gcaacgagcg 1020
caacccttgt tcactgttgc cagcacgtta tggtggggac tcagtggaga ccgccggggt 1080
caactcggag gaaggtgggg atgacgtcaa gtcatcatgc cccttatgtc cagggcttca 1140
cgcatgctac aatggctggt acagagagtg gcgagcctgt gagggtgagc gaatctcgga 1200
aagccggtct cagttcggat tggggtctgc aactcgacct catgaagtcg gagtcgctag 1260
taatcgcaga tcagcaacgc tgcggtgaat acgttcccgg ggcttgtaca caccgcccgt 1320
caagtcatga aagttggtaa cacccgaagc cggtggccta accgttgtgg gggagccgtc 1380
gaaggtggga ctggtgatta ggactaagtc gtaacaaggt aaccaagggc gaatt 1435

<210> SEQ ID NO 116
<211> LENGTH: 1332
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Actinomycetales, Family: Microbacteriaceae, Genus: Okibacterium
<220> FEATURE:
<221> NAME/KEY: misc_feature
<222> LOCATION: (1302)..(1303)
<223> OTHER INFORMATION: n is a, c, g, or t
<220> FEATURE:
<221> NAME/KEY: misc_feature
<222> LOCATION: (1332)..(1332)
<223> OTHER INFORMATION: n is a, c, g, or t

<400> SEQUENCE: 116
ttcaccaggg ttttagcgtg taaccgctct tgagggggga ccgccccca tgggattgaa 60 aacgggccct aattttttag gggggacaca agggggggatt ttttcccaat gggggaaagc 120
cttaatgaaa aaacccgggg gagggaaagg ccctttgggt ttaaaccttt tttccacgga 180
agaaaggaaa aggggcgtcc ctcagaaaaa ggcccgggta attagtggcc agcagccgcg 240
gtaataagtg ggggccaaga gttttccgaa attattgggg gaaagaagct tgtagggggt 300
ttgttcgctt ttggctggaa atccgggagg ttcaacctcc gggcctgcag tgggtacggg 360
cagattagag tgcggtaggg gagatttgaa atccctggtg tagcggtgga atgcgcagat 420
tcaggaggaa caccgatggc gaaggcagtt ctctgggccg taactgacgc tgaggagcga 480
aaggggcggg gagcaaacag ggttagatac cctggtagtc caccccgtaa acgttgggaa 540
ctagttgtgg ggtccattcc acggattccg tgacgcagct aacgcattaa gttccccgcc 600
tggggagtac ggccgcaagg ctaaaactca aaggaattga cggggacccg cacaagcggc 660
ggagcatgcg gattaattcg atgcaacgcg aagaacctta ccaaggcttg acatatacga 720
gaacgggcca gaaatggcca actctttgga cactcgtaaa caggtggtgc atggttgtcg 780
tcagctcgtg tcgtgagatg ttgggttaag tcccgcaacg agcgcaaccc tcgttctatg 840
ttgccagcac gtaatggtgg gaactcatgg gatactgccg gggtcaactc ggaggaaggt 900
ggggatgacg tcaaatcatc atgcccctta tgtcttgggc ttcacgcatg ctacaatggc 960
cggtacaaag ggctgcaata ccgcgaggtg gagcgaatcc caaaaagccg gtcccagttc 1020
ggattgaggt ctgcaactcg acctcatgaa gtcggagtcg ctagtaatcg cagatcagca 1080
acgctgcggt gaatacgttc ccgggtcttg tacacaccgc ccgtcaagtc atgaaagtcg 1140
gtaacacctg aagccggtgg cctaaccctt gtggagggag ccgtcgaagg tgggatcggt 1200
aattaggact aagtcgtaac aaggtaacca agggcgaatt ccacagtgga tatcaagctt 1260
atcgataccg tcgacctcga ggggggcccc ggtacccagc tnngtccctt tgtaaagacg 1320
ctagtggcac cn 1332

<210> SEQ ID NO 117
<211> LENGTH: 1431
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Actinomycetales, Family: Microbacteriaceae, Genus: Microbacterium

<400> SEQUENCE: 117
ccttagagtt tgatcctggc tcaggatgaa cgctggcggc gtgcttaaca catgcaagtc 60
gaacggtgaa cacggagctt gctctgtggg atcagtggcg aacgggtgag taacacgtga 120
gcaacctacc cctgactctg ggataagcgc tggaaacggc gtctaatact ggatacgagt 180
ggcgaccgca tggtcagcta ctggaaagat ttattggttg ggatgggct cgcggcctat 240 cagcttgttg gtgaggtaat ggctcaccaa ggcgtcgacg ggtagccggc ctgagagggt 300
gaccggccac actgggactg agacacggcc cagactccta cgggaggcag cagtggggaa 360
tattgcacaa tgggcgcaag cctgatgcag caacgccgcg tgagggatga cggccttcgg 420
gttgtaaacc tcttttagca gggaagaagc gaaagtgacg gtacctgcag aaaaagcgcc 480
ggctaactac gtgccagcag ccgcggtaat acgtagggcg caagcgttat ccggaattat 540
tgggcgtaaa gagctcgtag gcggtttgtc gcgtctgctg tgaaatccgg aggctcaacc 600
tccggcctgc agtgggtacg ggcagactag agtgcggtag gggagattgg aattcctggt 660
gtagcggtgg aatgcgcgcg aaagggtggg gagcaaacag gcttagatac cctggtagtc 720
caccccgtaa acgttgggaa ctagttgtgg ggtccattcc acggattccg tgacgcagct 780
aacgcattaa gttccccgcc tggggagtac ggccgcaagg ctaaaactca aaggaattga 840
cggggacccg cacaagcggc ggagcatgcg gattaattcg atgcaacgcg aagaacctta 900
ccaaggcttg acatatacga gaacgggcca gaaatggtca actctttgga cactcgtaaa 960
caggtggtgc atggttgtcg tcagctcgtg tcgtgagatg ttgggttaag tcccgcaacg 1020
agcgcaaccc tcgttctatg ttgccagcac gtaatggtgg gaactcatgg gatactgccg 1080
gggtcaactc ggaggaaggt ggggatgacg tcaaatcatc atgcccctta tgtcttgggc 1140
ttcacgcacg ctacaatggc cggtacaaag ggctgcaata ccgcgaggtg gagcgaatcc 1200
caaaaagccg gtcccagttc ggattgaggt ctgcaactcg acctcatgaa gtcggagtcg 1260
ctagtaatcg cagatcagca acgctgcggt gaatacgttc ccgggtcttg tacacaccgc 1320
ccgtcaagtc atgaaagtcg gtaacacctg aagccggtgg cctaaccctt gtggagggag 1380
ccgtcgaagg tgggatcggt aattaggact aagtcgtaac aaggtaacca a 1431

<210> SEQ ID NO 118
<211> LENGTH: 1530
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Actinomycetales, Family: Microbacteriaceae, Genus: Microbacterium

<400> SEQUENCE: 118
agagtttgat cctggctcag gatgaacgct ggcggcgtgc ttaacacatg caagtcgaac 60
ggtgaacacg gagcttgctc tgtgggatca gtggcgaacg ggtgagtaac acgtgagcaa 120
cctacccctg actctgggat aagcgctgga aacggcgtct aatactggat acgagtggcg 180
accgcatggt cagctactgg aaagatttat tggttgggga tgggctcgcg gcctatcagc 240
ttgttggtga ggtaatggct caccaaggcg tcgacgggta gccggcctga gagggtgacc 300
ggccacactg ggactgagac acggcccaga ctcctacggg aggcagcagt ggggaatatt 360
gcacaatggg cgcaagcctg atgcagcaac gccgcgtgag ggatgacggc cttcgggttg 420
taaacctctt ttagcaggga agaagcgaaa gtgacggtac ctgcagaaaa agcgccggct 480
aactacgtgc cagcagccgc ggtaatacgt agggcgcaag cgttatccgg aattattggg 540

```
cgtaaagagc tcgtaggcgg tttgtcgcgt ctgctgtgaa atccggaggc tcaacctccg    600

gcctgcagtg ggtacgggca gactagagtg cggtagggga gattggaatt cctggtgtag    660

cggtggaatg cgcagatatc aggaggaaca ccgatggcga aagcagatct ctgggccgta    720

actgacgctg aggagcgaaa gggtggggag caaacaggct tagataccct ggtagtccac    780

cccgtaaacg ttgggaacta gttgtggggt ccattccacg gattccgtga cgcagctaac    840

gcattaagtt ccccgcctgg ggagtacggc cgcaaggcta aaactcaaag gaattgacgg    900

ggacccgcac aagcggcgga gcatgcggat taattcgatg caacgcgaag aaccttacca    960

aggcttgaca tatacgagaa cgggccagaa atggtcgact ctttggacac tcgtaaacag   1020

gtggtgcatg gttgtcgtca gctcgtgtcg tgagatgttg ggttaagtcc cgcaacgagc   1080

gcaaccctcg ttctatgttg ccagcacgta atggtgggaa ctcatgggat actgccgggg   1140

tcaactcgga ggaaggtggg gatgacgtca aatcatcatg ccccttatgt cttgggcttc   1200

acgcatgcta caatggccgg tacaaagggc tgcaataccg cgaggtggag cgaatcccaa   1260

aaagccggtc ccagttcgga ttgaggtctg caactcgacc tcatgaagtc ggagtcgcta   1320

gtaatcgcag atcagcaacg ctgcggtgaa tacgttcccg ggtcttgtac acaccgcccg   1380

tcaagtcatg aaagtcggta acacctgaag ccggtggcct aacccttgtg gagggagccg   1440

tcgaaggtgg gatcggtaat taggactaag tcgtaacaag gtaaccaagg gcgaattcca   1500

cagtggatat caagcttatc gataccgtcg                                    1530
```

<210> SEQ ID NO 119
<211> LENGTH: 1451
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Actinomycetales, Family: Microbacteriaceae, Genus: Microbacterium

<400> SEQUENCE: 119

```
agagtttgat cctggctcag gatgaacgct ggcggcgtgc ttaacacatg caagtcgaac     60

ggtgaacacg gagcttgctc tgtgggatca gtggcgaacg ggtgagtaac acgtgagcaa    120

cctacccctg actctgggat aagcgctgga aacggcgtct aatactggat acgagtggcg    180

accgcatggt cagctactgg aaagatttat tggttgggga tgggctcgcg gcctatcagc    240

ttgttggtga ggtaatggct caccaaggcg tcgacgggta gccggcctga gagggtgacc    300

ggccacactg ggactgagac acggcccaga ctcctacggg aggcagcagc ggggaatatt    360

gcacaatggg cgcaagcctg atgcagcaac gccgcgtgag ggatgacggc cttcgggttg    420

taaacctctt ttagcaggga agaagcgaaa gtgacggtac ctgcagaaaa agcgccggct    480

aactacgtgc cagcagccgc ggtaatacgt agggcgcaag cgttatccgg aattattggg    540

cgtaaagagc tcgtaggcgg tttgtcgcgt ctgctgtgaa atccggaggc tcaacctccg    600

gcctgcagtg ggtacgggca gactagagtg cggtagggga gattggaatt cctggtgtag    660

cggtggaatg cgcagatatc tagataccct ggtagtccac cccgtaaacg ttgggaacta    720

gttgtggggt ccattccacg gattccgtga cgcagctaac gcattaagtt ccccgcctgg    780

ggagtacggc cgcaaggcta aaactcaaag gaattgacgg ggacccgcac aagcggcgga    840

gcatgcggat taattcgatg caacgcgaag aaccttacca aggcttgaca tatacgagaa    900

cgggccagaa atggtcaact ctttggacac tcgtaaacag gtggtgcatg gttgtcgtca    960

gctcgtgtcg tgagatgttg ggttaagtcc cgcaacgagc gcaaccctcg ttctatgttg   1020
```

-continued

```
ccagcacgta atggtgggaa ctcatgggat actgccgggg tcaactcgga ggaaggtggg   1080

gatgacgtca aatcatcatg ccccttatgt cttgggcttc acgcatgcta caatggccgg   1140

tacaaagggc tgcaataccg cgaggtggag cgaatcccaa aaagccggtc ccagttcgga   1200

ttgaggtctg caactcgacc tcatgaagtc ggagtcgcta gtaatcgcag atcagcaacg   1260

ctgcggtgaa tacgttcccg ggtcttgtac acaccgcccg tcaagtcatg aaagtcggta   1320

acacctgaag ccggtggcct aacccttgtg gagggagccg tcgaaggtgg gatcggtaat   1380

taggactaag tcgtaacaag gtaaccaagg gcgaattcca cagtggatat caagcttatc   1440

gataccgtcg a                                                        1451
```

```
<210> SEQ ID NO 120
<211> LENGTH: 1365
<212> TYPE: DNA
<213> ORGANISM: Unknown
<220> FEATURE:
<223> OTHER INFORMATION: Kingdom: Bacteria, Phylum: Bacteroidetes,
      Class: Flavobacteriia, Order: Flavobacteriales, Family:
      Flavobacteriaceae, Genus: Chryseobacterium

<400> SEQUENCE: 120

agagtttgat cctggctcag gatgaacgct agcgggaggc ctaacacatg caagccgagc     60

ggtatttatt cttcggaata gagagagcgg cgtacgggtg cggaacacgt gtgcaacctg    120

cctttatcag gggatagcc tttcgaaagg aagattaata ccccataata tattgaatgg    180

catcatttga tattgaaaac tccggtggat agagatgggc acgcgcaaga ttagatagtt    240

ggtagggtaa cggcctacca agtcagtgat ctttaggggg cctgagaggg tgatccccca    300

cactggtact gagacacgga ccagactcct acgggaggca gcagtgagga atattggaca    360

atgggtgaga gcctgatcca gccatcccgc gtgaaggacg acggccctat gggttgtaaa    420

cttcttttgt atagggataa acctttccac gtgtggaaag ctgaaggtac tatacgaata    480

agcaccggct aactccgtgc cagcagccgc ggtaatacgg agggtgcaag cgttatccgg    540

atttattggg tttaaagggt ccgtaggcgg atctgtaagt cagtggtgaa atctcatagc    600

ttaactatga aactgccatc gatactgcag gtcttgagta aagtagaagt ggctggaata    660

agtagtgtag cggtgaaatg catagatatt actttttttg ggtcttcgga ttcagagact    720

aagcgaaagt gataagttag ccacctgggg agtacgttcg caagaatgaa actcaaagga    780

attgacgggg gcccgcacaa gcggtggatt atgtggttta attcgatgat acgcgaggaa    840

ccttaccaag gcttaaatgg gaattgacag gtttagaaat agacttttct tcggacaatt    900

ttcaaggtgc tgcatggttg tcgtcagctc gtgccgtgag gtgttaggtt aagtcctgca    960

acgagcgcaa cccctgtcac tagttgccat cattcagttg ggactctag tgagactgcc   1020

tacgcaagta gagaggaagg tggggatgac gtcaaatcat cacggccctt acgccttggg   1080

ccacacacgt aatacaatgg ccggtacaga gggcagctac ctagcgatag gatgcgaatc   1140

tcgaaagccg gtctcagttc ggattggagt ctgcaactcg actctatgaa gctggaatcg   1200

ctagtaatcg catatcagcc atgatgcggt gaatacgttc ccgggccttg tacacaccgc   1260

ccgtcaagcc atggaagttt ggggtacctg aagtcggtga ccgtaacagg agctgcctag   1320

ggtaaaacaa gtaactaggg ctaagtcgta acaaggtaac caagg                   1365
```

```
<210> SEQ ID NO 121
<211> LENGTH: 1505
<212> TYPE: DNA
```

<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Oxalobacteraceae, Genus: Herbaspirillum

<400> SEQUENCE: 121
agagtttgat cctggctcag attgaacgct ggcggcatgc cttacacatg caagtcgaac 60
ggcagcatag gagcttgctc ctgatggcga gtggcgaacg ggtgagtaat atatcggaac 120
gtgccctaga gtgggggata actagtcgaa agactagcta ataccgcata cgatctacgg 180
atgaaagtgg gggatcgcaa gacctcatgc tcctggagcg gccgatatct gattagctag 240
ttggtggggt aaaagcctac caaggcaacg atcagtagct ggtctgagag gacgaccagc 300
cacactggga ctgagacacg gcccagactc ctacgggagg cagcagtggg gaattttgga 360
caatgggggc aaccctgatc cagcaatgcc gcgtgagtga agaaggcctt cgggttgtaa 420
agctcttttg tcagggaaga aacggtagta gcgaataact attactaatg acggtacctg 480
aagaataagc accggctaac tacgtgccag cagccgcggt aatacgtagg gtgcaagcgt 540
taatcggaat tactgggcgt aaagcgtgcg caggcggttg tgtaagtcag atgtgaaatc 600
cccgggctca acctgggaat tgcatttgag actgcacggc tagagtgtgt cagagggggg 660
tagaattcca cgtgtagcag tgaaatgcgt agatatgtgg aggaataccg atggcgaagg 720
cagccccctg ggataacact gacgctcatg cacgaaagcg tggggagcaa acaggattag 780
ataccctggt agtccacgcc ctaaacgatg tctactagtt gtcgggtctt aattgacttg 840
gtaacgcagc taacgcgtga agtagaccgc ctggggagta cggtcgcaag attaaaactc 900
aaaggaattg acggggaccc gcacaagcgg tggatgatgt ggattaattc gatgcaacgc 960
gaaaaacctt acctaccctt gacatggatg gaatcccgaa gagatttggg agtgctcgaa 1020
agagaaccat cacacaggtg ctgcatggct gtcgtcagct cgtgtcgtga gatgttgggt 1080
taagtcccgc aacgagcgca acccttgtca ttagttgcta cgaaagggca ctctaatgag 1140
actgccggtg acaaaccgga ggaaggtggg gatgacgtca agtcctcatg gcccttatgg 1200
gtagggcttc acacgtcata caatggtaca tacagagggc cgccaacccg cgagggggag 1260
ctaatcccag aaagtgtatc gtagtccgga ttggagtctg caactcgact ccatgaagtt 1320
ggaatcgcta gtaatcgcgg atcagcatgt cgcggtgaat acgttcccgg gtcttgtaca 1380
caccgcccgt cacaccatgg gagcgggttg taccagaagt gggtagccta accgcaagga 1440
gggcgctcac cacggtagga ttcgtgactg gggtgaagtc gtaacaaggt aaccaagggc 1500
gaatt 1505

<210> SEQ ID NO 122
<211> LENGTH: 1331
<212> TYPE: DNA
<213> ORGANISM: Unknown
<220> FEATURE:
<223> OTHER INFORMATION: Kingdom: Bacteria, Phylum: Bacteroidetes, Class: Flavobacteriia, Order: Flavobacteriales, Family: Flavobacteriaceae, Genus: Chryseobacterium

<400> SEQUENCE: 122
gtttgatcct ggctcaggat gaacgctagc gggaggccta acacatgcaa gccgagcggt 60
aggtttcctt cgggagactg agagcggcgc acgggtgcgg aacacgtgtg caacctgcct 120
ttatcagggg gatagccttt cgaaaggaag attaataccc cataatattt tgagtggcat 180
cacttaaaat tgaaaactcc ggtggataaa gatgggcacg cgcaagatta gatagttggt 240

```
gaggtaacgg ctcaccaagt ctacgatctt taggggggcct gagagggtga tcccccacac    300

tggtactgag acacggacca gactcctacg ggaggcagca gtgaggaata ttggacaatg    360

ggtgagagcc tgatccagcc atcccgcgtg aaggacgacg gccctatggg ttgtaaactt    420

cttttgtata gggataaacc tttccacgtg tggaaagctg aaggtactat acgaataagc    480

accggctaac tccgtgccag cagccgcggt aatacggagg gtgcaagcgt tatccggatt    540

tattgggttt aaagggtccg taggcggatc tgtaagtcag tggtgaaatc tcacaactta    600

actgtgaaac tgccattgat actgcaggtc ttgagtgttg ttgaagtagc tggaataagt    660

agtgtagcgg tgaaatgcat agatattact tcgtttttttg ggttttcgga ttcagagact    720

aagcgaaagt gataagttag ccacctgggg agtacggacg caagtctgaa actcaaagga    780

attgacgggg gcccgcacaa gcggtggatt atgtggttta attcgatgat acgcgaggaa    840

ccttaccaag gcttaaatgg gaaatgacag gtttagaaat agacttttct tcggacattt    900

ttcaaggtgc tgcatggttg tcgtcagctc gtgccgtgag gtgttaggtt aagtcctaca    960

acgagcgcaa cccctgtcac tagttgccat cattcagttg ggactctag tgagactgcc   1020

tacgcaagta gagaggaagg tggggatgac gtcaaatcat cacggccctt acgccttggg   1080

ccacacacgt aatacaatgg ccagtacaga gggcagctac caggcgactg gatgcgaatc   1140

tcgaaagctg gtctcagttc ggattggagt ctgcaactcg actctatgaa gctggaatcg   1200

ctagtaatcg cgcatcagcc atggcgcggt gaatacgttc ccgggccttg tacacaccgc   1260

ccgtcaagcc atggaagtct ggggtacctg aagtcggtga ccgtaacagg agctgcctag   1320

ggtaaaacag g                                                         1331
```

```
<210> SEQ ID NO 123
<211> LENGTH: 1308
<212> TYPE: DNA
<213> ORGANISM: Unknown
<220> FEATURE:
<223> OTHER INFORMATION: Kingdom: Bacteria, Phylum: Proteobacteria,
      Class: Alphaproteobacteria, Order: Rhizobiales, Family:
      Rhizobiaceae, Genus: Rhizobium

<400> SEQUENCE: 123

gccccgcagg ggagcggcag acgggtgagt aacgcgtggg aacgtaccct ttactacgga     60

ataacgcagg gaaacttgtg ctaataccgt atgtgccctt cgggggaaag atttatcggt    120

aagggatcgg cccgcgttgg attagctagt tggtggggta aaggcctacc aaggcgacga    180

tccatagctg gtctgagagg atgatcagcc acattgggac tgagacacgg cccaaactcc    240

tacgggaggc agcagtgggg aatattggac aatgggcgca agcctgatcc agccatgccg    300

cgtgagtgat gaaggcccta gggttgtaaa gctctttcac cggagaagat aatgacggta    360

tccggagaag aagccccggc taacttcgtg ccagcagccg cggtaatacg aaggggggcta    420

gcgttgttcg gaattactgg gcgtaaagcg cacgtaggcg gacatttaag tcaggggtga    480

aatcccagag ctcaactctg gaactgcctt tgatactggg tgtcttgagt atggaagagg    540

tgagtggaat tccgagtgta gaggtgaaat tcgtagatat tcggaggaac accagtggcg    600

aaggcggctc actggtccat tactgacgct gaggtgcgaa agcgtgggga gcaaacagga    660

ttagataccc tggtagtcca cgccgtaaac gatgaatgtt agccgtcggg cagtatactg    720

ttcggtggcg cagctaacgc attaaacatt ccgcctgggg agtacggtcg caagattaaa    780

actcaaagga attgacgggg gcccgcacaa gcggtggagc atgtggttta attcgaagca    840
```

-continued

```
acgcgcagaa ccttaccagc ccttgacatg cccggctacc tgcagagatg cagggttccc    900

ttcggggacc gggacacagg tgctgcatgg ctgtcgtcag ctcgtgtcgt gagatgttgg    960

gttaagtccc gcaacgagcg caaccctcgc ccttagttgc cagcatttag ttgggcactc   1020

taaggggact gccggtgata agccgagagg aaggtgggga tgacgtcaag tcctcatggc   1080

ccttacgggc tgggctacac acgtgctaca atggtggtga cagtgggcag cgagacagcg   1140

atgtcgagct aatctccaaa agccatctca gttcggattg cactctgcaa ctcgagtgca   1200

tgaagttgga atcgctagta atcgcggatc agcatgccgc ggtgaatacg ttcccgggcg   1260

ttgtacacac cgcccgtcac accatgggag ttggttttac ccgaaggt                1308
```

<210> SEQ ID NO 124
<211> LENGTH: 1455
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Phyllobacteriaceae, Genus: Mesorhizobium

<400> SEQUENCE: 124

```
ttcgccctta gagtttgatc ctggctcaga acgaacgctg gcggcaggct taacacatgc     60

aagtcgagcg ccccgcaagg ggagcggcag acgggtgagt aacgcgtggg aatctaccca    120

tcactacgga acaactccgg gaaactggag ctaataccgt atacgtcctt cgggagaaag    180

atttatcggt gatggatgag cccgcgttgg attagctagt tggtggggta atggcctacc    240

aaggcgacga tccatagctg gtctgagagg atgatcagcc acactgggac tgaggcacgg    300

cccagactcc tacgggaggc agcagtgggg aatattggac aatgggcgca agcctgatcc    360

agccatgccg cgtgagtgat gaaggcccta gggttgtaaa gctctttcaa cggtgaagat    420

aatgacggta accgtagaag aagccccggc taacttcgtg ccagcagccg cggtaatacg    480

aagggggcta gcgttgttcg gatttactgg gcgtaaagcg cacgtaggcg gattgttaag    540

ttaggggtga aatcccaggg ctcaaccctg gaactgcctt taatactggc aatctcgagt    600

ccggaagagg tgagtggaat tccgagtgta gaggtgaaat tcgtagatat tcggaggaac    660

accagtggcg aaggcggctc actggtccgg tactgacgct gaggtgcgaa agcgtgggga    720

gcaaacagga ttagataccc tggtagtcca cgctgtaaac gatggaagct agccgtcggc    780

aagtttactt gtcggtggcg cagctaacgc attaagcttc ccgcctgggg agtacagtcg    840

caagattaaa actcaaagga attgacgggg gcccgcacaa gcggtggagc atgtggttta    900

attcgaagca acgcgcagaa ccttaccagc ccttgacatc ccggtcgcgg cctagagaga    960

tttaggcctt cagttcggct ggaccggtga caggtgctgc atggctgtcg tcagctcgtg   1020

tcgtgagatg ttgggttaag tcccgcaacg agcgcaaccc tcgcccttag ttgccatcat   1080

tcagttgggc actctaaggg gactgccggt gataagccga gaggaaggtg gggatgacgt   1140

caagtcctca tggcccttac gggctgggct acacacgtgc tacaatggtg gtgacagtgg   1200

gcagcgagac cgcgaggtcg agctaatctc caaaagccat ctcagttcgg attgcactct   1260

gcaactcgag tgcatgaagt tggaatcgct agtaatcgcg gatcagcatg ccgcggtgaa   1320

tacgtccccg ggccttgtac acaccgcccg ccacaccatg ggagttggtt ttacccgaag   1380

gcgctgtgct aaccgcaagg aggcaggcga ccacggtagg gtcagcgact ggggtgaagt   1440

cgtaacaagg taacc                                                    1455
```

<210> SEQ ID NO 125
<211> LENGTH: 1523
<212> TYPE: DNA
<213> ORGANISM: Unknown
<220> FEATURE:
<223> OTHER INFORMATION: Kingdom: Bacteria, Phylum: Proteobacteria,
Class: Alphaproteobacteria, Order: Rhizobiales, Family:
Bradyrhizobiaceae, Genus: Rhodopseudomonas

<400> SEQUENCE: 125

```
agagtttgat cctggctcag agcgaacgct ggcggcaggc ttaacacatg caagtcgaac      60

gggcgtagca atacgtcagt ggcagacggg tgagtaacac gtgggaacgt accttttggt     120

tcggaacaac tgagggaaac ttcagctaat accggataag cccttacggg gaaagattta     180

tcgccgaaag atcggcccac gtctgattag ctagttggtg aggtaatggc tcaccaaggc     240

gacgatcagt agctggtctg agaggatgat cagccacatt gggactgaga cacggcccaa     300

actcctacgg gaggcagcag tggggaatat tggacaatgg gggaaaccct gatccagcca     360

tgccgcgtga gtgatgaagg ccctagggtt gtaaagctct tttgtgcggg aagataatga     420

cggtaccgca agaataagcc ccggctaact tcgtgccagc agccgcggta atacgaaggg     480

ggctagcgtt gctcggaatc actgggcgta aagggtgcgt aggcgggtct ttaagtcaga     540

ggtgaaagcc tggagctcaa ctccagaact gcctttgata ctgaggatct tgagtatggg     600

agaggtgagt ggaactgcga gtgtagaggt gaaattcgta gatattcgca agaacaccag     660

tggcgaaggc ggctcactgg cccataactg acgctgaggc acgaaagcgt ggggagcaaa     720

caggattaga taccctggta gtccacgccg taaacgatga atgccagccg ttagtgggtt     780

tactcactag tggcgcagct aacgctttaa gcattccgcc tggggagtac ggtcgcaaga     840

ttaaaactca aaggaattga cgggggcccg cacaagcggt ggagcatgtg gtttaattcg     900

acgcaacgcg cagaacctta ccagcccttg acatgtccag gaccggtcgc agagatgtga     960

ccttctcttc ggagcctgga gcacaggtgc tgcatggctg tcgtcagctc gtgtcgtgag    1020

atgttgggtt aagtcccgca acgagcgcaa cccccgtcct tagttgctac catttagttg    1080

agcactctaa ggagactgcc ggtgataagc cgcgaggaag gtggggatga cgtcaagtcc    1140

tcatggccct tacgggctgg gctacacacg tgctacaatg gcggtgacaa tgggatgcta    1200

aggggcgacc cctcgcaaat ctcaaaaagc cgtctcagtt cggattgggc tctgcaactc    1260

gagcccatga agttggaatc gctagtaatc gtggatcagc atgccacggt gaatacgttc    1320

ccgggccttg tacacaccgc ccgtcacacc atgggagttg gctttacctg aagacggtgc    1380

gctaaccagc aatggaggca gccggccacg gtagggtcag cgactggggt gaagtcgtaa    1440

caaggtaacc aagggcgaat tccacagtgg atatcaagct tatcgatacc gtcgacctcg    1500

aggggggggcc cggtacccag ctt                                          1523
```

<210> SEQ ID NO 126
<211> LENGTH: 1565
<212> TYPE: DNA
<213> ORGANISM: Unknown
<220> FEATURE:
<223> OTHER INFORMATION: Kingdom: Bacteria, Phylum: Proteobacteria,
Class: Betaproteobacteria, Order: Burkholderiales, Family:
Burkholderiaceae, Genus: Burkholderia

<400> SEQUENCE: 126

```
aagctgggta ccgggccccc cctcgaggtc gacggtatcg ataagcttga tatccactgt      60

ggaattcgcc cttagagttt gatcctggct cagattgaac gctggcggca tgccttacac     120
```

```
atgcaagtcg gacggcagcg cgggggcaac cctggcggcg agtggcgaac gggtgagtaa    180
tacatcggaa cgtgtcctgg agtgggggat agcccggcga aagccggatt aataccgcat    240
acgctctgtg gaggaaagcg ggggatcttc ggacctcgcg ctcaaggggc ggccgatggc    300
agattagcta gttggtgggg taaaggccta ccaaggcgac gatctgtagc tggtctgaga    360
ggacgaccag ccacactggg actgagacac ggcccagact cctacgggag gcagcagtgg    420
ggaattttgg acaatggggg caaccctgat ccagcaatgc cgcgtgtgtg aagaaggcct    480
tcgggttgta aagcactttt gtccggaaag aaaacgtctt ggctaatatc tggggcggat    540
gacggtaccg gaagaataag caccggctaa ctacgtgcca gcagccgcgg taatacgtag    600
ggtgcgagcg ttaatcggaa ttactgggcg taaagcgtgc gcaggcggtt cgctaagacc    660
gatgtgaaat ccccgggctt aacctgggaa ctgcattggc gactggcggg ctagagtatg    720
gcagaggggg gtagaattcc acgtgtagca gtgaaatgcg tagagatgtg gaggaatacc    780
gatggcgaag gcagccccct gggccaatac tgacgctcat gcacgaaagc gtggggagca    840
aacaggatta gataccctgg tagtccacgc cctaaacgat gtcaactagt tgtcgggtct    900
tcattgactt ggtaacgtag ctaacgcgtg aagttgaccg cctggggagt acggtcgcaa    960
gattaaaact caaaggaatt gacggggacc cgcacaagcg gtggatgatg tggattaatt   1020
cgatgcaacg cgaaaaacct tacctaccct tgacatgtac ggaatcctgc tgagaggtgg   1080
gagtgcccga aagggagctg taacacaggt gctgcatggc tgtcgtcagc tcgtgtcgtg   1140
agatgttggg ttaagtcccg caacgagcgc aacccttgtc cctagttgct acgcaagagc   1200
actctaggga gactgccggt gacaaaccgg aggaaggtgg ggatgacgtc aagtcctcat   1260
ggcccttatg ggtagggctt cacacgtcat acaatggtcg gaacagaggg ttgccaagcc   1320
gcgaggtgga gccaatccca gaaaaccgat cgtagtccgg atcgcagtct gcaactcgac   1380
tgcgtgaagc tggaatcgct agtaatcgcg gatcagcatg ccgcggtgaa tacgttcccg   1440
ggtcttgtac acaccgcccg tcacaccatg ggagtgggtt ttaccagaag tggctagtct   1500
aaccgcaagg aggacggtca ccacggtagg attcataact ggggtgaagt cgtaacaagg   1560
taacc                                                                1565
```

<210> SEQ ID NO 127
<211> LENGTH: 1506
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Oxalobacteraceae, Genus: Herbaspirillum

<400> SEQUENCE: 127

```
agagtttgat cctggctcag attgaacgct ggcggcatgc cttacacatg caagtcgaac     60
ggcagcatag gagcttgctc ctgatggcga gcggcgaacg ggtgagtaat atatcggaac    120
gtgccctaga gtgggggata actagtcgaa agactagcta ataccgcata cgatctacgg    180
atgaaagtgg gggatcgcaa gacctcatgc tcctggagcg gccgatatct gattagctag    240
ttggtggggt aaaagcctac caaggcaacg atcagtagct ggtctgagag gacgaccagc    300
cacactggga ctgagacacg gcccagactc ctacgggagg cagcagtggg gaattttgga    360
caatgggggc aaccctgatc cagcaatgcc gcgtgagtga agaaggcctt cgggttgtaa    420
agctcttttg tcagggaaga aacggtagta gcgaataact attactaatg acggtacctg    480
aagaataagc accggctaac tacgtgccag cagccgcggt aatacgtagg gtgcaagcgt    540
```

taatcggaat tactgggcgt aaagcgtgcg caggcggttg tgtaagtcag atgtgaaatc 600
cccgggctca acctgggaat tgcatttgag actgcacggc tagagtgtgt cagagggggg 660
tagaattcca cgtgtagcag tgaaatgcgt agatatgtgg aggaataccg atggcgaaag 720 cagcccccctg ggataacact gacgctcatg cacgaaagcg tggggagcaa acaggattag 780
ataccctggt agtccacgcc ctaaacgatg tctactagtt gtcgggtctt aattgacttg 840
gtaacgcagc taacgcgtga agtagaccgc ctggggagta cggtcgcaag attaaaactc 900
aaaggaattg acggggaccc gcacaagcgg tggatgatgt ggattaattc gatgcaacgc 960
gaaaaacctt acctaccctt gacatggatg gaatcccgaa gagatttggg agtgctcgaa 1020
agagaaccat cacacaggtg ctgcatggct gtcgtcagct cgtgtcgtga gatgttgggt 1080
taagtcccgc aacgagcgca acccttgtca ttagttgcta cgaaagggca ctctaatgag 1140
actgccggtg acaaaccgga ggaaggtggg gatgacgtca agtcctcatg gcccttatgg 1200
gtagggcttc acacgtcata caatggtaca tacagagggc cgccaacccg cgagggggag 1260
ctaatcccag aaagtgtatc gtagtccgga ttggagtctg caactcgact ccatgaagtt 1320
ggaatcgcta gtaatcgcgg atcagcatgt cgcggtgaat acgttcccgg gtcttgtaca 1380
caccgcccgt cacaccatgg gagcgggttt taccagaagt gggtagccta accgcaagga 1440
gggcgctcac cacggtagga ttcgtgactg gggtgaagtc gtaacaaggt aaccaagggc 1500
gaattc 1506

<210> SEQ ID NO 128
<211> LENGTH: 1483
<212> TYPE: DNA
<213> ORGANISM: Unknown
<220> FEATURE:
<223> OTHER INFORMATION: Kingdom: Archaea, Phylum: Crenarchaeota, Class: Thermoprotei, Order: Sulfolobales, Family: Sulfolobaceae, Genus: Sulfurisphaera
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (1463)..(1463)
<223> OTHER INFORMATION: n is a, c, g, or t
<220> FEATURE:
<221> NAME/KEY: misc_feature
<222> LOCATION: (1482)..(1483)
<223> OTHER INFORMATION: n is a, c, g, or t

<400> SEQUENCE: 128
gcgaactata tgtaccnctt attttttatt tacaaccttt taaatgtttg tggccagaga 60
aaataagcag atattatcaa aaatattttt tataaataaa gtgtggggcg atgaaattct 120
tcttggagaa ctccctgggg tgacctccct gtatgagata tatatagtaa ggggttattc 180
aaatataagg gatctttgct ggcgcttata gaaaattccc cgcataataa aatttgggga 240
taagcatttc ccgggggagg ctcaacactc ctaaagggat acccccccaa ggggaaaaca 300
ccacctcgga tttttttggg ggcccaattc gaataattcc cagggagaaa atttaacatt 360
aaccaaacct ggagaaaaaa agcccttggt aaaaaagcct ttttggggga aagaacttag 420
caatttagta aacttgtttg atgggaagtg caaaaaaaaa aacccccatt aatttcagcc 480
agcagcggga taaaaaggga gggaccaaat ctataagtaa ttatgtgaaa gaactcgaag 540
gggggatttt ggttaagtaa gataaataaa aggcgcggga tccactgcgg gggtctcctt 600

```
taaaggcggc ctgccgggag tttcgggggg aaaggggtta attgccggag cggggggatg    660

aagcgattag cattaggaac gacacccggg ggggaaggtt gtctcggcgt ttcaagacgc    720

tcaggaaggt aaagaaaggc gggcggaaaa gaccatagat aacatccctt gttcatcgca    780

ctcccacaaa aggaatctag gtagggggtg cattcccacg ggttcttggc ctgtagaata    840

aagactataa taagtccacc cccggggagg aatggcccgc gacaggtcta aaaacaaaag    900

aataatggag ggggggcgca aaacacggcg gaggcatggt gggtttttta ttatgacaac    960

aacggagaaa catcatcccg ggtttcatca tctatcagga aagcttctga ggaagggagt   1020

gcctcccttc ggggaacgat acaacacaag gtgacacggc ggtgctgcag ctcctgtggt   1080

gggaaaatgt gggatatact cccagaaacg agcaaccccc gttcactttt gtcaccacgg   1140

tatggtgggg cactcgaagg agactgccgg tgataaaccg gaggaaggtg gggaggacgt   1200

caattcttca tgccccttac gcccagggct acacacggct tccaatggtg gtaacaaggg   1260

ggagcaacct cgcgaggtca agcaaactcc ataaacccgt tcctagtccg gatgggagtc   1320

tgcaactggc ctccgagaag tggattcgt tggtattgct gaatcacaat gccgcggtga    1380

atacttctcc ggggcttgta cacaccgccc gtcacctcat gagagttggt agcaccagag   1440

cagtgggcct aaccttcggg gantctatat atacgcgtaa ann                     1483
```

<210> SEQ ID NO 129
<211> LENGTH: 1220
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family: Enterobacteriaceae, Genus: Kosakonia

<400> SEQUENCE: 129

```
ggagggggat aactactgga aacggtagct aataccgcat aacgtctcaa gaccaaagag     60

ggggaccttc gggcctcttg ccatcagatg tgcccagatg ggattagcta gtaggcgggg    120

taacggccca cctaggcgac gatccctagc tggtctgaga ggatgaccag ccacactgga    180

actgagacac ggtccacact cctacgggag gcagcagtgg ggaatattgc acaatgggcg    240

caagcctgat gcatccatgc cgcgtgtgtg aagaaggcct tcgggttgta aagcactttc    300

agcggggagg aaggcagtcc ggttaataac cgtgctgatt gacgttaccc gcagaagaag    360

caccggctaa ctccgtgcca gcagccgcgg taatacggag ggtgcaagcg ttaatcggaa    420

ttactgggcg taaagcgcac gcaggcggtc tgtcaagtcg gatgtgaaat ccccgggctc    480

aacctgggaa ctgcattcga aactggcagg ctggagtctc gtagagggag gtagaattcc    540

aggtgtagcg gtgaaatgcg tagagatctg gaggaatacc ggtggcgaaa gcggcctcct    600

ggacgaagac tgacgctcag gtgcgaaagc gtggggagca aacaggatta gataccctgg    660

tagtccacgc cgtaaacgat gtcgatttgg aggttgtgcc cttgaggcgt ggcttccgga    720

gctaacgcgt taaatcgacc gcctggggag tacggccgca aggttaaaac tcaaatgaat    780

tgacgggggc ccgcacaagc ggtggagcat gtggtttaat tcgatgcaac gcgaagaacc    840

ttacctggtc ttgacatcca cagaacctgg cagagatgcc ggggtgcctt cgggaactgt    900

gagacaggtg ctgcatggct gtcgtcagct cgtgttgtga aatgttgggt taagtcccgc    960

aacgagcgca acccttatcc tttgttgcca gcggttaggc cgggaactca aaggagactg   1020

ccagtgataa actggaggaa ggtggggatg acgtcaagtc atcatggccc ttacgaccag   1080

ggctacacac gtgctacaat ggcgcataca aagagaagcg acctcgcgag agcaagcgga   1140
```

cctcataaag tgcgtcgtag tccggattgg agtctgcaac tcgactccat gaagtcggaa 1200
tcgctagtaa tcgtgaatca 1220

<210> SEQ ID NO 130
<211> LENGTH: 1554
<212> TYPE: DNA
<213> ORGANISM: Unknown
<220> FEATURE:
<223> OTHER INFORMATION: Kingdom: Bacteria, Phylum: Actinobacteria,
Class: Actinobacteria, Order: Actinomycetales, Family:
Streptomycetaceae, Genus: Streptomyces

<400> SEQUENCE: 130
agagtttgat cctggctcag gacgaacgct ggcggcgtgc ttaacacatg caagtcgaac 60
gatgaaccac ttcggtgggg attagtggcg aacgggtgag taacacgtgg gcaatctgcc 120
cttcactctg ggacaagccc tggaaacggg gtctaatacc ggataacact gcggatcgca 180
tggtctgtgg ttaaaagctc cggcggtgaa gggtgagccc gcggcctatc agcttgttgg 240
tgaggtagtg gctcaccaag gcgacgacgg gtagccggcc tgagagggcg accggccaca 300
ctgggactga gacacggccc agactcctac gggaggcagc agtggggaat attgcacaat 360
gggcgaaagc ctgatgcagc gacgccgcgt gagggatgac ggccttcggg ttgtaaacct 420
ctttcagcag ggaagaagcg aaagtgacgg tacctgcaga agaagcgccg gctaactacg 480
tgccagcagc cgcggtaata cgtagggcgc aagcgttgtc cggaattatt gggcgtaaag 540
agctcgtagg cggcttgtca cgtcgattgt gaaagcccga ggcttaacct cgggtctgca 600
gtcgatacgg gctagctaga gtgtggtagg ggagatcgga attcctggcg tagcggtgaa 660
atgcgcagat atcaggagga acaccggtgg cgaaggcgga tctctgggcc attactgacg 720
ctgaggagcg aaagcgtggg gagcgaacag gattagatac cctggtagtc cacgccgtaa 780
acggcgggaa ctaggtgttg gcgacattcc acgtcgtcgg tgccgcagct aacgcattaa 840
gttccccgcc tggggagtac ggccgcaagg ctaaaactca aaggaattga cgggggcccg 900
cacaagcggc ggagcatgtg gcttaattcg acgcaacgcg aagaacctta ccaaggcttg 960
acatacaccg gaaacgtctg gagacaggcg ccccccttgtg gtcggtgtac aggtggtgca 1020
tggctgtcgt cagctcgtgt cgtgagatgt tgggttaagt cccgcaacga gcgcaaccct 1080
tgtcccgtgt tgccagcagg cccttgtggt gctggggact cacgggagac cgccggggtc 1140
aactcggagg aaggtgggga cgacgtcaag tcatcatgcc ccttatgtct tgggctgcac 1200
acgtgctaca atggccggta caatgagctg cgataccgtg aggtggagcg aatctcaaaa 1260
agccggtctc agttcggatt ggggtctgca actcgacccc atgaagtcgg agtcgctagt 1320
aatcgcagat cagcattgct gcggtgaata cgttcccggg ccttgtacac accgcccgtc 1380
acgtcacgaa agtcggtaac acccgaagcc ggtggcccaa cccttgtgga gggagctgtc 1440
gaaggtggga ctggcgattg ggacgaagtc gtaacaaggt aaccaagggc gaattccaca 1500
gtggatatca agcttatcga taccgtcgac ctcgaggggg ggcccggtac ccag 1554

<210> SEQ ID NO 131
<211> LENGTH: 1072
<212> TYPE: DNA
<213> ORGANISM: Unknown
<220> FEATURE:
<223> OTHER INFORMATION: Kingdom: Bacteria, Phylum: Fusobacteria,
Class: Fusobacteriia, Order: Fusobacteriales, Family:
Leptotrichiaceae, Genus: Sebaldella

<400> SEQUENCE: 131

```
agagtttgat cctggctcag atagatggta ggccaagaag aggacgcgag atgcgagaga     60
gacgaacgga tccacgtaag ggaacagggc gggcctgcgt gagctgaaga ggacattggt    120
agttccaaaa ccaccatgct cggctgcgtg ctgtccagcc ttagcctgaa gctcaaaatc    180
ggccttggag tcgagcatgt gcaggcttat catgaagtta ccgcgctcca cattcgggtt    240
cgatcgcggc atcgtcaagc tcagcgatac gtcatattct tgctgcgact tcatgggcgg    300
caattcgagt gatgcgatgc catatgggtt gacgccggag ctgcggccag caatgtcagc    360
gaaccacaac ttgaaattga ttacgatgcg atacgctgcg ctacataccc atactggagg    420
tggacaggca tcgtcaccac ctcatgggga agaaaattct ggaaaaagag agccgaagca    480
atggccgctg tgcaaaagag gatcacagca ccagacacca ggagcacgct attgacgaat    540
gcccgctgga ctggcttcga cgtgacgatg cgggcagtct cttgaagggt atcctgcgca    600
ggtaaagtgt cagtcgctta catctgtctg tccaattctg gagcgacaac tcaccatgct    660
aggccaaata tgtccgacgg tgcggactgc atggatgttg cgagagaagg gttggttgga    720
gtagtgtagc attcaaggga gaagcaaagc aatggagctg aggccgtgta tggcatgtga    780
acgtgggcag ctggagctca acagctccca cgtcatacca gggtacgtac tgcgcctgca    840
acaagggcac tgcattttag gtacatcacc aacagcaaca acagcaacaa caccaatgca    900
cagcaagcaa gaataataaa gttgaattga gaattaagaa agtatccatc cctagcttag    960
ctaagagaaa gggcagctca tacaattttg cctgcgtaac aaataccaaa cgtcaagtcg   1020
taacaaggta accaagggcg aattccacag tggatatcaa gcttatcgat ac           1072
```

<210> SEQ ID NO 132
<211> LENGTH: 1428
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Actinomycetales, Family: Microbacteriaceae, Genus: Curtobacterium

<400> SEQUENCE: 132

```
gtttgatcct ggctcaggac gaacgctggc ggcgtgctta acacatgcaa gtcgaacgat     60
gatgcccagc ttgctgggtg gattagtggc gaacgggtga gtaacacgtg agtaacctgc    120
ccctgactct gggataagcg ttggaaacga cgtctaatac tggatatgat cactggccgc    180
atggtctggt ggtggaaaga ttttttggtt ggggatggac tcgcggccta tcagcttgtt    240
ggtgaggtaa tggctcacca aggcgacgac gggtagccgg cctgagaggg tgaccggcca    300
cactgggact gagacacggc ccagactcct acgggaggca gcagtgggga atattgcaca    360
atgggcgaaa gcctgatgca gcaacgccgc gtgagggatg acggccttcg ggttgtaaac    420
ctcttttagt agggaagaag cgaaagtgac ggtacctgca gaaaaagcac cggctaacta    480
cgtgccagca gccgcggtaa tacgtagggt gcaagcgttg tccggaatta ttgggcgtaa    540
agagctcgta ggcggtttgt cgcgtctgct gtgaaatccc gaggctcaac ctcgggcttg    600
cagtgggtac gggcagacta gagtgcggta ggggagattg gaattcctgg tgtagcggtg    660
gaatgcgcag atatcagcga aagcatgggg agcgaacagg attagatacc ctggtagtcc    720
atgccgtaaa cgttgggcgc tagatgtagg gacctttcca cggtttctgt gtcgtagcta    780
acgcattaag cgccccgcct ggggagtacg gccgcaaggc taaaactcaa aggaattgac    840
gggggcccgc acaagcggcg gagcatgcgg attaattcga tgcaacgcga agaaccttac    900
```

```
caaggcttga catacaccgg aaacggccag agatggtcgc cccttgtgg tcggtgtaca     960

ggtggtgcat ggttgtcgtc agctcgtgtc gtgagatgtt gggttaagtc ccgcaacgag   1020

cgcaaccctc gttctatgtt gccagcgggt tatgccgggg actcatagga gactgccggg   1080

gtcaactcgg aggaaggtgg ggatgacgtc aaatcatcat gccccttatg tcttgggctt   1140

cacgcatgct acaatggccg gtacaaaggg ctgcgatacc gtaaggtgga gcgaatccca   1200

aaaagccggt ctcagttcgg attgaggtct gcaactcgac ctcatgaagt cggagtcgct   1260

agtaatcgca gatcagcaac gctgcggtga atacgttccc gggccttgta cacaccgccc   1320

gtcaagtcat gaaagtcggt aacacccgaa gccggtggcc taacccttgt ggaaggagcc   1380

gtcgaaggtg ggatcggtga ttaggactaa gtcgtaacaa ggtaacca                1428
```

<210> SEQ ID NO 133
<211> LENGTH: 349
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Moraxellaceae, Genus: Enhydrobacter

<400> SEQUENCE: 133

```
caaggcgacg atctgtaact ggtctgagag gatgatcaat cacaccggaa ctgagacaca     60

gtccggactc ctacgggagg cagcagtggg gaatattgga caatgggggc aaccctgatc    120

cagccatgcc gcgtgtgtga agaaggcctt ttggttgtaa agcactttaa gcagggagga    180

gaggctaatg gttaataccc attagattag acgttacctg cagaataagc accggctaac    240

tctgtgccag cagccgcggt aatacagagg gtgcgagcgt taatcggaat tactgggcgt    300

aaagcgagtg taggtggctc attaagtcac atgtgaaatc cccgggctt                349
```

<210> SEQ ID NO 134
<211> LENGTH: 231
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Sphingomonadales, Family: Sphingomonadaceae, Genus: Sphingomonas

<400> SEQUENCE: 134

```
ccttcgggtg ctagtggcgc acgggtgcgt aacgcgtggg aatctgccct ttggttcgga     60

ataacagttg gaaacgactg ctaataccgg atgatgacga aagtccaaag atttatcgcc    120

agaggatgag cccgcgtagg attagctagt tggtgtggta aaggcgcacc aaggcgacga    180

tccttagctg gtctgagagg atgatcagcc acactgggac tgagacacgg c             231
```

<210> SEQ ID NO 135
<211> LENGTH: 1254
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Sphingomonadales, Family: Sphingomonadaceae, Genus: Sphingomonas

<400> SEQUENCE: 135

```
ctagtggcgc acgggtgcgt aacgcgtggg aatctgccct ttggttcgga ataacagttg     60

gaaacgactg ctaataccgg atgatgacga aagtccaaag atttatcgcc agaggatgag    120
```

```
cccgcgtagg attagctagt tggtgtggta aaggcgcacc aaggcgacga tccttagctg    180

gtctgagagg atgatcagcc acactgggac tgagacacgg cccagactcc tacgggaggc    240

agcagtgggg aatattggac aatgggcgaa agcctgatcc agcaatgccg cgtgagtgat    300

gaaggcctta gggttgtaaa gctcttttac ccgggatgat aatgacagta ccgggagaat    360

aagctccggc taactccgtg ccagcagccg cggtaatacg gagggagcta gcgttgttcg    420

gaattactgg gcgtaaagcg cacgtaggcg gctttgtaag ttagaggtga aagcctggag    480

ctcaactcca gaactgcctt taagactgca tcgcttgaat ccaggagagg tgagtggaat    540

tccgagtgta gaggtgaaat tcgtagatat tcggaagaac accagtggcg aaggcggctc    600

actggactgg tattgacgct gaggtgcgaa agcgtgggga gcaaacagga ttagataccc    660

tggtagtcca cgccgtaaac gatgataact agctgtccgg ggacttggtc tttgggtggc    720

gcagctaacg cattaagtta tccgccctgg ggagtacggc cgcaaggtta aaactcaaat    780

gaattgacgg gggcctgcac aagcggtgga gcatgtggtt taattcgaag caacgcgcag    840

aaccttacca gcgtttgaca tgtccggacg atttccagag atggatctct tcccttcggg    900

gactggaaca caggtgctgc atggctgtcg tcagctcgtg tcgtgagatg ttgggttaag    960

tcccgcaacg agcgcaaccc tcgcctttag ttaccatcat ttagttgggg actctaaagg   1020

aaccgccggt gataagccgg aggaaggtgg ggatgacgtc aagtcctcat ggcccttacg   1080

cgctgggcta cacacgtgct acaatggcgg tgacagtggg cagcaaactc gcgagagtgc   1140

gctaatctcc aaaagccgtc tcagttcgga ttgttctctg caactcgaga gcatgaaggc   1200

ggaatcgcta gtaatcgcgg atcagcatgc cgcggtgaat acgttcccag gcct         1254
```

<210> SEQ ID NO 136
<211> LENGTH: 1317
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Actinomycetales, Family: Micromonosporaceae, Genus: Actinoplanes

<400> SEQUENCE: 136

```
gcggcgaacg ggtgagtaac acgtgagtaa cctgccctgg actatgggat aaccctcgga     60

aacgggggct aataccggat acgactgctg gccgcatggt tggtggtgga aagtttttcg    120

gtctgggatg ggctcgcggc ctatcagctt gttggtgggg tgatggccta ccaaggcgac    180

gacgggtagc cggcctgaga gggcgaccgg ccacactggg actgagacac ggcccagact    240

cctacgggag gcagcagtgg ggaatattgc acaatgggcg gaagcctgat gcagcgacgc    300

cgcgtgaggg atgacggcct tcgggttgta aacctctttc agcagggacg aagcgtgagt    360

gacggtacct gcagaagaag cgccggccaa ctacgtgcca gcagccgcgg taagacgtag    420

ggcgcgagcg ttgtccggat ttattgggcg taaagagctc gtaggcggct tgtcgcgtcg    480

tccgtgaaaa cctgcagctc aactgcaggc ttgcggtcga tacgggcagg ctagagttcg    540

gtaggggaga ctggaattcc tggtgtagcg gtgaaatgcg cagatatcag gaggaacacc    600

ggtggcgaag gcgggtctct gggccgatac tgacgctgag gagcgaaagc gtggggagcg    660

aacaggatta gataccctgg tagtccacgc tgtaaacgtt gggcgctagg tgtgggggc    720

ctctccggtt ctctgtgccg cagctaacgc attaagcgcc ccgcctgggg agtacggccg    780

caaggctaaa actcaaagga attgacgggg gcccgcacaa gcggcggagc atgcggatta    840

attcgatgca acgcgaagaa ccttacctgg gtttgacatg gccgcaaaac tgtcagagat    900
```

ggcaggtcct tcgggggcgg tcacaggtgg tgcatggctg tcgtcagctc gtgtcgtgag 960
atgttgggtt aagtcccgca acgagcgcaa ccctcgtccc atgttgccag caattcggtt 1020
ggggactcat gggagactgc cggggtcaac tcggaggaag gtggggatga cgtcaagtca 1080
tcatgcccct tatgtccagg gcttcacgca tgctacaatg gccggtacaa accgttgcga 1140
gcccgtgagg gggagcgaat cggaaaaagc cggtctcagt tcggatcggg gtctgcaact 1200
cgaccccgtg aagtcggagt cgctagtaat cgcagatcag caacgctgcg gtgaatacgt 1260
tcccgggcgg ggacacaccg cccgtcacgt cacgaaagtc ggcaacaccc gaagccg 1317

<210> SEQ ID NO 137
<211> LENGTH: 1514
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Beijerinckiaceae, Genus: Beijerinckia

<400> SEQUENCE: 137
gggtaccggg ccccccctcg aggtcgacgg tatcgataag cttgatatcc actgtggaat 60
tcgcccttag agtttgatcc tggctcagaa cgagcgctgg cggcaggctt aacacatgca 120
agtcgaacgc tcgtcttcgg acgggagtgg cagacgggtg agtaacacgt gggaacgtac 180
ccttcagttc ggaataaccc agggaaactt gggctaatac cggatacggc cgagaggcga 240
aaggtttact gctgaaggat cggcccgcgt ccgattagct tgttggtgtg gtaatggcgc 300
accaaggcat cgatcggtag ctggtctgag aggatggcca gccacattgg gactgagaca 360
cggcccaaac tcctacggga ggcagcagtg gggaatattg gacaatgggc gcaagcctga 420
tccagccatg ccgcgtgagt gatgaaggcc ttagggttgt aaagctcttt tacctgggaa 480
gatcatgacg gtaccaggag aataagcccc ggctaacttc gtgccagcag ccgcggtaat 540
acgaaggggg ctagcgttgt tcggatttac tgggcgtaaa gggcgcgtag gcggacctgt 600
aagtcagggg tgaaatcccg aggctcaacc tcggaactgc ctttgatact gtgggtcttg 660
agtccgggag aggtgagtgg aactgcgagt gtagaggtga aattcgtaga tattcgcaag 720
aacaccagtg gcgaaggcgg ctcactggcc cggaactgac gctgaggcgc gaaagcgtgg 780
ggagcaaaca ggattagata ccctggtagt ccacgcctta aacgatggat gctagccgtc 840
gggcagcttg ctgctctgtg gcgccgttaa cacattaagc atcccgcctg gggagtacgg 900
tcgcaagatt aaaactcaaa ggaattgacg gggcccgca caagcggtgg agcatgtggt 960
ttaattcgaa gcaacgcgca gaaccttacc agcctttgac atggcaggct cggacgagag 1020
atcgttcatt cccttcgggg acctgcacac aggtgctgca tggctgtcgt cagctcgtgt 1080
cgtgagatgt tgggttaagt cccgcaacga gcgcaaccca cgtcctcagt tgccatcatt 1140
cagttgggca ctctggggag actgccggtg ataagccgag aggaaggtgt ggatgacgtc 1200
aagtcctcat ggcccttacg ggctgggcta cacacgtgct acaatggcgg tgacagaggg 1260
acgctaaccc gcgagggtgt gccaatctct aaaatccgtc tcagttcgga ttgcactctg 1320
caactcgagt gcatgaagtt ggaatcgcta gtaatcgcgg atcagcacgc cgcggtgaat 1380
acgttcccgg gccttgtaca caccgcccgt cacaccatgg gagttggttt tacccgaagg 1440
cgtttcgcca accgcaagga ggcagacgac cacggtaggg tcagcgactg ggtgaagtc 1500 gtaacaaggt aacc 1514

<210> SEQ ID NO 138
<211> LENGTH: 1363
<212> TYPE: DNA
<213> ORGANISM: Unknown
<220> FEATURE:
<223> OTHER INFORMATION: Kingdom: Bacteria, Phylum: Proteobacteria,
Class: Gammaproteobacteria, Order: Enterobacteriales, Family:
Enterobacteriaceae, Genus: Erwinia

<400> SEQUENCE: 138

```
ttgctccttg ggtgacgagt ggcggacggg tgagtaatgt ctggggatct gcccgatgga      60
gggggataac tactggaaac ggtagctaat accgcataac gtcgcaagac caaagtgggg     120
gaccttcggg cctcacacca tcggatgaac ccagatggga ttagctagta ggtggggtaa     180
cggctcacct aggcgacgat ccctagctgg tctgagagga tgaccagcca cactggaact     240
gagacacggt ccagactcct acgggaggca gcagtgggga atattgcaca atgggcgcaa     300
gcctgatgca gccatgccgc gtgtatgaag aaggccttcg ggttgtaaag tactttcagc     360
ggggaggaag gcgataaggt taataacctt atcgattgac gttacccgca gaagaagcac     420
cggctaactc cgtgccagca gccgcggtaa tacggagggt gcaagcgtta atcggaatta     480
ctgggcgtaa agcgcacgca ggcggtctgt caagtcggat gtgaaatccc cgggcttaac     540
ctgggaactg cattcgaaac tggcaggctg gagtcttgta gaggggggta gaattccagg     600
tgtagcggtg aaatgcgtag agatctggag gaataccggt ggcgaaggcg gccccctgga     660
caaagactga cgctcaggtg cgaaagcgtg gggagcaaac aggattagat accctggtag     720
tccacgctgt aaacgatgtc gacttggagg ttgtgccctt gaggcgtggc ttccggagct     780
aacgcgttaa gtcgaccgcc tggggagtac ggccgcaagg ttaaaactca aatgaattga     840
cgggggcccg cacaagcggt ggagcatgtg gtttaattcg atgcaacgcg aagaacctta     900
cctggccttg acatccagag aatttagcag agatgcttga gtgccttcgg gaactgtgag     960
acaggtgctg catggctgtc gtcagctcgt gttgtgaaat gttgggttaa gtcccgcaac    1020
gagcgcaacc cttatccttt gttgccagcg attcggtcgg gaactcaaag gagactgccg    1080
gtgataaacc ggaggaaggt ggggatgacg tcaagtcatc atggccctta cggccagggc    1140
tacacacgtg ctacaatggc gcatacaaag agaagcgacc tcgcgagagc aagcggacct    1200
cataaagtgc gtcgtagtcc ggattggagt ctgcaactcg actccatgaa gtcggaatcg    1260
ctagtaatcg tagatcagaa tgctacggtg aatacgttcc ctgggccttg tacacaccgc    1320
ccgtcacacc atgggagtgg gttgcaaaag aagtaggtag cta                      1363
```

<210> SEQ ID NO 139
<211> LENGTH: 273
<212> TYPE: DNA
<213> ORGANISM: Unknown
<220> FEATURE:
<223> OTHER INFORMATION: Kingdom: Bacteria, Phylum: Proteobacteria,
Class: Alphaproteobacteria, Order: Rhizobiales, Family:
Bradyrhizobiaceae, Genus: Bradyrhizobium

<400> SEQUENCE: 139

```
aggacgtatt caccgtggcg tgctgatcca cgattactag cgattccaac ttcatgggct      60
cgagttgcag agcccaatcc gaactgagac ggctttttga gatttgcgaa gggtcgcccc     120
ttagcatccc attgtcaccg ccattgtagc acgtgtgtag cccagcccgt aagggccatg     180
aggacttgac gtcatcccca ccttcctcgc ggcttatcac cggcagtctc cttagagtgc     240
tcaactaaat ggtagcaact aaggacgggg gtt                                 273
```

<210> SEQ ID NO 140
<211> LENGTH: 261
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Bradyrhizobiaceae, Genus: Bradyrhizobium

<400> SEQUENCE: 140
cagggaaact tgtgctaata ccggataagc ccttacgggg aaagatttat cgccgaaaga 60
tcggcccgcg tctgattagc tagttggtga ggtaatggct caccaaggcg acgatcagta 120
gctggtctga gaggatgatc agccacattg ggactgagac acggcccaaa ctcctacggg 180
aggcagcagt ggggaatatt ggacaatggg cgcaagcctg atccagccat gccgcgtgag 240
tgatgaaggc cctacggttg t 261

<210> SEQ ID NO 141
<211> LENGTH: 419
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Bradyrhizobiaceae, Genus: Bradyrhizobium

<400> SEQUENCE: 141
aggacgtatt caccgtggcg tgctgatcca cgattactag cgattccaac ttcatgggct 60
cgagttgcag agcccaatcc gaactgagac ggctttttga gatttgcaaa gggtcgcccc 120
ttagcatccc attgtcaccg ccattgtagc acgtgtgtag cccagcccgt aagggccatg 180
aggacttgac gtcatcccca ccttcctcgc ggcttatcac cggcagtctc cttagagtgc 240
tcaactaaat ggtagcaact aaggacgggg gttgcgctcg ttgcgggact taacccaaca 300
tctcacgaca cgagctgacg acagccatgc agcacctgtc tccggtccag ccgaactgaa 360
gaactccgtc tctggagtcc gcgaccggga tgtcaagggc tggtaaggtt ctgcgcgtt 419

<210> SEQ ID NO 142
<211> LENGTH: 257
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Bradyrhizobiaceae, Genus: Bradyrhizobium

<400> SEQUENCE: 142
gggcgcaagc ctgatccagc catgccgcgt gagtgatgaa ggccctaggg ttgtaaagct 60
cttttgtgcg ggaagataat gacggtaccg caagaataag ccccggctaa cttcgtgcca 120
gcagccgcgg taatacgaag gggggctagcg ttgctcggaa tcactgggcg taaagggtgc 180
gtaggcgggt ctttaagtca ggggtgaaat cctggagctc aactccagaa ctgcctttgt 240
ctccgccgtt cgccggg 257

<210> SEQ ID NO 143
<211> LENGTH: 566
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family:

Bradyrhizobiaceae, Genus: Bradyrhizobium
<220> FEATURE:
<221> NAME/KEY: misc_feature
<222> LOCATION: (565)..(565)
<223> OTHER INFORMATION: n is a, c, g, or t

<400> SEQUENCE: 143
tgaatgccag ccgttagtgg gtttactcac tagtggcgca gctaacgctt taagcattcc 60
gcctcgggag tacggtcgca agattaaaac tcaaaggaat tgacgggggc ccgcacaagc 120
ggtggagcat gtggtttaat ttgacgcaac gcgcagaacc tcaccagccc ttgacatccc 180
ggtcgcggac tccagagacg gagttcttca gttcggctgg accggagaca ggtgctgcat 240
ggctgtcgtc agctcgtgtc gtgagatgtt gggttaagtc ccgcaacgag cgcaaccccc 300
gtccttagtt gctaccattt agttgagcac tctaaggaga ctgccggtga taagccgcga 360
ggaaggtggg gatgacgtca agtcctcatg gcccttacgg gctgggctac acacgtgcta 420
caatggcggt gacaatggga tgctaagggg cgaccctttg caaatctcaa aaagccgtct 480
cagttcggat tgggctctgc aactcgagcc catgaagttg gaatcgctag taatcgtgga 540
tcagcacgcc acggtgaata cgtcnc 566

<210> SEQ ID NO 144
<211> LENGTH: 429
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Bradyrhizobiaceae, Genus: Bradyrhizobium

<400> SEQUENCE: 144
gatcggcccg cgtctgatta gctagttggt gaggtaatgg ctcaccaagg cgacgatcag 60
tagctggtct gagaggatga tcagccacat tgggactgag acacggccca aactcctacg 120
ggaggcagca gtggggaata ttggacaatg ggcgcaagcc tgatccagcc atgccgcgtg 180
agtgatgaag gccctagggt tgtaaagctc ttttgtgcgg gaagataatg acggtaccgc 240
aagaataagc cccggctaac ttcgtgccag cagccgcggt aatacgaagg gggctagcgt 300
tgctcggaat cactgggcgt aaagggtgcg taggcgggtc tttaagtcag gggtgaaatc 360
ctggagctca actccagaac tgcctttgat actgaagatc ttgagttcgg gagaggtgag 420
tggaactgc 429

<210> SEQ ID NO 145
<211> LENGTH: 333
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Bradyrhizobiaceae, Genus: Bradyrhizobium

<400> SEQUENCE: 145
gcatgtggtt taattagacg caacgcgcag aacytcacca gcccttgaca tcccggtcgs 60
ggactccaga gamggagttc ttcagttcgg gtggacsgra gacaggtgct gcatggctgt 120
cgtcagctcg tgtcgtgaga tgttgggtta agtcccgcaa cgagcgcaac ccccgtcctt 180
agttgctacc atttagttga gcactctaag gagacygccg gtgataagcc gcgaggaagg 240
tggggatgac gtcaagtcct catggccctt acgggstggg ctacacacgt gctacaatgg 300
cggtgacaat gggatgcwaa ggggcgaccs ttt 333

<210> SEQ ID NO 146
<211> LENGTH: 240
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Bradyrhizobiaceae, Genus: Bradyrhizobium

<400> SEQUENCE: 146
ggttgtaaag ctcttttgtg cgggaagata atgaccgtac cgcaagaata agccccggct 60
aacttcgtgc cagcagccgc ggtaatacga agggggctag cgttgctcgg aatcactggg 120
cgtaaagggt gcgtaggcgg gtctttaagt caggggtgaa atcctggagc tcaactccag 180
aactgccttt gatactgaac atcttgagtt cgggagaggt gagtggaact gcgagtgtag 240

<210> SEQ ID NO 147
<211> LENGTH: 473
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Actinomycetales, Family: Intrasporangiaceae, Genus: Oryzihumus

<400> SEQUENCE: 147
ggccagtgag cgcgcgtaat acgactcact atagggcgaa ttggagctcc cgcggtgcgg 60
ccgctctaga actagtggat cccccgggct gcagcccaat gtggaattcg cccttagagt 120
ttgatcctgg ctcagttcgg attggggtct gcaactcgac cccatgaagt cggagttgct 180
agtaatcgca gatcagcatt gctgcggtga atacgttccc gggccttgta cacaccgccc 240
gtcacgtcac gaaagtcggt aacacccgaa gccggtggcc caaccccttg tgggagggag 300
ctgtcgaagg tgggactggc gattgggacg aagtcgtaac aaggtaacca agggcgaatt 360
ccacagtgga tatcaagctt atcgataccg tcgacctcga ggggggggcc ggtacccagc 420
ttttgttccc tttagtgagg gttaattgcg cgcttggcgt aatcatggtc ata 473

<210> SEQ ID NO 148
<211> LENGTH: 364
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Coriobacteriales, Family: Coriobacteriaceae, Genus: Adlercreutzia

<400> SEQUENCE: 148
ggccagtgag cgcgcgtaat acgactcact atagggcgaa ttggagctcc cgcggtgcgg 60
ccgctctaga actagtggat cccccgggct gcagcccaat gtggaattcg cccttggtta 120
ccttgttacg acttttactt cctctaaatg accgagtttg accaactttc cggcttgagg 180
tggtcgttgc caacctcctc gagccagtcc gaaggcctca ctgagccagg atcaaactct 240
aagggcgaat tccacagtgg atatcaagct tatcgatacc gtcgacctcg aggggggggcc 300 cggtacccag cttttgttcc ctttagtgag ggttaattgc gcgcttggcg taatcatggt 360
cata 364

<210> SEQ ID NO 149
<211> LENGTH: 166
<212> TYPE: DNA

<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Comamonadaceae, Genus: Variovorax

<400> SEQUENCE: 149
gggcactcta atgagactgc cggtgacaaa ccggaggaag gtggggatga cgtcaagtcc 60
tcatggccct tataggtggg gctacacacg tcatacaatg gctggtacaa agggttgcca 120
acccgcgagg gggagctaat cccataaaac cagtcgtagt ccggat 166

<210> SEQ ID NO 150
<211> LENGTH: 107
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Phyllobacteriaceae, Genus: Mesorhizobium

<400> SEQUENCE: 150
ctcccatggt gtgacgggcg gtgtgtacaa grcccgggaa cgtattcacc gcgrcatgct 60
gatccgcgat tactagcgat tccaacttca tgcactcgag ttgcaga 107

<210> SEQ ID NO 151
<211> LENGTH: 508
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Incertae Sedis XII, Genus: Exiguobacterium

<400> SEQUENCE: 151
agagtttgat cctggctcag gacgaacgct ggcggcgtgc ctaatacatg caagtcgagc 60
gcaggaagtc gacggaacct ttcgggggga agtcgatgga atgagcggcg gacgggtgag 120
taacacgtaa agaacctgcc ctcaggtctg ggataaccac gagaaatcgg ggctaatacc 180
ggatgggtca tcggaccgca tggtccgagg atgaaaggcg cttcggcgtc gcctggggat 240
ggctttgcgg tgcattagct agttggtggg gtaatggccc accaaggcga cgatgcatag 300
ccgacctgag agggtgatcg gccacactgg gactgagaca cggcccagac tcctacggga 360
ggcagcagta gggaatcttc cacaatggac gaaagtctga tggaacaacg ccgcgtgaac 420
gatgaaggcc ttcgggtcgt aaagttctgt tgtaagggaa gaacaagtgc cgcaggcaat 480
ggcggcacct tgacggtacc ttgcgaga 508

<210> SEQ ID NO 152
<211> LENGTH: 585
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Incertae Sedis XII, Genus: Exiguobacterium

<400> SEQUENCE: 152
ccctgaccgg tacagagatg taccttcccc ttcgggggca ggggtgacag gtggtgcatg 60
gttgtcgtca gctcgtgtcg tgagatgttg ggttaagtcc cgcaacgagc gcaacccttg 120
tccttagttg ccagcattca gttgggcact ctaaggagac tgccggtgac aaaccggagg 180
aaggtgggga tgacgtcaaa tcatcatgcc ccttatgagt tgggctacac acgtgctaca 240
atggacggta caaagggcag cgaagccgcg aggtggagcc aatcccagaa agccgttctc 300
agttcggatt gcaggctgca actcgcctgc atgaagtcgg aatcgctagt aatcgcaggt 360
cagcatactg cggtgaatac gttcccgggt cttgtacaca ccgcccgtca caccacgaga 420
gtttgtaaca cccgaagtcg gtgaggtaac cttagggagc cagccgccga aggtgggaca 480
gatgattggg gtgaagtcgt aacaaggtaa ccaagggcga attccacagt ggatatcaag 540
cttatcgata ccgtcgacct cgaggggggg cccggtaccc agctt 585

<210> SEQ ID NO 153
<211> LENGTH: 313
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Actinomycetales, Family: incertae_sedis, Genus: Sinosporangium

<400> SEQUENCE: 153
acggccagtg agcgcgcgta atacgactca ctatagggcg aattggagct cccgcggtgc 60
ggccgctcta gaactagtgg atcccccggg ctgcagccca atgtggaatt cgcccttggt 120
taccttgtta cgacttgcat gtgttaagca cgccgccagc gttcgtcctg agccaggatc 180
aaactctaag ggcgaattcc acagtggata tcaagcttat cgataccgtc gacctcgagg 240
gggggcccgg tacccagctt ttgttccctt tagtgagggt taattgcgcg cttggcgtaa 300
tcatggtcat agc 313

<210> SEQ ID NO 154
<211> LENGTH: 498
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Staphylococcaceae, Genus: Staphylococcus

<400> SEQUENCE: 154
agagtttgat cctggctcag gacgaacgct ggcggcgtgc ctaatacatg caagtcgagc 60
gaacagacga ggagcttgct cctctgacgt tagcggcgga cgggtgagta acacgtggat 120
aacctaccta taagactggg ataacttcgg gaaaccggag ctaataccgg ataatatatt 180
gaaccgcatg gttcaatagt gaaagacggt tttgctgtca cttatagatg gatccgcgcc 240
gcattagcta gttggtaagg taacggctta ccaaggcaac gatgcgtagc cgacctgaga 300
gggtgatcgg ccacactgga actgagacac ggtccagact cctacgggag gcagcagtag 360
ggaatcttcc gcaatgggcg aaagcctgac ggagcaacgc cgcgtgagtg atgaaggtct 420
tcggatcgta aaactctgtt attagggaag aacaaatgtg taagtaacta tgcacgtctt 480
gacggtacct aatcagaa 498

<210> SEQ ID NO 155
<211> LENGTH: 548
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Staphylococcaceae, Genus: Staphylococcus

<400> SEQUENCE: 155

-continued

```
agctgggtac cgggcccccc ctcgaggtcg acggtatcga taagcttgat atccactgtg     60

gaattcgccc ttggttacct tgttacgact tcaccccaat catttgtccc accttcgacg    120

gctagctcca aatggttact ccaccggctt cgggtgttac aaactctcgt ggtgtgacgg    180

gcggtgtgta caagacccgg gaacgtattc accgtagcat gctgatctac gattactagc    240

gattccagct tcatatagtc gagttgcaga ctacaatccg aactgagaac aactttatgg    300

gatttgcttg acctcgcggt ttcgctgccc tttgtattgt ccattgtagc acgtgtgtag    360

cccaaatcat aaggggcatg atgatttgac gtcatcccca ccttcctccg gtttgtcacc    420

ggcagtcaac ttagagtgcc caacttaatg atggcaacta agcttaaggg ttgcgctcgt    480

tgcgggactt aacccaacat ctcacgacac gagctgacga caaccatgca ccacctgtca    540

ctctgtcc                                                             548
```

```
<210> SEQ ID NO 156
<211> LENGTH: 465
<212> TYPE: DNA
<213> ORGANISM: Unknown
<220> FEATURE:
<223> OTHER INFORMATION: Kingdom: Bacteria, Phylum: Actinobacteria,
      Class: Actinobacteria, Order: Actinomycetales, Family:
      incertae_sedis, Genus: Sinosporangium

<400> SEQUENCE: 156

ggccagtgag cgcgcgtaat acgactcact atagggcgaa ttggagctcc cgcggtgcgg     60

ccgctctaga actagtggat cccccgggct gcagcccaat gtggaattcg cccttggtta    120

ccttgttacg acttcgtccc aatcgccagt cccaccttcg acagctccct cccacaaggg    180

gttgggccac cggcttcggg tgttaccgac tttcgtgacg tgacgggcgg tgtgtacaag    240

gcccgggaac gtattcaccg cagcaatgct gatctgcgat tactagcaac tccgacttca    300

tggggtcgag ttgcggaccc caatccgaac tgagccagga tcaaactcta agggcgaatt    360

ccacagtgga tatcaagctt atcgataccg tcgacctcga ggggggggccc ggtacccagc    420

ttttgttccc tttagtgagg gttaattgcg cgcttggcgt aatca                    465
```

```
<210> SEQ ID NO 157
<211> LENGTH: 536
<212> TYPE: DNA
<213> ORGANISM: Unknown
<220> FEATURE:
<223> OTHER INFORMATION: Kingdom: Bacteria, Phylum: Firmicutes, Class:
      Bacilli, Order: Bacillales, Family: Bacillaceae , Genus: Bacillus

<400> SEQUENCE: 157

agagtttgat cctggctcag gacgaacgct ggcggcgtgc ctaatacatg caagtcgagc     60

ggacagatgg gagcttgctc cctgatgtta gcggcggacg ggtgagtaac acgtgggtaa    120

cctgcctgta agactgggat aactccggga aaccggggct aataccggat ggttgtttga    180

accgcatggt tcagacataa aaggtggctt cggctaccac ttacagatgg acccgcggcg    240

cattagctag ttggtgaggt aacggctcac caaggcgacg atgcgtagcc gacctgagag    300

ggtgatcggc cacactggga ctgagacacg gcccagactc ctacgggagg cagcagtagg    360

gaatcttccg caatggacga aagtctgacg gagcaacgcc gcgtgagtga cgaaggtttt    420

cggatcgtaa agctctgttg ttagggaaga acaagtgccg ttcaaatagg gcggcacctt    480

gacggtacct aaccagaaag ccacggctaa ctacgtgcca gcagccgcgg taatac        536
```

```
<210> SEQ ID NO 158
```

<211> LENGTH: 584
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus

<400> SEQUENCE: 158
tttaattcga agcaacgcga agaaccttac caggtcttga catcctctga caatcctaga 60
gataggacgt ccccttcggg ggcagagtga caggtggtgc atggttgtcg tcagctcgtg 120
tcgtgagatg ttgggttaag tcccgcaacg agcgcaaccc ttgatcttag ttgccagcat 180
tcagttgggc actctaaggt gactgccggt gacaaaccgg aggaaggtgg ggatgacgtc 240
aaatcatcat gccccttatg acctgggcta cacacgtgct acaatggaca gaacaaaggg 300
cagcgaaacc gcgaggttaa gccaatccca caaatctgtt ctcagttcgg atcgcagtct 360
gcaactcgac tgcgtgaagc tggaatcgct agtaatcgcg gatcagcatg ccgcggtgaa 420
tacgttcccg ggccttgtac acaccgcccg tcacaccacg agagtttgta acacccgaag 480
tcggtgaggt aacctttatg gagccagccg ccgaaggtgg gacagatgat tggggtgaag 540
tcgtaacaag gtaaccaagg gcgaattcca cagtggatat caag 584

<210> SEQ ID NO 159
<211> LENGTH: 653
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Comamonadaceae, Genus: Variovorax

<400> SEQUENCE: 159
agagtttgat cctggctcag attgaacgct ggcggcatgc cttacacatg caagtcgaac 60
ggcagcacgg gagcaatcct ggtggcgagt ggcgaacggg tgagtaatac atcggaacgt 120
gcccaatcgt gggggataac gcagcgaaag ctgtgctaat accgcataag atctacggat 180
gaaagcaggg gatcgcaaga ccttgcgcga atggagcggc cgatggcaga ttaggtagtt 240
ggtgaggtaa aggctcacca agccttcgat ctgtagctgg tctgagagga cgaccagcca 300
cactgggact gagacacggc ccagactcct acgggaggca gcagtgggga attttggaca 360
atgggcgaaa gcctgatcca gccatgccgc gtgcaggatg aaggccttcg ggttgtaaac 420
tgcttttgta cggaacgaaa cggccttttc taataaagag ggctaatgac ggtaccgtaa 480
gaataagcac cggctaacta cgtgccagca gccgcggtaa tacgtagggt gcaagcgtta 540
atcggaatta ctgggcgtaa agcgtgcgca ggcggttatg taagacagtt gtgaaatccc 600
cgggctcaac ctgggaactg catctgtgac tgcatagcta gagtacggta gag 653

<210> SEQ ID NO 160
<211> LENGTH: 624
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Comamonadaceae, Genus: Variovorax

<400> SEQUENCE: 160
aggaattgac ggggacccgc acaagcggtg gatgatgtgg tttaattcga tgcaacgcga 60
aaaaccttac ccacctttga catgtacgga atttgccaga gatggcttag tgctcgaaag 120

-continued

```
agaaccgtaa cacaggtgct gcatggctgt cgtcagctcg tgtcgtgaga tgttgggtta    180

agtcccgcaa cgagcgcaac ccttgtcatt agttgctaca ttcagttggg cactctaatg    240

agactgccgg tgacaaaccg gaggaaggtg gggatgacgt caagtcctca tggcccttat    300

aggtggggct acacacgtca tacaatggct ggtacaaagg gttgccaacc cgcgaggggg    360

agctaatccc ataaaaccag tcgtagtccg gatcgcagtc agcaactcga ctgcgtgaag    420

tcggaatcgc tagtaatcgt ggatcagaat gtcacggtga atacgttccc gggtcttgta    480

cacaccgccc gtcacaccat gggagcgggt tctgccagaa gtagttagct taaccgcaag    540

gagggcgatt accacggcag ggttcgtgac tggggtgaag tcgtaacaag gtaaccaagg    600

gcgaattcca cagtggatat caag                                           624
```

```
<210> SEQ ID NO 161
<211> LENGTH: 512
<212> TYPE: DNA
<213> ORGANISM: Unknown
<220> FEATURE:
<223> OTHER INFORMATION: Kingdom: Archaea, Phylum: Crenarchaeota,
      Class: Thermoprotei, Order: Sulfolobales, Family: Sulfolobaceae,
      Genus: Stygiolobus

<400> SEQUENCE: 161

acgatgcata ggctgttacc gatttgggta gtgggtgtcg acgggtataa tgggcgggaa     60

gcagcaaaaa acgtcgacac agcgttgcag cgagaatgta tgcgcgacag gcatcgtggg    120

cacagtgacg ctggcttggt gttgaactat cgtcggttgc acctgcagat acgctggatt    180

agagccgtct agcgcctctt tagtcatggt gactagctgg gaagggcgag tcagggatcg    240

tgattggaaa cagcctcacg gccgtgtata cctagcccga tgcccttcgc gcggcggcga    300

gaatagagag agcgcgcgcc tggagagtgc gaccgtggca gcgcgatgcg ttagctgcga    360

atcgaggtcg tgtccttgtg acccagtgtg acgggcaaga gaacgacggc caggctccca    420

gccgccgcag gcagattgcg acggcatcaa gggccagagg cggcaggcaa tcatcgctca    480

cagcctccgc cggcgaccgt cctgctcgat ac                                  512


<210> SEQ ID NO 162
<211> LENGTH: 226
<212> TYPE: DNA
<213> ORGANISM: Unknown
<220> FEATURE:
<223> OTHER INFORMATION: Kingdom: Bacteria, Phylum: Proteobacteria,
      Class: Betaproteobacteria, Order: Burkholderiales, Family:
      Comamonadaceae, Genus: Variovorax

<400> SEQUENCE: 162

agatgttggg ttaagtcccg caacgagcgc aacccttgtc attagttgct acattcagtt     60

gggcactcta atgagactgc cggtgacaaa ccggaggaag gtggggatga cgtcaagtcc    120

tcatggccct tataggtggg gctacacacg tcatacaatg gctggtacaa agggttgcca    180

acccgcgagg gggagctaat cccataaaac cagtcgtagt ccggat                   226


<210> SEQ ID NO 163
<211> LENGTH: 538
<212> TYPE: DNA
<213> ORGANISM: Unknown
<220> FEATURE:
<223> OTHER INFORMATION: Kingdom: Bacteria, Phylum: Proteobacteria,
      Class: Alphaproteobacteria, Order: Rhizobiales, Family:
      Bradyrhizobiaceae, Genus: Bradyrhizobium

<400> SEQUENCE: 163
```

agagtttgat cctggctcag agcgaacgct ggcggcaggc ttaacacatg caagtcgagc 60
gggcatagca atatgtcagc ggcagacggg tgagtaacgc gtgggaacgt accttttggt 120
tcggaacaac acagggaaac ttgtgctaat accggataag cccttacggg gaaagattta 180
tcgccgaaag atcggcccgc gtctgattag ctagttggtg aggtaatggc tcaccaaggc 240
gacgatcagt agctggtctg agaggatgat cagccacatt gggactgaga cacggcccaa 300
actcctacgg gaggcagcag tggggaatat tggacaatgg gcgcaagcct gatccagcca 360
tgccgcgtga gtgatgaagg ccctagggtt gtaaagctct tttgtgcggg aagataatga 420
cggtaccgca agaataagcc ccggctaact tcgtgccagc agccgcggta atacgaaggg 480
ggctagcgtt gctcggaatc actgggcgta aagggtgcgt aggcgggtct ttaagtca 538

<210> SEQ ID NO 164
<211> LENGTH: 583
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Bradyrhizobiaceae, Genus: Bradyrhizobium
<220> FEATURE:
<221> NAME/KEY: misc_feature
<222> LOCATION: (4)..(4)
<223> OTHER INFORMATION: n is a, c, g, or t

<400> SEQUENCE: 164
attngacgca acgcgcagaa ccttaccagc ccttgacatc ccggtcgcgg actccagaga 60
cggagttctt cagttcggct ggaccggaga caggtgctgc atggctgtcg tcagctcgtg 120
tcgtgagatg ttgggttaag tcccgcaacg agcgcaaccc ccgtccttag ttgctaccat 180
ttagttgagc actctaagga gactgccggt gataagccgc gaggaaggtg gggatgacgt 240
caagtcctca tggcccttac gggctgggct acacacgtgc tacaatggcg gtgacaatgg 300
gatgctaagg ggcgaccctt cgcaaatctc aaaaagccgt ctcagttcgg attgggctct 360
gcaactcgag cccatgaagt tggaatcgct agtaatcgtg gatcagcacg ccacggtgaa 420
tacgttcccg ggccttgtac acaccgcccg tcacaccatg ggagttggtt ttacctgaag 480
acggtgcgct aaccgaaagg gggcagccgg ccacggtagg gtcagcgact ggggtgaagt 540
cgtaacaagg taaccaaggg cgaattccac agtggatatc aag 583

<210> SEQ ID NO 165
<211> LENGTH: 217
<212> TYPE: DNA
<213> ORGANISM: Unknown
<220> FEATURE:
<223> OTHER INFORMATION: Kingdom: Bacteria, Phylum: Firmicutes, Class: Bacilli, Order: Lactobacillales, Family: Carnobacteriaceae, Genus: Atopostipes

<400> SEQUENCE: 165
caggtggtgc atggttgtcg tcagctcgtg tcgtgagatg ttgggttaac tcccataacg 60
ggcgcaaccc ttattgttag ttgccagcat tcagttgggc actctagcga gactgccggt 120
gataaaccgg aggaaggtgg ggatgacgtc aaatcatcat gccccttatg agctgggcta 180
cacacgtgct acaatggacg gtacaacgag tggcgag 217

<210> SEQ ID NO 166
<211> LENGTH: 374
<212> TYPE: DNA

<213> ORGANISM: Unknown
<220> FEATURE:
<223> OTHER INFORMATION: Kingdom: Bacteria, Phylum: Firmicutes, Class: Bacilli, Order: Lactobacillales, Family: Carnobacteriaceae, Genus: Atopostipes

<400> SEQUENCE: 166
ttggtgaggt aatggctcac caaggcaacg atacttagcc gacctgagag ggtgatcggc 60
cacactggga ctgagacacg gcccatactc ctacgggagg cagcagtaag gaatcttcca 120
caatgggtgc aaacctgatg gagcaatgcc gcgtgaatga agaaggtctt cggatcgtaa 180
agttctgtta ttagagaaca acaagttgag gagtaactgc ctcagccttg acagtatcta 240
accagaaagt cacggctaac tacgtgccag cagccgcggt aatacgtagg tgacaagcgt 300
tgtccggaat tattgggcgt aaagggagcg cacgcggttg gaatagtctg atgtgaaagc 360
ccacggctta accg 374

<210> SEQ ID NO 167
<211> LENGTH: 552
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family: Enterobacteriaceae, Genus: Serratia

<400> SEQUENCE: 167
ggttaccttg ttacgacttc accccagtca tgaatcacaa agtggtaagc gccctcccga 60
aggttaagct acctacttct tttgcaaccc actcccatgg tgtgacgggc ggtgtgtaca 120
aggcccggga acgtattcac cgtagcattc tgatctacga ttactagcga ttccgacttc 180
atggagtcga gttgcagact ccaatccgga ctacgacgta ctttatgagg tccgcttgct 240
ctcgcgaggt cgcttctctt tgtatacgcc attgtagcac gtgtgtagcc ctactcgtaa 300
gggccatgat gacttgacgt catccccacc ttcctccagt ttatcactgg cagtctcctt 360
tgagtccccg gccgaaccgc tggcaacaaa ggataagggt tgcgctcgtt gcgggactta 420
acccaacatt tcacaacacg agctggcgac agccatgcag cacctgtctc agagttcccg 480
aaggcaccaa agcatctctg ctaagttctc tggatgtcaa gagtaggtaa ggttcttcgc 540
gttgcatcga at 552

<210> SEQ ID NO 168
<211> LENGTH: 533
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family: Enterobacteriaceae, Genus: Serratia

<400> SEQUENCE: 168
agttagccgg tgcttcttct gcgagtaacg tcaattgatg agcgtattaa gctcaccacc 60
ttcctcctcg ctgaaagtgc tttacaaccc gaaggccttc ttcacacacg cggcatggct 120
gcatcaggct tgcgcccatt gtgcaatatt ccccactgct gcctcccgta ggagtctgga 180
ccgtgtctca gttccagtgt ggctggtcat cctctcagac cagctaggga tcgtcgccta 240
ggtgagccat taccccacct actagctagt cccatctggg cgcatctgat ggcaagaggc 300
ccgaaggtcc ccctctttgg tcttgcgacg ttatgcggta ttagctaccg tttccagtag 360
ttatccccct ccatcaggca gtttcccaga cattactcac ccgtccgccg ctcgtcaccc 420
agagagcaag ctcccctgtg ctaccgctcg acttgcatgt gttaagcctg ccgccagcgt 480
tcaatctgag ccaggatcaa actctaaggg cgaattccac agtggatatc aag 533

<210> SEQ ID NO 169
<211> LENGTH: 566
<212> TYPE: DNA
<213> ORGANISM: Unknown
<220> FEATURE:
<223> OTHER INFORMATION: Kingdom: Archaea, Phylum: Crenarchaeota, Class: Thermoprotei, Order: Sulfolobales, Family: Sulfolobaceae, Genus: Sulfurisphaera

<400> SEQUENCE: 169
cagcaacaaa aggaccacca aagccgccca tggcggcagt ttgaagaacg gagaagagtg 60
aaccgacggt cacgaggccg atcttggctt acctaattgc ggcgatactt cctgtataat 120
gtcaactcca cgagccaagc aacgatacgg actgtctcac ctgcaacggg tcctgccgca 180
ctgaagccca ggaatcccag gaagttcgat gtaaactgcg cgaaaagaag gggacaaag 240 accctgccag cagcatttgt gggggagatg tgcttgtacc agggaggcgg aggtggaggg 300
aacattggag tacatcaagc agatgcactt gatgatgtcg gcgatgatga gaagtttaaa 360
cgcgattatg aagggtcggc tggctttgat aatcctcgcg cggaaggcgt tgccggccat 420
ggtgatgaaa gcgaggccgt agtgaagggg cgtgtcatgc gcttcgaggt gctcccggtc 480
ggcgtcgctg gcgtaggcgt gggcgtggga catgttttgt ggtgtctggc tgttgggata 540
tgggctataa cggtggtaat cgacga 566

<210> SEQ ID NO 170
<211> LENGTH: 604
<212> TYPE: DNA
<213> ORGANISM: Unknown
<220> FEATURE:
<223> OTHER INFORMATION: Kingdom: Bacteria, Phylum: Verrucomicrobia, Class: Opitutae, Order: Puniceicoccales, Family: Puniceicoccaceae, Genus: Coraliomargarita

<400> SEQUENCE: 170
gggctataac ggtggtaatc gacgaacaaa ataaagtttg cgggccgatc tcggcggagg 60
taaatgacgt caggaaagcg tggggagtga atgagaggga gagctttggc gcacgtgacg 120
tcgcgattta cctgaaattc gagtgccaca gcgcctcacc aaatactact gtatcacacg 180
ttggggtaga ggcatttgtc aggcttggaa aagtcaggca cgtcgtgatt attgcgacac 240
gctcgcgact tcctaatcgg accataccgg cagtgtttga gtcaaacaaa tcgccgatga 300
tgtcaccaat atatcggaat acactagcgc agaaacgtag tcattttcag cttgaactgg 360
ctgtacgcga aatatctcgg atttctgtga cctctggagg tgaacccaat tatgcttcta 420
tattggagat cttgagcaac gacaacatcg aagacaaata aaactttgcg ctaattccaa 480
taagataaac atgattcttt ctgcgtgtat catgagagca atctgagcca ggatcaaact 540
ctaagggcga attccacagt ggatatcaag cttatcgata ccgtcgacct cgaggggggg 600
cccg 604

<210> SEQ ID NO 171
<211> LENGTH: 668
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family:

Enterobacteriaceae, Genus: Enterobacter

<400> SEQUENCE: 171
ggttaccttg ttacgacttc accccagtca tgaatcacaa agtggtaagc gccctcccga 60
aggttaagct acctacttct tttgcaaccc actcccatgg tgtgacgggc ggtgtgtaca 120
aggcccggga acgtattcac cgtggcattc tgatccacga ttactagcga ttccgacttc 180
atggagtcga gttgcagact ccaatccgga ctacgacgca ctttatgagg tccgcttgct 240
ctcgcgaggt cgcttctctt tgtatgcgcc attgtagcac gtgtgtagcc ctggtcgtaa 300
gggccatgat gacttgacgt catccccacc ttcctccagt ttatcactgg cagtctcctt 360
tgagttcccg gccggaccgc tggcaacaaa ggataagggt tgcgctcgtt gcgggactta 420
acccaacatt tcacaacacg agctgacgac agccatgcag cacctgtctc agagttcccg 480
aaggcaccaa agcatctctg ctaagttctc tggatgtcaa gagtaggtaa ggttcttcgc 540
gttgcatcga attaaaccac atgctccacc gcttgtgcgg gcccccgtca attcatttga 600
gttttaacct tgcggccgta ctccccaggc ggtcgattta acgcgttagc tccggaagcc 660
acgcctca 668

<210> SEQ ID NO 172
<211> LENGTH: 564
<212> TYPE: DNA
<213> ORGANISM: Unknown
<220> FEATURE:
<223> OTHER INFORMATION: Kingdom: Bacteria, Phylum: Proteobacteria,
      Class: Gammaproteobacteria, Order: Enterobacteriales, Family:
      Enterobacteriaceae, Genus: Serratia

<400> SEQUENCE: 172
gtgcttcttc tgcgagtaac gtcaattgat gagcgtatta agctcaccac cttcctcctc 60
gctgaaagtg ctttacaacc cgaaggcctt cttcacacac gcggcatggc tgcatcaggc 120
ttgcgcccat tgtgcaatat tccccactgc tgcctcccgt aggagtctgg accgtgtctc 180
agttccagtg tggctggtca tcctctcaga ccagctaggg atcgtcgcct aggtgagcca 240
ttaccccacc tactagctaa tcccatctgg gcacatctga tggcaagagg cccgaaggtc 300
cccctctttg gtcttgcgac gttatgcggt attagctacc gtttccagta gttatccccc 360
tccatcaggc agtttcacag acattactca cccgtccgcc gctcgtcacc cagagagcaa 420
gctcccctgt gctaccactc gacttgcatg tgttaagcct gccgccagcg ttcaatctga 480
gccaggatca aactctaagg gcgaattcca cagtggatat caagcttatc gataccgtcg 540
acctcgaggg ggggcccggt accc 564

<210> SEQ ID NO 173
<211> LENGTH: 614
<212> TYPE: DNA
<213> ORGANISM: Unknown
<220> FEATURE:
<223> OTHER INFORMATION: Kingdom: Archaea, Phylum: Euryarchaeota, Class:
      Halobacteria, Order: Halobacteriales, Family: Halobacteriaceae,
      Genus: Halobaculum

<400> SEQUENCE: 173
agagtttgat cctggctcag attgggatca ggcccaacga cagtgcgacc cgagaagtcg 60
acacgctttc cagataggtt ctggcggaaa cggccgccct ttcccttgag acgctggcag 120
aaaccgcgca tcgtcttttg caggccttgt tgcttcaggc cgggcgagtc gctgttgatg 180
tacatggcaa tctgcaactg gagaaagtcc cactgctcca taggcacctg cagagggaag 240

```
ccgtcgcgca gaccggcacg gatgatgccg ctgatgtggg tgatgtcgcc aatcttgttg    300

gtgatgtcgt cttcggtagc accggcctcc tggaccaccg agggccggat gtagacaggc    360

ggcactggca cgtactccca tatcagcatc tccggccggg cgtcctcggg aatcatgtac    420

agcagctcgc agtcctcgtc agatatcctc ttgaagatgt tcagcacacg cagcgggtgc    480

atgtcgtcga cggccttctt cacgtgcttc tcgacatccg gattcccgac cttggccgtc    540

tcgaacgact ggtcgaactc ctgctttccg ggcggcagct tcttcacctt ggccgtggag    600

cggtcgtagg cgtc                                                      614


<210> SEQ ID NO 174
<211> LENGTH: 606
<212> TYPE: DNA
<213> ORGANISM: Unknown
<220> FEATURE:
<223> OTHER INFORMATION: Kingdom: Archaea, Phylum: Euryarchaeota, Class:
      Halobacteria, Order: Halobacteriales, Family: Halobacteriaceae,
      Genus: Halosimplex

<400> SEQUENCE: 174

cacacgcagc gggtgcatgt cgtcgacggc cttcttcacg tgcttctcga catccggatt     60

cccgaccttg gccgtctcga acgactggtc gaactcctgc tttccgggcg gcagcttctt    120

caccttggcc gtggagcggt cgtaggcgtc gtagcggcgg tggatgatct tcagcggatg    180

gccggcgact ttgcgcacag tgccgttgag gccgtggcag taggggcaga acttgcgctt    240

gcggcactcc tccatgatgc ggcgggcgag gttggtgcgc tgcaggttgt ccattccggg    300

gcggcgcatg ctgcgcaggt ggcgcttgcg ctcgtcgggc tcgagcaaca cgcgcgagca    360

gtccttgcat accgtgtgca gcacctcgat gatgtgcttg aggtagccga cgtggaagac    420

gggcagcgcg agcttgatgt ggccaaagtg gccgttgcac gtgtcgaggc cctcgccgca    480

cgtcttgcag aggccggtct tcgtcgagat gcccatgagg ggatccatgg ggccgtgctt    540

ggtgtgctgg cgctcgttgt tcggacctgg ggtgaagtcg taacaaggta accaagggcg    600

aattcc                                                               606


<210> SEQ ID NO 175
<211> LENGTH: 500
<212> TYPE: DNA
<213> ORGANISM: Unknown
<220> FEATURE:
<223> OTHER INFORMATION: Kingdom: Bacteria, Phylum: Proteobacteria,
      Class: Gammaproteobacteria, Order: Xanthomonadales, Family:
      Xanthomonadaceae, Genus: Luteibacter

<400> SEQUENCE: 175

ggacctaccc agacgtgggg gataacgtag ggaaacttac gctaataccg catacgtcct     60

acgggagaaa gcgggggatc gcaagacctc gcgcggttgg atggaccgat gtgcgattag    120

ctagttggta aggtagcggc ttaccaaggc gacgatcgct agctggtctg agaggatgat    180

cagccacact gggactgaga cacggcccag actcctacgg gaggcagcag tggggaatat    240

tggacaatgg gcgcaagcct gatccagcaa tgccgcgtgt gtgaagaagg ccctcgggtt    300

gtaaagcact tttatcagga gcgaaatctg caaggttaat acctttgcag tctgacggta    360

cctgaggaat aagcaccggc taactccgtg ccagcagccg cggtaatacg gagggtgcaa    420

gcgttaatcg gaattactgg gcgtaaagcg tgcgtaagcg gttcgttaag tctgttgtga    480

aagccccggg ctcaacctgg                                                500
```

<210> SEQ ID NO 176
<211> LENGTH: 543
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 176
cgcacaagcg gtggagtatg tggtttaatt cgatgcaacg cgaagaacct tacctggcct 60
tgacatgtcc ggaatccagc agagatgcag gagtgccttc gggaatcgga acacaggtgc 120
tgcatggctg tcgtcagctc gtgtcgtgag atgttgggtt aagtcccgca acgagcgcaa 180
cccttgtcct tagttgccag cgagtaatgt cgggaactct aaggagactg ccggtgacaa 240
accggaggaa ggtggggatg acgtcaagtc atcatggccc ttacggccag ggctacacac 300
gtactacaat ggtcggtaca gagggttgcg ataccgcgag gtggagctaa tcccagaaag 360
ccgatcccag tccggattgg agtctgcaac tcgactccat gaagtcggaa tcgctagtaa 420
tcgcagatca gctatgctgc ggtgaatacg ttcccgggcc ttgtacacac cgcccgtcac 480
accatgggag tgagctgctc cagaagccgt tagtctaacc gcaaggggga cgacgaccac 540
gga 543

<210> SEQ ID NO 177
<211> LENGTH: 582
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Actinomycetales, Family: Microbacteriaceae, Genus: Pseudoclavibacter

<400> SEQUENCE: 177
ggttaccttg ttacgactta gtcctaatca ccgatcccac cttcgacggc tccctccaaa 60
aggttgggcc accggctccg ggtgttaccg actttcatga cttgacgggc ggtgtgtaca 120
aggcccggga acgtattcac cgcagcgttg ctgatctgcg attactagcg actccgactt 180
catggggtcg agttgcagac cccaatccga actgagaccg gctttttggg attcgctcca 240
ccttgcggta ttgctgccct ttgtaccggc cattgtagca tgcgtgaagc ccaagacata 300
aggggcatga tgatttgacg tcatccccac cttcctccga gttgaccccg gcagtctcat 360
atgagttccc accattacgt gctggcaaca tacgacgagg gttgcgctcg ttgcgggact 420
taacccaaca tctcacgaca cgagctgacg acaaccatgc acaacctgta taccgacctt 480
gcggggcgac tatctctagc cgtttccggt atatgtcaag ccttggtaag gttcttcgcg 540
ttgcatcgaa ttaatccgca tgctccgccg cttgtgcggg cc 582

<210> SEQ ID NO 178
<211> LENGTH: 467
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Actinomycetales, Family: Microbacteriaceae, Genus: Zimmermannella

<400> SEQUENCE: 178
aagctgggta ccgggccccc cctcgaggtc gacggtatcg ataagcttga tatccactgt 60
ggaattcgcc cttagagttt gatcctggct caggacgaac gctggcggcg tgcttaacac 120

```
atgcaagtca aacgatgaac gaggagcttg ctcctccgga ttagtggcga acgggtgagt    180

aacacgtgag caacgtgccc aagactctgg aataacttcg ggaaaccgaa gctaataccg    240

gatacgagac gcgaaggcat cttcagcgtc tggaaagaac ttcggtcttg gatcggctca    300

cggcctatca gcttgtcggt gaggtaacgg ctcaccaagg cgacgacggg tagccggcct    360

gagagggtga ccggccacac tgggactgag acacggccca gactcctacg ggaggcagca    420

gtggggaata ttgcacaatg ggcgcaagcc tgatgcagca acgccgc                  467
```

<210> SEQ ID NO 179
<211> LENGTH: 1345
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family: Enterobacteriaceae, Genus: Serratia

<400> SEQUENCE: 179

```
ggcccgggaa cgtattcacc gtagcattct gatctacgat tactagcgat tccgacttca     60

tggagtcgag ttgcagactc caatccggac tacgacgtac tttatgaggt ccgcttgctc    120

tcgcgaggtc gcttctcttt gtatacgcca ttgtagcacg tgtgtagccc tactcgtaag    180

ggccatgatg acttgacgtc atccccacct tcctccagtt tatcactggc agtctccttt    240

gagttcccgg ccgaaccgct ggcaacaaag gataagggtt gcgctcgttg cgggacttaa    300

cccaacattt cacaacacga gctgacgaca gccatgcagc acctgtctca gagttcccga    360

aggcaccaat ccatctctgg aaagttctct ggatgtcaag agtaggtaag gttcttcgcg    420

ttgcatcgaa ttaaaccaca tgctccaccg cttgtgcggg cccccgtcaa ttcatttgag    480

ttttaacctt gcggccgtac tccccaggcg gtcgatttaa cgcgttagct ccggaagcca    540

cgcctcaagg gcacaacctc caaatcgaca tcgtttacag cgtggactac cagggtatct    600

aatcctgttt gctccccacg ctttcgcacc tgagcgtcag tcttcgtcca gggggccgcc    660

ttcgccaccg gtattcctcc agatctctac gcatttcacc gctacacctg gaattctacc    720

cccctctacg agactctagc ttgccagttt caaatgcagt tcccaggttg agcccgggga    780

tttcacatct gacttaacaa accgcctgcg tgcgctttac gcccagtaat tccgattaac    840

gcttgcaccc tccgtattac cgcggctgct ggcacggagt tagccggtgc ttcttctgcg    900

agtaacgtca attgatgaac gtattaagtt caccaccttc ctcctcgctg aaagtgcttt    960

acaacccgaa ggccttcttc acacacgcgg catggctgca tcaggcttgc gcccattgtg   1020

caatattccc cactgctgcc tcccgtagga gtctggaccg tgtctcagtt ccagtgtggc   1080

tggtcatcct ctcagaccag ctagggatcg tcgcctaggt gagccattac cccacctact   1140

agctaatccc atctgggcac atctgatggc aagaggcccg aaggtccccc tctttggtct   1200

tgcgacgtta tgcggtatta gctaccgttt ccagtagtta tccccctcca tcaggcagtt   1260

tcccagacat tactcacccg tccgccgctc gtcacccagg gagcaagctc ccctgtgcta   1320

ccgctcgact tgcatgtgtt aagcc                                         1345
```

<210> SEQ ID NO 180
<211> LENGTH: 595
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family:

Enterobacteriaceae, Genus: Serratia

<400> SEQUENCE: 180
agagtttgat cctggctcag attgaacgct ggcggcaggc ttaacacatg caagtcgagc 60
ggtagcacaa gggagcttgc tccctgggtg acgagcggcg gacgggtgag taatgtctgg 120
gaaactgcct gatggagggg gataactact ggaaacggta gctaataccg cataacgtcg 180
caagaccaaa gagggggacc ttcgggcctc ttgccatcag atgtgcccag atgggattag 240
ctagtaggtg gggtaatggc tcacctaggc gacgatccct agctggtctg agaggatgac 300
cagccacact ggaactgaga cacggtccag actcctacgg gaggcagcag tggggaatat 360
tgcacaatgg gcgcaagcct gatgcagcca tgccgcgtgt gtgaagaagg ccttcgggtt 420
gtaaagcact ttcagcgagg aggaaggtgg tgagcttaat acgctcatca attgacgtta 480
ctcgcagaag aagcaccggc taactccgtg ccagcagccg cggtaatacg gagggtgcaa 540
gcgttaatcg gaattactgg gcgtaaagcg cacgcaggcg gtttgttaag tcaga 595

<210> SEQ ID NO 181
<211> LENGTH: 549
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family: Enterobacteriaceae, Genus: Serratia

<400> SEQUENCE: 181
tgccttcggg aactctgaga caggtgctgc atggctgtcg tcagctcgtg ttgtgaaatg 60
ttgggttaag tcccgcaacg agcgcaaccc ttatcctttg ttgccagcgg ttcggccggg 120
aactcaaagg agactgccag tgataaactg gaggaaggtg gggatgacgt caagtcatca 180
tggcccttac gagtagggct acacacgtgc tacaatggcg tatacaaaga gaagcgacct 240
cgcgagagca agcggacctc ataaagtacg tcgtagtccg gattggagtc tgcaactcga 300
ctccatgaag tcggaatcgc tagtaatcgt agatcagaat gctacggtga atacgttccc 360
gggccttgta cacaccgccc gtcacaccat gggagtgggt tgcaaaagaa gtaggtagct 420
taaccttcgg gagggcgctt accactttgt gattcatgac tggggtgaag tcgtaacaag 480
gtaaccaagg gcgaattcca cagtggatat caagcttatc gataccgtcg acctcgaggg 540
ggggcccgg 549

<210> SEQ ID NO 182
<211> LENGTH: 564
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family: Enterobacteriaceae, Genus: Serratia

<400> SEQUENCE: 182
agagtttgat cctggctcag attgaacgct ggcggcaggc ttaacacatg caagtcgagc 60
ggtagcacaa gggagcttgc tccctgggtg acgagcggcg gacgggtgag taatgtctgg 120
gaaactgcct gatggagggg gataactact ggaaacggta gctaataccg cataacgtcg 180
caagaccaaa gagggggacc ttcgggcctc ttgccatcag atgtgcccag atgggattag 240
ctagtaggtg gggtaatggc tcacctaggc gacgatccct agctggtcta agaggatgac 300
cagccacact ggaactgaga cacggtccag actcctacgg gaggcagcag tggggaatat 360
tgcacaatgg gcgcaagcct gatgcagcca tgccgcgtgt gtgaagaagg ccttcgggtt 420
gtaaagcact ttcagcgagg aggaaggtgg tgagcttaat acgctcatca attgacgtta 480
ctcgcagaag aagcaccggc taactccgtg ccagcagccg cggtaatacg gagggtgcaa 540
gcgttaatcg gaattactgg gcgt 564

<210> SEQ ID NO 183
<211> LENGTH: 578
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family: Enterobacteriaceae, Genus: Serratia

<400> SEQUENCE: 183
tcgatgcaac gcgaagaacc ttacctactc ttgacatcca gagaactttc cagagatgga 60
ttggtgcctt cgggaactct gagacaggtg ctgcatggct gtcgtcagct cgtgttgtga 120
aatgttgggt taagtcccgc aacgagcgca acccttatcc tttgttgcca gcggttcggc 180
cgggaactca aaggagactg ccagtgataa actggaggaa ggtggggatg acgtcaagtc 240
atcatggccc ttacgagtag ggctacacac gtgctacaat ggcgtataca aagagaagcg 300
acctcgcgag agcaagcgga cctcataaag tacgtcgtag tccggattgg agtctgcaac 360
tcgactccat gaagtcggaa tcgctagtaa tcgtagatca gaatgctacg gtgaatacgt 420
tcccgggcct tgtacacacc gcccgtcaca ccatgggagt gggttgcaaa agaagtaggt 480
agcttaacct tcgggagggc gcttaccact ttgtgattca tgactggggt gaagtcgtaa 540
caaggtaacc aagggcgaat tccacagtgg atatcaag 578

<210> SEQ ID NO 184
<211> LENGTH: 651
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family: Enterobacteriaceae, Genus: Serratia

<400> SEQUENCE: 184
ggttaccttg ttacgacttc accccagtca tgaatcacaa agtggtaagc gccctcccga 60
aggttaagct acctacttct tttgcaaccc actcccatgg tgtgacgggc ggtgtgtaca 120
aggcccggga acgtattcac cgtagcattc tgatctacga ttactagcga ttccgacttc 180
atggagtcga gttgcagact ccaatccgga ctacgacgta ctttatgagg tccgcttgct 240
ctcgcgaggt cgcttctctt tgtatacgcc attgtagcac gtgtgtagcc ctactcgtaa 300
gggccatgat gacttgacgt catccccacc ttcctccagt ttatcactgg cagtctcctt 360
tgagttcccg gccgaaccgc tggcaacaaa ggataagggt tgcgctcgtt gcgggactta 420
acccaacatc tcacaacacg agctgacgac agccatgcag cacctgtctc agagttcccg 480
aaggcaccaa tccatctctg gaaagttctc tggatgtcaa gagtaggtaa ggttcttcgc 540
gttgcatcga attaaaccac atgctccacc gcttgtgcgg gcccccgtca attcatttga 600
gttttaacct tgcggccgta ctccccaggc ggtcgattta acgcgttagc t 651

<210> SEQ ID NO 185
<211> LENGTH: 564
<212> TYPE: DNA

<213> ORGANISM: Unknown
<220> FEATURE:
<223> OTHER INFORMATION: Kingdom: Bacteria, Phylum: Proteobacteria,
Class: Gammaproteobacteria, Order: Enterobacteriales, Family:
Enterobacteriaceae, Genus: Serratia

<400> SEQUENCE: 185
caccctccgt attaccgcgg ctgctggcac ggagttagcc ggtgcttctt ctgcgagtaa 60
cgtcaattga tgagcgtatt aagctcacca ccttcctcct cgctgaaagt gctttacaac 120
ccgaaggcct tcttcacaca cgcggcatgg ctgcatcagg cttgcgccca ttgtgcaata 180
ttccccactg ctgcctcccg taggagtctg gaccgtgtct cagttccagt gtggctggtc 240
atcctctcag accagctagg gatcgtcgcc taggttagcc attaccccac ctactagcta 300
atcccatctg ggcacatctg atggcaagag gcccgaaggt ccccctcttt ggtcttgcga 360
cgttatgcgg tattagctac cgtttccagt agttatcccc ctccatcagg cagtttccca 420
gacattactc acccgtccgc cgctcgtcac ccagggagca agctcccttg tgctaccgct 480
cgacttgcat gtgttaagcc tgccgccagc gttcaatctg agccaggatc aaactctaag 540
ggcgaattcc acagtggata tcaa 564

<210> SEQ ID NO 186
<211> LENGTH: 479
<212> TYPE: DNA
<213> ORGANISM: Unknown
<220> FEATURE:
<223> OTHER INFORMATION: Kingdom: Bacteria, Phylum: Proteobacteria,
Class: Gammaproteobacteria, Order: Enterobacteriales, Family:
Enterobacteriaceae, Genus: Serratia

<400> SEQUENCE: 186
gaaactgcct gatggagggg gataactact ggaaacggta gctaataccg cataacgtcg 60
caagaccaaa gagggggacc ttcgggcctc ttgccatcag atgtgcccag atgggattag 120
ctagtaggtg gggtaatggc taacctaggc gacgatccct agctggtctg agaggatgac 180
cagccacact ggaactgaga cacggtccag actcctacgg gaggcagcag tggggaatat 240
tgcacaatgg gcgcaagcct gatgcagcca tgccgcgtgt gtgaagaagg ccttcgggtt 300
gtaaagcact ttcagcgagg aggaaggtgg tgagcttaat acgctcatca attgacgtta 360
ctcgcagaag aagcaccggc taactccgtg ccagcagccg cggtaatacg gagggtgcaa 420
gcgttaatcg gaattactgg gcgtaaagcg cacgcaggcg gtttgttaag tcagatgtg 479

<210> SEQ ID NO 187
<211> LENGTH: 585
<212> TYPE: DNA
<213> ORGANISM: Unknown
<220> FEATURE:
<223> OTHER INFORMATION: Kingdom: Bacteria, Phylum: Proteobacteria,
Class: Gammaproteobacteria, Order: Enterobacteriales, Family:
Enterobacteriaceae, Genus: Serratia

<400> SEQUENCE: 187
gagtacggcc gcaaggttaa aactcaaatg aattgacggg ggcccgcaca agcggtggag 60
catgtggttt aattcgatgc aacgcgaaga accttaccta ctcttgacat ccagagaact 120
ttccagagat ggattggtgc cttcgggaac tctgagacag gtgctgcatg gctgtcgtca 180
gctcgtgttg tgaaatgttg ggttaagtcc cgcaacgagc gcaaccctta tcctttgttg 240
ccagcggttc ggccgggaac tcaaaggaga ctgccagtga taaactggag gaaggtgggg 300
atgacgtcaa gtcatcatgg cccttacgag tagggctaca cacgtgctac aatggcgtat 360
acaaagagaa gcgacctcgc gagagcaagc ggacctcata aagtacgtcg tagtccggat 420
tggagtctgc aactcgactc catgaagtcg gaatcgctag taatcgtaga tcagaatgct 480
acggtgaata cgttcccggg ccttgtacac accgcccgtc acaccatggg agtgggttgc 540
aaaagaagta ggtagcttaa ccttcgggag ggcgcttacc acttt 585

<210> SEQ ID NO 188
<211> LENGTH: 458
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family: Enterobacteriaceae, Genus: Serratia

<400> SEQUENCE: 188
ggcccgggaa cgtattcacc gtagcattct gatctacgat tactagcgat tccgacttca 60
tggagtcgag ttgcagactc caatccggac tacgacgtac tttatgaggt ccgcttgctc 120
tcgcgaggtc gcttctcttt gtatacgcca ttgtagcacg tgtgtagccc tactcgtaag 180
ggccatgatg acttgacgtc atccccacct tcctccagtt tatcactggc agtctccttt 240
gagttcccgg ccgaaccgct ggcaacaaag gataagggtt gcgctcgttg cgggacttaa 300
cccaacattt cacaacacga gctgacgaca gccatgcagc acctgtctca gagttcccga 360
aggcaccaat ccatctctgg aaagttctct ggatgtcaag agtaggtaag gttcttcgcg 420
ttgcatcgaa ttaaaccaca tgctccaccg cttgtgcg 458

<210> SEQ ID NO 189
<211> LENGTH: 619
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family: Enterobacteriaceae, Genus: Serratia

<400> SEQUENCE: 189
tacgagactc tagcttgcca gtttcaaatg cagttcccag gttgagcccg gggatttcac 60
atctgactta acaaaccgcc tgcgtgcgct ttacgcccag taattccgat taacgcttgc 120
accctccgta ttaccgcggc tgctggcacg gagttagccg gtgcttcttc tgcgagtaac 180
gtcaattgat gaacgtatta agttcaccac cttcctcctc gctgaaagtg ctttacaacc 240
cgaaggcctt cttcacacac gcggcatggc tgcatcaggc ttgcgcccat tgtgcaatat 300
tccccactgc tgcctcccgt aggagtctgg accgtgtctc agttccagtg tggctggtca 360
tcctctcaga ccagctaggg atcgtcgcct aggtgagcca ttaccccacc tactagctaa 420
tcccatctgg gcacatctga tggcaagagg cccgaaggtc cccctctttg gtcttgcgac 480
gttatgcggt attagctacc gtttccagta gttatccccc tccatcaggc agtttcccag 540
acattactca cccgtccgcc gctcgtcacc cagggagcaa gctcccctgt gctaccgctc 600
gacttgcatg tgttaagcc 619

<210> SEQ ID NO 190
<211> LENGTH: 404
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family:

Comamonadaceae, Genus: Variovorax

<400> SEQUENCE: 190
ccgcctgggg agtacggccg caaggttraa actcaaagga attgacgggg acccgcacaa 60
gcggtggatg atgtggttta attcgatgca acgcgaaaaa ccttacccac ctttgacatg 120
tacggaattt gccagagatg gyttagtgct kgaaagagaa ccgtaacaca ggtgctgcat 180
ggtctgtcgt cagctcgtgt cgtgagatgt tgggttaagt cccgcaacga gcgcaaccct 240
tgtcattagt tgctacattc agttgggcac tctaatgaga ctgccggtga caaaccggag 300
gaaggtgggg atgacgtcaa gtcctcatgg cccttatagg tggggctaca cacgtcatac 360
aatggctggt acaaagggtt gccaacccgc gagggggagc taat 404

<210> SEQ ID NO 191
<211> LENGTH: 625
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Comamonadaceae, Genus: Variovorax
<220> FEATURE:
<221> NAME/KEY: misc_feature
<222> LOCATION: (529)..(529)
<223> OTHER INFORMATION: n is a, c, g, or t

<400> SEQUENCE: 191
aaagctgtgc taataccgca taaratctac sgatgaaagc aggggatcgc aagaccttgc 60
gcgaatggag cggccgatgg cagattasgt agttggtgag gtaaaggctc accaagcctt 120
cgatctgtag ctggtctgag aggacgacca gccacactgg gactgagaca cggcccagac 180
tcctacggga ggcagcagtg gggaattttg gacaatgggc gaaagcctga tccagccatg 240
ccgcgtgcag gatgaaggcc ttcgggttgt aaactgcttt tgtacggaac gaaacggcct 300
tttctaataa agagggctaa tgacrgtacc gtaagaataa gcaccggcta actacgtgcc 360
agcagccgcg gtaatacgta gggtgcaagc gttaatcgga attactgggc gtaaagcgtg 420
cgcaggcggt tatgtaagac agttgtgaaa tccccgggct caacctggga actgcatctg 480
tgactgcata gctagagtac ggtagagggg gatggaattc crcgtgtanc agtgaaatgc 540
gtagatatgc ggaggaacac cgatggcgaa ggcaatcccc tggacctgta ctgacgctca 600
tgcacgaaag cgtggggagc aaaca 625

<210> SEQ ID NO 192
<211> LENGTH: 610
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus

<400> SEQUENCE: 192
ggagcgaaca ggattagata ccctggtagt ccacgccgta aacgatgagt gctaagtgtt 60
agggggtttc cgccccttag tgctgcagct aacgcattaa gcactccgcc tggggagtac 120
ggtcgcaaga ctgaaactca aaggaattga cgggggcccg cacaagcggt ggagcatgtg 180
gtttaattcg aagcaacgcg aagaacctta ccaggtcttg acatcctctg acaatcctag 240
agataggacg tccccttcgg gggcagagtg acaggtggtg catggttgtc gtcagctcgt 300
gtcgtgagat gttgggttaa gtcccgcaac gagcgcaacc cttgatctta gttgccagca 360

-continued ttcagttggg cactctaagg tgactgccgg tgacaaaccg gaggaaggtg gggatgacgt 420
caaatcatca tgccccttat gacctgggct acacacgtgc tacaatggac agaacaaagg 480
gcagcgaaac cgcgaggtta agccaatccc acaaatctgt tctcagttcg gatcgcagtc 540
tgcaactcga ctgcgtgaag ctggaatcgc tagtaatcgc ggatcagcat gccgcggtga 600
atacgttccc 610

<210> SEQ ID NO 193
<211> LENGTH: 480
<212> TYPE: DNA
<213> ORGANISM: Unknown
<220> FEATURE:
<223> OTHER INFORMATION: Kingdom: Archaea, Phylum: Nanohaloarchaeota, Class: Nanohaloarchaea, Order: Incertae sedis, Family: Incertae sedis, Genus: Candidatus Haloredivivus

<400> SEQUENCE: 193
actattccct ctactgttag accaaccgtt aagcggctca tgacctagcg ttggctctgg 60
cctggtgtct cgtagccgac gggtgacttc gccgcacgag cagtagtctg catgcccagg 120
tggttaggca acacggctag cggcagatcg cagtgaaagg gtgcggtgca cggttgcatc 180
tgttacggga agcgacgaca tcgctttctc gaggctctgc tgggagtaac aagttcaccg 240
cgaaatgcat ttttgctctc acgcaatata ttagtagccc gcacctgcct agcaccttta 300
agtgatcgcc acttgtcctt cccgttccac ccatgcattg attagcaata cacaaggcaa 360
cacaggacga ccaccctctc agcgcatgag tgcaacagca taatttctcc ctctcgccgc 420
aacagagatt gctgcgacca gaaaaacatc acagcgatta gcgatactcg tctccacata 480

<210> SEQ ID NO 194
<211> LENGTH: 451
<212> TYPE: DNA
<213> ORGANISM: Unknown
<220> FEATURE:
<223> OTHER INFORMATION: Kingdom: Archaea, Phylum: Euryarchaeota, Class: Archaeoglobi, Order: Archaeoglobales, Family: Archaeoglobaceae, Genus: Ferroglobus

<400> SEQUENCE: 194
tgagcgagag cgagcggagc ggtaggttgc gcaaggctag gtcttgaagt atctgtgcta 60
ataggcgata gattttgcat atgcgatatt gcgctcgctg cgaacatcgt ccatcgccgg 120
catcgtcgaa aagctgaacc cgctcctaca cctcgacccc gtcgtatacc tcccgcccga 180
actgaccttc cagatcctct cgtacctaga tcccgaaata ctattacgcg catcgacgct 240
gtcacgagca tggagggaga gggtgctgga cagccccctg tggaagctgc tgtttagatt 300
agaaggctgg aactctaact tcccgcaagt gcgcgcatac gaggacgctc agaggcagaa 360
gcgcgcagag ttcaaggaga aggagcgtaa gacgcgacat cgtgcagccg aagacacgga 420
ctacggcaag ccatcgcaca agaagcgtgt a 451

<210> SEQ ID NO 195
<211> LENGTH: 595
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 195
agtttgatca ttcagattga acgctggcgg catgcttaac acatgcaagt cgaacggcag 60

```
cacagcagag cttgctctgt gggtggcgag tggcggacgg gtgagtaatg catcgggacc    120

tacccagacg tgggggataa cgtagggaaa cttacgctaa taccgcatac gtcctacggg    180

agaaagcggg ggatcgcaag acctcgcgcg gttggatgga ccgatgtgcg attagctagt    240

tggtaaggta acggcttacc aaggcgacga tcgctagctg gtctgagagg atgatcagcc    300

acactgggac tgagacacgg cccagactcc tacgggaggc agcagtgggg aatattggac    360

aatgggcgca agcctgatcc agcaatgccg cgtgtgtgaa gaaggccctc gggttgtaaa    420

gcacttttat caggagcgaa atctgcaagg ttaatacctt tgcagtctga cggtacctga    480

ggaataagca ccggctaact ccgtgccagc agccgcggta atacggaggg tgcaagcgtt    540

aatcggaatt actgggcgta aagcgtgcgt aggcggttcg ttaagtctgt tgtga         595
```

<210> SEQ ID NO 196
<211> LENGTH: 572
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 196

```
ttcgatgcaa cgcgaagaac cttacctggc cttgacatgt ccggaatcca gcagagatgc     60

aggagtgcct tcgggaatcg gaacacaggt gctgcatggc tgtcgtcagc tcgtgtcgtg    120

agatgttggg ttaagtcccg caacgagcgc aacccttgtc cttagttgcc agcgagtaat    180

gtcgggaact ctaaggagac tgccggtgac aaaccggagg aaggtgggga tgacgtcaag    240

tcatcatggc ccttacggcc agggctacac acgtactaca atggtcggta cagagggttg    300

cgataccgcg aggtggagct aatcccagaa agccgatccc agtccggatt ggagtctgca    360

actcgactcc atgaagtcgg aatcgctagt aatcgcagat cagctatgct gcggtgaata    420

cgttcccggg ccttgtacac accgcccgtc acaccatggg agtgagctgc tccagaagcc    480

gttagtctaa ccgcaagggg gacgacgacc acggagtggt tcatgactgg ggtgaagtcg    540

taacaagggc gaattccaca gtggatatca ag                                  572
```

<210> SEQ ID NO 197
<211> LENGTH: 630
<212> TYPE: DNA
<213> ORGANISM: Unknown
<220> FEATURE:
<223> OTHER INFORMATION: Kingdom: Archaea, Phylum: Nanohaloarchaeota, Class: Nanohaloarchaea, Order: Incertae sedis, Family: Incertae sedis, Genus: Candidatus Haloredivivus

<400> SEQUENCE: 197

```
agtttgatca tggctcagat tgcagctgca aagctcgaga agaataatta cctcgaagta     60

ccatgtcgtt ctcgcactac tccagagatg caagatatca agcacctgca gagtgcccta    120

gactattccc tctactgtta gaccaaccgt taagcggctc atgacctagc gttggctctg    180

gcctggtgtc tcgtagccga cgggtgactt cgccgcacga gcagtagtct gcatgcccag    240

gtggttaggc aacacggcta gcggcagatc gcagtgaaag ggtgcggtgc acggttgcat    300

ctgttacggg aagcgacgac atcgctttct cgaggctctg ctgggagtaa caagttcacc    360

gcgaaatgca tttttgctct cacgcaatat attagtagcc cgcacctgcc tagcaccttt    420

aagtgatcgc cacttgtcct tcccgttcca cccatgcatt gattagcaat acacaaggca    480
```

acacaggacg accaccctct cagcgcatga gtgcaacagc ataatttctc cctctcgccg 540
caacagagat tgctgcgacc agaaaaacat cacagcgatt agcgatactc gtctccacat 600
aacttaaccc accgcgcgcg caccacaatg 630

<210> SEQ ID NO 198
<211> LENGTH: 630
<212> TYPE: DNA
<213> ORGANISM: Unknown
<220> FEATURE:
<223> OTHER INFORMATION: Kingdom: Archaea, Phylum: Euryarchaeota, Class: Archaeoglobi, Order: Archaeoglobales, Family: Archaeoglobaceae, Genus: Ferroglobus

<400> SEQUENCE: 198
ggagtcatcg tccagcctac ccgattgggt cctggctctg agcgagagcg agcggagcgg 60
taggttgcgc aaggctaggt cttgaagtat ctgtgctaat aggcgataga ttttgcatat 120
gcgatattgc gctcgctgcg aacatcgtcc atcgccggca tcgtcgaaaa gctgaacccg 180
ctcctacacc tcgaccccgt cgtatacctc ccgcccgaac tgaccttcca gatcctctcg 240
tacctagatc ccgaaatact attacgcgca tcgacgctgt cacgagcatg gagggagagg 300
gtgctggaca gccccctgtg gaagctgctg tttagattag aaggctggaa ctctaacttc 360
ccgcaagtgc gcgcatacga ggacgctcag aggcagaagc gcgcagagtt caaggagaag 420
gagcgtaaga cgcgacatcg tgcagccgaa gacacggact acggcaagcc atcgcacaag 480
aagcgtgtac gggagcggca gctgtttggc gagggctcag catcggagag tggtatacat 540
aacacgctag aaccgctgtc tattgaaggc tctaccggga atgcctgggg tgaagtcgta 600
acaagggcga attccacagt ggatatcaag 630

<210> SEQ ID NO 199
<211> LENGTH: 638
<212> TYPE: DNA
<213> ORGANISM: Unknown
<220> FEATURE:
<223> OTHER INFORMATION: Kingdom: Bacteria, Phylum: Actinobacteria, Class: Actinobacteria, Order: Actinomycetales, Family: Propionibacteriaceae, Genus: Propionibacterium

<400> SEQUENCE: 199
gaacgtattc accgcagcgt tgctgatctg cgattactag cgactccgac ttcatgaggt 60
cgagttgcag accccaatcc gaactgagac cggctttccg agattcactc accctcacag 120
gctcgccact ctctgtacca gccattgtag catgcgtgaa gccctggaca taaggggcat 180
gatgacttga cgtcatcccc accttcctcc gagttgaccc cggcggtctc cactgagtcc 240
ccaccataac gtgctggcaa cagtgaacaa gggttgcgct cgttgcggga cttaacccaa 300
catctcacga cacgagctga cgacagccat gcaccacctg tgaaccgacc ccaaaagagg 360
cacacccatc tctgagcact cccgatccat gtcaaaccca ggtaaggttc tacgcgttgc 420
atcgaattaa tccgcatgct ccgccgcttg tgcggggccc cgtcaattcc tttgagtttt 480
agccttgcgg ccgtactccc caggcggggt acttaaagcg ttagctacgg cacggaaccc 540
gtggaatgga ccccacacct agtacccacc gtttacagcg tggactacca gggtatctaa 600
gcctgttcgc tccccacgct ttcgctcctc agcgtcag 638

<210> SEQ ID NO 200
<211> LENGTH: 494
<212> TYPE: DNA
<213> ORGANISM: Unknown

<220> FEATURE:
<223> OTHER INFORMATION: Kingdom: Bacteria, Phylum: Proteobacteria, Class: Alphaproteobacteria, Order: Rhizobiales, Family: Bradyrhizobiaceae, Genus: Bradyrhizobium

<400> SEQUENCE: 200
agagtttgat cctggctcag agcgaacgct ggcggcaggc ttaacacatg caagtcgagc 60
gggcatagca atatgtcagc ggcagacggg tgagtaacgc gtgggaacgt accttttggt 120
tcggaacaac acagggaaac ttgtgctaat accggataag cccttacggg gaaagattta 180
tcgccgaaag atcggcccgc gtctgattag ctagttggtg aggtaatggc tcaccaaggc 240
gacgatcagt agctggtctg agaggatgat cagccacatt gggactgaga cacggcccaa 300
actcctacgg gaggcagcag tggggaatat tggacaatgg gcgcaagcct gatccagcca 360
tgccgcgtga gtgatgaagg ccctagggtt gtaaagctct tttgtgcggg aagataatga 420
cggtaccgca agaataagcc ccggctaact tcgtgccagc agccgcggta atacgaaggg 480
ggctagcatt gctc 494

<210> SEQ ID NO 201
<211> LENGTH: 627
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Bradyrhizobiaceae, Genus: Bradyrhizobium

<400> SEQUENCE: 201
ttcgacgcaa cgcgcagaac cttaccagcc cttgacatcc cggtcgcgga ctccagagac 60
ggagttcttc agttcggctg gaccggagac aggtgctgca tggctgtcgt cagctcgtgt 120
cgtgagatgt tgggttaagt cccgcaacga gcgcaacccc cgtccttagt tgctaccatt 180
tagttgagca ctctaaggag actgccggtg ataagccacg aggaaggtgg gtatgacgtc 240
aagtcctcat ggcccttacg ggctgggcta cacacgtgct acaatggcgg tgacaatggg 300
atgctaaggg gcgacccttc gcaaatctca aaaagccgtc tcagttcgga ttgggctctg 360
caactcgagc ccatgaagtt ggaatcgcta gtaatcgtgg atcagcacgc cacggtgaat 420
acgttcccgg gccttgtaca caccgcccgt cacaccatgg gagttggttt tacctgaaga 480
cggtgcgcta accgaaaggg ggcagccggc cacggtaggg tcagcgactg gggtgaagtc 540
gtaacaaggt aaccaagggc gaattccaca gtggatatca agcttatcga taccgtcgac 600
ctcgaggggg ggcccggtac ccagctt 627

<210> SEQ ID NO 202
<211> LENGTH: 493
<212> TYPE: DNA
<213> ORGANISM: Unknown
<220> FEATURE:
<223> OTHER INFORMATION: Kingdom: Bacteria, Phylum: Firmicutes, Class: Bacilli, Order: Lactobacillales, Family: Streptococcaceae, Genus: Streptococcus

<400> SEQUENCE: 202
agagtttgat cctggctcag gacgaacgct ggcggcgtgc ctaatacatg caagtagaac 60
gctgaaggag gagcttgctc ttctggatga gttgcgaacg ggtgagtaac gcgtaggtaa 120
cctgcctggt agcgggggat aactattgga aacgatagct aataccgcat aagagtagat 180
gttgcatgac atttacttaa aaggtgcaat tgcatcacta ccagatggac ctgcgttgta 240

```
ttagctagtt ggtgggataa cggctcacca aggcgacgat acatagccga cctgagaggg    300

tgatcggcca cactgggact gagacacggc ccagactcct acgggaggca gcagtaggga    360

atcttcggca atggacggaa gtctgaccga gcaacgccgc gtgagtgaag aaggttttcg    420

gatcgtaaag ctctgttgta agagaagaac gagtgtgaga gtggaaagtt cacactgtga    480

cggtatctta cca                                                       493


<210> SEQ ID NO 203
<211> LENGTH: 660
<212> TYPE: DNA
<213> ORGANISM: Unknown
<220> FEATURE:
<223> OTHER INFORMATION: Kingdom: Bacteria, Phylum: Firmicutes, Class:
      Bacilli, Order: Lactobacillales, Family: Streptococcaceae, Genus:
      Streptococcus

<400> SEQUENCE: 203

tgacgggggc ccgcacaagc ggtggagcat gtggtttaat tcgaagcaac gcgaagaacc     60

ttaccaggtc ttgacatccc tctgaccgct ctagagatag agctttcctt cgggacagag    120

gtgacaggtg gtgcatggtt gtcgtcagct cgtgtcgtga gatgttgggt taagtcccgc    180

aacgagcgca acccctattg ttagttgcca tcattcagtt gggcactcta gcgagactgc    240

cggtaataaa ccggaggaag gtggggatga cgtcaaatca tcatgcccct tatgacctgg    300

gctacacacg tgctacaatg gctggtacaa cgagtcgcaa gccggtgacg gcaagctaat    360

ctcttaaagc cagtctcagt tcggattgta ggctgcaact cgcctacatg aagtcggaat    420

cgctagtaat cgcggatcag cacgccgcgg tgaatacgtt cccgggcctt gtacacaccg    480

cccgtcacac cacgagagtt tgtaacaccc gaagtcggtg aggtaaccgt aaggagccag    540

ccgcctaagg tgggatagat gattggggtg aagtcgtaac aaggtaacca agggcgaatt    600

ccacagtgga tatcaagctt atcgataccg tcgacctcga ggggggggccc ggtacccagc    660


<210> SEQ ID NO 204
<211> LENGTH: 594
<212> TYPE: DNA
<213> ORGANISM: Unknown
<220> FEATURE:
<223> OTHER INFORMATION: Kingdom: Bacteria, Phylum: Firmicutes, Class:
      Bacilli, Order: Lactobacillales, Family: Streptococcaceae, Genus:
      Streptococcus
<220> FEATURE:
<221> NAME/KEY: misc_feature
<222> LOCATION: (565)..(565)
<223> OTHER INFORMATION: n is a, c, g, or t

<400> SEQUENCE: 204

agagtttgat cctggctcag gacgaacgct ggcggcgtgc ctaatacatg caagtagaac     60

gctgaaggag gagcttgctc ttctggatga gttgcgaacg ggtgagtaac gcgtaggtaa    120

cctgcctggt agcgggggat aactattgga aacgatagct aataccgcat aagagtagat    180

gttgcatgac atttacttaa aaggtgcaat tgcatcacta ccagatggac ctgcgttgta    240

ttagctagtt ggtgggataa cggctcacca aggcgacgat acatagccga cctgagaggg    300

tgatcggcca cactgggact gagacacggc ccagactcct acgggaggca gcagtaggga    360

atcttcggca atggacggaa gtctgaccga gcaacgccgc gtgagtgaag aaggttttcg    420

gatcgtaaag ctctgttgta agagaagaac gagtgtgaga gtggaaagtt cacactgtga    480

cggtatctta ccagaaaggg acggctaact acgtgccagc agccgcggta atacgtaggt    540

cccgagcgtt gtccggattt attangcgta aagcgagcgc aggcggttag ataa          594
```

<210> SEQ ID NO 205
<211> LENGTH: 730
<212> TYPE: DNA
<213> ORGANISM: Unknown
<220> FEATURE:
<223> OTHER INFORMATION: Kingdom: Bacteria, Phylum: Firmicutes, Class: Bacilli, Order: Lactobacillales, Family: Streptococcaceae, Genus: Streptococcus

<400> SEQUENCE: 205
tagtgccgta gctaacgcat taagcactcc gcctggggag tacgaccgca aggttgaaac 60
tcaaaggaat tgacgggggc ccgcacaagc ggtggagcat gtggtttaat tcgaagcaac 120
gcgaagamcc ttaccaggtc ttgacatccc tctgaccgct ctagagatag agctttcctt 180
cgggacagag gtgacaggtg gtgcatggtt gtcgtcagct cgtgtcgtga gatgttgggt 240
taagtcccgc aacgagcgca acccctattg ttagttgcca tcattcagtt gggcactcta 300
gcgagactgc cggtaataaa ccggaggaag gtggggatga cgtcaaatca tcatgcccct 360
tatgacctgg gctacacacg tgctacaatg gctggtacaa cgagtcgcaa gccggtgacg 420
gcaagctaat ctcttaaagc cagtctcagt tcggattgta ggctgcaact cgcctacatg 480
aagtcggaat cgctagtaat cgcggatcag cacgccgcgg tgaatacgtt cccgggcctt 540
gtacacaccg cccgtcacac cacgagagtt tgtaacaccc gaagtcggtg aggtaaccgt 600
aaggagccag ccgcctaagg tgggatagat gattggggtg aagtcgtaac aaggtaacca 660
agggcgaatt ccacagtgga tatcaagctt atcgataccg tcgacctcga ggggggggcc 720
ggtacccagc 730

<210> SEQ ID NO 206
<211> LENGTH: 857
<212> TYPE: DNA
<213> ORGANISM: Unknown
<220> FEATURE:
<223> OTHER INFORMATION: Kingdom: Bacteria, Phylum: candidate division WPS-2, Class: Incertae sedis, Order: Incertae sedis, Family: Incertae sedis, Genus: WPS-2 genera incertae sedis

<400> SEQUENCE: 206
catctatttg ccgtttgcac agcaggatcc tgtcgcaagt ggcatggggc taggattgtc 60
gctggtgaag cgcaatgttg atagccttgg aggcacagtc gatattgaga ccgatcaggc 120
ttttggcacc acggcaacaa tctctcttcg gactagggat attgtcgcgg aaacggacac 180
gcacttagag gccgacagca aaagtcaaat tcccgcagga atcataccat caatgccgaa 240
gcgaccaaaa gacagtttgc ctgtcatgca cgcctgcttt tacgctccaa gcacgtggct 300
acatcgccac gacaagaggg atgagcgatc cattgatctg gtattcgact cgctggccag 360
cacactgggc gagtggtacc agccggtact cagcctatgg caacgccaga agaagcatac 420
tatcccggat ttgatcttca tcagccaacg gaacttggca gagttcaagg aggaatgcgg 480
aaaagagttc gccaatgtca agaaagttgt gatctgcgcc gcgattggca agaacagctc 540
acaagatcga gagaggatac gtcaggcttc gactgttgca gatgctctga tcacgggtgc 600
ggtgttgccg tcgaagctct gggaagttgt tacgagctac tttccacgaa ttcttcagcc 660
tgaggcctct gctgacgacc agacacgcaa caacaagaac actggcatcc ggcccaagtc 720
cctgggctcc gatgaatcga gagaggcggt caatgaacaa aagaaggaca gtgacagctt 780
gcccagacat gtgcttccgg agcatgatct tgagaatgaa cagtcgtccc ataacgacag 840

-continued tgataagcag gtccccg 857

<210> SEQ ID NO 207
<211> LENGTH: 627
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Bradyrhizobiaceae, Genus: Afipia

<400> SEQUENCE: 207
ggttaccttg ttacgacttc accccagtcg ctgaccctac cgtggtcagc tgcccccctt 60
gcgggttagc gcactgcctt caggtagaac caactcccat ggtgtgacgg gcggtgtgta 120
caaggcccgg gaacgtattc accgtggcat gctgatccac gattactagc gattccaact 180
tcatgggctc gagttgcaga gcccaatccg aactgagacg gctttttgag atttgcgagg 240
ggtcgcccct ttgcatccca ttgtcaccgc cattgtagca cgtgtgtagc ccagcccgta 300
agggccatga ggacttgacg tcatccccac cttcctcgcg gcttatcacc ggcagtctcc 360
ttagagtgct caactaaatg gtagcaacta aggacggggg ttgcgctcgt tgcgggactt 420
aacccaacat ctcacgacac gagctgacga caaccatgca gcacctgtgc tctatgcccc 480
gaagggaagg ctccatctct ggtgccggtc atagacatgt caagggctgg taaggttctg 540
cgcgttgcgt cgaattaaac cacatgctcc accgcttgtg cgggcccccg tcaattcctt 600
tgagttttaa tcttgcgacc gtactcc 627

<210> SEQ ID NO 208
<211> LENGTH: 616
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Bradyrhizobiaceae, Genus: Rhodopseudomonas
<220> FEATURE:
<221> NAME/KEY: misc_feature
<222> LOCATION: (20)..(20)
<223> OTHER INFORMATION: n is a, c, g, or t

<400> SEQUENCE: 208
ctctgactta aaaacccgcn tacgcaccct ttacgcccag tgattccgag caacgctagc 60
ccccttcgta ttaccgcggc tgctggcacg aagttagccg gggcttattc ttacggtacc 120
gtcattatct tcccgtacaa aagagcttta caaccctagg gccttcatca ctcacgcggc 180
atggctggat caggcttgcg cccattgtcc aatattcccc actgctgcct cccgtaggag 240
tttgggccgt gtctcagtcc caatgtggct gatcatcctc tcagaccagc tactgatcgt 300
cgccttggta ggccattacc ctaccaacta gctaatcaga cgcgggccga tctttcggcg 360
ataaatcttt ccccgttagg gcttatccgg tattagctga agtttccctc agttgttccg 420
aaccaaaagg tacgttccca cgcgttactc acccgtctgc cactgacacc gaagtgcccg 480
ttcgacttgc atgtgttaag cctgccgcca gcgttcgctc tgagccagga tcaaactcta 540
agggcgaatt ccacagtgga tatcaagctt atcgataccg tcgacctcga ggggggggcc 600
ggtacccagc tttgtc 616

<210> SEQ ID NO 209
<211> LENGTH: 660
<212> TYPE: DNA
<213> ORGANISM: Unknown

<220> FEATURE:
<223> OTHER INFORMATION: Kingdom: Bacteria, Phylum: Firmicutes, Class: Bacilli, Order: Lactobacillales, Family: Streptococcaceae, Genus: Streptococcus

<400> SEQUENCE: 209
agagtttgat cctggctcag gacgaacgct ggcggcgtgc ctaatacatg caagtagaac 60
gctgaagaga ggagcttgct cttcttggat gagttgcgaa cgggtgagta acgcgtaggt 120
aacctgcctt gtagcggggg ataactattg gaaacgatag ctaataccgc ataacaatgg 180
atgacacatg tcatttattt gaaaggggca attgctccac tacaagatgg acctgcgttg 240
tattagctag taggtgaggt aacggctcac ctaggcgacg atacatagcc gacctgagag 300
ggtgatcggc cacactggga ctgagacacg gcccagactc ctacgggagg cagcagtagg 360
gaatcttcgg caatgggggc aaccctgacc gagcaacgcc gcgtgagtga agaaggtttt 420
cggatcgtaa agctctgttg taagtcaaga acgagtgtga gagtggaaag ttcacactgt 480
gacggtagct taccagaaag ggacggctaa ctacgtgcca gcagccgcgg taatacgtag 540
gtcccgagcg ttgtccggat ttattgggcg taaagcgagc gcaggcggtt tgataagtct 600
gaagttaaag gctgtggctc aaccatagtt cgctttggaa actgtcaaac ttgagtgcag 660

<210> SEQ ID NO 210
<211> LENGTH: 664
<212> TYPE: DNA
<213> ORGANISM: Unknown
<220> FEATURE:
<223> OTHER INFORMATION: Kingdom: Bacteria, Phylum: Firmicutes, Class: Bacilli, Order: Lactobacillales, Family: Streptococcaceae, Genus: Streptococcus

<400> SEQUENCE: 210
acgggggccc gcacaagcgg tggagcatgt ggtttaattc gaagcaacgc gaagaacctt 60
accaggtctt gacatcccga tgctatttct agagatagaa agttacttcg gtacatcggt 120
gacaggtggt gcatggttgt cgtcagctcg tgtcgtgaga tgttgggtta agtcccgcaa 180
cgagcgcaac ccctattgtt agttgccatc attcagttgg gcactctagc gagactgccg 240
gtaataaacc ggaggaaggt ggggatgacg tcaaatcatc atgcccctta tgacctgggc 300
tacacacgtg ctacaatggt tggtacaacg agttgcgagt cggtgacggc aagctaatct 360
cttaaagcca atctcagttc ggattgtagg ctgcaactcg cctacatgaa gtcggaatcg 420
ctagtaatcg cggatcagca cgccgcggtg aatacgttcc cgggccttgt acacaccgcc 480
cgtcacacca cgagagtttg taacacccga agtcagtgag gtaacctttt ggagccagcc 540
gcctaaggtg ggatagatga ttggggtgaa gtcgtaacaa ggtaaccaag ggcgaattcc 600
acagtggata tcaagcttat cgataccgtc gacctcgagg gggggcccgg tacccagctt 660
tgtc 664

<210> SEQ ID NO 211
<211> LENGTH: 716
<212> TYPE: DNA
<213> ORGANISM: Unknown
<220> FEATURE:
<223> OTHER INFORMATION: Kingdom: Bacteria, Phylum: Cyanobacteria, Class: Incertae sedis, Order: Incertae sedis, Family: Incertae sedis, Genus: Incertae sedis

<400> SEQUENCE: 211
ggttaccttg ttacgacttc actccagtca ctagccctgc cttcggcatc ccccccttg 60

```
tggttaaggt aacgacttcg ggcatggcca gcttccatag tgtgacgggc ggtgtgtaca    120

aggcccggga acgaattcac cgccgtatgg ctgaccggcg attactagcg attccgactt    180

catgcaggcg agttgcagcc tgtaatccga actgaggaca ggtttttgaa gttagctcac    240

cctcgcggga ttgcgatcct ttgtcccgcc cattgtagca cgtgtgtcgc ccagggcata    300

aggggcatga tgacttgacg tcatcctcac cttcctccgg cttatcaccg gcagtctgct    360

cagggttcca aacctaacgg tggcaactaa acacgagggt tgcgctcgtt gcgggactta    420

acccaacacc ttacggcacg agctgacgac agccatgcac cacctgtgtc cgcgttcccg    480

aaggcacccc tctctttcaa gaggattcgc ggcatgtcaa gccctggtaa ggttcttcgc    540

tttgcatcga attaaaccac atgctccacc gcttgtgcgg gcccccgtca attcctttga    600

gtttcattct tgcgaacgta ctccccaggc gggatactta acgcgttagc tacagcactg    660

cacgggtcgg tatacgcaca gcgcctagta tccatcgttt acggctagga ctactg        716
```

<210> SEQ ID NO 212
<211> LENGTH: 652
<212> TYPE: DNA
<213> ORGANISM: Unknown
<220> FEATURE:
<223> OTHER INFORMATION: Kingdom: Bacteria, Phylum: Cyanobacteria, Class: Incertae sedis, Order: Incertae sedis, Family: Incertae sedis, Genus: Incertae sedis

<400> SEQUENCE: 212

```
caccggaaat tccctctgcc cctaccgtac tccagcttag tagtttccac cgcctgtcca     60

gggttgagcc ctgggatttg acggcggact taaaaagcca cctacagacg ctttacgccc    120

aatcattccg gataacgctt gcatcctctg tcttaccgcg gctgctggca cagagttagc    180

cgatgcttat tccccagata ccgtcattgt ttcttctctg ggaaaagaag ttcacgaccc    240

gtgggccttc tacctccacg cggcattgct ccgtcaggct ttcgcccatt gcggaaaatt    300

ccccactgct gcctcccgta ggagtctggg ccgtgtctca gtcccagtgt ggctgatcat    360

cctctcggac cagctactga tcatcgcctt ggtaagctat tacctcacca actagctaat    420

cagacgcgag cccctcctca ggcggattcc tccttttgct cctcagccta cggggtatta    480

gcagccgttt ccagctgttg ttcccctccc aagggcaggt tcttacgcgt tactcacccg    540

tccgccactg gaaacaccac ttcccgtccg acttgcatgt gttaagcatg ccgccagcgt    600

tcatcctgag ccaggatcaa actctaaggg cgaattccac agtggatatc aa            652
```

<210> SEQ ID NO 213
<211> LENGTH: 627
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Pseudomonadales, Family: Pseudomonadaceae, Genus: Pseudomonas

<400> SEQUENCE: 213

```
agagtttgat cctggctcag attgaacgct ggcggcaggc ctaacacatg caagtcgagc     60

ggatgagaag agcttgctct tcgattcagc ggcggacggg tgagtaatac ctaggaatct    120

gcctggtagt gggggacaac gtttcgaaag gaacgctaat accgcatacg tcctacggga    180

gaaagcaggg gaccttcggg ccttgcgcta tcagatgagc ctaggtcgga ttagctagtt    240

ggtgaggtaa tggctcacca aggcgacgat ccgtaactgg tctgagagga tgatcagtca    300

cactggaact gagacacggt ccagactcct acgggaggca gcagtgggga atattggaca    360
```

```
atgggcgaaa gcctgatcca gccatgccgc gtgtgtgaag aaggtcttcg gattgtaaag    420

cactttaagt tgggaggaag ggcagtaagc taataccttg ctgttttgac gttaccgaca    480

gaataagcac cggctaactc tgtgccagca gccgcggtaa tacagagggt gcaagcgtta    540

atcggaatta ctgggcgtaa agcgcgcgta ggtggttcgt taagttggat gtgaaatccc    600

cgggctcaac ctgggaactg catccaa                                        627


<210> SEQ ID NO 214
<211> LENGTH: 662
<212> TYPE: DNA
<213> ORGANISM: Unknown
<220> FEATURE:
<223> OTHER INFORMATION: Kingdom: Bacteria, Phylum: Proteobacteria,
      Class: Gammaproteobacteria, Order: Pseudomonadales, Family:
      Pseudomonadaceae, Genus: Pseudomonas

<400> SEQUENCE: 214

cgcctgggga gtacggccgc aaggttaaaa ctcaaatgaa ttgacggggg cccgcacaag     60

cggtggagca tgtggtttaa ttcgaagcaa cgcgaagaac cttaccaggc cttgacatgc    120

agagaacttt ccagagatgg attggtgcct tcgggaactc tgacacaggt gctgcatggc    180

tgtcgtcagc tcgtgtcgtg agatgttggg ttaagtcccg taacgagcgc aacccttgtc    240

cttagttacc agcacgttat ggtgggcact ctaaggagac tgccggtgac aaaccggagg    300

aaggtgggga tgacgtcaag tcatcatggc ccttacggcc tgggctacac acgtgctaca    360

atggtcggta cagagggttg ccaagccgcg aggtggagct aatctcacaa aaccgatcgt    420

agtccggatc gcagtctgca actcgactgc gtgaagtcgg aatcgctagt aatcgcgaat    480

cagaatgtcg cggtgaatac gttcccgggc cttgtacaca ccgcccgtca caccatggga    540

gtgggttgca ccagaagtag ctagtctaac cttcgggagg acggttacca cggtgtgatt    600

catgactggg gtgaagtcgt aacaaggtaa ccaagggcga attccacagt ggatatcaag    660

ct                                                                   662


<210> SEQ ID NO 215
<211> LENGTH: 651
<212> TYPE: DNA
<213> ORGANISM: Unknown
<220> FEATURE:
<223> OTHER INFORMATION: Kingdom: Bacteria, Phylum: Firmicutes, Class:
      Bacilli, Order: Lactobacillales, Family: Lactobacillaceae, Genus:
      Lactobacillus

<400> SEQUENCE: 215

agagtttgat cctggctcag gacgaacgct ggcggcgtgc ctaatacatg caagtcgagc     60

gagtctgcct tgaagatcgg agtgcttgca ctctgtgaaa caagatacag gctagcggcg    120

gacgggtgag taacacgtgg gtaacctgcc caagagatcg ggataacacc tggaaacaga    180

tgctaatacc ggataacaac agatgatgcc tatcaactgt ttaaaagatg gttctgctat    240

cactcttgga tggacctgcg gtgcattagc tagttggtag ggtaacggcc taccaaggcg    300

atgatgcata gccgagttga gagactgatc ggccacattg ggactgagac acggcccaaa    360

ctcctacggg aggcagcagt agggaatctt ccacaatgga cgcaagtctg atggagcaac    420

gccgcgtgag tgaagaaggg tttcggctcg taaagctctg ttgttggtga agaaggacag    480

ggtagtaac tgacctttgt ttgacggtaa tcaattagaa agtcacggct aactacgtgc    540

cagcagccgc ggtaatacgt aggtggcaag cgttgtccgg atttattggg cgtaaagcga    600
```

gtgcaggcgg ctcgataagt ctgatgtgaa agccttcggc tcaaccggag a 651

<210> SEQ ID NO 216
<211> LENGTH: 666
<212> TYPE: DNA
<213> ORGANISM: Unknown
<220> FEATURE:
<223> OTHER INFORMATION: Kingdom: Bacteria, Phylum: Firmicutes, Class: Bacilli, Order: Lactobacillales, Family: Lactobacillaceae, Genus: Lactobacillus

<400> SEQUENCE: 216
tgacgggggc ccgcacaagc ggtggagcat gtggtttaat tcgaagcaac gcgaagaacc 60
ttaccaggtc ttgacatcca tagccagtct aagagattag atgttccctt cggggactat 120
gagacaggtg gtgcatggct gtcgtcagct cgtgtcgtga gatgttgggt taagtcccgc 180
aacgagcgca acccttgtca ttagttgcca gcattaagtt gggcactcta atgagactgc 240
cggtgacaaa ccggaggaag gtggggatga cgtcaagtca tcatgcccct tatgacctgg 300
gctacacacg tgctacaatg gacggtacaa cgagaagcga ccctgtgaag gcaagcggat 360
ctctgaaagc cgttctcagt tcggattgca ggctgcaact cgcctgcatg aggctggaat 420
cgctagtaat cgcaaatcag cacgttgcgg tgaatacgtt cccgggcctt gtacacaccg 480
cccgtcacac catgagagtc tgtaacgccc gaagccggcg ggataaccaa aaggagtcag 540
ccgtctaagg cgggacagat gattagggtg aagtcgtaac aaggtaacca agggcgaatt 600
ccacagtgga tatcaagctt atcgataccg tcgacctcga ggggggggcc ggtacccagc 660
tttgtc 666

<210> SEQ ID NO 217
<211> LENGTH: 699
<212> TYPE: DNA
<213> ORGANISM: Unknown
<220> FEATURE:
<223> OTHER INFORMATION: Kingdom: Bacteria, Phylum: Cyanobacteria, Class: Incertae sedis, Order: Incertae sedis, Family: Incertae sedis, Genus: Incertae sedis

<400> SEQUENCE: 217
agagtttgat cctggctcag gatgaacgct ggcggcatgc ttaacacatg caagtcggac 60
gggaagtggt gtttccagtg gcggacgggt gagtaacgcg taagaacctg cccttgggag 120
gggaacaaca gctggaaacg gctgctaata ccccgtaggc tgaggagcaa aaggaggaat 180
ccgcctgagg aggggctcgc gtctgattag ctagttggtg aggtaatagc ttaccaaggc 240
gatgatcagt agctggtccg agaggatgat cagccacact gggactgaga cacggcccag 300
actcctacgg gaggcagcag tggggaattt tccgcaatgg gcgaaagcct gacggagcaa 360
tgccgcgtgg aggtagaagg cccacgggtc gtgaacttct tttcccagag aagaaacaat 420
gacggtatct ggggaataag catcggctaa ctctgtgcca gcagccgcgg taagacagag 480
gatgcaagcg ttatccggaa tgattgggcg taaagcgtct gtaggtggct ttttaagtcc 540
gccgtcaaat cccagggctc aaccctggac aggcggtgga aactactaag ctggagtacg 600
gtaggggcag agggaatttc cggtggagcg gtgaaatgcg tagagatcgg aaagaacacc 660
aacggcgaaa gcgctctgct gggccgacac tggcactga 699

<210> SEQ ID NO 218
<211> LENGTH: 702
<212> TYPE: DNA
<213> ORGANISM: Unknown

<220> FEATURE:
<223> OTHER INFORMATION: Kingdom: Bacteria, Phylum: Cyanobacteria, Class: Incertae sedis, Order: Incertae sedis, Family: Incertae sedis, Genus: Incertae sedis

<400> SEQUENCE: 218
gggagtacgt tcgcaagaat gaaactcaaa ggaattgacg ggggcccgca caagcggtgg 60
agcatgtggt ttaattcgat gcaaagcgaa gaaccttacc agggcttgac atgccgcgaa 120
tcctcttgaa agagaggggt gccttcggga acgcggacac aggtggtgca tggctgtcgt 180
cagctcgtgc cgtaaggtgt tgggttaagt cccgcaacga gcgcaaccct cgtgtttagt 240
tgccaccgtt aggtttggaa ccctgagcag actgccggtg ataagccgga ggaaggtgag 300
gatgacgtcc agtcatcatg ccccttatgc cctgggcgac acacgtgcta caatgggcgg 360
gacaaaggat cgcaatcccg cgagggtgag ctaacttcaa aaacctgtcc tcagttcgga 420
ttgcaggctg caactcgcct gcatgaagtc ggaatcgcta gtaatcgccg gtcagccata 480
cggcggtgaa ttcgttcccg ggccttgtac acaccgcccg tcacactatg gaagctggcc 540
atgcccgaag tcgttacctt aaccacaagg ggggggatgc cgaaggcagg gctagtgact 600
ggagtgaagt cgtaacaagg taaccaaggg cgaattccac agtggatatc aagcttatcg 660
ataccgtcga cctcgagggg gggcccggta cccagctttg tc 702

<210> SEQ ID NO 219
<211> LENGTH: 536
<212> TYPE: DNA
<213> ORGANISM: Unknown
<220> FEATURE:
<223> OTHER INFORMATION: Kingdom: Bacteria, Phylum: Firmicutes, Class: Bacilli, Order: Lactobacillales, Family: Streptococcaceae, Genus: Streptococcus

<400> SEQUENCE: 219
agagtttgat cctggctcag gacgaacgct ggcggcgtgc ctaatacatg caagtagaac 60
gctgaagaga ggagcttgct cttcttggat gagttgcgaa cgggtgagta acgcgtaggt 120
aacctgcctg gtagcggggg ataactattg gaaacgatag ctaataccgc atgaaattgc 180
ttatcgcatg ataattaatt gaaagatgca attgcatcac taccagatgg acctgcgttg 240
tattagctag ttggtgaggt aacggctcac caaggcgacg atacatagcc gacctgagag 300
ggtgatcggc cacactggga ctgagacacg gcccagactc ctacgggagg cagcagtagg 360
gaatcttcgg caatgggggg aaccctgacc gagcaacgcc gcgtgagtga agaaggtttt 420
cggatcgtaa agctctgttg taagagaaga acgggtgtga gagtggaaag ttcacactgt 480
gacggtatct taccagaaag ggacggctaa ctacgtgcca gcagccgcgg taatac 536

<210> SEQ ID NO 220
<211> LENGTH: 660
<212> TYPE: DNA
<213> ORGANISM: Unknown
<220> FEATURE:
<223> OTHER INFORMATION: Kingdom: Bacteria, Phylum: Firmicutes, Class: Bacilli, Order: Lactobacillales, Family: Streptococcaceae, Genus: Streptococcus

<400> SEQUENCE: 220
gggcccgcac aagcggtgga gcatgtggtt taattcgaag caacgcgaag aaccttacca 60
ggtcttgaca tccctctgac cgctctagag atagagtttt ccttcgggac agaggtgaca 120
ggtggtgcat ggttgtcgtc agctcgtgtc gtgagatgtt gggttaagtc ccgcaacgag 180

-continued

```
cgcaacccct attgttagtt gccatcattg agttgggcac tctagcgaga ctgccggtaa    240

taaaccggag gaaggtgggg atgacgtcaa atcatcatgc cccttatgac ctgggctaca    300

cacgtgctac aatggctggt acaacgagtc gcaagccggt gacggcaagc taatctctga    360

aagccagtct cagttcggat tgtaggctgc aactcgccta catgaagtcg gaatcgctag    420

taatcgcgga tcagcacgcc gcggtgaata cgttcccggg ccttgtacac accgcccgtc    480

acaccacgag agtttgtaac acccgaagtc ggtgaggtaa ccgtaaggag ccagccgcct    540

aaggtgggat agatgattgg ggtgaagtcg taacaaggta accaagggcg aattccacag    600

tggatatcaa gcttatcgat accgtcgacc tcgagggggg gcccggtacc cagctttgtc    660
```

```
<210> SEQ ID NO 221
<211> LENGTH: 688
<212> TYPE: DNA
<213> ORGANISM: Unknown
<220> FEATURE:
<223> OTHER INFORMATION: Kingdom: Bacteria, Phylum: Proteobacteria,
      Class: Alphaproteobacteria, Order: Rhizobiales, Family:
      Rhizobiaceae, Genus: Rhizobium

<400> SEQUENCE: 221

agagtttgat cctggctcag aacgaacgct ggcggcaggc ttaacacatg caagtcgagc     60

gccccgcaag gggagcggca gacgggtgag taacgcgtgg gaatctaccc ttttctacgg    120

aataacgcag ggaaacttgt gctaataccg tatgtgtcct tcgggagaaa gatttatcgg    180

gaaaggatga gcccgcgttg gattagctag ttggtggggt aaaggcctac caaggcgacg    240

atccatagct ggtctgagag gatgatcagc cacattggga ctgagacacg gcccaaactc    300

ctacgggagg cagcagtggg gaatattgga caatgggcgc aagcctgatc cagccatgcc    360

gcgtgagtga tgaaggccct agggttgtaa agctctttca ccggagaaga taatgacggt    420

atccggagaa gaagccccgg ctaacttcgt gccagcagcc gcggtaatac gaagggggct    480

agcgttgttc ggatttactg ggcgtaaagc gcacgtaggc ggatcgatca gtcaggggtg    540

aaatcccagg gctcaaccct ggaactgcct ttgatactgt cgatctggag tatggaagag    600

gtaagtggaa ttccgagtgt agaggtgaaa ttcgtagata ttcggaggaa caccagtggc    660

gaaggcggct tactggtcca ttactgac                                       688
```

```
<210> SEQ ID NO 222
<211> LENGTH: 643
<212> TYPE: DNA
<213> ORGANISM: Unknown
<220> FEATURE:
<223> OTHER INFORMATION: Kingdom: Bacteria, Phylum: Proteobacteria,
      Class: Alphaproteobacteria, Order: Rhizobiales, Family:
      Rhizobiaceae, Genus: Rhizobium

<400> SEQUENCE: 222

agcggtggag catgtggttt aattcgaagc aacgcgcaga accttaccag cccttgacat     60

cctgtgttac ccgtagagat atggggtcca cttcggtggc gcagagacag gtgctgcatg    120

gctgtcgtca gctcgtgtcg tgagatgttg ggttaagtcc cgcaacgagc gcaaccctcg    180

cccttagttg ccagcatcca gttgggcact ctaaggggac tgccggtgat aagccgagag    240

gaaggtgggg atgacgtcaa gtcctcatgg cccttacggg ctgggctaca cacgtgctac    300

aatggtggtg acagtgggca gcgagcacgc gagtgtgagc taatctccaa aagccatctc    360

agttcggatt gcactctgca actcgagtgc atgaagttgg aatcgctagt aatcgcggat    420

cagcatgccg cggtgagtac gttcccgggc cttgtacaca ccgcccgtca caccatggga    480
```

gttggtttta cccgaaggta gtgcgctaac cgcaaggagg cagctaacca cggtagggtc 540
agcgactggg gtgaagtcgt aacaaggtaa ccaagggcga attccacagt ggatatcaag 600
cttatcgata ccgtcgacct cgaggggggg cccggtaccc agc 643

<210> SEQ ID NO 223
<211> LENGTH: 662
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Rhizobiaceae, Genus: Rhizobium

<400> SEQUENCE: 223
agagtttgat cctggctcag aacgaacgct ggcggcaggc ttaacacatg caagtcgagc 60
gccccgcaag gggagcggca gacgggtgag taacgcgtgg gaatctaccc ttttctacgg 120
aataacgcag ggaaacttgt gctaataccg tatgtgtcct tcgggagaaa gatttatcgg 180
gaaaggatga gcccgcgttg gattagctag ttggtggggt aaaggcctac caaggcgacg 240
atccatagct ggtctgagag gatgatcagc cacattggga ctgagacacg gcccaaactc 300
ctacgggagg cagcagtggg gaatattgga caatgggcgc aagcctgatc cagccatgcc 360
gcgtgagtga tgaaggccct agggttgtaa agctctttca ccggagaaga taatgacggt 420
atccggagaa gaagccccgg ctaacttcgt gccagcagcc gcggtaatac gaagggggct 480
agcgttgttc ggatttactg ggcgtaaagc gcccgtaggc ggatcgatca gtcaggggtg 540
aaatcccagg gctcaaccct ggaactgcct ttgatactgt cgatctggag tatggaagag 600
gtaagtggaa ttccgagtgt agaggtgaaa ttcgtagata ttcggaggaa caccagtggc 660
ga 662

<210> SEQ ID NO 224
<211> LENGTH: 626
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Rhizobiaceae, Genus: Rhizobium

<400> SEQUENCE: 224
aaggaattga cgggggcccg cacaagcggt ggagcatgtg gtttaattcg aagcaacgcg 60
cagaacctta ccagcccttg acatcctgtg ttacccgtag agatatgggg tccacttcgg 120
tggcgcagag acaggtgctg catggctgtc gtcagctcgt gtcgtgagat gttgggctaa 180
gtcccgcaac gagcgcaacc ctcgccctta gttgccagca ttcagttggg cactctaagg 240
ggactgccgg tgataagccg agaggaaggt ggggatgacg tcaagtcctc atggccctta 300
cgggctgggc tacacacgtg ctacaatggt ggtgacagtg ggcagcgagc acgcgagtgt 360
gagctaatct ccaaaagcca tctcagttcg gattgcactc tgcaactcga gtgcatgaag 420
ttggaatcgc tagtaatcgc ggatcagcat gccgcggtga atacgttccc gggccttgta 480
cacaccgccc gtcacaccat gggagttggt tttacccgaa ggtagtgcgc taaccgcaag 540
gaggcagcta accacggtag ggtcagcgac tggggtgaag tcgtaacaag gtaaccaagg 600
gcgaattcca cagtggatat caagct 626

<210> SEQ ID NO 225

<211> LENGTH: 661
<212> TYPE: DNA
<213> ORGANISM: Unknown
<220> FEATURE:
<223> OTHER INFORMATION: Kingdom: Bacteria, Phylum: Firmicutes, Class: Bacilli, Order: Lactobacillales, Family: Streptococcaceae, Genus: Streptococcus

<400> SEQUENCE: 225
agagtttgat cctggctcag gacgaacgct ggcggcgtgc ctaacacatg caagtagaac 60
gctgaagaga ggagcttgct cttcttggat gagttgcgaa cgggtgagta acgcgtaggt 120
agcctgcctg gtagcggggg ataactattg gaaacgatag ctaataccgc atgaaattgc 180
ttatcgcatg ataattaatt gaaagatgca attgcatcac taccagatgg acctgcgttg 240
tattagctag ttggtgaggt aacggctcac caaggcgacg atacatagcc gacctgagag 300
ggtgatcggc cacactggga ctgagacacg gcccagactc ctacgggagg cagcagtagg 360
gaatcttcgg caatgggggg aaccctgacc gagcaacgcc gcgtgagtga agaaggtttt 420
cggatcgtaa agctctgttg taagagaaga acgggtgtga gagtggaaag ttcacactgt 480
gacggtatct taccagaaag ggacggctaa ctacgtgcca gcagccgcgg taatacgtag 540
gtcccgagcg ttgtccggat ttattgggcg taaagcgagc gcaggcggtt agataagtct 600
gaagttaaag gctgtggctt aaccatagta tgctttggaa actgtttaac ttgagtgcag 660
a 661

<210> SEQ ID NO 226
<211> LENGTH: 663
<212> TYPE: DNA
<213> ORGANISM: Unknown
<220> FEATURE:
<223> OTHER INFORMATION: Kingdom: Bacteria, Phylum: Firmicutes, Class: Bacilli, Order: Lactobacillales, Family: Streptococcaceae, Genus: Streptococcus

<400> SEQUENCE: 226
cgggggcccg cacaagcggt ggagcatgtg gtttaattcg aagcaacgcg aagaacctta 60
ccaggtcttg acatccctct gaccgctcta gagatagagt tttccttcgg gacagaggtg 120
acaggtggtg catggttgtc gtcagctcgt gtcgtgagat gttgggttaa gtcccgcaac 180
gagcgcaacc cctattgtta gttgccatca ttgagttggg cactctagcg agactgccgg 240
taataaaccg gaggaaggtg gggatgacgt caaatcatca tgccccttat gacctgggct 300
acacacgtgc tacaatggct ggtacaacga gtcgcaagcc ggtgacggca agctaatctc 360
tgaaagccag tctcagttcg gattgtaggc tgcaactcgc ctacatgaag tcggaatcgc 420
tagtaatcgc ggatcagcac gccgcggtga atacgttccc gggccttgta cacaccgccc 480
gtcacaccac gagagtttgt aacacccgaa gtcggtgagg taaccgtaag gagccagccg 540
cctaaggtgg gatagatgat tggggtgaag tcgtaacaag gtaaccaagg gcgaattcca 600
cagtggatat caagcttatc gataccgtcg acctcgaggg ggggcccggt acccagcttt 660
gtc 663

<210> SEQ ID NO 227
<211> LENGTH: 696
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Bradyrhizobiaceae, Genus: Bradyrhizobium

<400> SEQUENCE: 227
ggttaccttg ttacgacttc accccagtcg ctgaccctac cgtggccggc tgcccccttt 60
cggttagcgc accgtcttca ggtaaaacca actcccatgg tgtgacgggc ggtgtgtaca 120
aggcccggga acgtattcac cgtggcgtgc tgatccacga ttactagcga ttccaacttc 180
atgggctcga gttgcagagc ccaatccgaa ctgagacggc tttttgagat ttgcgaaggg 240
tcgcccctta gcatcccatt gtcaccgcca ttgtagcacg tgtgtagccc agcccgtaag 300
ggccatgagg acttgacgtc atccccacct tcctcgcggc ttatcaccgg cagtctcctt 360
agagtgctca actaaatggt agcaactaag gacgggggtt gcgctcgttg cgggacttaa 420
cccaacatct cacgacacga gctgacgaca gccatgcagc acctgtctcc ggtccagccg 480
aactgaagaa ctccgtctct ggagtccgcg accgggatgt caagggctgg taaggttctg 540
cgcgttgcgt cgaattaaac cacatgctcc accgcttgtg cgggcccccg tcaattcctt 600
tgagttttaa tcttgcgacc gtactcccca ggcggaatgc ttaaagcgtt agctgcgcca 660
ctagtgagta aacccactaa cggctggcat tcatcg 696

<210> SEQ ID NO 228
<211> LENGTH: 597
<212> TYPE: DNA
<213> ORGANISM: Unknown
<220> FEATURE:
<223> OTHER INFORMATION: Kingdom: Bacteria, Phylum: Proteobacteria,
Class: Alphaproteobacteria, Order: Rhizobiales, Family:
Bradyrhizobiaceae, Genus: Bradyrhizobium

<400> SEQUENCE: 228
ggcagttctg gagttgagct ccaggatttc accccctgact taaagacccg cctacgcacc 60
ctttacgccc agtgattccg agcaacgcta gccccccttcg tattaccgcg gctgctggca 120
cgaagttagc cggggcttat tcttgcggta ccgtcattat cttcccgcac aaaagagctt 180
tacaacccta gggccttcat cactcacgcg gcatggctgg atcaggcttg cgcccattgt 240
ccaatattcc ccactgctgc ctcccgtagg agtttgggcc gtgtctcagt cccaatgtgg 300
ctgatcaccc tctcagacca gctactgatc gtcgccttgg tgagccatta cctcaccaac 360
tagctaatca gacgcgggcc gatctttcgg cgataaatct ttccccgtaa gggcttatcc 420
ggtattagca caagtttccc tgtgttgttc cgaaccaaaa ggtacgttcc cacgcgttac 480
tcacccgtct gccgctgaca tattgctatg cccgctcgac ttgcatgtgt taagcctgcc 540
gccagcgttc gctctgagcc aggatcaaac tctaagggcg aattccacag tggatat 597

<210> SEQ ID NO 229
<211> LENGTH: 682
<212> TYPE: DNA
<213> ORGANISM: Unknown
<220> FEATURE:
<223> OTHER INFORMATION: Kingdom: Bacteria, Phylum: Proteobacteria,
Class: Alphaproteobacteria, Order: Rhizobiales, Family:
Rhizobiaceae, Genus: Rhizobium

<400> SEQUENCE: 229
ggttaccttg ttacgacttc accccagtcg ctgaccctac cgtggttagc tgcctccttg 60
cggttagcgc actaccttcg ggtaaaacca actcccatgg tgtgacgggc ggtgtgtaca 120
aggcccggga acgtattcac cgcggcatgc tgatccgcga ttactagcga ttccaacttc 180
atgcactcga gttgcagagt gcaatccgaa ctgagatggc ttttggagat tagctcacac 240

-continued

```
tcgcgtgctc gctgcccact gtcaccacca ttgtagcacg tgtgtagccc agcccgtaag    300

ggccatgagg acttgacgtc atccccacct tcctctcggc ttatcaccgg cagtcccctt    360

agagtgccca actgaatgct ggcaactaag ggcgagggtt gcgctcgttg cgggacttaa    420

cccaacatct cacgacacga gctgacgaca gccatgcagc acctgtctct gcgccaccga    480

agtggacccc atatctctac gggtaacaca ggatgtcaag ggctggtaag gttctgcgcg    540

ttgcttcgaa ttaaaccaca tgctccaccg cttgtgcggg cccccgtcaa ttcctttgag    600

ttttaatctt gcgaccgtac tccccaggcg gaatgtttaa tgcgttagct gcgccaccga    660

acagtatact gcccgacggc ta                                             682


<210> SEQ ID NO 230
<211> LENGTH: 662
<212> TYPE: DNA
<213> ORGANISM: Unknown
<220> FEATURE:
<223> OTHER INFORMATION: Kingdom: Bacteria, Phylum: Proteobacteria,
      Class: Alphaproteobacteria, Order: Rhizobiales, Family:
      Rhizobiaceae, Genus: Rhizobium

<400> SEQUENCE: 230

actccagatc gacagtatca aaggcagttc cagggttgag ccctgggatt tcacccctga     60

ctgatcgatc cgcctacgtg cgctttacgc ccagtaaatc cgaacaacgc tagccccctt    120

cgtattaccg cggctgctgg cacgaagtta gccggggctt cttctccgga taccgtcatt    180

atcttctccg gtgaaagagc tttacaaccc tagggccttc atcactcacg cggcatggct    240

ggatcaggct tgcgcccatt gtccaatatt ccccactgct gcctcccgta ggagtttggg    300

ccgtgtctca gtcccaatgt ggctgatcat cctctcagac cagctatgga tcgtcgcctt    360

ggtaggcctt taccccacca actagctaat ccaacgcggg ctcatccttt cccgataaat    420

ctttctcccg aaggacacat acggtattag cacaagtttc cctgcgttat tccgtagaaa    480

agggtagatt cccacgcgtt actcacccgt ctgccgctcc ccttgcgggg cgctcgactt    540

gcatgtgtta agcctgccgc cagcgttcgt tctgagccag gatcaaactc taagggcgaa    600

ttccacagtg gatatcaagc tgatcgatac cgtcgacctc gaggggggc ccggtaccca     660

gc                                                                   662


<210> SEQ ID NO 231
<211> LENGTH: 653
<212> TYPE: DNA
<213> ORGANISM: Unknown
<220> FEATURE:
<223> OTHER INFORMATION: Kingdom: Bacteria, Phylum: Proteobacteria,
      Class: Betaproteobacteria, Order: Burkholderiales, Family:
      Burkholderiaceae, Genus: Polynucleobacter

<400> SEQUENCE: 231

agagtttgat cctggctcag attgaacgct ggcggcatgc cttacacatg caagtcgaac     60

ggcagcacgg gtgcttgcac ctggtggcga gtggcgaacg ggtgagtaat acatcggaac    120

gtaccttatc gtgggggata acgcagcgaa agttgcgcta ataccgcata cgccctgagg    180

gggaaagcgg gggaccgtaa ggcctcgcgc gattagagcg gccaatgtct gattagcttg    240

ttggtgaggt aaaagcttac caaggcgatg atcagtagct ggtctgagag gacgatcagc    300

cacactggga ctgagacacg gcccagactc ctacgggagg cagcagtggg gaattttgga    360

caatgggggc aaccctgatc cagcaatgcc gcgtgagtga agaaggcctt cgggttgtaa    420

agctcttttg tcagggaaga aacagcagct ctaacacagt ctgcgaatga cggtacctga    480
```

agaataagca ccggctaact acgtgccagc agccgcggta atacgtaggg tgcgagcgtt 540
aatcggaatt actgggcgta aagcgtgcgc aggcggttat acaagacagg cgtgaaatcc 600
ccgggcttaa cctgggaatg gcgtctgtga ctgtatagct agagtgtgtc aga 653

<210> SEQ ID NO 232
<211> LENGTH: 666
<212> TYPE: DNA
<213> ORGANISM: Unknown
<220> FEATURE:
<223> OTHER INFORMATION: Kingdom: Bacteria, Phylum: Proteobacteria, Class: Betaproteobacteria, Order: Burkholderiales, Family: Burkholderiaceae, Genus: Polynucleobacter

<400> SEQUENCE: 232
tgaagtcagc cgcctgggga gtacggtcgc aagattaaaa ctcaaaggaa ttgacgggga 60
cccgcacaag cggtggatga tgtggattaa ttcgatgcaa cgcgaaaaac cttacctacc 120
cttgacatgt cactaacgaa gtagagatac attaggtgcc cgtaagggaa agtgaacaca 180
ggtgctgcat ggctgtcgtc agctcgtgtc gtgagatgtt gggttaagtc ccgcaacgag 240
cgcaaccctt gtctttagtt gctacgcaag agcactctaa agagactgcc ggtgacaaac 300
cggaggaagg tggggatgac gtcaagtcct catggccctt atgggtaggg cttcacacgt 360
catacaatgg tgcgtacaga gggttgccaa cccgcgaggg ggagctaatc tcttaaaacg 420
catcgtagtc cggatcgtag tctgcaactc gactacgtga ggctggaatc gctagtaatc 480
gcggatcagc atgtcgcggt gaatacgttc ccgggtcttg tacacaccgc ccgtcacacc 540
atgggagtgg gttttgccag aagcagttag cctaaccgta aggagggcga ttgccacggc 600
agggttcatg actggggtga agtcgtaaca aggtaaccaa gggcgaattc cacagtggat 660
atcaag 666

<210> SEQ ID NO 233
<211> LENGTH: 623
<212> TYPE: DNA
<213> ORGANISM: Unknown
<220> FEATURE:
<223> OTHER INFORMATION: Kingdom: Bacteria, Phylum: Proteobacteria, Class: Alphaproteobacteria, Order: Rhizobiales, Family: Rhizobiaceae, Genus: Rhizobium

<400> SEQUENCE: 233
ggaattgacg gggcccgca caagcggtgg agcatgtggt ttaattcgaa gcaacgcgca 60
gaaccttacc agcccttgac atcctgtgtt acccgtagag atatggggtc cacttcggtg 120
gcgcagagac aggtgctgca tggctgtcgt cagctcgtgt cgtgagatgt tgggttaagt 180
cccgcaacga gcgcaaccct cgcccttagt tgccagcatt cagttgggca ctctaagggg 240
actgccggtg ataagccgag aggaaggtgg ggatgacgtc aagtcctcat ggcccttacg 300
ggctgggcta cacacgtgct acaatggtgg tgacagtggg cagcgagcac gcgagtgtga 360
gctaatctcc aaaagccatc tcagttcgga ttgcactctg caactcgagt gcatgaagtt 420
ggaatcgcta gtaatcgcgg atcagcatgc cgcggtgaat acgttcccgg gccttgtaca 480
caccgcccgt cacaccatgg gagttggttt tacccgaagg tagtgcgcta accgcaagga 540
ggcagctaac cacggtaggg tcagcgactg gggtgaagtc gtaacaaggt aaccaagggc 600
gaattccaca gtggatatca agc 623

<210> SEQ ID NO 234

```
<211> LENGTH: 711
<212> TYPE: DNA
<213> ORGANISM: Unknown
<220> FEATURE:
<223> OTHER INFORMATION: Kingdom: Bacteria, Phylum: Bacteroidetes,
      Class: Sphingobacteriia, Order: Sphingobacteriales, Family:
      Chitinophagaceae, Genus: Filimonas

<400> SEQUENCE: 234

cgttgagatt tgttctattt ctacttatac tcaggatcaa tcttgcattt atcttacaat     60

ctatgtattt tccacaactg catgcactag ttaccccaga tctgtaaagt ggatcccgat    120

ccaccaatga aacgcgccaa ggcgatctta cgcaggagcc aagtctcata gtatctcgat    180

ctggtcaggc actatacctg ttatttggtc aagcctgtgg aatcattgcg ttgactaatc    240

ttaaggggca tatgaagaat gaactatgtg atcagatgat ttaaaagaaa tacaaccttt    300

gttattggta ggtattatga aggtgaactt gtagtttgtg ggtcgcgctg tcttactact    360

ttaaaaaggt tgttactgcg gcaccaaaag ttattgctac acctcactat ccgtattcgg    420

acttggtctg aagttgtata ccagaaaact tactacgcaa catctcacct gggcaggtat    480

gtacggagtg ctcaccagga gctaaaagcc aaaggacaca agaattttat ccacactgaa    540

acaagaaaaa agcaacggga cacaagaaac gcacaaataa taagccatga aacacaaaac    600

agaccactcc ttgtctgcaa acttggtttg agataacacc ggaaacgaaa cacggattta    660

tggttagcag acacatcgac taggagcgat agtcaagcca aggtaccatt g             711


<210> SEQ ID NO 235
<211> LENGTH: 917
<212> TYPE: DNA
<213> ORGANISM: Unknown
<220> FEATURE:
<223> OTHER INFORMATION: Kingdom: Bacteria, Phylum: Bacteroidetes,
      Class: Sphingobacteriia, Order: Sphingobacteriales, Family:
      Chitinophagaceae, Genus: Filimonas

<400> SEQUENCE: 235

cccaatgtgg aattcgccct tgttacgact tcaccccagt ttccgacatc gcttatgcag     60

gttagtcagc gagatctgat cgccactaat gacgtctgca cggcacggga ttcattaaac    120

caggtggagc ctttcttcct gcgttgagat ttgttctatt tctacttata ctcaggatca    180

atcttgcatt tatcttacaa tctatgtatt ttccacaact gcatgcacta gttaccccag    240

atctgtaaag tggatcccga tccaccaatg aaacgcgcca aggcgatctt acgcaggagc    300

caagtctcat agtatctcga tctggtcagg cactatacct gttatttggt caagcctgtg    360

gaatcattgc gttgactaat cttaaggggc atatgaagaa tgaactatgt gatcagatga    420

tttaaaagaa atacaacctt tgttattggt aggtattatg aaggtgaact tgtagtttgt    480

gggtcgcgct gtcttactac tttaaaaagg ttgttactgc ggcaccaaaa gttattgcta    540

cacctcacta tccgtatccg gacttggtct gaagttgtat accagaaaac ttactacgca    600

acatctcacc tgggcaggta tgtacggagt gctcaccagg agctaaaagc caaaggacac    660

aagaatttta tccacactga aacaagaaaa aagcaacggg acacaagaaa cgcacaaata    720

ataagccatg aaacacaaaa cagaccactc cttgtctgca aacttggttt gagataacac    780

cggaaacgaa acacggattt atggttagca gacacatcga ctaggagcga tagtcaagcc    840

aaggtaccat tgatggggcg cgtcttccaa tctgagccat gatcaaacta agggcgaatt    900

ccacagtgga tatcaag                                                   917
```

<210> SEQ ID NO 236
<211> LENGTH: 709
<212> TYPE: DNA
<213> ORGANISM: Unknown
<220> FEATURE:
<223> OTHER INFORMATION: Kingdom: Bacteria, Phylum: Bacteroidetes, Class: Sphingobacteriia, Order: Sphingobacteriales, Family: Chitinophagaceae, Genus: Filimonas

<400> SEQUENCE: 236
accaagtttg cagacaagga gtggtctgtt ttgtgtttca tggcttatta tttgtgcgtt 60
tcttgtgtcc cgttgctttt ttcttgtttc agtgtggata aaattcttgt gtcctttggc 120
ttttagctcc tggtgagcac tccgtacata cctgcccagg tgagatgttg cgtagtaagt 180
tttctggtat acaacttcag accaagtccg aatacggata gtgaggtgta gcaataactt 240
ttggtgccgc agtaacaacc tttttaaagt agtaagacag cgcgacccac aaactacaag 300
ttcaccttca taatacctac caataacaaa ggttgtattt cttttaaatc atctgatcac 360
atagttcatt cttcatatgc cccttaagat tagtcaacgc aatgattcca caggcttgac 420
caaataacag gtatagtgcc tgaccagatc gagatactat gagacttggc tcctgcgtaa 480
gatcgccttg gcgcgtttca ttggtggatc gggatccact ttacagatct ggggtaacta 540
gtgcatgcag ttgtggaaaa tacatagatt gtaagataaa tgcaagattg atcctgagta 600
taagtagaaa tagaacaaat ctcaacgcag gaagaaaggc tccacctggt ttaatgaatc 660
ccgtgccgtg cagacgtcat tagtggcgat cagatctcgc tgactaacc 709

<210> SEQ ID NO 237
<211> LENGTH: 1333
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Dyella

<400> SEQUENCE: 237
agcttgctct gtgggtggcg agtggcggac gggtgagtaa tgcatcggga cctacccaga 60
cgtgggggat aacgtaggga aacttacgct aataccgcat acgtcctacg ggagaaagcg 120
ggggatcgca agacctcgcg cggttggatg gaccgatgtg cgattagctt gttggtgagg 180
taacggctca ccaaggcgac gatcgctagc tggtctgaga ggatgatcag ccacactggg 240
actgagacac ggcccagact cctacgggag gcagcagtgg ggaatattgg acaatgggcg 300
caagcctgat ccagcaatgc cgcgtgtgtg aagaaggccc tcgggttgta aagcactttt 360
atcaggagcg aaatctgcaa ggttaatacc tttgcagtct gacggtacct gaggaataag 420
caccggctaa ctccgtgcca gcagccgcgg taatacggag ggtgcaagcg ttaatcggaa 480
ttactgggcg taaagcgtgc gtaggcggtt cgttaagtct gttgtgaaag ccccgggctc 540
aacctgggaa tggcaatgga tactggcgag ctagagtgtg tcagaggatg gtggaattcc 600
cggtgtagcg gtgaaatgcg tagagatcgg gaggaacatc agtggcgaag gcggccatct 660
gggacaacac tgacgctgag gcacgaaagc gtggggagca aacaggatta gataccctgg 720
tagtccacgc cctaaacgat gcgaactgga tgttggtctc aactcggaga tcagtgtcga 780
agctaacgcg ttaagttcgc cgcctgggga gtacggtcgc aagactgaaa ctcaaaggaa 840
ttgacggggg cccgcacaag cggtggagta tgtggtttaa ttcgatgcaa cgcgaagaac 900
cttacctggc cttgacatgt ccggaatcca gcagagatgc aggagtgcct tcgggaatcg 960

```
gaacacaggt gctgcatggc tgtcgtcagc tcgtgtcgtg agatgttggg ttaagtcccg   1020

caacgagcgc aacccttgtc cttagttgcc agcgagtaat gtcgggaact ctaaggagac   1080

tgccggtgac aaaccggagg aaggtgggga tgacgtcaag tcatcatggc ccttacggcc   1140

agggctacac acgtactaca atggtcggta cagagggttg cgataccgcg aggtggagct   1200

aatcccagaa agccgatccc agtccggatt ggagtctgca actcgactcc atgaagtcgg   1260

aatcgctagt aatcgcagat cagctatgct gcggtgaata cgttcccggg ccttgtacac   1320

accgcccgtc aca                                                      1333
```

<210> SEQ ID NO 238
<211> LENGTH: 1177
<212> TYPE: DNA
<213> ORGANISM: Unknown
<220> FEATURE:
<223> OTHER INFORMATION: Kingdom: Bacteria, Phylum: Proteobacteria,
Class: Gammaproteobacteria, Order: Enterobacteriales, Family:
Enterobacteriaceae, Genus: Pantoea

<400> SEQUENCE: 238

```
tggggggtta aaggcccact tggggaggat cccagtttgt gtgaggggtg accagcccac     60

cggaaatggg acccggtccc gactcttacg gagggagcag tgggaatatt gcacaatggg    120

cccaaccctg atgcagccat gccgggttat gaagaggcct ttgggttgta aagtactttc    180

agcggggagg aaggcgatgc ggttataacc gcaccgattg acgttacccg cagaagaagc    240

acgggctaac tccgtgccag cagccgcggt aatacggagg gtgcaagcgt taatcggaat    300

tactgggcgt aaagcgcacg caggcggtct gttaagtcag atgtgaaatc cccgggctta    360

acctgggaac tgcatttgaa actggcaggc ttgagtcttg tagagggggg tagaattcca    420

ggtgtagcgg tgaaatgcgt agagatctgg aggaataccg gtggcgaagg cggccccctg    480

gacaaagact gacgctcagg tgcgaaagcg tggggagcaa acaggattag ataccctggt    540

agtccacgcc gtaaacgatg tcgacttgga ggttgttccc ttgaggagtg gcttccggag    600

ctaacgcgtt aagtcgaccg cctggggagt acggccgcaa ggttaaaact caaatgaatt    660

gacgggggcc cgcacaagcg gtggagcatg tggtttaatt cgatgcaacg cgaagaacct    720

tacctactct tgacatccag agaattcggc agagatgctt tagtgccttc gggaactgtg    780

agacaggtgc tgcatggctg tcgtcagctc gtgttgtgaa atgttgggtt aagtcccgca    840

acgagcgcaa cccttatcct ttgttgccag cgattcggtc gggaactcaa aggagactgc    900

cggtgataaa ccggaggaag gtggggatga cgtcaagtca tcatggccct tacgagtagg    960

gctacacacg tgctacaatg gcgcatacaa agagaagcga cctcgcgaga gcaagcggac   1020

ctcacaaagt gcgtcgtagt ccggatcgga gtctgcaact cgactccgtg aagtcggaat   1080

cgctagtaat cgtggatcag aatgccacgg tgaatacgtt cccgggcctt gtacacaccg   1140

cccgtcacac catgggagtg ggtgcaaaag aagtagg                            1177
```

<210> SEQ ID NO 239
<211> LENGTH: 1333
<212> TYPE: DNA
<213> ORGANISM: Unknown
<220> FEATURE:
<223> OTHER INFORMATION: Kingdom: Bacteria, Phylum: Proteobacteria,
Class: Gammaproteobacteria, Order: Xanthomonadales, Family:
Xanthomonadaceae, Genus: Luteibacter

<400> SEQUENCE: 239

```
agcttgctct gtgggtggcg agtggcggac gggtgagtaa tgcatcggga cctacccaga     60
```

```
cgtgggggat aacgtaggga aacttacgct aataccgcat acgtcctacg ggagaaagcg    120
ggggatcgca agacctcgcg cggttggatg gaccgatgtg cgattagcta gttggtaagg    180
taacggctta ccaaggcgac gatcgctagc tggtctgaga ggatgatcag ccacactggg    240
actgagacac ggcccagact cctacgggag gcagcagtgg ggaatattgg acaatgggcg    300
caagcctgat ccagcaatgc cgcgtgtgtg aagaaggccc tcgggttgta aagcactttt    360
atcaggagcg aaatctgcaa ggttaatacc tttgcagtct gacggtacct gaggaataag    420
caccggctaa ctccgtgcca gcagccgcgg taatacggag ggtgcaagcg ttaatcggaa    480
ttactgggcg taaagcgtgc gtaggcggtt cgttaagtct gttgtgaaag ccccgggctc    540
aacctgggaa tggcaatgga tactggcgag ctagagtgtg tcagaggatg gtggaattcc    600
cggtgtagcg gtgaaatgcg tagagatcgg gaggaacatc agtggcgaag gcggccatct    660
gggacaacac tgacgctgag gcacgaaagc gtggggagca aacaggatta gataccctgg    720
tagtccacgc cctaaacgat gcgaactgga tgttggtctc aactcggaga tcagtgtcga    780
agctaacgcg ttaagttcgc cgcctgggga gtacggtcgc aagactgaaa ctcaaaggaa    840
ttgacggggg cccgcacaag cggtggagta tgtggtttaa ttcgatgcaa cgcgaagaac    900
cttacctggc cttgacatgt ccggaatcca gcagagatgc aggagtgcct tcgggaatcg    960
gaacacaggt gctgcatggc tgtcgtcagc tcgtgtcgtg agatgttggg ttaagtcccg   1020
caacgagcgc aacccttgtc cttagttgcc agcgagtaat gtcgggaact ctaaggagac   1080
tgccggtgac aaaccggagg aaggtgggga tgacgtcaag tcatcatggc ccttacggcc   1140
agggctacac acgtactaca atggtcggta cagagggttg cgataccgcg aggtggagct   1200
aatcccagaa agccgatccc agtccggatt ggagtctgca actcgactcc atgaagtcgg   1260
aatcgctagt aatcgcagat cagctatgct gcggtgaata cgttcccggg ccttgtacac   1320
accgcccgtc aca                                                      1333
```

<210> SEQ ID NO 240
<211> LENGTH: 1333
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Dyella

<400> SEQUENCE: 240

```
agcttgctct gtgggtggcg agtggcggac gggtgagtaa tgcatcggga cctacccaga     60
cgtgggggat aacgtaggga aacttacgct aataccgcat acgtcctacg ggagaaagcg    120
ggggatcgca agacctcgcg cggttggatg gaccgatgtg cgattagctt gttggtgagg    180
taacggctca ccaaggcgac gatcgctagc tggtctgaga ggatgatcag ccacactggg    240
actgagacac ggcccagact cctacgggag gcagcagtgg ggaatattgg acaatgggcg    300
caagcctgat ccagcaatgc cgcgtgtgtg aagaaggccc tcgggttgta aagcactttt    360
atcaggagcg aaatctgcaa ggttaatacc tttgcagtct gacggtacct gaggaataag    420
caccggctaa ctccgtgcca gcagccgcgg taatacggag ggtgcaagcg ttaatcggaa    480
ttactgggcg taaagcgtgc gtaggcggtt cgttaagtct gttgtgaaag ccccgggctc    540
aacctgggaa tggcaatgga tactggcgag ctagagtgtg tcagaggatg gtggaattcc    600
cggtgtagcg gtgaaatgcg tagagatcgg gaggaacatc agtggcgaag gcggccatct    660
```

```
gggacaacac tgacgctgag gcacgaaagc gtggggagca aacaggatta gataccctgg    720

tagtccacgc cctaaacgat gcgaactgga tgttggtctc aactcggaga tcagtgtcga    780

agctaacgcg ttaagttcgc cgcctgggga gtacggtcgc aagactgaaa ctcaaaggaa    840

ttgacggggg cccgcacaag cggtggagta tgtggtttaa ttcgatgcaa cgcgaagaac    900

cttacctggc cttgacatgt ccggaatcca gcagagatgc aggagtgcct tcgggaatcg    960

gaacacaggt gctgcatggc tgtcgtcagc tcgtgtcgtg agatgttggg ttaagtcccg   1020

caacgagcgc aacccttgtc cttagttgcc agcgagtaat gtcgggaact ctaaggagac   1080

tgccggtgac aaaccggagg aaggtgggga tgacgtcaag tcatcatggc ccttacggcc   1140

agggctacac acgtactaca atggtcggta cagagggttg cgataccgcg aggtggagct   1200

aatcccagaa agccgatccc agtccggatt ggagtctgca actcgactcc atgaagtcgg   1260

aatcgctagt aatcgcagat cagctatgct gcggtgaata cgttcccggg ccttgtacac   1320

accgcccgtc aca                                                      1333
```

<210> SEQ ID NO 241
<211> LENGTH: 1333
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Xanthomonadales, Family: Xanthomonadaceae, Genus: Luteibacter

<400> SEQUENCE: 241

```
agcttgctct gtgggtggcg agtggcggac gggtgagtaa tgcatcggga cctacccaga     60

cgtgggggat aacgtaggga aacttacgct aataccgcat acgtcctacg ggagaaagcg    120

ggggatcgca agacctcgcg cggttggatg gaccgatgtg cgattagcta gttggtaagg    180

taacggctta ccaaggcgac gatcgctagc tggtctgaga ggatgatcag ccacactggg    240

actgagacac ggcccagact cctacgggag gcagcagtgg ggaatattgg acaatgggcg    300

caagcctgat ccagcaatgc cgcgtgtgtg aagaaggccc tcgggttgta aagcactttt    360

atcaggagcg aaatctgcaa ggttaatacc tttgcagtct gacggtacct gaggaataag    420

caccggctaa ctccgtgcca gcagccgcgg taatacggag ggtgcaagcg ttaatcggaa    480

ttactgggcg taaagcgtgc gtaggcggtt cgttaagtct gttgtgaaag ccccgggctc    540

aacctgggaa tggcaatgga tactggcgag ctagagtgtg tcagaggatg gtggaattcc    600

cggtgtagcg gtgaaatgcg tagagatcgg gaggaacatc agtggcgaag gcggccatct    660

gggacaacac tgacgctgag gcacgaaagc gtggggagca aacaggatta gataccctgg    720

tagtccacgc cctaaacgat gcgaactgga tgttggtctc aactcggaga tcagtgtcga    780

agctaacgcg ttaagttcgc cgcctgggga gtacggtcgc aagactgaaa ctcaaaggaa    840

ttgacggggg cccgcacaag cggtggagta tgtggtttaa ttcgatgcaa cgcgaagaac    900

cttacctggc cttgacatgt ccggaatcca gcagagatgc aggagtgcct tcgggaatcg    960

gaacacaggt gctgcatggc tgtcgtcagc tcgtgtcgtg agatgttggg ttaagtcccg   1020

caacgagcgc aacccttgtc cttagttgcc agcgagtaat gtcgggaact ctaaggagac   1080

tgccggtgac aaaccggagg aaggtgggga tgacgtcaag tcatcatggc ccttacggcc   1140

agggctacac acgtactaca atggtcggta cagagggttg cgataccgcg aggtggagct   1200

aatcccagaa agccgatccc agtccggatt ggagtctgca actcgactcc atgaagtcgg   1260

aatcgctagt aatcgcagat cagctatgct gcggtgaata cgttcccggg ccttgtacac   1320
```

accgcccgtc aca 1333

<210> SEQ ID NO 242
<211> LENGTH: 1326
<212> TYPE: DNA
<213> ORGANISM: Unknown
<220> FEATURE:
<223> OTHER INFORMATION: Kingdom: Bacteria, Phylum: Proteobacteria,
Class: Betaproteobacteria, Order: Burkholderiales, Family:
Burkholderiaceae, Genus: Ralstonia

<400> SEQUENCE: 242
agcttgctag attgatggcg agtggcgaac gggtgagtaa tacatcggaa cgtgccctgt 60
agtgggggat aactagtcga aagattagct aataccgcat acgacctgag ggtgaaagtg 120
ggggaccgca aggcctcatg ctataggagc ggccgatgtc tgattagcta gttggtgagg 180
taaaggctca ccaaggcgac gatcagtagc tggtctgaga ggacgatcag ccacactggg 240
actgagacac ggcccagact cctacgggag gcagcagtgg ggaattttgg acaatgggcg 300
aaagcctgat ccagcaatgc cgcgtgtgtg aggaaggcct tcgggttgta aagcactttt 360
gtccggaaag aaatggctct ggttaatacc tggggtcgat gacggtaccg gaagaataag 420
gaccggctaa ctacgtgcca gcagccgcgg taatacgtag ggtccaagcg ttaatcggaa 480
ttactgggcg taaagcgtgc gcaggcggtt gtgcaagacc gatgtgaaat ccccgagctt 540
aacttgggaa ttgcattggt gactgcacgg ctagagtgtg tcagaggggg gtagaattcc 600
acgtgtagca gtgaaatgcg tagagatgtg gaggaatacc gatggcgaag gcagccccct 660
gggataacac tgacgctcat gcacgaaagc gtggggagca aacaggatta gataccctgg 720
tagtccacgc cctaaacgat gtcaactagt tgttggggat tcatttcctt agtaacgtag 780
ctaacgcgtg aagttgaccg cctggggagt acggtcgcaa gattaaaact caaaggaatt 840
gacggggacc cgcacaagcg gtggatgatg tggattaatt cgatgcaacg cgaaaaacct 900
tacctaccct tgacatgcca ctaacgaagc agagatgcat taggtgctcg aaagagaaag 960
tggacacagg tgctgcatgg ctgtcgtcag ctcgtgtcgt gagatgttgg gttaagtccc 1020
gcaacgagcg caacccttgt ctctagttgc tacgaaaggg cactctagag agactgccgg 1080
tgacaaaccg gaggaaggtg gggatgacgt caagtcctca tggcccttat gggtagggct 1140
tcacacgtca tacaatggtg catacagagg gttgccaagc cgcgaggtgg agctaatccc 1200
agaaaatgca tcgtagtccg gatcgtagtc tgcaactcga ctacgtgaag ctggaatcgc 1260
tagtaatcgc ggatcagcat gccgcggtga atacgttccc gggtcttgta cacaccgccc 1320
gtcaca 1326

<210> SEQ ID NO 243
<211> LENGTH: 1330
<212> TYPE: DNA
<213> ORGANISM: Unknown
<220> FEATURE:
<223> OTHER INFORMATION: Kingdom: Bacteria, Phylum: Proteobacteria,
Class: Gammaproteobacteria, Order: Enterobacteriales, Family:
Enterobacteriaceae, Genus: Erwinia

<400> SEQUENCE: 243
agcttgctcc tcgggtgacg agtggcggac gggtgagtaa tgtctgggga tctgcccggt 60
agagggggat aaccactgga aacggtggct aataccgcat aatctcgcaa gagcaaagtg 120
ggggaccttc gggcctcaca ctaccggatg aacccagatg ggattagcca gctggtgagg 180
taacggctca ccagggcgac gatccctagc tggtctgaga ggatgaccag ccacactgga 240
actgagacac ggtccagact cctacgggag gcagcagtgg ggaatattgc acaatgggcg 300
caagcctgat gcagccatgc cgcgtgtatg aagaaggcct tcgggttgta aagtactttc 360
agcggggagg aagggtgaag agcgaataac ttttcacatt gacgttaccc gcagaagaag 420
caccggctaa ctccgtgcca gcagccgcgg taatacggag ggtgcaagcg ttaatcggaa 480
ttactgggcg taaagcgcac gcaggcggtc tgttaagtca gatgtgaaat ccccgggctc 540
aacccgggaa ctgcatttga aactggcagg cttgagtctc gtagaggggg gtggaattcc 600
aggtgtagcg gtgaaatgcg tagagatctg gaggaatacc ggtggcgaag gcggccccct 660
ggacgaagac tgacgctcag gtgcgaaagc gtggggagca aacaggatta gataccctgg 720
tagtccacgc cgtaaacgat gtcgatttgg aggctgtgag cttgactcgt ggcttccgta 780
gctaacgcgt taaatcgacc gcctggggag tacggccgca aggttaaaac tcaaatgaat 840
tgacgggggc ccgcacaagc ggtggagcat gtggtttaat tcgatgcaac gcgaagaacc 900
ttacctggtc ttgacatcca cggaatcggg cagagatgcc tgagtgcctt cgggagccgt 960
gagacaggtg ctgcatggct gtcgtcagct cgtgttgtga aatgttgggt taagtcccgc 1020
aacgagcgca acccttatcc tttgttgcca gcgattcggt cgggaactca aaggagactg 1080
ccggtgataa accggaggaa ggtggggatg acgtcaagtc atcatggccc ttacgaccag 1140
ggctacacac gtgctacaat ggcgcataca aagagaagcg acctcgcgag agcaagcgga 1200
cctcataaag tgcgtcgtag tccggatcgg agtctgcaac ccgactccgt gaagtcggaa 1260
tcgctagtaa tcgtggatca gaatgccacg gtgaatacgt tcccgggcct tgtacacacc 1320
gcccgtcaca 1330

<210> SEQ ID NO 244
<211> LENGTH: 684
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus

<400> SEQUENCE: 244
acagatggga gcttgctccc tgatgttagc ggcggacggg tgagtaacac gtgggtaacc 60
tgcctgtaag actgggataa ctccgggaaa ccggggctaa taccggatgg ttgtttgaac 120
cgcatggttc aaacataaaa ggtggcttcg gctaccactt acagatggac ccgcggcgca 180
ttagctagtt ggtgaggtaa tggctcacca aggcaacgat gcgtagccga cctgagaggg 240
tgatcggcca cactgggact gagacacggc ccagactcct acgggaggca gcagtaggga 300
atcttccgca atggacgaaa gtctgacgga gcaacgccgc gtgagtgatg aaggttttcg 360
gatcgtaaag ctctgttgtt agggaagaac aagtaccgtt cgaatagggc ggtaccttga 420
cggtacctaa ccagaaagcc acggctaact acgtgccagc agccgcggta atacgtaggt 480
ggcaagcgtt gtccggaatt attgggcgta aagggctcgc aggcggtttc ttaagtctga 540
tgtgaaagcc cccggctcaa ccggggaggg tcattggaaa ctggggaact tgagtgcaga 600
agaggagagt ggaattccac gtgtagcggt gaaatgcgta gagatgtgga ggaacaccag 660
tggcgaaggc gactctctgg tctg 684

<210> SEQ ID NO 245
<211> LENGTH: 1336
<212> TYPE: DNA

<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus

<400> SEQUENCE: 245

```
agcttgctcc ctgatgttag cggcggacgg gtgagtaaca cgtgggtaac ctgcctgtaa      60
gactgggata actccgggaa accggggcta ataccggatg cttgtttaac cgcatggttc     120
aaacataaaa ggtggcttcg gctaccactt acagatggac ccgcggcgca ttagctagtt     180
ggtgaggtaa tggctcacca aggcaacgat gcgtagccga cctgagaggg tgatcggcca     240
cactgggact gagacacggc ccagactcct acgggaggca gcagtaggga atcttccgca     300
atggacgaaa gtctgacgga gcaacgccgc gtgagtgatg aaggttttcg gatcgtaaag     360
ctctgttgtt agggaagaac aagtgccgtt caaatagggc ggcaccttga cggtacctaa     420
ccagaaagcc acggctaact acgtgccagc agccgcggta atacgtaggt ggcaagcgtt     480
gtccggaatt attgggcgta aagggctcgc aggcggtttc ttaagtctga tgtgaaagcc     540
cccggctcaa ccggggaggg tcattggaaa ctggggaact tgagtgcaga agaggagagt     600
ggaattccac gtgtagcggt gaaatgcgta gagatgtgga ggaacaccag tggcgaaggc     660
gactctcttc tgtaactgac gctgaggagc gaaagcgtgg ggagcgaaca ggattagata     720
ccctggtagt ccacgccgta aacgatgagt gctaagtgtt agggggtttc cgccccttag     780
tgctgcagct aacgcattaa gcactccgcc tggggagtac ggtcgcaaga ctgaaactca     840
aaggaattga cgggggcccg cacaagcggt ggagcatgtg gtttaattcg aagcaacgcg     900
aagaacctta ccaggtcttg acatcctctg acacccctag agatagggct tccccttcgg     960
gggcagagtg acaggtggtg catggttgtc gtcagctcgt gtcgtgagat gttgggttaa    1020
gtcccgcaac gagcgcaacc cttgatctta gttgccagca ttcagttggg cactctaagg    1080
tgactgccgg tgacaaaccg gaggaaggtg gggatgacgt caaatcatca tgccccttat    1140
gacctgggct acacacgtgc tacaatggac agaacaaagg gcagcgagac cgcgaggtta    1200
agccaatccc acaaatctgt tctcagttcg gatcgcagtc tgcaactcga ctgcgtgaag    1260
ctggaatcgc tagtaatcgc ggatcagcat gccgcggtga atacgttccc gggccttgta    1320
cacaccgccc gtcaca                                                   1336
```

<210> SEQ ID NO 246
<211> LENGTH: 1295
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus

<400> SEQUENCE: 246

```
gaaaccgggg ctaataccgg atggttgttt gaaccgcatg gttcaaacat aaaaggtggc      60
ttcggctacc acttacagat ggacccgcgg cgcattagct agttggtgag gtaacggctc     120
accaaggcaa cgatgcgtag ccgacctgag agggtgatcg gccacactgg gactgagaca     180
cggcccagac tcctacggga ggcagcagta gggaatcttc cgcaatggac gaaagtctga     240
cggagcaacg ccgcgtgagt gatgaaggtt ttcggatcgt aaagctctgt tgttagggaa     300
gaacaagtac cgttcgaata gggcggtacc ttgacggtac ctaaccagaa agccacggct     360
aactacgtgc cagcagccgc ggtaatacgt aggtggcaag cgttgtccgg aattattggg     420
cgtaaagggc tcgcaggcgg tttcttaagt ctgatgtgaa agcccccggc tcaaccgggg     480
```

agggtcattg gaaactgggg aacttgagtg cagaagagga gagtggaatt ccacgtgtag 540
cggtgaaatg cgtagagatg tggaggaaca ccagtggcga aggcgactct ctggtctgta 600
actgacgctg aggagcgaaa gcgtggggag cgaacaggat tagataccct ggtagtccac 660
gccgtaaacg atgagtgcta agtgttaggg ggtttccgcc ccttagtgct gcagctaacg 720
cattaagcac tccgcctggg gagtacggtc gcaagactga aactcaaagg aattgacggg 780
ggcccgcaca agcggtggag catgtggttt aattcgaagc aacgcgaaga accttaccag 840
gtcttgacat cctctgacaa tcctagagat aggacgtccc cttcgggggc agagtgacag 900
gtggtgcatg gttgtcgtca gctcgtgtcg tgagatgttg ggttaagtcc cgcaacgagc 960
gcaacccttg atcttagttg ccagcattca gttgggcact ctaaggtgac tgccggtgac 1020
aaaccggagg aaggtgggga tgacgtcaaa tcatcatgcc ccttatgacc tgggctacac 1080
acgtgctaca atggacagaa caaagggcag cgaaaccgcg aggttaagcc aatcccacaa 1140
atctgttctc agttcggatc gcagtctgca actcgactgc gtgaagctgg aatcgctagt 1200
aatcgcggat cagcatgccg cggtgaatac gttcccgggc cttgtacaca ccgcccgtca 1260
caccacgaga gtttgtaaca cccgaagtcg gtgag 1295

<210> SEQ ID NO 247
<211> LENGTH: 1337
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Bacillaceae , Genus: Bacillus

<400> SEQUENCE: 247
agcttgctcc ctgatgttag cggcggacgg gtgagtaaca cgtgggtaac ctgcctgtaa 60
gactgggata actccgggaa accggggcta ataccggatg gttgtttacc gcatggttca 120
aacataaaag gtggcttcgg ctaccactta cagatggacc cgcggcgcat tagctagttg 180
gtgaggtaac ggctcaccaa ggcaacgatg cgtagccgac ctgagagggt gatcggccac 240
actgggactg agacacggcc cagactccta cgggaggcag cagtagggaa tcttccgcaa 300
tggacgaaag tctgacggag caacgccgcg tgagtgatga aggttttcgg atcgtaaagc 360
tctgttgtta gggaagaaca agtaccgttc gaatagggcg gtaccttgac ggtacctaac 420
cagaaagcca cggctaacta cgtgccagca gccgcggtaa tacgtaggtg gcaagcgttg 480
tccggaatta ttgggcgtaa agggctcgca ggcggtttct taagtctgat gtgaaagccc 540
ccggctcaac cggggagggt cattggaaac tggggaactt gagtgcagaa gaggagagtg 600
gaattccacg tgtagcggtg aaatgcgtag agatgtggag gaacaccagt ggcgaaggcg 660
actctctggt ctgtaactga cgctgaggag cgaaagcgtg gggagcgaac aggattagat 720
accctggtag tccacgccgt aaacgatgag tgctaagtgt tagggggttt ccgcccctta 780
gtgctgcagc taacgcatta agcactccgc ctggggagta cggtcgcaag actgaaactc 840
aaaggaattg acgggggccc gcacaagcgg tggagcatgt ggtttaattc gaagcaacgc 900
gaagaacctt accaggtctt gacatcctct gacaatccta gagataggac gtccccttcg 960
ggggcagagt gacaggtggt gcatggttgt cgtcagctcg tgtcgtgaga tgttgggtta 1020
agtcccgcaa cgagcgcaac ccttgatctt agttgccagc attcagttgg gcactctaag 1080
gtgactgccg gtgacaaacc ggaggaaggt ggggatgacg tcaaatcatc atgcccctta 1140
tgacctgggc tacacacgtg ctacaatgga cagaacaaag ggcagcgaaa ccgcgaggtt 1200
aagccaatcc cacaaatctg ttctcagttc ggatcgcagt ctgcaactcg actgcgtgaa 1260
gctggaatcg ctagtaatcg cggatcagca tgccgcggtg aatacgttcc cgggccttgt 1320
acacaccgcc cgtcaca 1337

<210> SEQ ID NO 248
<211> LENGTH: 1338
<212> TYPE: DNA
<213> ORGANISM: Unknown
<220> FEATURE:
<223> OTHER INFORMATION: Kingdom: Bacteria, Phylum: Firmicutes, Class: Bacilli, Order: Bacillales, Family: Paenibacillaceae , Genus: Paenibacillus

<400> SEQUENCE: 248
agcttgcttc tccgatggtt agcggcggac gggtgagtaa cacgtaggca acctgccctc 60
aagtttggga caactaccgg aaacggtagc taataccgaa tagttgtttt tctcctgaag 120
gaaactggaa agacggagca atctgtcact tggggatggg cctgcggcgc attagctagt 180
tggtggggta acggctcacc aaggcgacga tgcgtagccg acctgagagg gtgatcggcc 240
acactgggac tgagacacgg cccagactcc tacgggaggc agcagtaggg aatcttccgc 300
aatgggcgaa agcctgacgg agcaatgccg cgtgagtgat gaaggttttc ggatcgtaaa 360
gctctgttgc cagggaagaa cgcttgggag agtaactgct ctcaaggtga cggtacctga 420
gaagaaagcc ccggctaact acgtgccagc agccgcggta atacgtaggg ggcaagcgtt 480
gtccggaatt attgggcgta aagcgcgcgc aggcggtcat ttaagtctgg tgtttaatcc 540
cggggctcaa ccccggatcg cactggaaac tgggtgactt gagtgcagaa gaggagagtg 600
gaattccacg tgtagcggtg aaatgcgtag atatgtggag gaacaccagt ggcgaaggcg 660
actctctggg ctgtaactga cgctgaggcg cgaaagcgtg gggagcaaac aggattagat 720
accctggtag tccacgccgt aaacgatgag tgctaggtgt taggggtttc gatacccttg 780
gtgccgaagt taacacatta agcactccgc ctggggagta cggtcgcaag actgaaactc 840
aaaggaattg acggggaccc gcacaagcag tggagtatgt ggtttaattc gaagcaacgc 900
gaagaacctt accaggtctt gacatccctc tgaccggtac agagatgtac ctttccttcg 960
ggacagagga gacaggtggt gcatggttgt cgtcagctcg tgtcgtgaga tgttgggtta 1020
agtcccgcaa cgagcgcaac ccttgatctt agttgccagc acttcgggtg ggcactctaa 1080
ggtgactgcc ggtgacaaac cggaggaagg tggggatgac gtcaaatcat catgcccctt 1140
atgacctggg ctacacacgt actacaatgg ccggtacaac gggcagtgaa accgcgaggt 1200
ggaacgaatc ctaaaaagcc ggtctcagtt cggattgcag gctgcaactc gcctgcatga 1260
agtcggaatt gctagtaatc gcggatcagc atgccgcggt gaatacgttc ccgggtcttg 1320
tacacaccgc ccgtcaca 1338

<210> SEQ ID NO 249
<211> LENGTH: 938
<212> TYPE: DNA
<213> ORGANISM: Unknown
<220> FEATURE:
<223> OTHER INFORMATION: Kingdom: Bacteria, Phylum: Proteobacteria, Class: Gammaproteobacteria, Order: Enterobacteriales, Family: Enterobacteriaceae, Genus: Pantoea

<400> SEQUENCE: 249
cagccgcggt aatacggagg gtgcaagcgt taatcggaat tactgggcgt aaagcgcacg 60
caggcggtct gttaagtcag atgtgaaatc cccgggctta acctgggaac tgcatttgaa 120
actggcaggc ttgagtctcg tagagggggg tagaattcca ggtgtagcgg tgaaatgcgt 180
agagatctgg aggaataccg gtggcgaagg cggccccctg gacgaagact gacgctcagg 240
tgcgaaagcg tggggagcaa acaggattag ataccctggt agtccacgcc gtaaacgatg 300
tcgacttgga ggttgttccc ttgaggagtg gcttccggag ctaacgcgtt aagtcgaccg 360
cctggggagt acggccgcaa ggttaaaact caaatgaatt gacgggggcc cgcacaagcg 420
gtggagcatg tggtttaatt cgatgcaacg cgaagaacct tacctactct tgacatccag 480
agaacttagc agagatgctt tggtgccttc gggaactgtg agacaggtgc tgcatggctg 540
tcgtcagctc gtgttgtgaa atgttgggtt aagtcccgca acgagcgcaa cccttatcct 600
ttgttgccag cgattcggtc gggaactcaa aggagactgc cggtgataaa ccggaggaag 660
gtggggatga cgtcaagtca tcatggccct tacgagtagg gctacacacg tgctacaatg 720
gcgcatacaa agagaagcga cctcgcgaga gcaagcggac ctcataaagt gcgtcgtagt 780
ccggatcgga gtctgcaact cgactccgtg aagtcggaat cgctagtaat cgtggatcag 840
aatgccacgg tgaatacgtt cccgggcctt gtacacaccg cccgtcacac catgggagtg 900
ggttgcaaaa gaagtaggta gcttaacctt cgggaggg 938

<210> SEQ ID NO 250
<211> LENGTH: 505
<212> TYPE: DNA
<213> ORGANISM: Unknown
<220> FEATURE:
<223> OTHER INFORMATION: Kingdom: Fungi, Phylum: Ascomycota, Class: Pezizomycotina, Order: Sordariomycetes, Family: Xylariomycetidae, Genus: Pestalotiopsis

<400> SEQUENCE: 250
cggagggatc attacagagt tatctaactc ccaaacccat gtgaacttac cttttgttgc 60
ctcggcagtg cctaccctgt agccagttac cctgtaacga actaccctgt agcgcctgcc 120
gatggaccat taaactcttg ttatttttaa gtaatctgag cgtcttattt taataagtca 180
aaactttcaa caacggatct cttggttctg gcatcgatga agaacgcagc gaaatgcgat 240
aagtaatgtg aattgcagaa ttcagtgaat catcgaatct ttgaacgcac attgcgccca 300
ttagtattct agtgggcatg cctgttcgag cgtcatttca acccttaagc ctagcttagt 360
attgggaatc gactgtattg tcgttcttca aattcaacgg cggatttata gcaatctctg 420
aacgtagtaa tctttatctc gtttttgaaa tactataaac ctcagccgct aaacccccca 480
attttaatgg ttgacctcgg atcag 505

<210> SEQ ID NO 251
<211> LENGTH: 1119
<212> TYPE: DNA
<213> ORGANISM: Unknown
<220> FEATURE:
<223> OTHER INFORMATION: Kingdom: Fungi, Phylum: Ascomycota, Class: Eurotiomycetes, Order: Chaetothyriales, Family: Herpotrichiellaceae, Genus: Phaeomoniella

<400> SEQUENCE: 251
tgagttaggg tctcttttag agcccgaatc tccaaccctt tgttaaaaac actttgttgc 60
tttggcaggc ccgtcttatc ctttaaccgg gagacgaccg ccgggggcgt ttagtcacct 120
ctggtccgtg cttgccgata gcctattaaa aattctttat taaattatgt ctgaaaaatt 180
ataactaaat ataattaaaa cttttaacaa cggatctctt ggttctggca tcgatgaaga 240

```
acgcagcgaa atgcgataag taatgtgaat tgcagacttc agtgaatcat cgaatctttg    300
aacgcacatt gcgccctttg gtattccgaa gggcatgcct gttcgagcgt cattatcaac    360
cctcaagccc ggcttgttat tggtccctta tcgttaaaga taggcccgaa agataatggc    420
ggcgtcacaa atgaccccag atgcagcgag cttatacagc atacattgaa aggtttttgt    480
ggcccggcct taacgagaag caattctcaa ttttttacag gttgacctcg gatcaggtag    540
gaatacccgc tgaacttaag catatcaata agcggaggaa aagaaaccaa cagggattgc    600
ctcagtaacg gcgagtgaag cggcaatagc tcaaatttga aatctggctc ttcgagtccg    660
agttgtaatt tgtagaggat gtttcgggtg cgcccgcagt ttaagttcct tggaacagga    720
cgtcatagag ggtgagaatc ccgtcttgaa ctgtacggca agtccatgtg aaactccttc    780
gacgagtcga gttgtttggg aatgcagctc aaaatgggag gtaaatttct tctaaagcta    840
aatattggcc agagaccgat agcgcacaag tagagtgatc gaaagatgaa aagcactttg    900
aaaagagagt taaacagtat gtgaaattgt taaaagggaa gcgtttgcaa ccagacttgt    960
ttctaacagt tctaccgcag ttctctgtgg cttattctgt tagtccaggc cagcatcagt   1020
ttgggtggct cgttaaaggc cttgggaatg tatctactcc ttcgggtgta gacttatagc   1080
cctcggtgta atagggtcta cctggactga ggtacgcgc                          1119
```

<210> SEQ ID NO 252
<211> LENGTH: 1099
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Sordariomycetes, Family: Xylariomycetidae, Genus: Biscogniauxia

<400> SEQUENCE: 252

```
ggaggacatt agcgagttat cataaactcc aaaacccctg tgaacttacc tatgttgcct     60
cggcaggtcg tggtgtgtag cggtgaccac tgggtcgctt gcctcgcacc acgctgaaaa    120
gacctgtcaa aggaccccta aactctgttt ttacaactgt atctctgagt ctattataca    180
aataagttaa aactttcaac aacggatctc ttggctctgg catcgatgaa gaacgcagcg    240
aaatgcgata agtaatgtga attgcagaat tcagtgaatc atcgaatctt tgaacgcaca    300
ttgcgcctga tagtattctg tcaggcatgc ctgttcgagc gtcatttcaa cccccaagcc    360
ctatttgctt gacgttggga gtttacggag acgtaattcc tcaaatatag tggcggagct    420
aggtcgtgct ctaagcgtag taaccacaat tctcgcttct gcagccggct taggtcctgc    480
cgtaaaaccc ctatattttt ttattggttg acctcggatc aggtaggaat acccgctgaa    540
cttaagcata tcaataagcg gaggaaaaga aaccaacagg gattgcccta gtaacggcga    600
gtgaagcggc aacagctcaa atttgaaatc tggccctcgg gtccgagttg taatttgcag    660
aggatgcttt tggcgcggtg ccttccgagt tccctggaac gggacgcctt agagggtgag    720
agccccgtac ggttggacac caagcctctg taaagctcct tcgacgagtc gagtagtttg    780
ggaatgctgc tctaaatggg aggtaaattt cttctaaagc taaataccgg ccagagaccg    840
atagcgcaca agtagagtga tcgaaagatg aaaagcactt tgaaaagagg gttaaatagc    900
acgtgaaatt gttgaaaggg aagcgtttac ggccagacct tttcctggcg gatcatctgg    960
tgttctcacc agtgcactcc gccaggttta ggccagcatc ggctcccgta gggggataaa   1020
agcagtggga aagtagctcc ctcgggagtg ttatagcccg ctgcacaata cccttacagg   1080
```

ggccgaggac cgcgctctg 1099

<210> SEQ ID NO 253
<211> LENGTH: 1120
<212> TYPE: DNA
<213> ORGANISM: Unknown
<220> FEATURE:
<223> OTHER INFORMATION: Kingdom: Fungi, Phylum: Ascomycota, Class:
Eurotiomycetes, Order: Chaetothyriales, Family:
Herpotrichiellaceae, Genus: Phaeomoniella

<400> SEQUENCE: 253
tgagttaggg tctctttaga gcccgaatct ccaacccttt gttaaaaaca ctttgttgct 60
ttggcaggcc cgtcctatcc cttcaccggg agacgaccgc cgggggcgtt tagtcacctc 120
tggtcagtgc ttgccgatag cctattaaaa attctttatt aaataatgtc tgaaaaatta 180
taactaaata taattaaaac ttttaacaac ggatctcttg gttctggcat cgatgaagaa 240
cgcagcgaaa tgcgataagt aatgtgaatt gcagacttca gtgaatcatc gaatctttga 300
acgcacattg cgccctttgg tattccgaag ggcatgcctg ttcgagcgtc attatcaacc 360
ctcaagcccg gcttgttatt gggttcttat cgttaaagat aggcccgaaa gataatggcg 420
gcgtcacaaa tgaccccaga tgcagcgagc ttatacagca tacatcgaaa ggtttttgtg 480
gcccggcctt aacgagaagc aattctcaat tttttacagg ttgacctcgg atcaggtagg 540
aatacccgct gaacttaagc atatcaataa gcggaggaaa agaaaccaac agggattgcc 600
tcagtaacgg cgagtgaagc ggcaatagct caaatttgaa atctggctct tcgagtccga 660
gttgtaattt gtagaggatg tttcgggtgc gcccgcagtt taagttcctt ggaacaggac 720
gtcatagagg gtgagaatcc cgtcttgaac tgtacggcaa gtccatgtga aactccttcg 780
acgagtcgag ttgtttggga atgcagctca aaatgggagg taaatttctt ctaaagctaa 840
atattggcca gagaccgata gcgcacaagt agagtgatcg aaagatgaaa agcactttga 900
aaagagagtt aaacagtatg tgaaattgtt aaaagggaag cgtttgcaac cagacttgtt 960
tctaacagtt ctaccgcagt tctctgtggc ttattctgtt agtccaggcc agcatcagtt 1020
tgggtggctc gttaaaggcc ttgggaatgt atctactcct tcgggtgtag acttatagcc 1080
ctcggtgtaa tagggtctac ctggactgag gtacgcgctt 1120

<210> SEQ ID NO 254
<211> LENGTH: 1025
<212> TYPE: DNA
<213> ORGANISM: Unknown
<220> FEATURE:
<223> OTHER INFORMATION: Kingdom: Fungi, Phylum: Ascomycota, Class:
Sordariomycetes, Order: , Family:

<400> SEQUENCE: 254
attactgagt tatctaaact cccaaccctt tgtgaacctt accgtcgttg cctcggcggg 60
ctgtacttac cctgtagcta ccctgtagct acccggtagg tgcgctccaa gcccgccggt 120
ggaccactaa attctatttt actactgtat ctctgaatgc ttcaacttaa taagttaaaa 180
ctttcaacaa cggatctctt ggttctggca tcgatgaaga acgcagcgaa atgcgataag 240
taatgtgaat tgcagaattc agtgaatcat cgaatctttg aacgcacatt gcgcccatta 300
gtattctagt gggcatgcct attcgagcgt catttcaacc cttaagccta gttgcttagt 360
gttgggaatc tgccctgtat ttatagggca gttccttaaa gtgatcggcg gagttagggc 420
atactctaag cgtagtaata ttcttctcgc ttctgtagtt gtcctggcgg cttgccgtta 480

-continued

```
aaccccctata tttctagtgg ttgacctcgg attaggtagg aatacccgct gaacttaagc    540

atatcaataa gcggaggaaa agaaaccaac agggattgcc ctagtaacgg cgagtgaagc    600

ggcaacagct caaatttgaa atctggccct agcggtccga gttgtaattt gtagaggatg    660

cttttggtta ggtgccttct gagttccctg gaacgggacg ccagagaggg tgagagcccc    720

gtacggttgg acaccgagcc tctatatagc tccttcgacg agtcgagtag tttgggaatg    780

ctgctctaaa tgggaggtaa atttcttcta aagctaaata ccggccagag accgatagcg    840

cacaagtaga gtgatcgaaa gatgaaaagt actttgaaaa gagggttaaa tagcacgtga    900

aattgttgaa agggaagcgt ttgcgaccag actttttcca ggcggatcat cctgtgttct    960

caccggtgca cttcgcctgg tttaggccag catcggttct cttaggggga taaaggcctg   1020

gggaa                                                               1025
```

<210> SEQ ID NO 255
<211> LENGTH: 592
<212> TYPE: DNA
<213> ORGANISM: Unknown
<220> FEATURE:
<223> OTHER INFORMATION: Kingdom: Fungi, Phylum: Ascomycota, Class: Eurotiomycetes, Order: Chaetothyriales, Family:

<400> SEQUENCE: 255

```
tgcttaagtt cagcgggtat tcctacctaa tccgaggtca acctttgaat ttagttaaat     60

tgctttaacg taaaggggcc ggaccacaaa gaccacctca gtgtatgcta taagctcgct    120

gcacctgggg tcattcatga cgccgccatt atctttcggg cctatcttta acgataaggg    180

acccaataac aagccgggct tgagggttga taatgacgct cgaataggca tgcccttcgg    240

aataccaaag ggcgcaatgt gcgttcaaag attcgatgat tcactgaatt ctgcaattca    300

cattacttat cgcatttcgc tgcgttcttc atcgatgcca gaaccaagag atccgttgtt    360

gaaagtttta attaaatttt aattaaagat tcagacttca taattataaa gaatttagat    420

tggctactga caagcactga ccagaggtga cttaacccct ccggcggccc cgaaaggcgg    480

gcctgccaaa gcaacaaagt agttaaacat agggttggag gttcgggccc agaggaccct    540

aactcagtaa tgatccttcc gcaggttcac ctacggaaac cttgttacga ct            592
```

<210> SEQ ID NO 256
<211> LENGTH: 601
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Incertae sedis, Genus: Phoma
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (592)..(592)
<223> OTHER INFORMATION: n is a, c, g, or t

<400> SEQUENCE: 256

```
aaatcacggt tcgtaggtga acctgcggaa ggatcattac ctagagttgt aggctttgcc     60

tgctatctct tacccatgtc ttttgagtac cttcgtttcc tcggcgggtc cgcccgccga    120

ttggacaatt taaaccattt gcagttgcaa tcagcgtctg aaaaaactta atagttacaa    180

ctttcaacaa cggatctctt ggttctggca tcgatgaaga acgcagcgaa atgcgataag    240
```

```
tagtgtgaat tgcagaattc agtgaatcat cgaatctttg aacgcacatt gcgccccttg    300

gtattccatg gggcatgcct gttcgagcgt catttgtacc ctcaagcttt gcttggtgtt    360

gggtgtttgt ctcgcctctg cgcgtagact cgcctcaaaa aaattggcag ccggtgtatt    420

gatttcggag cgcagtacat ctcgcgcttt gcactcaaaa ctgacsacrt ccaaaagtac    480

atttttacac tcttgacctc ggatcaggta gggatacccg ctgaacttaa gcatatcata    540

ggcgagagga aatcangtag gaatacccgc tgaacttaag catatcaata gncggaggaa    600

a                                                                    601


<210> SEQ ID NO 257
<211> LENGTH: 1007
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Pleosporales, Family: Pleosporaceae,
      Genus: Alternaria
<220> FEATURE:
<221> NAME/KEY: misc_feature
<222> LOCATION: (156)..(156)
<223> OTHER INFORMATION: n is a, c, g, or t

<400> SEQUENCE: 257

agtcgacggc agcgcggggc aacctggcgg cgagtggcga acgggtgagt aatatatcgg     60

aacgtaccca aaagtggggg ataacgtagc gaaagttacg ctaataccgc atacgatcta    120

cggatgaaag tgggggacct tcgggccttg tgctcntgga gcggccgata tctgattagc    180

tagttggtga ggtaaaggct caccaaggcg acgatcagta gctggtctga gaggacgacc    240

agccacactg gaactgagac acggtccaga ctcctacggg aggcagcagt ggggaatttt    300

ggacaatggg cgcaagcctg atccagcaat gccgcgtgag tgaagaaggc cttcgggttg    360

taaagctctt ttgtcaggga agaaacggct gaggctaata tcctcggcta atgacggtac    420

ctgaagaata agcaccggct aactacgtgc cagcagccgc ggtaatacgt agggtgcaag    480

cgttaatcgg aattactggg cgtaaagcgt gcgcaggcgg ttttgtaagt ctgacgtgaa    540

atccccgggc tcaacctggg aattgcgatg gagactgcaa ggcttgaatc tggcagaggg    600

gggtagaatt ccacgtgtag cagtgaaatg cgtagagatg tggaggaaca ccgatggcga    660

aggcagcccc ctgggtcaag attgacgctc atgcacgaaa gcgggcactc taatgagact    720

gccggtgaca aaccggagga aggtggggat gacgtcaagt cctcatggcc cttatgggta    780

gggcttcaca cgtcatacaa tggtacatac agagggccgc caacccgcga gggggagcta    840

atcccagaaa gtgtatcgta gtccggatcg cagtctgcaa ctcgactgcg tgaagttgga    900

atcgctagta atcgcggatc agcatgtcgc ggtgaatacg ttcccgggtc ttgtacacac    960

cgcccgtcac accatgggag cgggtttacc agaagtagga gctaacc                 1007


<210> SEQ ID NO 258
<211> LENGTH: 592
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Dothideales, Family: Dothioraceae, Genus:
      Aureobasidium

<400> SEQUENCE: 258

tttaatagtc gtagtgactg cggaaggatc attaaagagt aagggtgctc agcgcccgac     60

ctccaaccct ctgttgttaa aactaccttg ttgctttggc gggaccgctc ggtctcgagc    120
```

cgctggggat tcgtcccagg cgagcgcccg ccagagttaa accaaactct tgttatataa 180
accggtcgtc tgagttaaaa ttttgaataa atcaaaactt tcaacaacgg atctcttggt 240
tctcgcatcg atgaagaacg cagcgaaatg cgataagtaa tgtgaattgc agaattcagt 300
gaatcatcga atctttgaac gcacattgcg ccccttggta ttccgagggg catgcctgtt 360
cgagcgtcat tacaccactc aagctatgct tggtattggg cgtccgtccc ttcgggggcg 420
cgccttaaag acctcggcga ggcctcaccg gctttaggcg tagtagaatt tattcgaacg 480
tctgtcaatg gagaggactt ctgccgactg aaacctttta tatttttcta ggttgacctc 540
ggatcaggta gggatacccg ctgaacttaa gcatatcaat agccggagga aa 592

<210> SEQ ID NO 259
<211> LENGTH: 574
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Coniochaetales, Family: Coniochaetaceae, Genus: Lecythophora

<400> SEQUENCE: 259
ttcacggttc gtggtgaacc agcggaggga tcattacaag aagccgaaag gctacttcaa 60
accatcgtga acttatccaa gttgcttcgg cggcgcggct cccctcgcgg ggtgccgcag 120
ccccgccccc tcgggggtgg tgggcgcccg ccggaggtat taaactctcc cgtattatag 180
tggtatttct gagtaaaaac aaataagtta aaactttcaa caacggatct cttggttctg 240
gcatcgatga agaacgcagc gaaatgcgat aagtaatgtg aattgcagaa ttcagtgaat 300
catcgaatct ttgaacgcac attgcgcccg ctagtattct agcgggcatg cctgttcgag 360
cgtcatttca accctcaagc cctgcttggt gttggggccc tacggctgcc gtaggccctg 420
aaaagaagtg gcgggctcgc tgcaactccg agcgtagtaa ttcattatct cgctagggag 480
gcgcggcggt gctcctgccg ttaaagacca tctttaacca aaggttgacc tcggatcagg 540
taggaatacc cgctgaactt aagcatatca taaa 574

<210> SEQ ID NO 260
<211> LENGTH: 662
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Dothideales, Family: Dothioraceae, Genus: Hormonema
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (184)..(184)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:

<221> NAME/KEY: misc_feature
<222> LOCATION: (355)..(355)
<223> OTHER INFORMATION: n is a, c, g, or t
<220> FEATURE:
<221> NAME/KEY: misc_feature
<222> LOCATION: (397)..(398)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (527)..(527)
<223> OTHER INFORMATION: n is a, c, g, or t

<400> SEQUENCE: 260
tttaacacgg ttccgaggga cctgcggaag gatcattaan gagttgcgtg gaaatctccc 60
gcaaacctca accctgttgt tgttataact accttgttgc tttggcgtgg accgtccggt 120
tcgccggact gccagggccc ttaggggccg cggtaagcgc ccgccagagt cnaaccaaac 180
tctngttttt aaccggtcgt ctgagtacaa gtttaaatta aattaaaact ttcaacaaag 240
gatctcttgg ttctcgcatc gatgaagaac gcagcgaaat gcgataagta atgtgaattg 300
cagaattcag tgaatcatng aatctttgaa cgcacattgc gcccnttggt attcngaggg 360
gcatgcctgt tcgagcgtca ttacaccatt caagctnngc ttggtattag gcattcgtcc 420
tcctncacgg tgggcgggcc tcaaaaatct cggcggagcc tttccagctt tgggcgtagt 480
agaatttcta atcacgtctt taaacggaga ggtttccact gccgctnaac cttttatttt 540
tcaggttgac ctcggatcac gtagggatac ccgctgaact taagcatatc aaaacccgga 600
ggaatttatt tgggtgacct cagatcaggt agggataccc gctgaactta agcatatcat 660
ag 662

<210> SEQ ID NO 261
<211> LENGTH: 552
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Sporormiaceae, Genus: Preussia

<400> SEQUENCE: 261
aaaaacacgg ttcgtaggtg aacctgcgga aggatcatta tcgtagggct tcggccctgt 60
cgagatagaa cccttgcctt tttgagtacc tttcgtttcc tcggcaggct cgcctgccaa 120
tggggaccac aaaaaacact ttgcagtacc tgtaacagtc tgaacaaaca aaacaaaaat 180
caaaactttc aacaacggat ctcttggttc tggcatcgat gaagaacgca gcgaaatgcg 240
ataagtagtg tgaattgcag aattcagtga atcatcgaat ctttgaacgc acattgcgcc 300
ctttggtatt ccttagggca tgcctgttcg agcgtcattt aaaccttcaa gctaagcttg 360
gtgttgggtg actgtccgct tcactgcgga ctcgcctcaa aattattggc ggccggtaca 420
ttggcttcga gcgcagcaga aacgcgaact cgggcccgtc gtattggctc ccagaagcta 480
tcttcacaat tttgacctcg gatcaggtag ggatacccgc tgaacttaag catatcataa 540
ccgcggagga aa 552

<210> SEQ ID NO 262
<211> LENGTH: 1383
<212> TYPE: DNA
<213> ORGANISM: Unknown

<220> FEATURE:
<223> OTHER INFORMATION: Kingdom: Fungi, Phylum: Ascomycota, Class: Sordariomycetes, Order: Coniochaetales, Family: Coniochaetaceae, Genus: Lecythophora

<400> SEQUENCE: 262

```
gcagtcgacg gcagcacggg agcaatcctg gtggcgagtg gcgaacgggt gagtaataca     60

tcggaacgtg cccaatcgtg gggataacg cagcgaaagc tgtgctaata ccgcatacga    120

tctacggatg aaagcagggg accgcaaggc cttgcgcgaa tggagcggcc gatggcagat    180

taggtagttg gtgaggtaaa ggctcaccaa gccttcgatc tgtagctggt ctgagaggac    240

gaccagccac actgggactg agacacggcc cagactccta cgggaggcag cagtggggaa    300

ttttggacaa tgggcgaaag cctgatccag caatgccgcg tgcaggatga aggccttcgg    360

gttgtaaact gcttttgtac ggaacgaaac ggttctttct aataaagaga gctaatgacg    420

gtaccgtaag aataagcacc ggctaactac gtgccagcag ccgcggtaat acgtagggtg    480

caagcgttaa tcggaattac tgggcgtaaa gcgtgcgcag gcggttatgt aagacagttg    540

tgaaatcccc gggctcaacc tgggaattgc atctgtgact gcatagctag agtacggtag    600

agggggatgg aattccgcgt gtagcagtga aatgcgtaga tatgcggagg aacaccgatg    660

gcgaaggcaa tcccctggac ctgtactgac gctcatgcac gaaagcgtgg ggagcaaaca    720

ggattagata ccctggtagt ccacgcccta aacgatgtca actggttgtt gggtcttcac    780

tgactcagta acgaagctaa cgcgtgaagt tgaccgcctg gggagtacgg ccgcaaggtt    840

gaaactcaaa ggaattgacg gggacccgca caagcggtgg atgatgtggt ttaattcgat    900

gcaacgcgaa aaaccttacc cacctttgac atgtacggaa tttaccagag atggtttagt    960

gctcgaaaga gaaccgtaac acaggtgctg catggctgtc gtcagctcgt gtcgtgagat   1020

gttgggttaa gtcccgcaac gagcgcaacc cttgtcatta gttgctacat ttagttgggc   1080

actctaatga gactgccggt gacaaaccgg aggaaggtgg ggatgacgtc aagtcctcat   1140

ggcccttata ggtggggcta cacacgtcat acaatggctg gtacaaaggg ttgccaaccc   1200

gcgaggggga gctaatccca taaaaccagt cgtagtccgg atcgcagtct gcaactcgac   1260

tgcgtgaagt cggaatcgct agtaatcgtg gatcagaatg tcacggtgaa tacgttcccg   1320

ggtcttgtac acaccgcccg tcacaccatg ggagcgggtt ctgccagaag tagttagcca   1380

acc                                                                 1383
```

<210> SEQ ID NO 263
<211> LENGTH: 533
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Incertae sedis, Family: Incertae sedis, Genus: Monodictys

<400> SEQUENCE: 263

```
aacacggttc gtatgtacct gcggaaggat cattatcgta gggcttcggc cctgtcgaga     60

tagaaccctt gcctttttga gtacctcttg tttcctcggc gggctcgccc gccgatggac    120

ccccccaaaa aacactttgc agtacctgta atagtctgaa caacaaacaa aaattaaaac    180

tttcaacaac ggatctcttg gttctggcat cgatgaagaa cgcagcgaaa tgcgataagt    240

agtgtgaatt gcagaattca gtgaatcatc gaatctttga acgcacattg cgccctttgg    300

tattccttag ggcatgcctg ttcgagcgtc atttaaacct tcaagctcag cttggtgttg    360
```

-continued

```
ggtgactgtc cccctcaaaa gggactcgcc tcaaaatcat tggcggccgg tacgttggct    420

tcgagcgcag cagaaacgcg aactcggaga ctttgtgtcg gctcccagaa gccatcttta    480

aattttgacc tcggatcagg tagggatacc cgctgaactt aagcatatca taa           533
```

```
<210> SEQ ID NO 264
<211> LENGTH: 598
<212> TYPE: DNA
<213> ORGANISM: Unknown
<220> FEATURE:
<223> OTHER INFORMATION: Kingdom: Fungi, Phylum: Ascomycota, Class:
      Sordariomycetes, Order: Xylariales, Family: Amphisphaeriaceae,
      Genus: Pestalotiopsis

<400> SEQUENCE: 264

ccacacggtc cgtggtgaca gcggagggat cattatagag ttttttaaac tcccaaccca     60

tgtgaactta ccattgttgc ctcggcagaa gctacctggt taccttacct tggaacggcc    120

taccctgtag cgccttaccc tggaacggcc taccctgtaa cggctgccgg tggactacca    180

aactcttgtt attttattgt aatctgagcg tcttatttta ataagtcaaa actttcaaca    240

acggatctct tggttctggc atcgatgaag aacgcagcga aatgcgataa gtaatgtgaa    300

ttgcagaatt cagtgaatca tcgaatcttt gaacgcacat tgcgcccatt agtattctag    360

tgggcatgcc tgttcgagcg tcatttcaac ccttaagcct agcttagtgt tgggagccta    420

ctgcttttgc tagcggtagc tcctgaaata caacggcgga tctgcgatat cctctgagcg    480

tagtaatttt tatctcgctt ttgactggag ttgcagcgtc tttagccgct aaacccccca    540

atttttaatg gttgacctcg gatcaggtag gaatacccgc tgaacttaag catatcta      598
```

```
<210> SEQ ID NO 265
<211> LENGTH: 542
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Capnodiales, Family: Mycosphaerellaceae,
      Genus: Cladosporium

<400> SEQUENCE: 265

aataaacagt tcgtagtgac cgcggaggga tcattacaag tgaccccggt ctaaccaccg     60

ggatgttcat aaccctttgt tgtccgactc tgttgcctcc ggggcgaccc tgccttcggg    120

cgggggctcc gggtggacac ttcaaactct tgcgtaactt tgcagtctga gtaaacttaa    180

ttaataaatt aaaactttta acaacggatc tcttggttct ggcatcgatg aagaacgcag    240

cgaaatgcga taagtaatgt gaattgcaga attcagtgaa tcatcgaatc tttgaacgca    300

cattgcgccc cctggtattc cggggggcat gcctgttcga gcgtcatttc accactcaag    360

cctcgcttgg tattgggcaa cgcggtccgc cgcgtgcctc aaatcgaccg gctgggtctt    420

ctgtccccta agcgttgtgg aaactattcg ctaaagggtg ttcgggaggc tacgccgtaa    480

aacaacccca tttctaaggt tgacctcgat caggtaggga tacccgctga acttaagcat    540

at                                                                   542
```

```
<210> SEQ ID NO 266
<211> LENGTH: 578
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Botryosphaeriales, Family:
      Botryosphaeriaceae, Genus: Botryosphaeria
```

<400> SEQUENCE: 266
aacacggttc gtagggacct gcggaaggat cattaccgag ttgattcggg ctccggcccg 60
atcctcccac cctttgtgta cctacctctg ttgctttggc gggccgcggt cctccgcggc 120
cgcccccctc cccgggggt ggccagcgcc cgccagagga ccatcaaact ccagtcagta 180
aacgatgcag tctgaaaaac atttaataaa ctaaaacttt caacaacgga tctcttggtt 240
ctggcatcga tgaagaacgc agcgaaatgc gataagtaat gtgaattgca gaattcagtg 300
aatcatcgaa tctttgaacg cacattgcgc cctttggtat tccgaagggc atgcctgttc 360
gagcgtcatt acaaccctca agctctgctt ggtattgggc accgtccttt gcgggcgcgc 420
ctcaaagacc tcggcggtgg cgtcttgcct caagcgtagt agaacataca tctcgcttcg 480
gagcgcaggg cgtcgcccgc cggacgaacc ttctgaactt ttctcaaggt tgacctcgga 540
tcaggtaggg atacccgctg aacttaagca tatcatag 578

<210> SEQ ID NO 267
<211> LENGTH: 645
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Botryosphaeriales, Family: Botryosphaeriaceae, Genus: Phyllosticta

<400> SEQUENCE: 267
aacacggttc gtagtgacct gcggaaggat cattactgaa aatgtaataa acccttcagg 60
ttttggaagg gggagccgtc aaaagcttcc ctggtacatg cctcacccct tgtatatcta 120
ccatgttgct ttggcgggcc gacccggttt cgacccgggc ggccggcgcc cccagcctgc 180
ttgccaggcc aggacgcccg gccaagtgcc cgccagtata caaaactcca gcgattattt 240
tgtgtagtcc tgagaattta ttcaataaat taaaactttc aacaacggat ctcttggttc 300
tggcatcgat gaagaacgca gcgaaatgcg ataagtaatg tgaattgcag aattcagtga 360
atcatcgaat ctttgaacgc acattgcgcc ctctggcatt ccggagggca tgcctgttcg 420
agcgtcattt caaccctcaa gctctgcttg gtattgggcg acgtctgctg tcagacgcgc 480
ctggaagacc tcggcgacgg cattccagcc tcgagcgtag tagtaaaata tctcgctttg 540
gaggatgggg tgacggcttg ccggacaacc gacctctggt catttttttcc aaggttgacc 600 tcggatcagg tagggatacc cgctgaactt aagcatatat aggcg 645

<210> SEQ ID NO 268
<211> LENGTH: 600
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Montagnulaceae, Genus: Paraconiothyrium

<400> SEQUENCE: 268
aaacacggtt cgtagtgacc tgcggaagga tcattatcta ttccatgagg tgcggtcgcg 60
gccctcggcg ggagcaacag ctaccgtcgg gcggtagagg taacactttc acgcgccgca 120
tgtctgaatc cttttttttac gagcaccttt cgttctcctt cggcggggca acctgccgtt 180
ggaacctatc aaaacctttt tttgcatcta gcattacctg ttctgataca aacaatcgtt 240
acaactttca acaatggatc tcttggctct ggcatcgatg aagaacgcag cgaaatgcga 300
taagtagtgt gaattgcaga attcagtgaa tcatcgaatc tttgaacgca cattgcgccc 360
cttggtattc catggggcat gcctgttcga gcgtcatcta caccctcaag ctctgcttgg 420
tgttgggcgt ctgtcccgcc tctgcgcgcg gactcgcccc aaattcattg gcagcggtcc 480
ttgcctcctc tcgcgcagca cattgcgctt ctcgaggtgc gcggcccgcg tccacgaagc 540
aacattaccg tctttgacct cggatcaggt agggataccc gctgaactta agcatatctg 600

<210> SEQ ID NO 269
<211> LENGTH: 615
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Xylariales, Family: Amphisphaeriaceae, Genus: Pestalotiopsis

<400> SEQUENCE: 269
aaaacacggt ctgttgtgaa ccagcggagg gatcattata gagttttcta aactcccaac 60
ccatgtgaac ttaccattgt tgcctcggca gaagctacct ggttacctta ccttggaacg 120
gcctaccctg tagcgcctta ccctggaacg gcctaccctg taacggctgc cggtggacta 180
ccaaactctt gttattatat tgtaatctga gcgtcttatt ttaataagtc aaaactttca 240
acaacggatc tcttggttct ggcatcgatg aagaacgcag cgaaatgcga taagtaatgt 300
gaattgcaga attcagtgaa tcatcgaatc tttgaacgca cattgcgccc attagtattc 360
tagtgggcat gcctgttcga gcgtcatttc aacccttaag cctagcttag tgttgggagc 420
ctactgcttt tgctagcggt agctcctgaa atacaacggc ggatctgcga tatcctctga 480
gcgtagtaat tttatctcg cttttgactg gagttgcagc gtctttagcc gctaaacccc 540
ccaattttta atggttgacc tcggatcagg taggaatacc cgctgaactt aagcatatca 600
taggccgaaa ggaaa 615

<210> SEQ ID NO 270
<211> LENGTH: 604
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Montagnulaceae, Genus: Paraconiothyrium

<400> SEQUENCE: 270
ttacacggtt cgtaggtgaa cctgcggaag gatcattatc tattccatga ggtgcggtcg 60
cggccctcgg cgggagcaac agctaccgtc gggcggtaga ggtaacactt tcacgcgccg 120
catgtctgaa tcctttttt acgagcacct ttcgttctcc ttcggcgggg caacctgccg 180
ttggaaccta tcaaaacctt tttttgcatc tagcattacc tgttctgata caaacaatcg 240
ttacaacttt caacaatgga tctcttggct ctggcatcga tgaagaacgc agcgaaatgc 300
gataagtagt gtgaattgca gaattcagtg aatcatcgaa tctttgaacg cacattgcgc 360
cccttggtat tccatggggc atgcctgttc gagcgtcatc tacaccctca agctctgctt 420
ggtgttgggc gtctgtcccg cctctgcgcg cggactcgcc ccaaattcat tggcagcggt 480
ccttgcctcc tctcgcgcag cacattgcgc ttctcgaggt gcgcggcccg cgtccacgaa 540
gcaacattac cgtctttgac ctcggatcag gtagggatac ccgctgaact taagcatatc 600
ataa 604

<210> SEQ ID NO 271
<211> LENGTH: 586
<212> TYPE: DNA
<213> ORGANISM: Unknown
<220> FEATURE:
<223> OTHER INFORMATION: Kingdom: Fungi, Phylum: Ascomycota, Class: Eurotiomycetes, Order: Eurotiales, Family: Trichocomaceae, Genus: Penicillium

<400> SEQUENCE: 271

```
aaaaaacaag gtttccgtag gtgaacctgc ggaaggatca ttaccgagtg agggccctct     60

gggtccaacc tcccacccgt gtttatcgta ccttgttgct tcggcgggcc cgccgcaagg    120

ccgccggggg gcatctgccc tctggcccgc gcccgccgaa gacaccattg aacgctgtct    180

gaagattgca gtctgagcaa ttagttaaat aacttaaaac tttcaacaac ggatctcttg    240

gttccggcat cgatgaagaa cgcagcgaaa tgcgatacgt aatgtgaatt gcagaattca    300

gtgaatcatc gagtctttga acgcacattg cgccccctgg tattccgggg ggcatgcctg    360

tccgagcgtc attgctgccc tcaagcacgg cttgtgtgtt gggctccgtc ctccttccgg    420

ggggacgggc ccgaaaggca gcggcggcac cgcgtccggt cctcgagcgt atggggcttc    480

gtcacccgct ctgcaggccc ggccggcgct tgccgacaca tcaatctttt ttccaggttg    540

acctcggatc aggtagggat acccgctgaa cttaagcata tcatag                  586
```

<210> SEQ ID NO 272
<211> LENGTH: 1083
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Xylariales, Family: Xylariaceae

<400> SEQUENCE: 272

```
ggatcattac tgagttatct aaactcccaa ccctttgtga accttaccgt cgttgcctcg     60

gcgggctgta cttaccctgt agctaccctg tagctacccg gtaggtgcgc tccaagcccg    120

ccggtggacc actaaattct attttactac tgtatctctg aatgcttcaa cttaataagt    180

taaaactttc aacaacggat ctcttggttc tggcatcgat gaagaacgca gcgaaatgcg    240

ataagtaatg tgaattgcag aattcagtga atcatcgaat ctttgaacgc acattgcgcc    300

cattagtatt ctagtgggca tgcctattcg agcgtcattt caacccttaa gcctagttgc    360

ttagtgttgg gaatctgccc tgtatttata gggcagttcc ttaaagtgat cggcggagtt    420

agggcatact ctaagcgtag taatattctt ctcgcttctg tagttgtcct ggcggcttgc    480

cgttaaaccc ctatatttct agtggttgac ctcggattag gtaggaatac ccgctgaact    540

taagcatatc aataagcgga ggaaaagaaa ccaacaggga ttgccctagt aacggcgagt    600

gaagcggcaa cagctcaaat ttgaaatctg gccctagcgg tccgagttgt aatttgtaga    660

ggatgctttt ggttaggtgc cttctgagtt ccctggaacg ggacgccaga gagggtgaga    720

gccccgtacg gttggacacc gagcctctat atagctcctt cgacgagtcg agtagtttgg    780

gaatgctgct ctaaatggga ggtaaatttc ttctaaagct aaataccggc cagagaccga    840

tagcgcacaa gtagagtgat cgaaagatga aaagtacttt gaaaagaggg ttaaatagca    900

cgtgaaattg ttgaaaggga agcgtttgcg accagacttt ttccaggcgg atcatccggt    960

gttctcaccg gtgcacttcg cctggtttag gccagcatcg gttctcttag gggataaag    1020

gcctggggaa cgtagctcct tcgggagtgt tatagcccct agcgtaatac ccttcggggg   1080

acc                                                                 1083
```

<210> SEQ ID NO 273
<211> LENGTH: 1078
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Xylariales, Family: Xylariaceae

<400> SEQUENCE: 273
ttatctaaac tcccaaccct ttgtgaacct taccgtcgtt gcctcggcgg gctgtactta 60
ccctgtagct accctgtagc tacccggtag gtgcgctcca agcccgccgg tggaccacta 120
aattctattt tactactgta tctctgaatg cttcaactta ataagttaaa actttcaaca 180
acggatctct tggttctggc atcgatgaag aacgcagcga aatgcgataa gtaatgtgaa 240
ttgcagaatt cagtgaatca tcgaatcttt gaacgcacat tgcgcccatt agtattctag 300
tgggcatgcc tattcgagcg tcatttcaac ccttaagcct agttgcttag tgttgggaat 360
ctgccctgta tttatagggc agttccttaa agtaatcggc ggagttaggg catactctaa 420
gcgtagtaat attcttctcg cttctgtagt tgtcctggcg gcttgccgtt aaacccctat 480
atttctagtg gttgacctcg gattaggtag gaatacccgc tgaacttaag catatcaata 540
agcggaggaa aagaaaccaa cagggattgc cctagtaacg gcgagtgaag cggcaacagc 600
tcaaatttga aatctggccc tagcggtccg agttgtaatt tgtagaggat gcttttggtt 660
aggtgccttc tgagttccct ggaacgggac gccagagagg gtgagagccc cgtacggttg 720
gacaccgagc ctctatatag ctccttcgac gagtcgagta gtttgggaat gctgctctaa 780
atgggaggta aatttcttct aaagctaaat accggccaga gaccgatagc gcacaagtag 840
agtgatcgaa agatgaaaag tactttgaaa agagggttaa atagcacgtg aaattgttga 900
aagggaagcg tttgcgacca gactttttcc aggcggatca tcctgtgttc tcaccggtgc 960
acttcgcctg gtttaggcca gcatcggttc tcttaggggg ataaaggcct ggggaacgta 1020
gctccttcgg gagtgttata gcccctagcg taataccctt cgggggaccg aggaacgc 1078

<210> SEQ ID NO 274
<211> LENGTH: 1046
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: , Family:

<400> SEQUENCE: 274
ctgctaccct gtaggaccta ccctggacct accccgtagc tgctacccgg taagcacgct 60
aaacggcctg ccggcggtct tctaaactct tgtcagttat tgtgaaattc tgaatatcta 120
aaacataata agttaaaact ttcaacaacg gatctcttgg ttctggcatc gatgaagaac 180
gcagcgaaat gcgataagta atgtgaattg cagaattcag tgaatcatcg aatctttgaa 240
cgcacattgc gcccattagt attctagtgg gcatgcctgt tcgagcgtca ttttgaccct 300
taagcccctg ttgcttagtg ttgggagtct acgactatgg cgtagctcct taaagttagt 360
tggcggagtt agggtatact ctcagcgtag taaaaatttt cctcgctttt gtagttatcc 420
caactatagc cattaaaccc ttttattttt tttctaaagg ttgacctcgg atcaggtagg 480
aatacccgct gaacttaagc atatcaataa gcggaggaaa agaaaccaac agggattgcc 540
ttagtaacgg cgagtgaagc ggcaacagct caaatttgaa atctggcctt cgggtccgag 600
ttgtaatttg tagaggatgc ttttggcgcg gtgccttcca agttccctgg aacgggacgc 660
cttagagggt gagagccccg tacggttgga cgcctagcct ctgtaaagct ccttcgacga 720
gtcgagtagt ttgggaatgc tgctctaaat gggaggtaaa cttcttctaa agctaaatac 780
cggccagaga ccgatagcgc acaagtagag tgatcgaaag atgaaaagca ctttgaaaag 840
agggttaaat agcacgtgaa attgttgaaa gggaagcgtt tgcgaccaga ctttctctag 900
gcggatcatc cggtgttctc accggtgcac ttcgcctagt ttaggccagc atcggtttct 960
gtagggggat aaaggcctgg ggaatgtggc tccctcggga gtgttatagc cccttgcgta 1020 ataccttttgc ggggaccgag gaccgc 1046

<210> SEQ ID NO 275
<211> LENGTH: 1092
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Xylariales, Family: Xylariaceae

<400> SEQUENCE: 275
ggatcattac tgagttatct aaactcccaa ccctttgtga accttaccgt cgttgcctcg 60
gcgggctgta cttaccctgt agctaccctg tagctacccg gtaggtgcgc tccaagcccg 120
ccggtggacc actaaattct attttactac tgtatctctg aatgcttcaa cttaataagt 180
taaaactttc aacaacggat ctcttggttc tggcatcgat gaagaacgca gcgaaatgcg 240
ataagtaatg tgaattgcag aattcagtga atcatcgaat ctttgaacgc acattgcgcc 300
cattagtatt ctagtgggca tgcctattcg agcgtcattt caacccttaa gcctagttgc 360
ttagtgttgg gaatctgccc tgtatttata gggcagttcc ttaaagtgat cggcggagtt 420
agggcatact ctaagcgtag taatattctt ctcgcttctg tagttgtcct ggcggcttgc 480
cgttaaaccc ctatatttct agtggttgac ctcggattag gtaggaatac ccgctgaact 540
taagcatatc aataagcgga ggaaaagaaa ccaacaggga ttgccctagt aacggcgagt 600
gaagcggcaa cagctcaaat ttgaaatctg gccctagcgg tccgagttgt aatttgtaga 660
ggatgctttt ggttaggtgc cttctgagtt ccctggaacg ggacgccaga gagggtgaga 720
gccccgtacg gttggacacc gagcctctat atagctcctt cgacgagtcg agtagtttgg 780
gaatgctgct ctaaatggga ggtaaatttc ttctaaagct aaataccggc cagagaccga 840
tagcgcacaa gtagagtgat cgaaagatga aaagtacttt gaaaagaggg ttaaatagca 900
cgtgaaattg ttgaaaggga agcgtttgcg accagacttt ttccaggcgg atcatccggt 960
gttctcaccg gtgcacttcg cctggtttag gccagcatcg gttctcttag ggggataaag 1020
gcctggggaa cgtagctcct tcgggagtgt tatagcccct agcgtaatac ccttcggggg 1080
accgaggaac gc 1092

<210> SEQ ID NO 276
<211> LENGTH: 1039
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Xylariales, Family: Xylariaceae

<400> SEQUENCE: 276
tgcctcggcg ggctgtactt accctgtagc taccctgtag ctacccggta ggtgcgctcc 60
aagcccgccg gtggaccact aaattctatt ttactactgt atctctgaat gcttcaactt 120

-continued

```
aataagttaa aactttcaac aacggatctc ttggttctgg catcgatgaa gaacgcagcg    180

aaatgcgata agtaatgtga attgcagaat tcagtgaatc atcgaatctt tgaacgcaca    240

ttgcgcccat tagtattcta gtgggcatgc ctattcgagc gtcatttcaa cccttaagcc    300

tagttgctta gtgttgggaa tctgccctgt atttataggg cagttcctta aagtgatcgg    360

cggagttagg gcatactctg agcgtagtaa tattcttctc gcttctgtag ttgtcctggc    420

ggcttgccgt taaaccccta tatttctagt ggttgacctc ggattaggta ggaatacccg    480

ctgaacttaa gcatatcaat aagcggagga aaagaaacca acagggattg ccctagtaac    540

ggcgagtgaa gcggcaacag ctcaaatttg aaatctggcc ctagcggtcc gagttgtaat    600

ttgtagagga tgcttttggt taggtgcctt ctgagttccc tggaacggga cgccagagag    660

ggtgagagcc ccgtacggtt ggacaccgag cctctatata gctccttcga cgagtcgagt    720

agtttgggaa tgctgctcta aatgggaggt aaatttcttc taaagctaaa taccggccag    780

agaccgatag cgcacaagta gagtgatcga aagatgaaaa gtactttgaa aagagggtta    840

aatagcacgt gaaattgttg aaagggaagc gtttgcgacc agactttttc caggcggatc    900

atccggtgtt ctcaccggtg cacttcgcct ggtttaggcc agcatcggtt ctcttagggg    960

gataaaggcc tggggaacgt agctccttcg ggagtgttat agcccctagc gtaataccct   1020

tcgggggacc gaggaacgc                                                1039
```

```
<210> SEQ ID NO 277
<211> LENGTH: 543
<212> TYPE: DNA
<213> ORGANISM: Unknown
<220> FEATURE:
<223> OTHER INFORMATION: Kingdom: Fungi, Phylum: Ascomycota, Class:
      Sordariomycetes, Order: Hypocreales, Family: Nectriaceae, Genus:
      Fusarium

<400> SEQUENCE: 277

cattaccgag ttattcaact catcaaccct gtgaacatac ctaaacgttg cttcggcggg     60

aatagacggc cccgtgaaac gggccgcccc cgccagagga cccttaactc tgtttctata    120

atgtttcttc tgagtaaaac aagcaaataa attaaaactt tcaacaacgg atctcttggc    180

tctggcatcg atgaagaacg cagcgaaatg cgataagtaa tgtgaattgc agaattcagt    240

gaatcatcga atctttgaac gcacattgcg cccgccagta ttctggcggg catgcctgtt    300

cgagcgtcat tacaaccctc aggcccccgg gcctggcgtt ggggatcggc ggagcctctc    360

tgtgggcaca cgccgtcccc caaatacagt ggcggtcccg ccgcagcttc catcgcgtag    420

tagctaacac ctcgcgactg gagagcggcg cggccacgcc gtaaaacacc caacttttct    480

gaagttgacc tcgaatcagg taggaatacc cgctgaactt aagcatatca ataagcggag    540

gaa                                                                  543
```

```
<210> SEQ ID NO 278
<211> LENGTH: 545
<212> TYPE: DNA
<213> ORGANISM: Unknown
<220> FEATURE:
<223> OTHER INFORMATION: Kingdom: Fungi, Phylum: Ascomycota, Class:
      Sordariomycetes, Order: Hypocreales, Family: Nectriaceae, Genus:
      Fusarium

<400> SEQUENCE: 278

cattaccgag ttatacaact catcaaccct gtgaacatac ctataacgtt gcctcggcgg     60
```

gaacagacgg ccccgtaaca cgggccgccc ccgccagagg accccctaac tctgtttcta 120
taatgtttct tctgagtaaa caagcaaata aattaaaact ttcaacaacg gatctcttgg 180
ctctggcatc gatgaagaac gcagcgaaat gcgataagta atgtgaattg cagaattcag 240
tgaatcatcg aatctttgaa cgcacattgc gcccgccagt attctggcgg gcatgcctgt 300
tcgagcgtca ttacaaccct caggcccccg ggcctggcgt tggggatcgg cggaagcccc 360
ctgcgggcac aacgccgtcc cccaaataca gtggcggtcc cgccgcagct tccattgcgt 420
agtagctaac acctcgcaac tggagagcgg cgcggccacg ccgtaaaaca cccaacttct 480
gaatgttgac ctcgaatcag gtaggaatac ccgctgaact taagcatatc aataagcgga 540
ggaaa 545

<210> SEQ ID NO 279
<211> LENGTH: 644
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Hypocreales, Family: Nectriaceae, Genus: Fusarium
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (625)..(627)
<223> OTHER INFORMATION: n is a, c, g, or t

<400> SEQUENCE: 279
ttggaagtaa aagtcgtaac aaggtctccg ttggtgaacc agcgnnggga tcattaccga 60
gtttacaact cccaaaccca atgtgaacgt taccaaactg ttgcctcggc gggatctctg 120
ccccgggtgc gtcgcagccc cggaccaagg cgcccgccgg aggaccaacc taaaactctt 180
attgtatacc ccctcgcggg ttttttttata atctgagcct tctcggcgcc tctcgtaggc 240
gtttcgaaaa tgaatcaaaa ctttcaacaa cggatctctt ggttctggca tcgatgaaga 300
acgcagcgaa atgcgataag taatgtgaat tgcagaattc agtgaatcat cgaatctttg 360
aacgcacatt gcgcccgcca gtattctggc gggcatgcct gtccgagcgt catttcaacc 420
ctcgaacccc tccgggggt cggcgttggg gatcggccct cccttagcgg gtggccgtct 480
ccgaaataca gtggcggtct cgccgcagcc tctcctgcgc agtagtttgc acactcgcat 540
cgggagcgcg gcgcgtccac agccgttaaa cacccaactt ctgaaatgtt gacctcggat 600
caggtaggaa tacccgctga acttnnncat atcaataagc ggga 644

<210> SEQ ID NO 280
<211> LENGTH: 403
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Hypocreales, Family: Nectriaceae, Genus: Nectria
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t
<220> FEATURE:
<221> NAME/KEY: misc_feature
<222> LOCATION: (380)..(381)
<223> OTHER INFORMATION: n is a, c, g, or t
<220> FEATURE:
<221> NAME/KEY: misc_feature
<222> LOCATION: (386)..(387)
<223> OTHER INFORMATION: n is a, c, g, or t

<400> SEQUENCE: 280
cattaccgag ttattcactc atcaaccctg tgaacttacc taaacgttgc ttcggcggga 60
acagacggcc ctgtaaaacg ggccgccccc gccagaggac ccctaactct gtttctatta 120
tgtttcttct gagtaaaaca agcaaataaa ttaaaacttt caacaacgga tctcttggct 180
ctggcatcga tgaagaacgc agcgaaatgc gataagtaat gtgaattgca gaattcagtg 240
aatcatcgaa tctttgaacg cacattgcgc ccgccagtat tctggcgggc atgcctgttc 300
gagcgtcatt acaaccctca ggcccccggg cctggcgttg gggatcggcg ganccccctg 360
cgggnacncg ccgtccccn natacnntgg cggtcccgcc gca 403

<210> SEQ ID NO 281
<211> LENGTH: 569
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Hypocreales, Family: Nectriaceae, Genus: Fusarium

<400> SEQUENCE: 281
gtaacaaggt ctccgttggt gaaccagcgg agggatcatt accgagttta caactcccaa 60
acccctgtga acataccaat tgttgcctcg gcggatcagc ccgctcccgg taaaacggga 120
cggcccgcca gaggacccct aaactctgtt tctatatgta acttctgagt aaaaccataa 180
ataaatcaaa actttcaaca acggatctct tggttctggc atcgatgaag aacgcagcaa 240
aatgcgataa gtaatgtgaa ttgcagaatt cagtgaatca tcgaatcttt gaacgcacat 300
tgcgcccgcc agtattctgg cgggcatgcc tgttcgagcg tcatttcaac cctcaagccc 360
tcgggtttgg tgttggggat cggcgagccc ttgcggcaag ccggccccga aatctagtgg 420
cggtctcgct gcagcttcca ttgcgtagta gtaaaaccct cgcaactggt acgcggcgcg 480
gccaagccgt taaaccccca acttctgaat gttgacctcg gatcaggtag gaatacccgc 540
tgaacttaag catatcaata agcggagga 569

<210> SEQ ID NO 282
<211> LENGTH: 563
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Xylariales, Family: Xylariaceae, Genus: Xylaria

<400> SEQUENCE: 282
ttggaagtaa aagtcgtaac aaggtctccg ttggtgaacc agcggaggga tcattaaaga 60
gttataacaa ctcccaaacc cctgtgaaca tacctcatgt tgcctcggca ggtcgcgcct 120
cggtgccctg ccggcggccc acgaaactct gtttagcatt aaattctgaa cttataacta 180
aatcagttaa aactttcaac aacggatctc ttggttctgg catcgatgaa gaacgcagcg 240
aaatgcgata agtaatgtga attgcagaat tcagtgaatc atcgaatctt tgaacgcaca 300
ttgcgcccat tagtattcta gtgggcatgc ctgttcgagc gtcatttcaa cccttaagcc 360
ctcgttgctt agcgttggga gcctacaagc actgtagctc cccaaagtta gtggcggagt 420
cggttcacac cccagacgta gtaagatttc acctcgcctg tagttggacc ggtcccctgc 480
cgtaaaacac ataattttct caaggttgac ctcggatcag gtaggaatac ccgctgaact 540
taagcatatc aataagcgga gga 563

<210> SEQ ID NO 283
<211> LENGTH: 678
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Xylariales, Family: Xylariaceae, Genus: Hypoxylon

<400> SEQUENCE: 283
ttggaagtaa aagtcgtaac aaggtctccg ttggtgaacc agcggaggga tcattactga 60
gttatcaaaa ctccaaaccc tttgtgaacc ttaccatcgt tgcctcggcg tgagctacgg 120
ctaccctgta actaccctgg agctacccta gagttaccct atagctaccc tgcacttacc 180
ctgcagctac cctatagcta ccctggagct accctggagc taccctgtag tcggcttcgg 240
cccgccgaag gaccgttaaa ctcttgtttt taccactgtt tctctgaatt ttaaaccaaa 300
ataagttaaa actttcaaca acggatctct tggttctggc atcgatgaag aacgcagcga 360
aatgcgataa gtaatgtgaa ttgcagaatt cagtgaatca tcgaatcttt gaacgcacat 420
tgcgcccatt agtattctag tgggcatgcc tattcgagcg tcatttcgac cctaagccc 480 ctgttgctta gcgttgggaa tctacggcgt agttcctcaa agttagtggc ggagttaggg 540
tacactctca gcgtagtaat ttctctcgct cgtgtggtgg ccctggctgc tagccgttaa 600
aacccctata ttttctagtg gttgacctcg gattaggtag gaatacccgc tgaacttaag 660
catatcaata agcggagg 678

<210> SEQ ID NO 284
<211> LENGTH: 531
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Hypocreales, Family: Nectriaceae, Genus: Fusarium

<400> SEQUENCE: 284
attaccgagt ttacaactcc caaacccctg tgaacatacc aattgttgcc tcggcggatc 60
agcccgctcc cggtaaaacg ggacggcccg ccagaggacc cctaaactct gtttctatat 120
gtaacttctg agtaaaacca taaataaatc aaaactttca acaacggatc tcttggttct 180
ggcatcgatg aagaacgcag caaaatgcga taagtaatgt gaattgcaga attcagtgaa 240
tcatcgaatc tttgaacgca cattgcgccc gccagtattc tggcgggcat gcctgttcga 300
gcgtcatttc aaccctcaag ccctcgggtt tggtgttggg gatcggcgag cccttgcggc 360
aagccggccc cgaaatctag tggcggtctc gctgcagctt ccattgcgta gtagtaaaac 420
cctcgcaact ggtacgcggc gcggccaagc cgttaaaccc ccaacttctg aatgttgacc 480
tcggatcagg taggaatacc cgctgaactt aagcatatca ataagcggag g 531

<210> SEQ ID NO 285
<211> LENGTH: 609
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Xylariales, Family: Xylariaceae, Genus: Xylaria

<400> SEQUENCE: 285

```
tggaagtaaa agtcgtaaca aggtctccgt tggtgaacca gcggagggat cattaaagag     60
ttttctacaa ctcccaaacc cctgtgaaca tacctttgt tgcctcggca ggcctcgcct    120
accttgtagt gcccctacgc tgtaggggcc tacctgggga gtgcgggggg gccctgccgg    180
cggcccgcga aactctgttt agcactgaat tctgaacata taactaaata agttaaaact    240
ttcaacaacg gatctcttgg ttctggcatc gatgaagaac gcagcgaaat gcgataagta    300
atgtgaattg cagaattcag tgaatcatcg aatctttgaa cgcacattgc gcccattagt    360
attctagtgg gcatgcctgt tcgagcgtca tttcaaccct taagcccctg ttgcttagcg    420
ttgggagcct acggcagcgt agctccccaa agttagtggc gtggtcggtt cacactccag    480
acgtagtaaa ttttcacctc gcctgtagtc ggaccggtcc cctgccgtaa aacaccccaa    540
tttccaaagg ttgacctcgg atcaggtagg aatacccgct gaacttaagc atatcaataa    600
gcggaggaa                                                           609
```

<210> SEQ ID NO 286
<211> LENGTH: 679
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Xylariales, Family: Xylariaceae, Genus: Xylaria

<400> SEQUENCE: 286

```
tggaagtaaa agtcgtaaca aggtctccgt tggtgaacca gcggagggat cattactgag     60
ttatcaaaac tccaaaccct ttgtgaacct taccgtcgtt gcctcggcgt gagctacggc    120
taccctgtaa ctaccctgga gctaccctag agttacccta tagctaccct gcacttaccc    180
tgcagctacc ctatagctac cctggagcta ccctggagct accctgtagt cggcttcggc    240
ccgccgaagg accgttaaac tcttgttttt accactgttt ctctgaattt taaactaaaa    300
taagttaaaa ctttcaacaa cggatctctt ggttctggca tcgatgaaga acgcagcgaa    360
atgcgataag taatgtgaat tgcagaattc agtgaatcat cgaatctytg aacgcacatt    420
gcgcccatta gtattctagy gggcatgcct attcgagcgt catttcgacc cctaagcccc    480
tgttgcttag cgttgggaat ctacggcgta gttcctcaaa gttagtggcg gagttagggt    540
acactctcag cgtagtaatt tctctcgctc gtgtggtggc cctggctgct agccgttaaa    600
acccctaaat tttctagtgg ttgacctcgg attaggtagg aatacccgct gaacttaagc    660
atatcaataa agcggagga                                                679
```

<210> SEQ ID NO 287
<211> LENGTH: 538
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Hypocreales, Family: Nectriaceae, Genus: Fusarium

<400> SEQUENCE: 287
cattaccgag ttatacaact catcaaccct gtgaacatac ctaaaacgtt gcttcggcgg 60
gaacagacgg ccccgtaaca cgggccgccc ccgccagagg accccctaac tctgtttcta 120
ttatgtttct tctgagtaaa acaagcaaat aaattaaaac tttcaacaac ggatctcttg 180
gctctggcat cgatgaagaa cgcagcgaaa tgcgataagt aatgtgaatt gcagaattca 240
gtgaatcatc gaatctttga acgcacattg cgcccgccag tattctggcg ggcatgcctg 300
ttcgagcgtc attacaaccc tcaggccccc gggcctggcg ttggggatcg gcgaggcgcc 360
ccctgcgggc acacgccgtc ccccaaatac agtggcggtc ccgccgcagc ttccattgcg 420
tagtagctaa cacctcgcaa ctggagagcg gcgcggccat gccgtaaaac acccaacttc 480
tgaatgttga cctcgaatca ggtaggaata cccgctgaac ttaagcatat caataagc 538

<210> SEQ ID NO 288
<211> LENGTH: 1012
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Sporormiaceae, Genus: Preussia

<400> SEQUENCE: 288
aacacccttg acctttttga gtaccttttc gtttcctcgg caggctcgcc tgccaacggg 60
gaccccaaaa acgctttgta atacctgtca ttgtctgata taacaagcaa aaattaaaac 120
tttcaacaac ggatctcttg gttctggcat cgatgaagaa cgcagcgaaa tgcgataagt 180
agtgtgaatt gcagaattca gtgaatcatc gaatctttga acgcacattg cgccctttgg 240
tattccttag ggcatgcctg ttcgagcgtc atttaaacct tcaagctcag cttggtgatg 300
ggtgactgtc ctcccctcgc ggggggactc gcctcaaaaa cattggcggc cggtacattg 360
gcttcgagcg cagcagaaac gcggtctcga gcccggtgga tcggctccca taagcctctt 420
cttttatttt gacctcggat caggtaggga tacccgctga acttaagcat atcaataagc 480
ggaggaaaag aaaccaacag ggattgccct agtaacggcg agtgaagcgg caacagctca 540
aatttgaaat ctggcccttt cagggtccga gttgtaattt gtagagggtg ctttggcgtt 600
ggctgtggtc taagttcctt ggaacaggac gtcgcagagg gtgagaatcc cgtatgtggc 660
cgccagtctt cgccgtgtaa agccccttcg acgagtcgag ttgtttggga atgcagctct 720
aaatgggagg taaatttctt ctaaagctaa atattggcca gagaccgata gcgcacaagt 780
agagtgatcg aaagatgaaa agcactttgg aaagagagtc aaaaagcacg tgaaattgtt 840
gaaagggaag cgcttgcagc cagacttgcc tgtagttgct catccgggct tttgcccggt 900
gcactcttct atgggcaggc cagcatcagt cccagcggtt ggataaatgc ctgttgaatg 960
tacctctctt cggggaggac ttatagcctc gggcggcata caaccagccg gg 1012

<210> SEQ ID NO 289
<211> LENGTH: 907
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Sporormiaceae, Genus: Preussia

<400> SEQUENCE: 289
tttcctcggt caggctcgcc tgccaacggg gaccccaaaa acgctttgta atacctgtca 60
ttgtctgata taacaagcaa aaattaaaac tttcaacaac ggatctcttg gttctggcat 120
cgatgaagaa cgcagcgaaa tgcgataagt agtgtgaatt gcagaattca gtgaatcatc 180
gaatctttga acgcacattg cgccctttgg tattccttag ggcatgcctg ttcgagcgtc 240
atttaaacct tcaagctcag cttggtgatg ggtgactgtc ctcccctcgc ggggggactc 300
gcctcaaaaa cattggcggc cggtacattg gcttcgagcg cagcagaaac gcggtctcga 360
gcccggtgga tcggctccca taagcctctt cttttatttt gacctcggat caggtaggga 420
tacccgctga acttaagcat atcaataagc ggaggaaaag aaaccaacag ggattgccct 480
agtaacggcg agtgaagcgg caacagctca aatttgaaat ctggcccttt cagggtccga 540
gttgtaattt gtagagggtg ctttggcgtt ggctgtggtc taagttcctt ggaacaggac 600
gtcgcagagg gtgagaatcc cgtatgtggc cgccagtctt cgccgtgtaa agccccttcg 660
acgagtcgag ttgtttggga atgcagctct aaatgggagg taaatttctt ctaaagctaa 720
atattggcca gagaccgata gcgcacaagt agagtgatcg aaagatgaaa agcactttgg 780
aaagagagtc aaaaagcacg tgaaattgtt gaaagggaag cgcttgcagc cagacttgcc 840
tgtagttgct catccgggct tttgcccggt gcactcttct atgggcaggc cagcatcagt 900
cccagcg 907

<210> SEQ ID NO 290
<211> LENGTH: 1025
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Sporormiaceae, Genus: Preussia

<400> SEQUENCE: 290
cccattcgag ataacaccct tgccttttg agtacctttt cgtttcctcg gcaggctcgc 60
ctgccaacgg ggaccccaaa aacgctttgt aatacctgtc attgtctgat ataacaagca 120
aaaattaaaa ctttcaacaa cggatctctt ggttctggca tcgatgaaga acgcagcgaa 180
atgcgataag tagtgtgaat tgcagaattc agtgaatcat cgaatctttg aacgcacatt 240
gcgccctttg gtattcctta gggcatgcct gttcgagcgt catttaaacc ttcaagctca 300
gcttggtgat gggtgactgt cctcccctcg cggggggact cgcctcaaaa acattggcgg 360
ccggtacatt ggcttcgagc gcagcagaaa cgcggtctcg agcccggtgg atcggctccc 420
ataagcctct tcttttattt tgacctcgga tcaggtaggg atacccgctg aacttaagca 480
tatcaataag cggaggaaaa gaaaccaaca gggattgccc tagtaacggc gagtgaagcg 540
gcaacagctc aaatttgaaa tctggccctt tcagggtccg agttgtaatt tgtagagggt 600
gctttggcgt tggctgtggt ctaagttcct tggaacagga cgtcgcagag ggtgagaatc 660
ccgtatgtgg ccgccagtct tcgccgtgta aagccccttc gacgagtcga gttgtttggg 720
aatgcagctc taaatgggag gtaaatttct tctaaagcta aatattggcc agagaccgat 780
agcgcacaag tagagtgatc gaaagatgaa aagcactttg gaaagagagt caaaaagcac 840
gtgaaattgt tgaaagggaa gcgcttgcag ccagacttgc ctgtagttgc tcatccgggc 900
ttttgcccgg tgcactcttc tatgggcagg ccagcatcag tcccagcggt tggataaatg 960
cctgttgaat gtacctctct tcggggagga cttatagcct cgggcggcat acaaccagcc 1020
gggat 1025

<210> SEQ ID NO 291
<211> LENGTH: 585
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Hypocreales, Family: Nectriaceae, Genus: Fusarium
<220> FEATURE:
<221> NAME/KEY: misc_feature
<222> LOCATION: (15)..(15)
<223> OTHER INFORMATION: n is a, c, g, or t

<400> SEQUENCE: 291

```
ttggaagtaa aagtngtaac aaggtctccg ttggtgaacc agcggaggga tcattaccga     60

gtttacaact cccaaacccc tgtgaacata ccaattgttg cctcggcgga tcagcccgct    120

cccggtaaaa cgggacggcc cgccagagga cccctaaact ctgtttctat atgtaacttc    180

tgagtaaaac cataaataaa tcaaaacttt caacaacgga tctcttggtt ctggcatcga    240

tgaagaacgc agcaaaatgc gataagtaat gtgaattgca gaattcagtg aatcatcgaa    300

tctttgaacg cacattgcgc ccgccagtat tctggcgggc atgcctgttc gagcgtcatt    360

tcaaccctca agccctcggg tttggtgttg gggatcggcg agcccttgcg gcaagccggc    420

cccgaaatct agtggcggtc tcgctgcagc ttccattgcg tagtagtaaa accctcgcaa    480

ctggtacgcg gcgcggccaa gccgttaaac cccaacttc tgaatgttga cctcggatca    540

ggtaggaata cccgctgaac ttaagcatat caataagcgg aggaa                    585
```

<210> SEQ ID NO 292
<211> LENGTH: 534
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Hypocreales, Family: Nectriaceae, Genus: Fusarium

<400> SEQUENCE: 292

```
tcattaccga gtttacaact cccaaacccc tgtgaacata ccaattgttg cctcggcgga     60

tcagcccgct cccggtaaaa cgggacggcc cgccagagga cccctaaact ctgtttctat    120

atgtaacttc tgagtaaaac cataaataaa tcaaaacttt caacaacgga tctcttggtt    180

ctggcatcga tgaagaacgc agcaaaatgc gataagtaat gtgaattgca gaattcagtg    240

aatcatcgaa tctttgaacg cacattgcgc ccgccagtat tctggcgggc atgcctgttc    300

gagcgtcatt tcaaccctca agccctcggg tttggtgttg gggatcggcg agcccttgcg    360

gcaagccggc cccgaaatct agtggcggtc tcgctgcagc ttccattgcg tagtagtaaa    420

accctcgcaa ctggtacgcg gcgcggccaa gccgttaaac cccaacttc tgaatgttga    480

cctcggatca ggtaggaata cccgctgaac ttaagcatat caataagcgg agga          534
```

<210> SEQ ID NO 293
<211> LENGTH: 584
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Hypocreales, Family: Nectriaceae, Genus: Fusarium

<400> SEQUENCE: 293

```
ttggaagtaa aagtcgtaac aaggtctccg ttggtgaacc agcggaggga tcattaccga     60
```

-continued

```
gtttacaact cccaaacccc tgtgaacata ccaattgttg cctcggcgga tcagcccgct    120

cccggtaaaa cgggacggcc cgccagagga cccctaaact ctgtttctat atgtaacttc    180

tgagtaaaac cataaataaa tcaaaacttt caacaacgga tctcttggtt ctggcatcga    240

tgaagaacgc agcaaaatgc gataagtaat gtgaattgca gaattcagtg aatcatcgaa    300

tctttgaacg cacattgcgc ccgccagtat tctggcgggc atgcctgttc gagcgtcatt    360

tcaaccctca agccctcggg tttggtgttg gggatcggcg agcccttgcg gcaagccggc    420

cccgaaatct agtggcggtc tcgctgcagc ttccattgcg tagtagtaaa accctcgcaa    480

ctggtacgcg gcgcggccaa gccgttaaac cccaacttc tgaatgttga cctcggatca    540

ggtaggaata cccgctgaac ttaagcatat caataagcgg agga                     584
```

<210> SEQ ID NO 294
<211> LENGTH: 1009
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Sporormiaceae, Genus: Preussia

<400> SEQUENCE: 294

```
gggcttcggc ccattcgaga taacaccctt gcctttttga gtaccttttc gtttcctcgg     60

caggctcgcc tgccaacggg gaccccaaaa acgctttgta atacctgtca ttgtctgata    120

taacaagcaa aaattaaaac tttcaacaac ggatctcttg gttctggcat cgatgaagaa    180

cgcagcgaaa tgcgataagt agtgtgaatt gcagaattca gtgaatcatc gaatctttga    240

acgcacattg cgcccttttgg tattccttag ggcatgcctg ttcgagcgtc atttaaacct    300

tcaagctcag cttggtgatg ggtgactgtc ctcccctcgc ggggggactc gcctcaaaaa    360

cattggcggc cggtacattg gcttcgagcg cagcagaaac gcggtctcga gcccggtgga    420

tcggctccca taagcctctt cttttatttt gacctcggat caggtaggga tacccgctga    480

acttaagcat atcaataagc ggaggaaaag aaaccaacag ggattgccct agtaacggcg    540

agtgaagcgg caacagctca aatttgaaat ctggcccttt cagggtccga gttgtaattt    600

gtagagggtg ctttggcgtt ggctgtggtc taagttcctt ggaacaggac gtcgcagagg    660

gtgagaatcc cgtatgtggc cgccagtctt cgccgtgtaa agccccttcg acgagtcgag    720

ttgtttggga atgcagctct aaatgggagg taaatttctt ctaaagctaa atattggcca    780

gagaccgata gcgcacaagt agagtgatcg aaagatgaaa agcactttgg aaagagagtc    840

aaaaagcacg tgaaattgtt gaaagggaag cgcttgcagc cagacttgcc tgtagttgct    900

catccgggct tttgcccggt gcactcttct acgggcaggc cagcatcagt cccagcggtt    960

ggataaatgc ctgttgaatg tacctctctt cggggaggac ttatagcct               1009
```

<210> SEQ ID NO 295
<211> LENGTH: 1078
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Montagnulaceae, Genus: Paraconiothyrium

<400> SEQUENCE: 295

```
ggtgttggtt gcggcctccg ggggttctcc ccccgggtgg tagaggtaac actctcacgc     60
```

-continued

```
gccacatgcc ttaatccttt ttttacgagc acctttcgtt ctccttcggt ggggcaacct    120

gccgctggaa cttatcaaaa accttttttt gcatctagca ttacctgttc tgatacaaac    180

aatcgttaca actttcaaca atggatctct tggctctggc atcgatgaag aacgcagcga    240

aatgcgataa gtagtgtgaa ttgcagaatt cagtgaatca tcgaatcttt gaacgcacat    300

tgcgcccctt ggtattccat ggggcatgcc tgttcgagcg tcatctacac cctcaagctc    360

tgcttggtgt tgggcgtctg tcccgcctct gcgcgcggac tcgccccaaa ttcattggca    420

gcggtccttg cctcctctcg cgcagcacat tgcgcttctc gaggtgcgcg ggccgcgtcc    480

acgaagcaac attaccgtct ttgacctcgg atcaggtagg gatacccgct gaacttaagc    540

atatcaataa gcggaggaaa agaaaccaac agggattgcc ctagtaacgg cgagtgaagc    600

ggcaacagct caaatttgaa atctggctct ctttgggggt ccgagttgta atttgcagag    660

gatgctttgg cattggcggc ggtctaagtt ccttggaaca ggacatcgca gagggtgaga    720

atcccgtacg tgggcgcctg cctttgccgt gtaaagctcc ttcgacgagt cgagttgttt    780

gggaatgcag ctctaaatgg gaggtaaatt tcttctaaag ctaaataccg gccagagacc    840

gatagcgcac aagtagagtg atcgaaagat gaaaagtact ttggaaagag agtcaaaaag    900

cacgtgaaat tgttgaaagg gaagcgcttg cagccagact tgcccgcagt tgctcaccta    960

ggctttggcc tggggcactc ttctgtgggc aggccagcat cagtttgggc ggttggataa   1020

aggcctctgt cacgtatctt ccttcgggaa gaccttatag gggaggcgta atgcaacc     1078


<210> SEQ ID NO 296
<211> LENGTH: 1006
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Pleosporales, Family: Montagnulaceae,
      Genus: Paraconiothyrium

<400> SEQUENCE: 296

ggtggtagag gtaacactct cacgcgccac atgccttaat cctttttta cgagcacctt      60

tcgttctcct tcggtggggc aacctgccgc tggaacttat caaaaacctt tttttgcatc    120

tagcattacc tgttctgata caaacaatcg ttacaacttt caacaatgga tctcttggct    180

ctggcatcga tgaagaacgc agcgaaatgc gataagtagt gtgaattgca gaattcagtg    240

aatcatcgaa tctttgaacg cacattgcgc cccttggtat tccatggggc atgcctgttc    300

gagcgtcatc tacaccctca agctctgctt ggtgttgggc gtctgtcccg cctctgcgcg    360

cggactcgcc ccaaattcat tggcagcggt ccttgcctcc tctcgcgcag cacattgcgc    420

ttctcgaggt gcgcgggccg cgtccacgaa gcaacattac cgtctttgac ctcggatcag    480

gtagggatac ccgctgaact taagcatatc aataagcgga ggaaaagaaa ccaacaggga    540

ttgccctagt aacggcgagt gaagcggcaa cagctcaaat ttgaaatctg gctctctttg    600

ggggtccgag ttgtaatttg cagaggatgc tttggcattg gcggcggtct aagttccttg    660

gaacaggaca tcgcagaggg tgagaatccc gtacgtgggc gcctgccttt gccgtgtaaa    720

gctccttcga cgagtcgagt tgtttgggaa tgcagctcta aatgggaggt aaatttcttc    780

taaagctaaa taccggccag agaccgatag cgcacaagta gagtgatcga aagatgaaaa    840

gtactttgga aagagagtca aaaagcacgt gaaattgttg aaagggaagc gcttgcagcc    900

agacttgccc gcagttgctc acctaggctt tggcctgggg cactcttctg tgggcaggcc    960

agcatcagtt tgggcggttg gataaaggcc tctgtcacgt atcttc                  1006
```

<210> SEQ ID NO 297
<211> LENGTH: 1050
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family:

<400> SEQUENCE: 297
ttacctagag ttgtaggctt tgcctgctat ctcttaccca tgtcttttga gtacttacgt 60
ttcctcggcg ggtccgcccg ccgactggac aatttaaacc ctttgcagtt gcaatcagcg 120
tctgaaaaaa cttaatagtt acaactttca acaacggatc tcttggttct ggcatcgatg 180
aagaacgcag cgaaatgcga taagtagtgt gaattgcaga attcagtgaa tcatcgaatc 240
tttgaacgca cattgcgccc cttggtattc catggggcat gcctgttcga gcgtcatttg 300
taccttcaag ctctgcttgg tgttgggtgt ttgtctcgcc tctgcgtgta gactcgcctt 360
aaaacaattg gcagccggcg tattgatttc ggagcgcagt acatctcgcg ctttgcactc 420
ataacgacga cgtccaaaag tacattttta cactcttgac ctcggatcag gtagggatac 480
ccgctgaact taagcatatc aataagcgga ggaaaagaaa ccaacaggga ttgccctagt 540
aacggcgagt gaagcggcaa cagctcaaat ttgaaatctg gcgtctttgg cgtccgagtt 600
gtaatttgca gagggcgctt tggcattggc agcggtccaa gttccttgga acaggacgtc 660
acagagggtg agaatcccgt acgtggtcgc tagcctttac cgtgtaaagc cccttcgacg 720
agtcgagttg tttgggaatg cagctctaaa tgggaggtaa atttcttcta aagctaaata 780
ctggccagag accgatagcg cacaagtaga gtgatcgaaa gatgaaaagc actttggaaa 840
gagagttaaa aagcacgtga aattgttgaa agggaagcgc ttgcagccag acttgcctgt 900
agttgctcat ccgggtttct acccggtgca ctcttctata ggcaggccag catcagtttg 960
ggcggttgga taaaggtctc tgtcatgtac ctctcttcgg ggagaactta taggggagac 1020
gacatgcaac cagcccggac tgaggtccgc 1050

<210> SEQ ID NO 298
<211> LENGTH: 579
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Coniochaetales, Family: Coniochaetaceae, Genus: Lecythophora

<400> SEQUENCE: 298
gtaacaaggt ctccgttggt gaaccagcgg agggatcatt acaagaagcc gaaaggctac 60
ttcaaaccat cgcgaactcg tccaagttgc ttcggcggcg cggcacccct taacgggggc 120
gccgcagccc tgcctctccg gaggtttggg gcgcccgccg gaggtacgaa actctgtatt 180
atagtggcat ctctgagtat aaaacaaata agttaaaact ttcaacaacg gatctcttgg 240
ttctggcatc gatgaagaac gcagcgaaat gcgataagta atgtgaattg cagaattcag 300
tgaatcatcg aatctttgaa cgcacattgc gcccggtagt actctaccgg gcatgcctgt 360
tcgagcgtca tttcaaccct caagccctgc ttggtgttgg ggccctacgg ctgccgtagg 420
ccctgaaagg aagtggcggg ctcgctacaa ctccgagcgt agtaattcat tatctcgcta 480
gggaggttgc ggcgtgctcc tgccgttaaa gacccatctt taaccaaggt tgacctcgga 540
tcaggtagga atacccgctg aacttaagca tatcaataa 579

<210> SEQ ID NO 299
<211> LENGTH: 550
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Incertae sedis, Genus: Phoma

<400> SEQUENCE: 299
gtaacaaggt ttccgtaggt gaacctgcgg aaggatcatt acctagagtt gtaggctttg 60
cctgctatct cttacccatg tcttttgagt acttacgttt cctcggcggg tccgcccgcc 120
gactggacaa tttaaaccct ttgcagttgc aatcagcgtc tgaaaaaact taatagttac 180
aactttcaac aacggatctc ttggttctgg catcgatgaa gaacgcagcg aaatgcgata 240
agtagtgtga attgcagaat tcagtgaatc atcgaatctt tgaacgcaca ttgcgcccct 300
tggtattcca tggggcatgc ctgttcgagc gtcatttgta ccttcaagct ctgcttggtg 360
ttgggtgttt gtctcgcctc tgcgtgtaga ctcgccttaa aacaattggc agccggcgta 420
ttgatttcgg agcgcagtac atctcgcgct ttgcactcat aacgacgacg tccaaaagta 480
catttttaca ctcttgacct cggatcaggt agggataccc gctgaactta agcatatcaa 540
taagcggagg 550

<210> SEQ ID NO 300
<211> LENGTH: 1030
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Sordariales, Family: Sordariaceae, Genus: Neurospora

<400> SEQUENCE: 300
tcgcgaatct tacccgtacg gttgcctcgg cgctggcggt ccggaaggcc ctcgggcccc 60
ccggatcctc gggtctcccg ctcgcgggag gctgcccgcc ggagtgccga aaccaaactc 120
ttgatatttt atgtctctct gagtaaactt ttaaataagt caaaactttc aacaacggat 180
ctcttggttc tggcatcgat gaagaacgca gcgaaatgcg ataagtaatg tgaattgcag 240
aattcagtga atcatcgaat ctttgaacgc acattgcgct cgccagtatt ctggcgagca 300
tgcctgttcg agcgtcattt caaccatcaa gctctgcttg cgttggggat ccgcgtctga 360
cgcggtccct caaaaacagt ggcgggctcg ctagtcacac cgagcgtagt aactctacat 420
cgctatggtc gtgcggcggg ttcttgccgt aaaacccccc aatttttaag gttgacctcg 480
gatcaggtag gaatacccgc tgaacttaag catatcaata agcggaggaa aagaaaccaa 540
cagggattgc cctagtaacg gcgagtgaag cggcaacagc tcaaatttga aatctggctt 600
cggcccgagt tgtaatttgt agaggaaact tttggtgagg caccttctga gtcccttgga 660
acagggcgcc atagagggtg agagccccgt atagtcggat gccgatccaa tgtaaagttc 720
cttcgacgag tcgagtagtt tgggaatgct gctcaaaatg ggaggtaaat ttcttctaaa 780
gctaaatata ggccagagac cgatagcgca caagtagagt gatcgaaaga tgaaaagcac 840
tttgaaaaga gggttaaata gcacgtgaaa ttgttgaaag ggaagcgttt gtgaccagac 900
ttgcgccgtt ccgatcatcc ggtgttctca ccggtgcact cggggcggct caggccagca 960
tcggttttgg tgggggata aaggttcggg gaacgtagct cctccgggag tgttatagcc 1020
ccgggcgtaa 1030

<210> SEQ ID NO 301
<211> LENGTH: 1025
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: , Family:

<400> SEQUENCE: 301
ggcttcggcc ctgtcgagat agaacccttg cctttttgag tacctcttgt ttcctcggcg 60
ggctcgcccg ccgatggacc ccccaaaaaa cactttgcag tacctgtaat agtctgaaca 120
acaaacaaaa attaaaactt tcaacaacgg atctcttggt tctggcatcg atgaagaacg 180
cagcgaaatg cgataagtag tgtgaattgc agaattcagt gaatcatcga atctttgaac 240
gcacattgcg ccctttggta ttccttaggg catgcctgtt cgagcgtcat ttaaaccttc 300
aagctcagct tggtgttggg tgactgtccc ctcaaaagga ctcgcctcaa aatcattggc 360
ggccggtacg ttggcttcga gcgcagcaga aacgcgaact cggagactgt gtgtcggctc 420
ccagaagcca tctttaaatt ttgacctcgg atcaggtagg gatacccgct gaacttaagc 480
atatcaataa gcggaggaaa agaaaccaac agggattgcc ctagtaacgg cgagtgaagc 540
ggcaacagct caaatttgaa atctggctct ttcagggtcc gagttgtaat ttgtagaggg 600
tgctttggag ttgactgtgg tctaagttcc ttggaacagg acgtcgcaga gggtgagaat 660
cccgtatgtg gccgccagtc ttcgccgtgt aaagcccctt cgacgagtcg agttgtttgg 720
gaatgcagct ctaaatggga ggtaaatttc ttctaaagct aaatattggc cagagaccga 780
tagcgcacaa gtagagtgat cgaaagatga aaagcacttt ggaaagagag tcaaaaagca 840
cgtgaaattg ttgaaaggga agcgcttgca gccagacttg cctgtagttg ctcatccggg 900
cttttgcccg gtgcactctt ctacaggcag gccagcatca gtcctggcgg ttggataaat 960
gcctgctaaa tgtacctctc ttcggggagg acttatagtt tcaggcggca tacaaccagc 1020
cggga 1025

<210> SEQ ID NO 302
<211> LENGTH: 958
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Capnodiales, Family: Davidiellaceae, Genus: Cladosporium

<400> SEQUENCE: 302
aaccctttga tttccgactc tgttgcctcc ggggcgaccc tgccttcggg cgggggctcc 60
gggtggacac ttcaaactct tgcgtaactt tgcagtctga gtaaacttaa ttaataaatt 120
aaaactttta acaacggatc tcttggttct ggcatcgatg aagaacgcag cgaaatgcga 180
taagtaatgt gaattgcaga attcagtgaa tcatcgaatc tttgaacgca cattgcgccc 240
cctggtattc cggggggcat gcctgttcga gcgtcatttc accactcaag cctcgcttgg 300
tattgggcaa cgcggtccgc cgcgtgcctc aaatcgtccg gctgggtctt ctgtccccta 360
agcgttgtgg aaactattcg ctaaagggtg ttcgggaggc tacgccgtaa aacaacccca 420
tttctaaggt tgacctcgga tcaggtaggg atacccgctg aacttaagca tatcaataag 480
cggaggaaaa gaaaccaaca gggattgctc tagtaacggc gagtgaagca gcaatagctc 540

```
aaatttgaaa tctggcgtct tcgacgtccg agttgtaatt tgtagaggat gcttctgagt    600

ggccaccgac ctaagttcct tggaacagga cgtcatagag ggtgagaatc ccgtatgcgg    660

tcggaaaggc gctctatacg tagctccttc gacgagtcga gttgtttggg aatgcagctc    720

taaatgggag gtaaatttct tctaaagcta aatattggcc agagaccgat agcgcacaag    780

tagagtgatc gaaagatgaa aagcactttg gaaagagagt taaaaagcac gtgaaattgt    840

taaaagggaa gggattgcaa ccagacttgc tcgcggtgtt ccgccggtct tctgaccggt    900

ctactcgccg cgttgcaggc cagcatcgtc tggtgccgct ggataagact tgaggaat      958
```

<210> SEQ ID NO 303
<211> LENGTH: 957
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Sporormiaceae, Genus: Preussia

<400> SEQUENCE: 303

```
taccttttcg tttcctcggc aggctcgcct gccaacgggg accccaaaaa cgctttgtaa     60

tacctgtcat tgtctgatat aacaagcaaa aattaaaact ttcaacaacg gatctcttgg    120

ttctggcatc gatgaagaac gcagcgaaat gcgataagta gtgtgaattg cagaattcag    180

tgaatcatcg aatctttgaa cgcacattgc gcccctttggt attccttagg gcatgcctgt    240

tcgagcgtca tttaaacctt caagctcagc ttggtgatgg gtgactgtcc tcccctcgcg    300

gggggactcg cctcaaaaac attggcggcc ggtacattgg cttcgagcgc agcagaaacg    360

cggtctcgag cccggtggat cggctcccat aagcctcttc ttttattttg acctcggatc    420

aggtagggat acccgctgaa cttaagcata tcaataagcg gaggaaaaga aaccaacagg    480

gattgcccta gtaacggcga gtgaagcggc aacagctcaa atttgaaatc tggccctttc    540

agggtccgag ttgtaatttg tagagggtgc tttggcgttg gctgtggtct aagttccttg    600

gaacaggacg tcgcagaggg tgagaatccc gtatgtggcc gccagtcttc gccgtgtaaa    660

gccccttcga cgagtcgagt tgtttgggaa tgcagctcta aatgggaggt aaatttcttc    720

taaagctaaa tattggccag agaccgatag cgcacaagta gagtgatcga aagatgaaaa    780

gcactttgga aagagagtca aaaagcacgt gaaattgttg aaagggaagc gcttgcagcc    840

agacttgcct gtagttgctc atccgggctt ttgcccggtg cactcttcta tgggcaggcc    900

agcatcagtc ccagcggttg gataaatgcc tgttgaatgt acctctcttc ggggagg       957
```

<210> SEQ ID NO 304
<211> LENGTH: 905
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Capnodiales, Family: Davidiellaceae, Genus: Cladosporium

<400> SEQUENCE: 304

```
ggcgggggct ccgggtggac acttcaaact cttgcgtaac tttgcagtct gagtaaactt     60

aattaataaa ttaaaacttt taacaacgga tctcttggtt ctggcatcga tgaagaacgc    120

agcgaaatgc gataagtaat gtgaattgca gaattcagtg aatcatcgaa tctttgaacg    180

cacattgcgc cccctggtat tccgggggc atgcctgttc gagcgtcatt tcaccactca    240

agcctcgctt ggtattgggc aacgcggtcc gccgcgtgcc tcaaatcgtc cggctgggtc    300
```

ttctgtcccc taagcgttgt ggaaactatt cgctaaaggg tgttcgggag gctacgccgt 360
aaaacaaccc catttctaag gttgacctcg gatcaggtag ggatacccgc tgaacttaag 420
catatcaata agcggaggaa aagaaaccaa cagggattgc tctagtaacg gcgagtgaag 480
cagcaatagc tcaaatttga aatctggcgt cttcgacgtc cgagttgtaa tttgtagagg 540
atgcttctga gtggccaccg acctaagttc cttggaacag gacgtcatag agggtgagaa 600
tcccgtatgc ggtcggaaag gcgctctata cgtagctcct tcgacgagtc gagttgtttg 660
ggaatgcagc tctaaatggg aggtaaattt cttctaaagc taaatattgg ccagagaccg 720
atagcgcaca agtagagtga tcgaaagatg aaaagcactt tggaaagaga gttaaaaagc 780
acgtgaaatt gttaaaaggg aagggattgc aaccagactt gctcgcggtg ttccgccggt 840
cttctgaccg gtctactcgc cgcgttgcag gccagcatcg tctggtgccg ctggataaga 900
cttga 905

<210> SEQ ID NO 305
<211> LENGTH: 990
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Pleosporales Incertae sedis, Genus: Periconia

<400> SEQUENCE: 305
tcgagataac acccttgcct ttttgagtac cttttcgttt cctcggcagc tcgcctgcca 60
acggggaccc caaaaacgct ttgtaatacc tgtcattgct gatataacaa gcaaaaatta 120
aaactttcaa caacggatct cttggtttgg catcgatgaa gaacgcagcg aaatgcgata 180
agtagtgtga attgcaaatt cagtgaatca tcgaatcttt gaacgcacat tgcgcccttt 240
ggtatcctta gggcatgcct gttcgagcgt catttaaacc ttcaagctca gcttgtgatg 300
ggtgactgtc ctcccctcgc ggggggactc gcctcaaaaa catggcggcc ggtacattgg 360
cttcgagcgc agcagaaacg cggtctcgag ccggtggatc ggctcccata agcctcttct 420
tttattttga cctcggatca gtagggatac ccgctgaact taagcatatc aataagcgga 480
ggaaaagaaa caacagggat tgccctagta acggcgagtg aagcggcaac agctcaaatt 540
gaaatctggc cctttcaggg tccgagttgt aatttgtaga gggtgcttgg cgttggctgt 600
ggtctaagtt ccttggaaca ggacgtcgca gagggtggaa tcccgtatgt ggccgccagt 660
cttcgccgtg taaagcccct tcgacggtcg agttgtttgg gaatgcagct ctaaatggga 720
ggtaaatttc ttctaagcta aatattggcc agagaccgat agcgcacaag tagagtgatc 780
gaaaatgaaa agcactttgg aaagagagtc aaaaagcacg tgaaattgtt gaagggaagc 840
gcttgcagcc agacttgcct gtagttgctc atccgggctt ttcccggtgc actcttctat 900
gggcaggcca gcatcagtcc cagcggttgg aaaatgcctg ttgaatgtac ctctcttcgg 960
ggaggactta tagcctcggg ggcatacaac 990

<210> SEQ ID NO 306
<211> LENGTH: 980
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Pleosporales Incertae sedis, Genus: Periconia

<400> SEQUENCE: 306
agatagaacc cttgcctttt tgagtacctc ttgtttcctc ggcgggctcc ccgccgatgg 60
accccccaaa aaacactttg cagtacctgt aatagtctaa caacaaacaa aaattaaaac 120
tttcaacaac ggatctcttg gttctggatc gatgaagaac gcagcgaaat gcgataagta 180
gtgtgaattg cagaatcagt gaatcatcga atctttgaac gcacattgcg ccctttggta 240
ttcctagggc atgcctgttc gagcgtcatt taaaccttca agctcagctt ggtgtgggtg 300
actgtcccct caaaaggact cgcctcaaaa tcattggcgg ccgtacgttg gcttcgagcg 360
cagcagaaac gcgaactcgg agactgtgtg tcgctcccag aagccatctt taaattttga 420
cctcggatca ggtagggata ccgctgaact taagcatatc aataagcgga ggaaaagaaa 480
ccaacaggga tgccctagta acggcgagtg aagcggcaac agctcaaatt tgaaatctgc 540
tctttcaggg tccgagttgt aatttgtaga gggtgctttg gagttgacgt ggtctaagtt 600
ccttggaaca ggacgtcgca gagggtgaga atcccgttgt ggccgccagt cttcgccgtg 660
taaagcccct tcgacgagtc gagttgttgg gaatgcagct ctaaatggga ggtaaatttc 720
ttctaaagct aaatatggcc agagaccgat agcgcacaag tagagtgatc gaaagatgaa 780
aagcctttgg aaagagagtc aaaaagcacg tgaaattgtt gaaagggaag cgctgcagcc 840
agacttgcct gtagttgctc atccgggctt ttgcccggtg catcttctac aggcaggcca 900
gcatcagtcc tggcggttgg ataaatgcct gtaaatgtac ctctcttcgg ggaggactta 960
tagtttcagg cggcatacaa 980

<210> SEQ ID NO 307
<211> LENGTH: 915
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Pleosporaceae, Genus: Alternaria

<400> SEQUENCE: 307
tttcctcggc gggtccgccc gccgactgga caatttaaac cctttgcagt gcaatcagcg 60
tctgaaaaaa cttaatagtt acaactttca acaacggact cttggttctg gcatcgatga 120
agaacgcagc gaaatgcgat aagtagttga attgcagaat tcagtgaatc atcgaatctt 180
tgaacgcaca ttgcgccctt ggtattccat ggggcatgcc tgttcgagcg tcatttgtac 240
cttcagctct gcttggtgtt gggtgtttgt ctcgcctctg cgtgtagact cgcctaaaac 300
aattggcagc cggcgtattg atttcggagc gcagtacatc tcggctttgc actcataacg 360
acgacgtcca aaagtacatt tttacactct tgcctcggat caggtaggga tacccgctga 420
acttaagcat atcaataagc gaggaaaaga aaccaacagg gattgcccta gtaacggcga 480
gtgaagcggc acagctcaaa tttgaaatct ggcgtctttg gcgtccgagt tgtaatttga 540
gagggcgctt tggcattggc agcggtccaa gttccttgga acaggacgca cagagggtga 600
gaatcccgta cgtggtcgct agcctttacc gtgtaaaccc cttcgacgag tcgagttgtt 660
tgggaatgca gctctaaatg ggaggtaatt tcttctaaag ctaaatactg gccagagacc 720
gatagcgcac aagtaagtga tcgaaagatg aaaagcactt tggaaagaga gttaaaaagc 780
acgtaaattg ttgaaaggga agcgcttgca gccagacttg cctgtagttg ctctccgggt 840
ttctacccgg tgcactcttc tataggcagg ccagcatcag ttgggcggtt ggataaaggt 900
ctctgtcatg tacct 915

<210> SEQ ID NO 308
<211> LENGTH: 958
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Pleosporales Incertae sedis, Genus: Periconia

<400> SEQUENCE: 308
tacctcttgt ttcctcggcg ggctcgcccg ccgatggacc ccccaaaaac actttgcagt 60
acctgtaata gtctgaacaa taaacaaaaa ttaaaacttc aacaacggat ctcttggttc 120
tggcatcgat gaagaacgca gcgaaatcga taagtagtgt gaattgcaga attcagtgaa 180
tcatcgaatc tttgaagcac attgcgccct ttggtattcc ttagggcatg cctgttcgag 240
cgtcattaaa ccttcaagct cagcttggtg ttgggtgact gtcccccctca aaaggactcg 300 cctcaaaatc attggcggcc ggtacgttgg cttcgagcgc agcgaaacgc gaactcggag 360
actttgtgtc ggctcccaga agccatcttt aattttgacc tcggatcagg tagggatacc 420
cgctgaactt aagcatatca aaagcggagg aaaagaaacc aacagggatt gccctagtaa 480
cggcgagtga gcggcaacag ctcaaatttg aaatctggct ctttcagggt ccgagttgta 540
tttgtagagg gtgctttgga gttgactgtg gtctaagttc cttggaacgg acgtcgcaga 600
gggtgagaat cccgtatgtg gccgccagtc ttcgccggta aagcccccttc gacgagtcga 660 gttgtttggg aatgcagctc taaatggagg taaatttctt ctaaagctaa atattggcca 720
gagaccgata gcgcaaagta gagtgatcga aagatgaaaa gcactttgga aagagagtca 780
aaaacacgtg aaattgttga aagggaagcg cttgcagcca gacttgcctg tagtgctcat 840
ccgggctttt gcccggtgca ctcttctaca ggcaggccag cacagtcctg gcggttggat 900
aaatgcctgc taaatgtacc tctcttcggg gggacttata gtttcaggcg gcatacaa 958

<210> SEQ ID NO 309
<211> LENGTH: 875
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Pleosporaceae, Genus: Alternaria

<400> SEQUENCE: 309
actggacaat ttaaaccctt tgcagttgca atcagcgtct gaaaaacata tagttacaac 60
tttcaacaac ggatctcttg gttctggcat cgatgaagac gcagcgaaat gcgataagta 120
gtgtgaattg cagaattcag tgaatcacga atctttgaac gcacattgcg ccccttggta 180
ttccatgggg catgccgttc gagcgtcatt tgtaccttca agctttgctt ggtgttgggt 240
gtttgctcgc ctctgcgtgt agactcgcct taaaacaatt ggcagccggc gtatgatttc 300
ggagcgcagt acatctcgcg ctttgcactc ataacgacga cgtcaaaagt acatttttac 360
actcttgacc tcggatcagg tagggatacc cgtgaactta agcatatcaa taagcggagg 420
aaaagaaacc aacagggatt gcctagtaac ggcgagtgaa gcggcaacag ctcaaatttg 480
aaatctggcg ctttggcgtc cgagttgtaa tttgcagagg gcgctttggc attggcagcg 540
tccaagttcc ttggaacagg acgtcacaga gggtgagaat cccgtacggg tcgctagcct 600
ttaccgtgta aagccccttc gacgagtcga gttgtttgga atgcagctct aaatgggagg 660
taaatttctt ctaaagctaa atactgccag agaccgatag cgcacaagta gagtgatcga 720
aagatgaaaa gcacttggaa agagagttaa aaagcacgtg aaattgttga aagggaagcg 780
cttgagccag acttgcctgt agttgctcat ccgggtttct acccggtgca ctctctatag 840
gcaggccagc atcagtttgg gcggttggat aaagg 875

<210> SEQ ID NO 310
<211> LENGTH: 983
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Pleosporales Incertae sedis, Genus: Periconia

<400> SEQUENCE: 310
tacctttcgt ttcctcggca ggctcgcctg ccaatgggga ccacaaaaaa cactttgcag 60
tacctgtaac agtctgaaca aacaaaacaa aaattaaaac tttcaacaac ggatctcttg 120
gttctggcat cgatgaagaa cgcagcgaaa tgcgataagt agtgtgaatt gcagaattca 180
gtgaatcatc gaatctttga acgcacattg cgccctttgg tattccttag ggcatgcctg 240
ttcgagcgtc atttaaacct tcaagctaag cttggtgttg ggtgactgtc cgcttcactg 300
cggactcgcc tcaaaattat tggcggccgg tacattggct tcgagcgcag cagaaacgcg 360
aactcgggcc cgtcgtattg gctcccagaa gctatcttca caattttgac ctcggatcag 420
gtagggatac ccgctgaact taagcatatc aataagcgga ggaaaagaaa ccaacaggga 480
ttgccctagt aacggcgagt gaagcggcaa cagctcaaat ttgaaatctg gctctttcag 540
ggtccgagtt gtaatttgta gagggtgctt tggagttgac tgtggtctaa gttccttgga 600
acaggacgtc gcagagggtg agaatcccgt atgtggccgc cagtcttctc cgtgtaaagc 660
cccttcgacg agtcgagttg tttgggaatg cagctctaaa tgggaggtaa atttcttcta 720
aagctaaata ttggccagag accgatagcg cacaagtaga gtgatcgaaa gatgaaaagc 780
actttggaaa gagagtcaaa aagcacgtga aattgttgaa agggaagcgc ttgcagccag 840
acttgcctgt agttgctcat ccgggctttt gcccggtgca ctcttctata ggcaggccag 900
catcagtcgc ggcggttgga taaatgtctg cacaatgtac ctctcttcgg ggaggactta 960
tagggcaggc ggcatacaac cag 983

<210> SEQ ID NO 311
<211> LENGTH: 969
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Capnodiales, Family: Davidiellaceae, Genus: Cladosporium

<400> SEQUENCE: 311
tccgactctg ttgcctccgg ggcgaccctg ccttcgggcg ggggctccgg tggacacttc 60
aaactcttgc gtaactttgc agtctgagta aacttaataa taaattaaaa cttttaacaa 120
cggatctctt ggttctggca tcgatgagaa cgcagcgaaa tgcgataagt aatgtgaatt 180
gcagaattca gtgaatatcg aatctttgaa cgcacattgc gccccctggt attccggggg 240
gcatgctgtt cgagcgtcat ttcaccactc aagcctcgct tggtattggg caaccggtcc 300
gccgcgtgcc tcaaatcgac cggctgggtc ttctgtcccc taacgttgtg gaaactattc 360
gctaaagggt gttcgggagg ctacgccgta aacaaccccca tttctaaggt tgacctcgga 420
tcaggtaggg atacccgctg acttaagcat atcaataagc ggaggaaaag aaaccaacag 480
ggattgctct gtaacggcga gtgaagcagc aatagctcaa atttgaaatc tggcgtcttg 540
acgtccgagt tgtaatttgt agaggatgct tctgagtaac caccgaccaa gttccttgga 600
acaggacgtc atagagggtg agaatcccgt atgcggtgga aaggtgctct atacgtagct 660
ccttcgacga gtcgagttgt ttgggatgca gctctaaatg ggaggtaaat ttcttctaaa 720
gctaaatatt ggccaagacc gatagcgcac aagtagagtg atcgaaagat gaaaagcact 780
ttggaagaga gttaaaaagc acgtgaaatt gttaaaaggg aagggattgc aacagacttg 840
ctcgcggtgt tccgccggtc ttctgaccgg tctactcgcc gcttgcaggc cagcatcgtc 900
tggtgccgct ggataagact tgaggaatgt actccctcgg gagtgttata gcctcttgtg 960
atgcagcga 969

<210> SEQ ID NO 312
<211> LENGTH: 255
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Dothideales, Family:

<400> SEQUENCE: 312
ggtgctcagc gcccgacctc caaccctctg ttgttaaaac taccttgttg ctttggcggg 60
accgcccggt ctccgagccg ccggggccct caccggccca ggcgagcgcc cgccagagtt 120
aaaccaaact cttgttataa accggtcgtc tgagtaaaag tttttaataa atcaaaactt 180
tcaacaacgg atctcttggt tctcgcatcg atgaagaacg cagcgaaatg cgataagtaa 240
tgtgaattgc agaat 255

<210> SEQ ID NO 313
<211> LENGTH: 255
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Leptosphaeriaceae, Genus: Coniothyrium

<400> SEQUENCE: 313
ttgacctgcc ctgtctgaat attctaccca tgtcttttgc gtactatttg tttccttggt 60
gggcttgccc accattagga cactataaaa ccttttgtaa ttgcagtcag cgtcagaaat 120
aacttaatag ttacaacttt caacaacgga tctcttggtt ctggcatcga tgaagaacgc 180
agcgaaatgc gataagtagt gtgaattgca gaattcagtg aatcatcgaa tctttgaacg 240
cacattgcgc ccctt 255

<210> SEQ ID NO 314
<211> LENGTH: 1024
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Pleosporaceae, Genus: Alternaria

<400> SEQUENCE: 314
tgtaggcttt gcctgctatc tcttacccat gtcttttgag tacttacgtt tcctcggcgg 60
gtccgcccgc cgactggaca atttaaaccc tttgcagttg caatcagcgt ctgaaaaaac 120

```
ttaatagtta caactttcaa caacggatct cttggttctg gcatcgatga agaacgcagc    180
gaaatgcgat aagtagtgtg aattgcagaa ttcagtgaat catcgaatct ttgaacgcac    240
attgcgcccc ttggtattcc atggggcatg cctgttcgag cgtcatttgt accttcaagc    300
tctgcttggt gttgggtgtt tgtctcgcct ctgcgtgtag actcgcctta aaacaattgg    360
cagccggcgt attgatttcg gagcgcagta catctcgcgc tttgcactca taacgacgac    420
gtccaaaagt acatttttac actcttgacc tcggatcagg tagggatacc cgctgaactt    480
aagcatatca ataagcggag gaaaagaaac caacagggat tgccctagta acggcgagtg    540
aagcggcaac agctcaaatt tgaaatctgg cgtctttggc gtccgagttg taatttgcag    600
agggcgcttt ggcattggca gcggtccaag ttccttggaa caggacgtca cagagggtga    660
gaatcccgta cgtggtcgct agcctttacc gtgtaaagcc ccttcgacga gtcgagttgt    720
ttgggaatgc agctctaaat gggaggtaaa tttcttctaa agctaaatac tggccagaga    780
ccgatagcgc acaagtagag tgatcgaaag atgaaaagca ctttggaaag agagttaaaa    840
agcacgtgaa attgttgaaa gggaagcgct tgcagccaga cttgcctgta gttgctcatc    900
cgggtttcta cccggtgcac tcttctatag gcaggccagc atcagtttgg gcggttggat    960
aaaggtctct gtcatgtacc tctcttcggg gagaacttat aggggagacg acatgcaacc   1020
agcc                                                                1024
```

<210> SEQ ID NO 315
<211> LENGTH: 973
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Pleosporaceae, Genus: Alternaria

<400> SEQUENCE: 315

```
actcttgcct agtctgcgtg aatattcacc catgtttttg cgtacttctt gtttccttgg     60
tgggctcgcc cgccaaatgg acactgttaa accttttgta attgcagtca gcgtcagtac    120
aatttaatta ttacaacttt caacaacgga tctcttggtt ctggcatcga tgaagaacgc    180
agcgaaatgc gatacgtagt gtgaattgca gaattcagtg aatcatcgaa tctttgaacg    240
cacattgcgc ccattggtat tccaatgggc atgcctgttc gagcgtcatt tgtaccctca    300
agctttgctt ggtgttgggc gtttgtcctg cgggactcgc cttaaaacga ttggcagccg    360
gcacactggt ttggagcgca gcacaaattg cggtctagcc atgaatgtcg gcgtccatga    420
agccctattt cacttttgac ctcggatcag gtagggatac ccgctgaact taagcatatc    480
aataagcgga ggaaaagaaa ccaacaggga ttgcctcagt aacggcgagt gaagcggcat    540
cagctcaaat ttgaaatctg gctctttcag ggtccgagtt gtaatttgca gagggcgctt    600
tggcataggc agcgattcaa gtcccttgga acagggcgtc acagagggtg agaatcccgt    660
acgtggtcgc tagctcttgc cgtgtaaagc cccttcgacg agtcgagttg tttgggaatg    720
cagctctaaa tgggaggtaa atttcttcta aagctaaata ctggccagag accgatagcg    780
cacaagtaga gtgatcgaaa gatgaaaaaa actttggaaa gagagttaaa cagcatgtga    840
aattgttgaa agggaagcgc ttgcagccag acttgcctgt agttgctcat ccgggctctt    900
gcccggtgca ctcttctgta ggcaggccag catcagtttg ggcggttgga taaaggtctc    960
tgtcatgtac cgc                                                       973
```

<210> SEQ ID NO 316
<211> LENGTH: 930
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Pleosporales Incertae sedis, Genus: Periconia

<400> SEQUENCE: 316

```
tcctcggcag gctcgcctgc caatggggac cccaacaaac actttgcagt acctgtaaac     60
agtctgaaca aactttaaaa attaaaactt tcaacaacgg atctcttggt tctggcatcg    120
atgaagaacg cagcgaaatg cgataagtag tgtgaattgc agaattcagt gaatcatcga    180
atctttgaac gcacattgcg ccctttggta ttccttaggg catgcctgtt cgagcgtcat    240
ttaaaccttc aagctcagct tggtgttggg tgactgtccg cttgcggact cgcctcaaaa    300
tgattggcgg ccggtacttt tggcttcgag cgcagcagaa acgcgaactc gaggcctgtg    360
tgctggctcc cagaagctat cttcacaatt ttgacctcgg atcaggtagg gatacccgct    420
gaacttaagc atatcaataa gcggaggaaa agaaaccaac agggattgcc ctagtaacgg    480
cgagtgaagc ggcaacagct caaatttgaa atctggctct ttcagggtcc gagttgtaat    540
ttgtagaggg tgctttggag ttgactgtgg tctaagttcc ttggaacagg acgtcgcaga    600
gggtgagaat cccgtatgtg gccgccagtc ttcgccgtgt aaagcccctt cgacgagtcg    660
agttgtttgg gaatgcagct ctaaatggga ggtaaatttc ttctaaagct aaatattggc    720
cagagaccga tagcgcacaa gtagagtgat cgaaagatga aaagcacttt ggaaagagag    780
tcaaaaagca cgtgaaattg ttgaaaggga agcgcttgca gccagacttg cctgtagttg    840
ctcatccggg cttttgcccg gtgcactctt ctatgggcag gccagcatca gtcctggcgg    900
tcggataaat gcctgctgaa tgtacctctc                                     930
```

<210> SEQ ID NO 317
<211> LENGTH: 1046
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Pleosporales Incertae sedis, Genus: Periconia

<400> SEQUENCE: 317

```
tatcgtaggg cttcggccct gtcgagatag aacccttgcc tttttgagta cctcttgttt     60
cctcggcggg ctcgcccgcc gatggacccc ccaaaaaaca ctttgcagta cctgtaatag    120
tctgaacaac aaacaaaaat taaaactttc aacaacggat ctcttggttc tggcatcgat    180
gaagaacgca gcgaaatgcg ataagtagtg tgaattgcag aattcagtga atcatcgaat    240
ctttgaacgc acattgcgcc ctttggtatt ccttagggca tgcctgttcg agcgtcattt    300
aaaccttcaa gctcagcttg gtgttgggtg actgtccccc tcaaaaggga ctcgcctcaa    360
aatcattggc ggccggtacg ttggcttcga gcgcagcaga aacgcgaact cggagacttt    420
gtgtcggctc ccagaagcca tctttaaatt ttgacctcgg atcaggtagg gatacccgct    480
gaacttaagc atatcaataa gcggaggaaa agaaaccaac agggattgcc ctagtaacgg    540
cgagtgaagc ggcaacagct caaatttgaa atctggctct ttcagggtcc gagttgtaat    600
ttgtagaggg tgctttggag ttgactgtgg tctaagttcc ttggaacagg acgtcgcaga    660
gggtgagaat cccgtatgtg gccgccagtc ttcgccgtgt aaagcccctt cgacgagtcg    720
```

-continued agttgtttgg gaatgcagct ctaaatggga ggtaaatttc ttctaaagct aaatattggc 780
cagagaccga tagcgcacaa gtagagtgat cgaaagatga aaagcacttt ggaaagagag 840
tcaaaaagca cgtgaaattg ttgaaaggga agcgcttgca gccagacttg cctgtagttg 900
ctcatccggg cttttgcccg gtgcactctt ctacaggcag gccagcatca gtcctggcgg 960
ttggataaat gcctgctaaa tgtacctctc ttcggggagg acttatagtt tcaggcggca 1020
tacaaccagc cgggattgag gtccgc 1046

<210> SEQ ID NO 318
<211> LENGTH: 990
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Capnodiales, Family: Davidiellaceae, Genus: Cladosporium

<400> SEQUENCE: 318
tccgactctg ttgcctccgg ggcgaccctg ccttcgggcg ggggctccgg gtggacactt 60
caaactcttg cgtaactttg cagtctgagt aaacttaatt aataaattaa aacttttaac 120
aacggatctc ttggttctgg catcgatgaa gaacgcagcg aaatgcgata agtaatgtga 180
attgcagaat tcagtgaatc atcgaatctt tgaacgcaca ttgcgccccc tggtattccg 240
gggggcatgc ctgttcgagc gtcatttcac cactcaagcc tcgcttggta ttgggcaacg 300
cggtccgccg cgtgcctcaa atcgaccggc tgggtcttct gtcccctaag cgttgtggaa 360
actattcgct aaagggtgtt cgggaggcta cgccgtaaaa caaccccatt tctaaggttg 420
acctcggatc aggtagggat acccgctgaa cttaagcata tcaataagcg gaggaaaaga 480
aaccaacagg gattgctcta gtaacggcga gtgaagcagc aatagctcaa atttgaaatc 540
tggcgtcttc gacgtccgag ttgtaatttg tagaggatgc ttctgagtaa ccaccgacct 600
aagttccttg gaacaggacg tcatagaggg tgagaatccc gtatgcggtc ggaaaggtgc 660
tctatacgta gctccttcga cgagtcgagt tgtttgggaa tgcagctcta aatgggaggt 720
aaatttcttc taaagctaaa tattggccag agaccgatag cgcacaagta gagtgatcga 780
aagatgaaaa gcactttgga aagagagtta aaaagcacgt gaaattgtta aaagggaagg 840
gattgcaacc agacttgctc gcggtgttcc gccggtcttc tgaccggtct actcgccgcg 900
ttgcaggcca gcatcgtctg gtgccgctgg ataagacttg aggaatgtag ctccctcggg 960
agtgttatag cctcttgtga tgcagcgagc 990

<210> SEQ ID NO 319
<211> LENGTH: 1036
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Pleosporaceae, Genus: Alternaria

<400> SEQUENCE: 319
tacctagagt tgtaggcttt gcctgctatc tcttacccat gtcttttgag caccttatgt 60
ttcctcggtg ggctcgcccg ccgaatggac aaaatttaaa ccctttgtag tttgtaatca 120
gcgtctgaaa aaaacttaat agttacaact ttcaacaacg gatctcttgg ttctggcatc 180
gatgaagaac gcagcgaaat gcgataagta gtgtgaattg cagaattcag tgaatcatcg 240
aatctttgaa cgcacattgc gccccttggt attccatggg gcatgcctgt tcgagcgtca 300
tttgtacctt caagctttgc ttggtgttgg gtgtttgtct cgcctttgcg tgtagactcg 360
ccttaaaaca attggcagcc ggcgtattga tttcggagcg cagtacatct cgcgctttgc 420
actcataacg gtggcgtcca aaagtacatt tttacactct tgacctcgga tcaggtaggg 480
atacccgctg aacttaagca tatcaataag cggaggaaaa gaaaccaaca gggattgccc 540
tagtaacggc gagtgaagcg gcaacagctc aaatttgaaa tctggcgtct ttggcgtccg 600
agttgtaatt tgcagagggc gctttggcat tggcagcggt ccaagttcct tggaacagga 660
cgtcacagag ggtgagaatc ccgtacgtgg tcgctagcct ttaccgtgta aagccccttc 720
gacgagtcga gttgtttggg aatgcagctc taaatgggag gtaaatttct tctaaagcta 780
aatactggcc agagaccgat agcgcacaag tagagtgatc gaaagatgaa aagcactttg 840
gaaagagagt taaaaagcac gtgaaattgt tgaaagggaa gcgcttgcag ccagacttgc 900
ctgtagttgc tcatccgggt ttctacccgg tgcactcttc tacaggcagg ccagcatcag 960
tttgggcggt tggataaagg tctctgtcat gtacctctct tcggggagaa cttatagggg 1020
agacgacatg caacca 1036

<210> SEQ ID NO 320
<211> LENGTH: 986
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Pleosporales Incertae sedis, Genus: Periconia

<400> SEQUENCE: 320 acctttcgt ttcctcggca ggctcgcctg ccaacgggga ccccaaaaac gctttgtaat 60
acctgtcatt gtctgatata acaagcaaaa attaaaactt tcaacaacgg atctcttggt 120
tctggcatcg atgaagaacg cagcgaaatg cgataagtag tgtgaattgc agaattcagt 180
gaatcatcga atctttgaac gcacattgcg ccctttggta ttccttaggg catgcctgtt 240
cgagcgtcat ttaaaccttc aagctcagct tggtgatggg tgactgtcct cccctcgcgg 300
ggggactcgc ctcaaaaaca ttggcggccg gtacattggc ttcgagcgca gcagaaacgc 360
ggtctcgagc ccggtggatc ggctcccata agcctcttct tttattttga cctcggatca 420
ggtagggata cccgctgaac ttaagcatat caataagcgg aggaaaagaa accaacaggg 480
attgccctag taacggcgag tgaagcggca acagctcaaa tttgaaatct ggccctttca 540
gggtccgagt tgtaatttgt agagggtgct ttggcgttgg ctgtggtcta agttccttgg 600
aacaggacgt cgcagagggt gagaatcccg tatgtggccg ccagtcttcg ccgtgtaaag 660
ccccttcgac gagtcgagtt gtttgggaat gcagctctaa atgggaggta aatttcttct 720
aaagctaaat attggccaga gaccgatagc gcacaagtag agtgatcgaa agatgaaaag 780
cactttggaa agagagtcaa aaagcacgtg aaattgttga aagggaagcg cttgcagcca 840
gacttgcctg tagttgctca tccgggcttt tgcccggtgc actcttctac gggcaggcca 900
gcatcagtcc cagcggttgg ataaatgcct gttgaatgta cctctcttcg gggaggactt 960
atagcctcgg gcggcataca accagc 986

<210> SEQ ID NO 321
<211> LENGTH: 255
<212> TYPE: DNA
<213> ORGANISM: Unknown

<220> FEATURE:
<223> OTHER INFORMATION: Kingdom: Fungi, Phylum: Ascomycota, Class:
      Dothideomycetes, Order: Pleosporales, Family: Sporormiaceae,
      Genus: Preussia

<400> SEQUENCE: 321

```
tacctcttgt ttcctcggcg ggctcgcccg ccgatggacc ccccaaaaaa cactttgcag     60

tacctgtaat agtctgaaca acaaacaaaa attaaaactt tcaacaacgg atctcttggt    120

tctggcatcg atgaagaacg cagcgaaatg cgataagtag tgtgaattgc agaattcagt    180

gaatcatcga atctttgaac gcacattgcg ccctttggta ttccttaggg catgcctgtt    240

cgagcgtcat ttaaa                                                     255
```

<210> SEQ ID NO 322
<211> LENGTH: 1042
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Pleosporales, Family: Sporormiaceae

<400> SEQUENCE: 322

```
atcttatcgt agggcttcgg ccctgtcgag atagaaccct tgcctttttg agtacctttc     60

gtttcctcgg caggctcgcc tgccaatggg gaccacaaaa aacactttgc agtacctgta    120

acagtctgaa caaacaaaac aaaaattaaa actttcaaca acggatctct tggttctggc    180

atcgatgaag aacgcagcga aatgcgataa gtagtgtgaa ttgcagaatt cagtgaatca    240

tcgaatcttt gaacgcacat tgcgcccttt ggtattcctt agggcatgcc tgttcgagcg    300

tcatttaaac cttcaagcta agcttggtgt tgggtgactg tccgcttcac tgcggactcg    360

cctcaaaatt attggcggcc ggtacattgg cttcgagcgc agcagaaacg cgaactcggg    420

cccgtcgtat tggctcccag aagctatctt cacaattttg acctcggatc aggtagggat    480

acccgctgaa cttaagcata tcaataagcg gaggaaaaga aaccaacagg gattgcccta    540

gtaacggcga gtgaagcggc aacagctcaa atttgaaatc tggctctttc agggtccgag    600

ttgtaatttg tagagggtgc tttggagttg actgtggtct aagttccttg gaacaggacg    660

tcgcagaggg tgagaatccc gtatgtggcc gccagtcttc tccgtgtaaa gccccttcga    720

cgagtcgagt tgtttgggaa tgcagctcta aatgggaggt aaatttcttc taaagctaaa    780

tattggccag agaccgatag cgcacaagta gagtgatcga aagatgaaaa gcactttgga    840

aagagagtca aaaagcacgt gaaattgttg aaagggaagc gcttgcagcc agacttgcct    900

gtagttgctc atccgggctt ttgcccggtg cactcttcta taggcaggcc agcatcagtc    960

gcggcggttg gataaatgtc tgcacaatgt acctctcttc ggggaggact tatagggcag   1020

gcggcataca accagctgcg at                                            1042
```

<210> SEQ ID NO 323
<211> LENGTH: 1036
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Pleosporales, Family: Sporormiaceae,
      Genus: Preussia

<400> SEQUENCE: 323

```
ttgggcttcg gcccattcga gataacaccc ttgccttttt gagtaccttt tcgtttcctc     60

ggcaggctcg cctgccaacg gggaccccaa aaacgctttg taatacctgt cattgtctga    120
```

tataacaagc aaaaattaaa actttcaaca acggatctct tggttctggc atcgatgaag 180
aacgcagcga aatgcgataa gtagtgtgaa ttgcagaatt cagtgaatca tcgaatcttt 240
gaacgcacat tgcgcccttt ggtattcctt agggcatgcc tgttcgagcg tcatttaaac 300
cttcaagctc agcttggtga tgggtgactg tcctcccctc gcggggggac tcgcctcaaa 360
aacattggcg gccggtacat tggcttcgag cgcagcagaa acgcggtctc gagcccggtg 420
gatcggctcc cataagcctc ttcttttatt ttgacctcgg atcaggtagg gatacccgct 480
gaacttaagc atatcaataa gcggaggaaa agaaaccaac agggattgcc ctagtaacgg 540
cgagtgaagc ggcaacagct caaatttgaa atctggccct ttcagggtcc gagttgtaat 600
ttgtagaggg tgctttggcg ttggctgtgg tctaagttcc ttggaacagg acgtcgcaga 660
gggtgagaat cccgtatgtg gccgccagtc ttcgccgtgt aaagcccctt cgacgagtcg 720
agttgtttgg gaatgcagct ctaaatggga ggtaaatttc ttctaaagct aaatattggc 780
cagagaccga tagcgcacaa gtagagtgat cgaaagatga aaagcacttt ggaaagagag 840
tcaaaaagca cgtgaaattg ttgaaaggga agcgcttgca gccagacttg cctgtagttg 900
ctcatccggg cttttgcccg gtgcactctt ctatgggcag gccagcatca gtcccagcgg 960
ttggataaat gcctgttgaa tgtacctctc ttcggggagg acttatagcc tcgggcggca 1020
tacaaccagc cgggat 1036

<210> SEQ ID NO 324
<211> LENGTH: 984
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Sporormiaceae, Genus: Preussia

<400> SEQUENCE: 324
tacctttcgt ttcctcggca ggctcgcctg ccaatgggga ccacaaaaaa cactttgcag 60
tacctgtaac agtctgaaca aacaaaacaa aaattaaaac tttcaacaac ggatctcttg 120
gttctggcat cgatgaagaa cgcagcgaaa tgcgataagt agtgtgaatt gcagaattca 180
gtgaatcatc gaatctttga acgcacattg cgccctttgg tattccttag ggcatgcctg 240
ttcgagcgtc atttaaacct tcaagctaag cttggtgttg ggtgactgtc cgcttcactg 300
cggactcgcc tcaaaattat tggcggccgg tacattggct tcgagcgcag cagaaacgcg 360
aactcgggcc cgtcgtattg gctcccagaa gctatcttca caattttgac ctcggatcag 420
gtagggatac ccgctgaact taagcatatc aataagcgga ggaaaagaaa ccaacaggga 480
ttgccctagt aacggcgagt gaagcggcaa cagctcaaat ttgaaatctg gctctttcag 540
ggtccgagtt gtaatttgta gagggtgctt tggagttgac tgtggtctaa gttccttgga 600
acaggacgtc gcagagggtg agaatcccgt atgtggccgc cagtcttctc cgtgtaaagc 660
cccttcgacg agtcgagttg tttgggaatg cagctctaaa tgggaggtaa atttcttcta 720
aagctaaata ttggccagag accgatagcg cacaagtaga gtgatcgaaa gatgaaaagc 780
actttggaaa gagagtcaaa aagcacgtga aattgttgaa agggaagcgc ttgcagccag 840
acttgcctgt agttgctcat ccgggctttt ttgcccggtg cactcttcta taggcaggcc 900
agcatcagtc gcggcggttg gataaatgtc tgcacaatgt acctctcttc ggggaggact 960
tatagggcag gcggcataca acca 984

<210> SEQ ID NO 325
<211> LENGTH: 578
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Botryosphaeriales, Family: Botryosphaeriaceae, Genus: Botryosphaeria

<400> SEQUENCE: 325
aacacggttc gtagggacct gcggaaggat cattaccgag ttgattcggg ctccggcccg 60
atcctcccac cctttgtgta cctacctctg ttgctttggc gggccgcggt cctccgcggc 120 cgccccccctc cccgggggggt ggccagcgcc cgccagagga ccatcaaact ccagtcagta 180
aacgatgcag tctgaaaaac atttaataaa ctaaaacttt caacaacgga tctcttggtt 240
ctggcatcga tgaagaacgc agcgaaatgc gataagtaat gtgaattgca gaattcagtg 300
aatcatcgaa tctttgaacg cacattgcgc cctttggtat tccgaagggc atgcctgttc 360
gagcgtcatt acaaccctca agctctgctt ggtattgggc accgtccttt gcgggcgcgc 420
ctcaaagacc tcggcggtgg cgtcttgcct caagcgtagt agaacataca tctcgcttcg 480
gagcgcaggg cgtcgcccgc cggacgaacc ttctgaactt ttctcaaggt tgacctcgga 540
tcaggtaggg atacccgctg aacttaagca tatcatag 578

<210> SEQ ID NO 326
<211> LENGTH: 600
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Botryosphaeriales, Family: Botryosphaeriaceae, Genus: Microdiplodia

<400> SEQUENCE: 326
aaacacggtt cgtagtgacc tgcggaagga tcattatcta ttccatgagg tgcggtcgcg 60
gccctcggcg ggagcaacag ctaccgtcgg gcggtagagg taacactttc acgcgccgca 120
tgtctgaatc cttttttttac gagcaccttt cgttctcctt cggcggggca acctgccgtt 180
ggaacctatc aaaacctttt tttgcatcta gcattacctg ttctgataca aacaatcgtt 240
acaactttca acaatggatc tcttggctct ggcatcgatg aagaacgcag cgaaatgcga 300
taagtagtgt gaattgcaga attcagtgaa tcatcgaatc tttgaacgca cattgcgccc 360
cttggtattc catggggcat gcctgttcga gcgtcatcta caccctcaag ctctgcttgg 420
tgttgggcgt ctgtcccgcc tctgcgcgcg gactcgcccc aaattcattg gcagcggtcc 480
ttgcctcctc tcgcgcagca cattgcgctt ctcgaggtgc gcggcccgcg tccacgaagc 540
aacattaccg tctttgacct cggatcaggt agggataccc gctgaactta agcatatctg 600

<210> SEQ ID NO 327
<211> LENGTH: 615
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Xylariales, Family: Amphisphaeriaceae, Genus: Pestalotiposis

<400> SEQUENCE: 327
aaaacacggt ctgttgtgaa ccagcggagg gatcattata gagttttcta aactcccaac 60
ccatgtgaac ttaccattgt tgcctcggca gaagctacct ggttacctta ccttggaacg 120
gcctaccctg tagcgcctta ccctggaacg gcctaccctg taacggctgc cggtggacta 180
ccaaactctt gttattatat tgtaatctga gcgtcttatt ttaataagtc aaaactttca 240
acaacggatc tcttggttct ggcatcgatg aagaacgcag cgaaatgcga taagtaatgt 300
gaattgcaga attcagtgaa tcatcgaatc tttgaacgca cattgcgccc attagtattc 360
tagtgggcat gcctgttcga gcgtcatttc aacccttaag cctagcttag tgttgggagc 420
ctactgcttt tgctagcggt agctcctgaa atacaacggc ggatctgcga tatcctctga 480
gcgtagtaat ttttatctcg cttttgactg gagttgcagc gtctttagcc gctaaacccc 540
ccaattttta atggttgacc tcggatcagg taggaatacc cgctgaactt aagcatatca 600
taggccgaaa ggaaa 615

<210> SEQ ID NO 328
<211> LENGTH: 645
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Botryosphaeriales, Family: Botryosphaeriaceae, Genus: Phyllosticta

<400> SEQUENCE: 328
aacacggttc gtagtgacct gcggaaggat cattactgaa aatgtaataa acccttcagg 60
ttttggaagg gggagccgtc aaaagcttcc ctggtacatg cctcacccct tgtatatcta 120
ccatgttgct ttggcgggcc gacccggttt cgacccgggc ggccggcgcc cccagcctgc 180
ttgccaggcc aggacgcccg gccaagtgcc cgccagtata caaaactcca gcgattattt 240
tgtgtagtcc tgagaattta ttcaataaat taaaactttc aacaacggat ctcttggttc 300
tggcatcgat gaagaacgca gcgaaatgcg ataagtaatg tgaattgcag aattcagtga 360
atcatcgaat ctttgaacgc acattgcgcc ctctggcatt ccggagggca tgcctgttcg 420
agcgtcattt caaccctcaa gctctgcttg gtattgggcg acgtctgctg tcagacgcgc 480
ctggaagacc tcggcgacgg cattccagcc tcgagcgtag tagtaaaata tctcgctttg 540
gaggatgggg tgacggcttg ccggacaacc gacctctggt catttttccc aaggttgacc 600
tcggatcagg tagggatacc cgctgaactt aagcatatat aggcg 645

<210> SEQ ID NO 329
<211> LENGTH: 1371
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Pleosporaceae, Genus: Alternaria

<400> SEQUENCE: 329
gattgcccta gtacggcgag tgaagcggca cagctcaaat ttgaaatctg gctcttttag 60
agtccgagtt gtaatttgca gagggcgctt tggctttggc agcggtccaa gttccttgga 120
acaggacgtc acagagggtg agaatcccgt acgtggtcgc tggctattgc cgtgtaaagc 180
cccttcgacg agtcgagttg tttgggaatg cagctctaaa tgggaggtac atttcttcta 240
aagctaaata ttggccagag accgatagcg cacaagtaga gtgatcgaaa gatgaaaagc 300
actttggaaa gagagtcaaa cagcacgtga aattgttgaa agggaagcgc ttgcagccag 360
acttgcttac agttgctcat ccgggtttct acccggtgca ctcttctgta ggcaggccag 420
catcagtttg ggcggtagga taaaggtctc tgtcacgtac ctcctttcgg ggaggcctta 480
taggggagac gacatactac cagcctggac tgaggtccgc gcatctgcta ggatgctggc 540
gtaatggctg taagcggccc gtcttgaaac acggaccaag gagtctaaca tctatgcgag 600
tgtttgggtg tcaagcccga gcgcgtaatg aaagtgaacg gaggtgggaa cccgcaaggg 660
tgcaccatcg accgatcctg atgtcttcgg aaggatttga gtaagagcat ggctgttggg 720
acccgaaaga tggtgaacta tgcttgaata gggtgaagcc agaggaaact ctggtggagg 780
ctcgcagcgg ttctgacgtg caaatcgatc gtcaaatttg ggcatagggg cgaaagacta 840
atcgaactat ctagtagctg gttcctgccg aagtttccct caggatagca gtaacgtatt 900
cagttttatg aggtaaagcg aatgattaga ggcctggggg ttgaaacaac cttcacctat 960
tctcaaactt taaatatgta agaagtcctt gttacttaat tgaacgtgga cagttgaatg 1020
aaacgttatt agtgggccat tttggtaag cagaactggc gatgcgggat gaaccgaacg 1080
aggggttaaa gtgccggaat atacgctcat cagacaccac aaaaggtgtt ggttcatcta 1140
gacagcagga cggtggccat ggaagtcgga atccgctaag gagtgtgtaa caactcacct 1200
gccgaatgaa ctagccctga aaatggatgg cgctcaagcg tgttacttat accccctccgc 1260 tggggcaaaa tttacgcccc agcgagtagg caggcgtgga ggtccgtgac gaagccttgg 1320
gggtgacccc gggtcgaacg gcctctagtg cagatctggg ggggtagtaa a 1371

<210> SEQ ID NO 330
<211> LENGTH: 574
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Coniochaetales, Family: Coniochaetaceae, Genus: Lecythophora

<400> SEQUENCE: 330
ttcacggttc gtggtgaacc agcggaggga tcattacaag aagccgaaag gctacttcaa 60
accatcgtga acttatccaa gttgcttcgg cggcgcggct cccctcgcgg ggtgccgcag 120
ccccgccccc tcgggggtgg tgggcgcccg ccggaggtat taaactctcc cgtattatag 180
tggtatttct gagtaaaaac aaataagtta aaactttcaa caacggatct cttggttctg 240
gcatcgatga agaacgcagc gaaatgcgat aagtaatgtg aattgcagaa ttcagtgaat 300
catcgaatct ttgaacgcac attgcgcccg ctagtattct agcgggcatg cctgttcgag 360
cgtcatttca accctcaagc cctgcttggt gttggggccc tacggctgcc gtaggccctg 420
aaaagaagtg gcgggctcgc tgcaactccg agcgtagtaa ttcattatct cgctagggag 480
gcgcggcggt gctcctgccg ttaaagacca tctttaacca aaggttgacc tcggatcagg 540
taggaatacc cgctgaactt aagcatatca taaa 574

<210> SEQ ID NO 331
<211> LENGTH: 604
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Botryosphaeriales, Family: Botryosphaeriaceae, Genus: Microdiplodia

<400> SEQUENCE: 331
ttacacggtt cgtaggtgaa cctgcggaag gatcattatc tattccatga ggtgcggtcg 60
cggccctcgg cgggagcaac agctaccgtc gggcggtaga ggtaacactt tcacgcgccg 120
catgtctgaa tcctttttttt acgagcacct ttcgttctcc ttcggcgggg caacctgccg 180
ttggaaccta tcaaaacctt tttttgcatc tagcattacc tgttctgata caaacaatcg 240
ttacaacttt caacaatgga tctcttggct ctggcatcga tgaagaacgc agcgaaatgc 300
gataagtagt gtgaattgca gaattcagtg aatcatcgaa tctttgaacg cacattgcgc 360
cccttggtat tccatggggc atgcctgttc gagcgtcatc tacaccctca agctctgctt 420
ggtgttgggc gtctgtcccg cctctgcgcg cggactcgcc ccaaattcat tggcagcggt 480
ccttgcctcc tctcgcgcag cacattgcgc ttctcgaggt gcgcggcccg cgtccacgaa 540
gcaacattac cgtctttgac ctcggatcag gtagggatac ccgctgaact taagcatatc 600
ataa 604

<210> SEQ ID NO 332
<211> LENGTH: 539
<212> TYPE: DNA
<213> ORGANISM: Unknown
<220> FEATURE:
<223> OTHER INFORMATION: Kingdom: Fungi, Phylum: Ascomycota, Class: Sordariomycetes, Order: Xylariales, Family: Xylariaceae, Genus: Daldinia

<400> SEQUENCE: 332
actgagttat ctaaactccc aaccctttgt gaaccttacc gtcgttgcct cggcgggctg 60
tacttaccct gtagctaccc tgtagctacc cggtaggtgc gctccaagcc cgccggtgga 120
ccactaaatt ctattttact actgtatctc tgaatgcttc aacttaataa gttaaaactt 180
tcaacaacgg atctcttggt tctggcatcg atgaagaacg cagcgaaatg cgataagtaa 240
tgtgaattgc agaattcagt gaatcatcga atctttgaac gcacattgcg cccattagta 300
ttctagtggg catgcctatt cgagcgtcat ttcaaccctt aagcctagtt gcttagtgtt 360
gggaatctgc cctgtattta tagggcagtt ccttaaagtg atcggcggag ttagggcata 420
ctctaagcgt agtaatattc ttctcgcttc tgtagttgtc ctggcggctt gccgttaaac 480
ccctatattt ctagtggttg acctcggatt aggtaggaat acccgctgaa cttaagcat 539

<210> SEQ ID NO 333
<211> LENGTH: 612
<212> TYPE: DNA
<213> ORGANISM: Unknown
<220> FEATURE:
<223> OTHER INFORMATION: Kingdom: Fungi, Phylum: Zygomycota, Class: Mucoromycotina, Order: Mucorales, Family: Mucoraceae, Genus: Mucor
<220> FEATURE:
<221> NAME/KEY: misc_feature
<222> LOCATION: (605)..(606)
<223> OTHER INFORMATION: n is a, c, g, or t

<400> SEQUENCE: 333
cattaaataa tcaataatct tggctatgtc cattattatc tatttactgt gaactgtatt 60
attatttgac atttgaggga tgttccaatg ttataaggat agacattgga aatgttaacc 120
gagtcataat caggtttagg cctggtatcc tattattatt taccaaatga attcagaatt 180
aatattgtaa catagaccta aaaaatctat aaaacaactt ttaacaacgg atctcttggt 240
tctcgcatcg atgaagaacg tagcaaagtg cgataactag tgtgaattgc atattcagtg 300
aatcatcgag tctttgaacg caacttgcgc tcattggtat tccaatgagc acgcctgttt 360
cagtatcaaa acaaaccctc tattcaactt ttgttgtata ggattattgg gggcctctcg 420
atctgtatag atcttgaaat ccttgaaatt tactaaggcc tgaacttgtt taaatgcctg 480

-continued

```
aactttttttt taatataaag gaaagctctt gtaattgact ttgatggggc ctcccaaata    540

aatctctttt aaatttgatc tgaaatcagg cgggattacc cgctgaactt aagcatatca    600

ataannggag ga                                                        612
```